(12) United States Patent
Yokoyama et al.

(10) Patent No.: US 10,593,884 B2
(45) Date of Patent: Mar. 17, 2020

(54) ORGANIC ELECTROLUMINESCENT DEVICE

(71) Applicant: Hodogaya Chemical Co., Ltd., Tokyo (JP)

(72) Inventors: Norimasa Yokoyama, Tokyo (JP); Shuichi Hayashi, Tokyo (JP); Takeshi Yamamoto, Tokyo (JP); Naoaki Kabasawa, Tokyo (JP); Daizou Kanda, Tokyo (JP); Kazunori Togashi, Tokyo (JP); Shunji Mochizuki, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 276 days.

(21) Appl. No.: 15/541,842

(22) PCT Filed: Jan. 4, 2016

(86) PCT No.: PCT/JP2016/050005
§ 371 (c)(1),
(2) Date: Jul. 6, 2017

(87) PCT Pub. No.: WO2016/111254
PCT Pub. Date: Jul. 14, 2016

(65) Prior Publication Data
US 2018/0006235 A1    Jan. 4, 2018

(30) Foreign Application Priority Data

Jan. 6, 2015  (JP) ................ 2015-001119
Jun. 19, 2015 (JP) ................ 2015-123597

(51) Int. Cl.
*H01L 51/50* (2006.01)
*H01L 51/00* (2006.01)
(Continued)

(52) U.S. Cl.
CPC ........ *H01L 51/0059* (2013.01); *C07C 211/54* (2013.01); *C07C 211/61* (2013.01);
(Continued)

(58) Field of Classification Search
None
See application file for complete search history.

(56) References Cited

U.S. PATENT DOCUMENTS 9,123,897 B2    9/2015 Yokoyama et al.
2004/0170863 A1* 9/2004 Kim ................ C07C 13/72
                                        428/690
(Continued)

FOREIGN PATENT DOCUMENTS

JP  2013-118288  * 6/2013 ........... H01L 51/50
TW  201342681 A  10/2013
(Continued)

OTHER PUBLICATIONS

International Search Report dated Mar. 8, 2016, issued for PCT/JP2016/050005.
(Continued)

*Primary Examiner* — Gregory D Clark
(74) *Attorney, Agent, or Firm* — Locke Lord LLP; James E. Armstrong, IV; Nicholas J. DiCeglie, Jr.

(57) ABSTRACT

In the organic electroluminescent device having at least an anode, a hole injection layer, a first hole injection layer, a second hole injection layer, a light emitting layer, an electron transport layer and a cathode in this order, the hole injection layer includes an arylamine compound of the following general formula (1) and an electron acceptor.

[Chemical Formula 1]

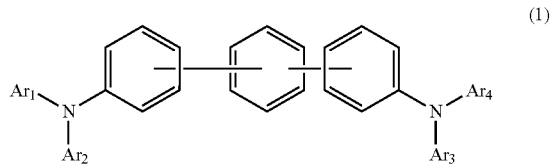

In the formula, $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group.

19 Claims, 1 Drawing Sheet

← 9 CATHODE
← 8 ELECTRON INJECTION LAYER
← 7 ELECTRON TRANSPORT LAYER
← 6 LIGHT EMITTING LAYER
← 5 SECOND HOLE TRANSPORT LAYER
← 4 FIRST HOLE TRANSPORT LAYER
← 3 HOLE INJECTION LAYER
← 2 TRANSPARENT ANODE
← 1 GLASS SUBSTRATE

(51) Int. Cl.
*C07D 401/10* (2006.01)
*C07C 211/54* (2006.01)
*C09K 11/06* (2006.01)
*C07C 211/61* (2006.01)
*C07D 209/88* (2006.01)
*C07C 211/60* (2006.01)
*H01L 51/52* (2006.01)

(52) U.S. Cl.
CPC ......... *C07D 209/88* (2013.01); *C07D 401/10* (2013.01); *C09K 11/06* (2013.01); *H01L 51/006* (2013.01); *H01L 51/0061* (2013.01); *H01L 51/0067* (2013.01); *H01L 51/50* (2013.01); *C07C 211/60* (2013.01); *H01L 51/001* (2013.01); *H01L 51/0052* (2013.01); *H01L 51/0056* (2013.01); *H01L 51/0058* (2013.01); *H01L 51/0072* (2013.01); *H01L 51/0073* (2013.01); *H01L 51/508* (2013.01); *H01L 51/5012* (2013.01); *H01L 51/5016* (2013.01); *H01L 51/5064* (2013.01); *H01L 51/5072* (2013.01); *H01L 51/5088* (2013.01); *H01L 51/5206* (2013.01); *H01L 51/5221* (2013.01); *H01L 2251/552* (2013.01)

(56) References Cited

U.S. PATENT DOCUMENTS

| 2013/0193414 | A1* | 8/2013 | Werner ................. C09K 11/06 257/40 |
| 2014/0374721 | A1 | 12/2014 | Yokoyama et al. |
| 2015/0380657 | A1 | 12/2015 | Yokoyama et al. |
| 2016/0126464 | A1 | 5/2016 | Yokoyama et al. |
| 2017/0179398 | A1* | 6/2017 | Yokoyama ............. C09K 11/06 |

FOREIGN PATENT DOCUMENTS

| WO | 2013/054764 A | 4/2013 |
| WO | 2013083712 A1 | 6/2013 |
| WO | 2014/129201 A1 | 8/2014 |
| WO | 2014/199567 A1 | 12/2014 |

OTHER PUBLICATIONS

Office Action dated Sep. 30, 2018, issued for the Chinese patent application No. 201680005179.7 and Japanese translation thereof.
Office Action issued in corresponding Japanese Patent Application No. JP 2017-030713, dated Oct. 29, 2019.

* cited by examiner

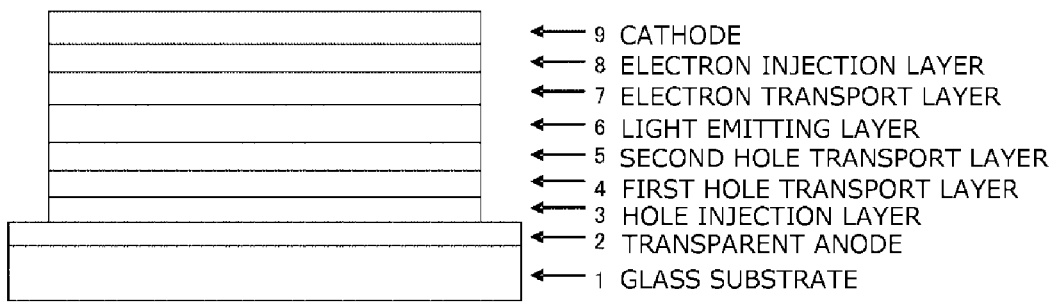

ORGANIC ELECTROLUMINESCENT DEVICE

TECHNICAL FIELD

The present invention relates to an organic electroluminescent device which is a preferred self-luminous device for various display devices. Specifically, this invention relates to organic electroluminescent devices (hereinafter referred to as organic EL devices) using specific arylamine compounds doped with an electron acceptor.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to Non-Patent Document 1, for example).

Further, there have been attempts to use triplet excitons for further improvements of luminous efficiency, and the use of a phosphorescence-emitting compound has been examined (refer to Non-Patent Document 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 3, for example).

The light emitting layer can be also fabricated by doping a charge-transporting compound generally called a host material, with a fluorescent compound, a phosphorescence-emitting compound, or a delayed fluorescent-emitting material. As described in the Non-Patent Document, the selection of organic materials in an organic EL device greatly influences various device characteristics such as efficiency and durability (refer to Non-Patent Document 2, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving the hole injection capability and the electron blocking capability of blocking injected electrons from the cathode, and high luminous efficiency can be obtained by confining excitons generated in the light emitting layer. The role of a hole transport material is therefore important, and there is a need for a hole transport material that has a high hole injection capability, a high hole mobility, a high electron blocking capability, and a high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (NPD) and various aromatic amine derivatives are known as the hole transport materials used for the organic EL device (refer to Patent Documents 1 and 2, for example). Although NPD has a desirable hole transport capability, its glass transition point (Tg), which is an index of heat resistance, is as low as 96° C., which causes the degradation of device characteristics by crystallization under a high-temperature condition (refer to Non-Patent Document 4, for example). The aromatic amine derivatives described in the Patent Documents include a compound known to have an excellent hole mobility of 10$^{-3}$ cm$^2$/Vs or higher (refer to Patent Documents 1 and 2, for example). However, since the compound is insufficient in terms of electron blocking capability, some of the electrons pass through the light emitting layer, and improvements in luminous efficiency cannot be expected. For such a reason, a material with a higher electron blocking capability, a more stable thin-film state and higher heat resistance is needed for higher efficiency. Although an aromatic amine derivative having high durability is reported (refer to Patent Document 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as the heat resistance and the hole injection capability (refer to Patent Documents 4 and 5, for example). Further, it is proposed that the hole injection capability can be improved by p-doping materials such as trisbromophenylamine hexachloroantimony, radialene derivatives, and F4-TCNQ into a material commonly used for the hole injection layer or the hole transport layer (refer to Patent Document 6 and Non-Patent Document 5). However, while the devices using these compounds for the hole injection layer or the hole transport layer have been improved in lower driving voltage and heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport capabilities, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport capabilities, stability as a thin film and durability.

CITATION LIST

Patent Documents

Patent Document 1: JP-A-8-048656
Patent Document 2: Japanese Patent No. 3194657
Patent Document 3: Japanese Patent No. 4943840
Patent Document 4: JP-A-2006-151979
Patent Document 5: WO2008/62636
Patent Document 6: WO2014/009310
Patent Document 7: WO2005/115970
Patent Document 8: JP-A-7-126615
Patent Document 9: JP-A-2005-108804
Patent Document 10: WO2011/059000
Patent Document 11: WO2003/060956
Patent Document 12: KR-A-2013-060157
Patent Document 13: WO2013/054764

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Appl. Phys. Let., 98, 083302 (2011)
Non-Patent Document 4: Organic EL Symposium, the 3rd Regular presentation Preprints, pp. 13 to 14 (2006)
Non-Patent Document 5: Appl. Phys. Let., 89, 253506 (2006)

SUMMARY OF THE INVENTION

Technical Problem

An object of the present invention is to provide an organic EL device having low driving voltage, high luminous efficiency and a long lifetime, by combining various materials for an organic EL device, which are excellent, as materials for an organic EL device having high luminous efficiency and high durability, in hole and electron injection/transport capabilities, electron blocking capability, stability in thin-film state and durability, so as to allow the respective materials to effectively reveal their characteristics.

Physical properties of the organic EL device to be provided by the present invention include (1) low turn on voltage, (2) low actual driving voltage, (3) high luminous efficiency and high power efficiency, and (4) a long lifetime.

Solution to Problem

For achieving the object, the present inventors, who pay attention to the fact that an arylamine material doped with an electron acceptor is excellent in the hole injection/transport capabilities and the stability and durability of the thin film, select a particular arylamine compound (having a particular structure), and produce various organic EL devices using a particular arylamine compound (having a particular structure) doped with an electron acceptor as a material of a hole injection layer for performing efficiently the injection/transport of holes from the anode, and combined therewith a particular arylamine compound (having a particular structure) not doped with an electron acceptor as a material of a hole transport layer, and the devices are earnestly evaluated for characteristics. The present inventors also produce various organic EL devices having a hole transport layer containing a first hole transport layer and a second hole transport layer, for which two kinds of particular arylamine compounds are selected respectively, and having a combination of materials of the first hole transport layer and the second hole transport layer, so as to inject and transport holes efficiently to the light emitting layer, and the devices are earnestly evaluated for characteristics. Furthermore, the present inventors produce various organic EL devices using a compound having an anthracene ring structure, a compound having a pyrimidine ring structure, or a compound having a benzotriazole ring structure, having a particular structure as a material of an electron transport layer, which is combined to provide good carrier balance, and the devices are earnestly evaluated for characteristics. As a result, the present invention has been completed.

According to the present invention, the following organic EL devices are provided.

1) An organic EL device having at least an anode, a hole injection layer, a first hole transport layer, a second hole transport layer, a light emitting layer, an electron transport layer, and a cathode, in this order, wherein the hole injection layer contains an arylamine compound of the following general formula (1) and an electron acceptor:

[Chemical Formula 1]

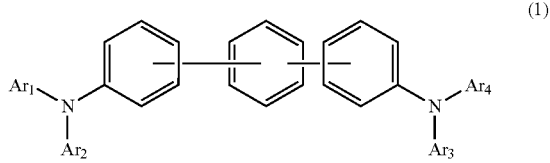

In the formula, $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group.

2) The organic EL device of 1), wherein the electron acceptor is an electron acceptor selected from trisbromophenylamine hexachloroantimony, tetracyanoquinodimethane (TCNQ), 2,3,5,6-tetrafluoro-tetracyano-1,4-benzoquinodimethane (F4TCNQ), and a radialene derivative.

3) The organic EL device of 1) or 2), wherein the electron acceptor is a radialene derivative of the following general formula (2):

[Chemical Formula 2]

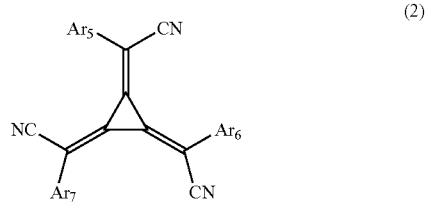

In the formula, $Ar_5$ to $Ar_7$ may be the same or different, and represent an aromatic hydrocarbon group, an aromatic heterocyclic group, or a condensed polycyclic aromatic group, having an electron acceptor group as a substituent.

4) The organic EL device of anyone of 1) to 3), wherein the first hole transport layer or the second hole transport layer contains only a hole transport arylamine compound.

5) The organic EL device of anyone of 1) to 3), wherein the first hole transport layer and the second hole transport layer each contain only a hole transport arylamine compound.

6) The organic EL device of 4) to 5), wherein the first hole transport layer contains an arylamine compound having a structure in which two to six triphenylamine structures are joined within a molecule via a single bond or a divalent group that does not contain a heteroatom.

7) The organic EL device of 6), wherein the arylamine compound having a structure in which two to six triphenylamine structures are joined within a molecule via a single bond or a divalent group that does not contain a heteroatom is an arylamine compound of the following general formula (3).

[Chemical Formula 3]

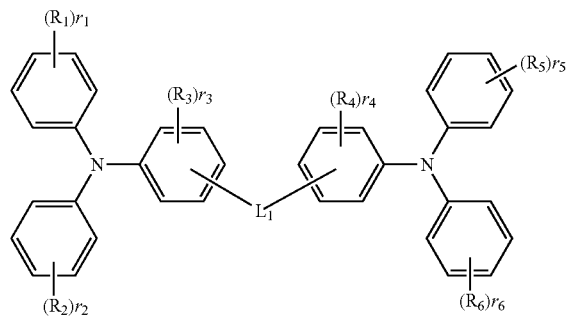

(3)

branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_1$ to $r_6$ may be the same or different, $r_1$, $r_2$, $r_5$, and $r_6$ representing an integer of 0 to 5, and $r_3$ and $r_4$ representing an integer of 0 to 4. When $r_1$, $r_2$, $r_5$, and $r_6$ are an integer of 2 to 5, or when $r_3$ and $r_4$ are an integer of 2 to 4, $R_1$ to $R_6$, a plurality of which bind to the same benzene ring, may be the same or different and may bind to each other via a single bond, substituted or unsubstituted methylene, an oxygen atom, or a sulfur atom to form a ring. $L_1$ represents a divalent linking group or a single bond.

8) The organic EL device of 6), wherein the arylamine compound having a structure in which two to six triphenylamine structures are joined within a molecule via a single bond or a divalent group that does not contain a heteroatom is an arylamine compound of the following general formula (4).

[Chemical Formula 4]

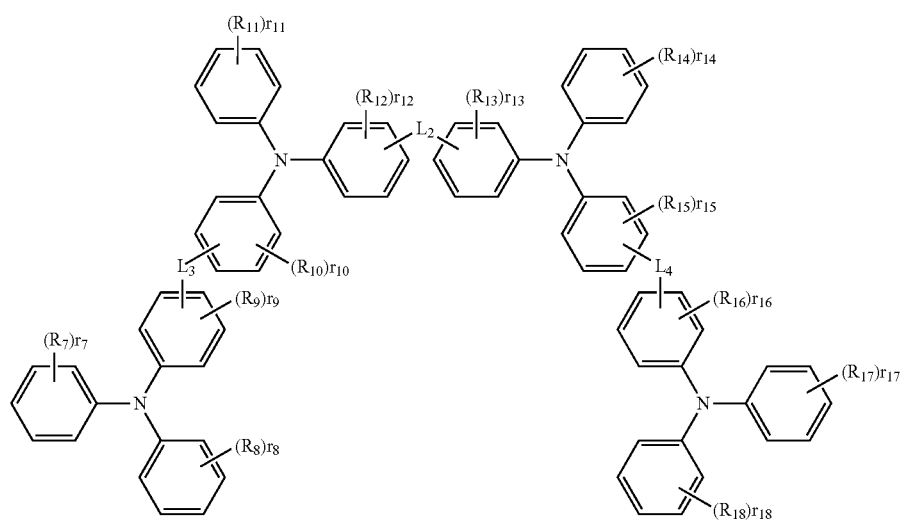

(4)

In the formula, $R_1$ to $R_6$ represent a deuterium atom, a fluorine atom, a chlorine atom, cyano, nitro, linear or In the formula, $R_7$ to $R_{18}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_7$ to $r_{18}$ may be the same or different, $r_7$, $r_8$, $r_{11}$, $r_{14}$, $r_{17}$, and $r_{18}$ representing an integer of 0 to 5, and $r_9$, $r_{10}$, $r_{11}$ $r_{13}$, $r_{15}$, and $r_{16}$ representing an integer of 0 to 4. When $r_7$, $r_8$, $r_{11}$, $r_{14}$, $r_{17}$, and $r_{18}$ are an integer of 2 to 5, or when $r_9$, $r_{10}$, $r_{12}$, $r_{13}$, $r_{15}$, and $r_{16}$ are an integer of 2 to 4, $R_7$ to $R_{18}$, a plurality of which bind to the same benzene ring, may be the same or different and may bind to each other via a single bond, substituted or unsubstituted methylene, an oxygen atom, or a sulfur atom to form a ring. $L_2$, $L_3$, and $L_4$ may be the same or different, and represent a divalent linking group or a single bond.

9) The organic EL device of 4) or 5), wherein the second hole transport layer contains an arylamine compound of the following general formula (5).

[Chemical Formula 5]

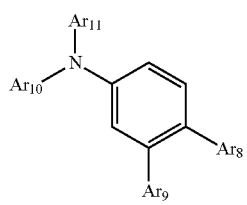

(5)

In the formula, $Ar_8$ to $Ar_{11}$ may be the same or different, and represent a substituted or unsubstituted aromatic hydrocarbon group, a substituted or unsubstituted aromatic heterocyclic group, or a substituted or unsubstituted condensed polycyclic aromatic group.

10) The organic EL device of 4) or 5), wherein the second hole transport layer contains an arylamine compound of the following general formula (10).

[Chemical Formula 6]

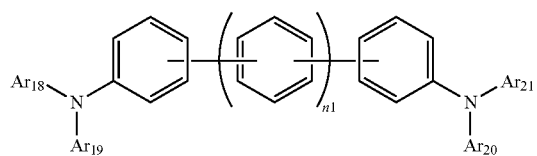

(10)

In the formula, $Ar_{18}$ to $Ar_{21}$ may be the same or different, and represent a substituted or unsubstituted aromatic hydrocarbon group, a substituted or unsubstituted aromatic heterocyclic group, or a substituted or unsubstituted condensed polycyclic aromatic group, and n1 represents an integer of 2 to 4.

11) The organic EL device of any one of 1) to 10), wherein the electron transport layer has a LUMO level of 2.9 to 3.4 eV.

12) The organic EL device of any one of 1) to 10), wherein the electron transport layer contains a compound of the following formula (6) having an anthracene ring structure.

[Chemical Formula 7]

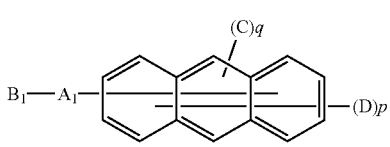

(6)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $B_1$ represents a substituted or unsubstituted aromatic heterocyclic group. C represents a substituted or unsubstituted aromatic hydrocarbon group, a substituted or unsubstituted aromatic heterocyclic group, or a substituted or unsubstituted condensed polycyclic aromatic group. D may be the same or different, and represents a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. p represents 7 or 8, and q represents 1 or 2 while maintaining a relationship that a sum of p and q is 9.

13) The organic EL device of any one of 1) to 10), wherein the electron transport layer contains a compound of the following general formula (7) having a pyrimidine ring structure.

[Chemical Formula 8]

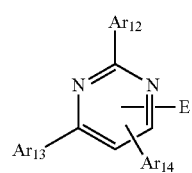

(7)

In the formula, $Ar_{12}$ represents a substituted or unsubstituted aromatic hydrocarbon group, a substituted or unsubstituted aromatic heterocyclic group, or a substituted or unsubstituted condensed polycyclic aromatic group. $Ar_{13}$ and $Ar_{14}$ may be the same or different, and represent a hydrogen atom, a substituted or unsubstituted aromatic hydrocarbon group, a substituted or unsubstituted aromatic heterocyclic group, or a substituted or unsubstituted condensed polycyclic aromatic group. E represents a monovalent group of the following structural formula (8). Herein, $Ar_{13}$ and $Ar_{14}$ are not simultaneously a hydrogen atom.

[Chemical Formula 9]

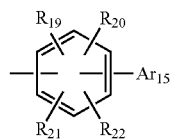
(8)

In the formula, $Ar_{15}$ represents a substituted or unsubstituted aromatic heterocyclic group. $R_{19}$ to $R_{22}$ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group, where $R_{19}$ to $R_{22}$ may bind to $Ar_{15}$ via a single bond, substituted or unsubstituted methylene, an oxygen atom, or a sulfur atom to form a ring.

14) The organic EL device of any one of 1) to 10), wherein the electron transport layer contains a compound of the following general formula (9) having a benzotriazole ring structure.

[Chemical Formula 10]

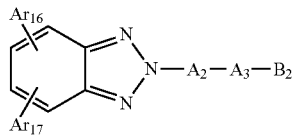
(9)

In the formula, $Ar_{16}$ represents a substituted or unsubstituted aromatic hydrocarbon group, a substituted or unsubstituted aromatic heterocyclic group, or a substituted or unsubstituted condensed polycyclic aromatic group. $Ar_{17}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group. $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $A_3$ represents a divalent group of substituted or unsubstituted condensed polycyclic aromatics, or a single band. $B_2$ represents a substituted or unsubstituted aromatic heterocyclic group.

15) The organic EL device of any one of 1) to 14), wherein the light emitting layer contains a blue light emitting dopant.

16) The organic EL device of 15), wherein the light emitting layer contains a pyrene derivative as the blue light emitting dopant.

17) The organic EL device of any one of 1) to 16), wherein the light emitting layer contains an anthracene derivative.

18) The organic EL device of 17), wherein the light emitting layer contains a host material which is the anthracene derivative.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic hydrocarbon group", the "substituted aromatic heterocyclic group", or the "substituted condensed polycyclic aromatic group" represented by $Ar_1$ to $Ar_4$ in the general formula (1) include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl; arylvinyls such as styryl and naphthylvinyl; acyls such as acetyl and benzoyl; and silyls, such as trimethylsilyl and triphenylsilyl. These substituents may be further substituted with the exemplified substituents above. These substituents may bind to each other via a single bond, substituted or unsubstituted methylene, an oxygen atom, or a sulfur atom to form a ring.

Specific examples of the "electron acceptor group" in the "aromatic hydrocarbon group, aromatic heterocyclic group, or condensed polycyclic aromatic ring having an electron acceptor group as a substituent" represented by $Ar_5$ to $Ar_7$ in the general formula (2) include a fluorine atom, a chlorine atom, a bromine atom, cyano, trimethylfluoro, and nitro.

Examples of the "aromatic hydrocarbon group", the "aromatic heterocyclic group", or the "condensed polycyclic aromatic group" in the "aromatic hydrocarbon group, aromatic heterocyclic group, or condensed polycyclic aromatic ring having an electron acceptor group as a substituent" represented by $Ar_5$ to $Ar_7$ in the general formula (2) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, in addition to the electron acceptor group, and specific examples of the substituent include a deuterium atom; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl. These substituents may be further substituted with the exemplified substituents or electron acceptor groups above. These substituents may bind to each other via a single bond, substituted or unsubstituted methylene, an oxygen atom, or a sulfur atom to form a ring.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_6$ in the general formula (3) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_6$ in the general formula (3) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_6$ in the general formula (3) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_6$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_6$ in the general formula (3) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aryloxy group" in the "substituted or unsubstituted aryloxy group" represented by $R_1$ to $R_6$ in the general formula (3) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (3), $r_1$ to $r_6$ may be the same or different, $r_1$, $r_2$, $r_5$, and $r_6$ representing an integer of 0 to 5, and $r_3$ and $r_4$ representing an integer of 0 to 4. When $r_1$, $r_2$, $r_5$, and $r_6$ are an integer of 2 to 5, or when $r_3$ and $r_4$ are an integer of 2 to 4, $R_1$ to $R_6$, a plurality of which bind to the same benzene ring, may be the same or different and may bind to each other via a single bond, substituted or unsubstituted methylene, an oxygen atom, or a sulfur atom to form a ring.

Examples of the "divalent linking group" represented by $L_1$ in the general formula (3) include "linear or branched alkylenes of 1 to 6 carbon atoms", such as methylene, ethylene, n-propylene, isopropylene, n-butylene, isobutylene, tert-butylene, n-pentylene, isopentylene, neopentylene, and n-hexylylene; "cycloalkylenes of 5 to 10 carbon atoms", such as cyclopentylylene, cyclohexylylene, and adamantylylene; "linear or branched alkenylenes of 2 to 6 carbon atoms", such as vinylene, arylene, isopropenylene, and butenylene; "divalent groups of aromatic hydrocarbons" that result from the removal of two hydrogen atoms from aromatic hydrocarbons, such as benzene, biphenyl, terphenyl, and tetrakisphenyl; and "divalent groups of condensed polycyclic aromatics" that result from the removal of two hydrogen atoms from condensed polycyclic aromatics, such as naphthalene, anthracene, acenaphthalene, fluorene, phenanthrene, indane, pyrene, and triphenylene.

These divalent groups may have a substituent. Examples of the substituent of the "linear or branched alkylene of 1 to 6 carbon atoms", the "cycloalkylene of 5 to 10 carbon atoms", or the "linear or branched alkenylene of 2 to 6 carbon atoms" include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_6$ in the general formula (3), and examples of the substituent in the "divalent group of aromatic hydrocarbons" or the "divalent group of condensed polycyclic aromatics" include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1).

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_7$ to $R_{18}$ in the general formula (4) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_6$ in the general formula (3), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_7$ to $R_{18}$ in the general formula (4) include the same groups exemplified as the groups for the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_6$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_7$ to $R_{18}$ in the general formula (4) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy" in the "substituted or unsubstituted aryloxy" represented by $R_7$ to $R_{18}$ in the general formula (4) include the same groups exemplified as the groups for the "aryloxy" in the "substituted or unsubstituted aryloxy" represented by $R_1$ to $R_6$ in the general formula (3), and possible embodiments may also be the same embodiments as the exemplified embodiments.

In the general formula (4), $r_7$ to $r_{18}$ may be the same or different, $r_7$, $r_8$, $r_{11}$, $r_{14}$, $r_{17}$, and $r_{18}$ representing an integer of 0 to 5, and $r_9$, $r_{10}$, $r_{12}$, $r_{13}$, $r_{15}$ and $r_{16}$ representing an integer of 0 to 4. When $r_7$, $r_8$, $r_{11}$, $r_{14}$, $r_{17}$, and $r_{18}$ is an integer of 2 to 5, or $r_9$, $r_{10}$, $r_{12}$, $r_{13}$, $r_{15}$ and $r_{16}$ is an integer of 2 to 4, $R_7$ to $R_{18}$, a plurality of which bind to the same benzene ring, may be the same or different and may bind to each other via a single bond, substituted or unsubstituted methylene, an oxygen atom, or a sulfur atom to form a ring.

Examples of the "divalent linking group" represented by $L_2$, $L_3$, and $L_4$ in the general formula (4) include the same groups exemplified as the groups for the "divalent linking group" represented by $L_1$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_8$ to $Ar_{11}$ in the general formula (5) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic hydrocarbon", the "aromatic heterocyclic ring", or the "condensed polycyclic aromatics" of the "substituted or unsubstituted aromatic hydrocarbon", the "substituted or unsubstituted aromatic heterocyclic ring", or the "substituted or unsubstituted condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (6) include benzene, biphenyl, terphenyl, tetrakisphenyl, styrene, naphthalene, anthracene, acenaphthalene, fluorene, phenanthrene, indane, pyrene, triphenylene, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

The "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (6) is a divalent group that results from the removal of two hydrogen atoms from the above "aromatic hydrocarbon", "aromatic heterocyclic ring", or "condensed polycyclic aromatics".

These divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic heterocyclic group" in the "substituted or unsubstituted aromatic heterocyclic group" represented by $B_1$ in the general formula (6) include triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic heterocyclic group" represented by $B_1$ in the general formula (6) include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; cycloalkyls of 5 to 10 carbon atoms such as cyclopentyl, cyclohexyl, 1-adamantyl, and 2-adamantyl; linear or branched alkyloxys of 1 to 6 carbon atoms such as methyloxy, ethyloxy, and propyloxy; cycloalkyloxys of 5 to 10 carbon atoms such as cyclopentyloxy, cyclohexyloxy, 1-adamantyloxy, and 2-adamantyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl; aryloxys such as phenyloxy, biphenylyloxy, naphthyloxy, anthracenyloxy, and phenanthrenyloxy; arylvinyls such as styryl and naphthylvinyl; and acyls such as acetyl and benzoyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by C in the general formula (6) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). When a plurality of these groups binds to the same anthracene ring (when q is 2), these groups may be the same or different.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "linear or branched alkyl of 1 to 6 carbon atoms" represented by D in the general formula (6) include methyl, ethyl, n-propyl, isopropyl, n-butyl, isobutyl, tert-butyl, n-pentyl, isopentyl, neopentyl, and n-hexyl.

The plural groups represented by D may be the same or different, and may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by D in the general formula (6) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). The plural groups represented by D may be the same or different, and may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{12}$, $Ar_{13}$, and $Ar_{14}$ in the general formula (7) include phenyl, biphenylyl, terphenylyl, tetrakisphenyl, styryl, naphthyl, anthracenyl, acenaphthenyl, phenanthrenyl, fluorenyl, indenyl, pyrenyl, perylenyl, fluoranthenyl, triphenylenyl, spirobifluorenyl, furyl, thienyl, benzofuranyl, benzothienyl, dibenzofuranyl, and dibenzothienyl.

These groups may have a substituent, and specific examples of the substituent include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, triphenylenyl, and spirobifluorenyl; aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, azafluorenyl, diazafluorenyl, carbolinyl, azaspirobifluorenyl, and diazaspirobifluorenyl; arylvinyls such as styryl and naphthylvinyl; and acyls such as acetyl and benzoyl. These substituents may be further substituted with the exemplified substituents above.

These substituents may bind to each other via a single bond, substituted or unsubstituted methylene, an oxygen atom, or a sulfur atom to form a ring. These substituents may bind to $Ar_{12}$, $Ar_{13}$, or $Ar_{14}$ that bind to the substituents, via an oxygen atom or a sulfur atom to form a ring.

Specific examples of the "aromatic heterocyclic group" in the "substituted or unsubstituted aromatic heterocyclic group" represented by $Ar_{15}$ in the structural formula (8) include triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, azafluorenyl, diazafluorenyl, naphthyridinyl, phenanthrolinyl, acridinyl, carbolinyl, azaspirobifluorenyl, and diazaspirobifluorenyl.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_{12}$, $Ar_{13}$, or $Ar_{14}$ in the general formula (7), and possible embodiments may also be the same embodiments as the exemplified embodiments.

Specific examples of the "linear or branched alkyl of 1 to 6 carbon atoms" represented by $R_{19}$ to $R_{22}$ in the structural formula (8) include methyl, ethyl, n-propyl, i-propyl, n-butyl, 2-methylpropyl, tert-butyl, n-pentyl, 3-methylbutyl, tert-pentyl, n-hexyl, iso-hexyl, and tert-hexyl.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{19}$ to $R_{22}$ in the structural formula (8) include phenyl, biphenylyl, terphenylyl, tetrakisphenyl, styryl, naphthyl, anthracenyl, acenaphthenyl, phenanthrenyl, fluorenyl, indenyl, pyrenyl, perylenyl, fluoranthenyl, triphenylenyl, spirobifluorenyl, triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, azafluorenyl, diazafluorenyl, naphthyridinyl, phenanthrolinyl, acridinyl, carbolinyl, phenoxazinyl, phenothiazinyl, phenazinyl, azaspirobifluorenyl, and diazaspirobifluorenyl.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_{12}$, $Ar_{13}$, or $Ar_{14}$ in the general formula (7), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{16}$ and $Ar_{17}$ in the structural formula (9) include phenyl, biphenylyl, terphenylyl, tetrakisphenyl, styryl, naphthyl, anthracenyl, acenaphthenyl, phenanthrenyl, fluorenyl, indenyl, pyrenyl, pyridyl, triazinyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, and acridinyl.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic hydrocarbon", the "aromatic heterocyclic ring", or the "condensed polycyclic aromatics" of the "substituted or unsubstituted aromatic hydrocarbon", the "substituted or unsubstituted aromatic heterocyclic ring", or the "substituted or unsubstituted condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_2$ in the general formula (9) include benzene, biphenyl, terphenyl, tetrakisphenyl, styrene, naphthalene, anthracene, acenaphthalene, fluorene, phenanthrene, indane, pyrene, triphenylene, pyridine, bipyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

The "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_2$ in the general formula (9) is a divalent group that results from the removal of two hydrogen atoms from the above "aromatic hydrocarbon", "aromatic heterocyclic ring", or "condensed polycyclic aromatics".

These divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "condensed polycyclic aromatics" of the "substituted or unsubstituted condensed polycyclic aromatics" in the "divalent group of a substituted or unsubstituted condensed polycyclic aromatics" represented by $A_3$ in the general formula (9) include naphthalene, anthracene, acenaphthalene, fluorene, phenanthrene, indane, pyrene, and triphenylene.

The "divalent group of a substituted or unsubstituted condensed polycyclic aromatics" represented by $A_3$ in the general formula (9) is a divalent group that results from the removal of two hydrogen atoms from the above "condensed polycyclic aromatics".

These divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic heterocyclic group" in the "substituted or unsubstituted aromatic heterocyclic group" represented by $B_2$ in the structural formula (9) include pyridyl, bipyridyl, triazinyl, pyrimidinyl, furyl, pyrrolyl, thienyl, quinolyl, isoquinolyl, benzofuranyl, benzothienyl, indolyl, carbazolyl, carbolinyl, benzoxazolyl, benzothiazolyl, quinoxalinyl, benzoimidazolyl, pyrazolyl, dibenzofuranyl, dibenzothienyl, naphthyridinyl, phenanthrolinyl, and acridinyl.

These groups may have a substituent, and examples of the substituent include the same substituents exemplified as the "substituent" in the "substituted aromatic heterocyclic group" represented by $B_1$ in the general formula (6), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{18}$ to $Ar_{21}$ in the general formula (10) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

$Ar_1$ to $Ar_4$ in the general formula (1) are preferably the "substituted or unsubstituted aromatic hydrocarbon group", the "substituted or unsubstituted sulfur-containing aromatic heterocyclic group", or the "substituted or unsubstituted condensed polycyclic aromatic group", and further preferably phenyl, biphenylyl, terphenylyl, naphthyl, phenanthryl, fluorenyl, or dibenzothienyl.

The "substituent" in the "substituted aromatic hydrocarbon group", the "substituted aromatic heterocyclic group", or the "substituted condensed polycyclic aromatic group" represented by $Ar_1$ to $Ar_4$ in the general formula (1) is preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", and further preferably a deuterium atom, phenyl, biphenylyl, naphthyl, or vinyl. It is preferable that these groups bind to each other via a single bond to form a condensed aromatic ring.

Examples of the electron acceptor, with which the arylamine compound represented by the general formula (1) is doped, in the hole injection layer of the organic EL device of the present invention include trisbromophenylamine hexachloroantimony, tetracyanoquinodimethane (TCNQ), 2,3,5,6-tetrafluoro-tetracyano-1,4-benzoquinodimethane (F4TCNQ), and a radialene derivative (see, for example, JP-A-2011-100621), and the radialene derivative of the general formula (2) is preferably used.

$Ar_5$ to $Ar_7$ in the general formula (2) are preferably the "aromatic hydrocarbon group", the "condensed polycyclic aromatic group", or pyridyl, and further preferably phenyl, biphenylyl, terphenylyl, naphthyl, phenanthryl, fluorenyl, or pyridyl, and the "electron acceptor group" therein is preferably a fluorine atom, a chlorine atom, cyano, or trifluoromethyl.

An embodiment is preferable that $Ar_5$ to $Ar_7$ in the general formula (2) are at least partially, preferably completely, substituted by the "electron acceptor group".

$Ar_5$ to $Ar_7$ in the general formula (2) are preferably phenyl that is completely substituted by a fluorine atom, a chlorine atom, cyano, or trifluoromethyl, such as tetrafluoropyridyl, tetrafluoro(trifluoromethyl)phenyl, cyanotetrafluorophenyl, dichlorodifluoro(trifluoromethyl)phenyl, or pentafluorophenyl, or pyridyl.

$R_1$ to $R_6$ in the general formula (3) are preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", further preferably a deuterium atom, phenyl, biphenylyl, naphthyl, or vinyl, and particularly preferably a deuterium atom, phenyl, or biphenylyl. It is also preferable that these groups bind to each other via a single bond to form a condensed aromatic ring.

$r_1$ to $r_6$ in the general formula (3) are preferably an integer of 0 to 3, and further preferably an integer of 0 to 2.

The "divalent linking group" represented by $L_1$ in the general formula (3) is preferably methylene, the "cycloalkyl of 5 to 10 carbon atoms", the "divalent group of an aromatic hydrocarbon", or the "divalent group of condensed polycyclic aromatics", or a single bond, further preferably divalent groups represented by the following structural formulae (B)

to (G), or a single bond, and particularly preferably a divalent group represented by the following structural formula (B) or (D).

In the following structural formula (B) in the general formula (3), n2 is preferably an integer of 1 to 3, and further preferably 2 or 3.

[Chemical Formula 11]

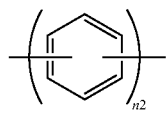
(B)

In the formula, n2 represents an integer of 1 to 4.

[Chemical Formula 12]

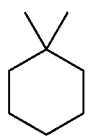
(C)

[Chemical Formula 13]

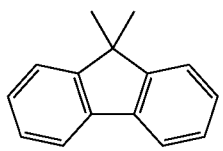
(D)

[Chemical Formula 14]

—CH$_2$—
(E)

[Chemical Formula 15]

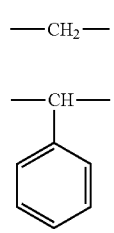
(F)

[Chemical Formula 16]

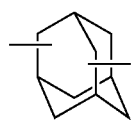
(G)

$R_7$ to $R_{18}$ in the general formula (4) are preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", and further preferably a deuterium atom, phenyl, biphenylyl, naphthyl, or vinyl. It is also preferable that these groups bind to each other via a single bond to form a condensed aromatic ring. A deuterium atom, phenyl, and biphenylyl are particularly preferable.

$r_7$ to $r_{18}$ in the general formula (4) are preferably an integer of 0 to 3, and further preferably an integer of 0 to 2.

The "divalent linking groups" represented by $L_2$ to $L_4$ in the general formula (4) are preferably methylene, the "cycloalkylene of 5 to 10 carbon atoms", the "divalent group of an aromatic hydrocarbon", or the "divalent group of condensed polycyclic aromatics", or a single bond, further preferably divalent groups represented by the structural formulae (B) to (G), or a single bond, and still further preferably a divalent group represented by the structural formula (B) or (D), or a single bond.

In the structural formula (B) in the general formula (4), n2 is preferably 1 or 2, and further preferably 1.

$Ar_8$ in the general formula (5) is preferably the "substituted or unsubstituted aromatic hydrocarbon group" or the "substituted or unsubstituted condensed polycyclic aromatic group", and further preferably phenyl, biphenylyl, terphenylyl, naphthyl, phenanthrenyl, anthracenyl, fluorenyl, carbazolyl, indolyl, dibenzofuranyl, or dibenzothienyl.

$Ar_9$ in the general formula (5) is preferably the "substituted or unsubstituted aromatic hydrocarbon group" or the "substituted or unsubstituted condensed polycyclic aromatic group", further preferably phenyl, biphenylyl, terphenylyl, naphthyl, phenanthrenyl, anthracenyl, or fluorenyl, still further preferably phenyl, and particularly unsubstituted phenyl.

The arylamine compound of the general formula (5) is preferably an arylamine compound of the following general formula (5a) or the following general formula (5b).

[Chemical Formula 17]

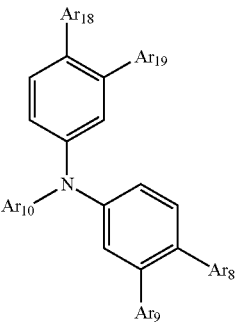
(5a)

In the formula, $Ar_8$ to $Ar_{10}$ have the same meanings as shown for the general formula (5). $Ar_{18}$ to $Ar_{19}$ may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 18]

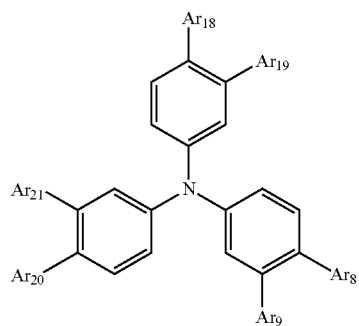
(5b)

In the formula, $Ar_8$ to $Ar_9$ have the same meanings as shown for the general formula (5). $Ar_{18}$ to $Ar_{21}$ may be the same or different, and represent a substituted or unsubstituted aromatic hydrocarbon group, a substituted or unsubstituted aromatic heterocyclic group, or a substituted or unsubstituted condensed polycyclic aromatic group.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{18}$ to $Ar_{21}$ in the general formula (5a) and the general formula (5b) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (5a), it is preferable that $Ar_8$ and $Ar_{18}$ are the same groups, and $Ar_9$ and $Ar_{19}$ are the same groups.

In the general formula (5b), it is preferable that $Ar_8$, $Ar_{18}$, and $Ar_{20}$ are the same groups, and $Ar_9$, $Ar_{19}$, and $Ar_{21}$ are the same groups.

The "substituent" in the "substituted aromatic hydrocarbon group", the "substituted aromatic heterocyclic group", or the "substituted condensed polycyclic aromatic group" represented by $Ar_8$ to $Ar_{11}$ in the general formula (5) is preferably a deuterium atom, a linear or branched alkyl of 1 to 6 carbon atoms that may have a substituent, a linear or branched alkenyl of 2 to 6 carbon atoms that may have a substituent, the "substituted or unsubstituted aromatic hydrocarbon group", or the "substituted or unsubstituted condensed polycyclic aromatic group", and further preferably a deuterium atom, phenyl, biphenylyl, naphthyl, or vinyl. It is preferable that these groups bind to each other via a single bond to form a condensed aromatic ring.

The "aromatic heterocyclic group" in the "substituted or unsubstituted aromatic heterocyclic group" represented by $B_1$ in the general formula (6) is preferably a nitrogen-containing aromatic heterocyclic group, such as pyridyl, pyrimidinyl, pyrrolyl, quinolyl, isoquinolyl, indolyl, carbazolyl, benzoxazolyl, benzothiazolyl, quinoxalinyl, benzoimidazolyl, pyrazolyl, or carbolinyl, and further preferably pyridyl, pyrimidinyl, quinolyl, isoquinolyl, indolyl, pyrazolyl, benzoimidazolyl, or carbolinyl.

For p and q in the general formula (6), p represents 7 or 8, and q represents 1 or 2, while maintaining the relationship, in which the sum of p and q (p+q) is 9.

$A_1$ in the general formula (6) is preferably the "divalent group of a substituted or unsubstituted aromatic hydrocarbon" or the "divalent group of substituted or unsubstituted condensed polycyclic aromatics", and further preferably divalent groups that result from the removal of two hydrogen atoms from benzene, biphenyl, naphthalene, or phenanthrene.

The compound having an anthracene ring structure of the general formula (6) is preferably a compound having an anthracene ring structure of the following general formula (6a), the following general formula (6b), or the following general formula (6c).

[Chemical Formula 19]

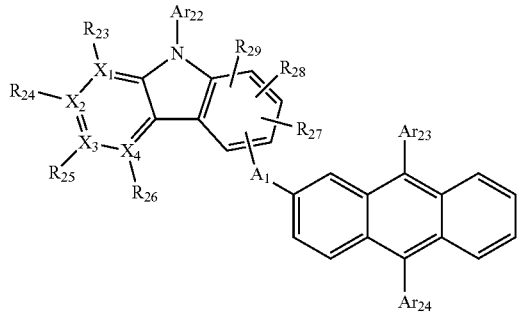

(6a)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{22}$, $Ar_{23}$, and $Ar_{24}$ may be the same or different, and represent a substituted or unsubstituted aromatic hydrocarbon group, a substituted or unsubstituted aromatic heterocyclic group, or a substituted or unsubstituted condensed polycyclic aromatic group. $R_{23}$ to $R_{29}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where these groups may bind to each other via a single bond, substituted or unsubstituted methylene, an oxygen atom, or a sulfur atom to form a ring. $X_1$, $X_2$, $X_3$, and $X_4$ represent a carbon atom or a nitrogen atom, and only one of $X_1$, $X_2$, $X_3$, and $X_4$ is a nitrogen atom. In this case, the nitrogen atom does not have the hydrogen atom or substituent for $R_{23}$ to $R_{26}$.

[Chemical Formula 20]

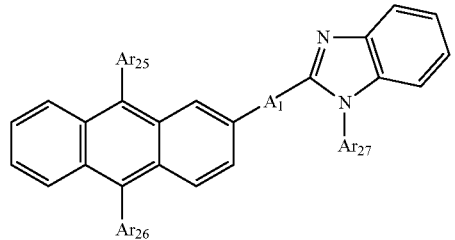

(6b)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{25}$, $Ar_{26}$, and $Ar_{27}$ may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 21]

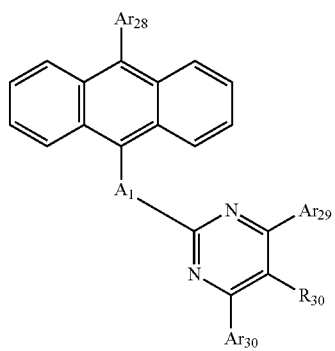

(6c)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{28}$, $Ar_{29}$, and $Ar_{30}$ may be the same or different, and represent a substituted or unsubstituted aromatic hydrocarbon group, a substituted or unsubstituted aromatic heterocyclic group, or a substituted or unsubstituted condensed polycyclic aromatic group. $R_{30}$ represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{22}$, $Ar_{23}$ and $Ar_{24}$ in the general formula (6a) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{23}$ to $R_{29}$ in the general formula (6a) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_{23}$ to $R_{29}$ in the general formula (6a) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{23}$ to $R_{29}$ in the general formula (6a) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_{23}$ to $R_{29}$ in the general formula (6a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{23}$ to $R_{29}$ in the general formula (6a) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aryloxy group" in the "substituted or unsubstituted aryloxy group" represented by $R_{23}$ to $R_{29}$ in the general formula (6a) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (6a), $X_1$, $X_2$, $X_3$, and $X_4$ represent a carbon atom or a nitrogen atom, and only one of $X_1$, $X_2$, $X_3$, and $X_4$ is a nitrogen atom. In this case, the nitrogen atom does not have the hydrogen atom or substituent for $R_{23}$ to $R_{26}$. That is, $R_{23}$ does not exist when $X_1$ is a nitrogen atom, $R_{24}$ does not exist when $X_2$ is a nitrogen atom, $R_{25}$ does not exist when $X_3$ is a nitrogen atom, and $R_{26}$ does not exist when $X_4$ is a nitrogen atom.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{25}$, $Ar_{26}$, and $Ar_{27}$ in the general formula (6b) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{28}$, $Ar_{29}$, and $Ar_{30}$ in the general formula (6c) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{30}$ in the general formula (6c) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{23}$ to $R_{29}$ in the general formula (6a).

These groups may have a substituent. Examples of the substituent include the same groups exemplified as the "substituent" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{23}$ to $R_{29}$ in the general formula (6a), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{30}$ in the general formula (6c) include the same groups exemplified as the "substituent" in the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{23}$ to $R_{29}$ in the general formula (6a).

These groups may have a substituent. Examples of the substituent include the same groups exemplified as the "substituent" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{23}$ to $R_{29}$ in the general formula (6a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{30}$ in the general formula (6c) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy group" in the "substituted or unsubstituted aryloxy group" represented by $R_{30}$ in the general formula (6c) include the same groups exemplified as the groups for the "aryloxy group" in the "substituted or unsubstituted aryloxy group" represented by $R_{23}$ to $R_{29}$ in the general formula (6a).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

$Ar_{12}$ in the general formula (7) is preferably phenyl, biphenylyl, naphthyl, anthracenyl, acenaphthenyl, phenanthrenyl, fluorenyl, indenyl, pyrenyl, perylenyl, fluoranthenyl, triphenylenyl, spirobifluorenyl, an oxygen-containing aromatic heterocyclic group, such as furyl, benzofuranyl, and dibenzofuranyl, or a sulfur-containing aromatic heterocyclic group, such as thienyl, benzothienyl, and dibenzothienyl, and further preferably phenyl, biphenylyl, naphthyl, phenanthrenyl, fluorenyl, pyrenyl, fluoranthenyl, triphenylenyl, spirobifluorenyl, dibenzofuranyl, or dibenzothienyl. The phenyl group preferably has a substituted or unsubstituted condensed polycyclic aromatic group or a phenyl group as a substituent, and further preferably has a substituent selected from naphthyl, phenanthrenyl, pyrenyl, fluoranthenyl, triphenylenyl, spirobifluorenyl, or phenyl, and it is also preferable that the substituent of the phenyl group and the phenyl group bind to each other via an oxygen atom or a sulfur atom to form a ring.

$Ar_{13}$ in the general formula (7) is preferably phenyl that has a substituent, substituted or unsubstituted spirobifluorenyl, an oxygen-containing aromatic heterocyclic group, such as furyl, benzofuranyl, and dibenzofuranyl, or a sulfur-containing aromatic heterocyclic group, such as thienyl, benzothienyl, and dibenzothienyl. The substituent of the phenyl in this case is preferably an aromatic hydrocarbon group, such as phenyl, biphenylyl, and terphenylyl, a condensed polycyclic aromatic group, such as naphthyl, acenaphthenyl, phenanthrenyl, fluorenyl, indenyl, pyrenyl, perylenyl, fluoranthenyl, triphenylenyl, and spirobifluorenyl, an oxygen-containing aromatic heterocyclic group, such as furyl, benzofuranyl, and dibenzofuranyl, or a sulfur-containing aromatic heterocyclic group, such as thienyl, benzothienyl, and dibenzothienyl, and further preferably phenyl, naphthyl, phenanthrenyl, fluorenyl, pyrenyl, fluoranthenyl, triphenylenyl, spirobifluorenyl, dibenzofuranyl, or dibenzothienyl, and it is also preferable that the substituent of the phenyl group and the phenyl group bind to each other via an oxygen atom or a sulfur atom to form a ring.

$Ar_{14}$ in the general formula (7) is preferably a hydrogen atom, phenyl that has a substituent, substituted or unsubstituted spirobifluorenyl, an oxygen-containing aromatic heterocyclic group, such as furyl, benzofuranyl, and dibenzofuranyl, or a sulfur-containing aromatic heterocyclic group, such as thienyl, benzothienyl, and dibenzothienyl. The substituent of the phenyl in this case is preferably an aromatic hydrocarbon group, such as phenyl, biphenylyl, and terphenylyl, a condensed polycyclic aromatic group, such as naphthyl, acenaphthenyl, phenanthrenyl, fluorenyl, indenyl, pyrenyl, perylenyl, fluoranthenyl, triphenylenyl, and spirobifluorenyl, an oxygen-containing aromatic heterocyclic group, such as furyl, benzofuranyl, and dibenzofuranyl, or a sulfur-containing aromatic heterocyclic group, such as thienyl, benzothienyl, and dibenzothienyl, and further preferably phenyl, naphthyl, phenanthrenyl, fluorenyl, pyrenyl, fluoranthenyl, triphenylenyl, spirobifluorenyl, dibenzofuranyl, or dibenzothienyl, and it is also preferable that the substituent of the phenyl group and the phenyl group bind to each other via an oxygen atom or a sulfur atom to form a ring.

In the general formula (7), it is preferable that $Ar_{12}$ and $Ar_{13}$ are not the same as each other from the viewpoint of thin film stability. When $Ar_{12}$ and $Ar_{13}$ are the same groups, the groups may have different substituents and may be substituted on different positions.

In the general formula (7), $Ar_{13}$ and $Ar_{14}$ may be the same groups, but there may be a possibility that the compound is easily crystallized due to the high symmetry of the entire molecule, and from the viewpoint of thin film stability, it is preferable that $Ar_{13}$ and $Ar_{14}$ are not the same as each other, and $Ar_{13}$ and $Ar_{14}$ are not simultaneously a hydrogen atom.

In the general formula (7), it is preferable that one of $Ar_{13}$ and $Ar_{14}$ is a hydrogen atom.

Examples of the compound of the general formula (7) having a pyrimidine ring structure include compounds of the following general formula (7a) and general formula (7b) having pyrimidine ring structures with different bonding patterns of substituents.

[Chemical Formula 22]

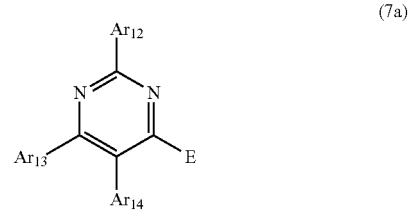

(7a)

In the formula, $Ar_{12}$, $Ar_{13}$, $Ar_{14}$, and E have the same meanings as shown for the general formula (7).

[Chemical Formula 23]

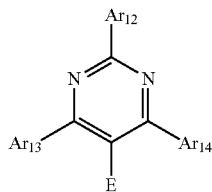

(7b)

In the formula, $Ar_{12}$, $Ar_{13}$, $Ar_{14}$, and E have the same meanings as shown for the general formula (7).

$Ar_{15}$ in the general formula (8) is preferably a nitrogen-containing heterocyclic group, such as triazinyl, pyridyl, pyrimidinyl, pyrrolyl, quinolyl, isoquinolyl, indolyl, carbazolyl, benzoxazolyl, benzothiazolyl, quinoxalinyl, benzoimidazolyl, pyrazolyl, azafluorenyl, diazafluorenyl, naphthyridinyl, phenanthrolinyl, acridinyl, carbolinyl, azaspirobifluorenyl, or diazaspirobifluorenyl, further preferably triazinyl, pyridyl, pyrimidinyl, quinolyl, isoquinolyl, indolyl, quinoxalinyl, azafluorenyl, diazafluorenyl, benzoimidazolyl, naphthyridinyl, phenanthrolinyl, acridinyl, azaspirobifluorenyl, or diazaspirobifluorenyl, and particularly preferably pyridyl, pyrimidinyl, quinolyl, isoquinolyl, indolyl, azafluorenyl, diazafluorenyl, quinoxalinyl, benzoimidazolyl, naphthyridinyl, phenanthrolinyl, acridinyl, azaspirobifluorenyl, or diazaspirobifluorenyl.

In the general formula (8), the binding position of $Ar_{15}$ on the benzene ring is preferably the meta-position with respect to the binding position to the pyrimidine ring of the general formula (7) as shown in the following structural formula (8a) from the viewpoint of thin film stability.

[Chemical Formula 24]

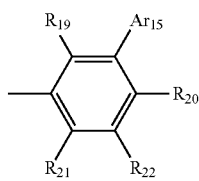

(8a)

In the formula, $Ar_{15}$ and $R_{19}$ to $R_{22}$ have the same meanings as shown for the general formula (8).

$Ar_{16}$ and $Ar_{17}$ in the general formula (9) are preferably the "substituted or unsubstituted aromatic hydrocarbon group", the "substituted or unsubstituted condensed polycyclic aromatic group", pyridyl, dibenzothienyl, carbazolyl, or dibenzofuranyl, further preferably phenyl, biphenylyl, terphenylyl, naphthyl, anthracenyl, phenanthrenyl, fluorenyl, indenyl, pyrenyl, pyridyl, carbazolyl, or dibenzofuranyl, and particularly preferably phenyl, biphenylyl, terphenylyl, naphthyl, anthracenyl, phenanthrenyl, or fluorenyl.

The substituent that these groups may have is preferably the "aromatic hydrocarbon group", the "aromatic heterocyclic group", and the "condensed polycyclic aromatic group", such as phenyl, biphenylyl, terphenylyl, tetrakisphenyl, styryl, naphthyl, anthracenyl, acenaphthenyl, phenanthrenyl, fluorenyl, indenyl, pyrenyl, pyridyl, triazinyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, or acridinyl, further preferably phenyl, biphenylyl, naphthyl, anthracenyl, phenanthrenyl, fluorenyl, pyrenyl, pyridyl, triazinyl, pyrimidinyl, quinolyl, isoquinolyl, indolyl, carbazolyl, quinoxalinyl, benzoimidazolyl, pyrazolyl, phenanthrolinyl, or acridinyl, and particularly preferably phenyl, naphthyl, anthracenyl, pyridyl, quinolyl, or isoquinolyl.

$A_2$ in the general formula (9) is preferably the "divalent group of a substituted or unsubstituted aromatic hydrocarbon", the "divalent group of substituted or unsubstituted condensed polycyclic aromatics", pyridylene, or bipyridylene, further preferably divalent groups that are derived from benzene, biphenyl, naphthalene, anthracene, fluorene, phenanthrene, pyrene, or pyridine, and particularly preferably divalent groups that are derived from benzene, naphthalene, or pyridine.

$A_3$ in the general formula (9) is preferably a single bond or divalent groups that are derived from naphthalene, anthracene, fluorene, phenanthrene, or pyrene, and further preferably a single bond or divalent groups that are derived from naphthalene or anthracene.

$B_2$ in the general formula (9) is preferably a nitrogen-containing aromatic heterocyclic group, such as pyridyl, bipyridyl, triazinyl, pyrimidinyl, pyrrolyl, quinolyl, isoquinolyl, indolyl, carbazolyl, carbolinyl, benzoxazolyl, benzothiazolyl, quinoxalinyl, benzoimidazolyl, pyrazolyl, naphthyridinyl, phenanthrolinyl, or acridinyl, further preferably pyridyl, bipyridyl, pyrimidinyl, quinolyl, isoquinolyl, indolyl, carbolinyl, quinoxalinyl, benzoimidazolyl, naphthyridinyl, or phenanthrolinyl, and particularly preferably pyridyl, quinolyl, or isoquinolyl.

In the general formula (9), when $A_2$ is a divalent group that results from the removal of two hydrogen atoms from substituted or unsubstituted benzene, and $A_3$ is a single bond, $B_2$ is preferably pyridyl, or a nitrogen-containing aromatic heterocyclic group having a condensed polycyclic structure, such as bipyridyl, quinolyl, isoquinolyl, indolyl, carbazolyl, carbolinyl, benzoxazolyl, benzothiazolyl, quinoxalinyl, benzoimidazolyl, naphthyridinyl, phenanthrolinyl, or acridinyl, further preferably pyridyl, bipyridyl, quinolyl, isoquinolyl, indolyl, carbolinyl, quinoxalinyl, benzoimidazolyl, naphthyridinyl, or phenanthrolinyl, and particularly preferably pyridyl, bipyridyl, quinolyl, or isoquinolyl.

In the general formula (9), when $B_2$ is pyridyl or bipyridyl, and $A_3$ is a single bond, $A_2$ is further preferably divalent groups that result from the removal of two hydrogen atoms from benzene, biphenyl, naphthalene, anthracene, fluorene, phenanthrene, or pyrene, or a single bond, and particularly preferably divalent groups that results from the removal of two hydrogen atoms from benzene or biphenyl, or a single bond.

$Ar_{18}$ to $Ar_{21}$ in the general formula (10) are preferably the "substituted or unsubstituted aromatic hydrocarbon group", the "substituted or unsubstituted oxygen-containing aromatic heterocyclic group", or the "substituted or unsubstituted condensed polycyclic aromatic group", and further preferably phenyl, biphenylyl, terphenylyl, naphthyl, phenanthryl, fluorenyl, or dibenzothienyl.

In the general formula (10), $Ar_{18}$ and $Ar_{19}$, or $Ar_{20}$ and $Ar_{21}$ are preferably different groups, and $Ar_{18}$ and $Ar_{19}$, and $Ar_{20}$ and $Ar_{21}$ are further preferably different groups.

In the general formula (10), n1 is preferably 2 or 3.

The bonding pattern of the phenylenes in the general formula (10) is preferably not a bonding pattern, in which all the bonds are 1,4-bonds, but is preferably a bonding pattern, in which a 1,2-bond or a 1,3-bond is mixed therein, from the viewpoint of thin film stability influencing the device lifetime, and consequently, the aryldiamine derivative having bonded thereto four phenylenes (when n is 2), five phenylenes (when n is 3), or six phenylenes (when n is 4) is preferably a compound having phenylenes that do not linearly bind each other, such as 1,1':3',1":3",1'''-quaterphenyldiamine, 1,1':3',1":2",1'''':3''',1''''-quinquephenyldiamine, 1,1':3',1":3",1''':3''',1''''-quinquephenyldiamine, 1,1':2',1":2",1'''-quaterphenyldiamine, 1,1':3',1":3",1'''-quaterphenyldiamine, 1,1':4',1":2",1''':4''',1''''-quinquephenyldiamine, 1,1':2',1":3",1''':2''',1''''-quinguephenyldiamine, 1,1':4',1":3",1''':4''',1''''-quinguephenyldiamine, or 1,1':2',1":2",1''':2''',1''''-quinguephenyldiamine.

The arylamine compound of the general formula (1) preferably used in the organic EL device of the present invention can be used as a constitutive material of a hole injection layer or a hole transport layer of an organic EL device. The compound has high hole mobility and is a preferred compound as a material of a hole injection layer or a hole transport layer.

The radialene derivative of the general formula (2) preferably used in the organic EL device of the present invention is a preferred compound as a p-type doping material for a material generally used in a hole injection layer or a hole transport layer of an organic EL device.

The arylamine compound of general formula (3) having two triphenylamine structures in the molecule and the arylamine compound of general formula (4) having four triphenylamine structures in the molecule preferably used in the organic EL device of the present invention are a preferred compound as a constitutive material of a hole injection layer or a hole transport layer of an organic EL device.

The arylamine compound of the general formula (5) or the general formula (10) preferably used in the organic EL device of the present invention can be used as a constitutive material of a hole transport layer or an electron blocking layer of an organic EL device. The compound has a high electron blocking capability and is a preferred compound as a material of a layer adjacent to a light emitting layer on the side of an anode.

The compound of the general formula (6) having an anthracene ring structure preferably used in the organic EL device of the present invention is a preferred compound as a material of an electron transport layer of an organic EL device.

The compound of the general formula (7) having a pyrimidine ring structure preferably used in the organic EL device of the present invention is a preferred compound as a material of an electron transport layer of an organic EL device.

The compound of the general formula (9) having a benzotriazole ring structure preferably used in the organic EL device of the present invention is a preferred compound as a material of an electron transport layer of an organic EL device.

The organic EL device of the present invention combines the materials for an organic EL device excellent in hole injection/transport capabilities, stability and durability as a thin film, taking the carrier balance into consideration. Therefore, as compared to the ordinary organic EL devices, the hole transport efficiency from the anode to the light emitting layer is improved (and furthermore the hole transport layer is constituted by two layers including the first hole transport layer and the second hole transport layer, for which two kinds of particular arylamine compounds (having particular structure) are selected respectively and combined), and thereby the luminous efficiency is improved, and the durability of the organic EL device is improved, while retaining the lower driving voltage.

Thus, an organic EL device having a low driving voltage, a high light emission efficiency, and a long lifetime can be attained.

Effects of the Invention

The organic EL device of the present invention can achieve an organic EL device having excellent hole injection/transport capabilities, low driving voltage, and high luminous efficiency, as a result of attaining efficient hole injection/transport from the electrode to the hole transport layer, by selecting the particular arylamine compound (having the particular structure) that can effectively achieves the hole injection/transport roles, as the material of the hole injection layer, and subjecting the electron acceptor to p-type doping.

An organic EL device having high efficiency, low driving voltage and a long lifetime can be achieved as a result of attaining good carrier balance, by selecting the two kinds of particular arylamine compounds (having the particular structures) without p-type doping as the materials of the first hole transport layer and the second hole transport layer.

The organic EL device of the present invention can improve the luminous efficiency, particularly the durability, while retaining the low driving voltage of the conventional organic EL devices.

BRIEF DESCRIPTION OF THE DRAWINGS

FIG. 1 is a diagram illustrating the configuration of the organic EL devices of Examples 67 to 82 and Comparative Examples 1 to 4.

MODE FOR CARRYING OUT THE INVENTION

The following presents specific examples of preferred compounds among the arylamine compounds of the general formula (1) preferably used in the organic EL device of the present invention. The present invention, however, is not restricted to these compounds.

[Chemical Formula 25]

(1-1)

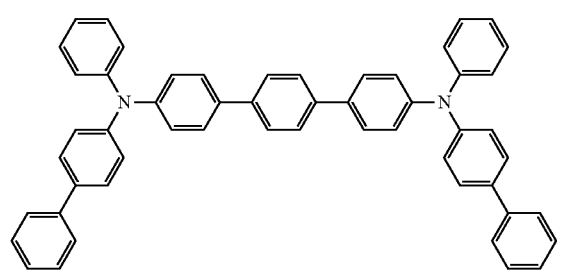

[Chemical Formula 26]

(1-2)

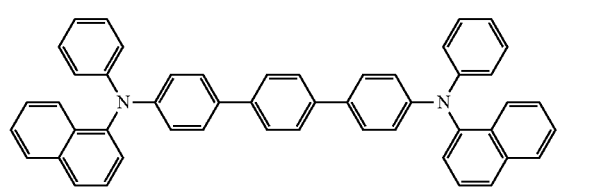

-continued
[Chemical Formula 27]
(1-3)
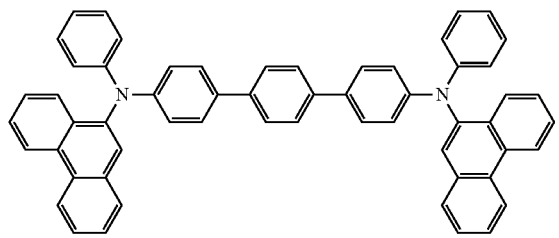
[Chemical Formula 28]
(1-4)
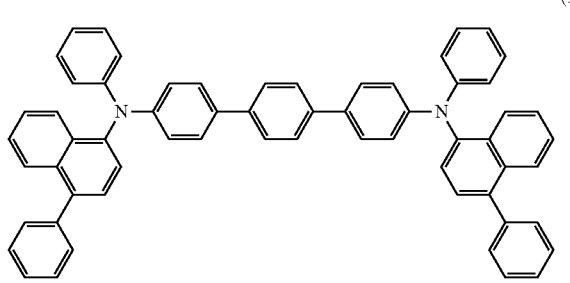
[Chemical Formula 29]
(1-5)
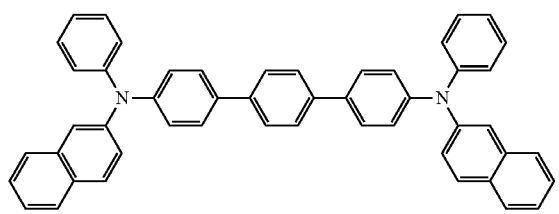
[Chemical Formula 30]
(1-6)
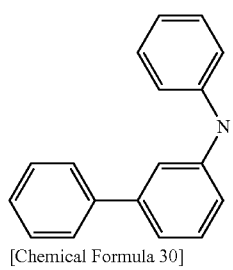
[Chemical Formula 31]
(1-7)
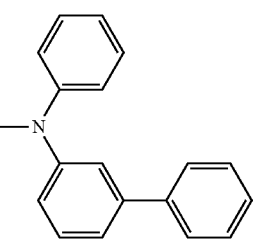
[Chemical Formula 32]
(1-8)
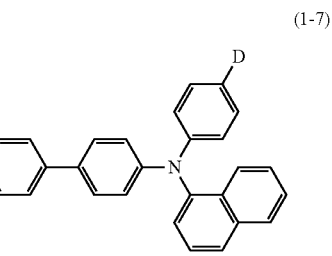
[Chemical Formula 33]
(1-9)
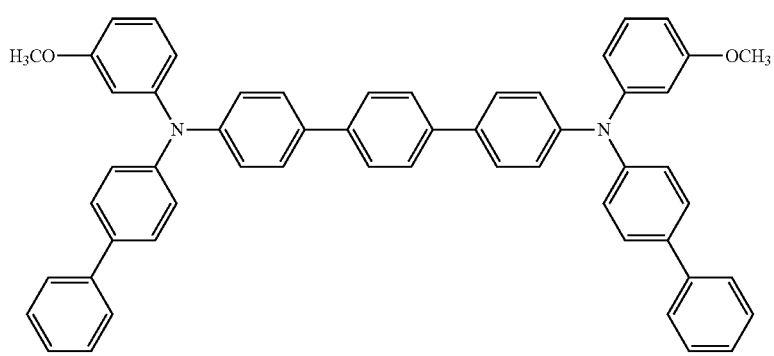
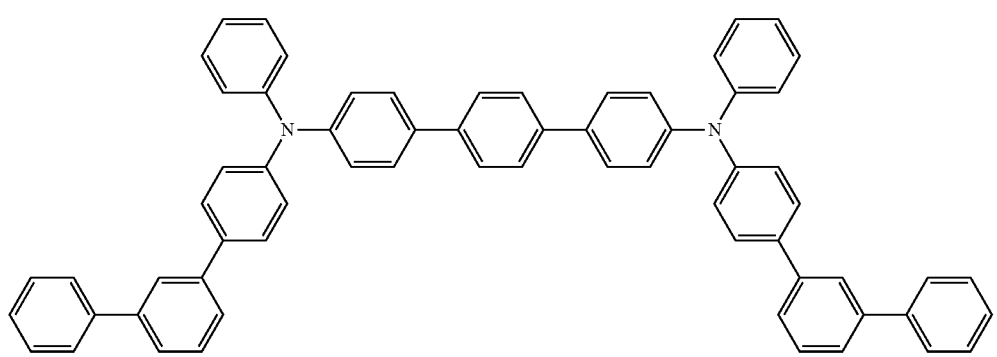

[Chemical Formula 34]
(1-10)
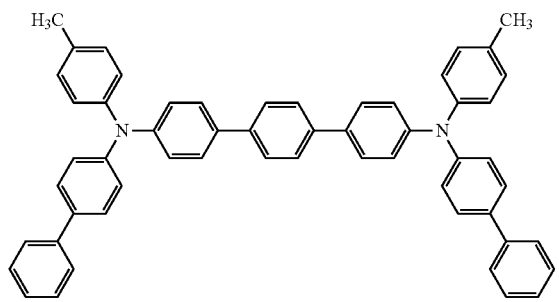
[Chemical Formula 35]
(1-11)
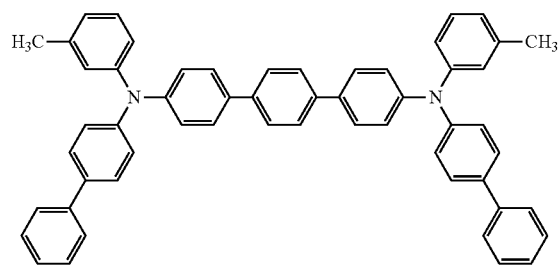
[Chemical Formula 36]
(1-12)
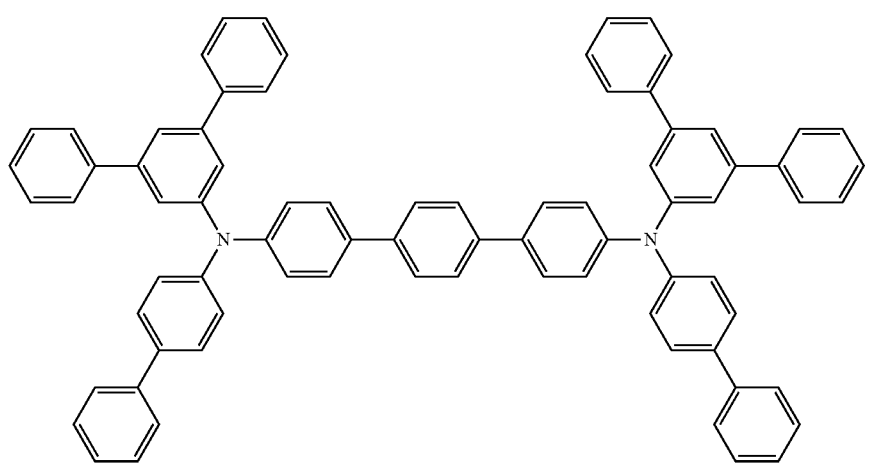
[Chemical Formula 37]
(1-13)
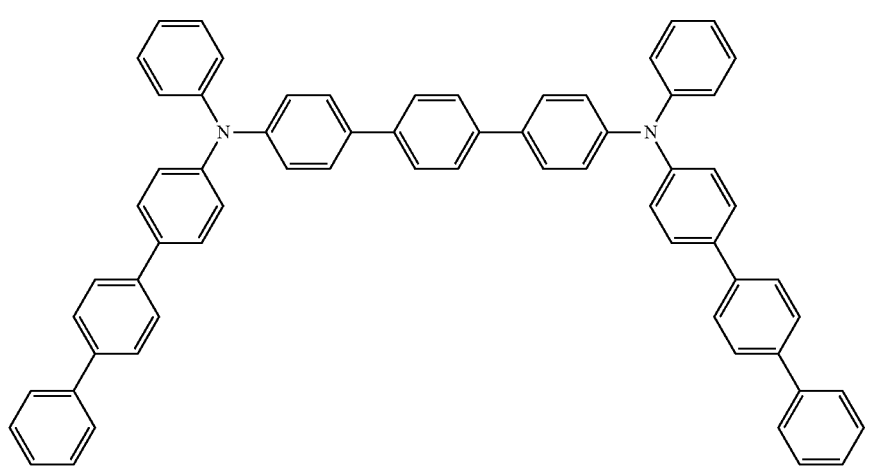

[Chemical Formula 38]
(1-14)
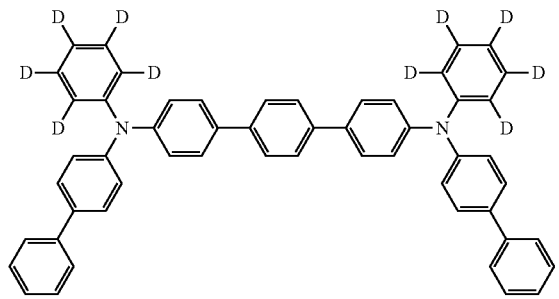
[Chemical Formula 39]
(1-15)
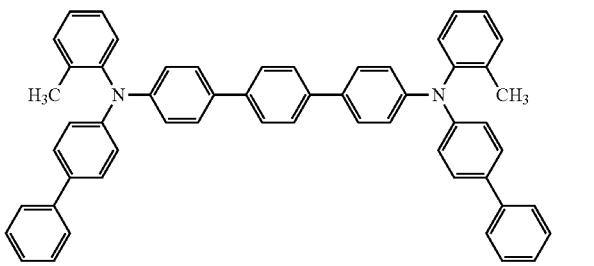
[Chemical Formula 40]
(1-16)
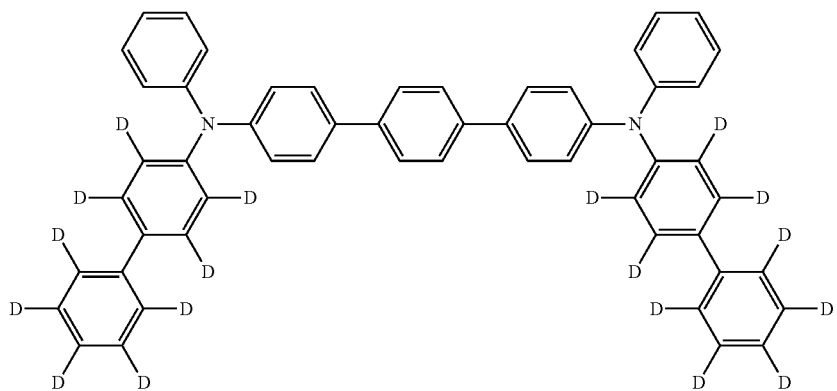
[Chemical Formula 41]
(1-17)
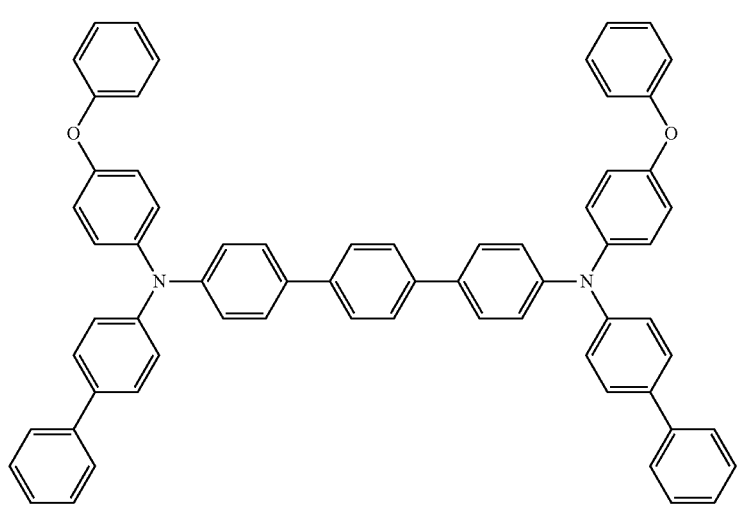

[Chemical Formula 42]
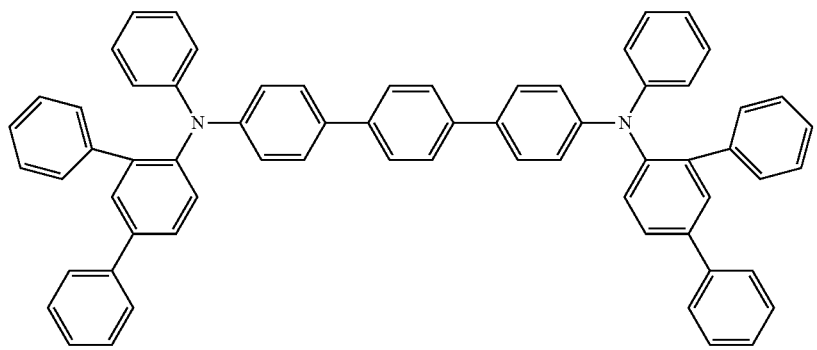
(1-18)
[Chemical Formula 43]
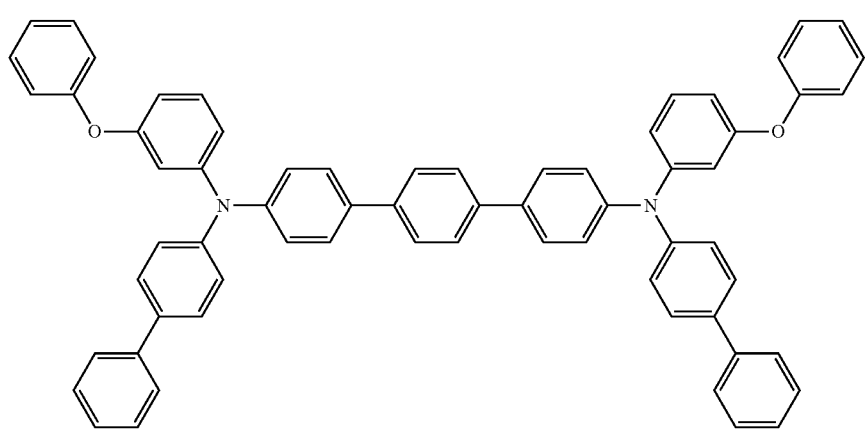
(1-19)
[Chemical Formula 44]
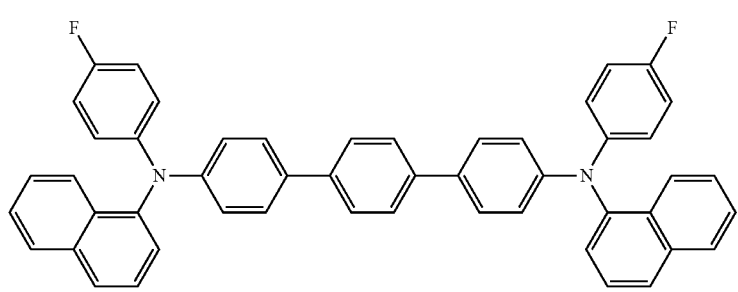
(1-20)

[Chemical Formula 45]
(1-21)
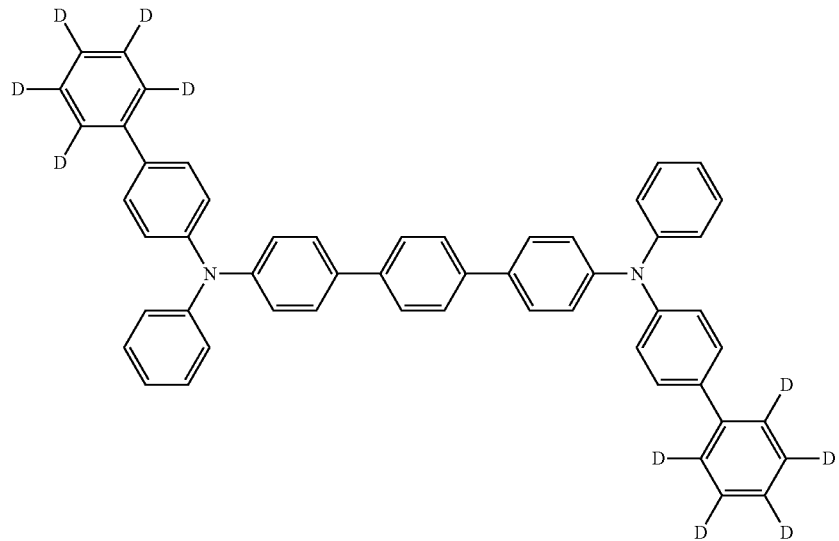
[Chemical Formula 46]
(1-22)
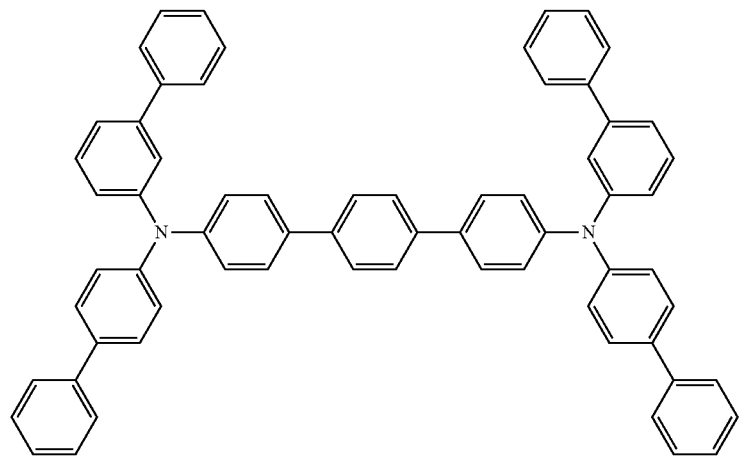
[Chemical Formula 47]
(1-23)
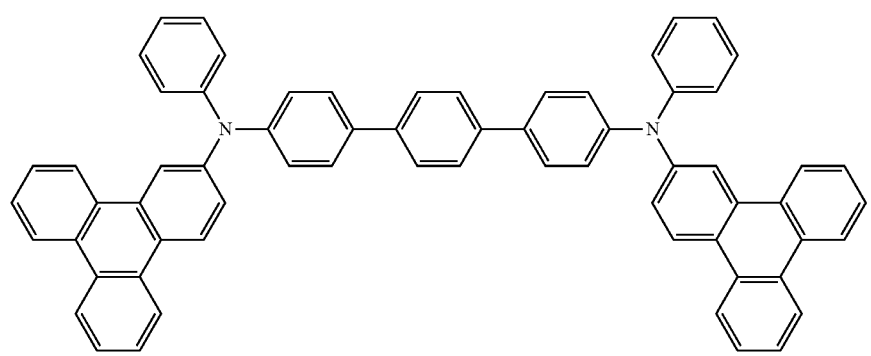

[Chemical Formula 48]
(1-24)
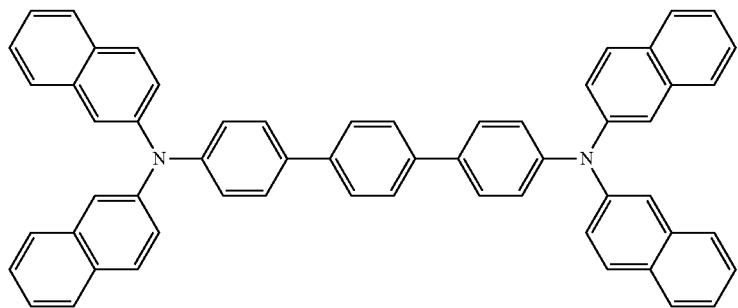
[Chemical Formula 49]
(1-25)
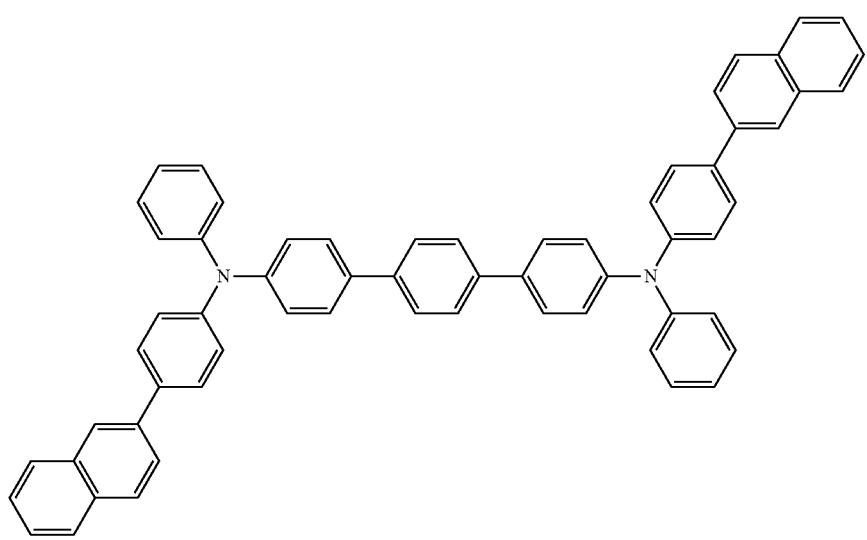
[Chemical Formula 50]
(1-26)
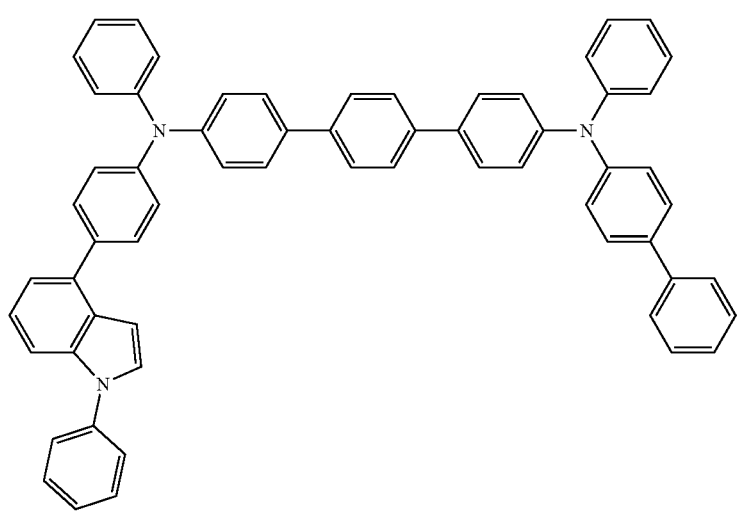

[Chemical Formula 51]
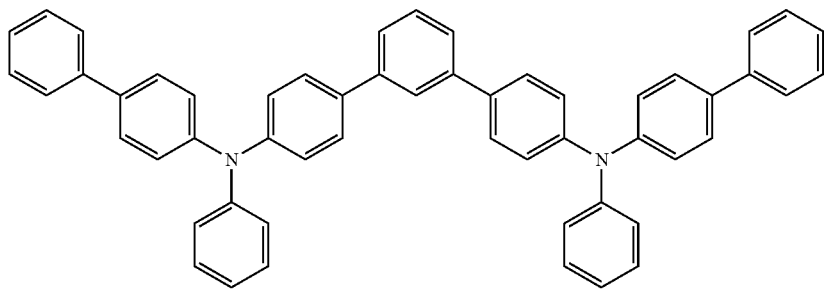
(1-27)
[Chemical Formula 52]
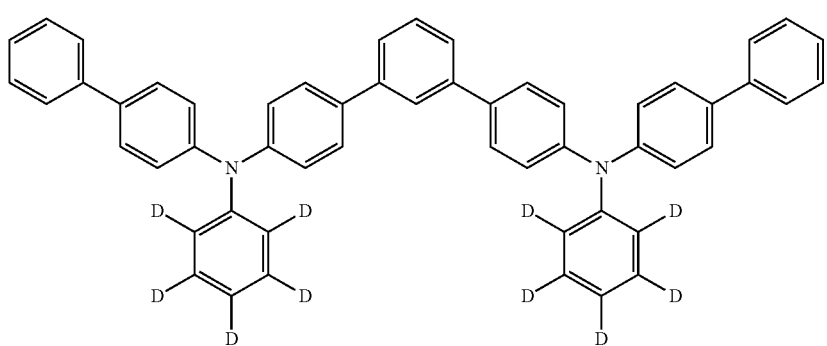
(1-28)
[Chemical Formula 53]
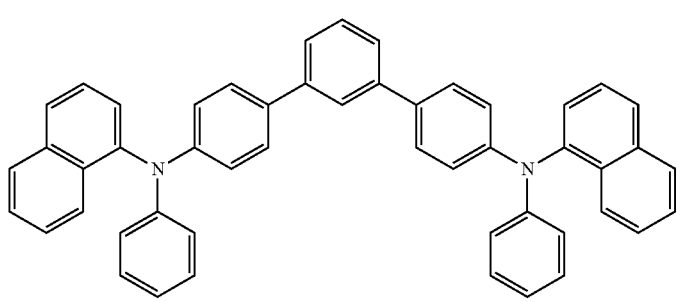
(1-29)
[Chemical Formula 54]
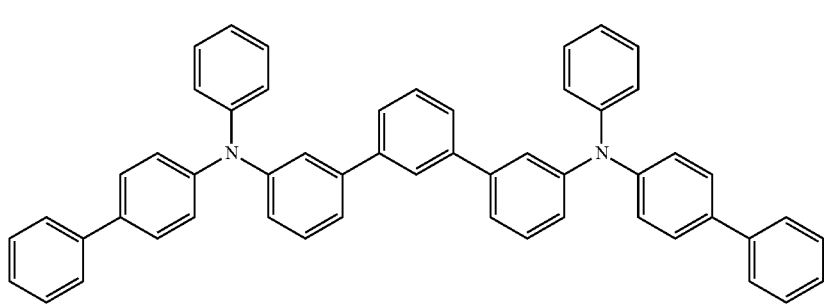
(1-30)

[Chemical Formula 55]
(1-31)
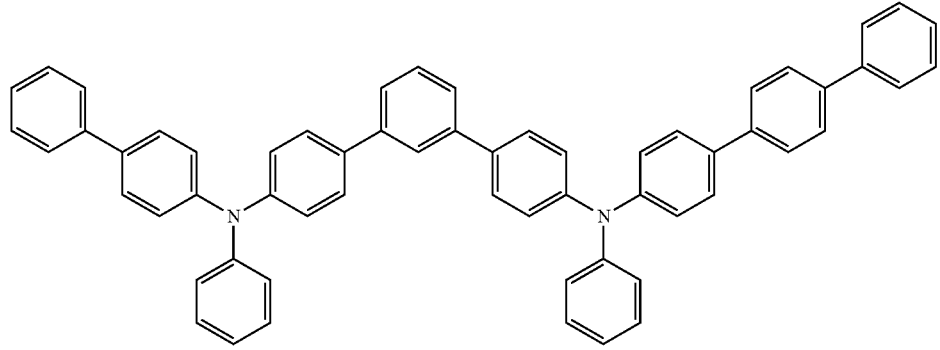
[Chemical Formula 56]
(1-32)
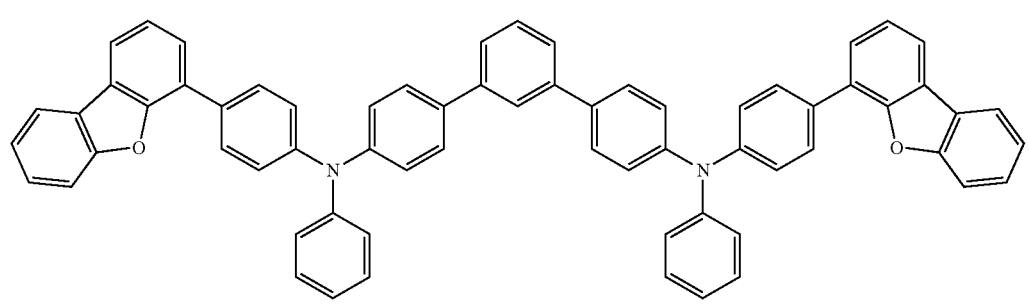
[Chemical Formula 57]
(1-33)
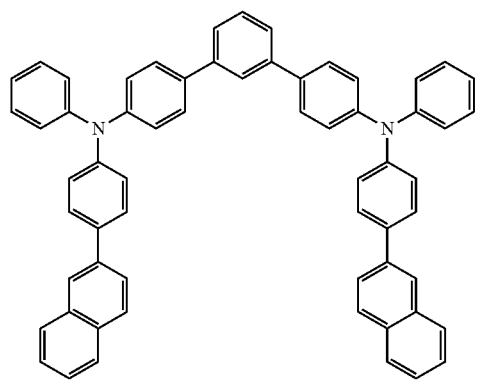
[Chemical Formula 58]
(1-34)
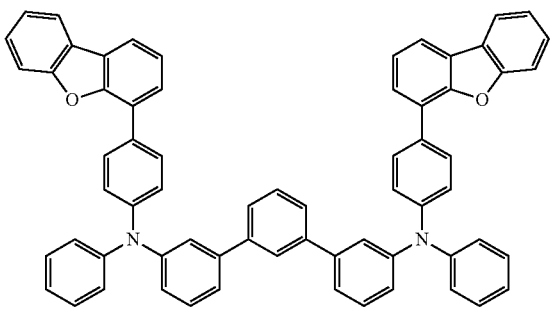
[Chemical Formula 59]
(1-35)
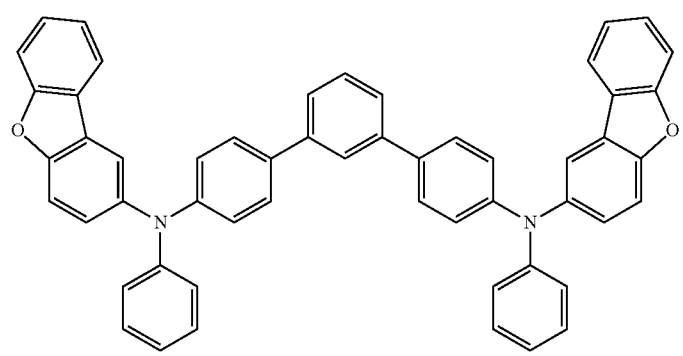

[Chemical Formula 60]
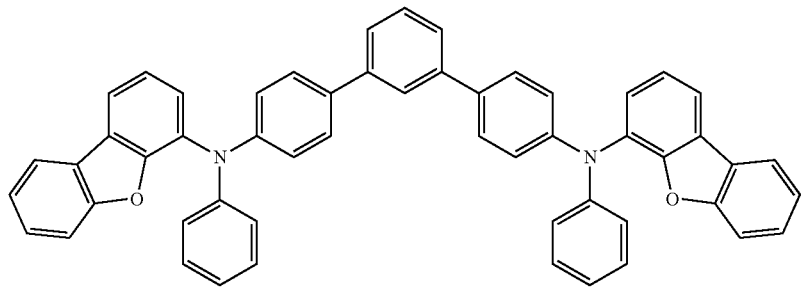
(1-36)
[Chemical Formula 61]
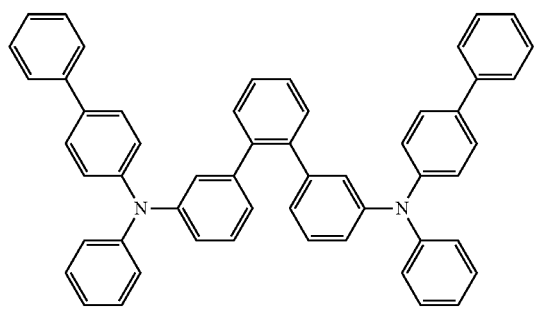
(1-37)
[Chemical Formula 62]
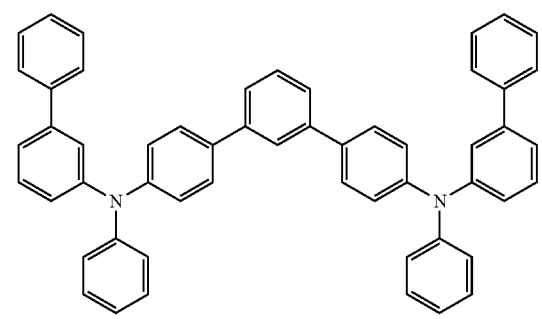
(1-38)
[Chemical Formula 63]
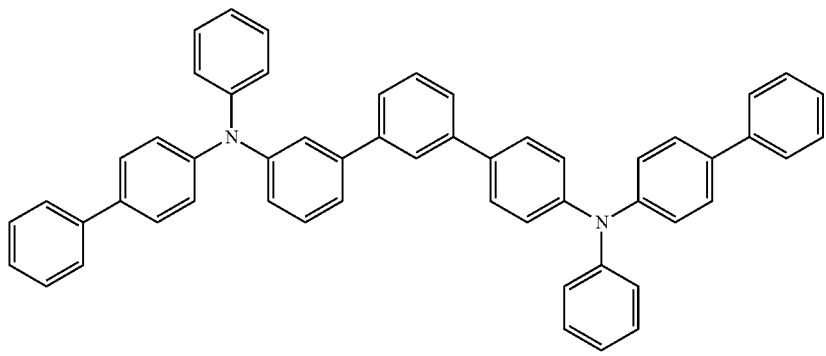
(1-39)
[Chemical Formula 64]
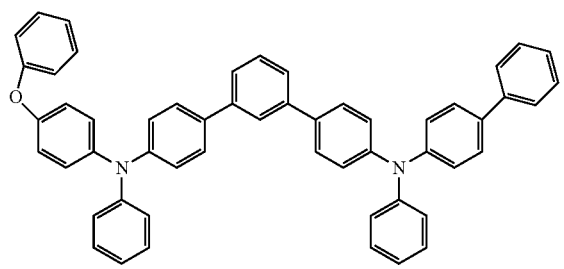
(1-40)
[Chemical Formula 65]
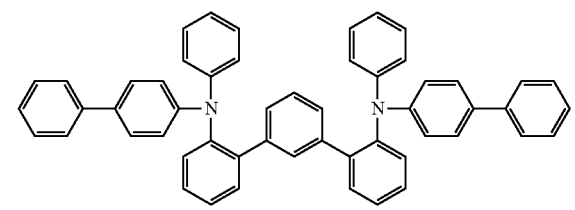
(1-41)

[Chemical Formula 66]
(1-42)
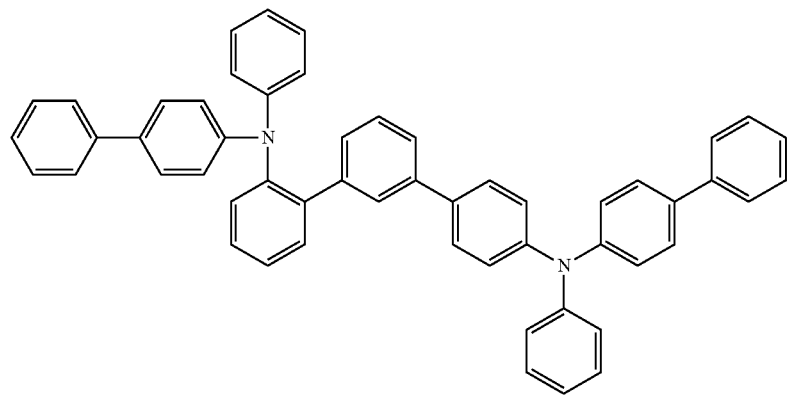
[Chemical Formula 67]
(1-43)
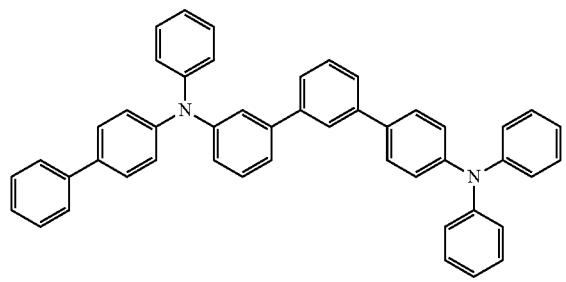
[Chemical Formula 68]
(1-44)
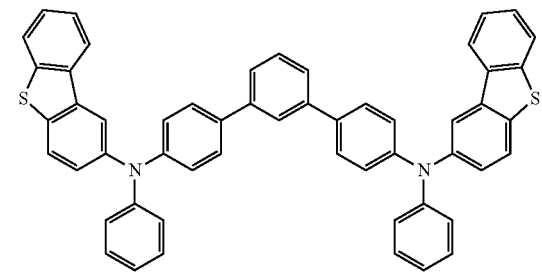
[Chemical Formula 69]
(1-45)
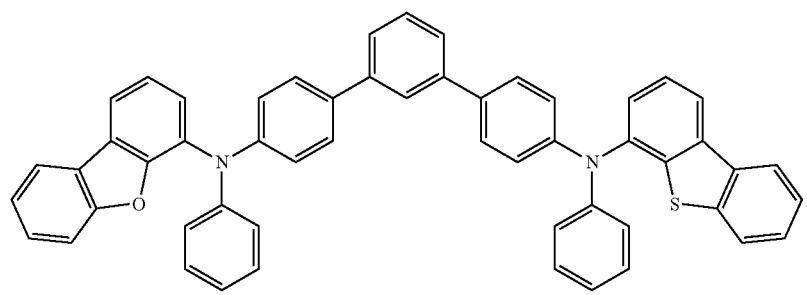
[Chemical Formula 70]
(1-46)
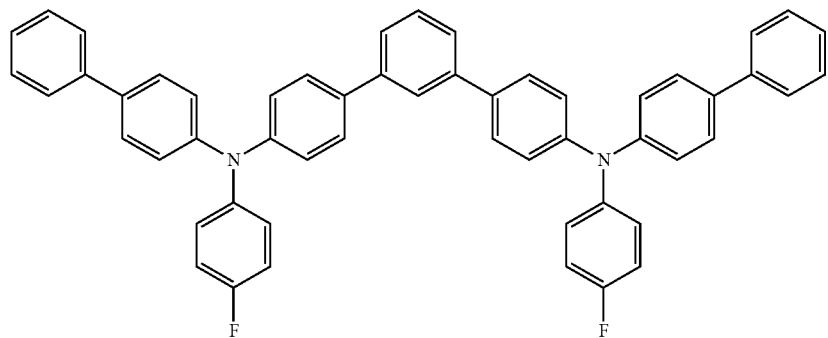

[Chemical Formula 71]
(1-47)
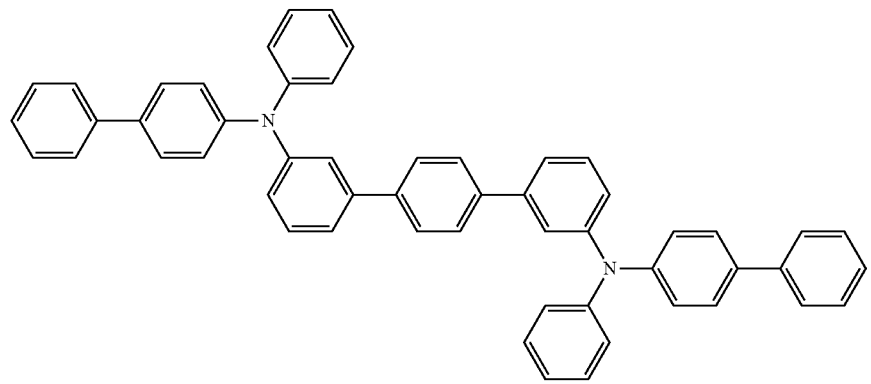
[Chemical Formula 72]
(1-48)
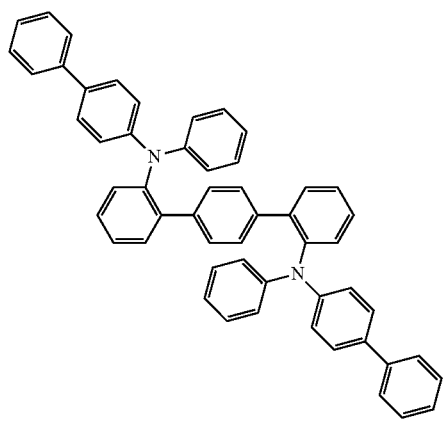
[Chemical Formula 73]
(1-49)
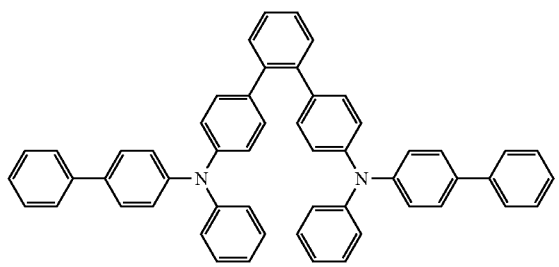
[Chemical Formula 74]
(1-50)
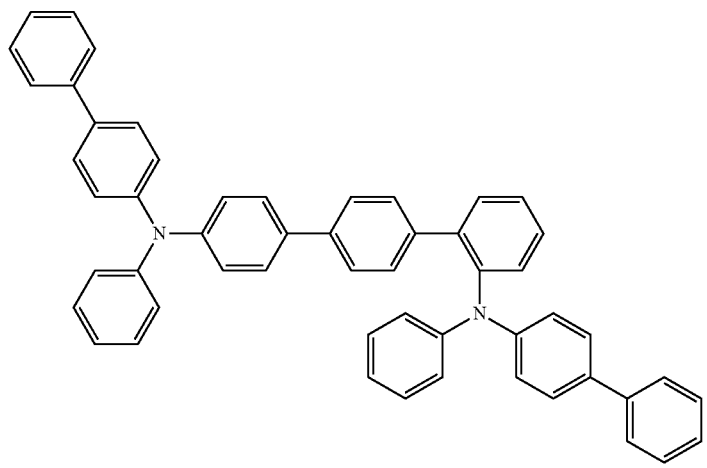

[Chemical Formula 75]
(1-51)
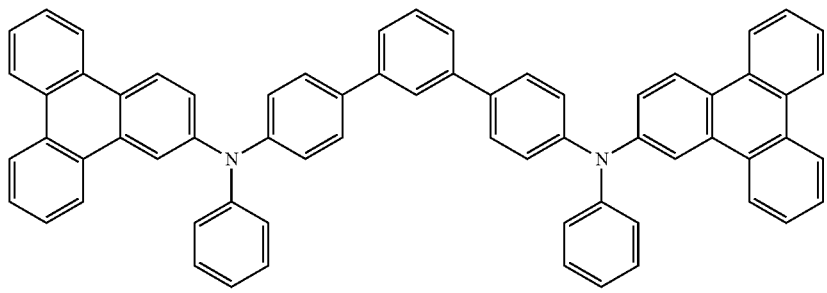
[Chemical Formula 76]
(1-52)
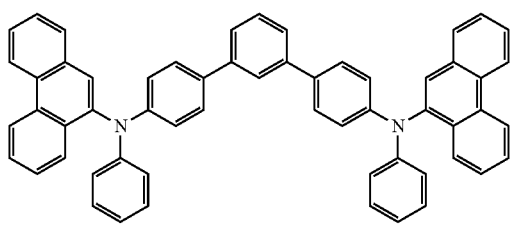
[Chemical Formula 77]
(1-53)
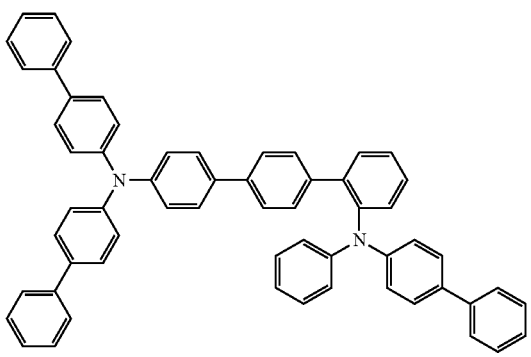
[Chemical Formula 78]
(1-54)
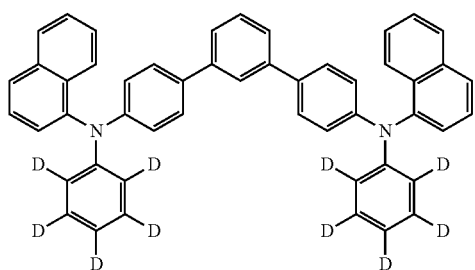
[Chemical Formula 79]
(1-55)
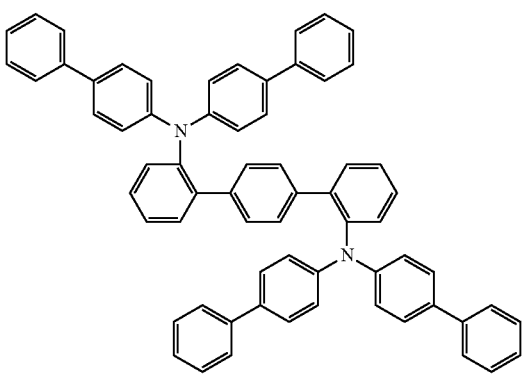
[Chemical Formula 80]
(1-56)
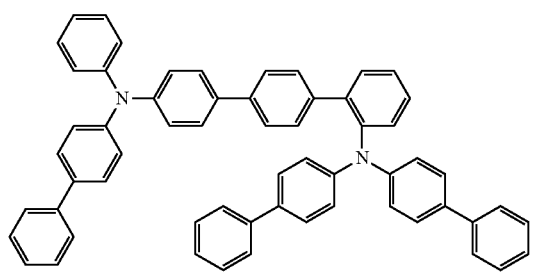
[Chemical Formula 81]
(1-57)
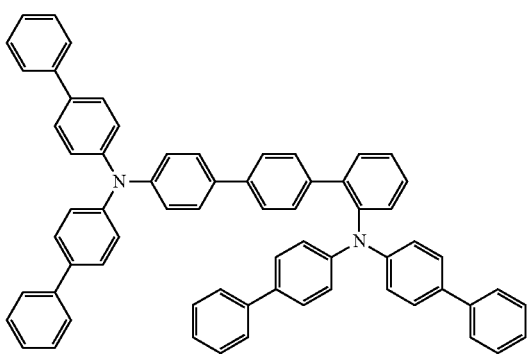

[Chemical Formula 82]
(1-58)
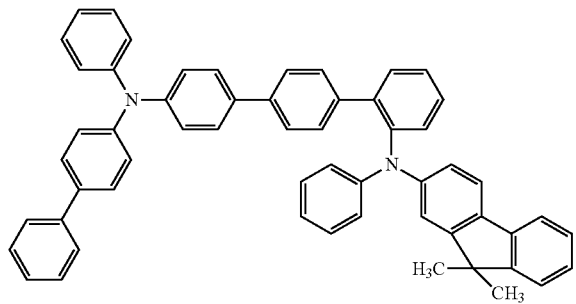
[Chemical Formula 83]
(1-59)
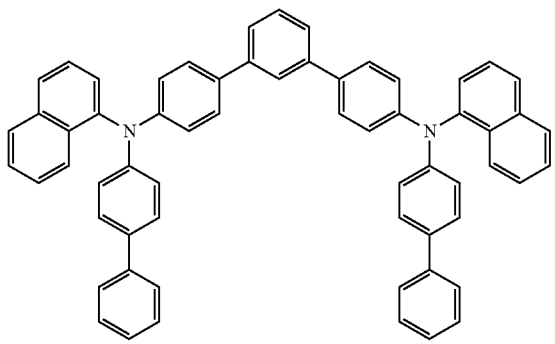
[Chemical Formula 84]
(1-60)
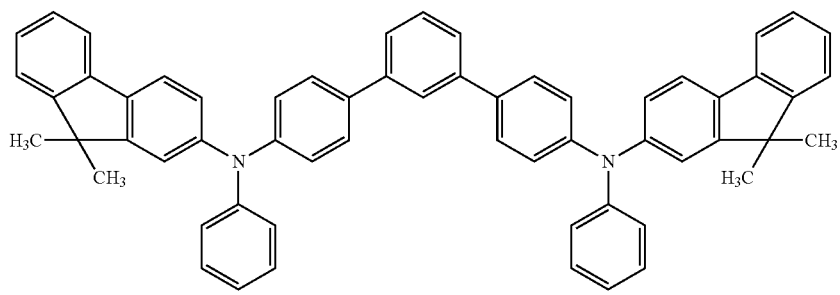
[Chemical Formula 85]
(1-61)
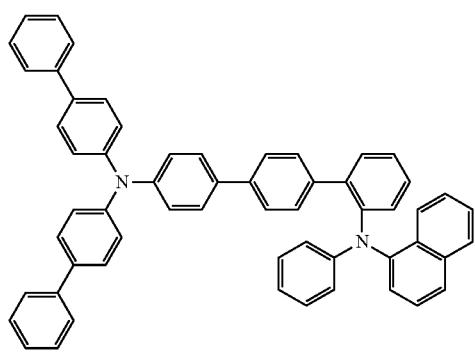
[Chemical Formula 86]
(1-62)
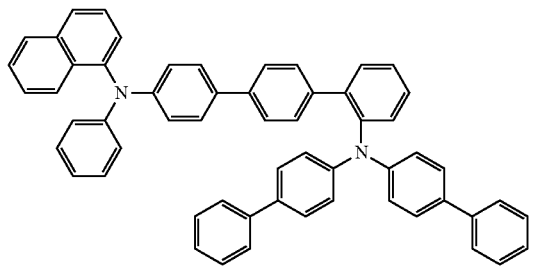
[Chemical Formula 87]
(1-63)
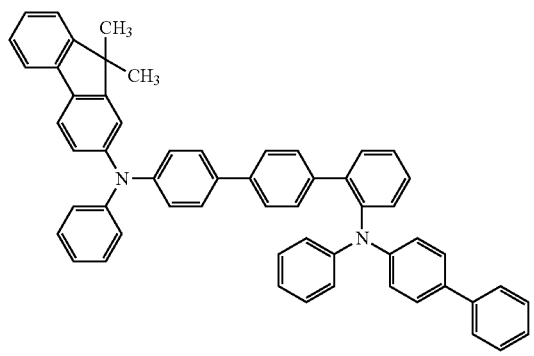
[Chemical Formula 88]
(1-64)
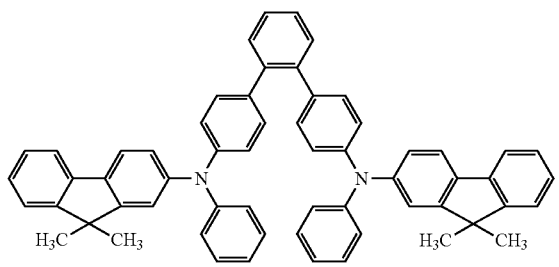

-continued
(1-65)
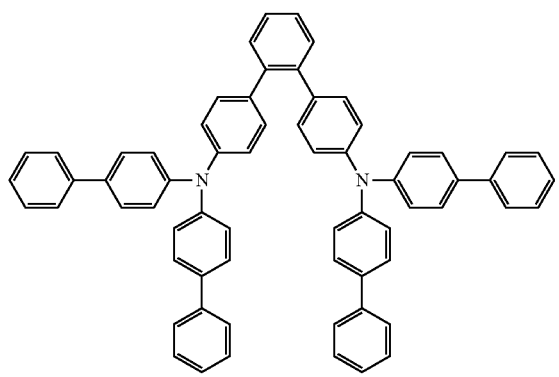
(1-66)
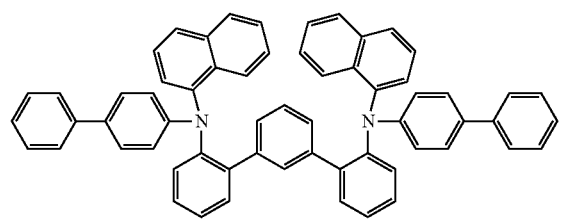
(1-67)
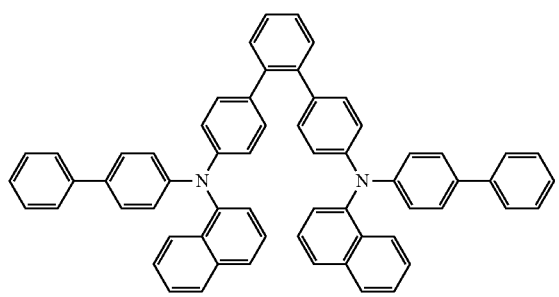
(1-68)
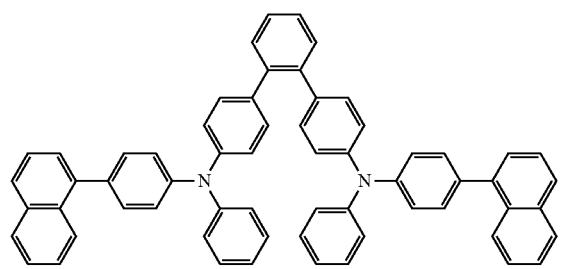
(1-69)
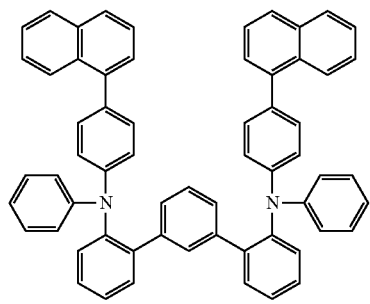
(1-70)
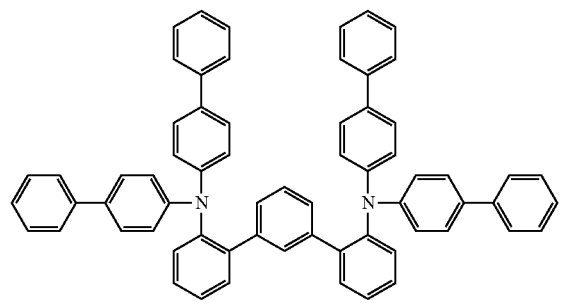
(1-71)
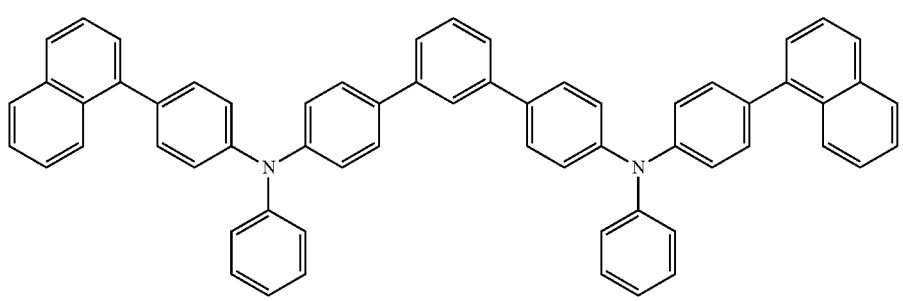

[Chemical Formula 96]
(1-72)
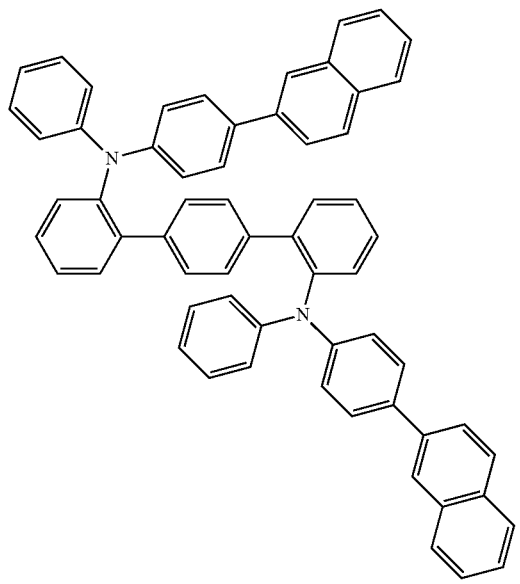
[Chemical Formula 97]
(1-73)
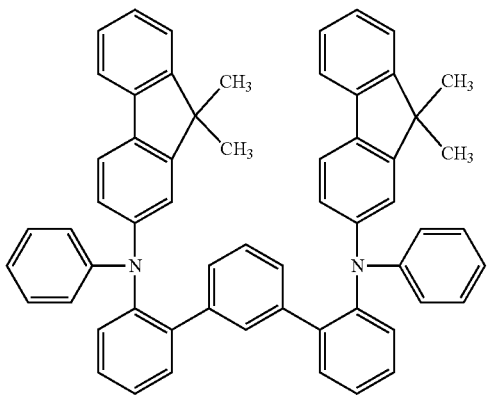
[Chemical Formula 98]
(1-74)
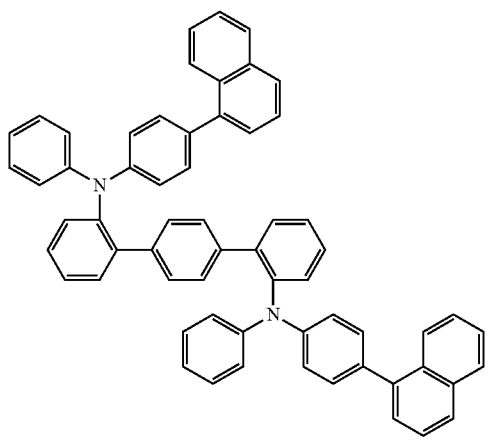
[Chemical Formula 99]
(1-75)
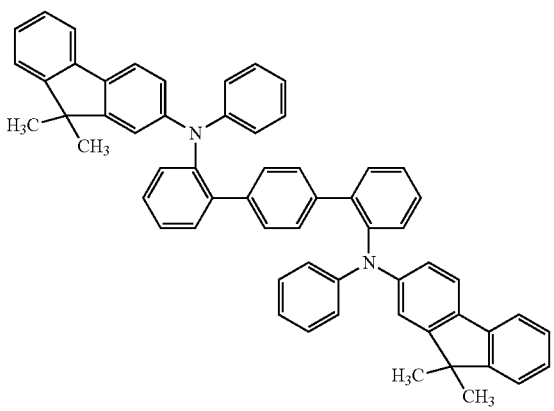
[Chemical Formula 100]
(1-76)
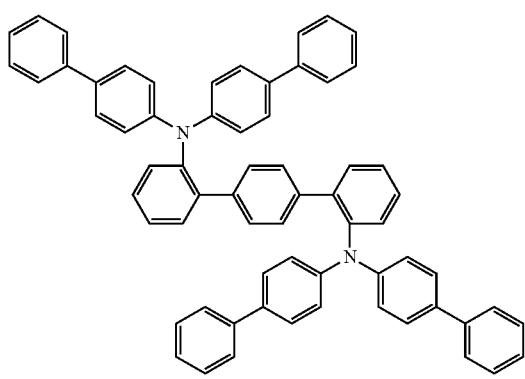
[Chemical Formula 101]
(1-77)
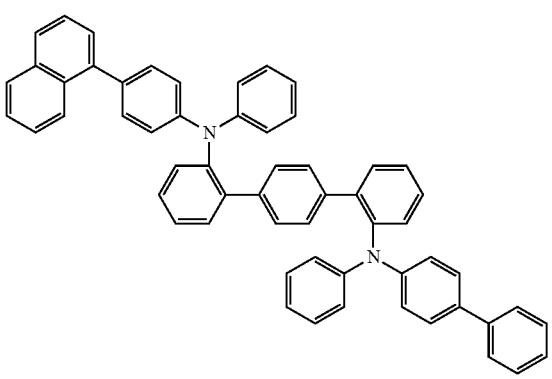

-continued
(1-78)
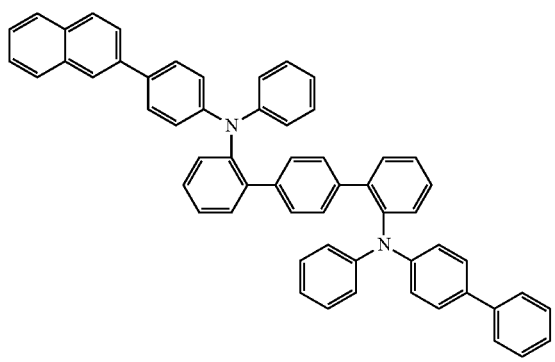
(1-79)
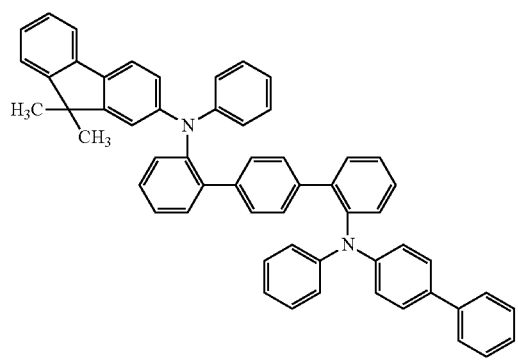
(1-80)
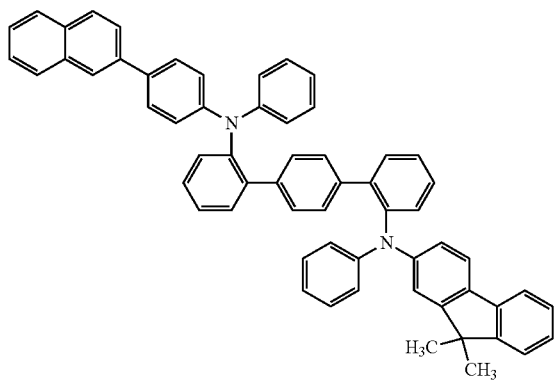
(1-81)
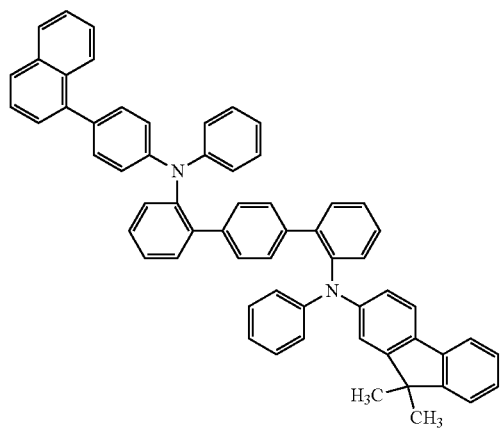
(1-82)
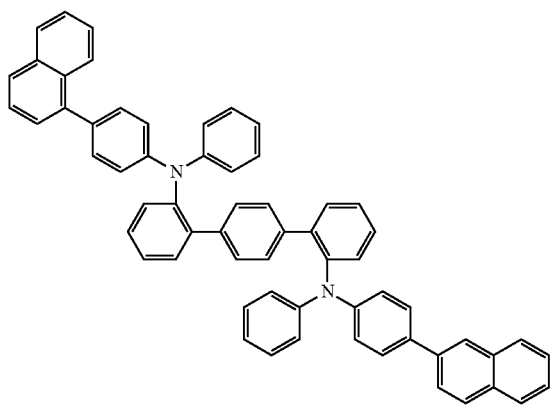
(1-83)
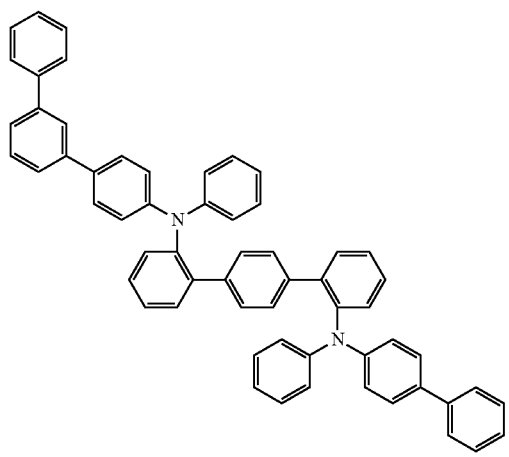

-continued
[Chemical Formula 108]
(1-84)
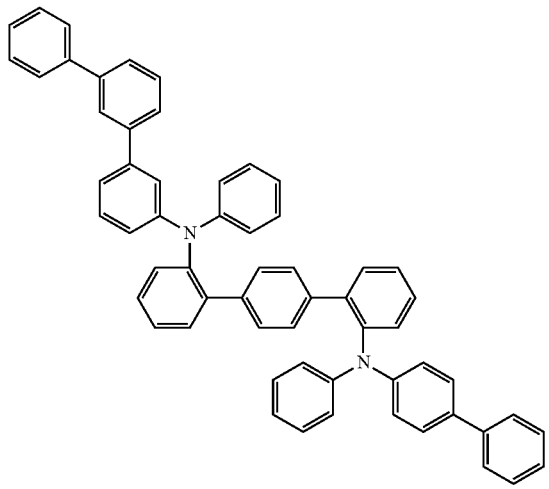
[Chemical Formula 109]
(1-85)
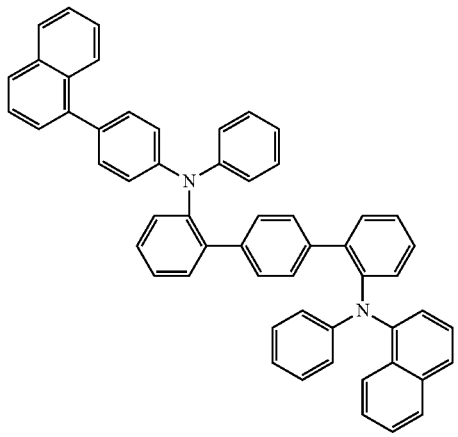
[Chemical Formula 110]
(1-86)
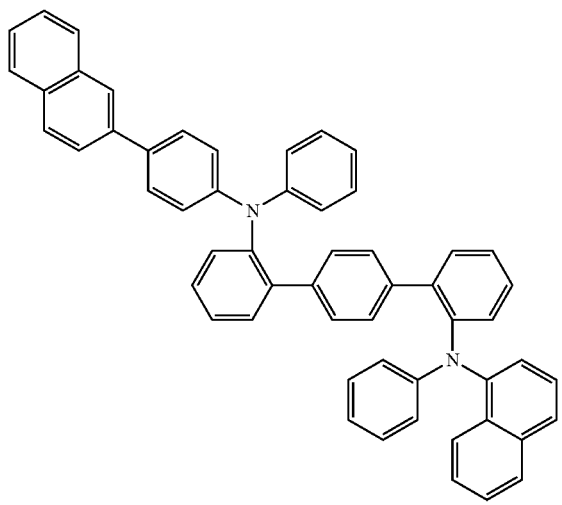
[Chemical Formula 111]
(1-87)
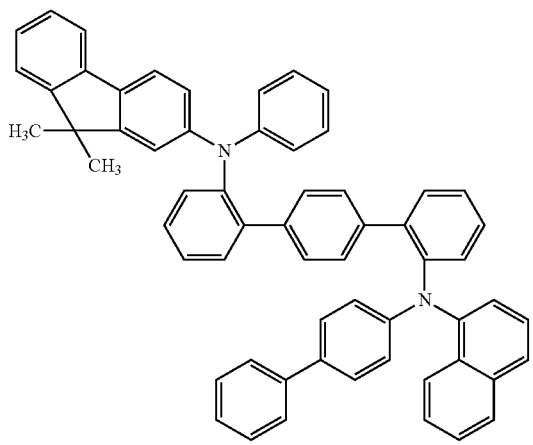
[Chemical Formula 112]
(1-88)
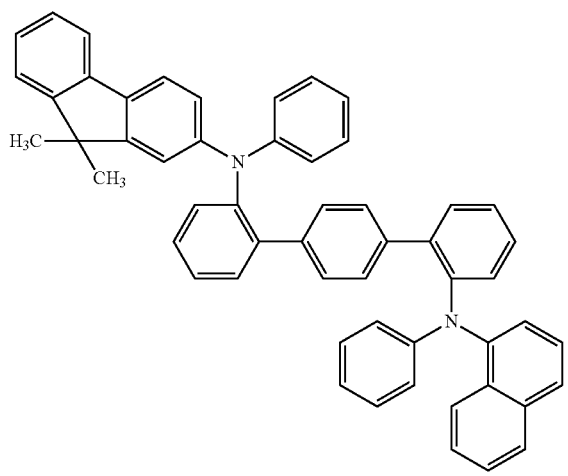
[Chemical Formula 113]
(1-89)
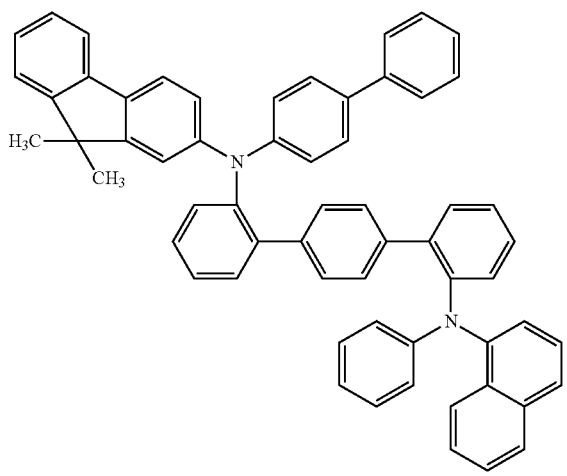

[Chemical Formula 114]

(1-90)

[Chemical Formula 115]

(1-91)

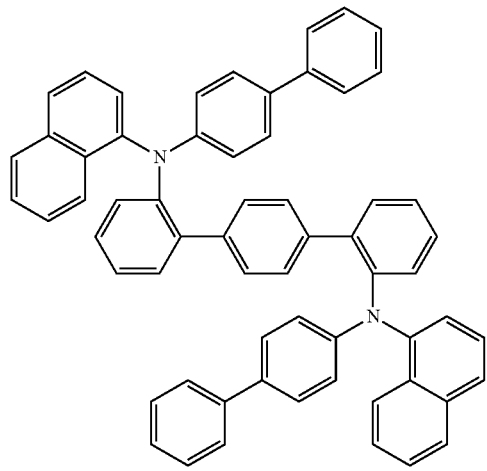

[Chemical Formula 116]

(1-92)

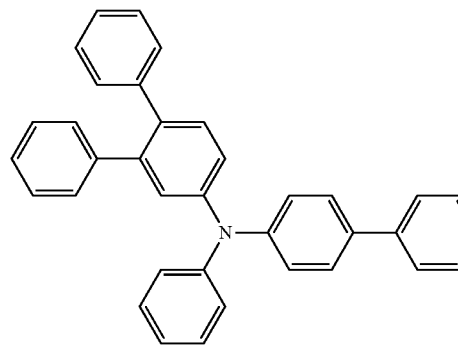

The arylamine compounds described above can be synthesized according to the known methods (refer to Patent Document 7, for example).

The following presents specific examples of preferred compounds among the arylamine compounds of the general formula (3) preferably used in the organic EL device of the present invention. The present invention, however, is not restricted to these compounds.

[Chemical Formula 117]

(3-1)

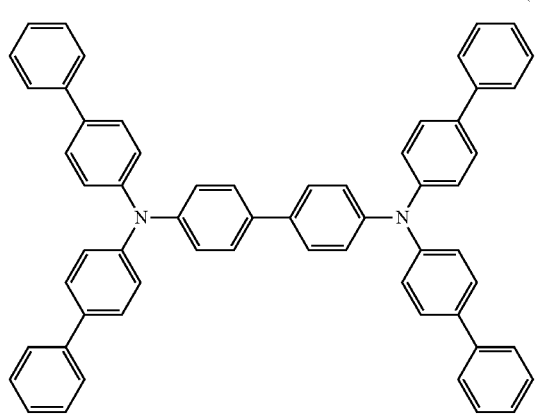

[Chemical Formula 118]

(3-2)

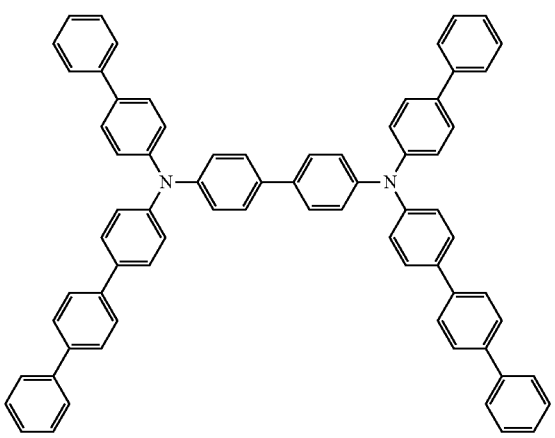

[Chemical Formula 119]
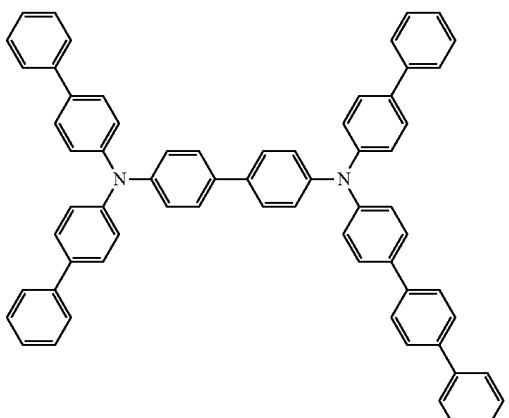
(3-3)
[Chemical Formula 120]
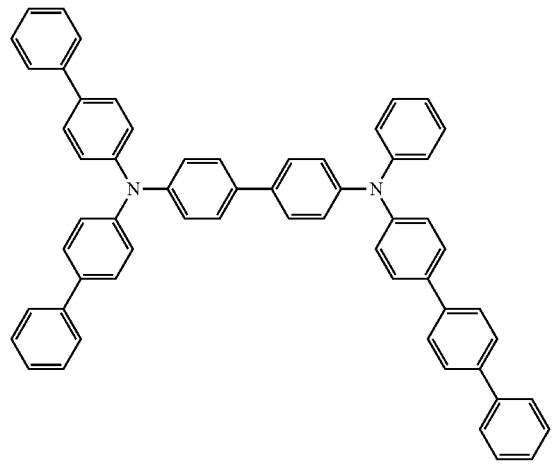
(3-4)
[Chemical Formula 121]
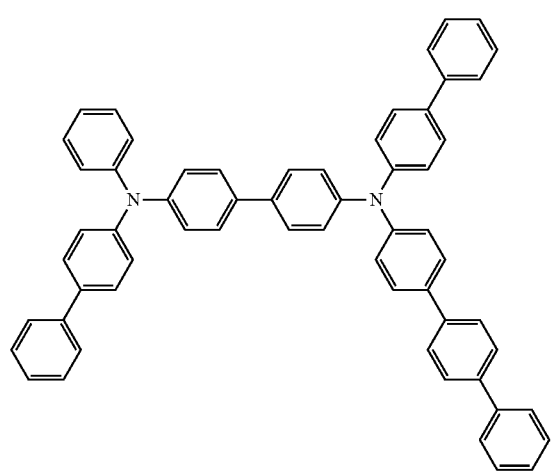
(3-5)
[Chemical Formula 122]
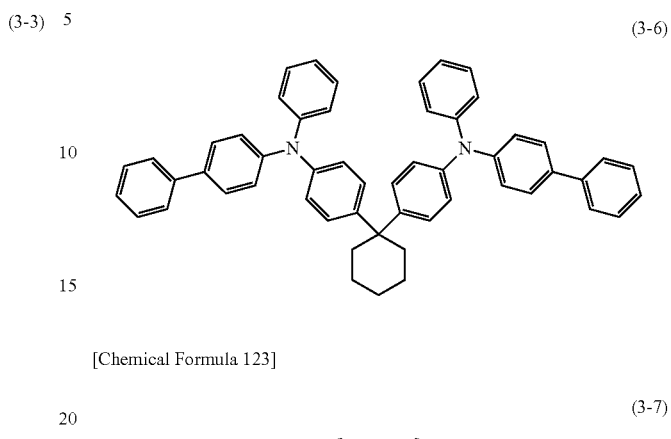
(3-6)
[Chemical Formula 123]
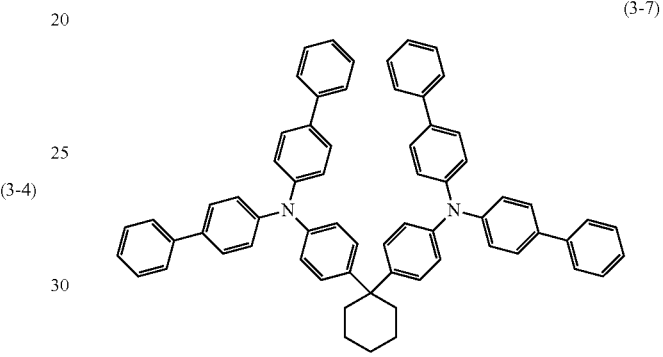
(3-7)
[Chemical Formula 124]
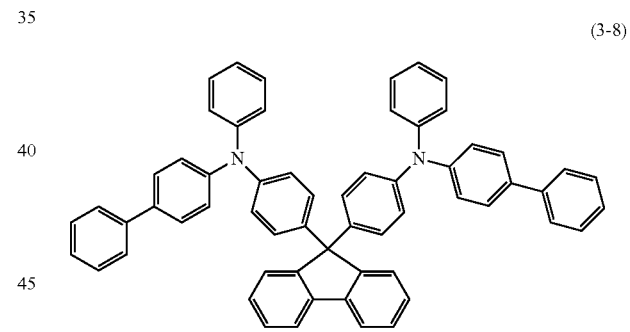
(3-8)
[Chemical Formula 125]
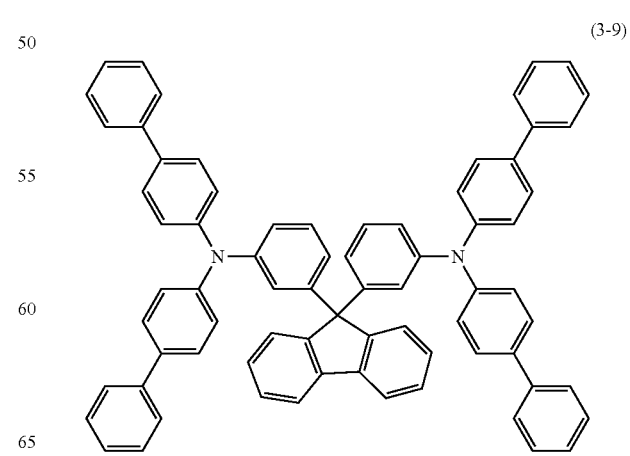
(3-9)

[Chemical Formula 126]
(3-10)
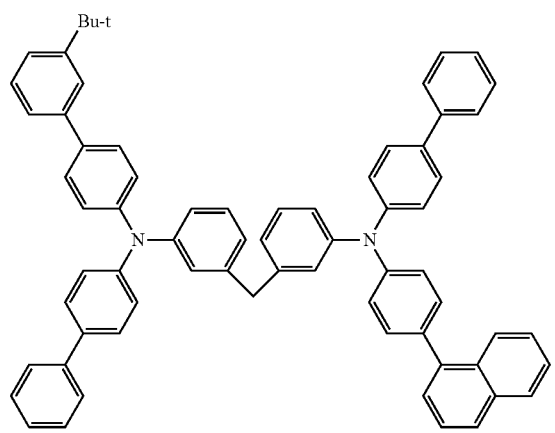
[Chemical Formula 127]
(3-11)
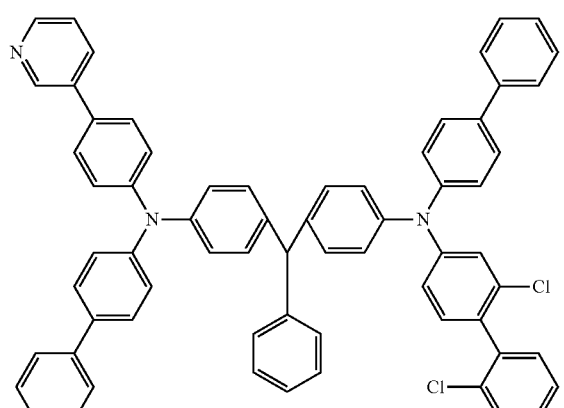
[Chemical Formula 128]
(3-12)
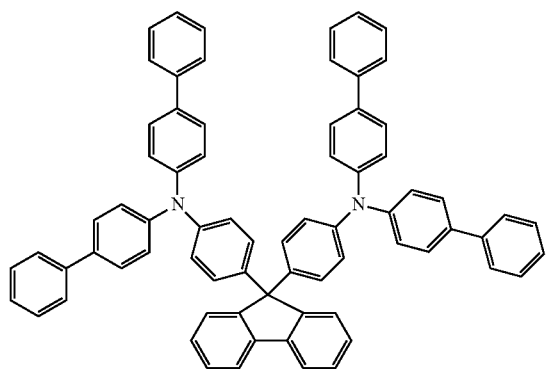
[Chemical Formula 129]
(3-13)
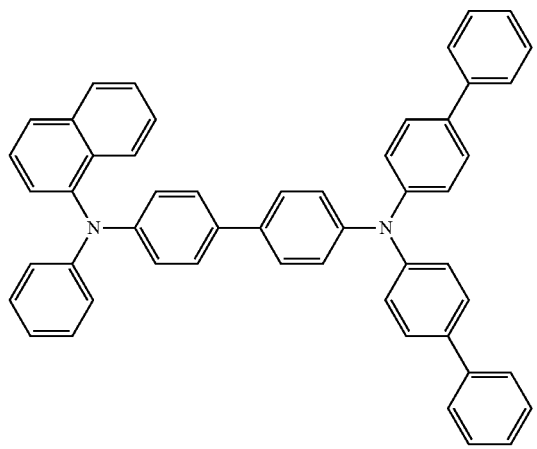
[Chemical Formula 130]
(3-14)
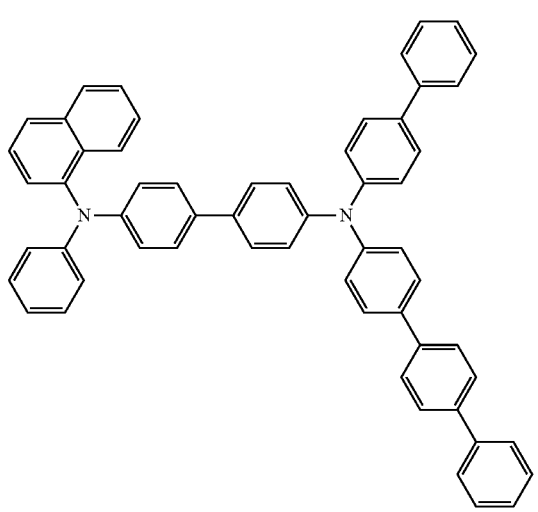
[Chemical Formula 131]
(3-15)
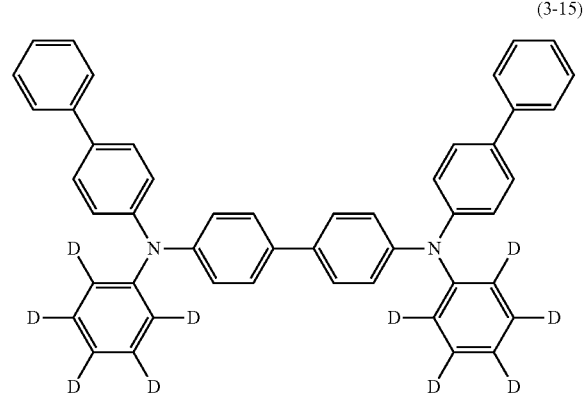

[Chemical Formula 132]
(3-16)
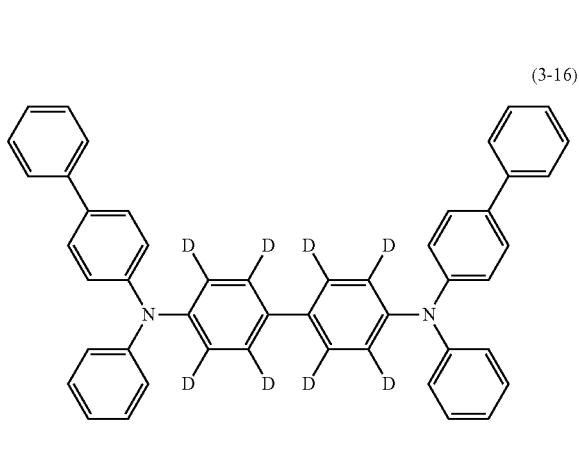
[Chemical Formula 133]
(3-17)
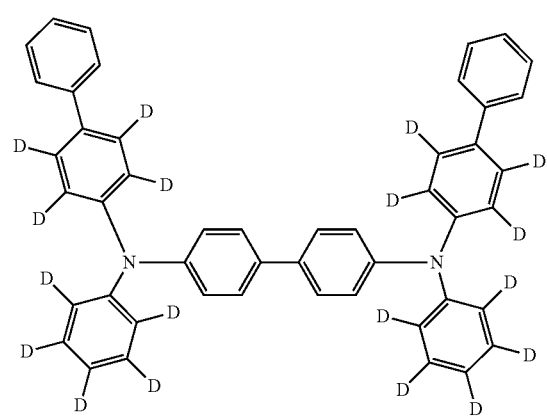
[Chemical Formula 134]
(3-18)
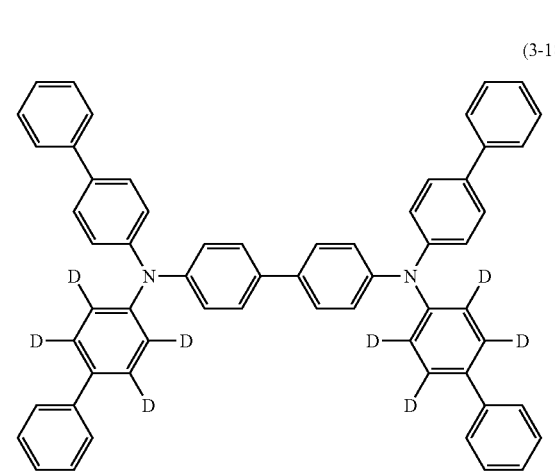
[Chemical Formula 135]
(3-19)
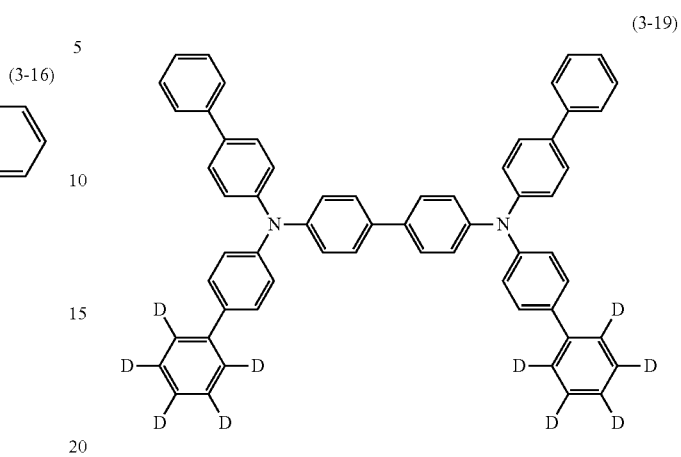
[Chemical Formula 136]
(3-20)
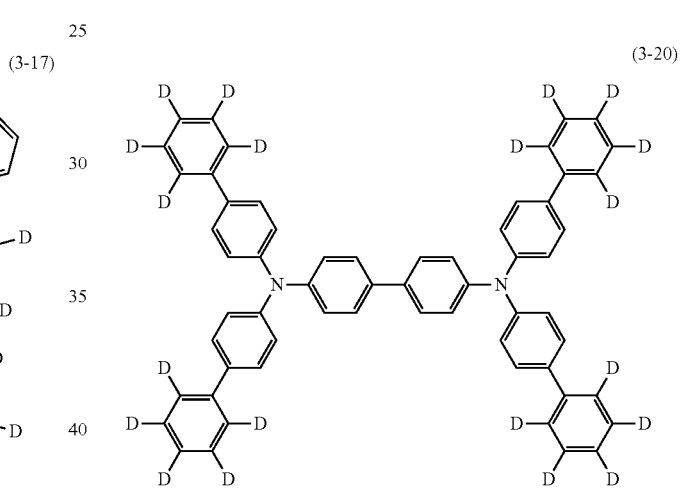
[Chemical Formula 137]
(3-21)
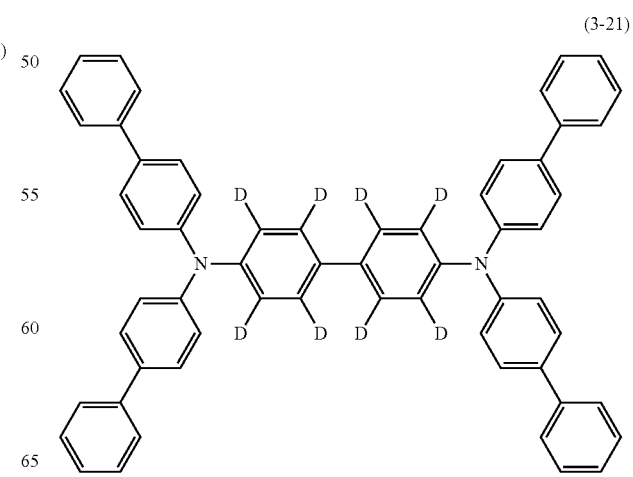

[Chemical Formula 138]

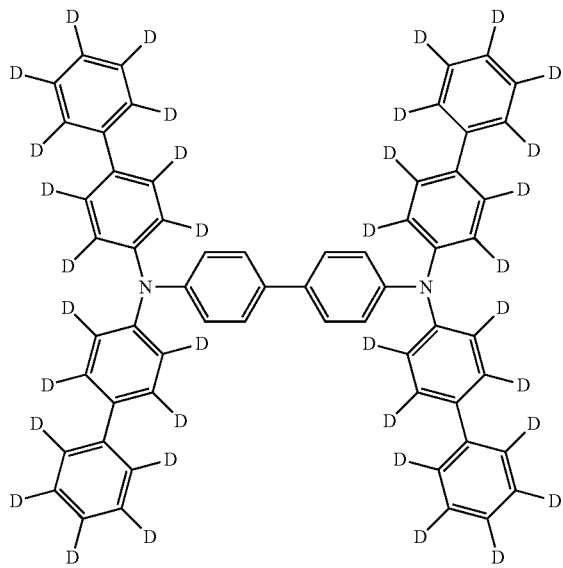

(3-22)

[Chemical Formula 139]

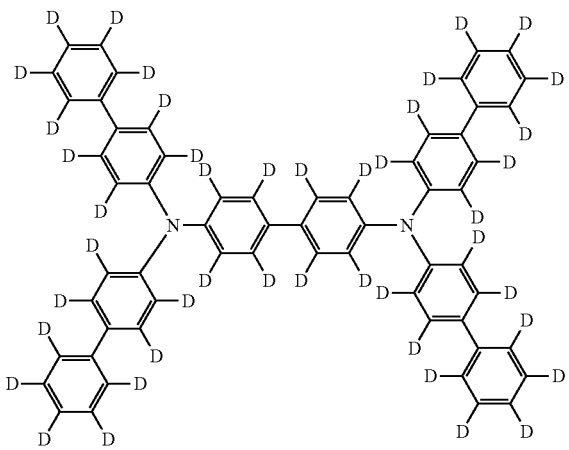

The following presents specific examples of preferred compounds of the arylamine compounds having two triphenylamine structures in the molecule among the arylamine compounds having a structure in which two to six triphenylamine structures in the molecule bind via a single bond or a divalent group that does not contain a heteroatom preferably used in the organic EL device of the present invention, in addition to the arylamine compounds of general formula (3). The present invention, however, is not restricted to these compounds.

[Chemical Formula 140]

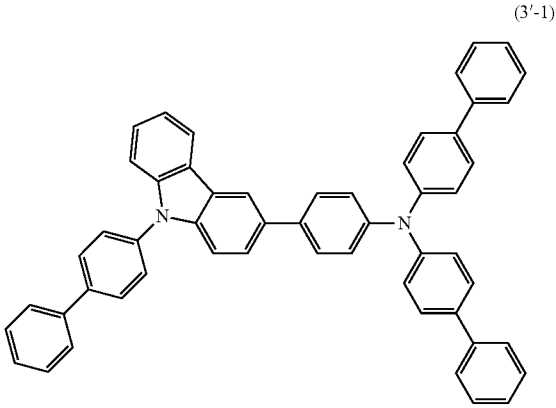

(3'-1)

[Chemical Formula 141]

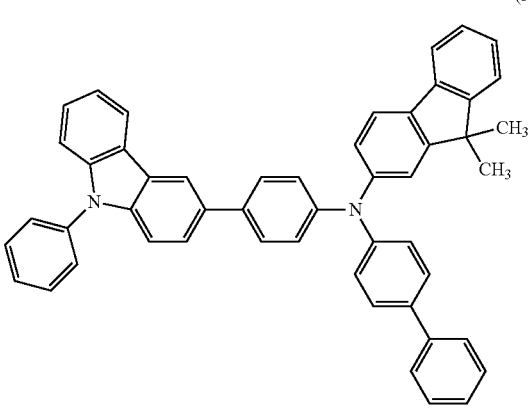

(3'-2)

The following presents specific examples of preferred compounds among the arylamine compounds of the general formula (4) preferably used in the organic EL device of the present invention. The present invention, however, is not restricted to these compounds.

[Chemical Formula 142]
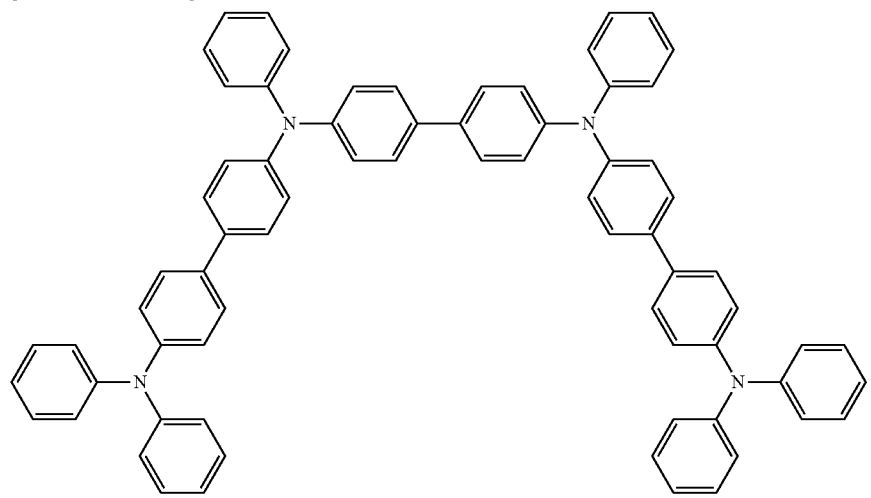
(4-1)
[Chemical Formula 143]
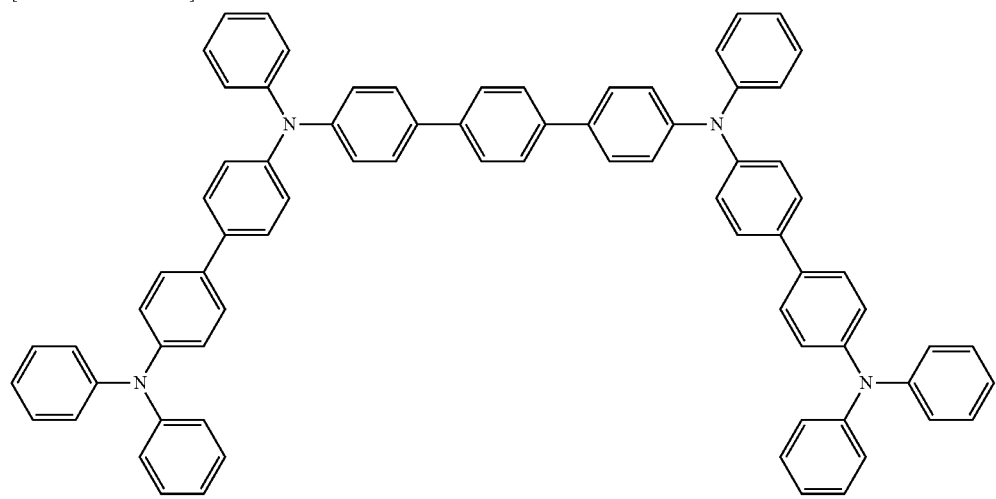
(4-2)
[Chemical Formula 144]
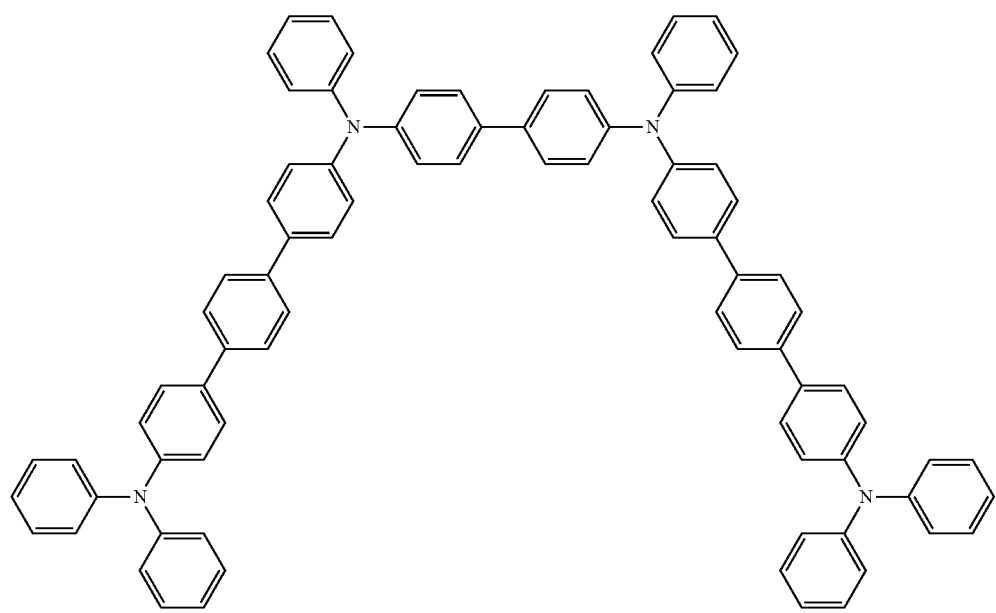
(4-3)

[Chemical Formula 145]
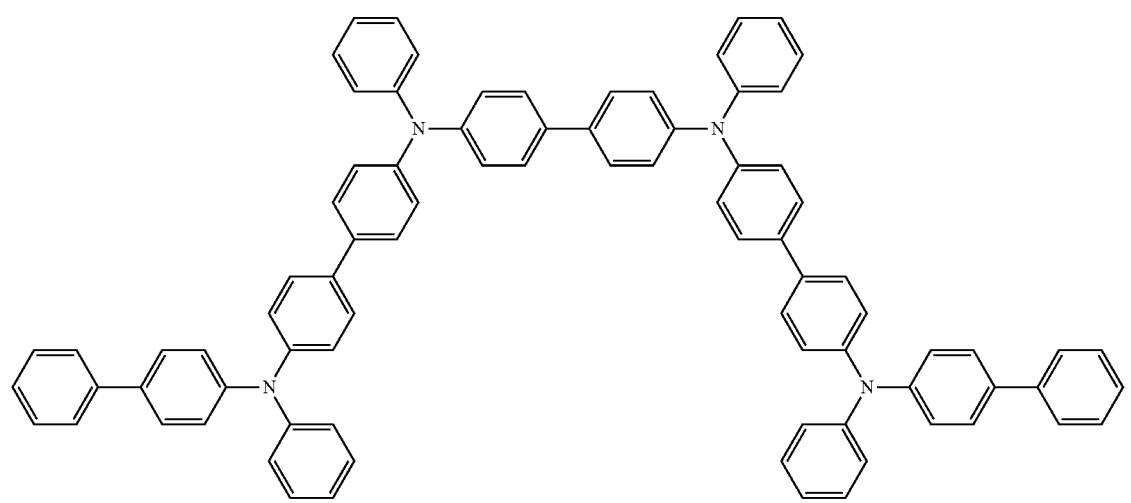
(4-4)
[Chemical Formula 146]
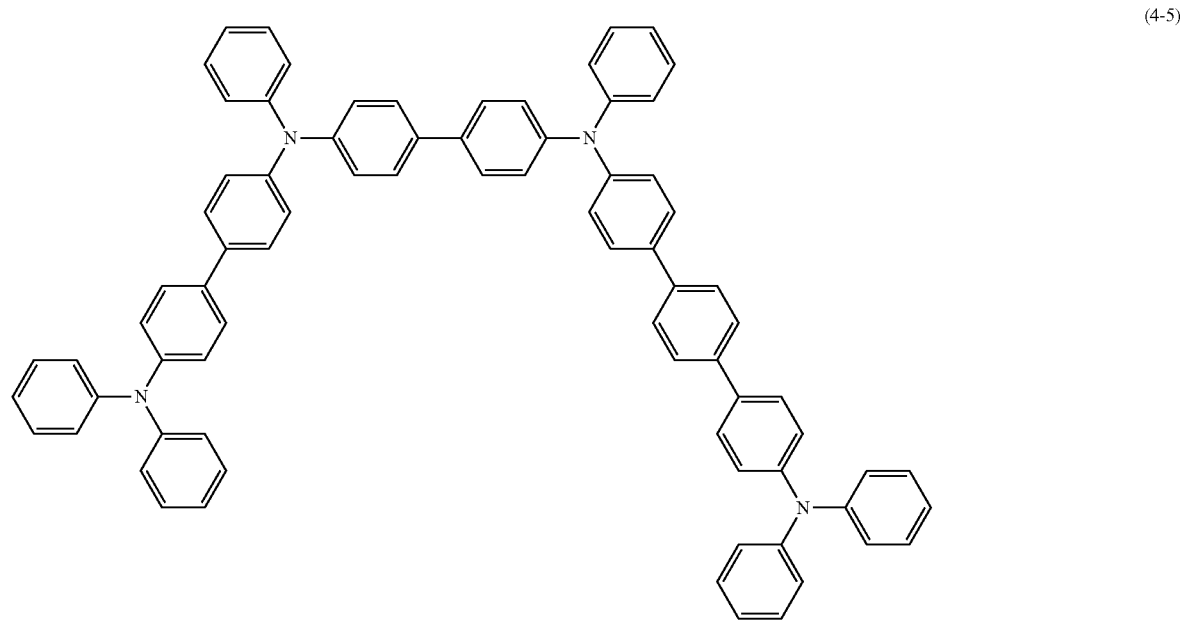
(4-5)

[Chemical Formula 147]
(4-6)
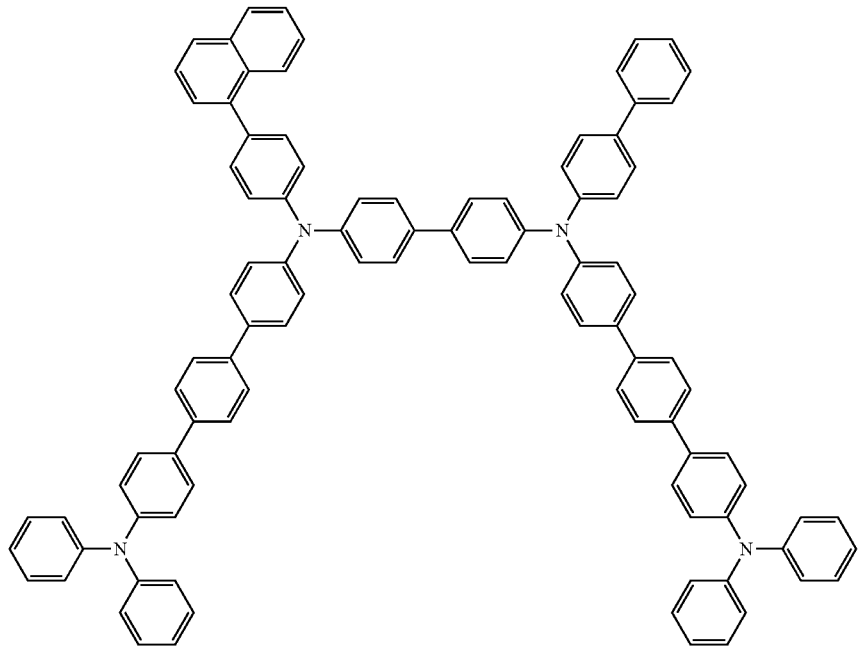
[Chemical Formula 148]
(4-7)
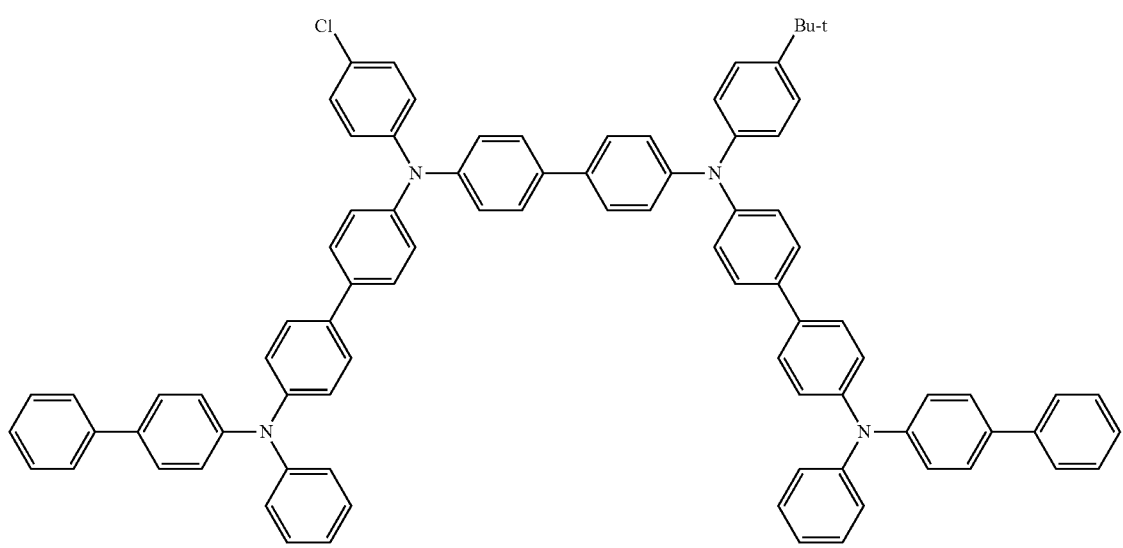

[Chemical Formula 149]
(4-8)
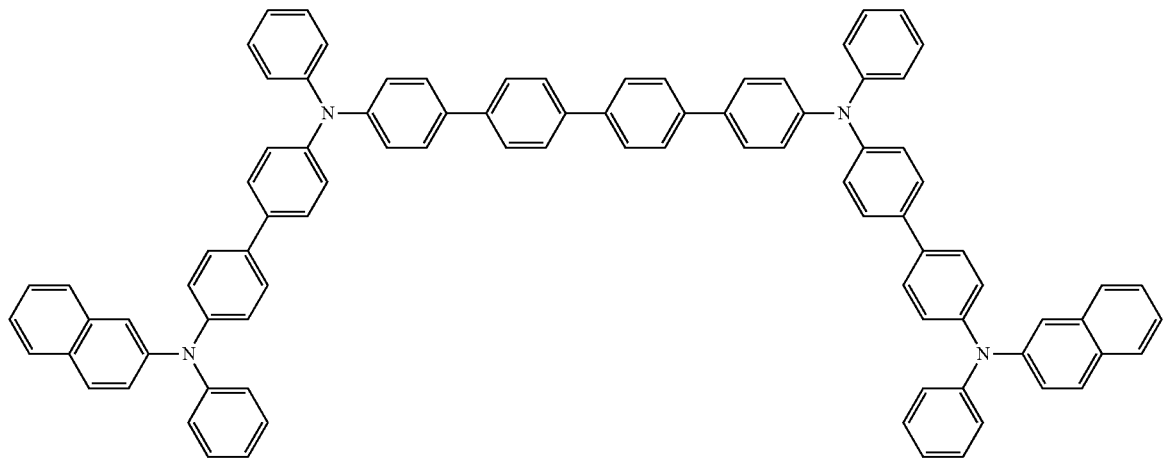
[Chemical Formula 150]
(4-9)
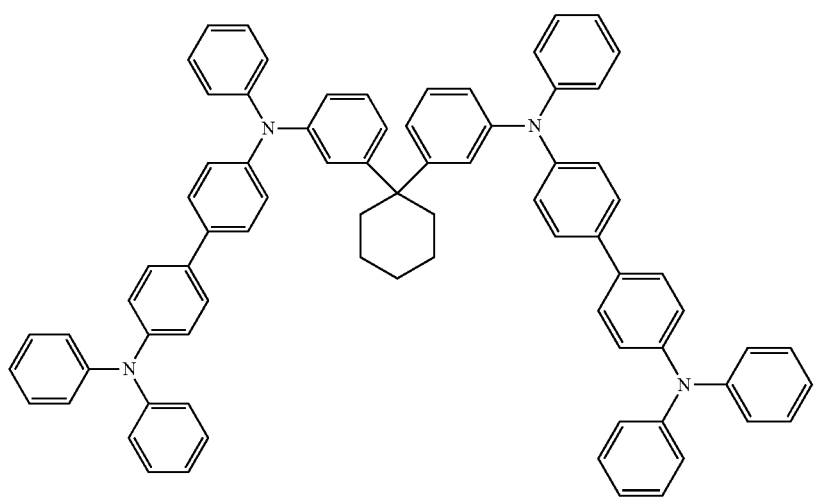
[Chemical Formula 151]
(4-10)
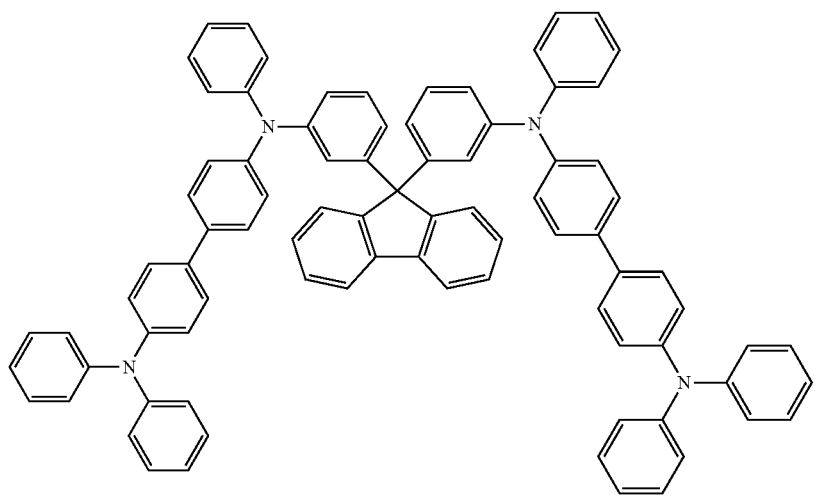

[Chemical Formula 152]
(4-11)
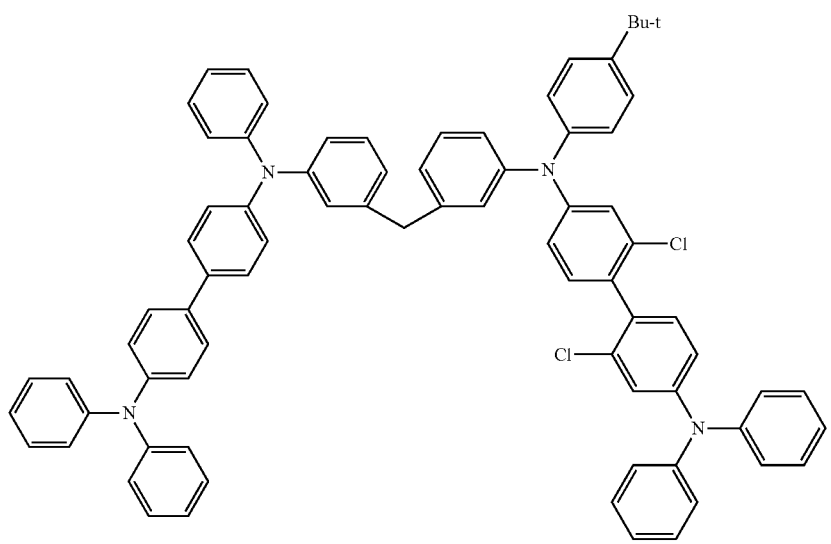
[Chemical Formula 153]
(4-12)
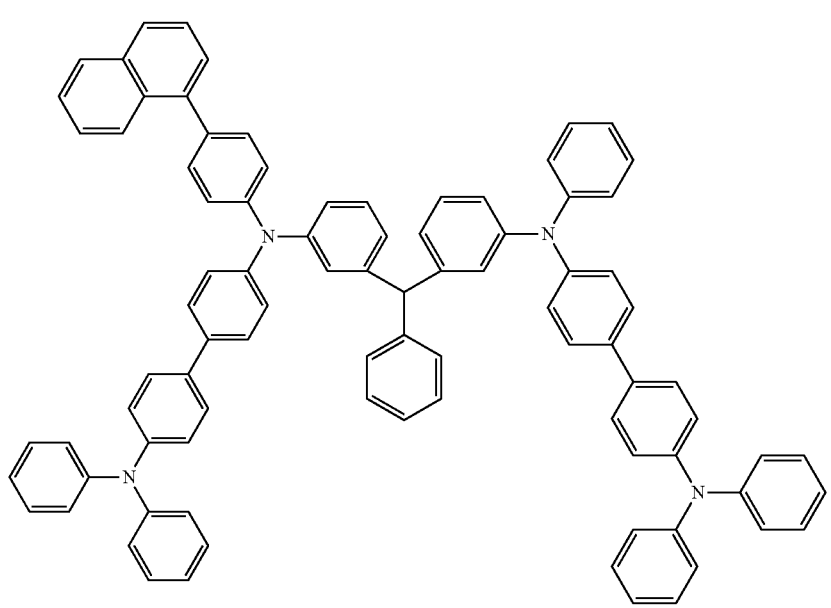
[Chemical Formula 154]
(4-13)
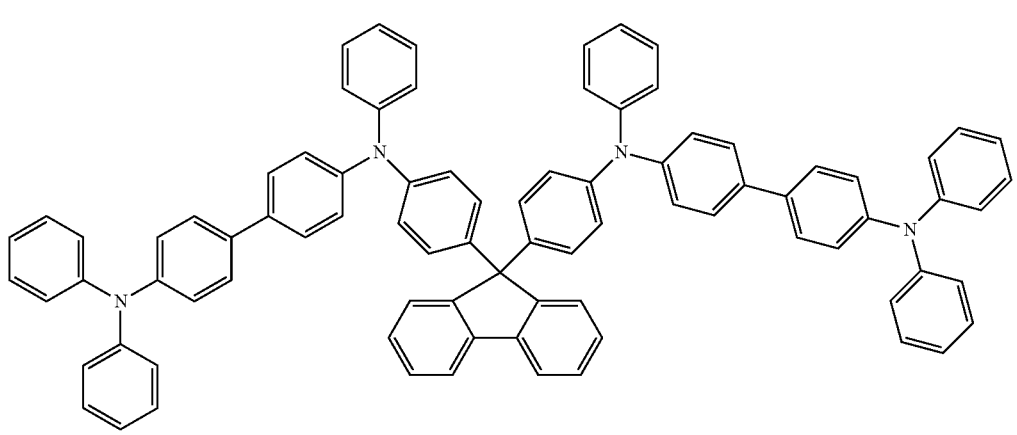

[Chemical Formula 155]
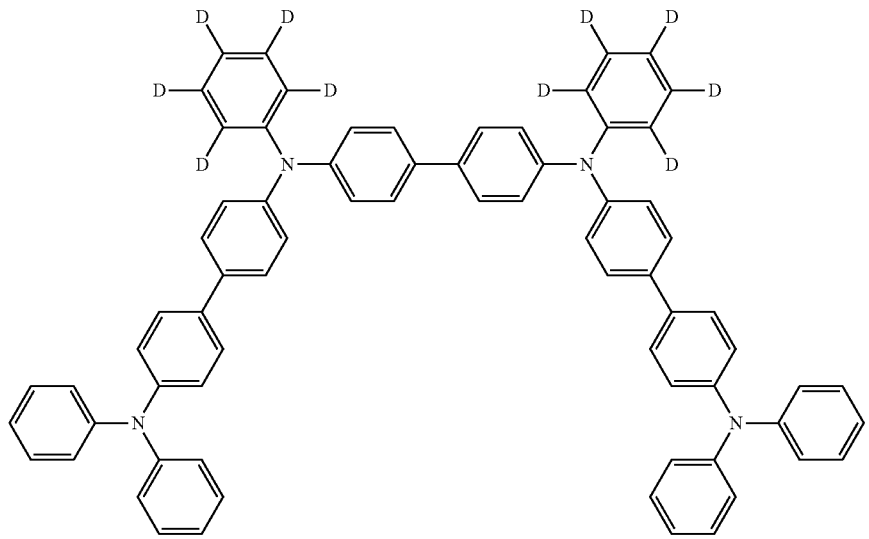
(4-14)
[Chemical Formula 156]
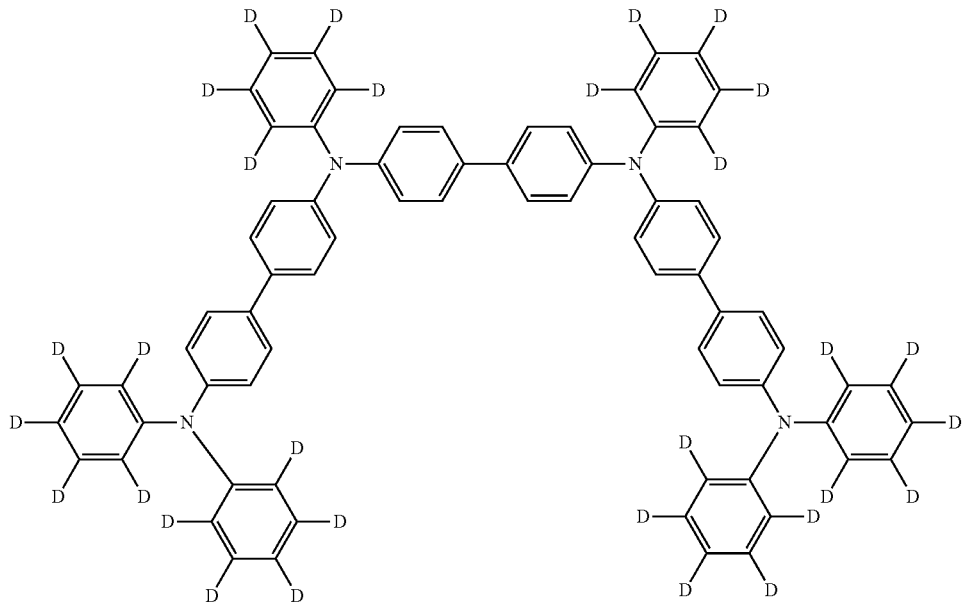
(4-15)

[Chemical Formula 157]

(4-16)

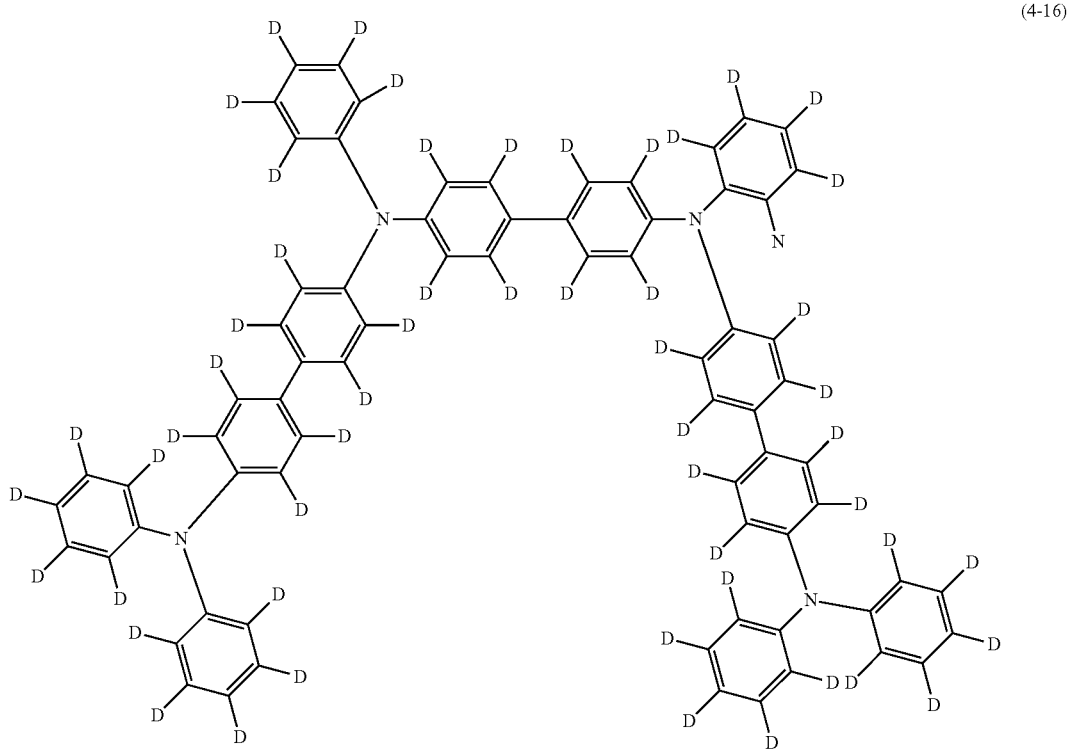

[Chemical Formula 158]

(4-17)

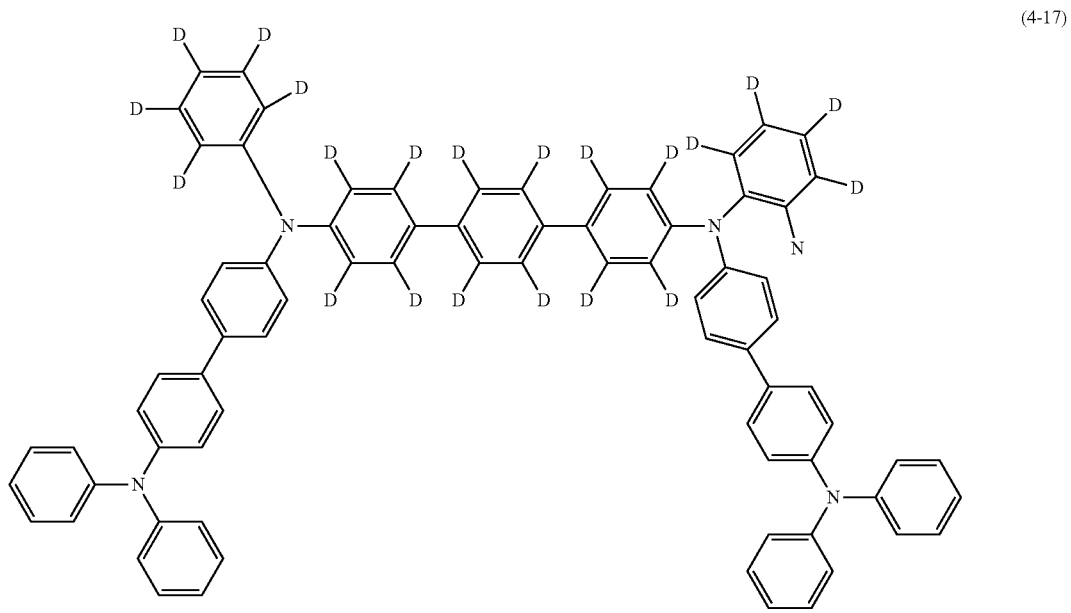

The arylamine compounds of the general formula (3) and the arylamine compounds of the general formula (4) can be synthesized by a known method (refer to Patent Documents 1 and 8 to 9, for example).

The following presents specific examples of preferred compounds among the arylamine compounds of the general formula (5) preferably used in the organic EL device of the present invention. The present invention, however, is not restricted to these compounds.

[Chemical Formula 159]
(5-1)
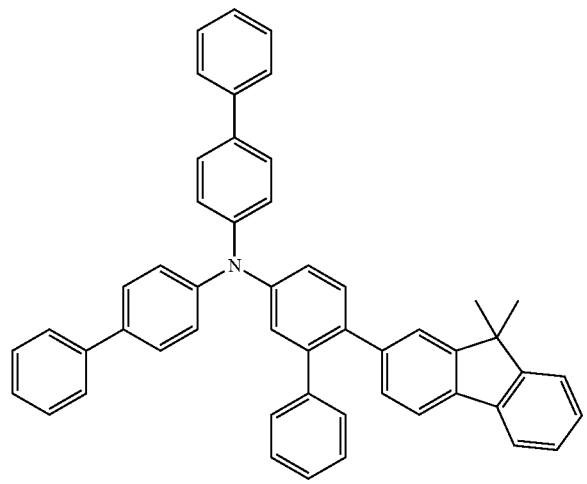
[Chemical Formula 160]
(5-2)
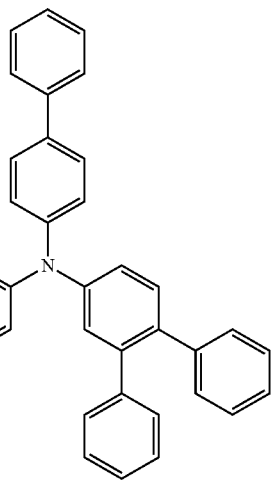
[Chemical Formula 161]
(5-3)
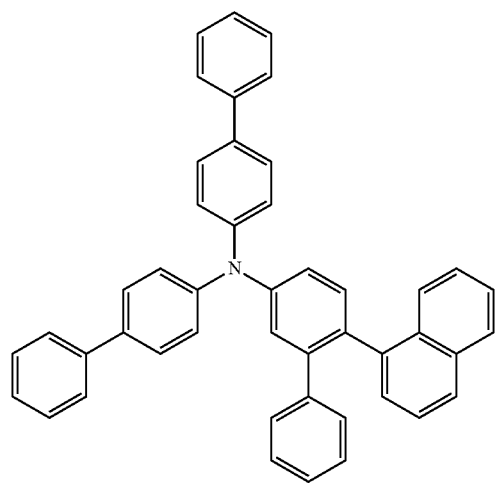
[Chemical Formula 162]
(5-4)
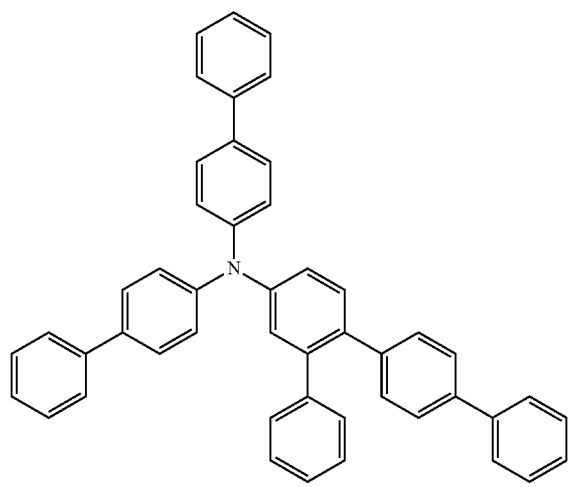
[Chemical Formula 163]
(5-5)
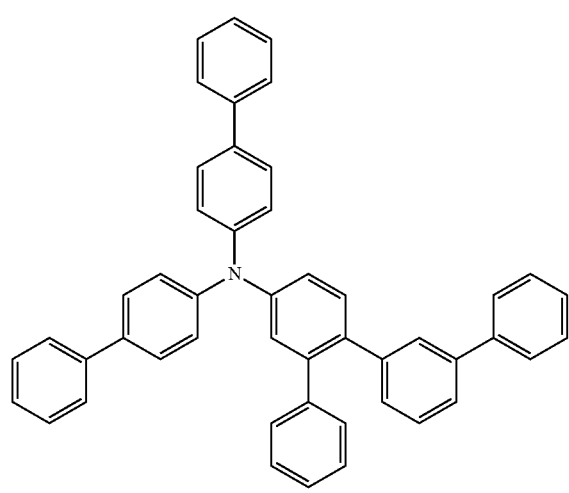
[Chemical Formula 164]
(5-6)
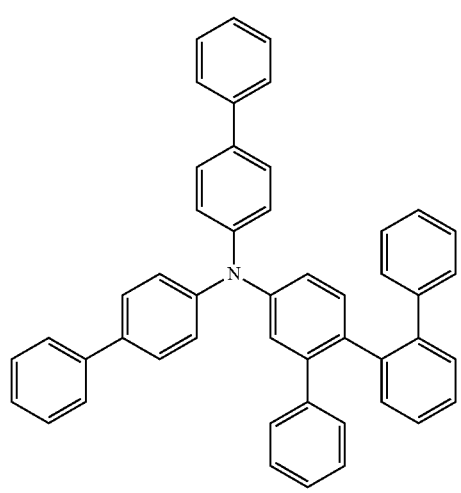

-continued
[Chemical Formula 165]
(5-7)
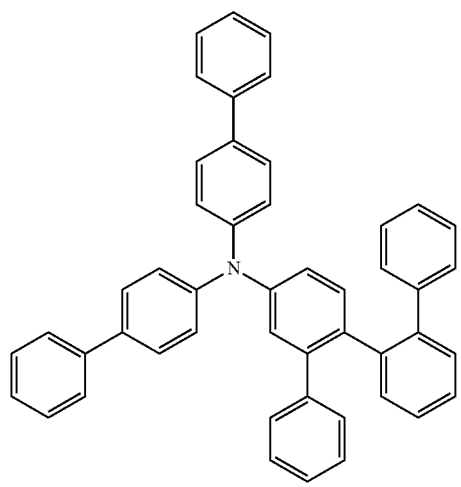
[Chemical Formula 166]
(5-8)
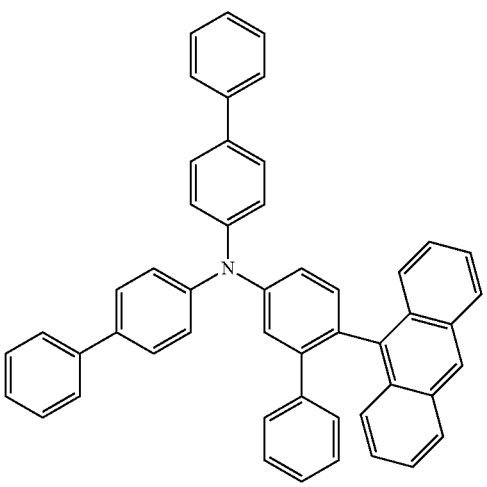
[Chemical Formula 167]
(5-9)
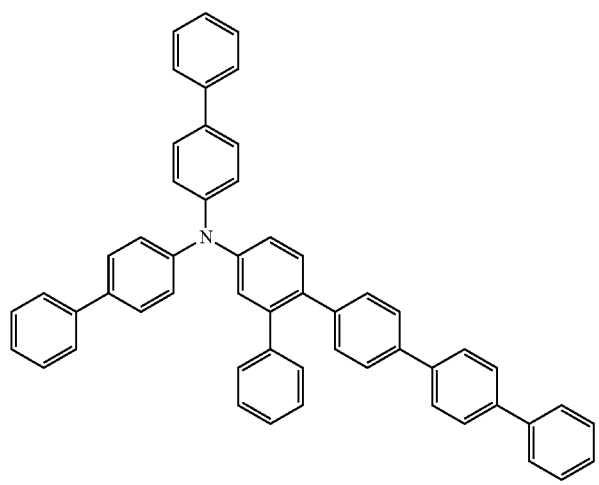
[Chemical Formula 168]
(5-10)
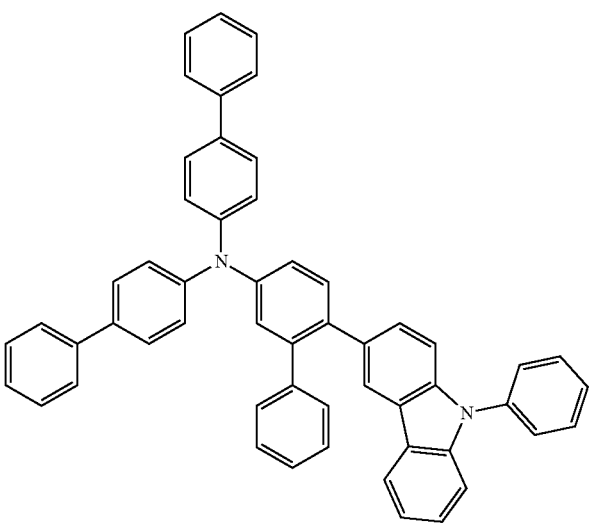
[Chemical Formula 169]
(5-11)
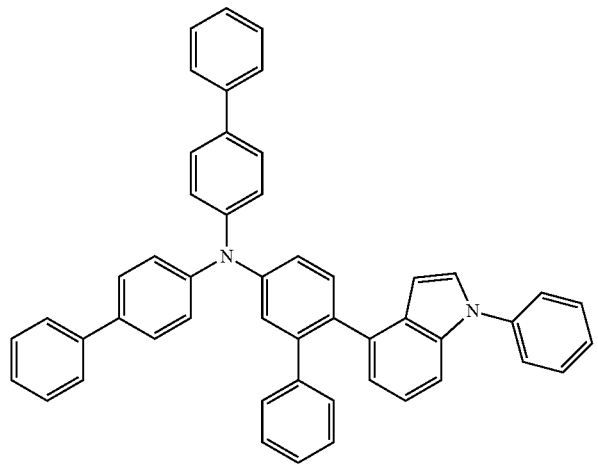
[Chemical Formula 170]
(5-12)
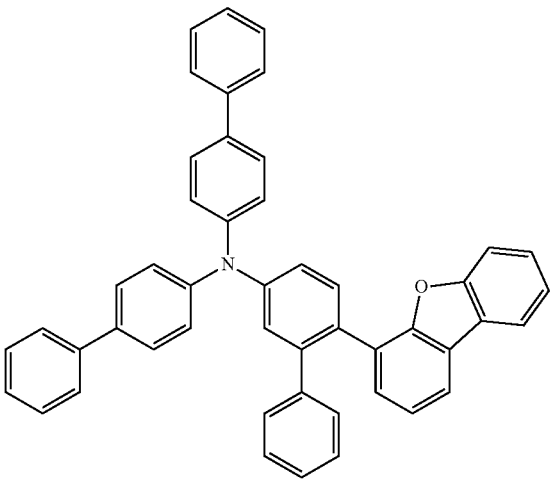

[Chemical Formula 171]
(5-13)
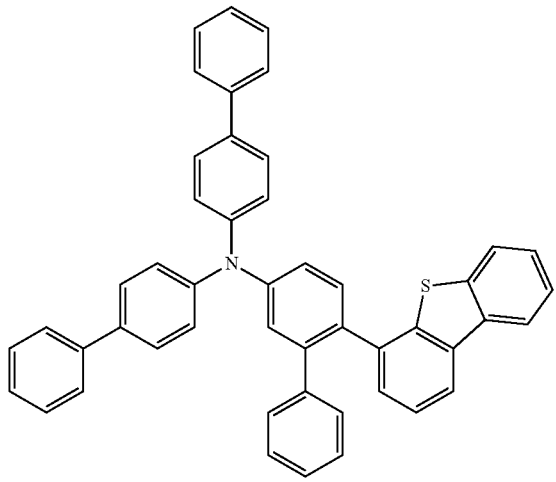
[Chemical Formula 172]
(5-14)
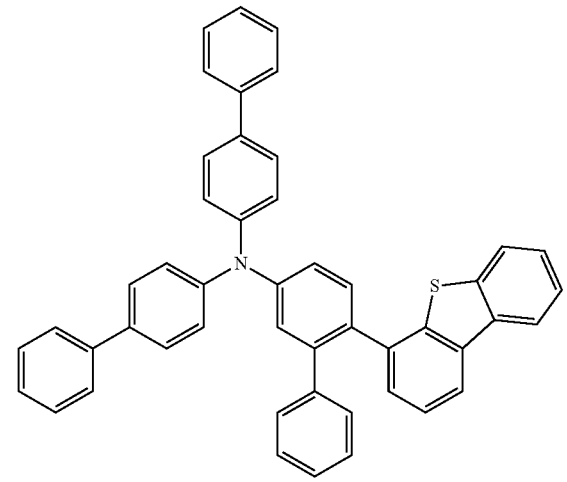
[Chemical Formula 173]
(5-15)
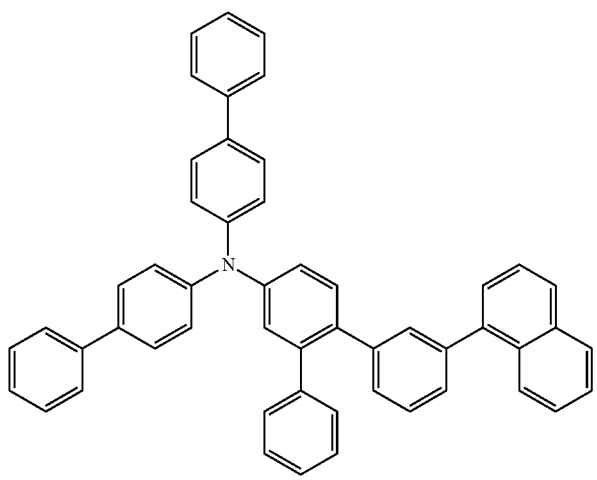
[Chemical Formula 174]
(5-16)
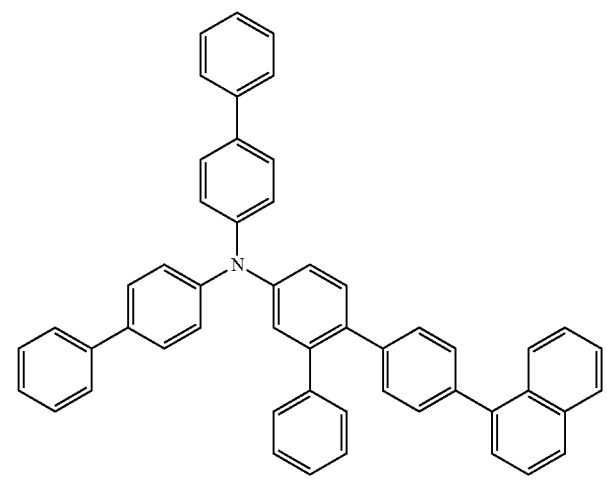
[Chemical Formula 175]
(5-17)
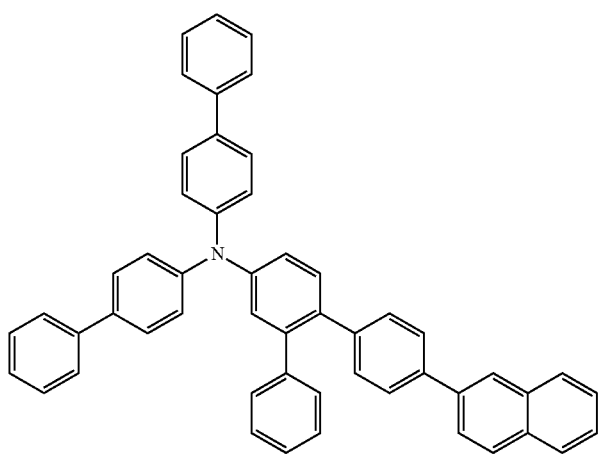
[Chemical Formula 176]
(5-18)
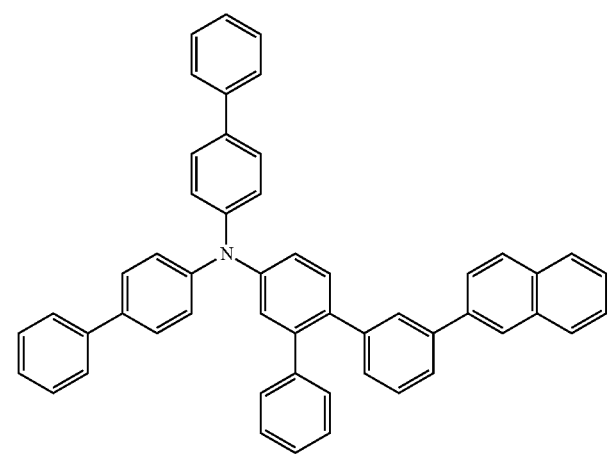

[Chemical Formula 177]
(5-19)
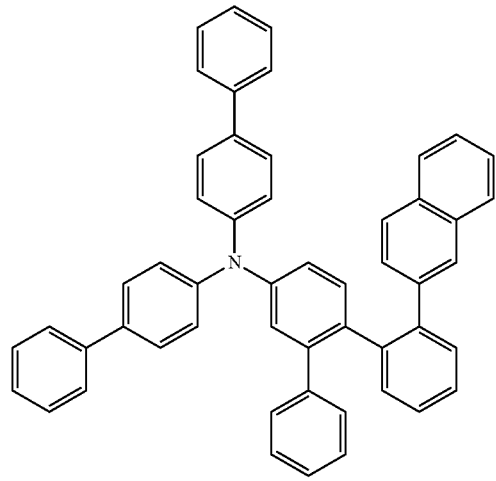
[Chemical Formula 178]
(5-20)
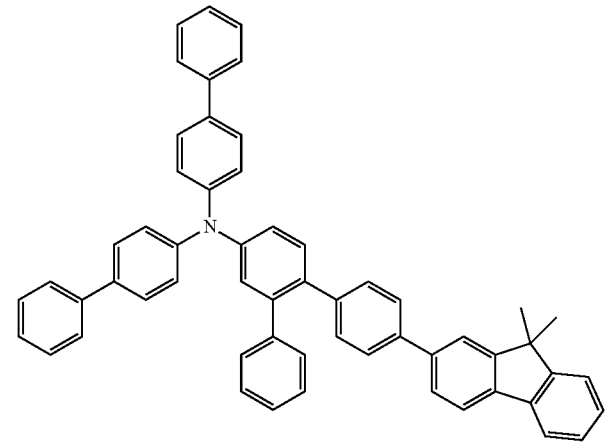
[Chemical Formula 179]
(5-21)
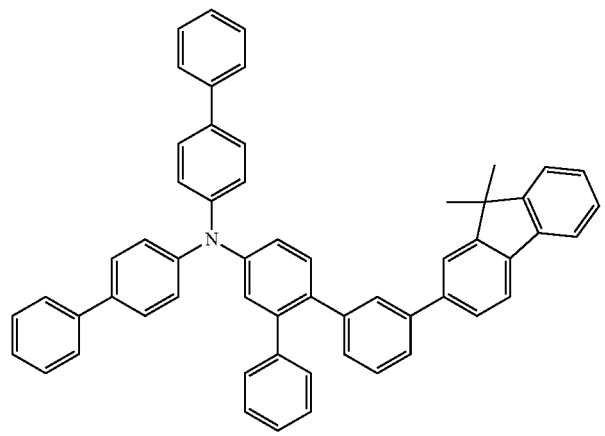
[Chemical Formula 180]
(5-22)
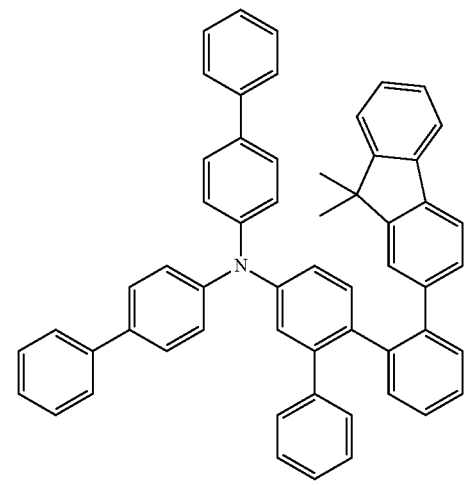
[Chemical Formula 181]
(5-23)
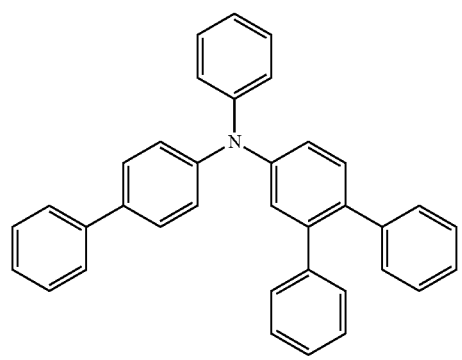
[Chemical Formula 182]
(5-24)
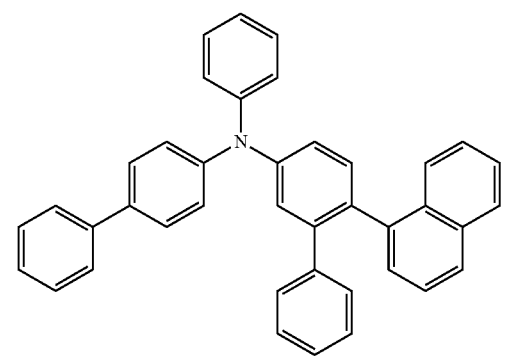

-continued
[Chemical Formula 183]
(5-25)
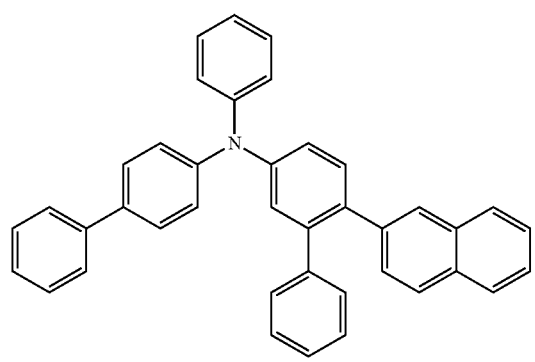
[Chemical Formula 184]
(5-26)
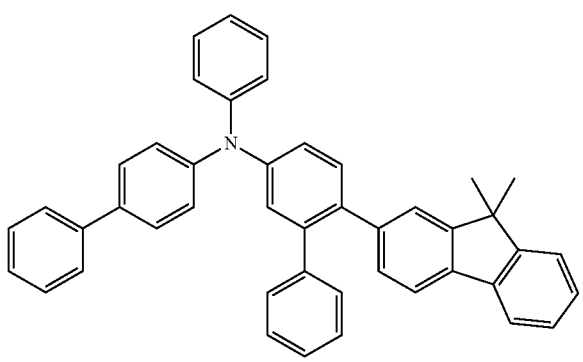
[Chemical Formula 185]
(5-27)
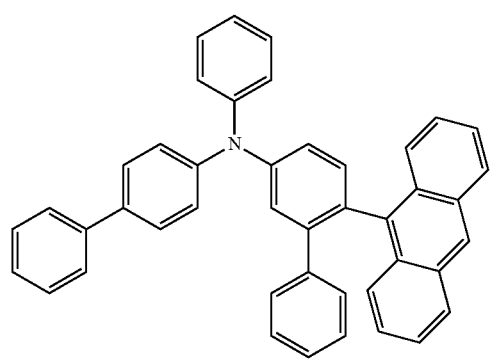
[Chemical Formula 186]
(5-28)
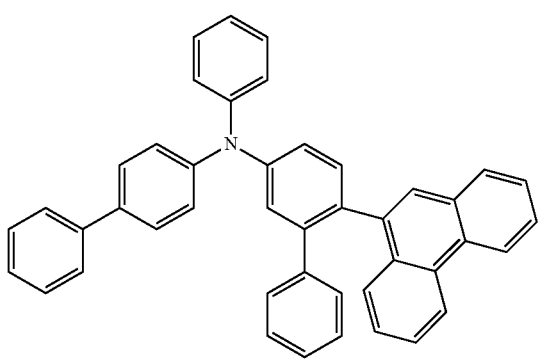
[Chemical Formula 187]
(5-29)
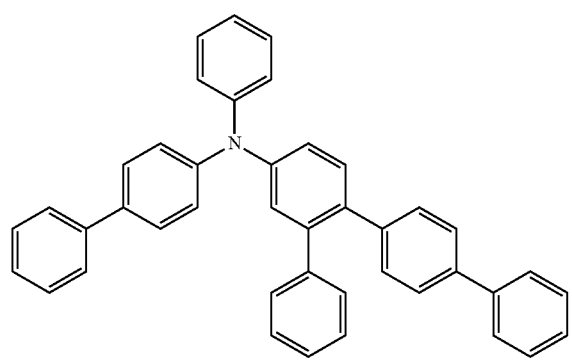
[Chemical Formula 188]
(5-30)
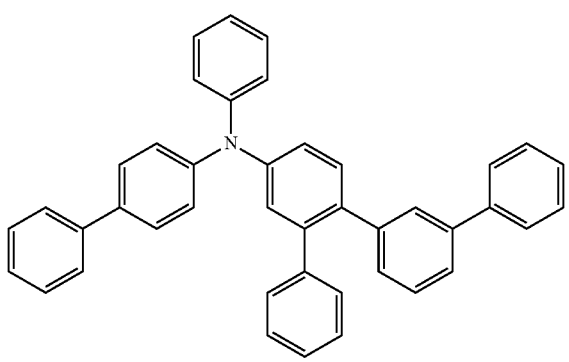
[Chemical Formula 189]
(5-31)
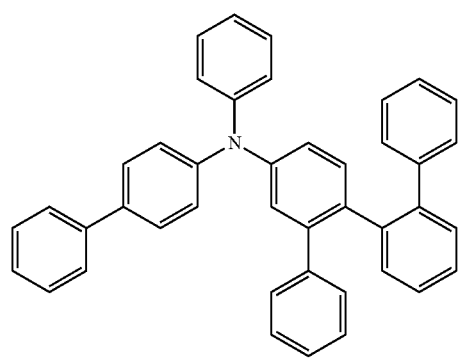
[Chemical Formula 190]
(5-32)
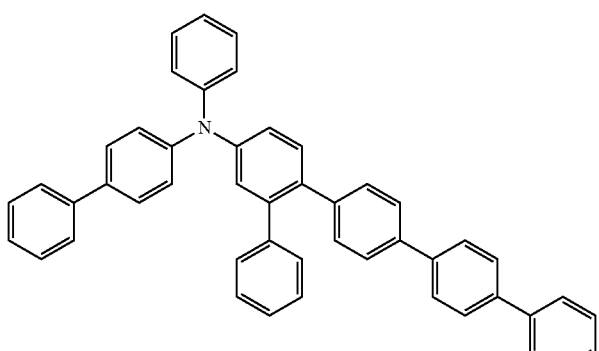

[Chemical Formula 191]
(5-33)
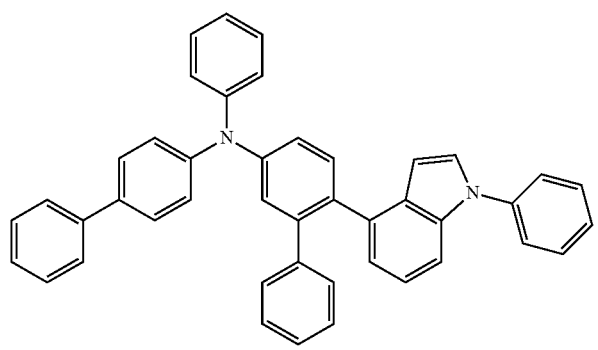
[Chemical Formula 192]
(5-34)
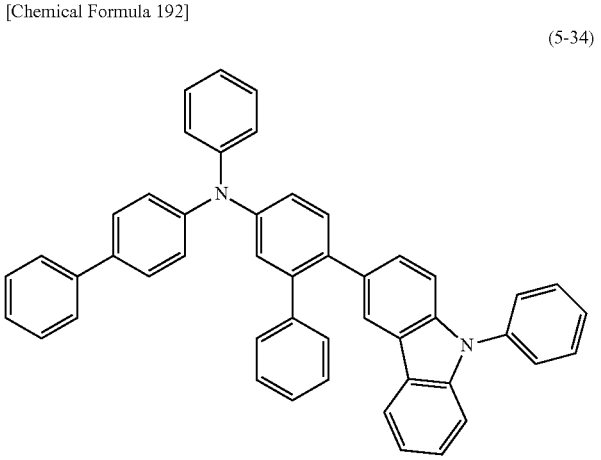
[Chemical Formula 193]
(5-35)
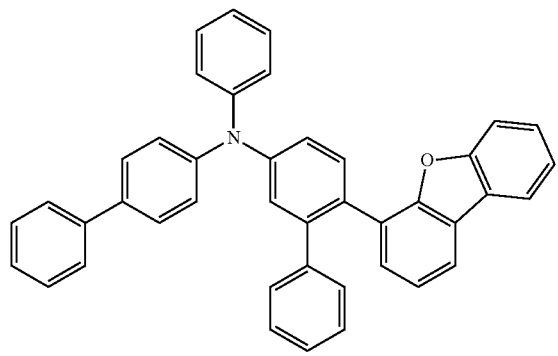
[Chemical Formula 194]
(5-36)
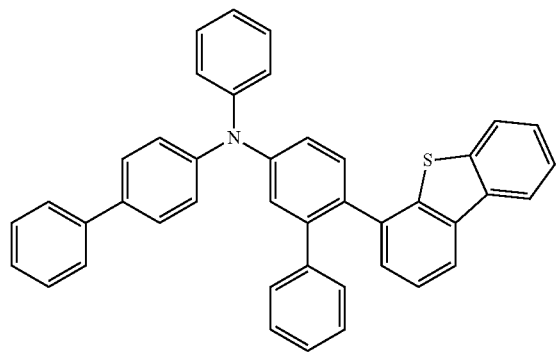
[Chemical Formula 195]
(5-37)
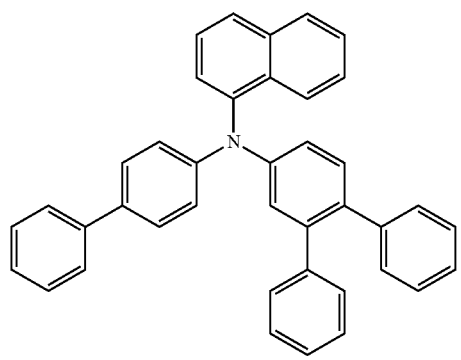
[Chemical Formula 196]
(5-38)
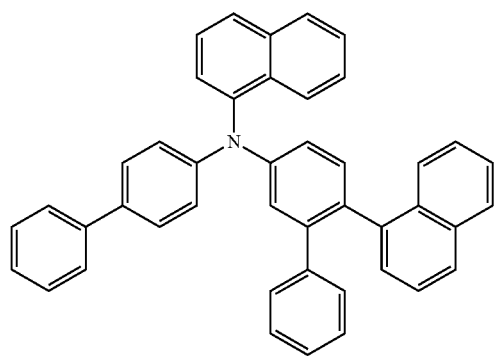
[Chemical Formula 197]
(5-39)
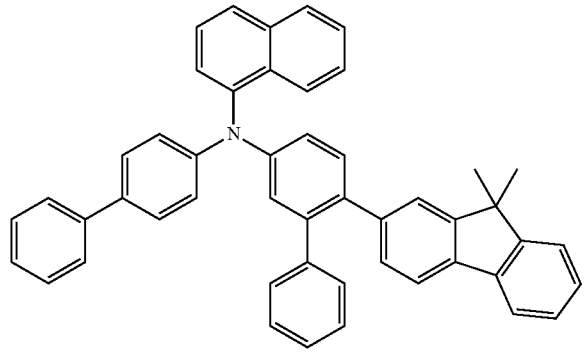
[Chemical Formula 198]
(5-40)
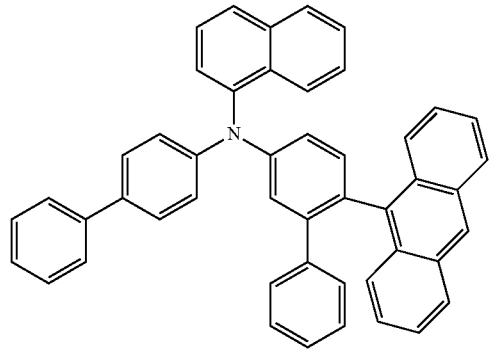

[Chemical Formula 199]
(5-41)
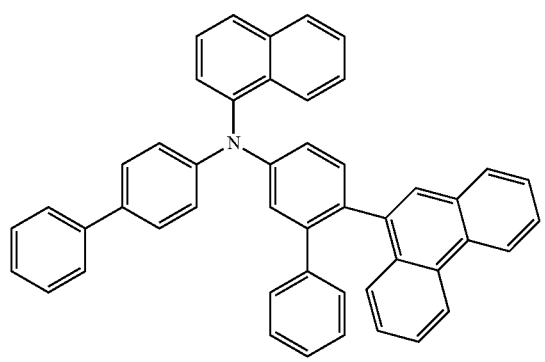
[Chemical Formula 200]
(5-42)
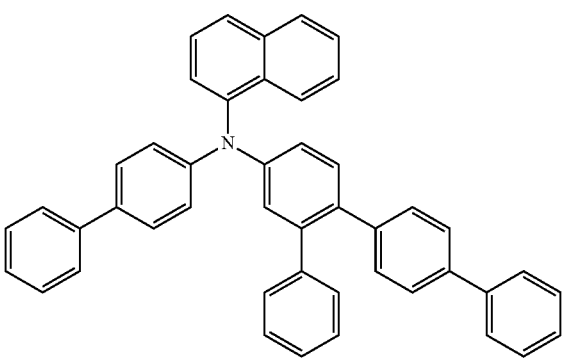
[Chemical Formula 201]
(5-43)
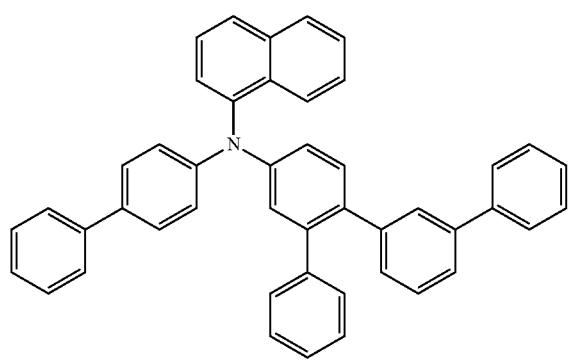
[Chemical Formula 202]
(5-44)
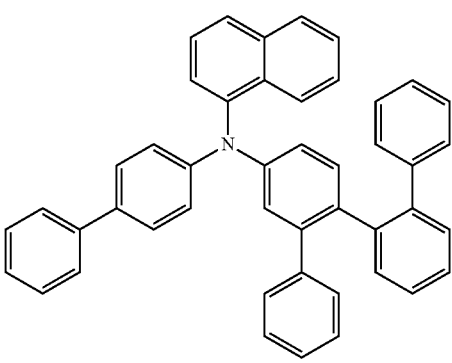
[Chemical Formula 203]
(5-45)
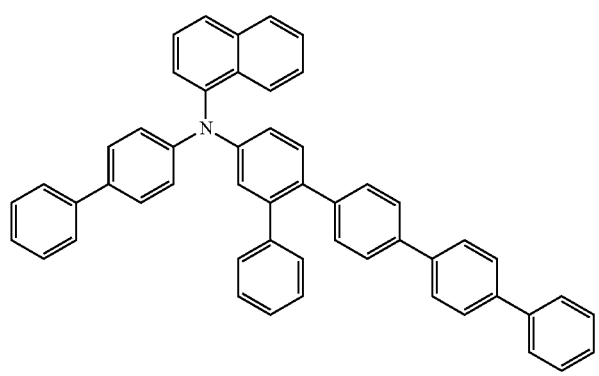
[Chemical Formula 204]
(5-46)
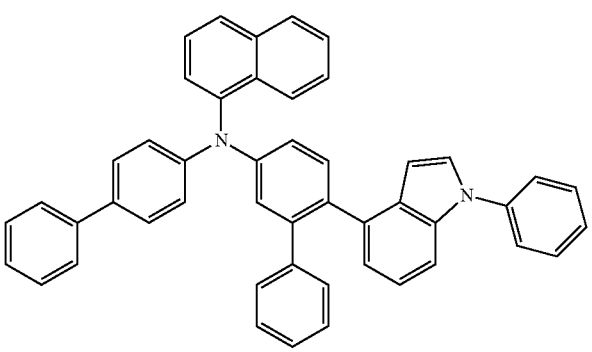
[Chemical Formula 205]
(5-47)
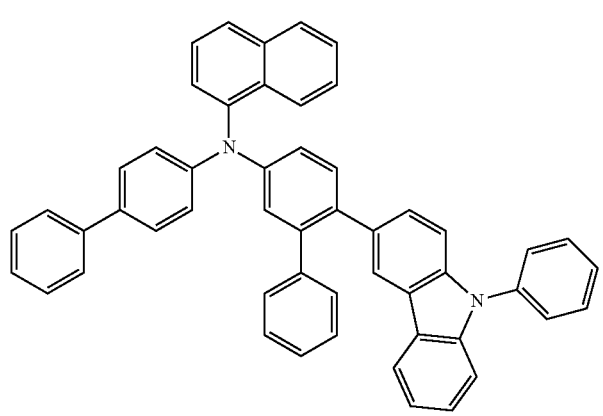
[Chemical Formula 206]
(5-48)
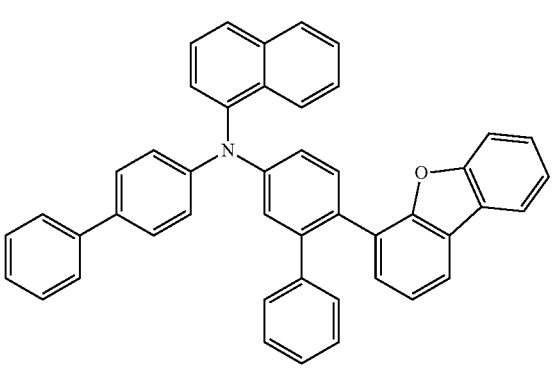

-continued
[Chemical Formula 207]
(5-49)
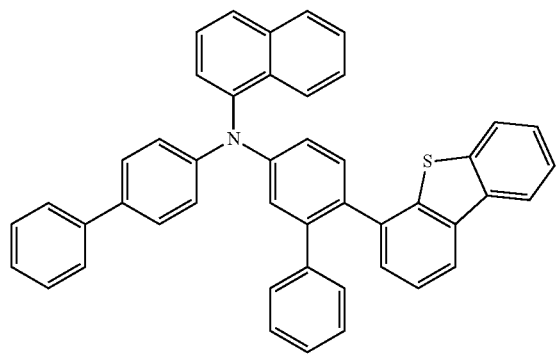
[Chemical Formula 208]
(5-50)
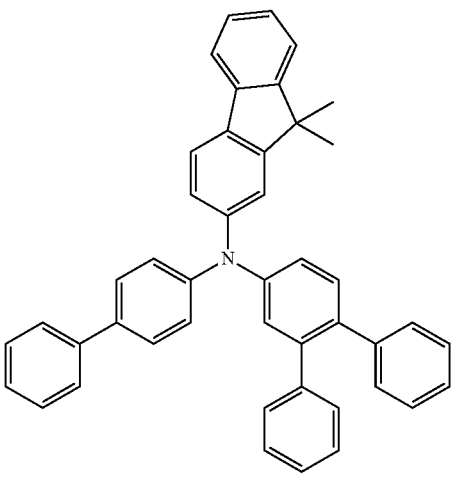
[Chemical Formula 209]
(5-51)
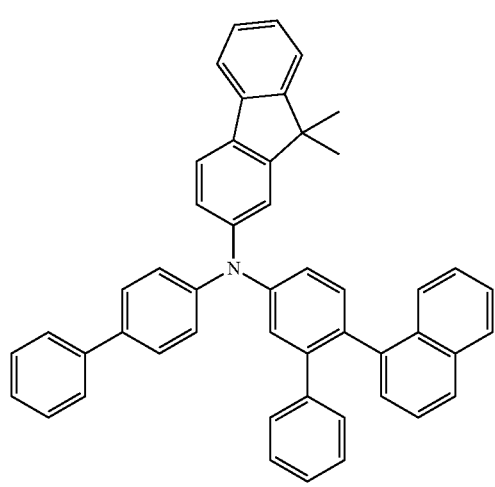
[Chemical Formula 210]
(5-52)
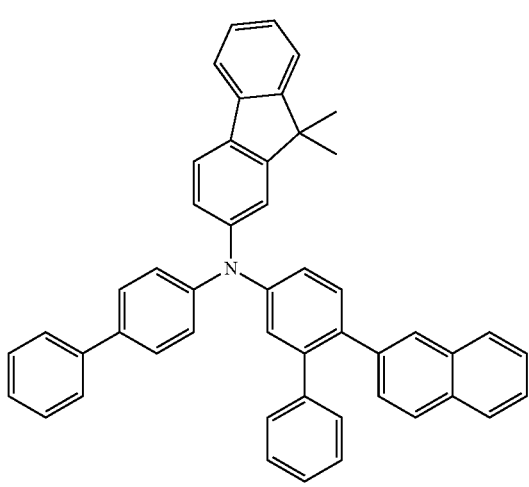
[Chemical Formula 211]
(5-53)
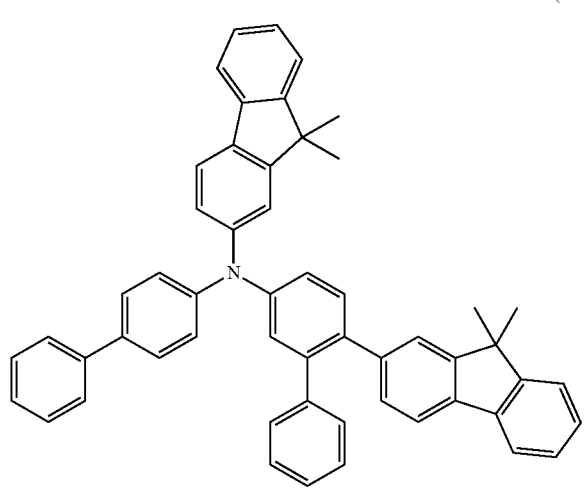
[Chemical Formula 212]
(5-54)
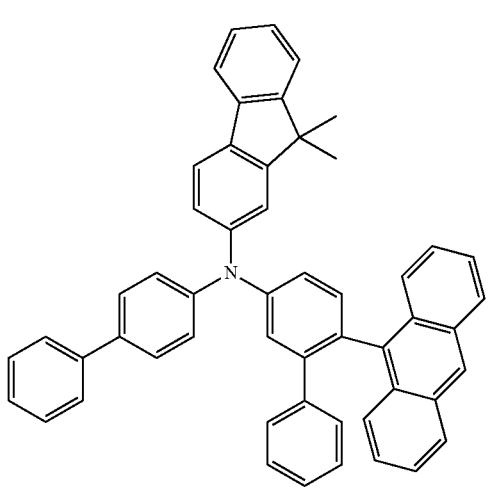

[Chemical Formula 213]
(5-55)
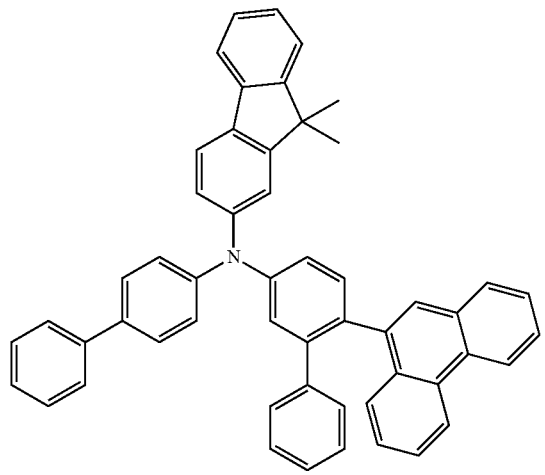
[Chemical Formula 214]
(5-56)
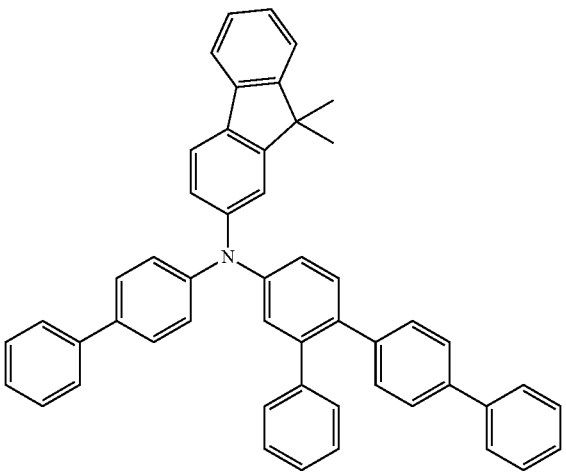
[Chemical Formula 215]
(5-57)
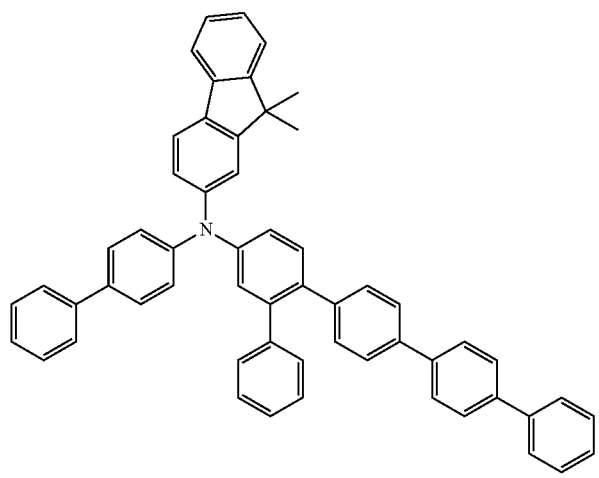
[Chemical Formula 216]
(5-58)
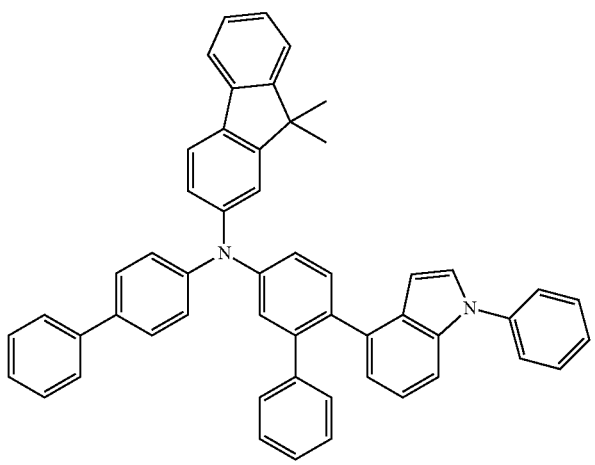
[Chemical Formula 217]
(5-59)
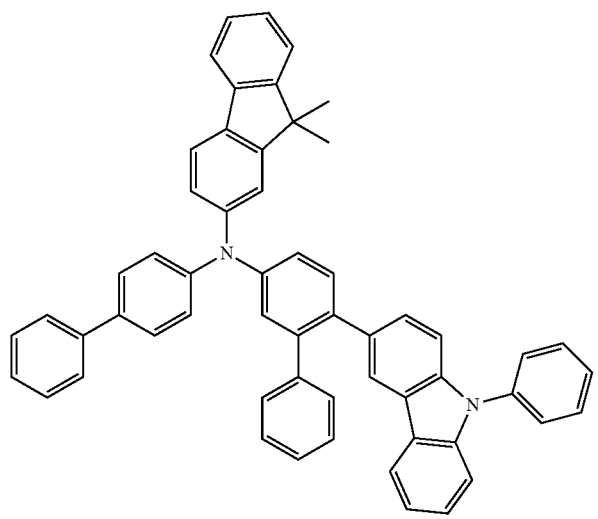
[Chemical Formula 218]
(5-60)
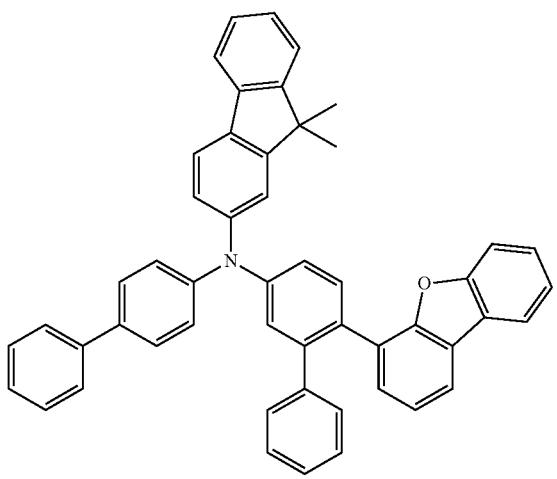

[Chemical Formula 219]
(5-61)
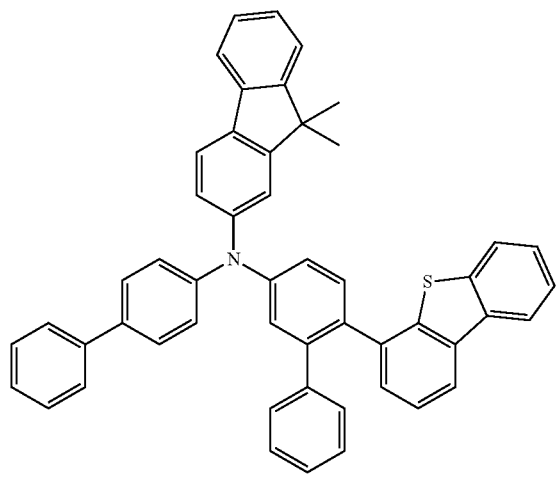
[Chemical Formula 220]
(5-62)
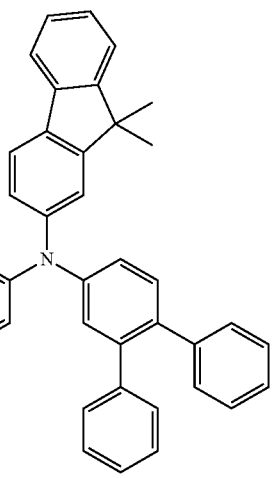
[Chemical Formula 221]
(5-63)
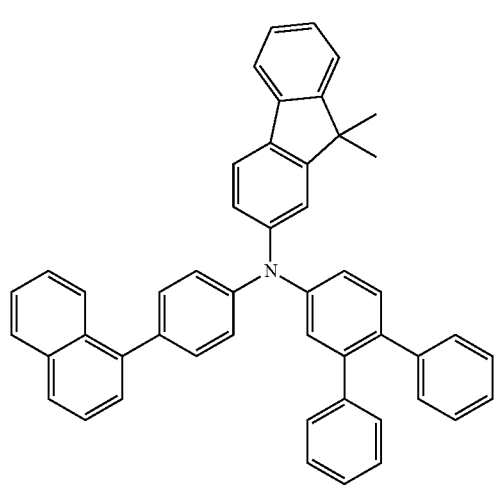
[Chemical Formula 222]
(5-64)
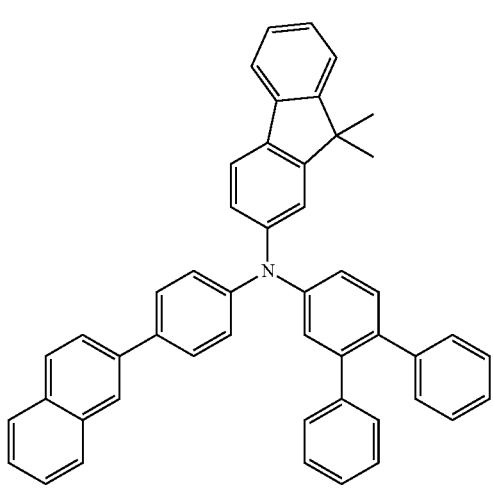
[Chemical Formula 223]
(5-65)
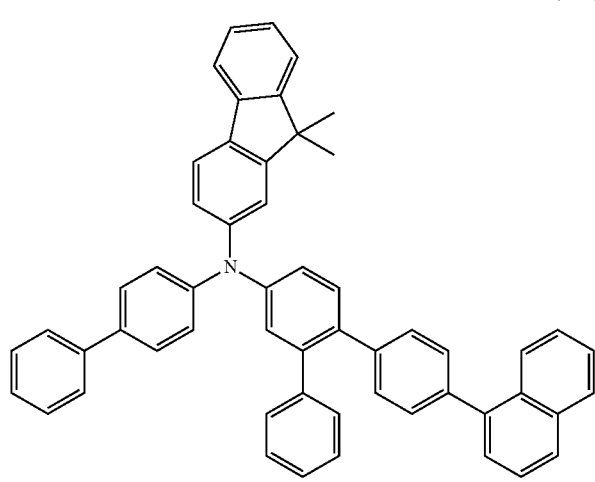
[Chemical Formula 224]
(5-66)
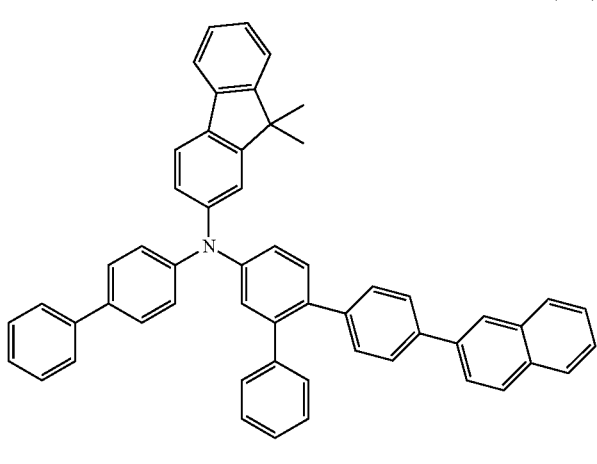

[Chemical Formula 225]
(5-67)
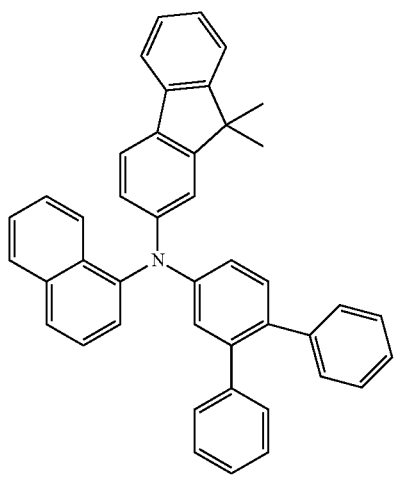
[Chemical Formula 226]
(5-68)
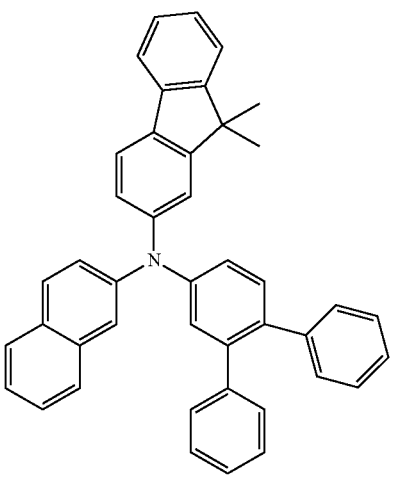
[Chemical Formula 227]
(5-69)
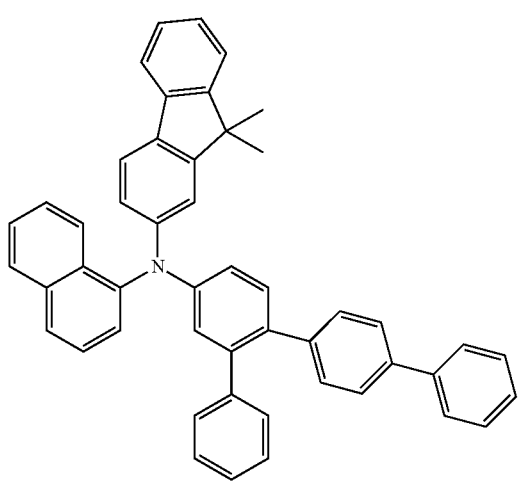
[Chemical Formula 228]
(5-70)
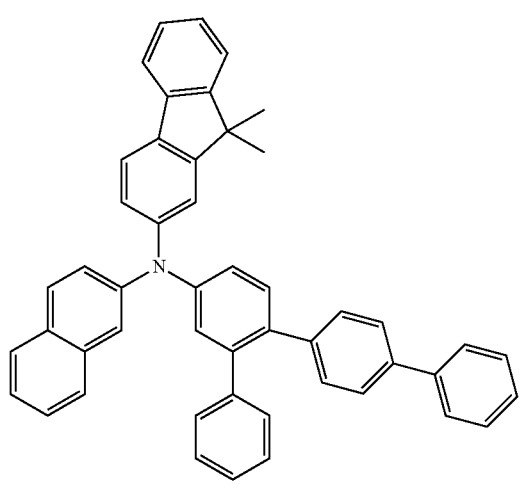
[Chemical Formula 229]
(5-71)
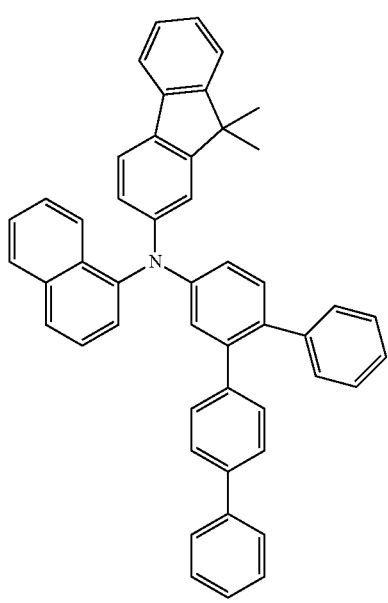
[Chemical Formula 230]
(5-72)
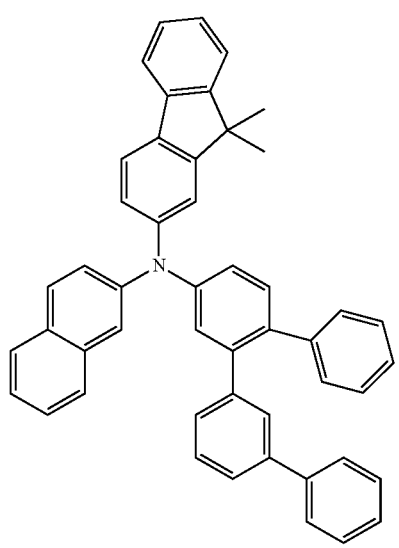

[Chemical Formula 231]
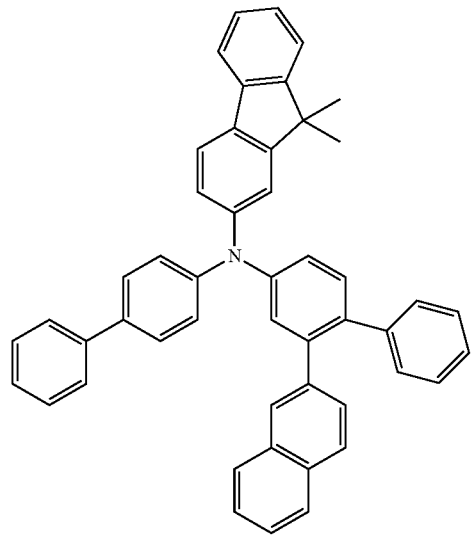
(5-73)
[Chemical Formula 232]
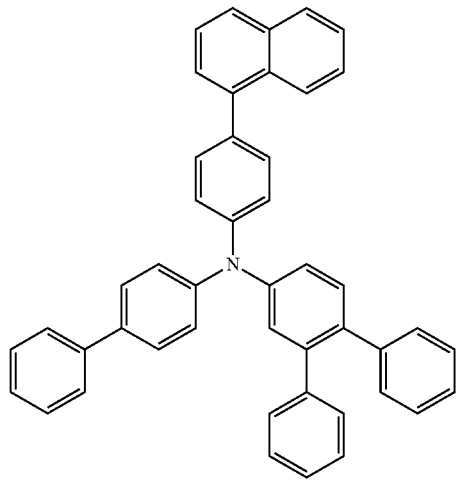
(5-74)
[Chemical Formula 233]
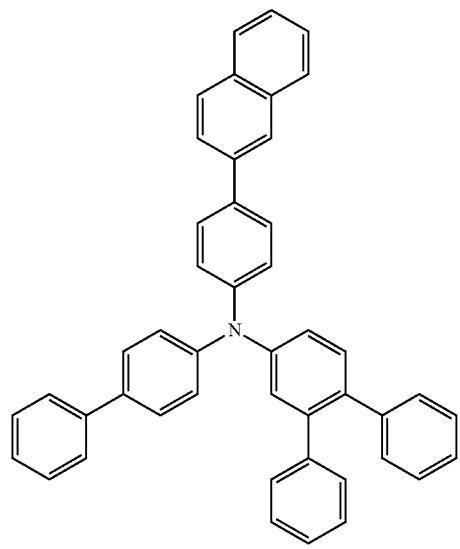
(5-75)
[Chemical Formula 234]
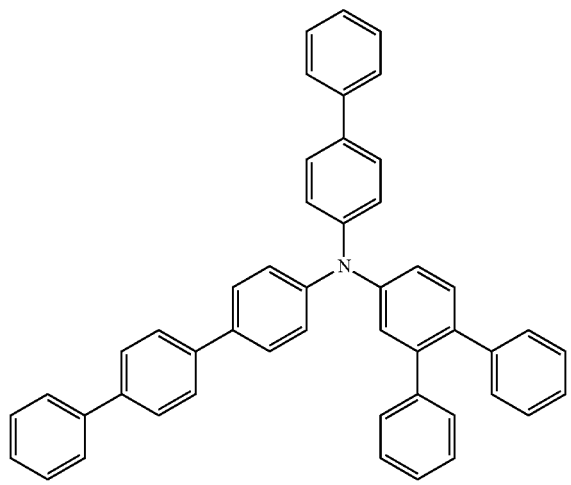
(5-76)

[Chemical Formula 235]
(5-77)
[Chemical Formula 236]
(5-78)
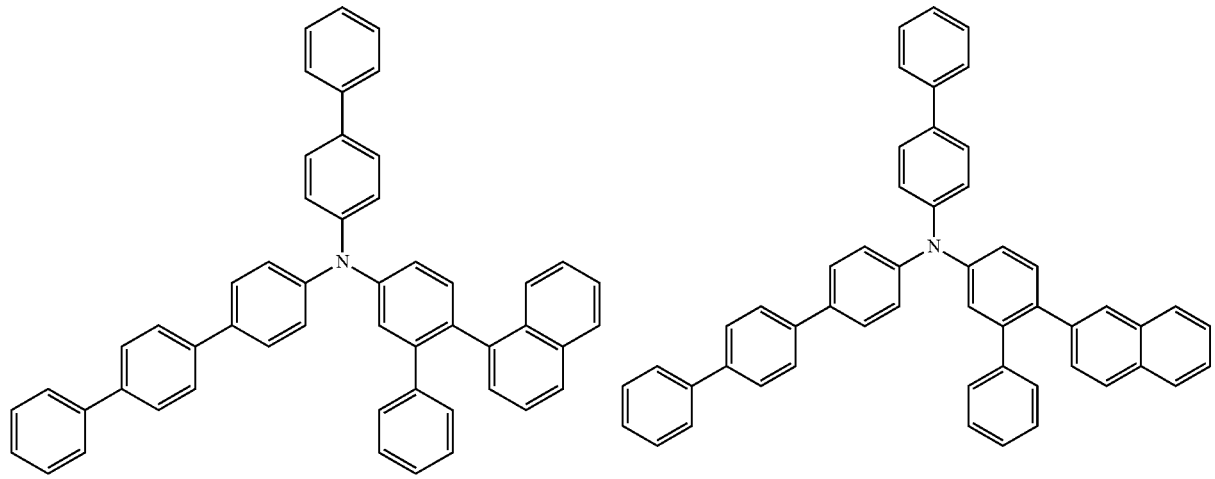
[Chemical Formula 237]
(5-79)
[Chemical Formula 238]
(5-80)
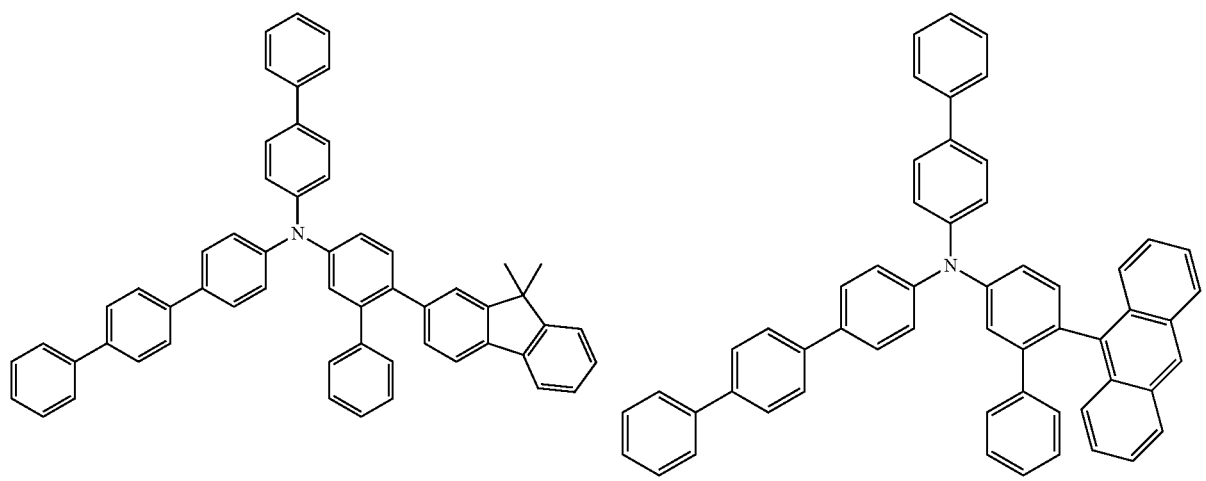
[Chemical Formula 239]
(5-81)
[Chemical Formula 240]
(5-82)
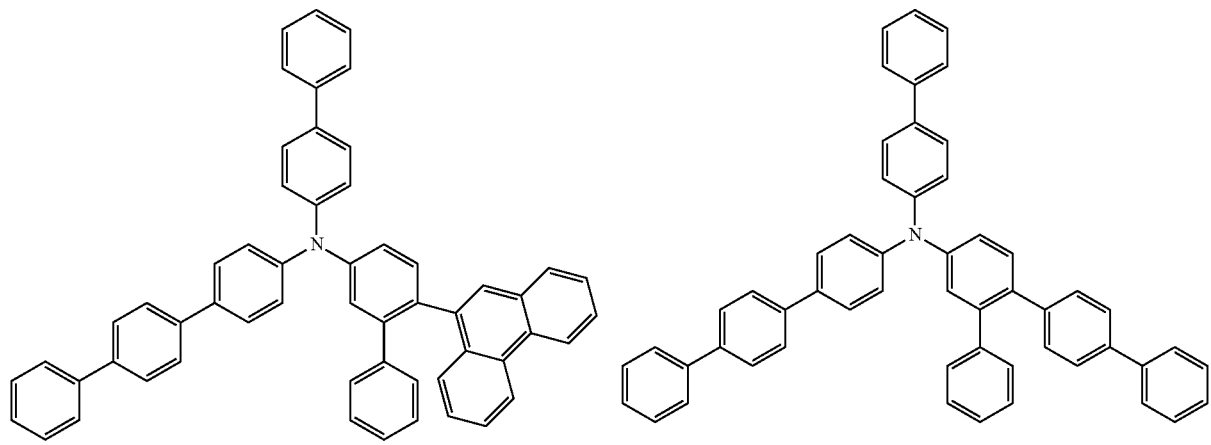

[Chemical Formula 241]
(5-83)
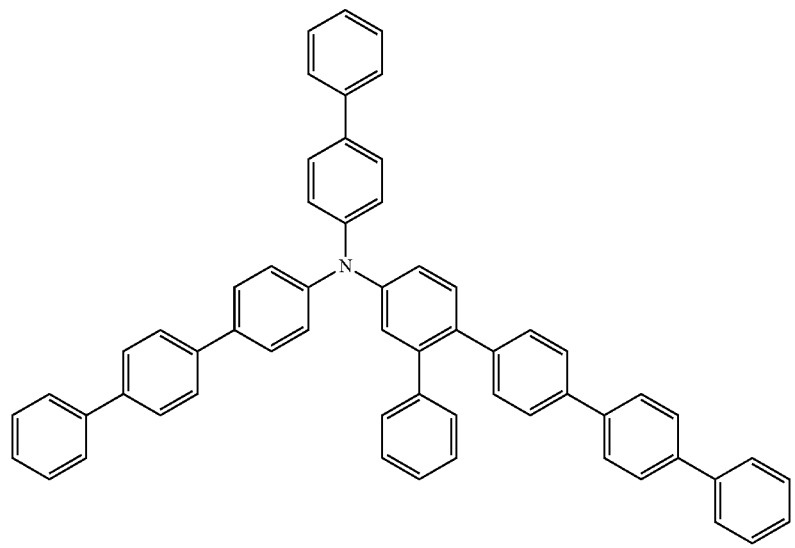
[Chemical Formula 242]
(5-84)
[Chemical Formula 243]
(5-85)
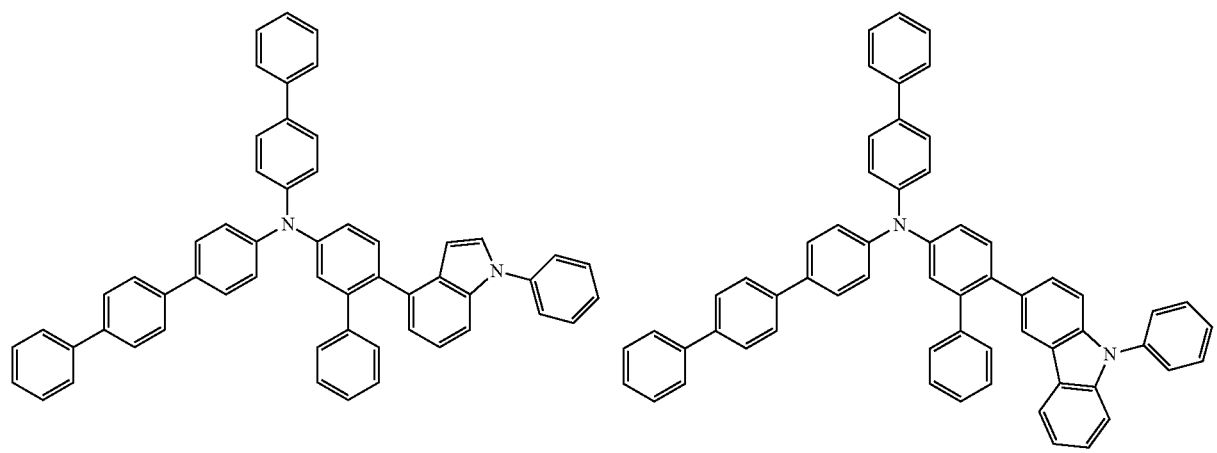
[Chemical Formula 244]
(5-86)
[Chemical Formula 245]
(5-87)
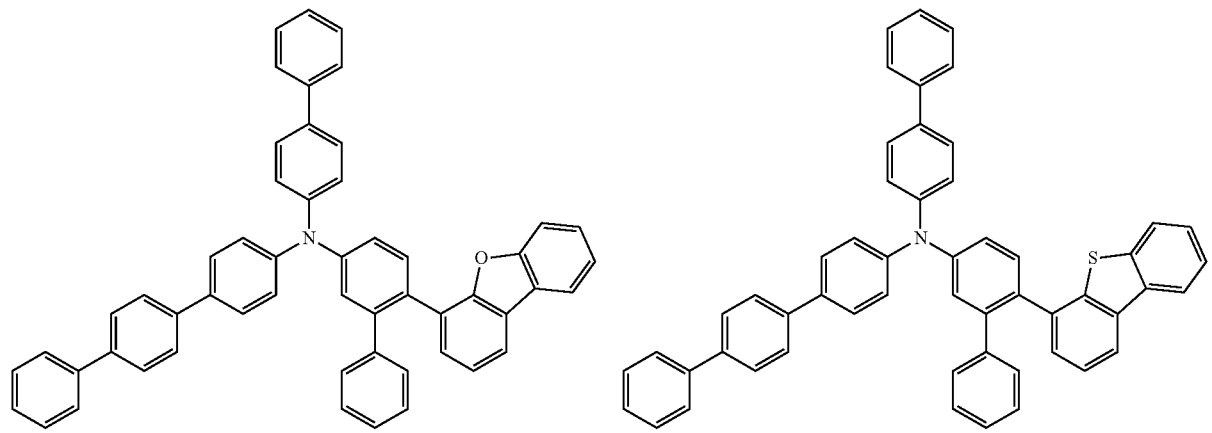

[Chemical Formula 246]
(5-88)
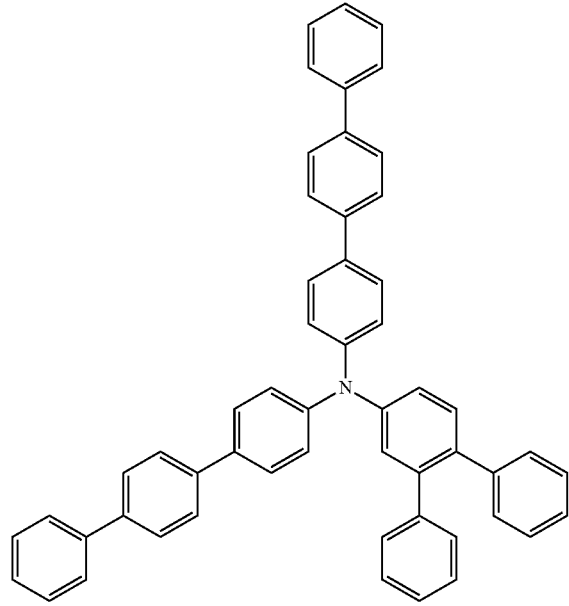
[Chemical Formula 247]
(5-89)
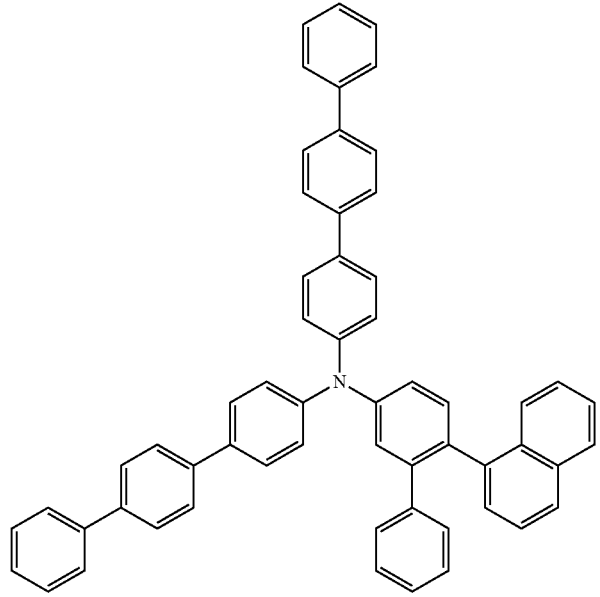
[Chemical Formula 248]
(5-90)
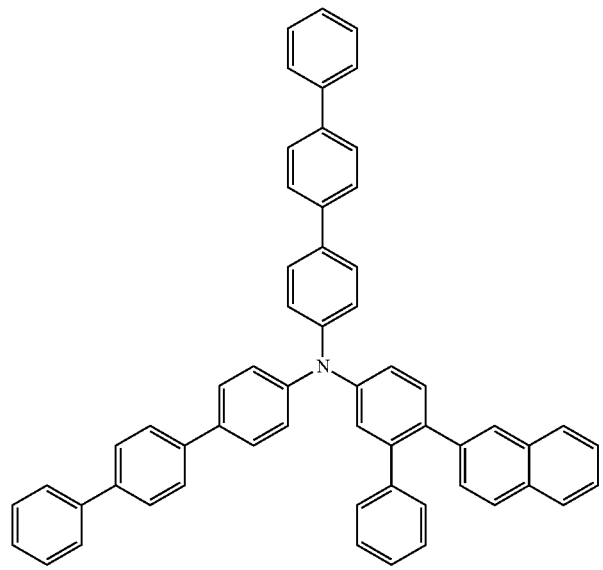
[Chemical Formula 249]
(5-91)
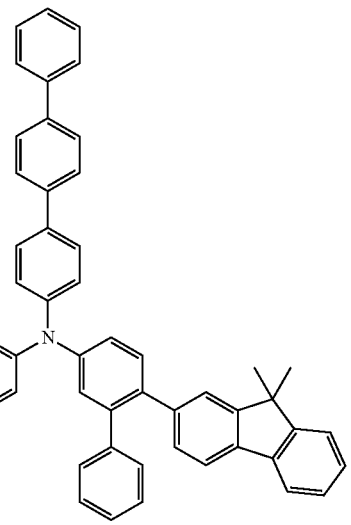

[Chemical Formula 250]
(5-92)
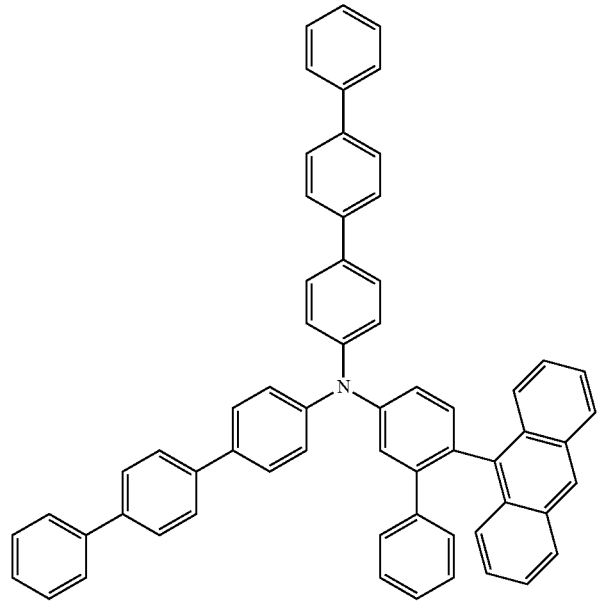
[Chemical Formula 251]
(5-93)
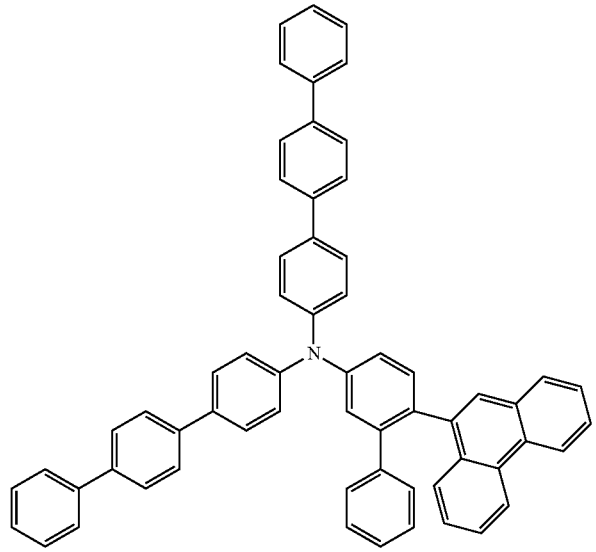
[Chemical Formula 252]
(5-94)
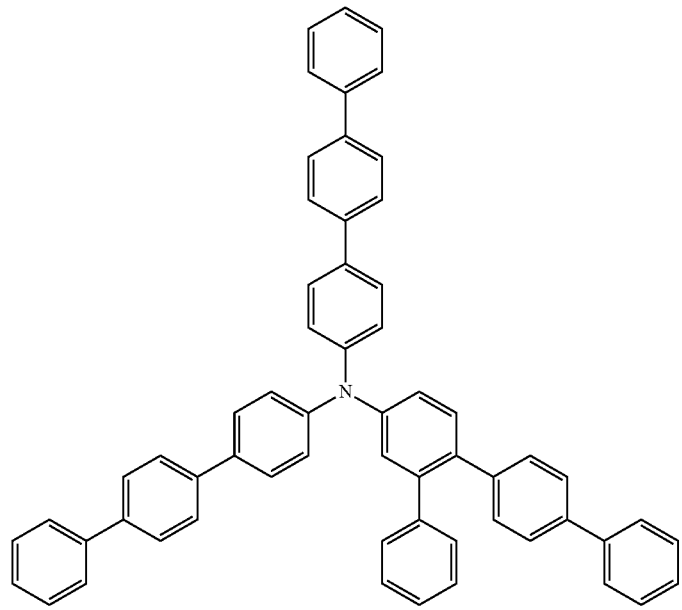

[Chemical Formula 253]
(5-95)
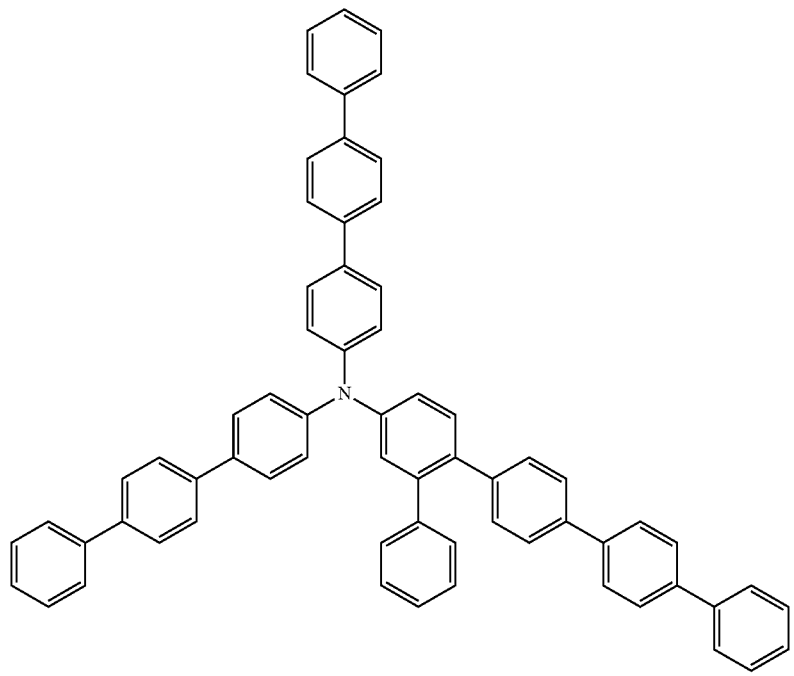
[Chemical Formula 254]
(5-96)
[Chemical Formula 255]
(5-97)
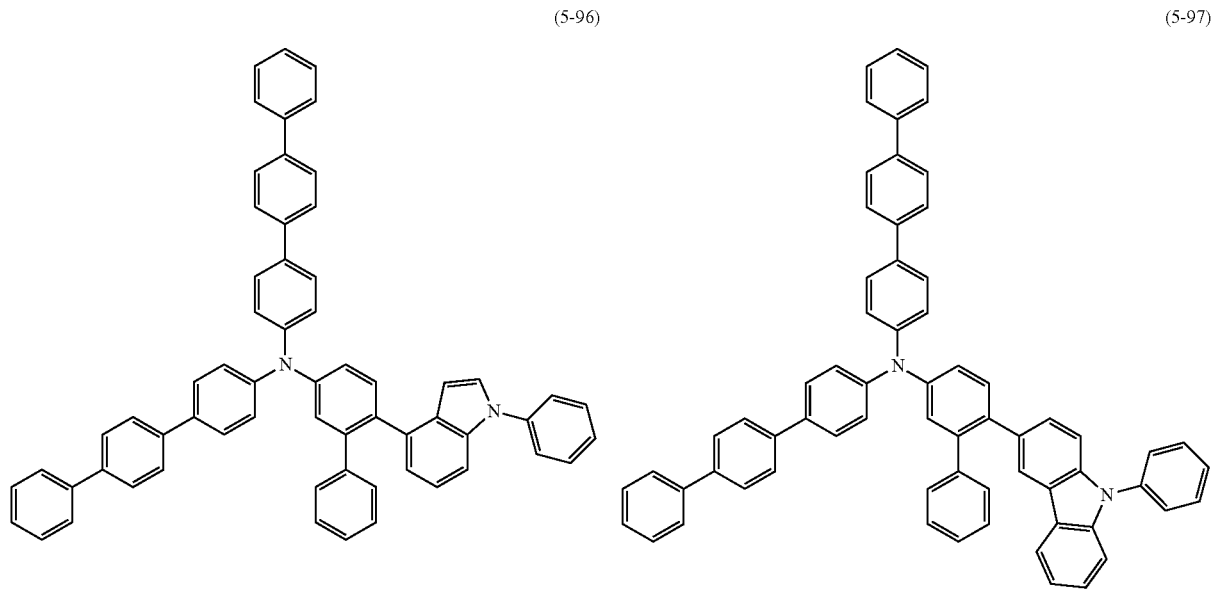

[Chemical Formula 256]
(5-98)
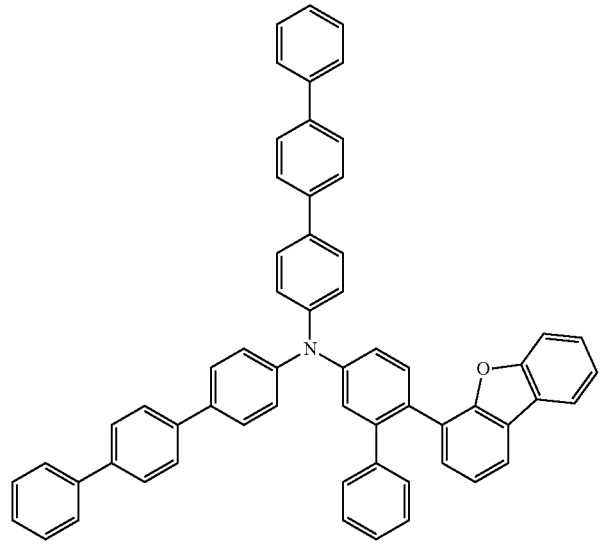
[Chemical Formula 257]
(5-99)
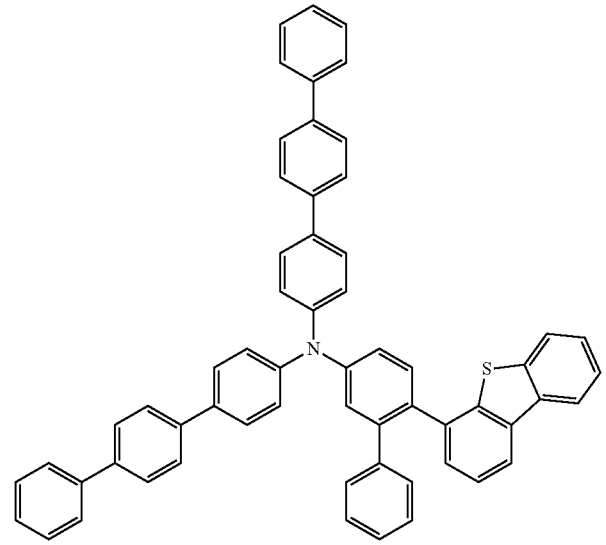
[Chemical Formula 258]
(5-100)
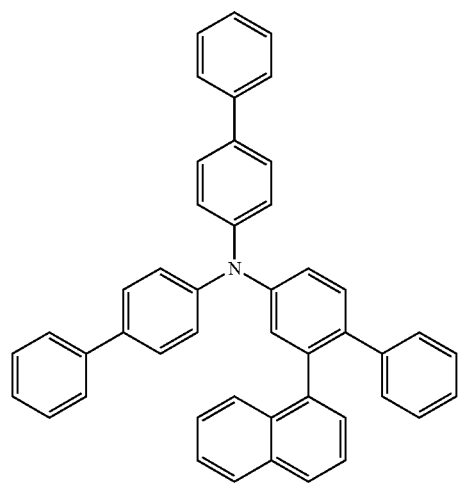
[Chemical Formula 259]
(5-101)
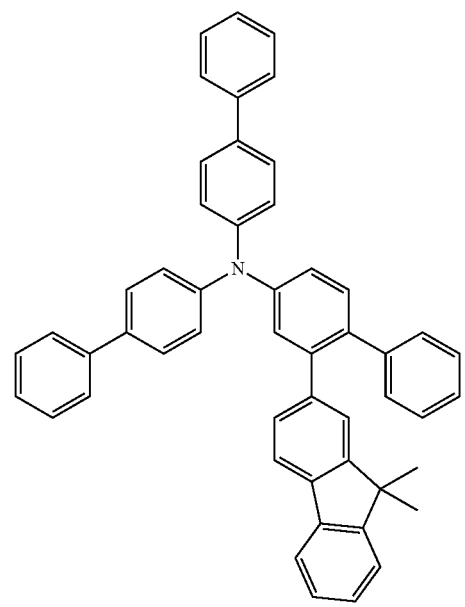

[Chemical Formula 260]
(5-102)
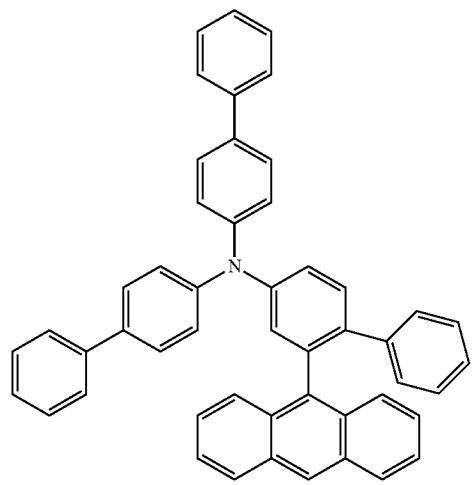
[Chemical Formula 261]
(5-103)
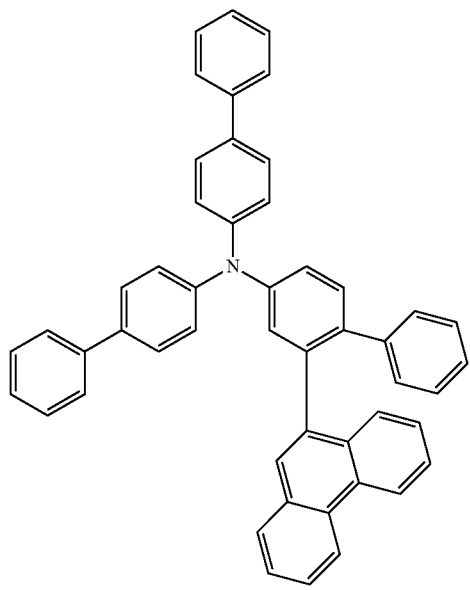
[Chemical Formula 262]
(5-104)
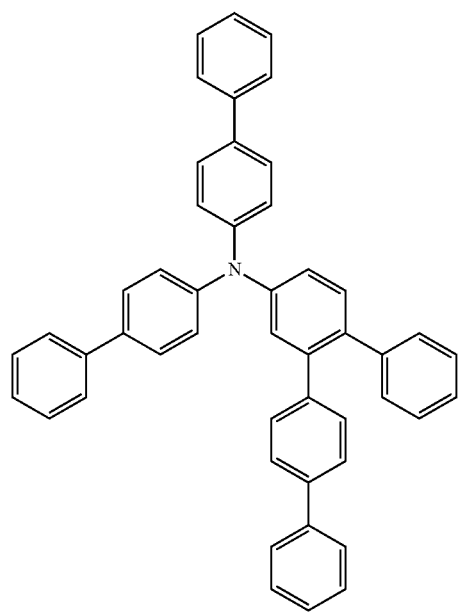
[Chemical Formula 263]
(5-105)
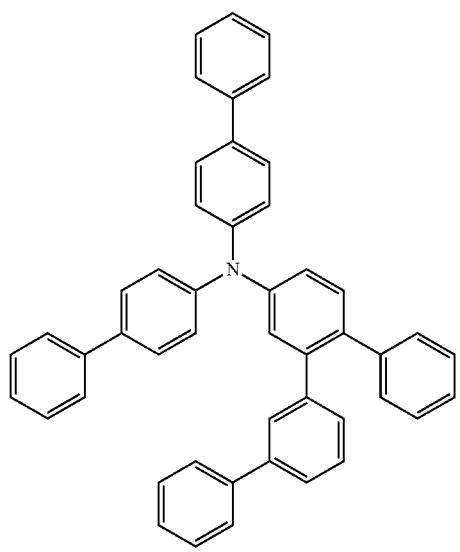

[Chemical Formula 264]
(5-106)
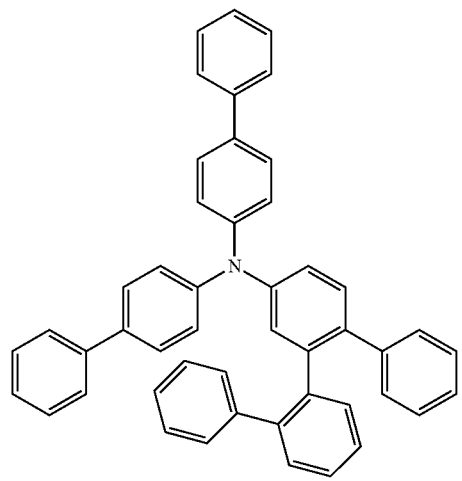
[Chemical Formula 265]
(5-107)
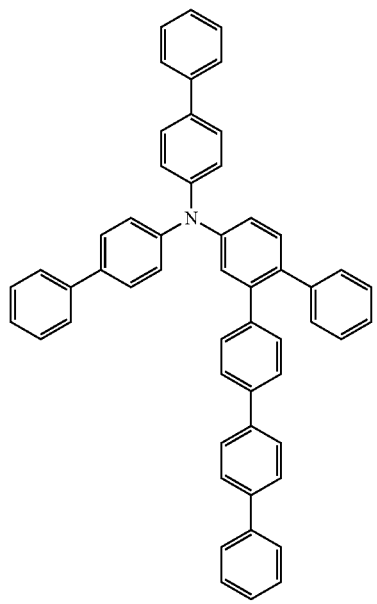
[Chemical Formula 266]
(5-108)
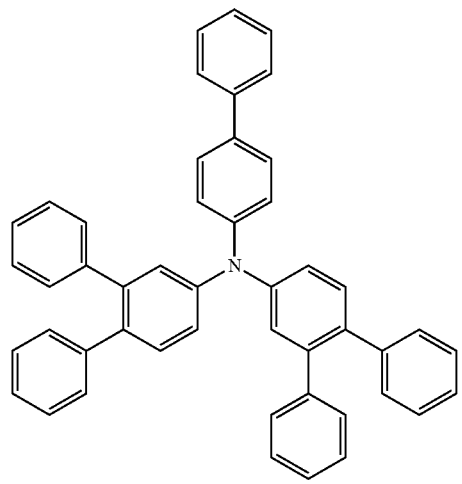
[Chemical Formula 267]
(5-109)
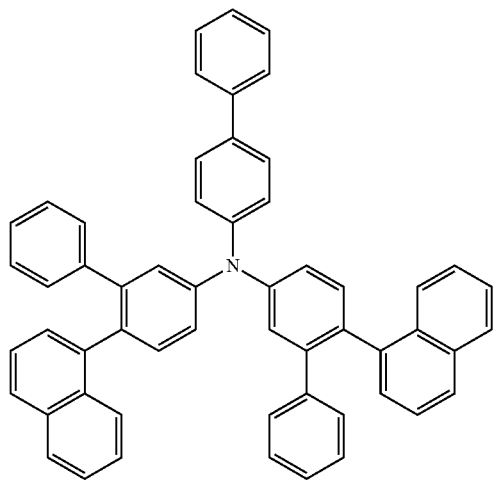

[Chemical Formula 268]
(5-110)
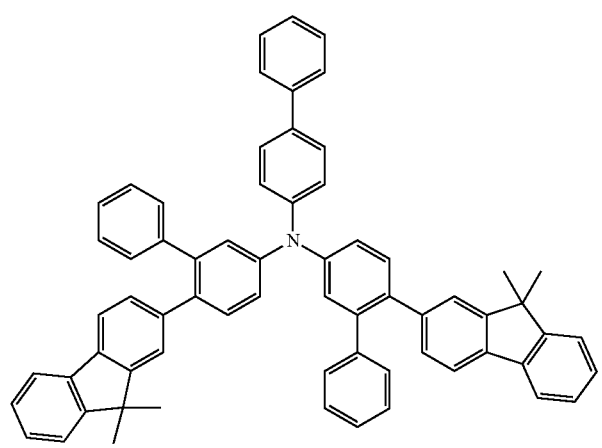
[Chemical Formula 269]
(5-111)
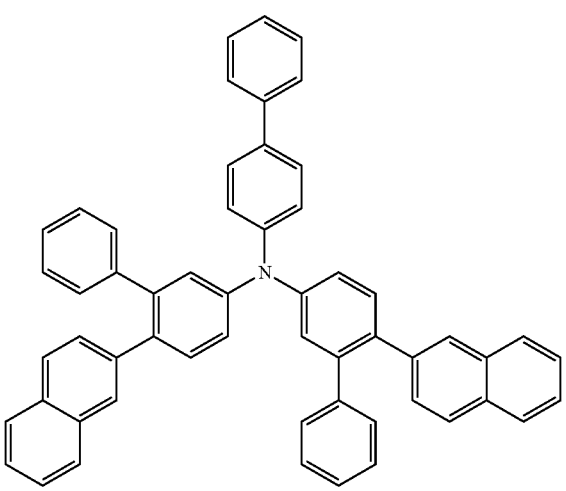
[Chemical Formula 270]
(5-112)
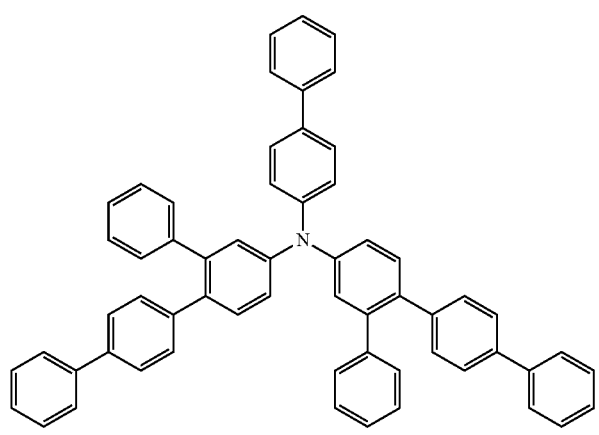
[Chemical Formula 271]
(5-113)
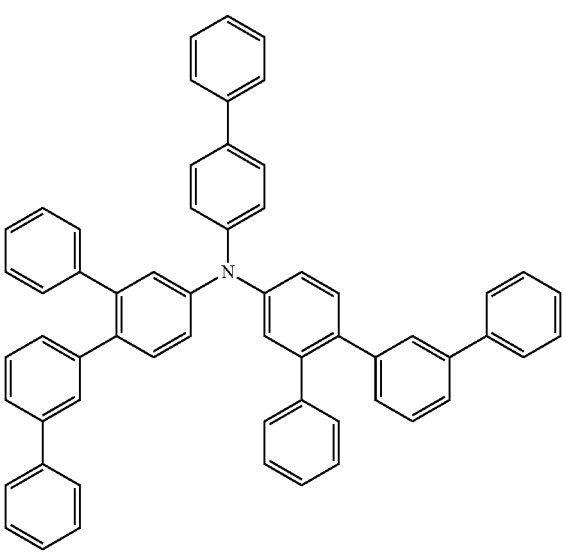
[Chemical Formula 272]
(5-114)
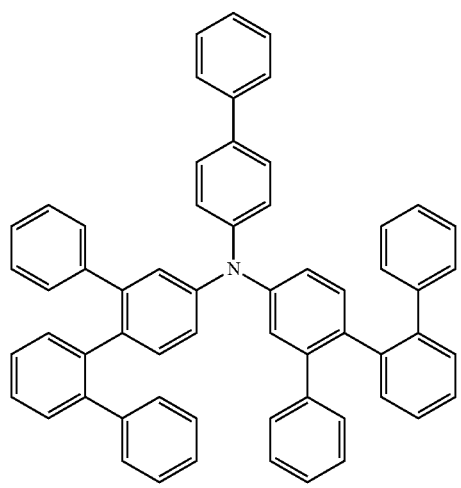
[Chemical Formula 273]
(5-115)
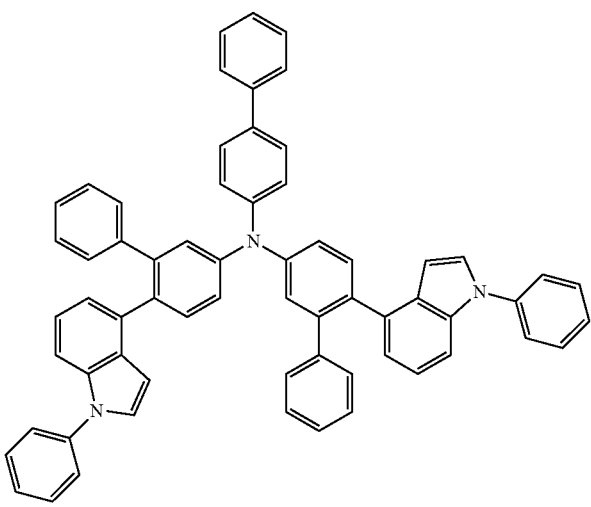

[Chemical Formula 274]
(5-116)
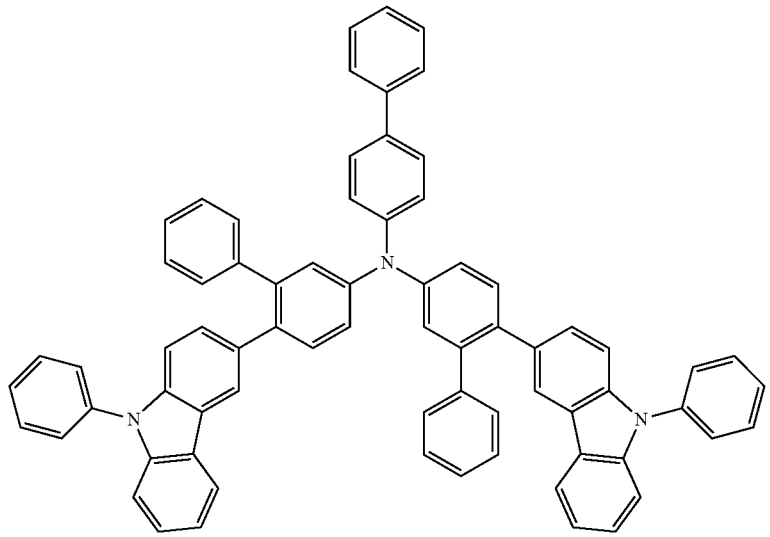
[Chemical Formula 275]
(5-117)
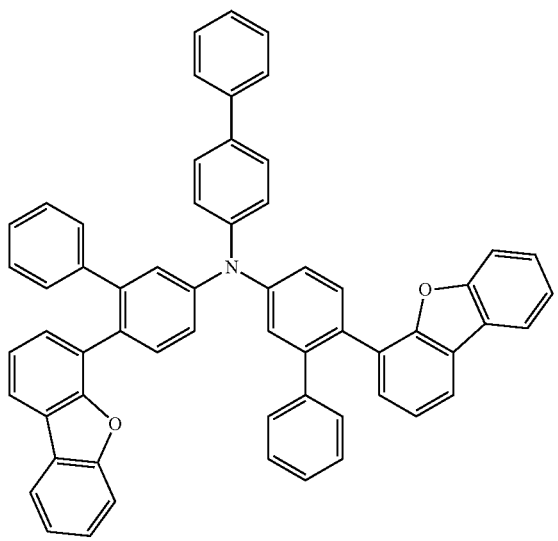
[Chemical Formula 276]
(5-118)
[Chemical Formula 277]
(5-119)
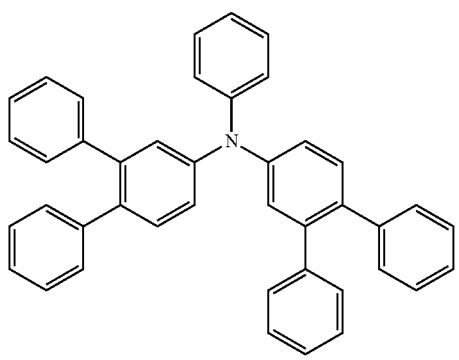
[Chemical Formula 278]
(5-120)
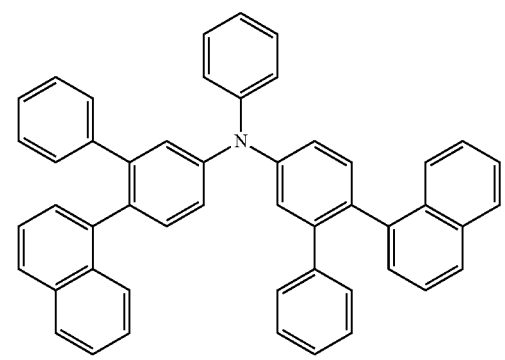

[Chemical Formula 279] (5-121)　　　[Chemical Formula 280] (5-122)
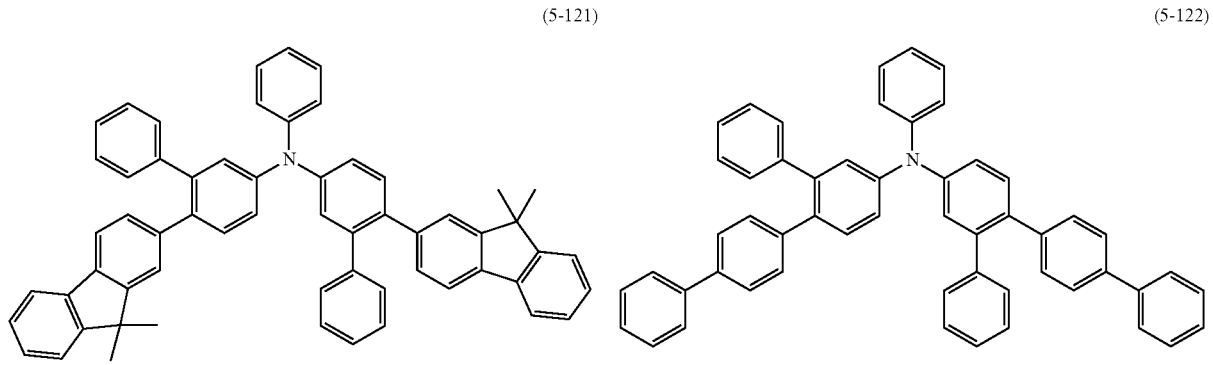
[Chemical Formula 281] (5-123)　　　[Chemical Formula 282] (5-124)
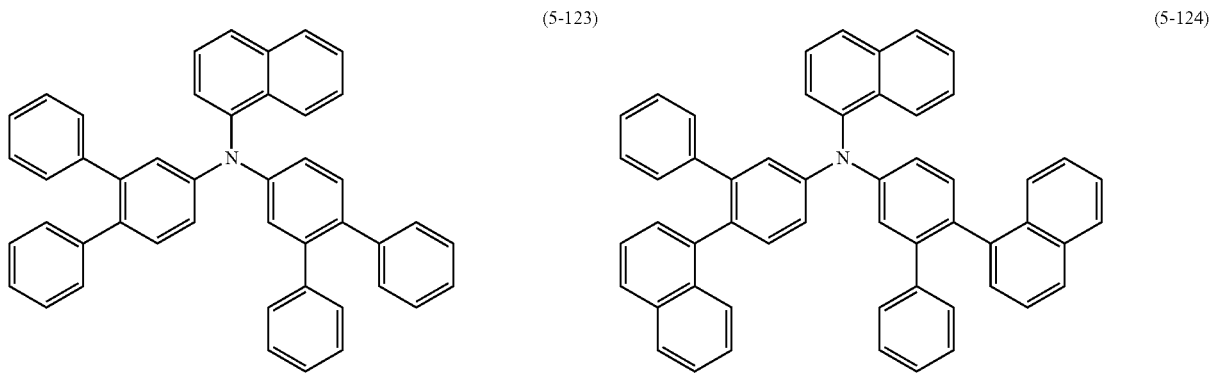
[Chemical Formula 283] (5-125)　　　[Chemical Formula 284] (5-126)
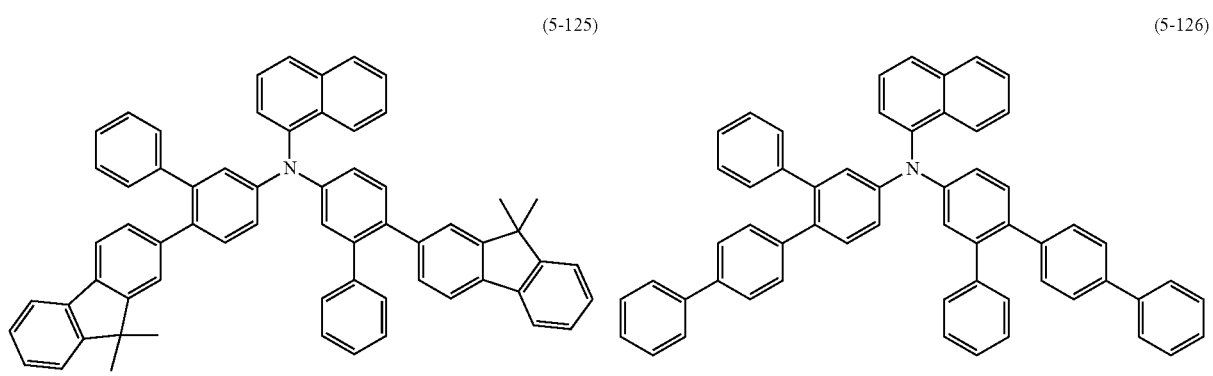

[Chemical Formula 285]
(5-127)
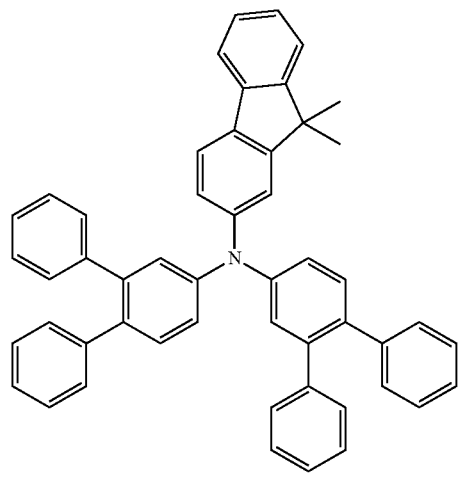
[Chemical Formula 286]
(5-128)
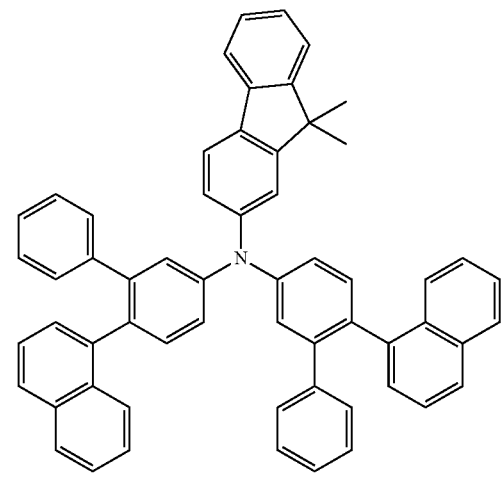
[Chemical Formula 287]
(5-129)
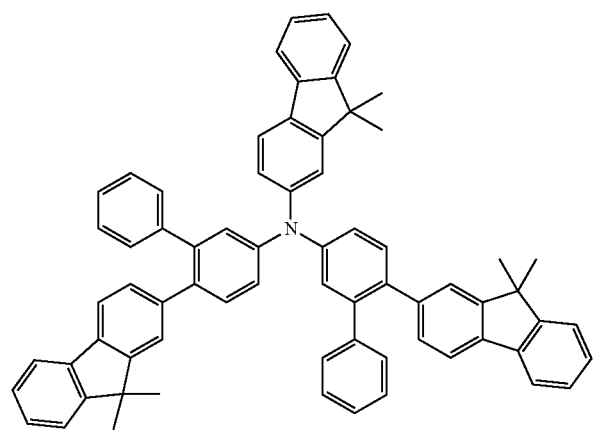
[Chemical Formula 288]
(5-130)
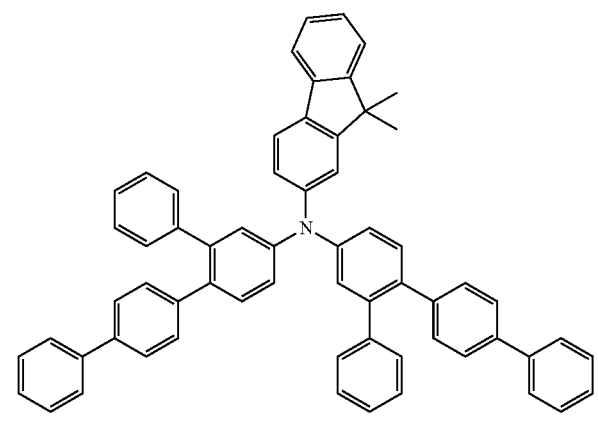
[Chemical Formula 289]
(5-131)
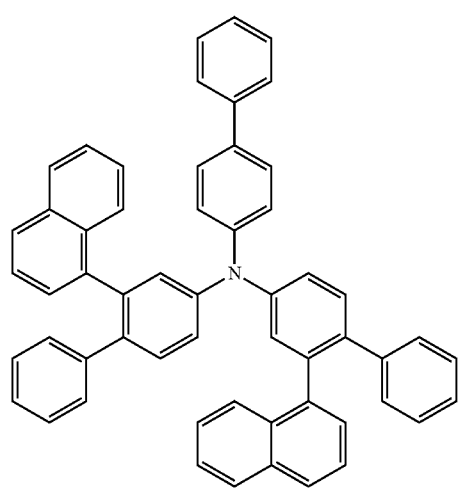
[Chemical Formula 290]
(5-132)
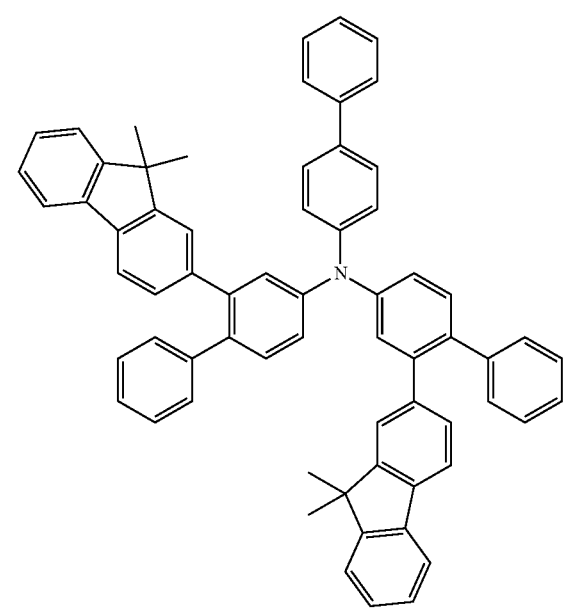

[Chemical Formula 291]
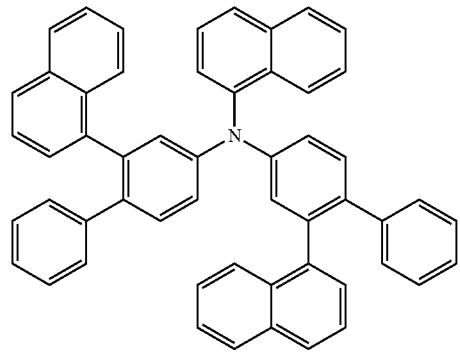
(5-133)
[Chemical Formula 292]
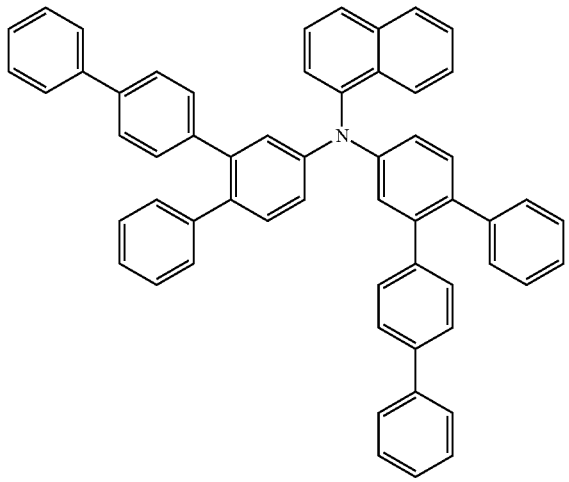
(5-134)
[Chemical Formula 293]
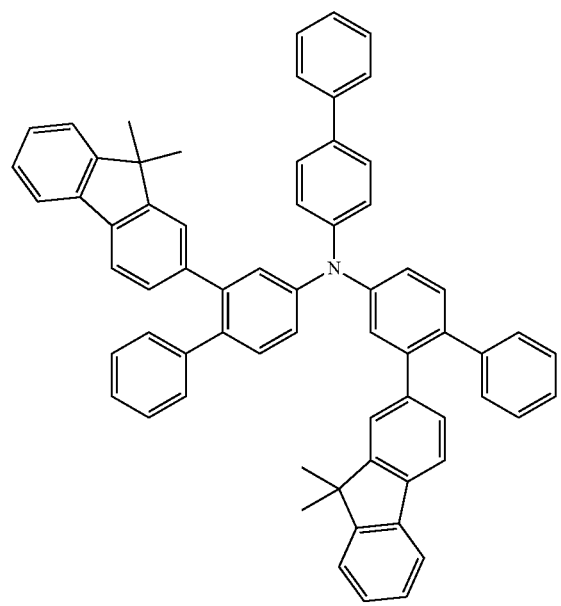
(5-135)
[Chemical Formula 294]
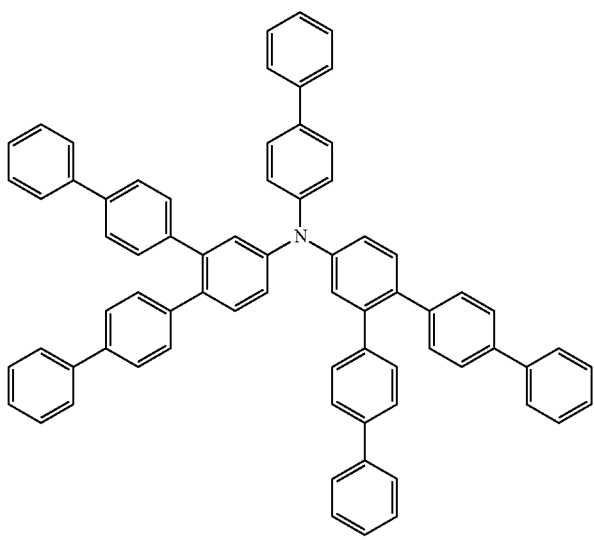
(5-136)

[Chemical Formula 295] (5-137)
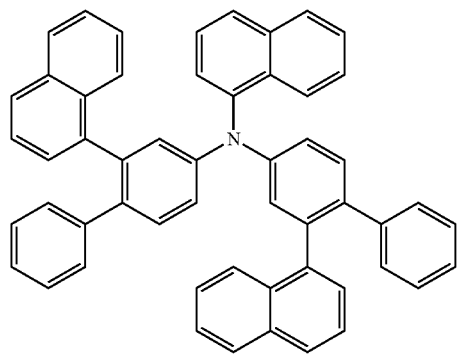
[Chemical Formula 296] (5-138)
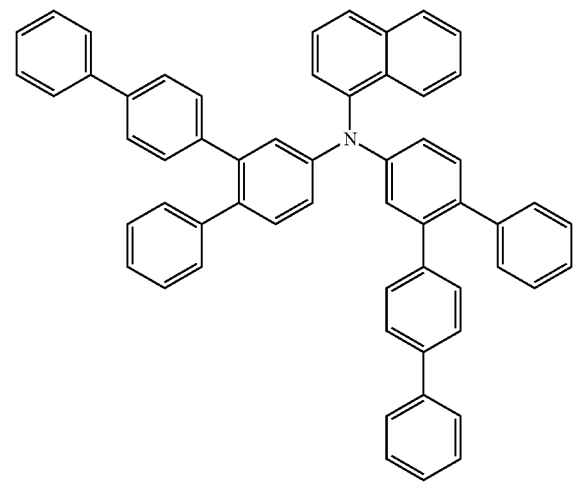
[Chemical Formula 297] (5-139)
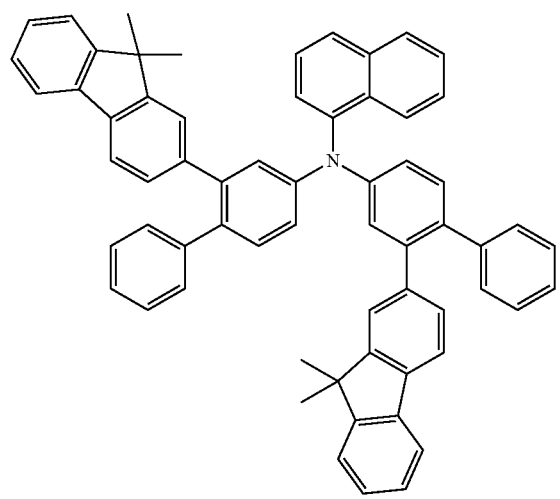
[Chemical Formula 298] (5-140)
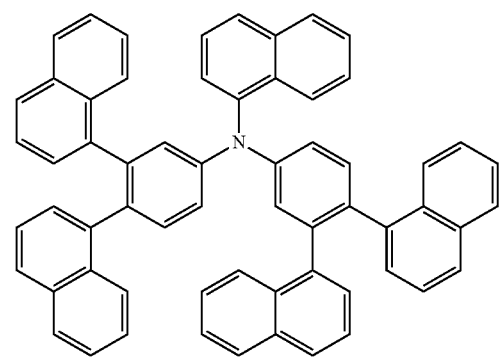
[Chemical Formula 299] (5-141)
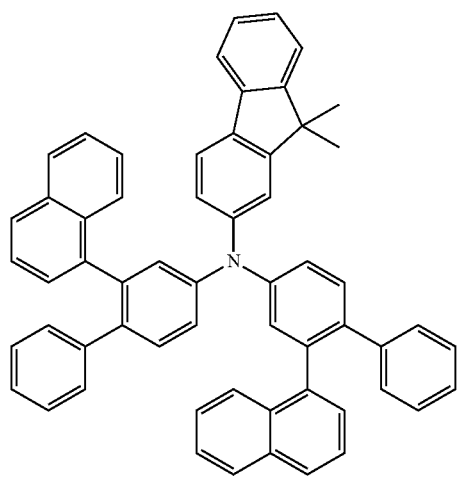
[Chemical Formula 300] (5-142)
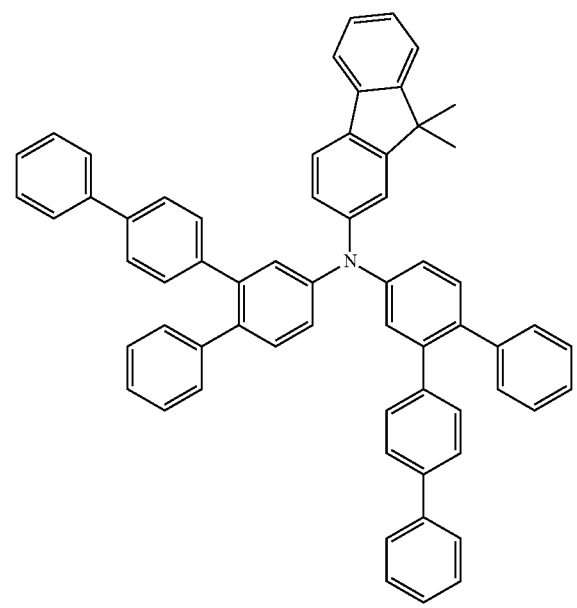

[Chemical Formula 301]
(5-143)
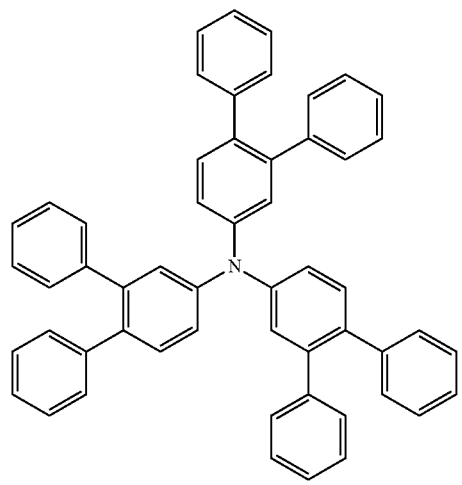
[Chemical Formula 302]
(5-144)
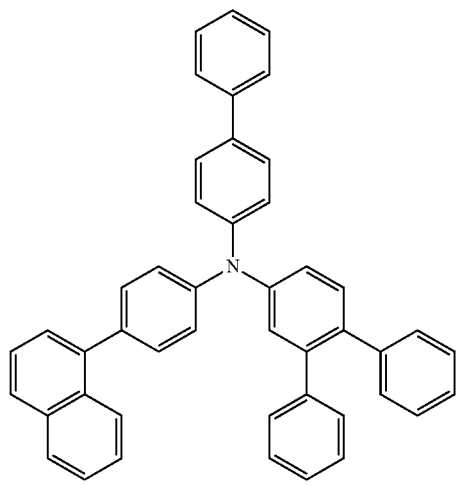
[Chemical Formula 303]
(5-145)
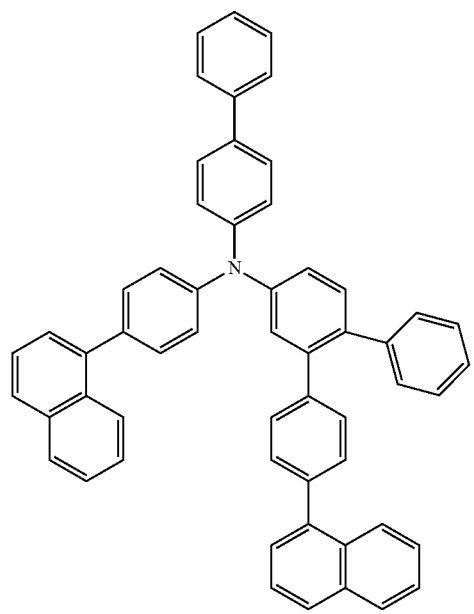
[Chemical Formula 304]
(5-146)
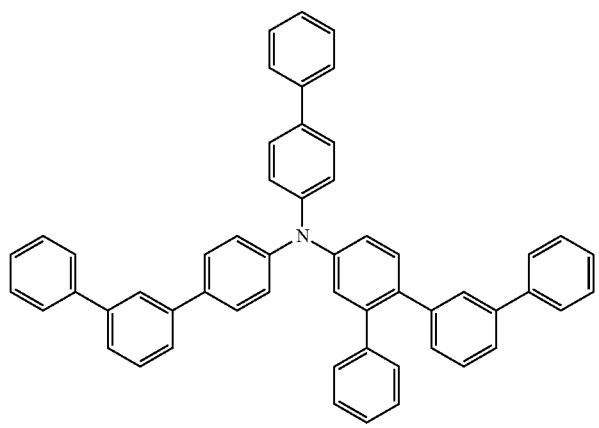

[Chemical Formula 305]
(5-147)
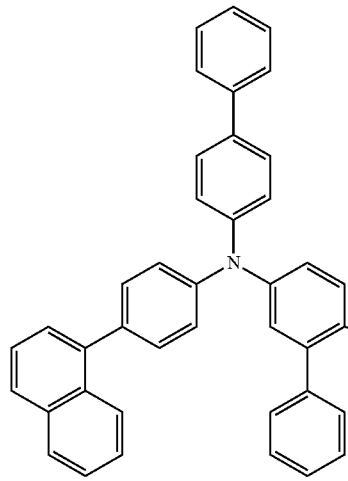
[Chemical Formula 306]
(5-148)
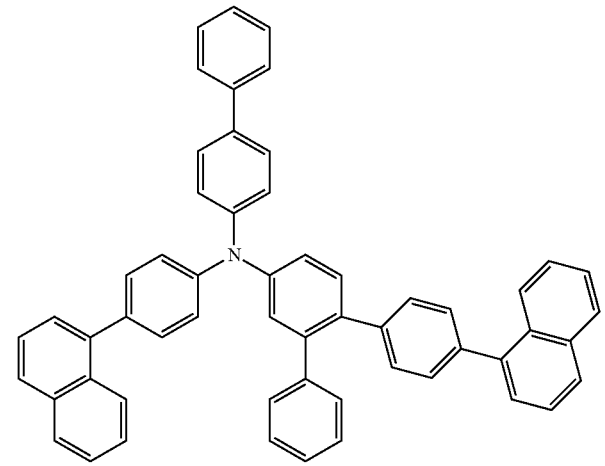
[Chemical Formula 307]
(5-149)
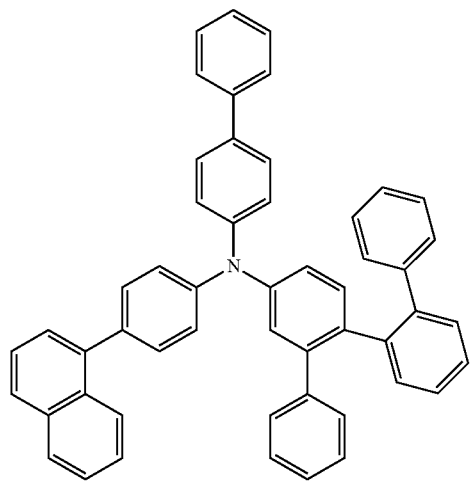
[Chemical Formula 308]
(5-150)
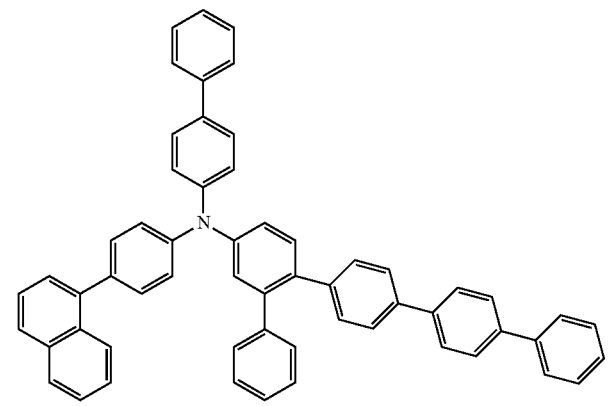
[Chemical Formula 309]
(5-151)
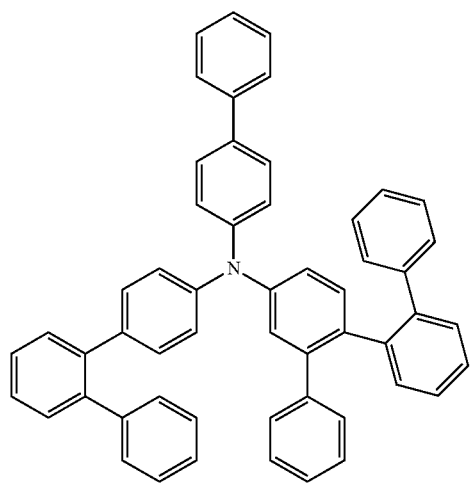
[Chemical Formula 310]
(5-152)
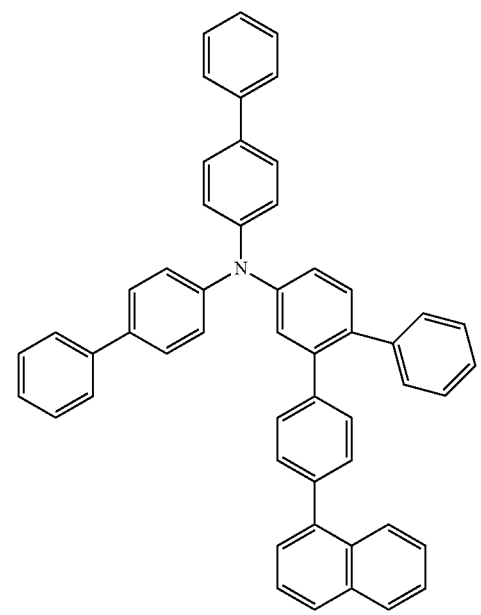

-continued
[Chemical Formula 311]
(5-153)
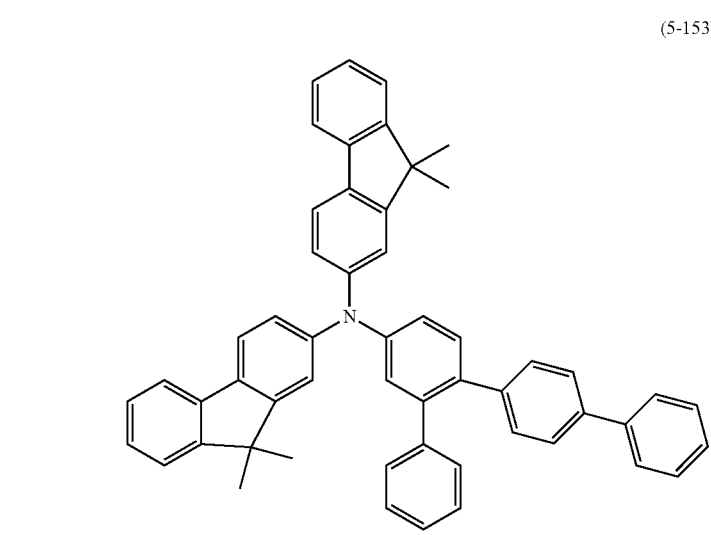
[Chemical Formula 312]
(5-154)
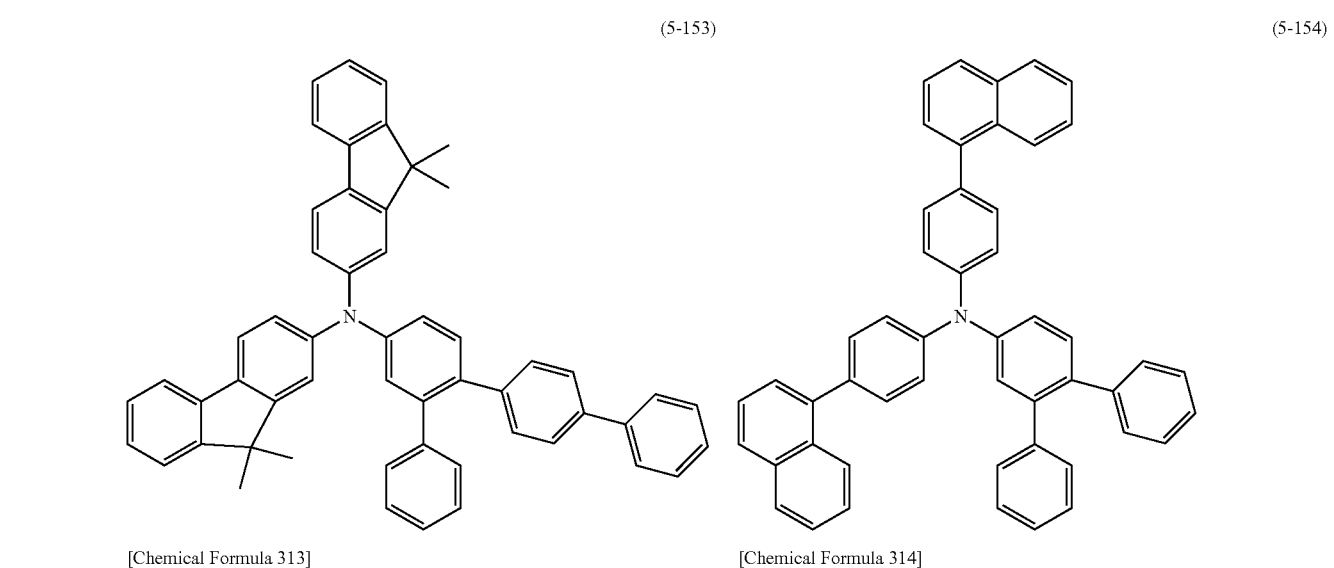
[Chemical Formula 313]
(5-155)
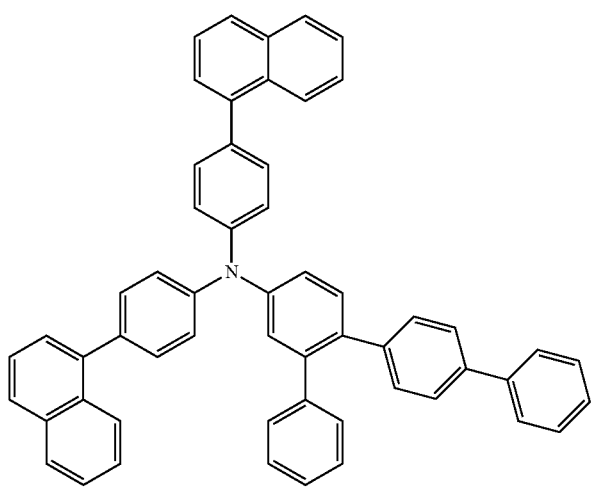
[Chemical Formula 314]
(5-156)
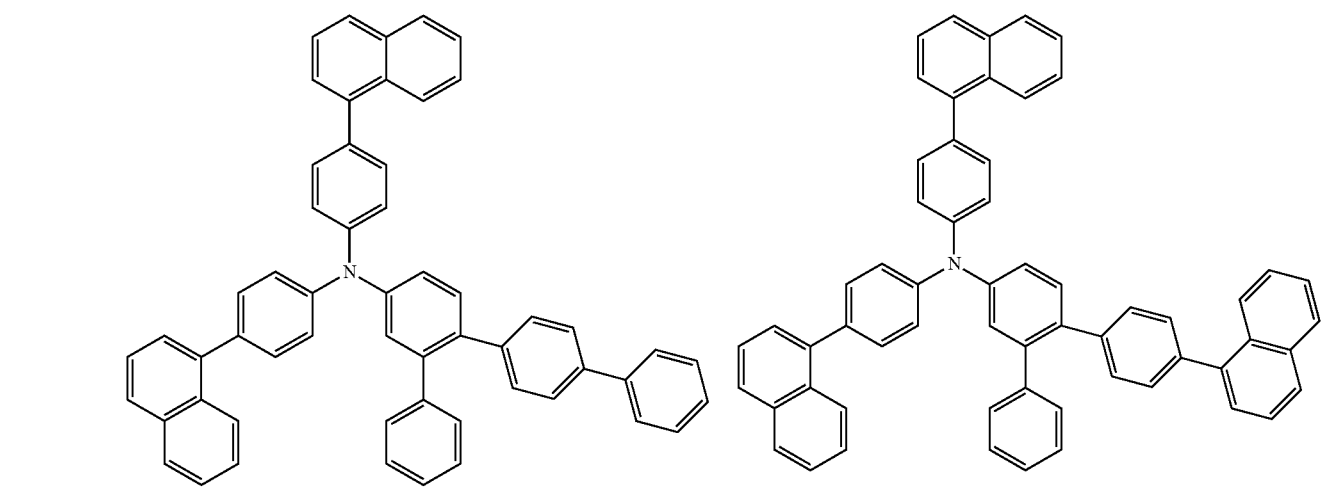
[Chemical Formula 315]
(5-157)
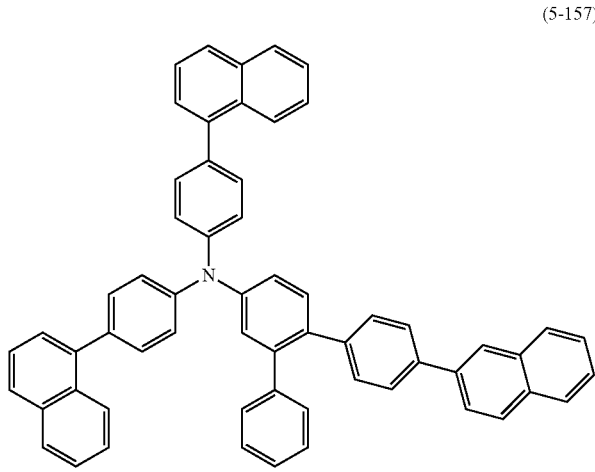
[Chemical Formula 316]
(5-158)
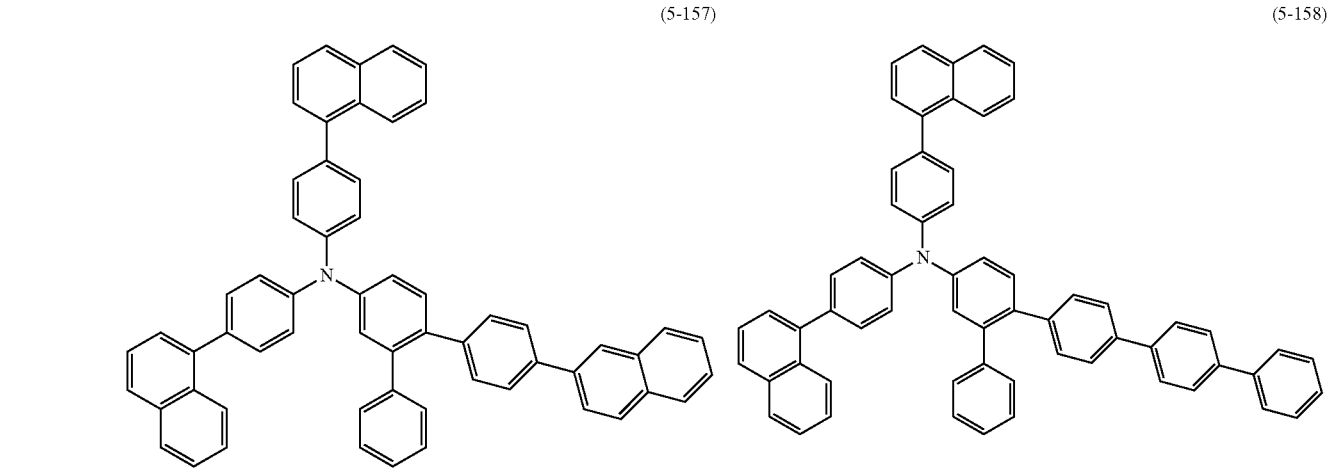

-continued
[Chemical Formula 317]
(5-159)
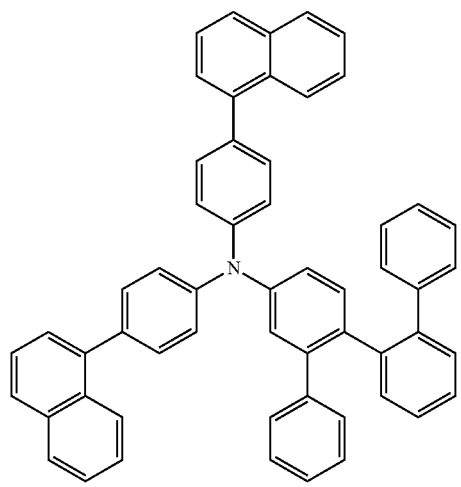
[Chemical Formula 318]
(5-160)
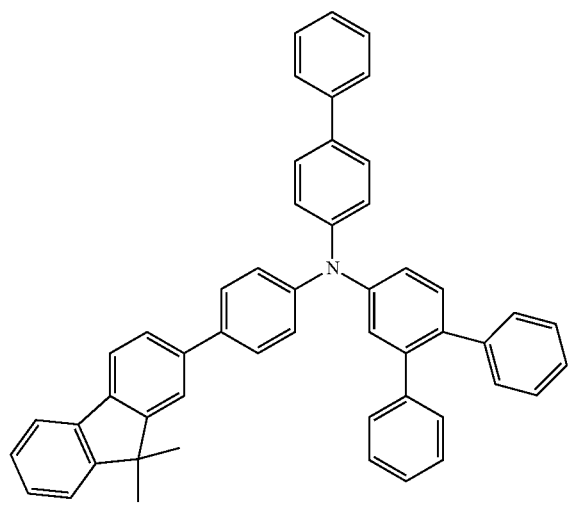
[Chemical Formula 319]
(5-161)
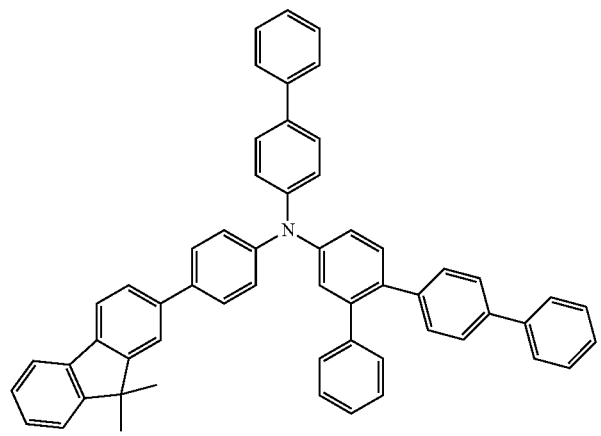
[Chemical Formula 320]
(5-162)
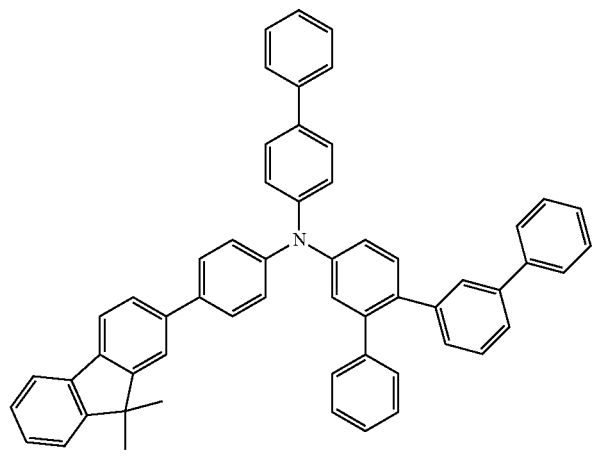
[Chemical Formula 321]
(5-163)
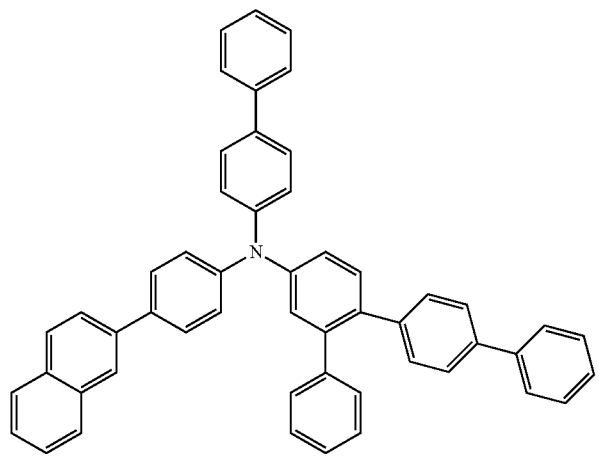
[Chemical Formula 322]
(5-164)
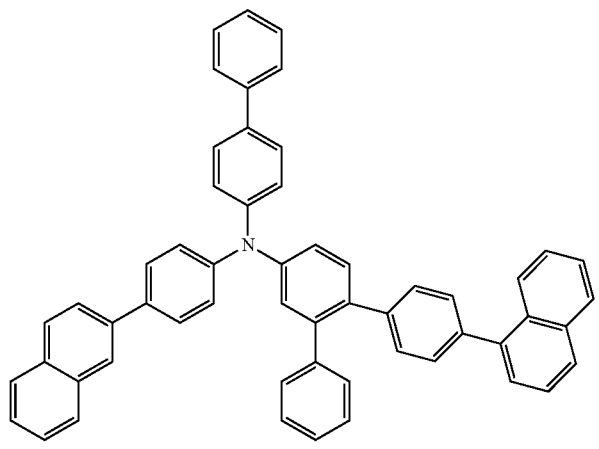

[Chemical Formula 323]
(5-165)
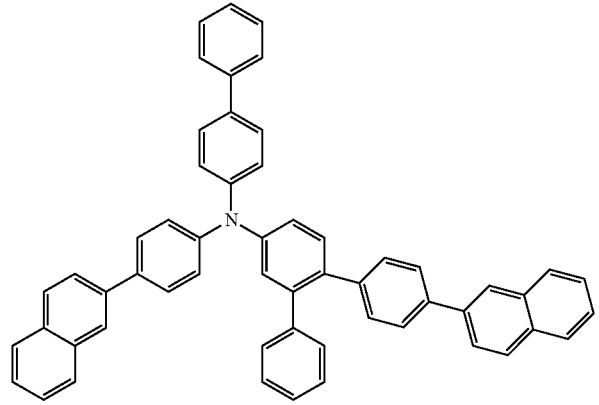
[Chemical Formula 324]
(5-166)
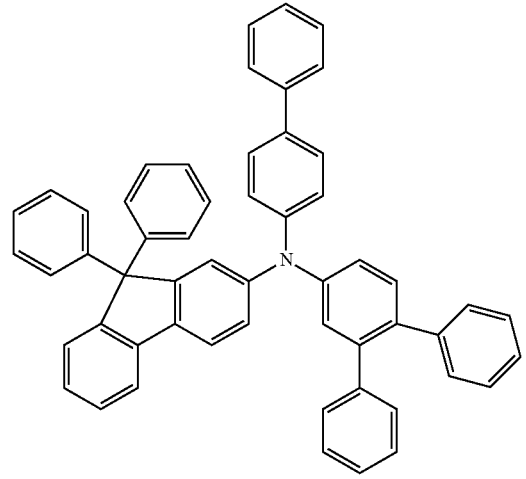
[Chemical Formula 325]
(5-167)
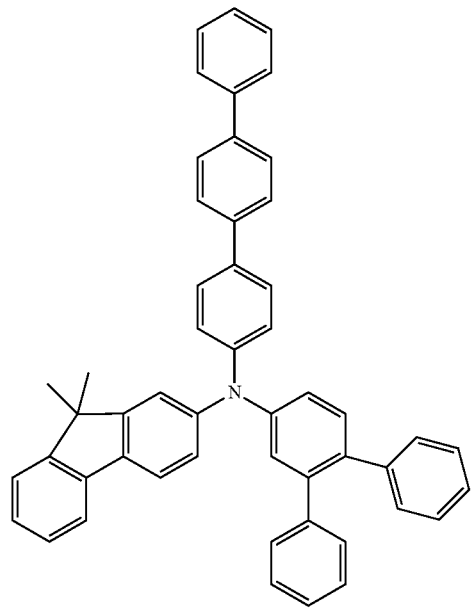
[Chemical Formula 326]
(5-168)
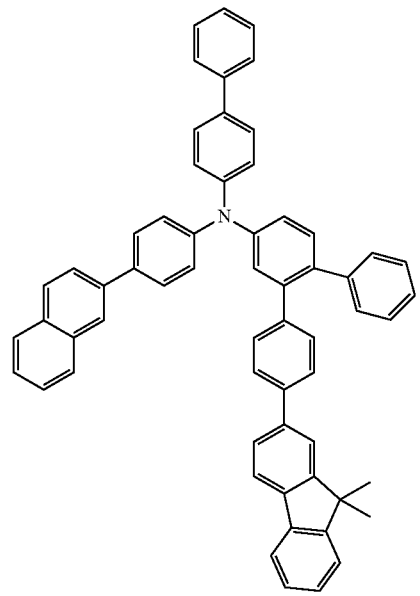

[Chemical Formula 327]
(5-169)
[Chemical Formula 328]
(5-170)
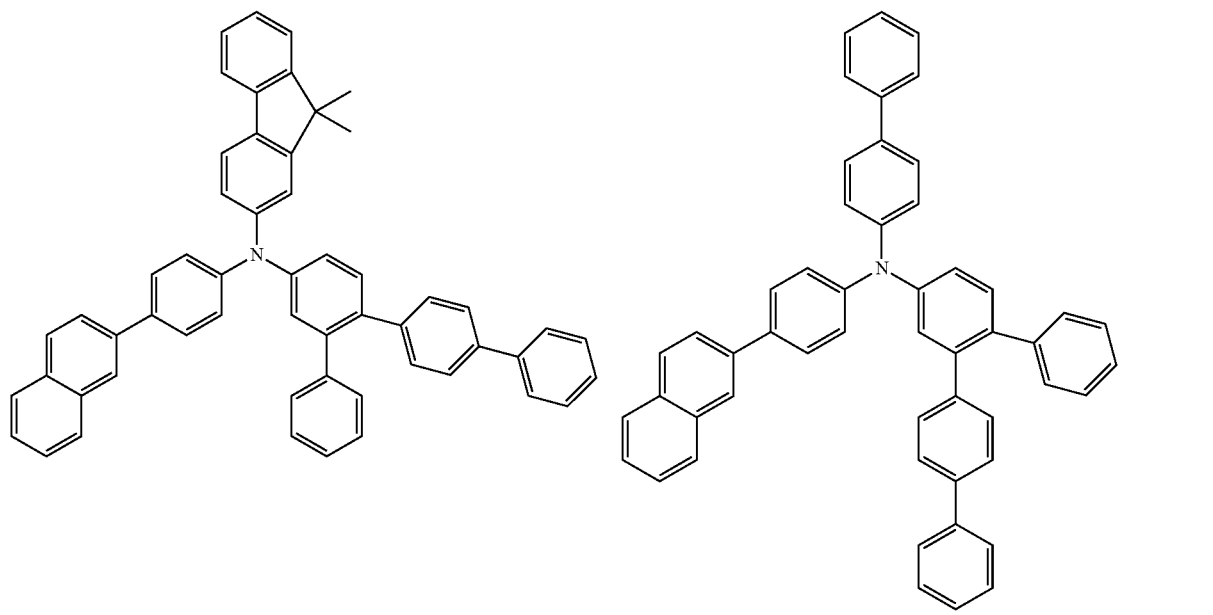
[Chemical Formula 329]
(5-171)
[Chemical Formula 330]
(5-172)
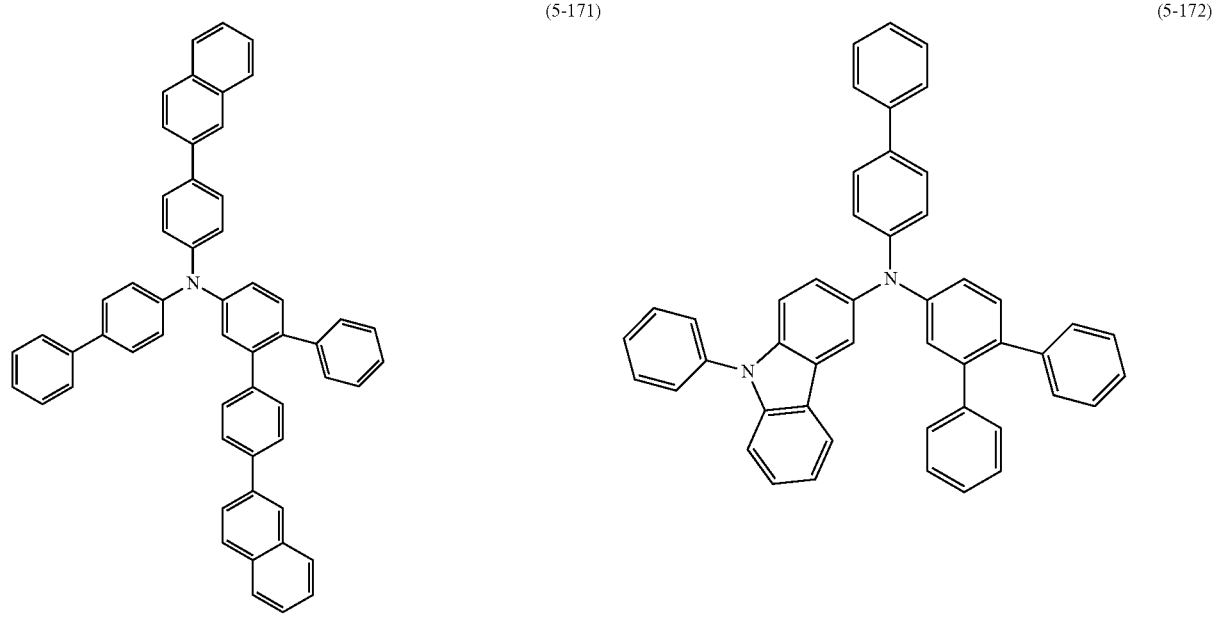

[Chemical Formula 331]
(5-173)
[Chemical Formula 331]
(5-174)
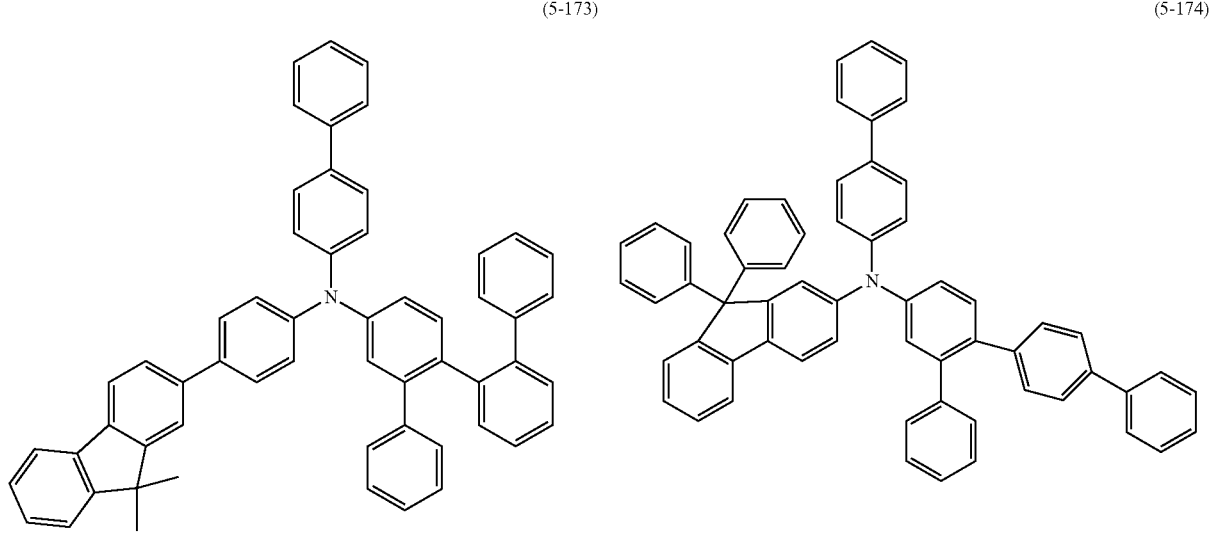
[Chemical Formula 333]
(5-175)
[Chemical Formula 334]
(5-176)
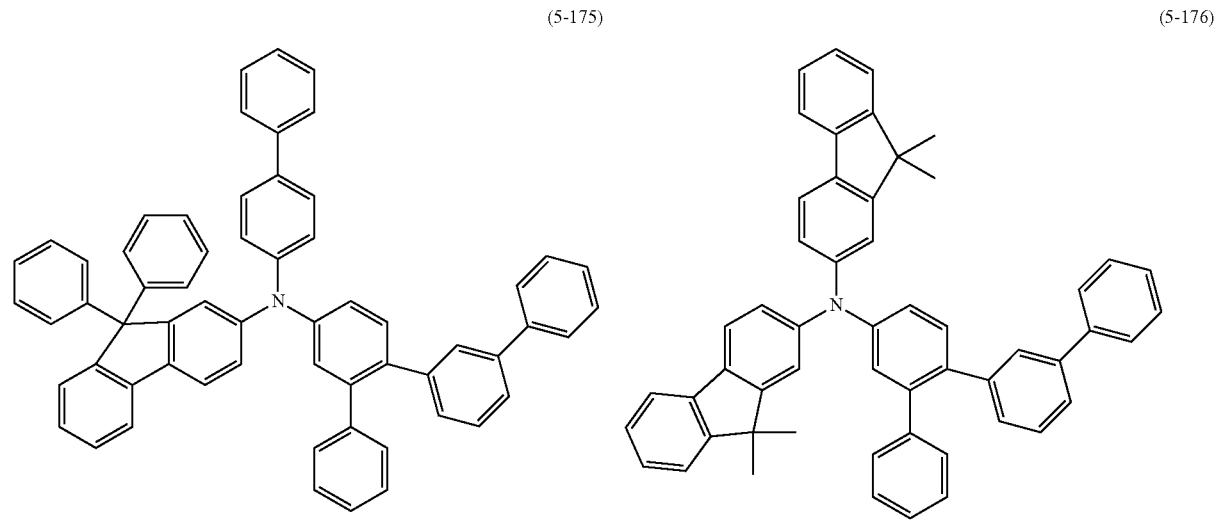

[Compound Formula 335]
(5-177)
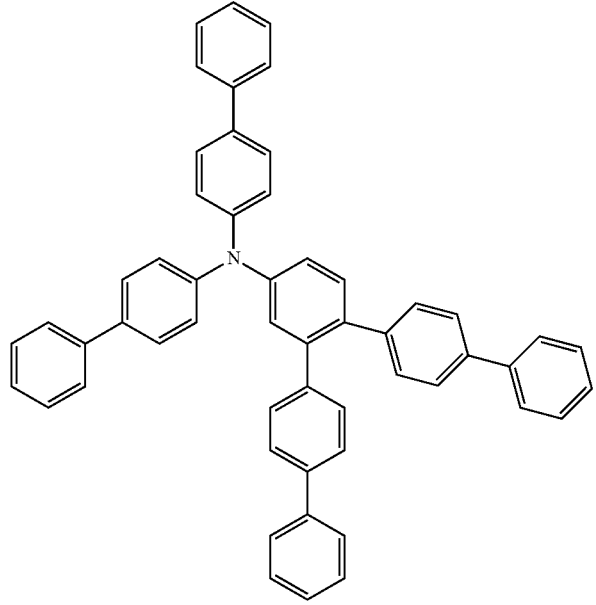
[Compound Formula 336]
(5-178)
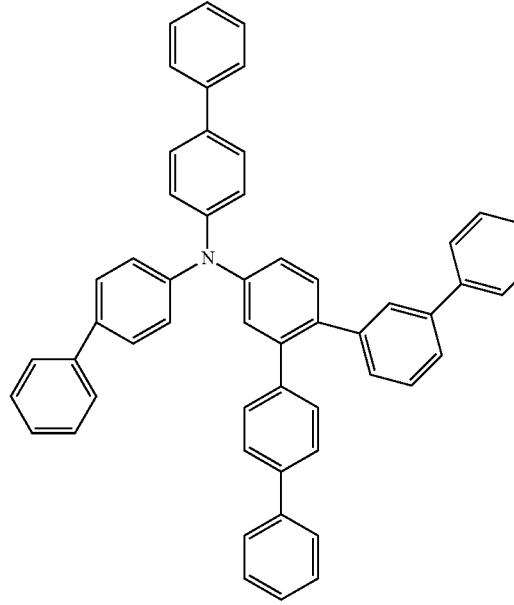
[Compound Formula 337]
(5-179)
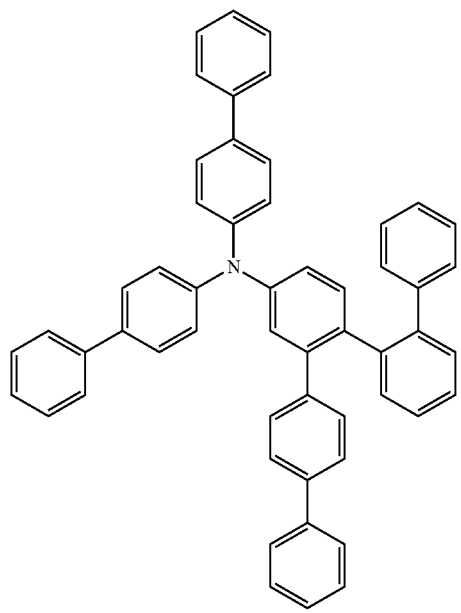
[Compound Formula 338]
(5-180)
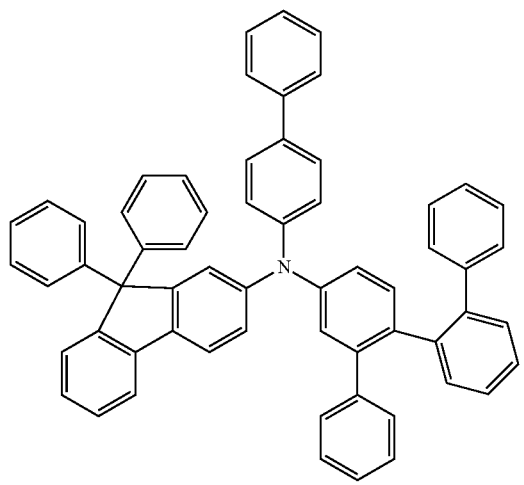

[Chemical Formula 339]
(5-181)
[Chemical Formula 340]
(5-182)
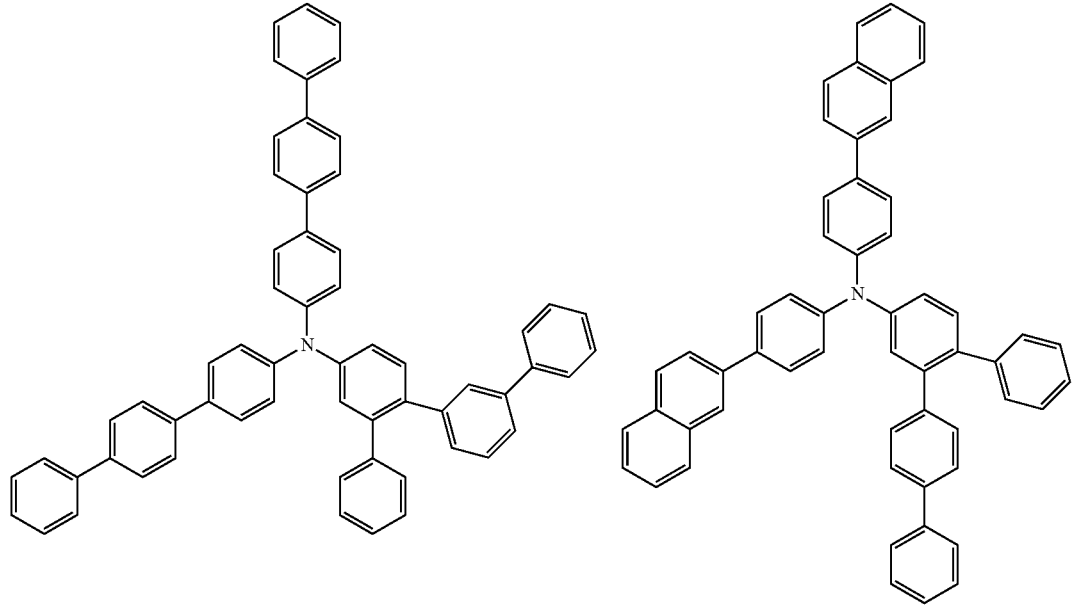
[Chemical Formula 341]
(5-183)
[Chemical Formula 342]
(5-184)
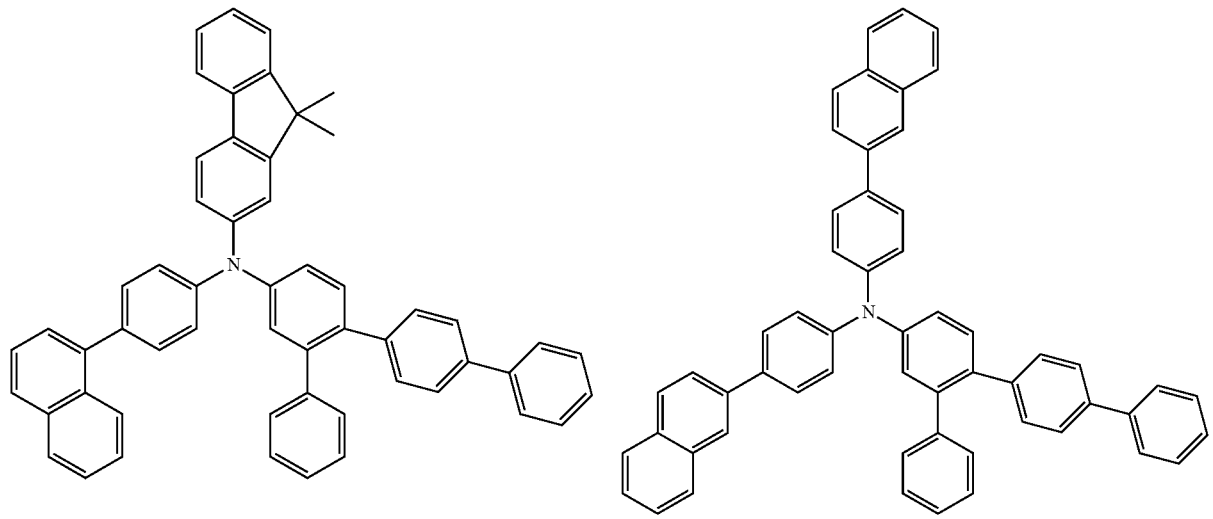

[Chemical Formula 343]
(5-184)
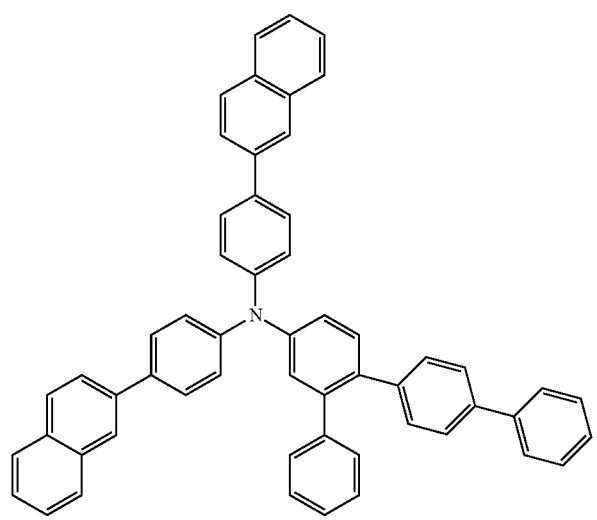
[Chemical Formula 344]
(5-185)
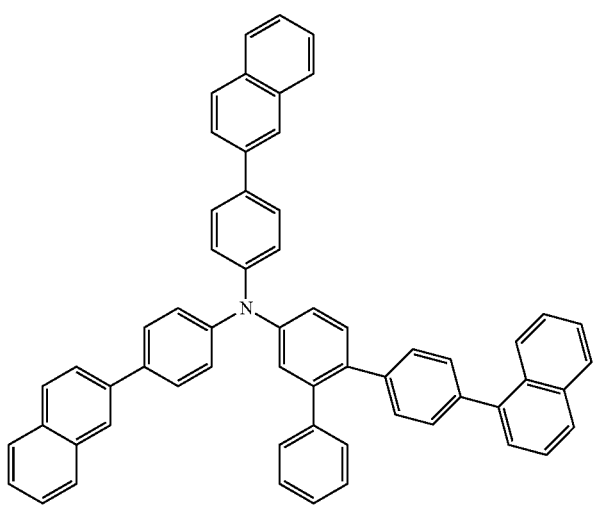
[Chemical Formula 344]
(5-186)
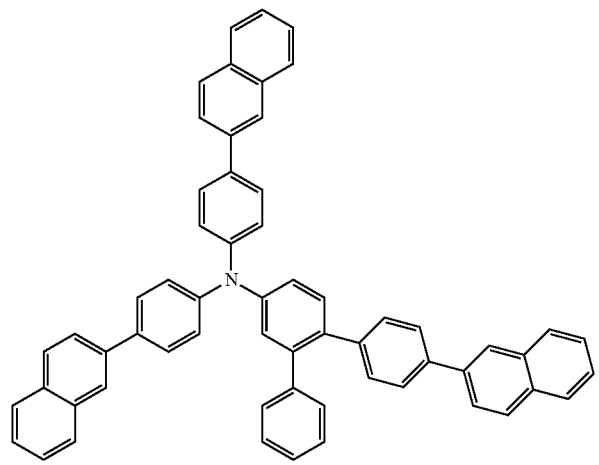
[Chemical Formula 345]
(5-187)
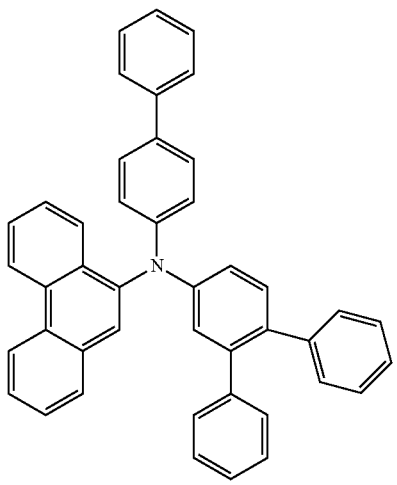
[Chemical Formula 346]
(5-188)
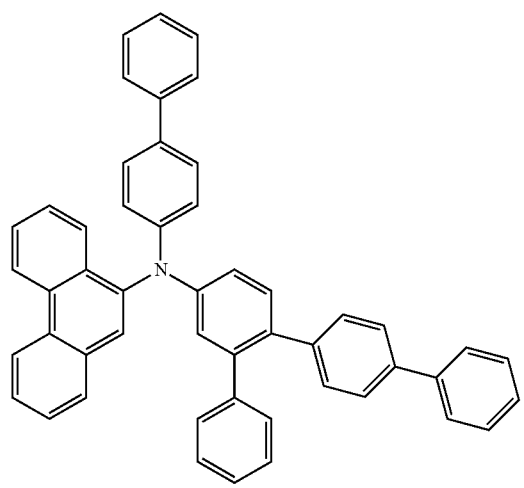
[Chemical Formula 347]
(5-189)
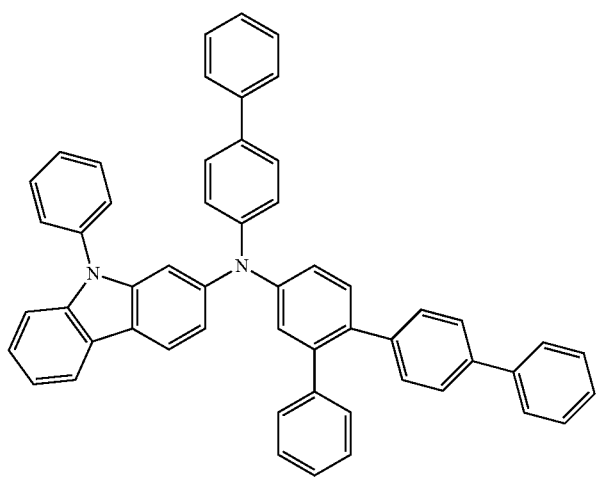

[Chemical Formula 348]
(5-190)
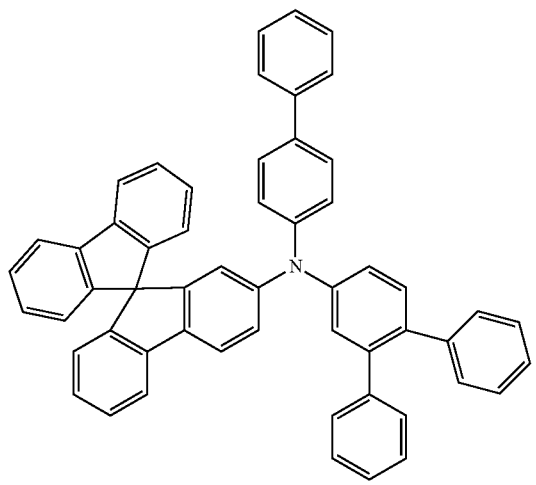
[Chemical Formula 349]
(5-191)
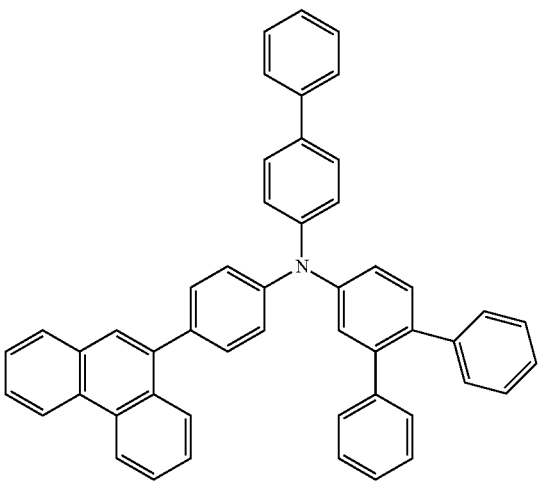
[Chemical Formula 350]
(5-192)
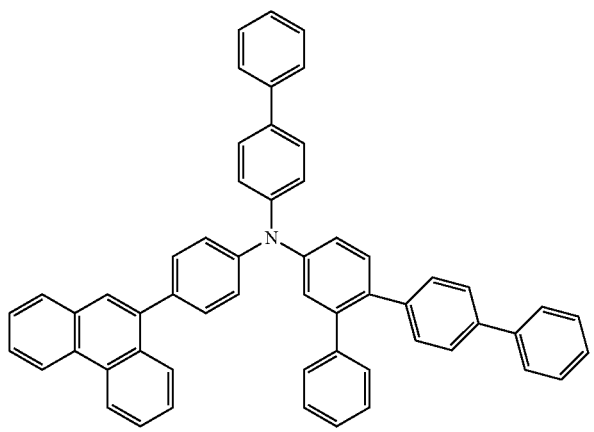
[Chemical Formula 351]
(5-193)
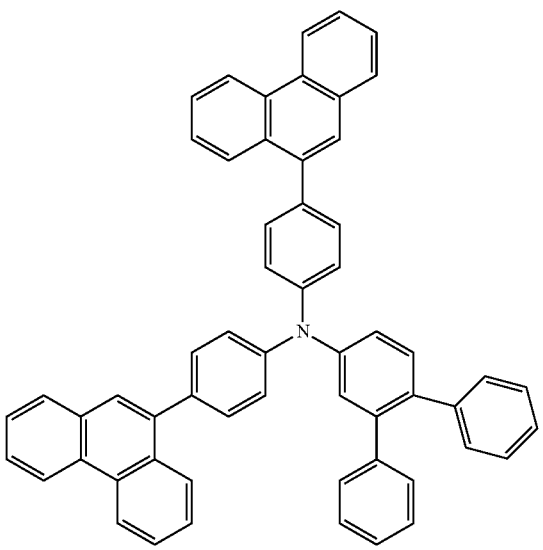
[Chemical Formula 352]
(5-194)
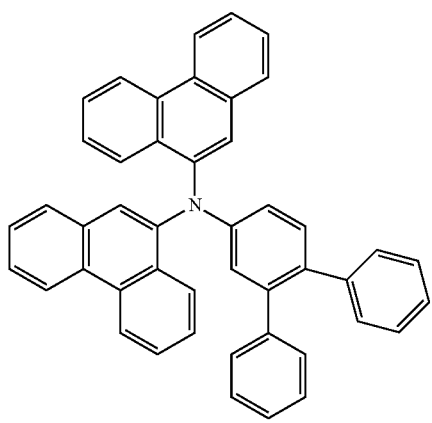
[Chemical Formula 353]
(5-195)
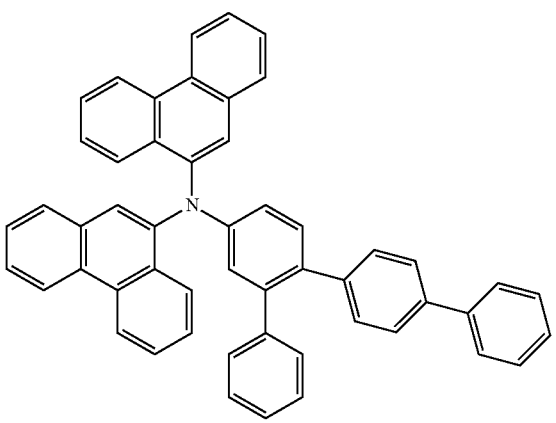

[Chemical Formula 354]
(5-196)
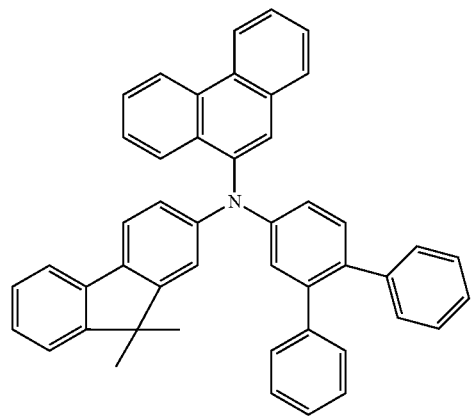
[Chemical Formula 355]
(5-197)
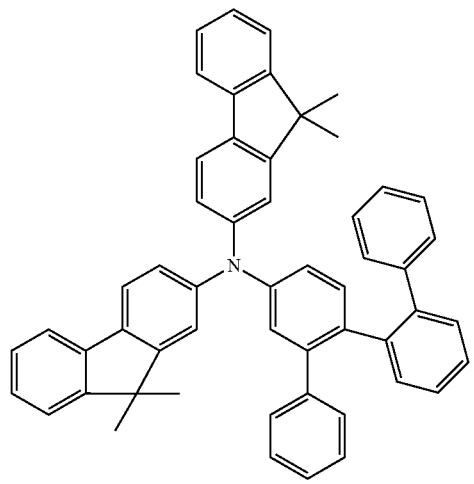
[Chemical Formula 356]
(5-198)
[Chemical Formula 357]
(5-199)
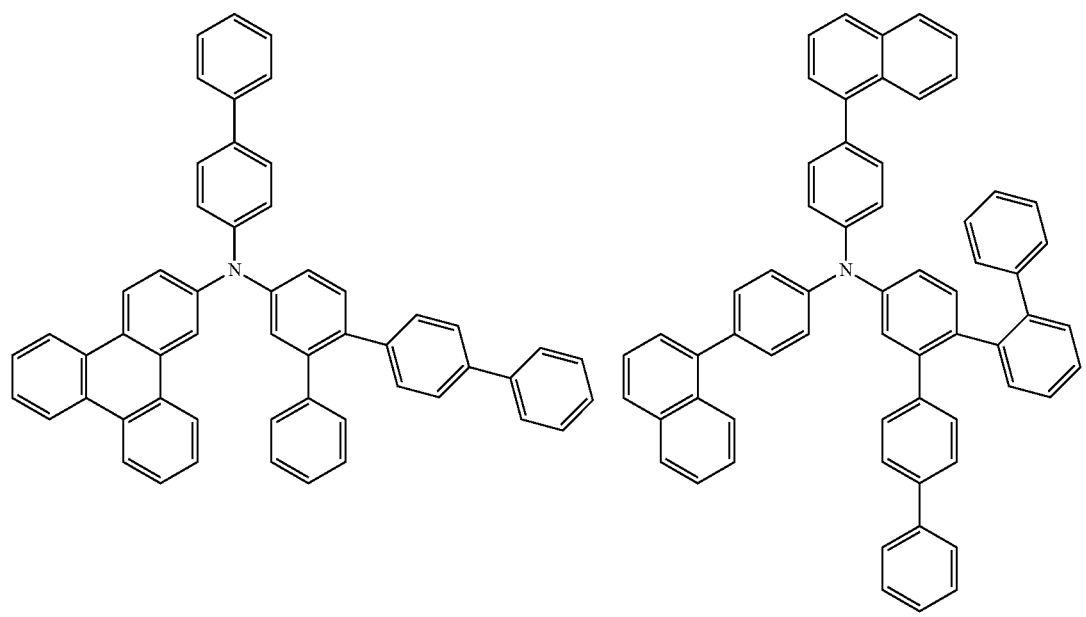

[Chemical Formula 358]
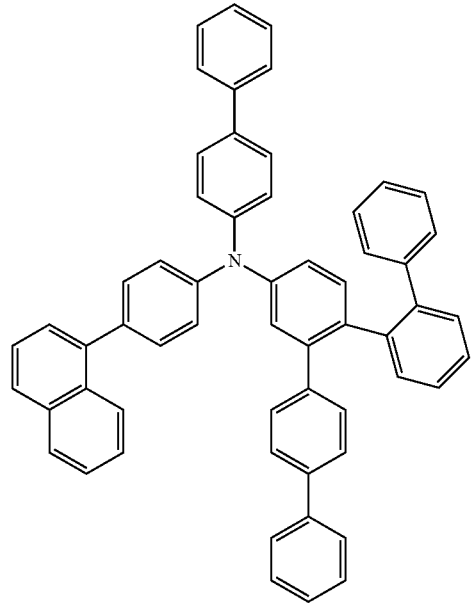
(5-200)
[Chemical Formula 359]
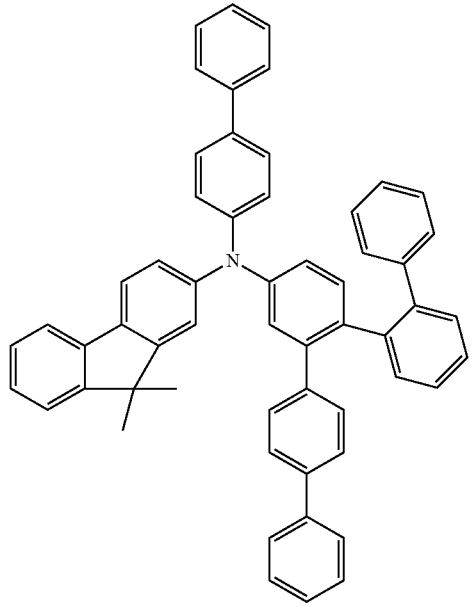
(5-201)
[Chemical Formula 360]
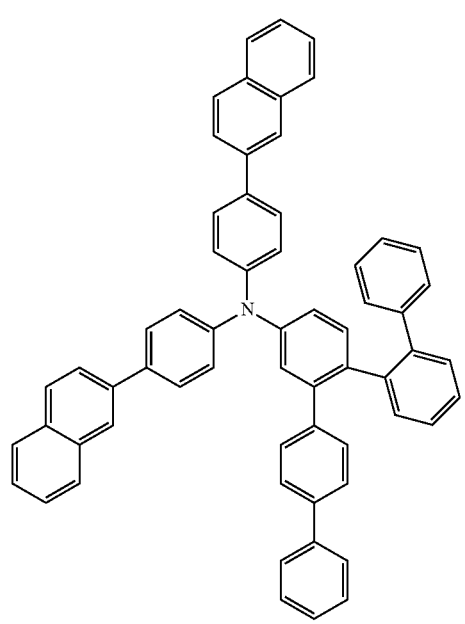
(5-202)
[Chemical Formula 361]
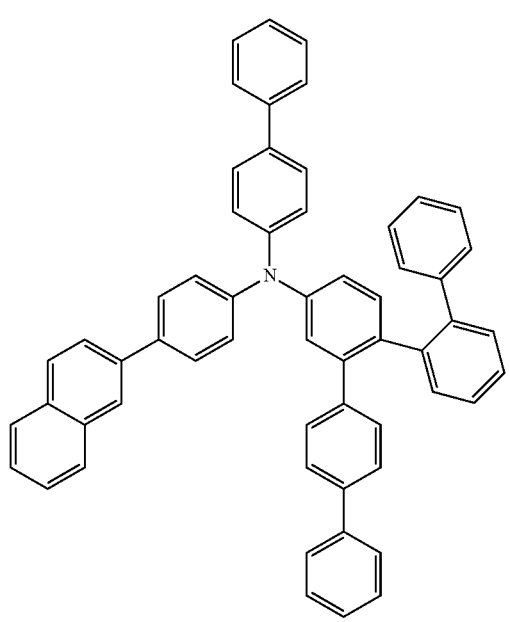
(5-203)

[Chemical Formula 362]
(5-204)
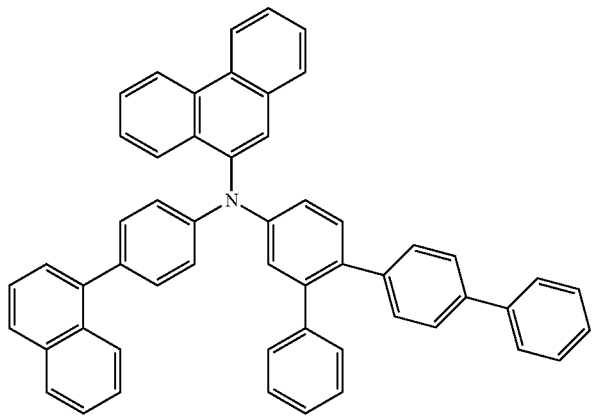
[Chemical Formula 363]
(5-205)
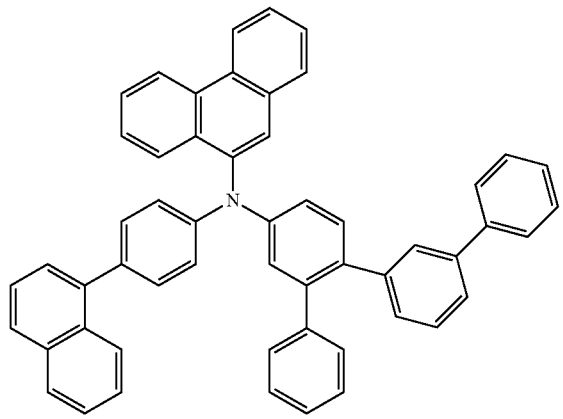
[Chemical Formula 364]
(5-206)
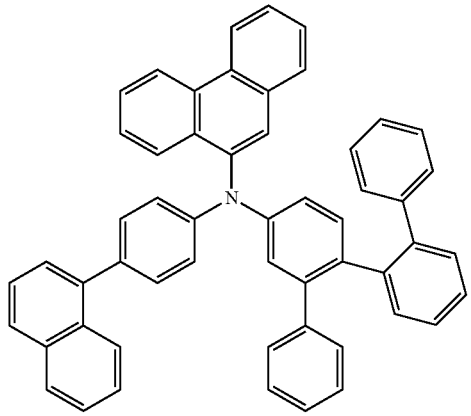
[Chemical Formula 365]
(5-207)
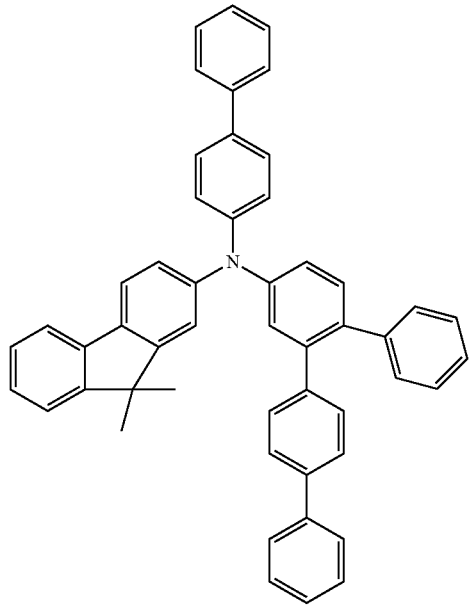
[Chemical Formula 366]
(5-208)
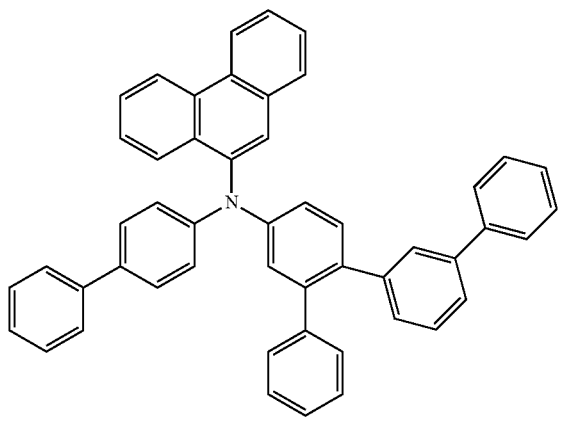
[Chemical Formula 367]
(5-209)
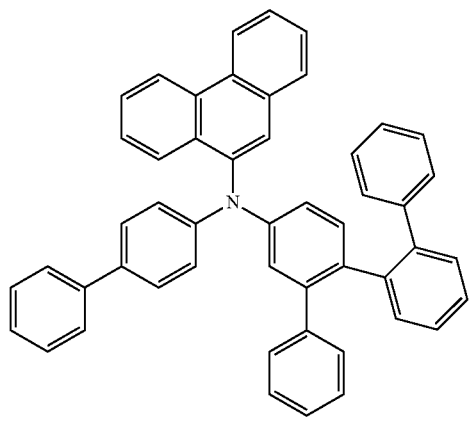

[Chemical Formula 368]
(5-210)
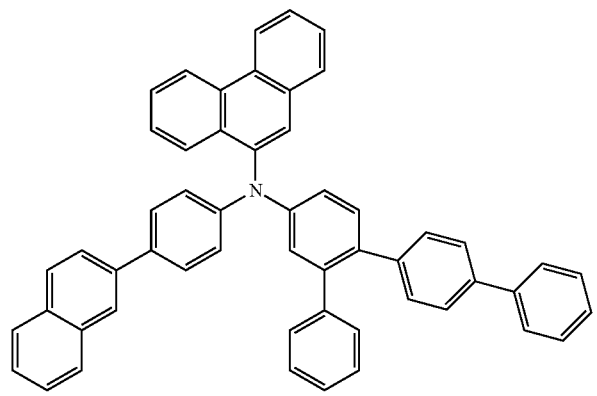
[Chemical Formula 369]
(5-211)
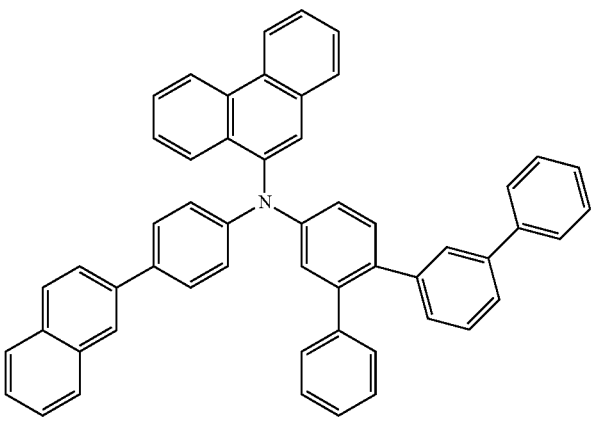
[Chemical Formula 370]
(5-212)
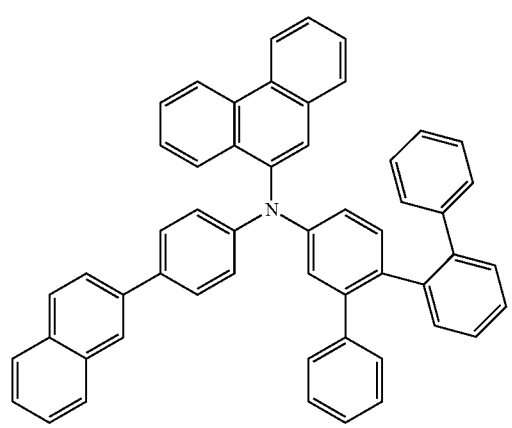
[Chemical Formula 371]
(5-213)
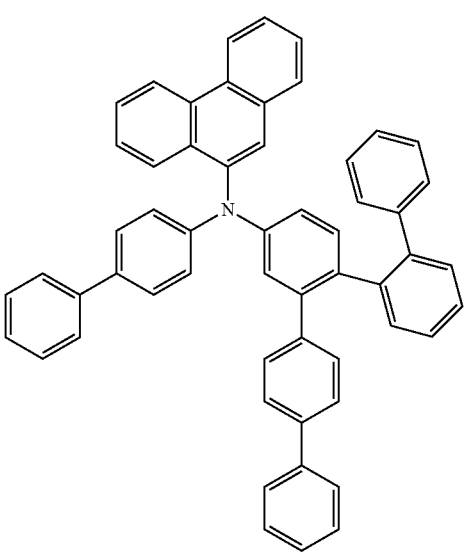
[Chemical Formula 372]
(5-214)
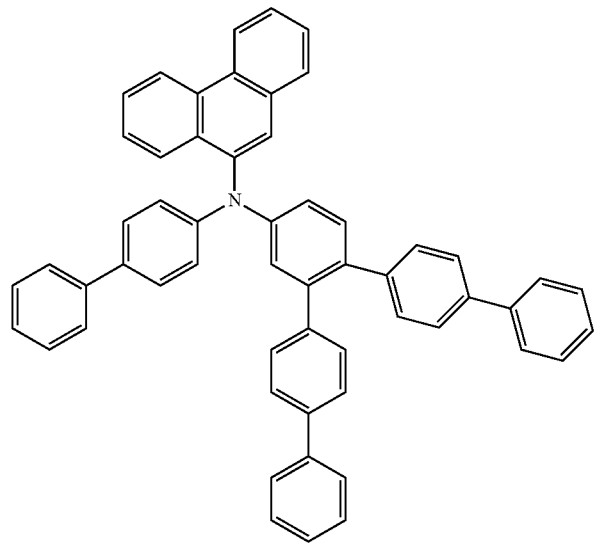
[Chemical Formula 373]
(5-215)
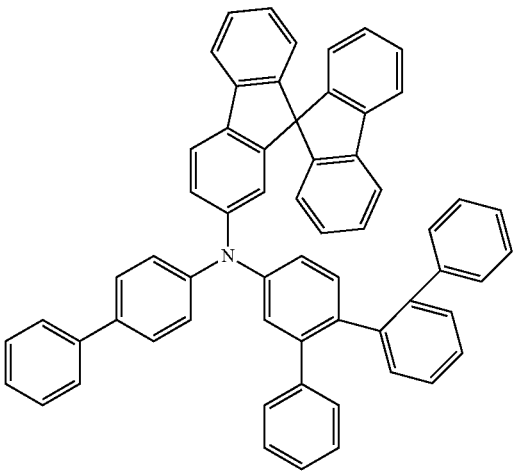

[Chemical Formula 374]

(5-216)

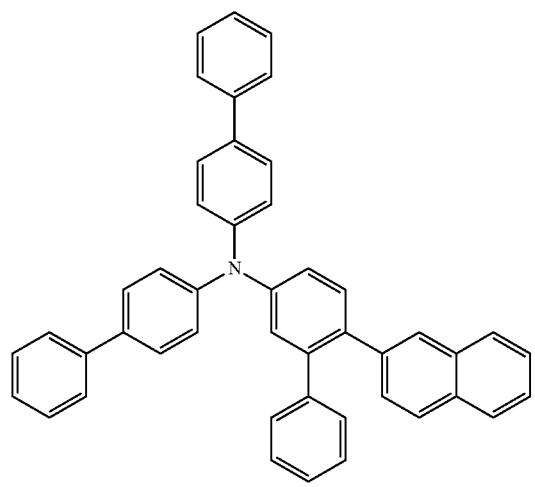

[Chemical Formula 375]

(5-217)

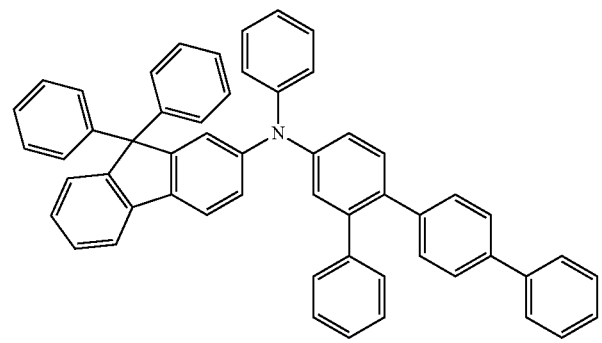

The following presents specific examples of preferred compounds among the compounds of the general formula (6a) preferably used in the organic EL device of the present invention and having an anthracene ring structure. The present invention, however, is not restricted to these compounds.

[Chemical Formula 376]

(6a-1)

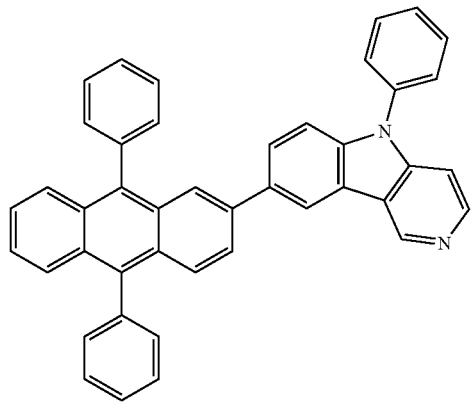

[Chemical Formula 377]

(6a-2)

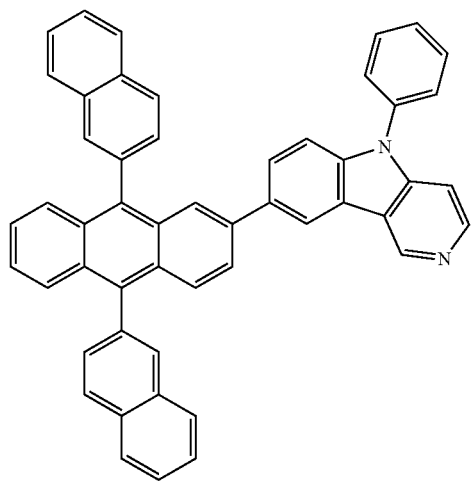

[Chemical Formula 378]

(6a-3)

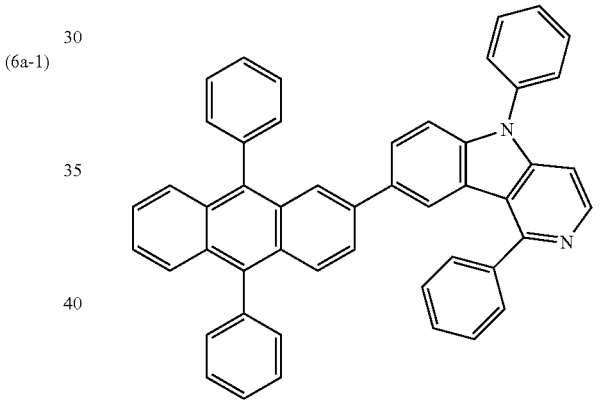

[Chemical Formula 379]

(6a-4)

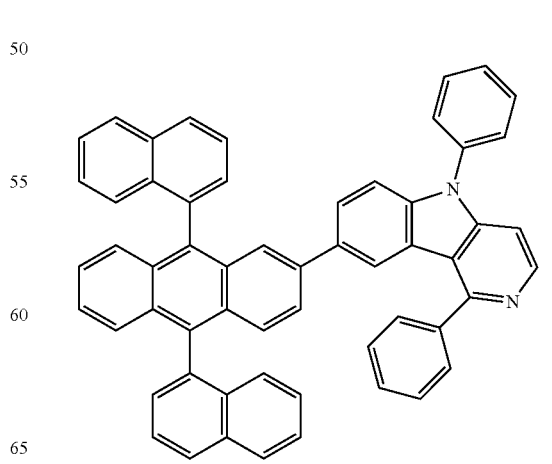

[Chemical Formula 380]
(6a-5)
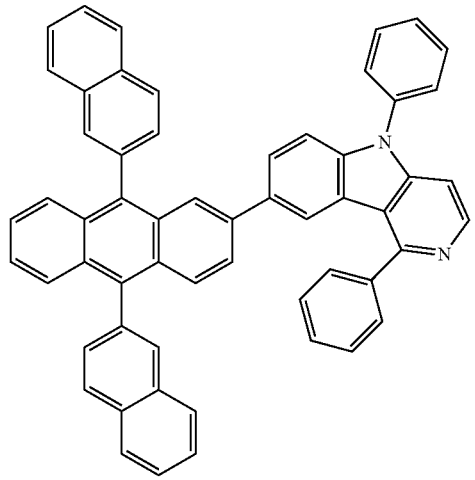
[Chemical Formula 381]
(6a-6)
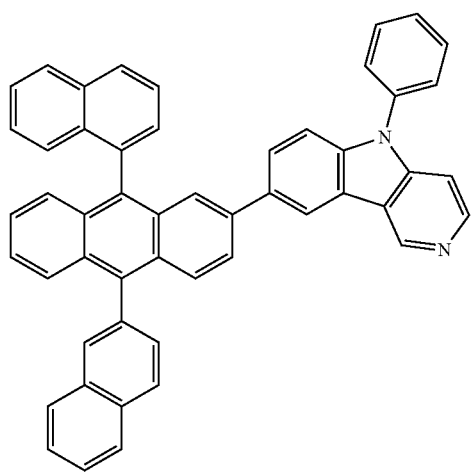
[Chemical Formula 382]
(6a-7)
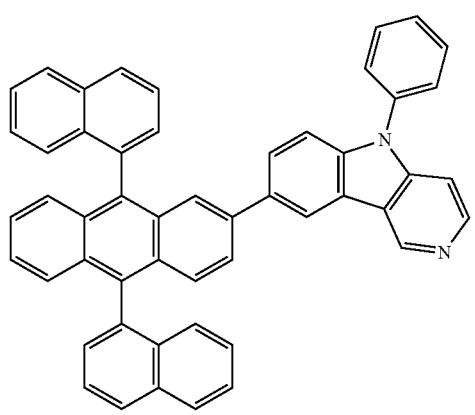
[Chemical Formula 383]
(6a-8)
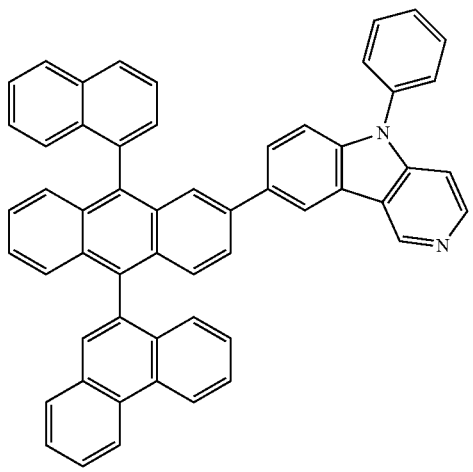
[Chemical Formula 384]
(6a-9)
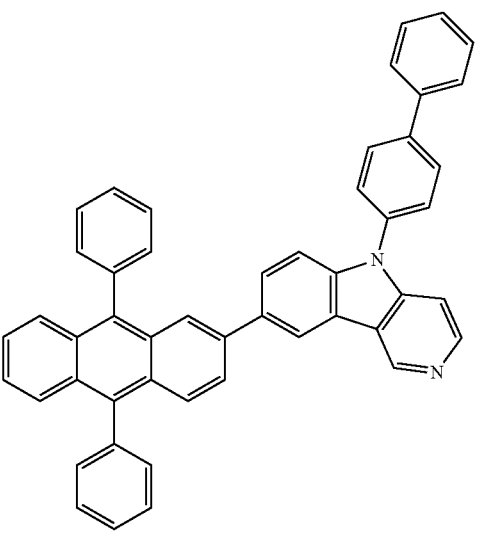
[Chemical Formula 385]
(6a-10)
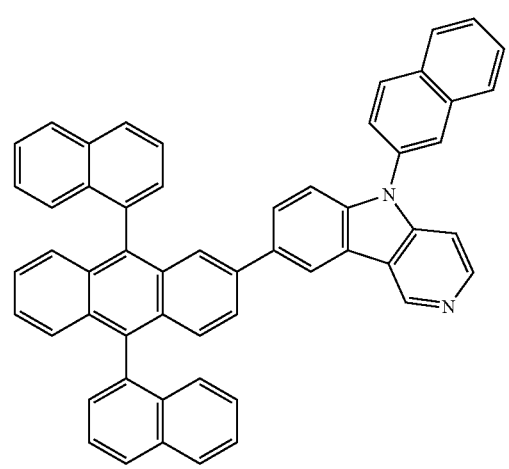

[Chemical Formula 386]
(6a-11)
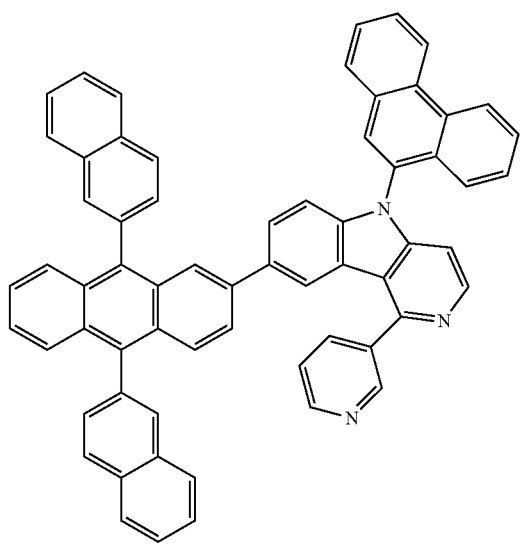
[Chemical Formula 387]
(6a-12)
[Chemical Formula 388]
(6a-13)
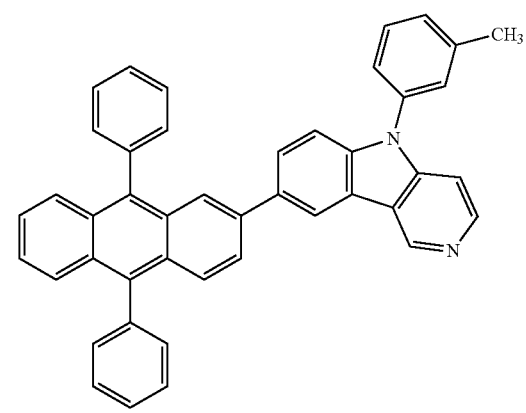
[Chemical Formula 389]
(6a-14)
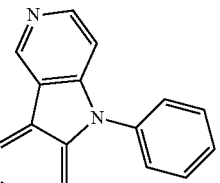
[Chemical Formula 390]
(6a-15)
[Chemical Formula 391]
(6a-16)
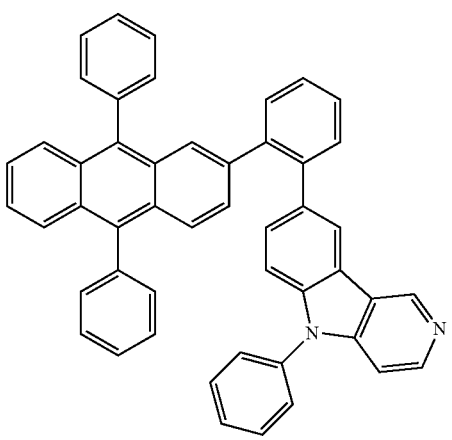

[Chemical Formula 392]

(6a-17)

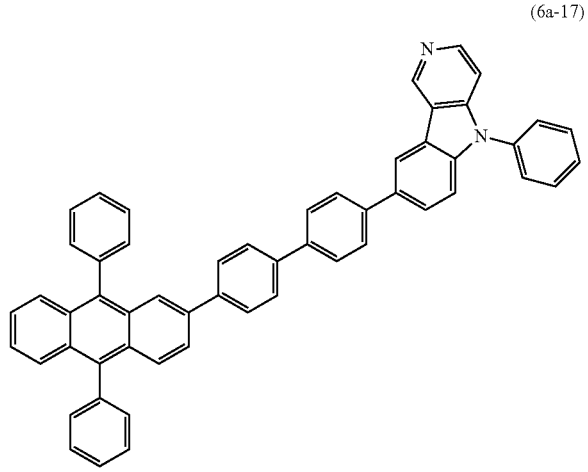

[Chemical Formula 393]

(6a-18)

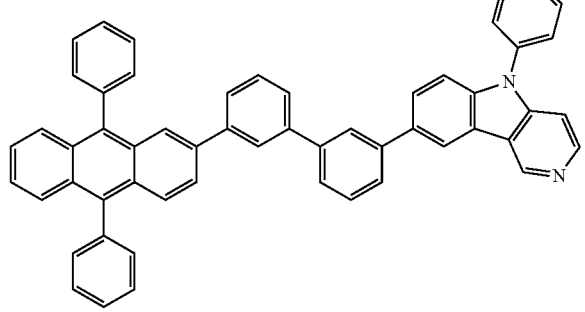

[Chemical Formula 394]

(6a-19)

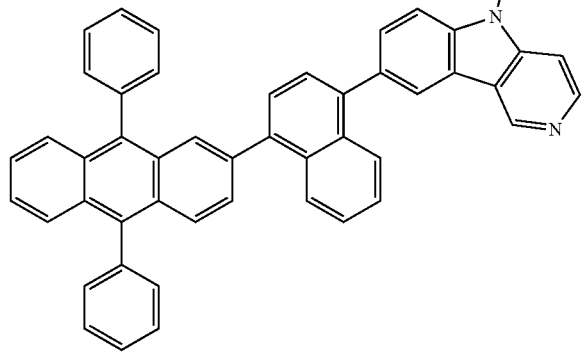

[Chemical Formula 395]

(6a-20)

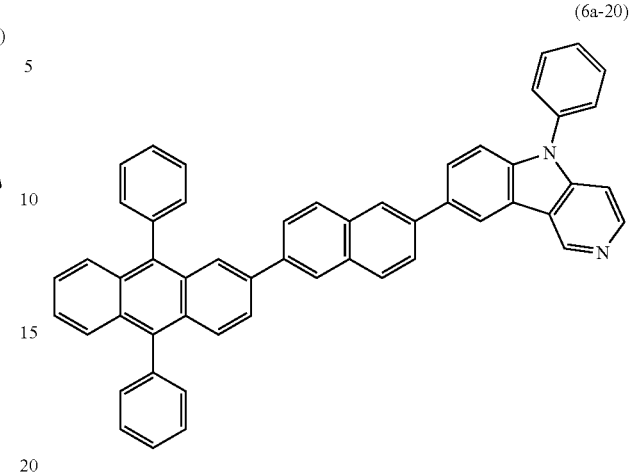

The following presents specific examples of preferred compounds among the compounds of the general formula (6b) preferably used in the organic EL device of the present invention and having an anthracene ring structure. The present invention, however, is not restricted to these compounds.

[Chemical Formula 396]

(6b-1)

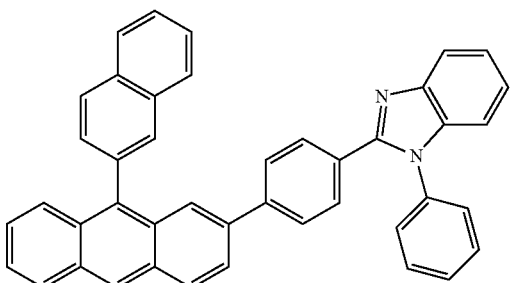

[Chemical Formula 397]

(6b-2)

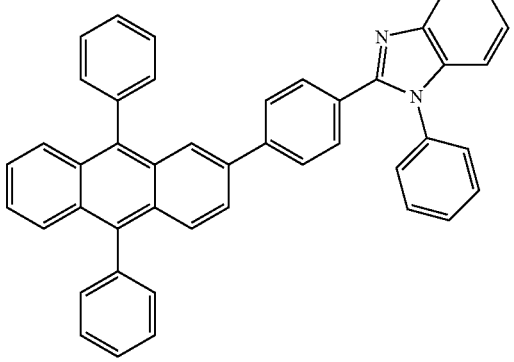

[Chemical Formula 398]
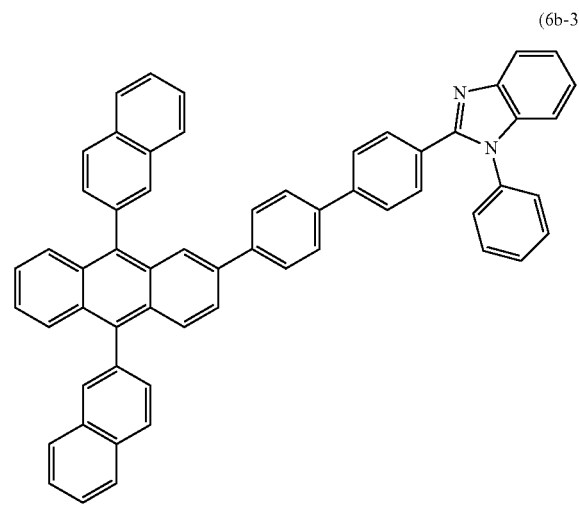
(6b-3)
[Chemical Formula 399]
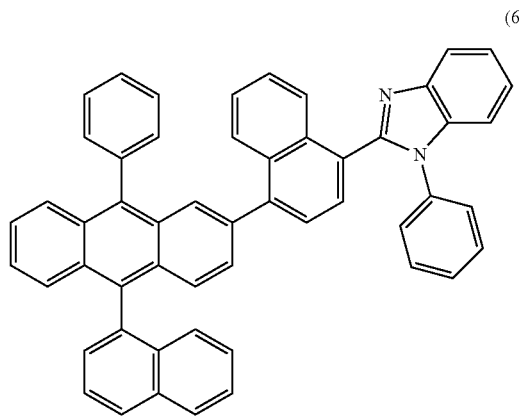
(6b-4)
[Chemical Formula 400]
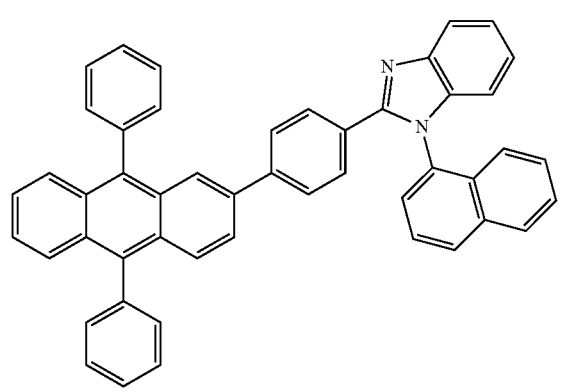
(6b-5)
[Chemical Formula 401]
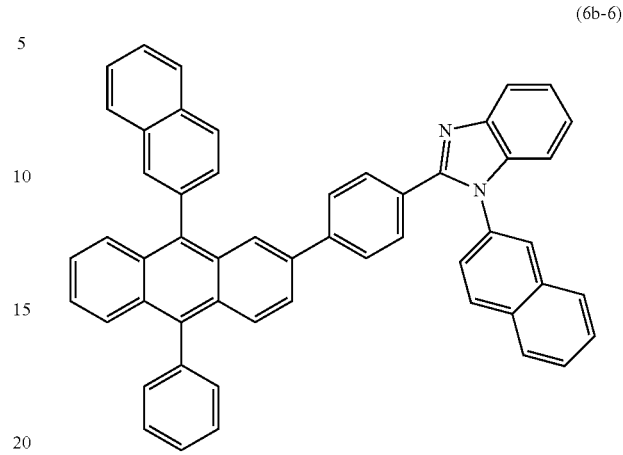
(6b-6)
[Chemical Formula 402]
(6b-7)
[Chemical Formula 403]
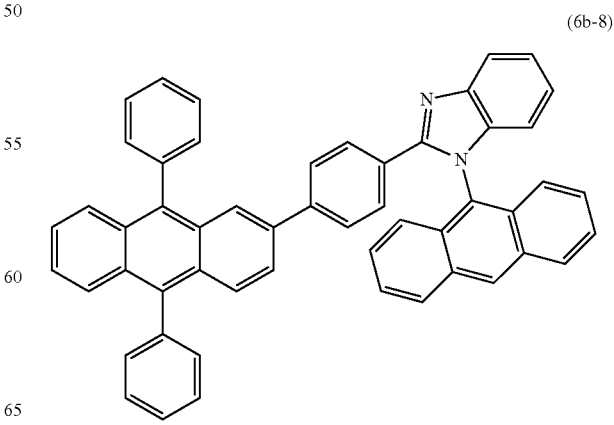
(6b-8)

[Chemical Formula 404]
(6b-9)
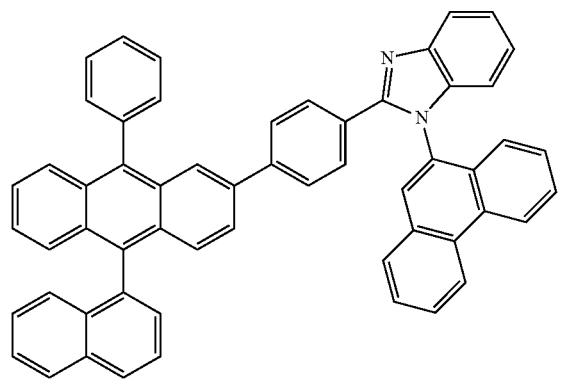
[Chemical Formula 405]
(6b-10)
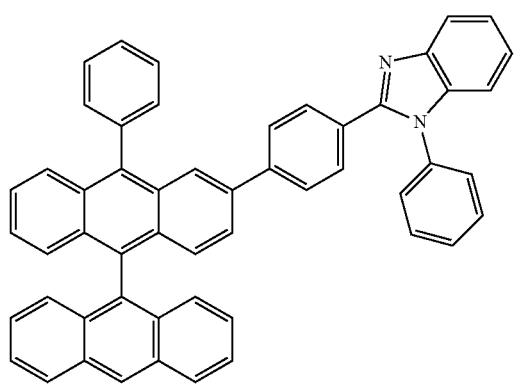
[Chemical Formula 406]
(6b-11)
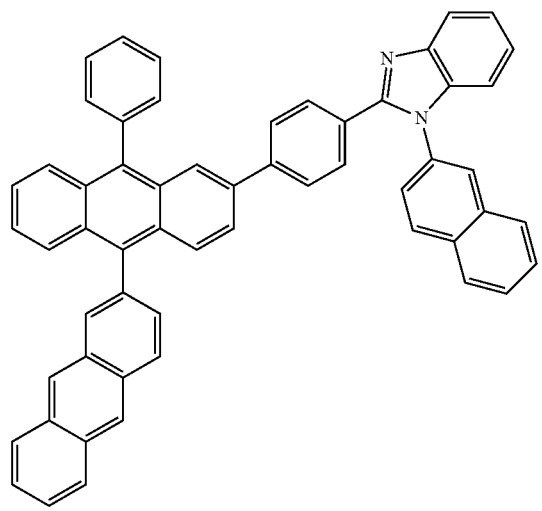
[Chemical Formula 407]
(6b-12)
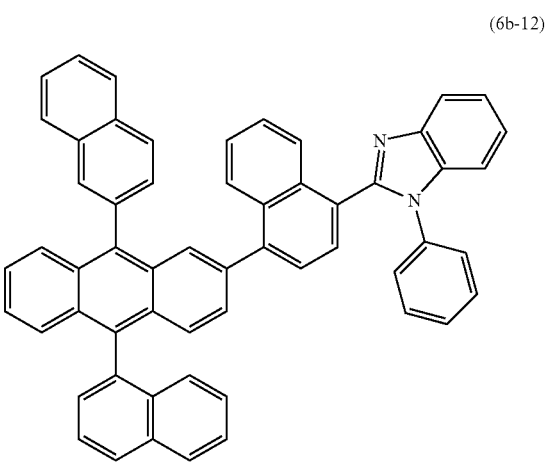
[Chemical Formula 408]
(6b-13)
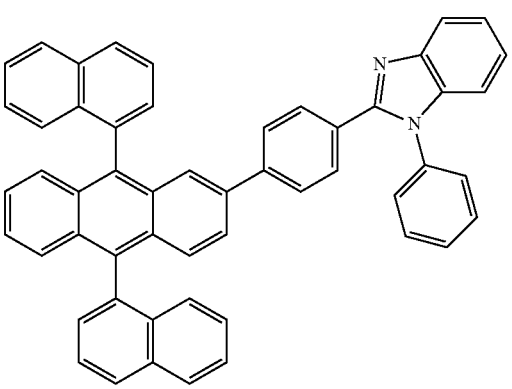
[Chemical Formula 409]
(6b-14)
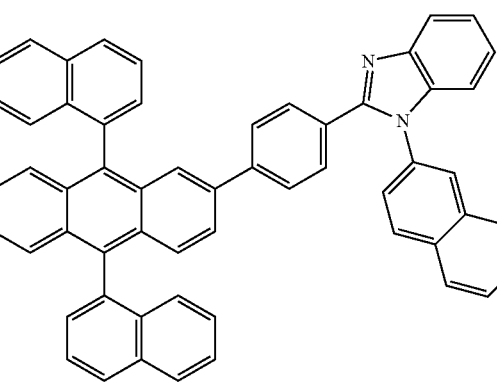

[Chemical Formula 410]

(6b-15)

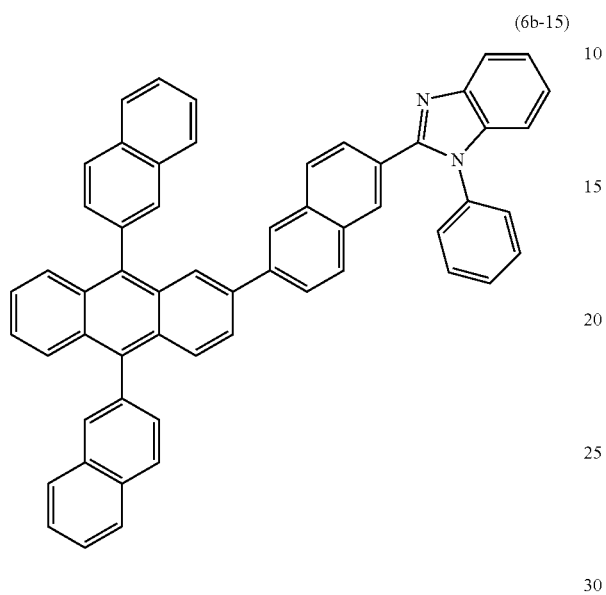

[Chemical Formula 411]

(6b-16)

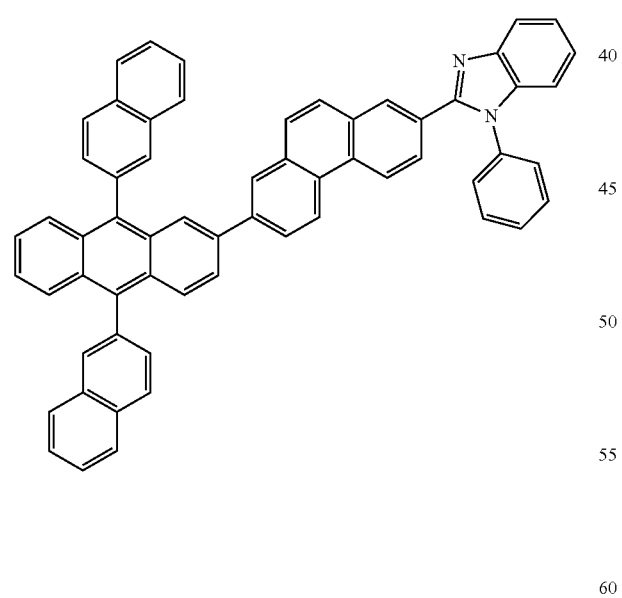

[Chemical Formula 412]

(6c-1)

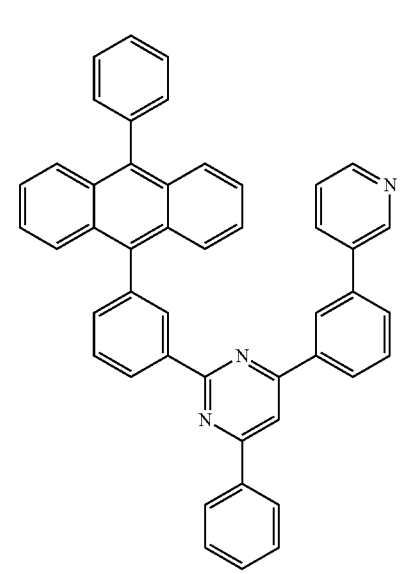

[Chemical Formula 413]

(6c-2)

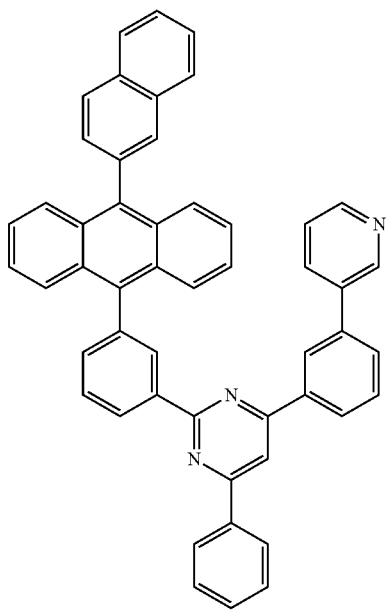

The following presents specific examples of preferred compounds among the compounds of the general formula (6c) preferably used in the organic EL device of the present invention and having an anthracene ring structure. The present invention, however, is not restricted to these compounds.

[Chemical Formula 414]
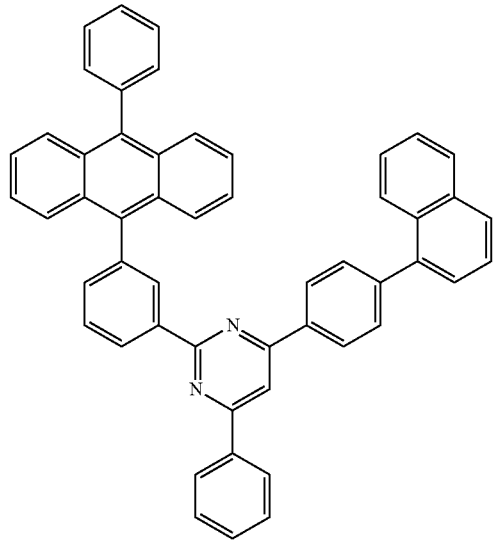
(6c-3)
[Chemical Formula 415]
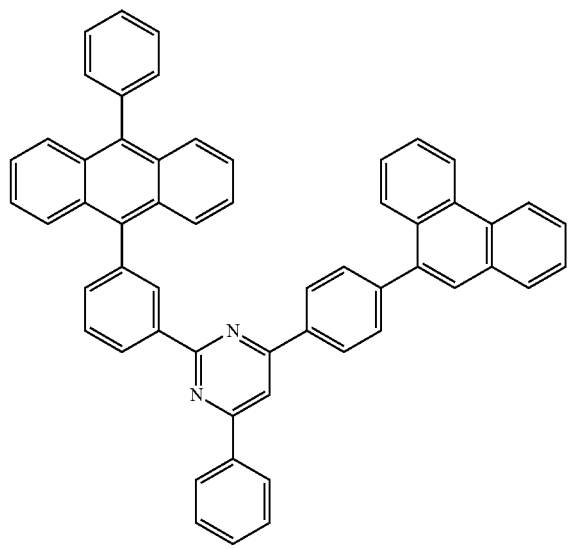
(6c-4)
[Chemical Formula 416]
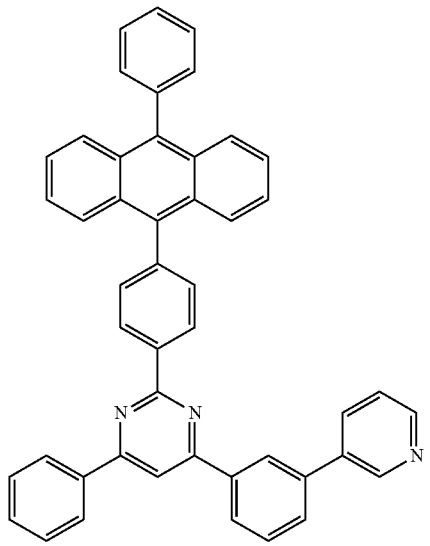
(6c-5)
[Chemical Formula 417]
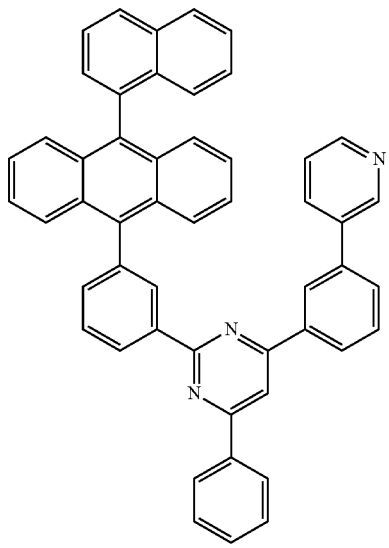
(6c-6)

[Chemical Formula 418]
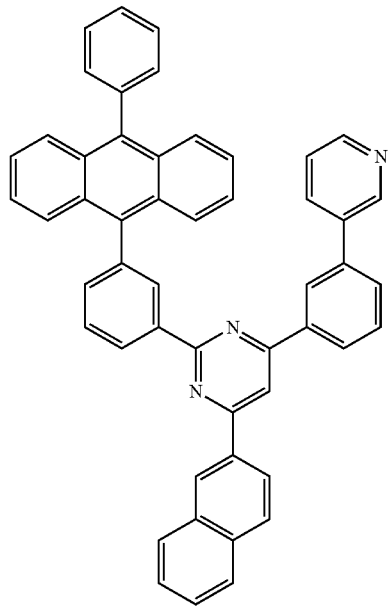
(6c-7)
[Chemical Formula 419]
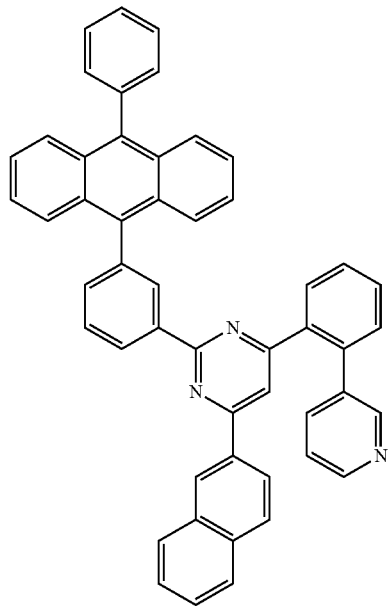
(6c-8)
[Chemical Formula 420]
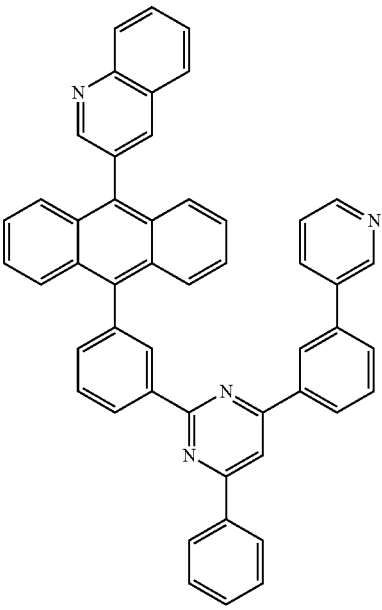
(6c-9)
[Chemical Formula 421]
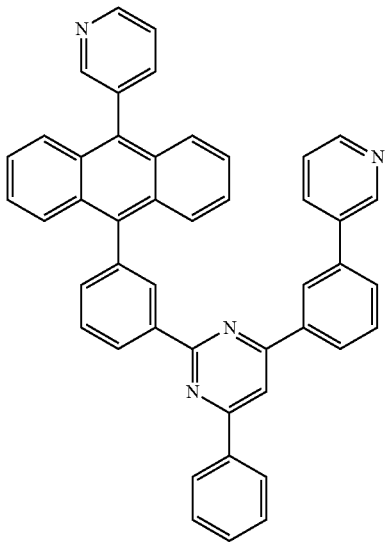
(6c-10)

[Chemical Formula 422]
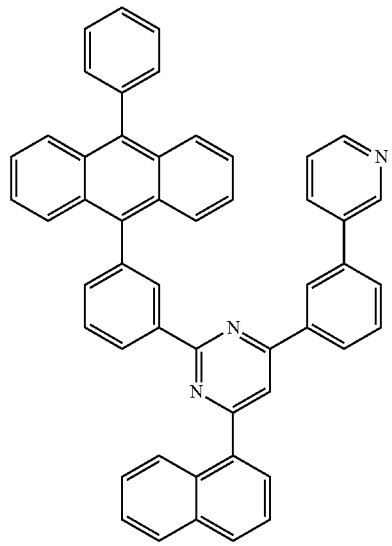
(6c-11)
[Chemical Formula 423]
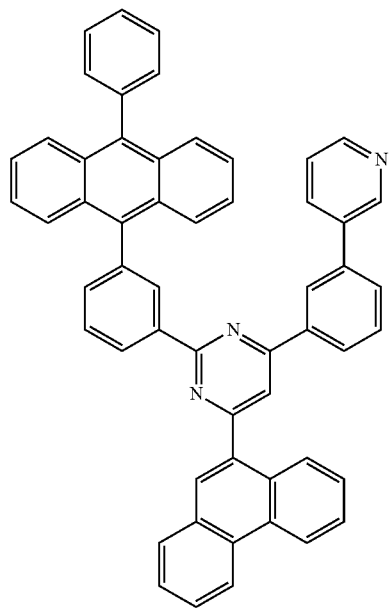
(6c-12)
[Chemical Formula 424]
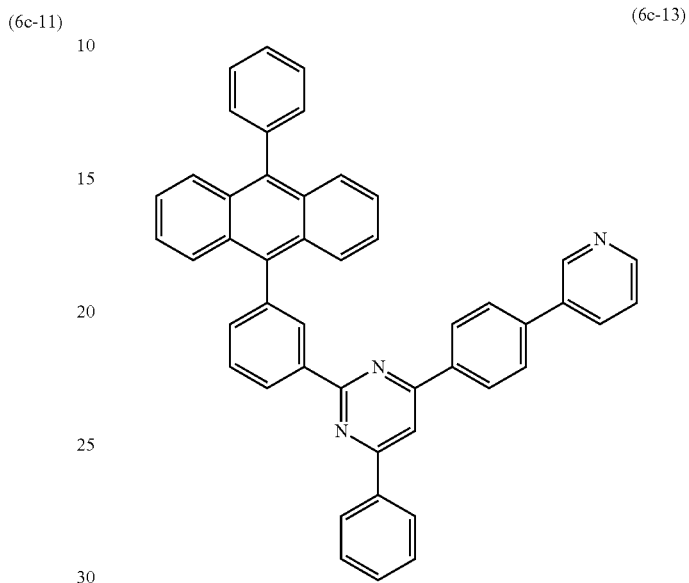
(6c-13)
[Chemical Formula 425]
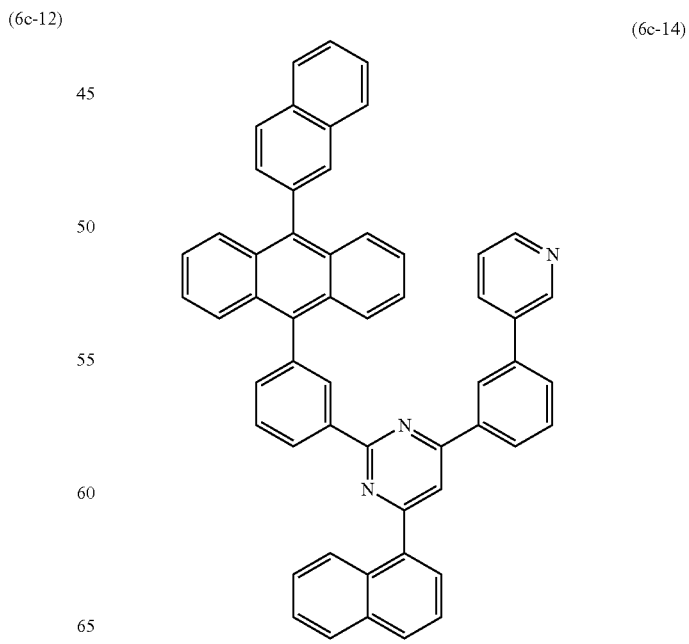
(6c-14)

[Chemical Formula 426]
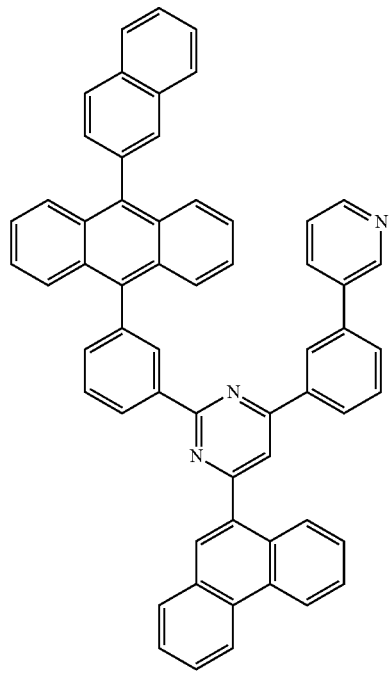
(6c-15)
[Chemical Formula 427]
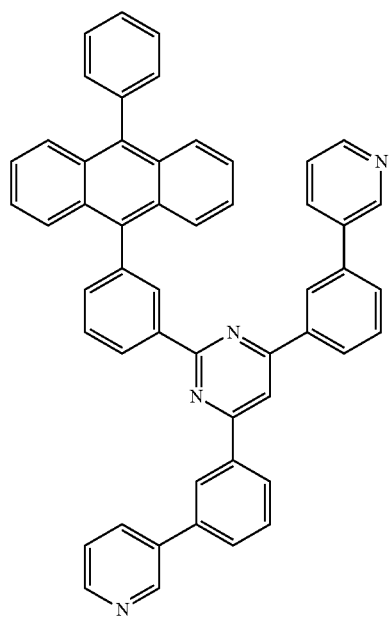
(6c-16)
[Chemical Formula 428]
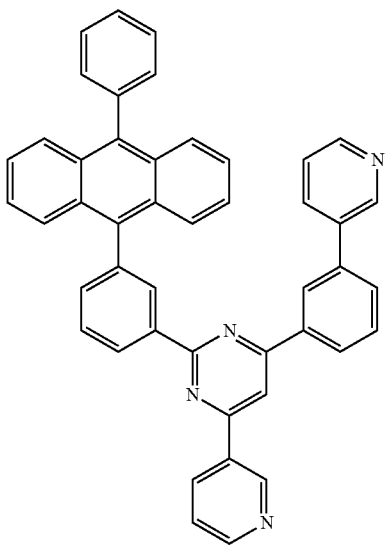
(6c-17)
[Chemical Formula 429]
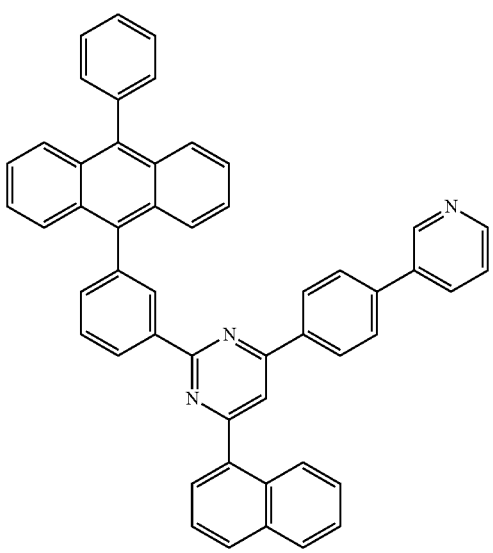
(6c-18)

[Chemical Formula 430]
(6c-19)
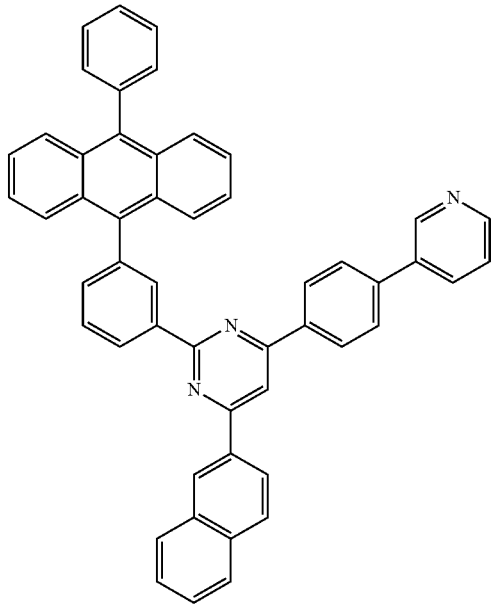
[Chemical Formula 431]
(6c-20)
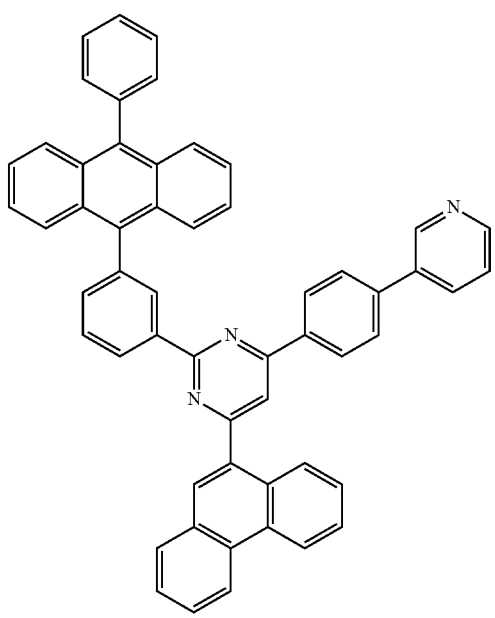
[Chemical Formula 432]
(6c-21)
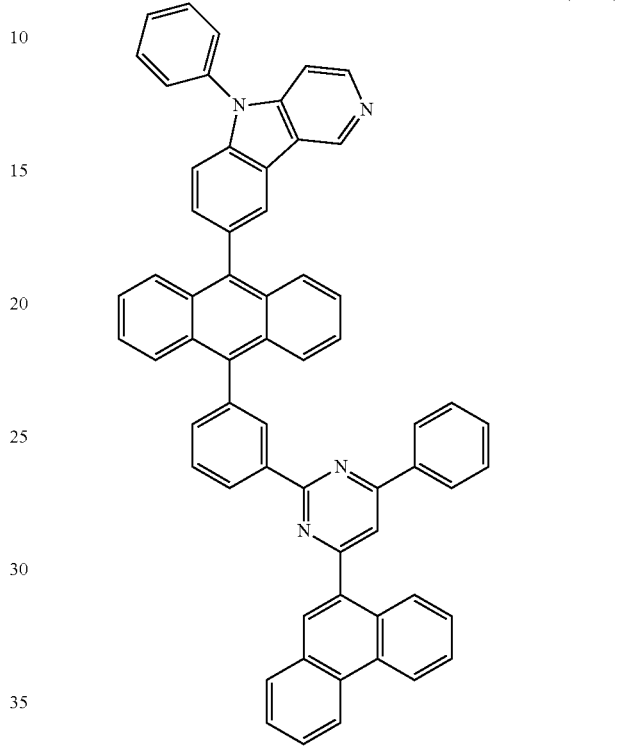
[Chemical Formula 433]
(6c-22)
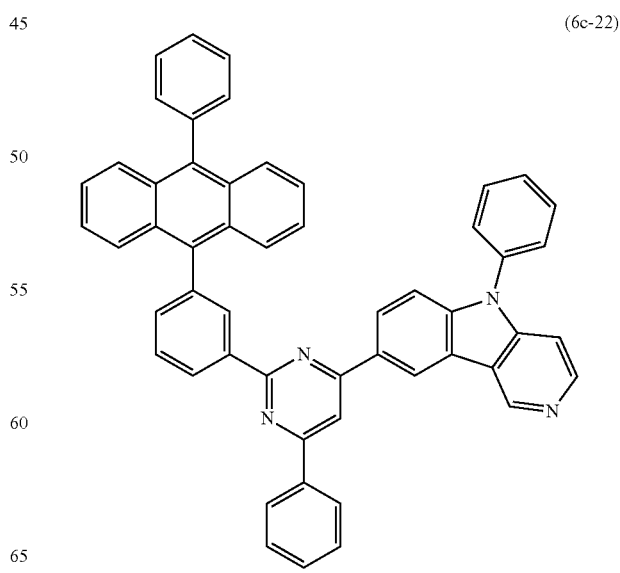

[Chemical Formula 434]
(6c-23)
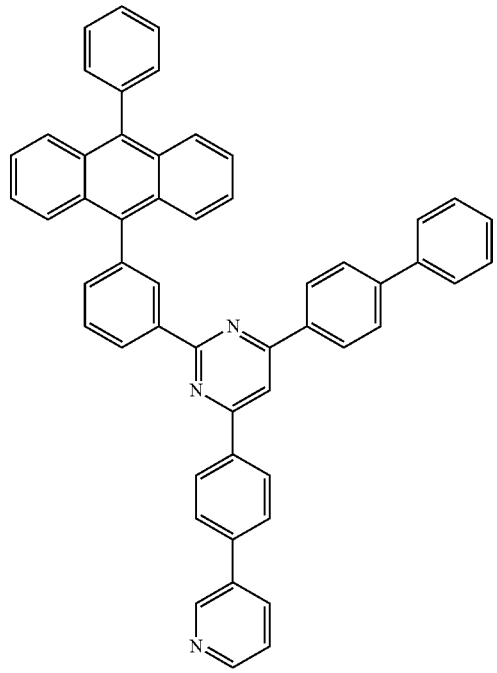
[Chemical Formula 435]
(6c-24)
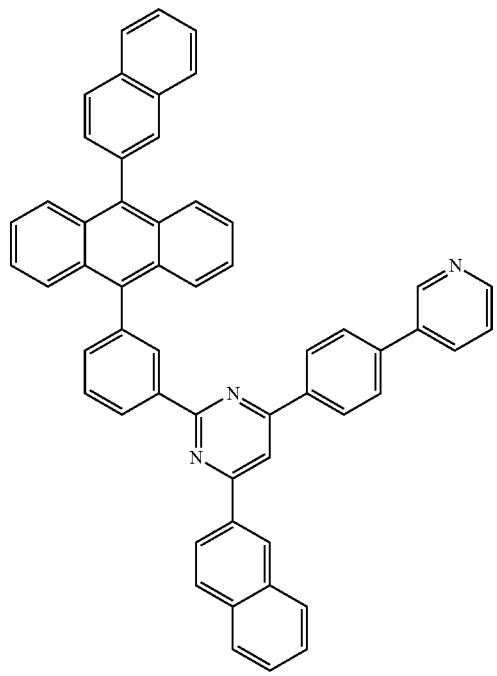
[Chemical Formula 436]
(6c-25)
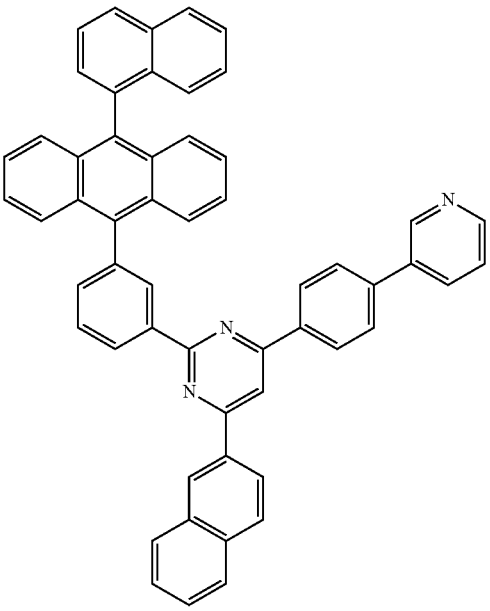
[Chemical Formula 437]
(6c-26)
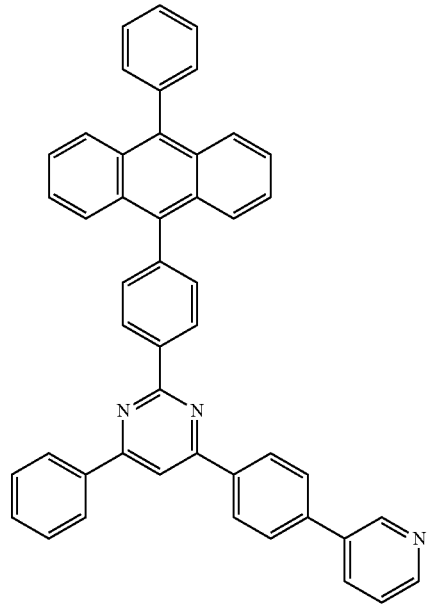

[Chemical Formula 438]

(6c-27)

[Chemical Formula 439]

(6c-28)

[Chemical Formula 440]

(6c-29)

[Chemical Formula 441]

(6c-30)

The compounds described above having an anthracene ring structure can be synthesized according to a known method (refer to Patent Documents 10 to 12, for example).

The following presents specific examples of preferred compounds among the compounds of the general formula (7) preferably used in the organic EL device of the present invention and having a pyrimidine ring structure. The present invention, however, is not restricted to these compounds.

[Chemical Formula 442]
(7-1)
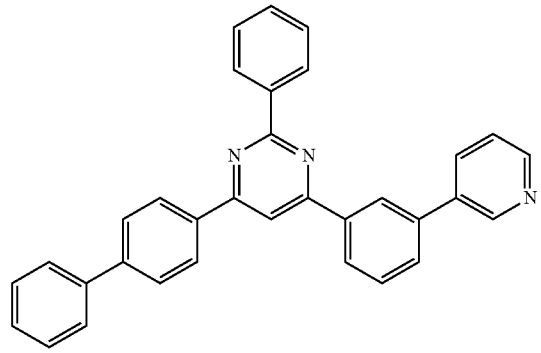
[Chemical Formula 443]
(7-2)
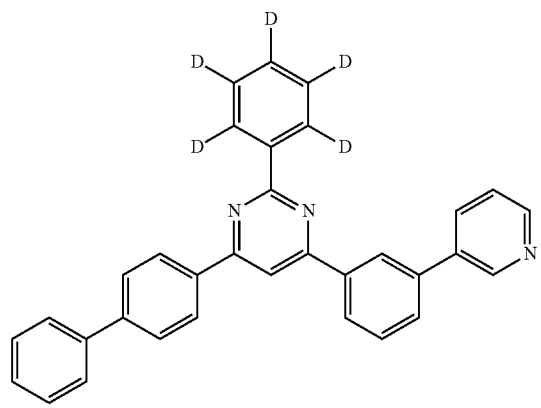
[Chemical Formula 444]
(7-3)
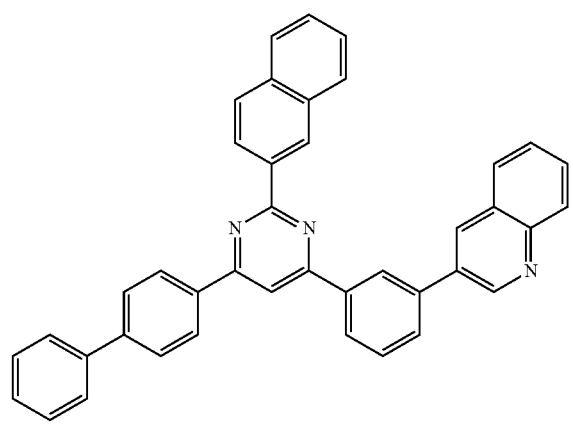
[Chemical Formula 445]
(7-4)
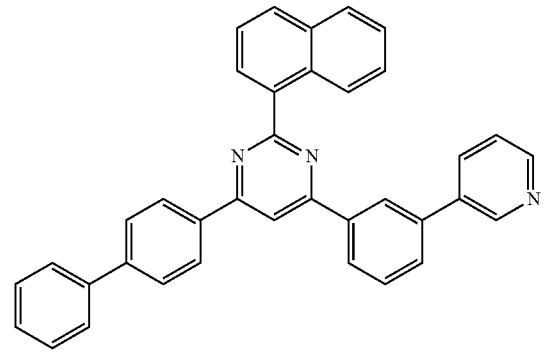
[Chemical Formula 446]
(7-5)
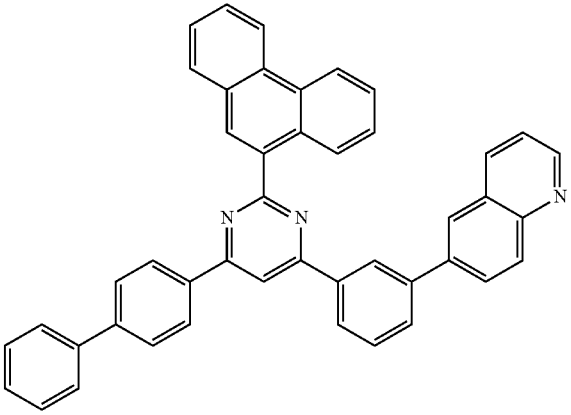
[Chemical Formula 447]
(7-6)
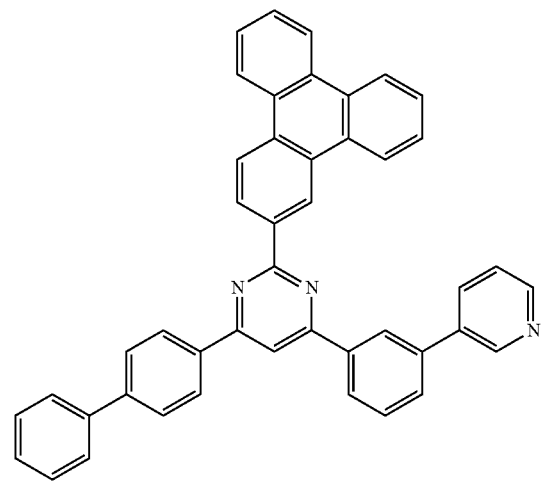

[Chemical Formula 448]
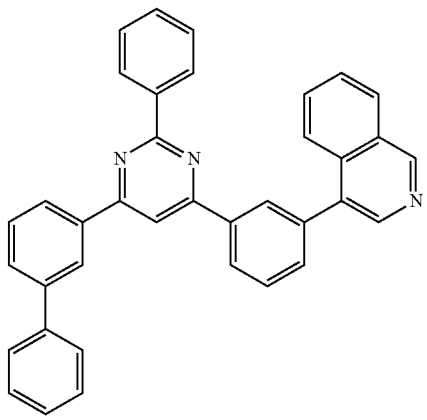
(7-7)
[Chemical Formula 449]
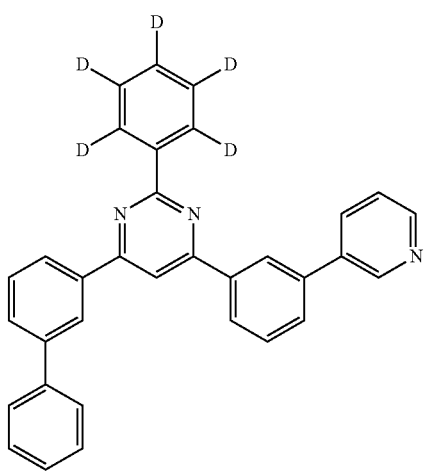
(7-8)
[Chemical Formula 450]
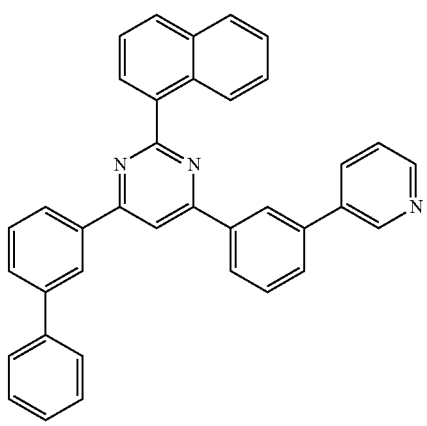
(7-9)
[Chemical Fromula 451]
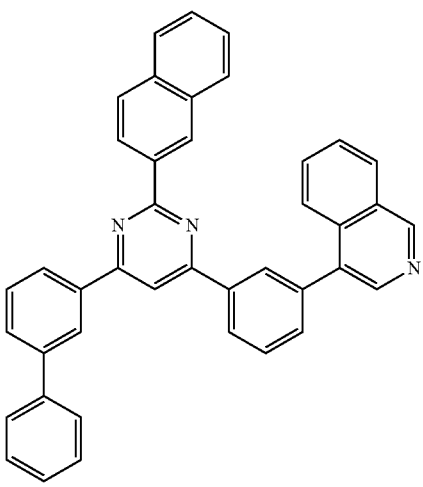
(7-10)
[Chemical Fromula 452]
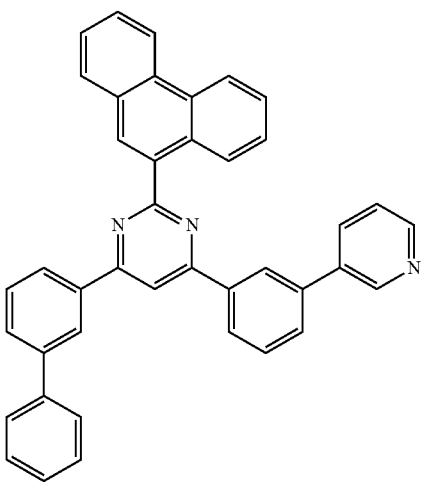
(7-11)
[Chemical Fromula 453]
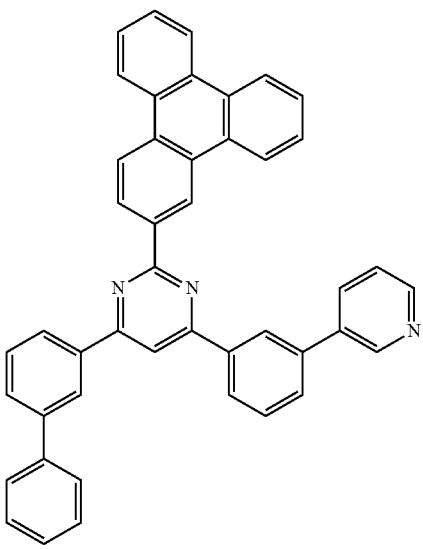
(7-12)

[Chemical Formula 454]
(7-13)
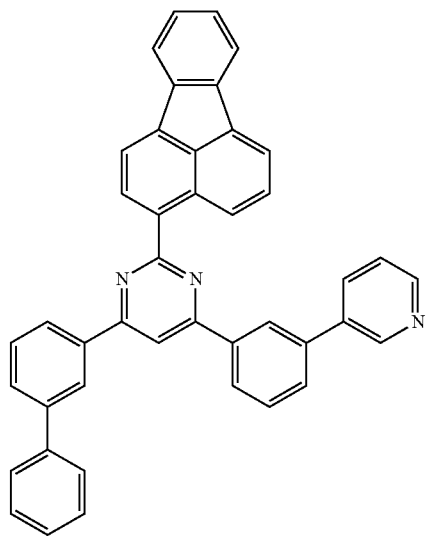
[Chemical Formula 455]
(7-14)
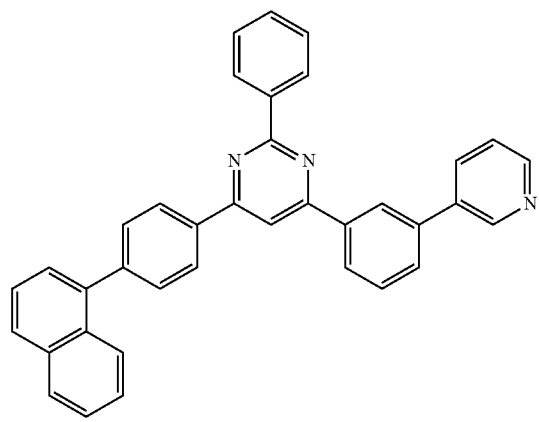
[Chemical Formula 456]
(7-15)
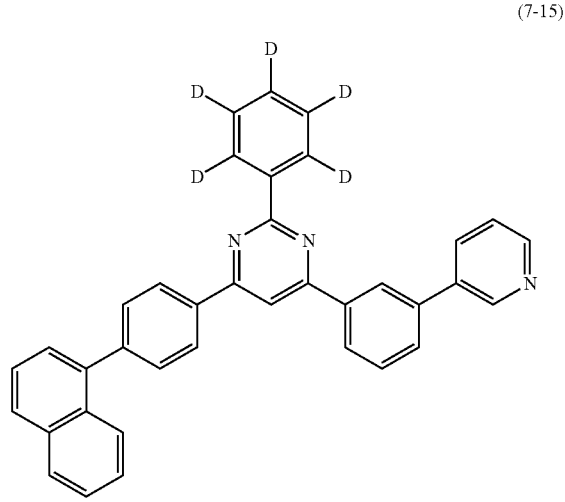
[Chemical Formula 457]
(7-16)
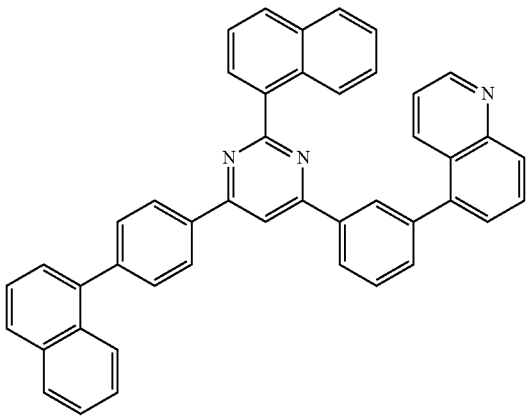
[Chemical Formula 458]
(7-17)
[Chemical Formula 459]
(7-18)
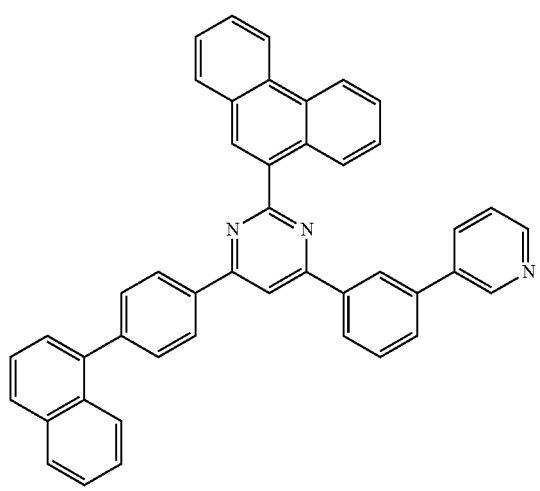

[Chemical Formula 460]
(7-19)
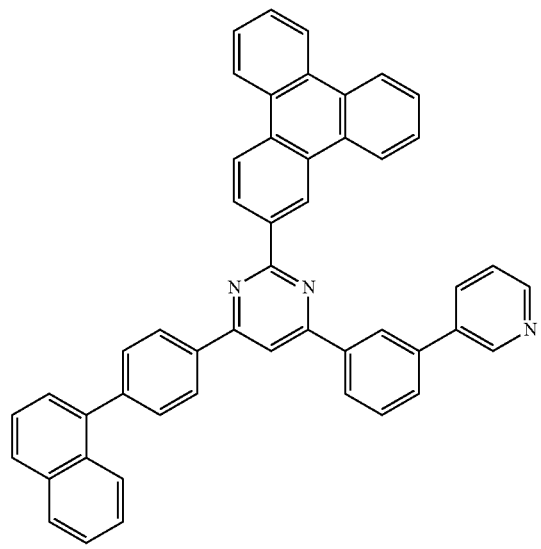
[Chemical Formula 461]
(7-20)
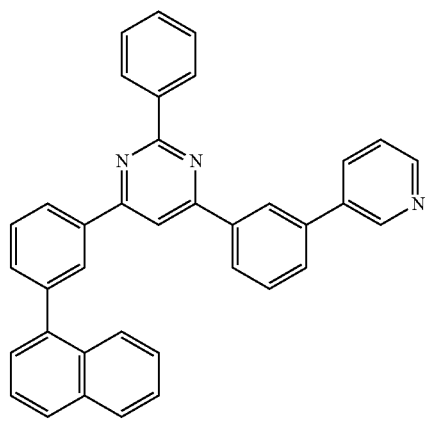
[Chemical Formula 462]
(7-21)
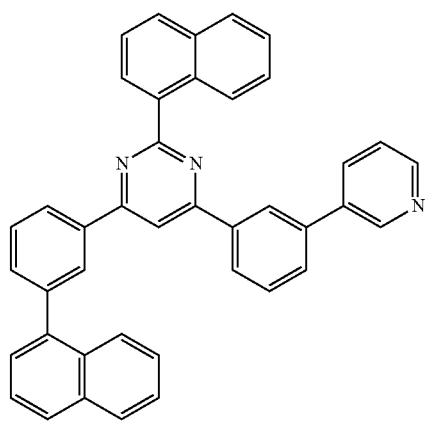
[Chemical Formula 463]
(7-22)
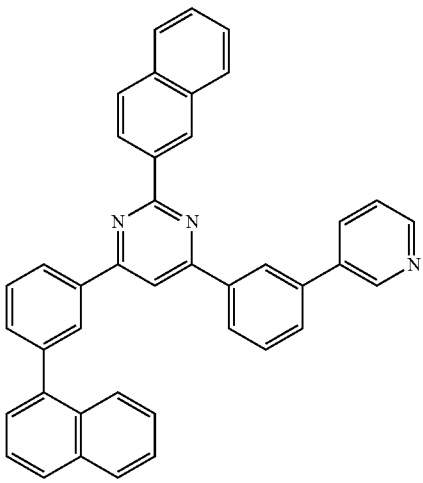
[Chemical Formula 464]
(7-23)
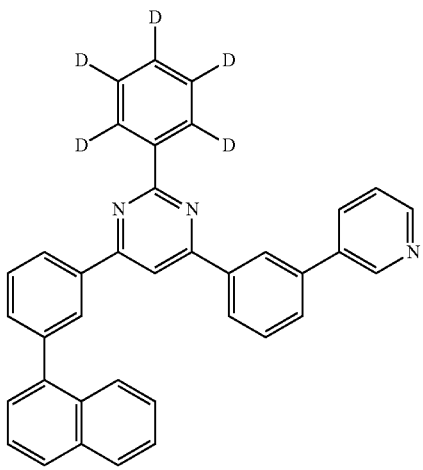
[Chemical Formula 465]
(7-24)
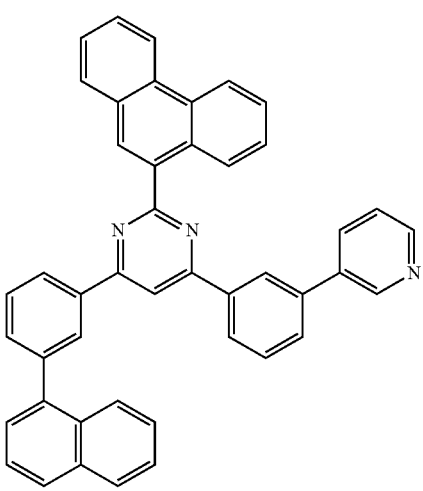

[Chemical Formula 466]
(7-25)
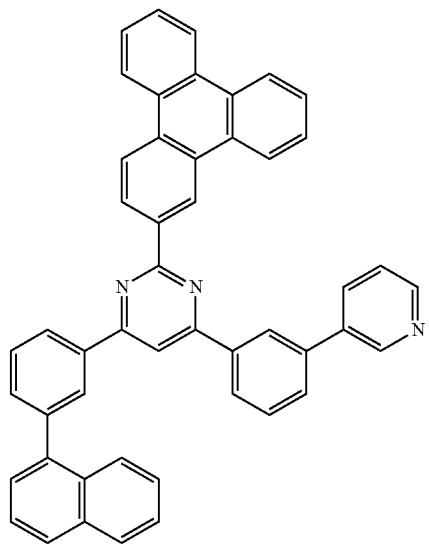
[Chemical Formula 467]
(7-26)
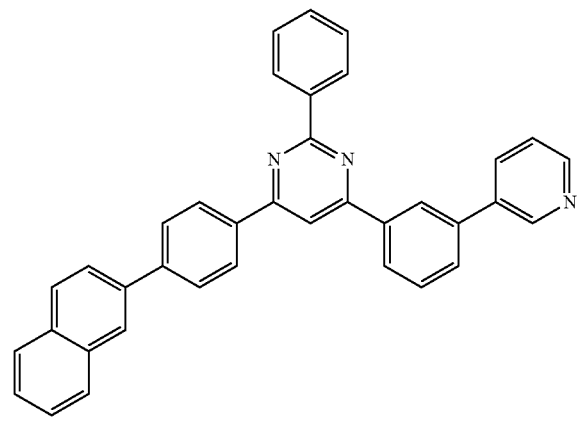
[Chemical Formula 468]
(7-27)
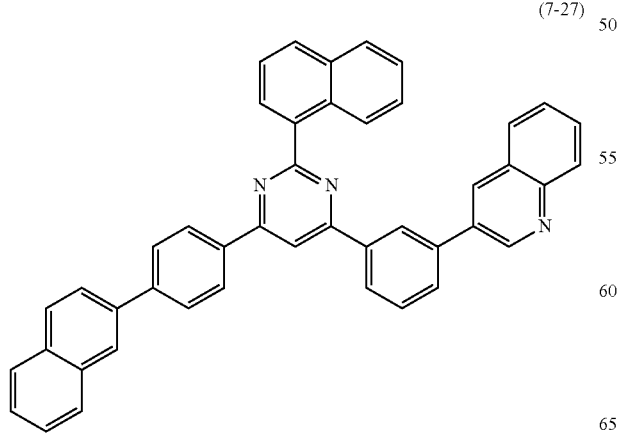
[Chemical Formula 469]
(7-28)
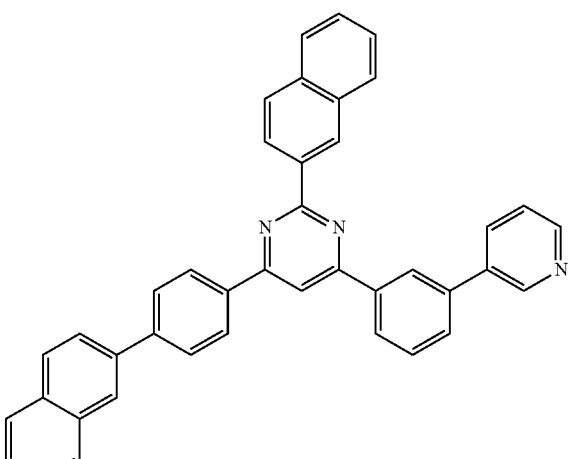
[Chemical Formula 470]
(7-29)
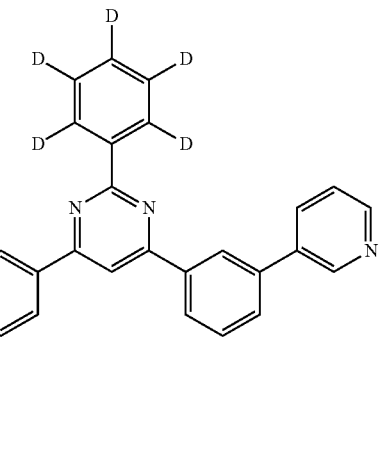
[Chemical Formula 471]
(7-30)
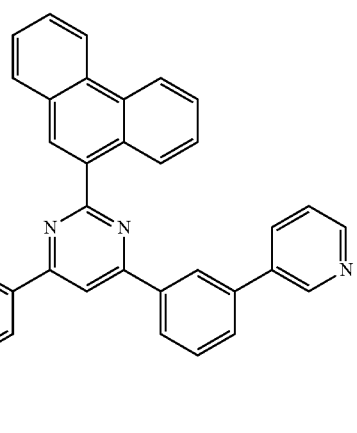

[Chemical Formula 472]
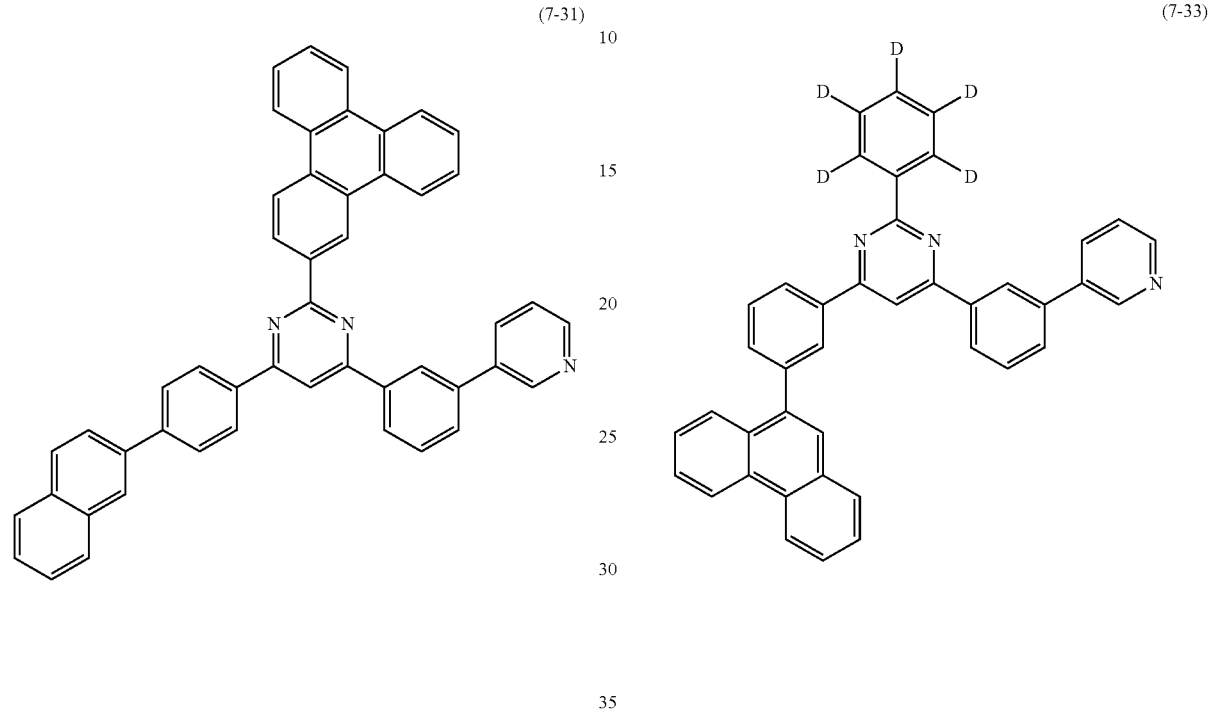
[Chemical Formula 473]
[Chemical Formula 474]
[Chemical Formula 475]
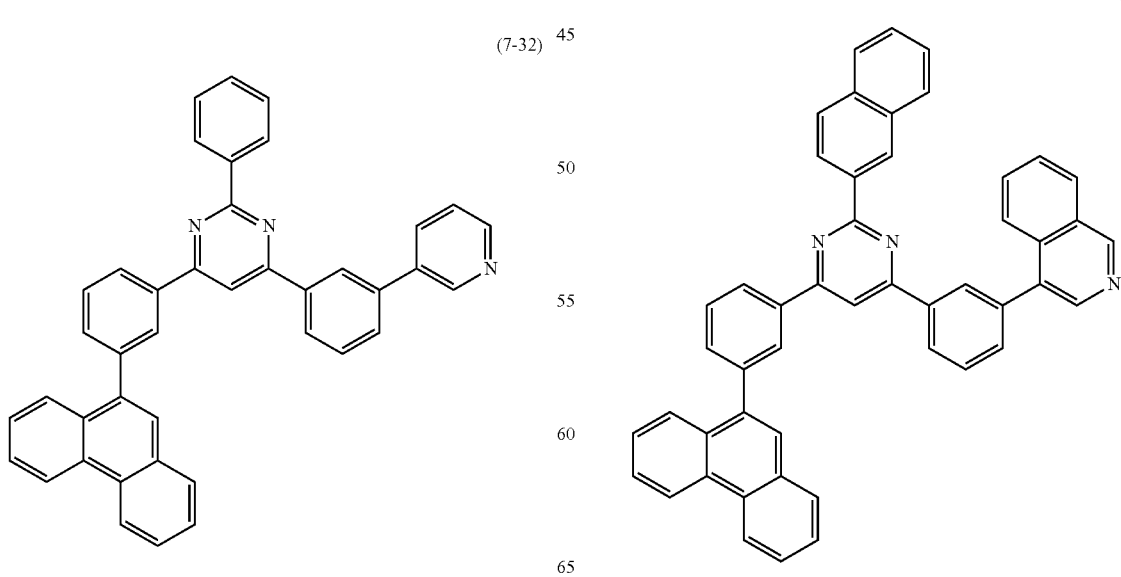

[Chemical Formula 476]
(7-35)
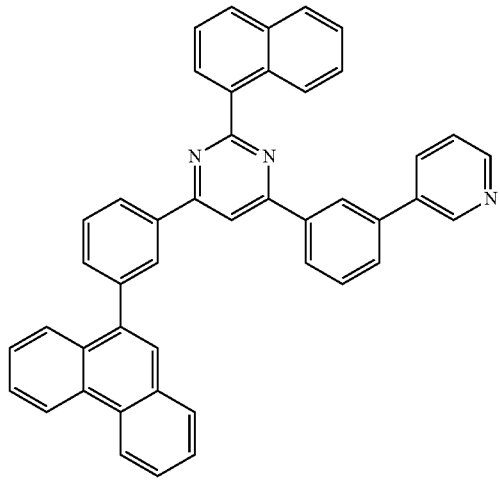
[Chemical Formula 477]
(7-36)
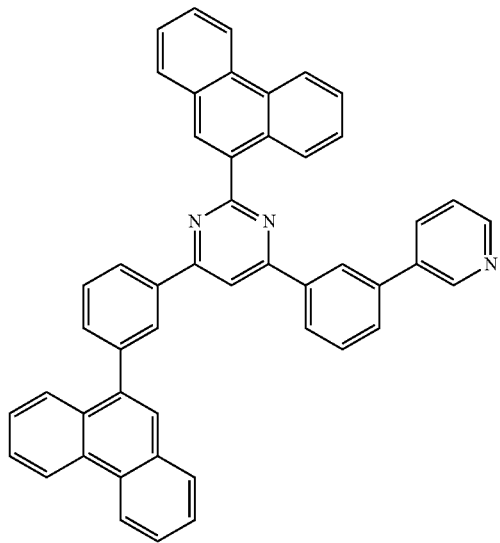
[Chemical Formula 478]
(7-37)
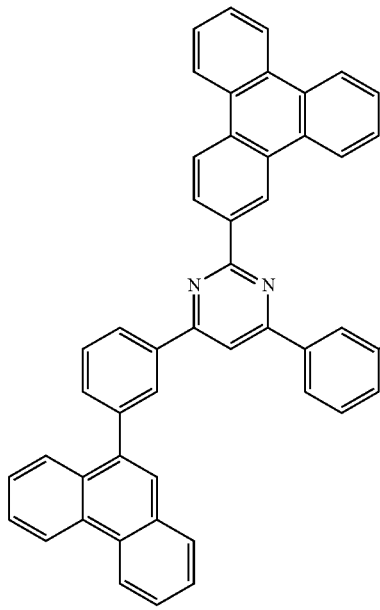
[Chemical Formula 479]
(7-38)
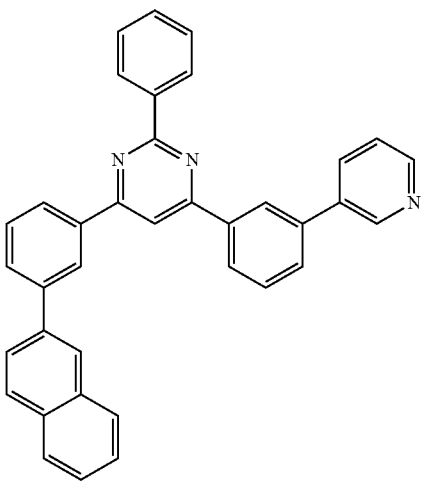
[Chemical Formula 480]
(7-39)
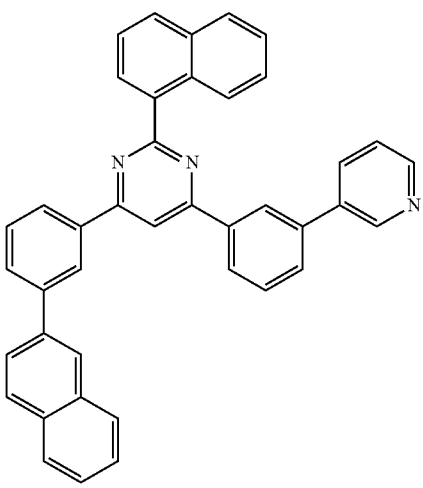

[Chemical Formula 481]
(7-40)
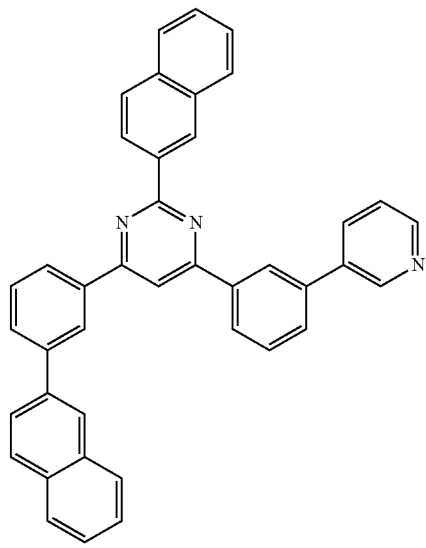
[Chemical Formula 482]
(7-41)
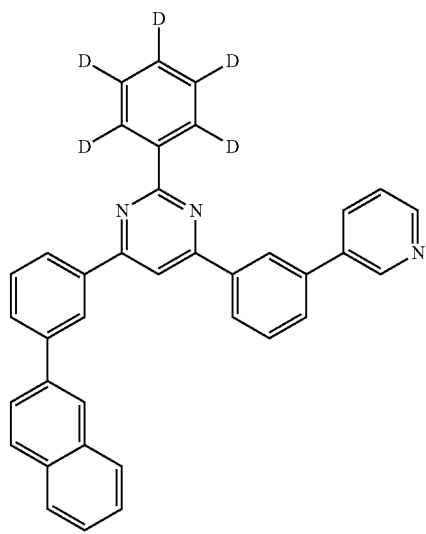
[Chemical Formula 483]
(7-42)
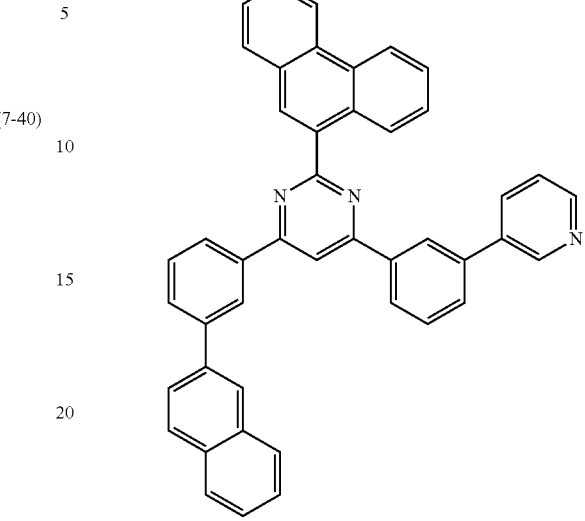
[Chemical Formula 484]
(7-43)
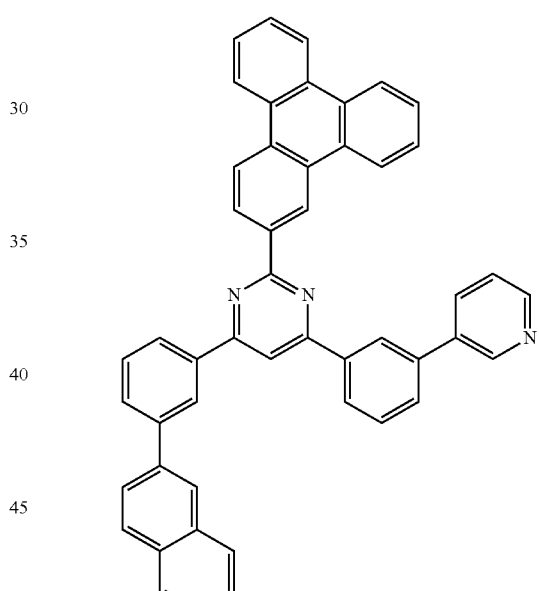
[Chemical Formula 485]
(7-44)
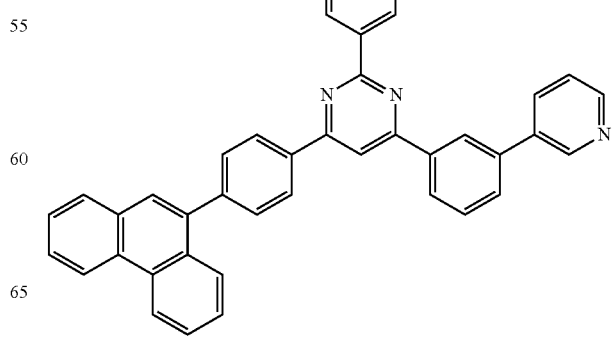

[Chemical Formula 486]
(7-45)
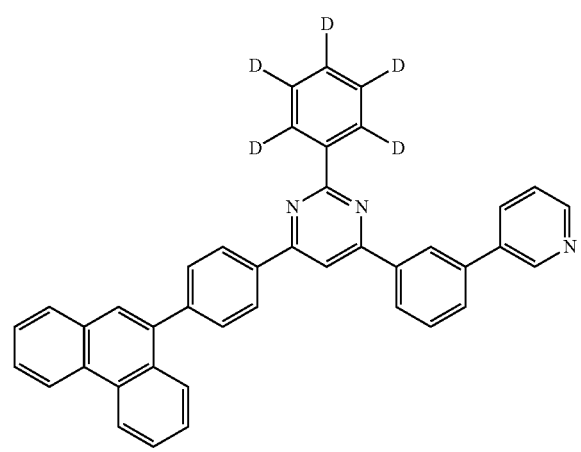
[Chemical Formula 487]
(7-46)
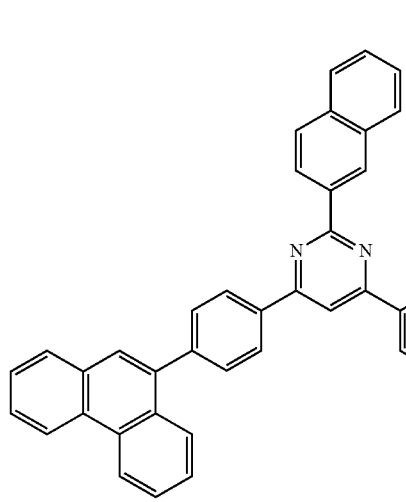
[Chemical Formula 488]
(7-47)
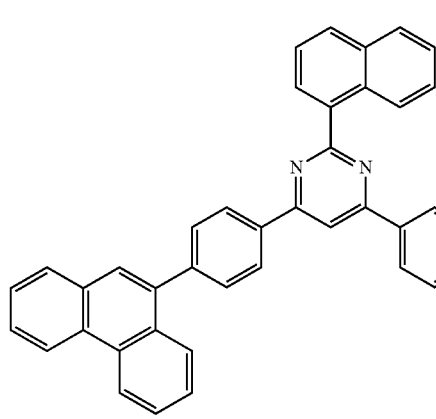
[Chemical Formula 489]
(7-48)
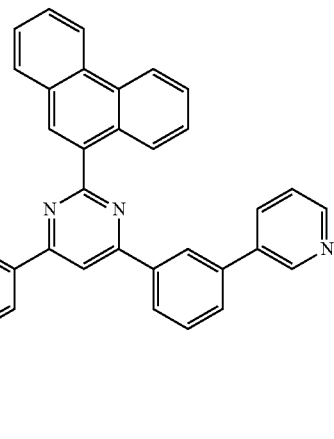
[Chemical Formula 490]
(7-49)
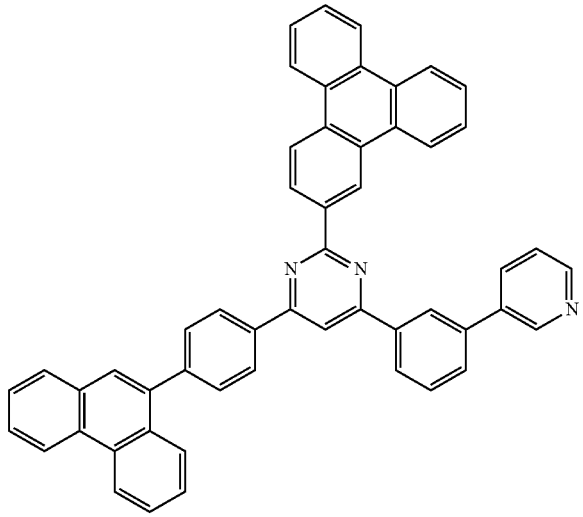
[Chemical Formula 491]
(7-50)
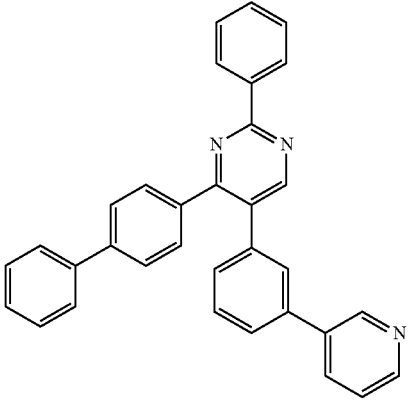

[Chemical Formula 492]
(7-51)
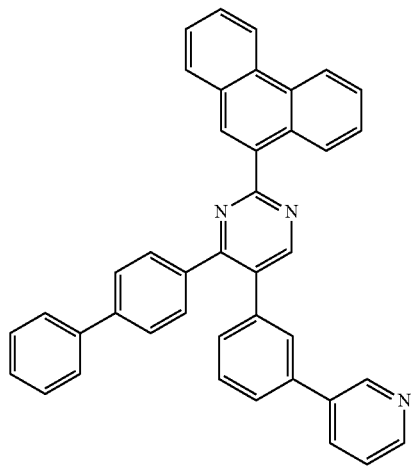
[Chemical Formula 493]
(7-52)
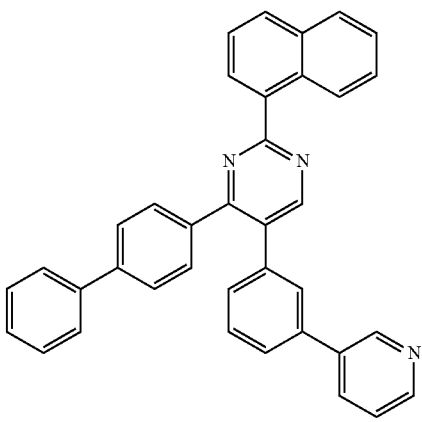
[Chemical Formula 494]
(7-53)
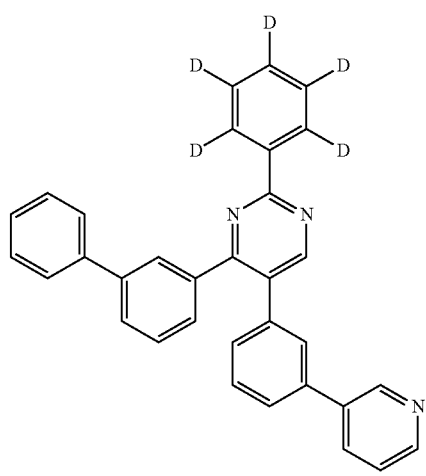
[Chemical Formula 495]
(7-54)
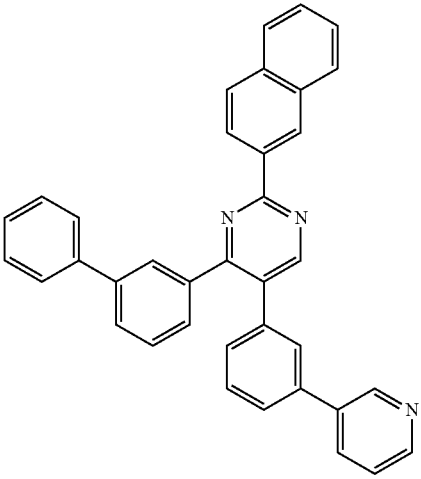
[Chemical Formula 496]
(7-55)
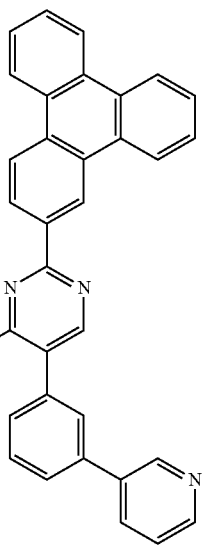
[Chemical Formula 497]
(7-56)
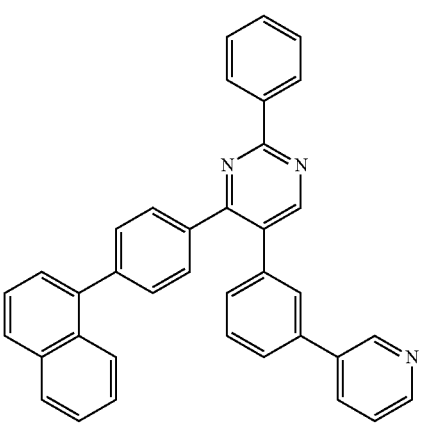

[Chemical Formula 498]
(7-57)
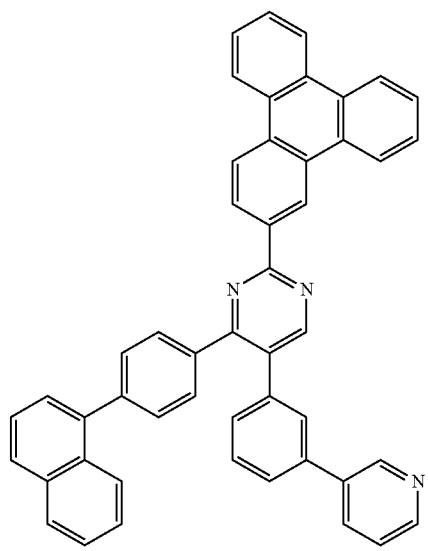
[Chemical Formula 499]
(7-58)
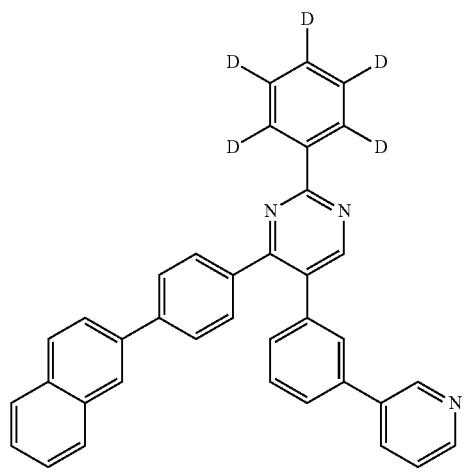
[Chemical Formula 500]
(7-59)
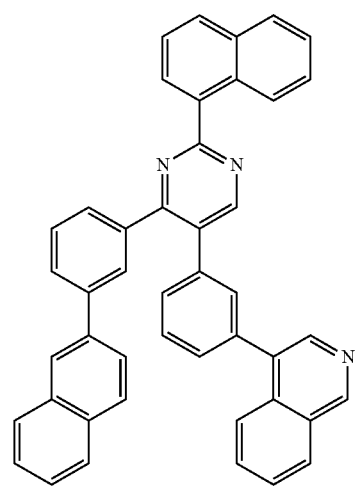
[Chemical Formula 501]
(7-60)
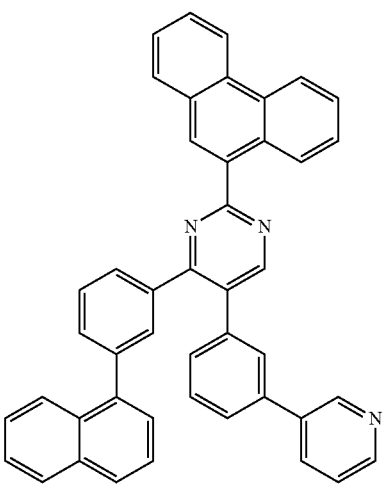
[Chemical Formula 502]
(7-61)
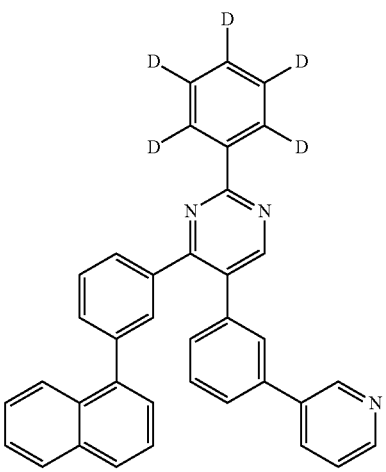
[Chemical Formula 503]
(7-62)
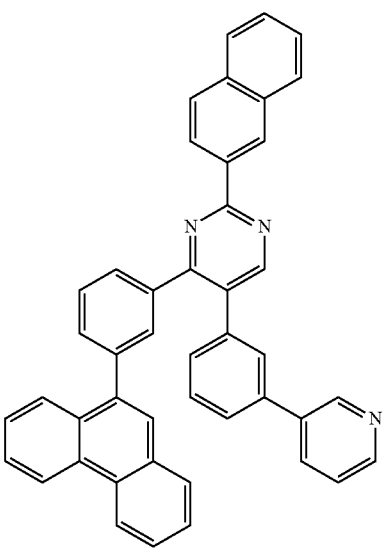

[Chemical Formula 504]
(7-63)
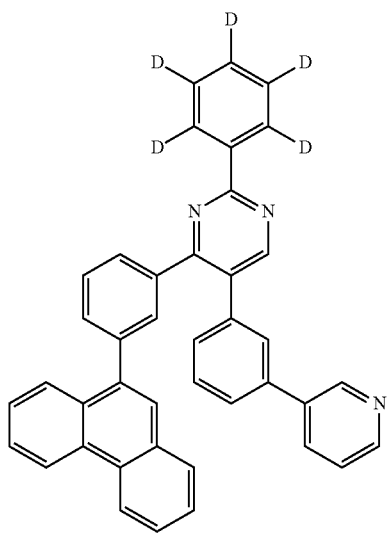
[Chemical Formula 505]
(7-64)
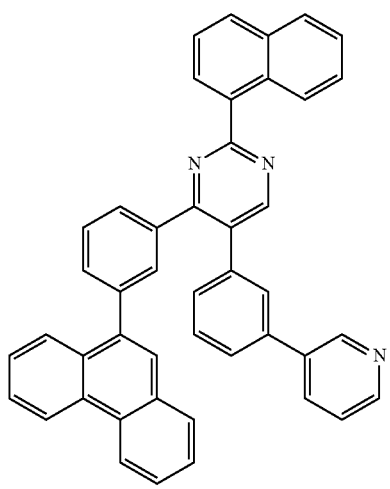
[Chemical Formula 506]
(7-65)
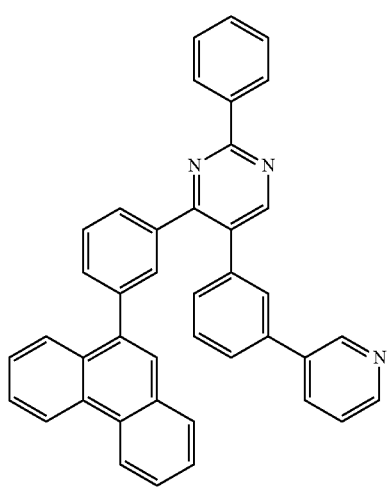
[Chemical Formula 507]
(7-66)
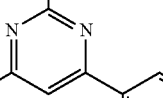
[Chemical Formula 508]
(7-67)
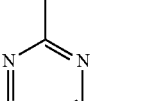
[Chemical Formula 509]
(7-68)
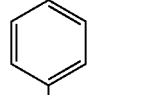

[Chemical Formula 510]
(7-69)
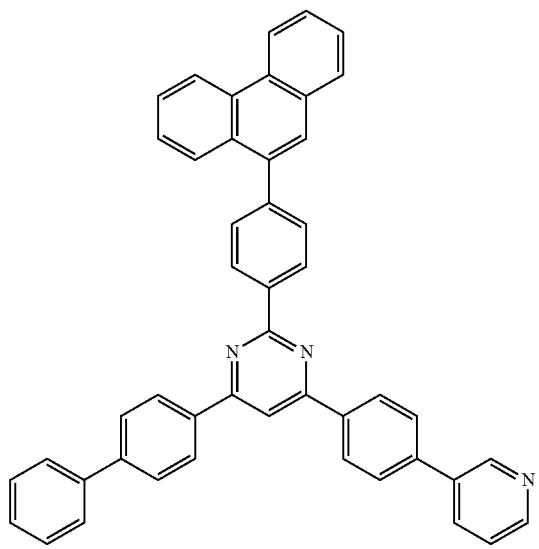
[Chemical Formula 511]
(7-70)
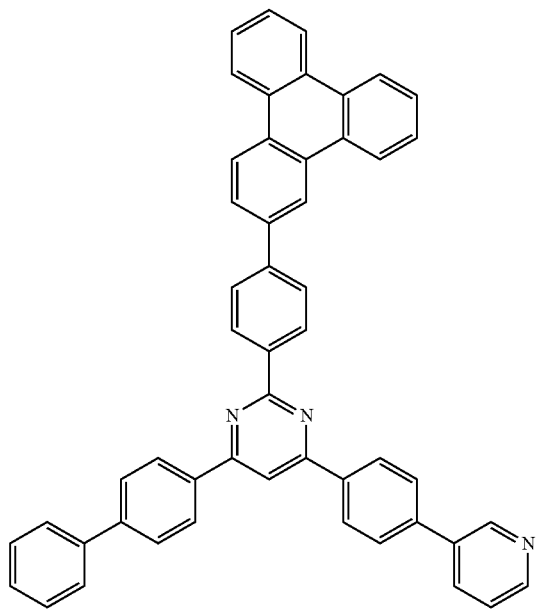
[Chemical Formula 512]
(7-71)
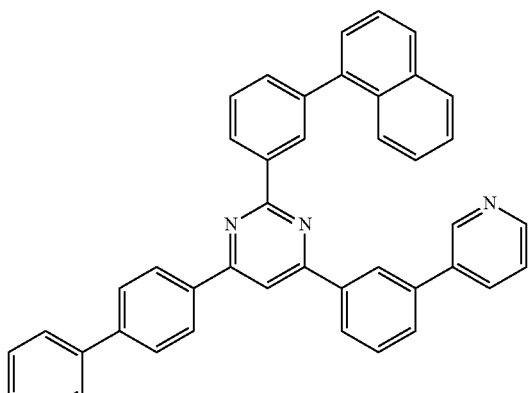
[Chemical Formula 513]
(7-72)
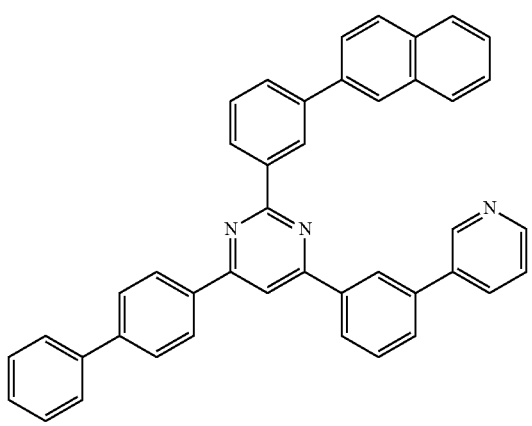
[Chemical Formula 514]
(7-73)
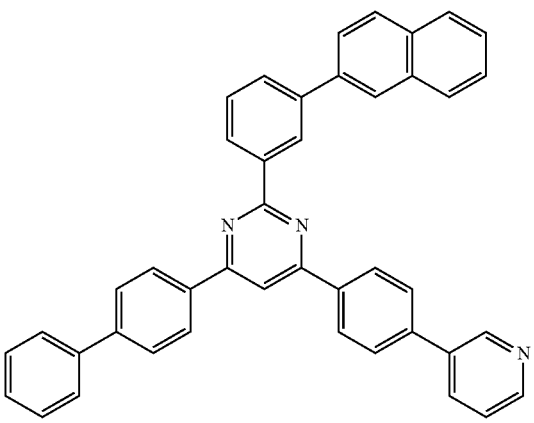

[Chemical Formula 515]
(7-74)
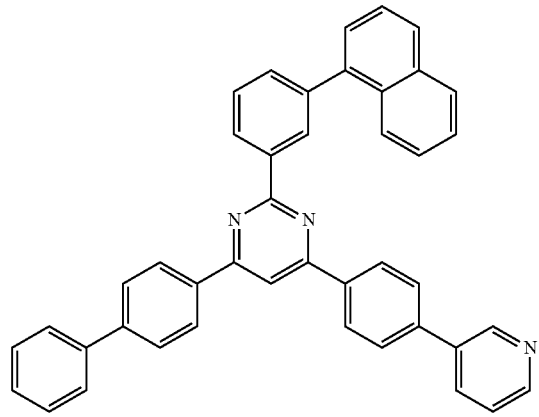
[Chemical Formula 516]
(7-75)
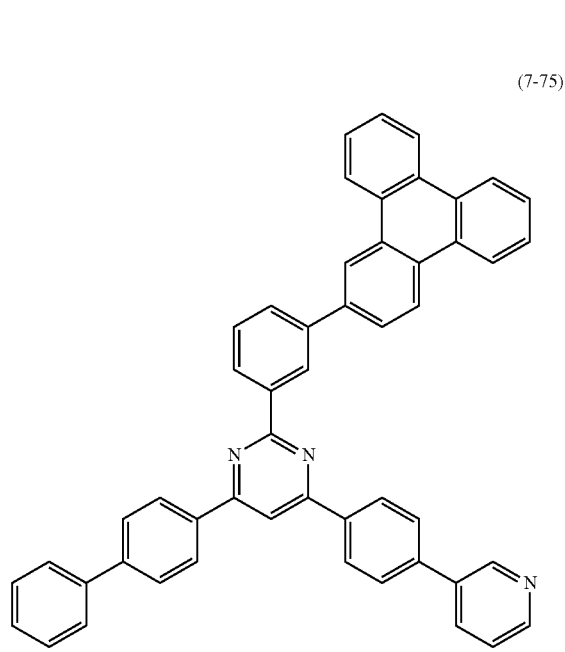
[Chemical Formula 517]
(7-76)
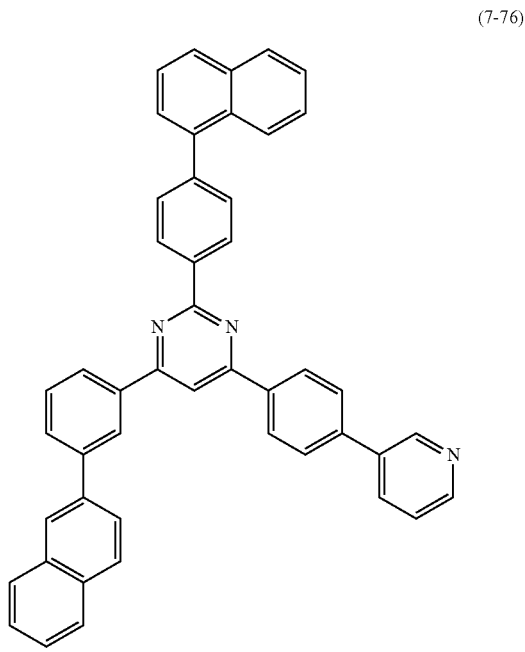
[Chemical Formula 518]
(7-77)
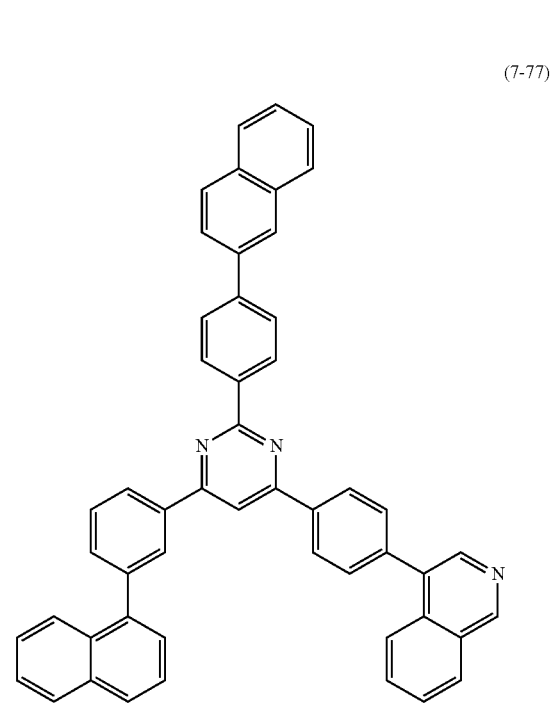

[Chemical Formula 519]
(7-78)
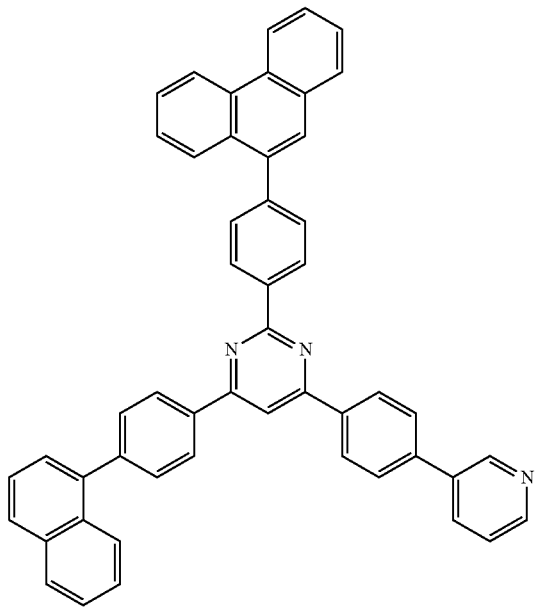
[Chemical Formula 520]
(7-79)
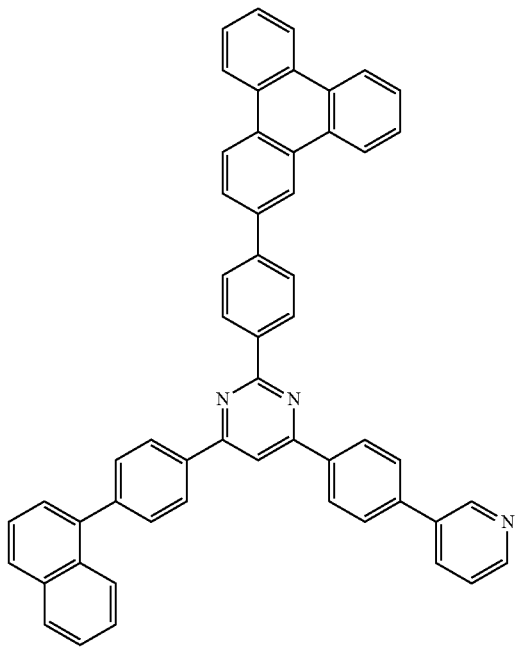
[Chemical Formula 521]
(7-80)
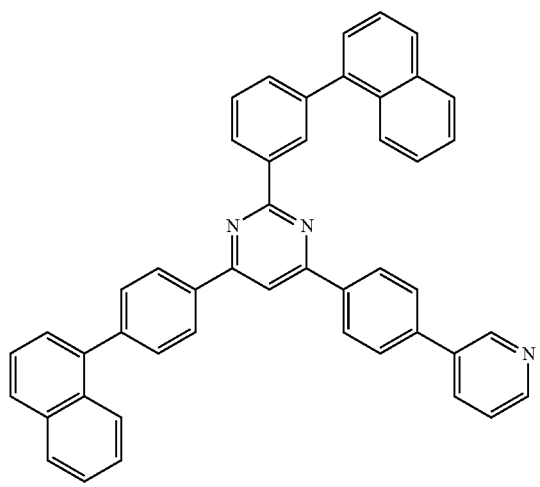
[Chemical Formula 522]
(7-81)
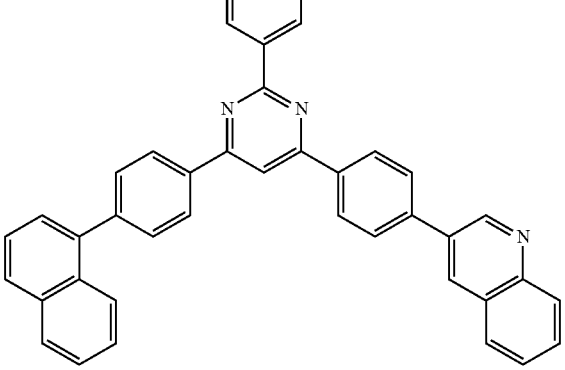
[Chemical Formula 523]
(7-82)
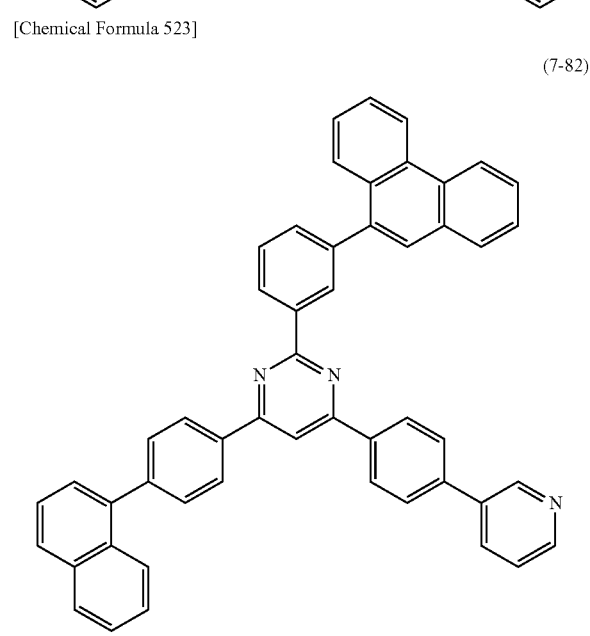

[Chemical Formula 524]
(7-83)
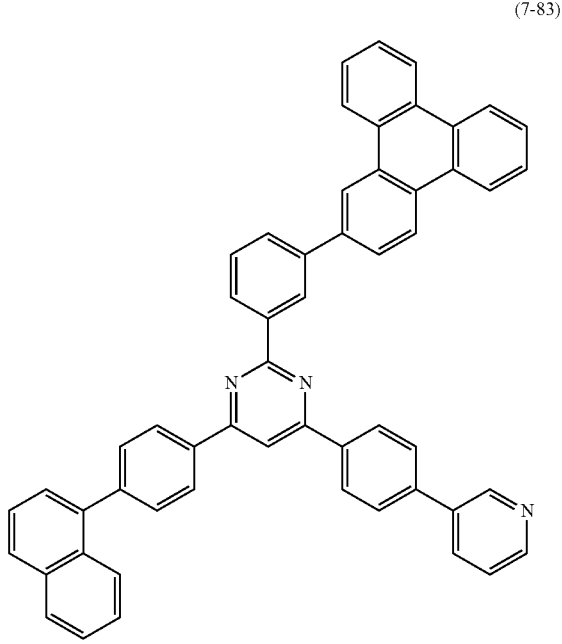
[Chemical Formula 525]
(7-84)
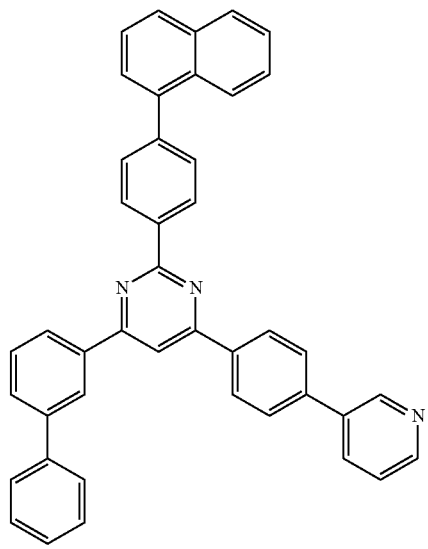
[Chemical Formula 526]
(7-85)
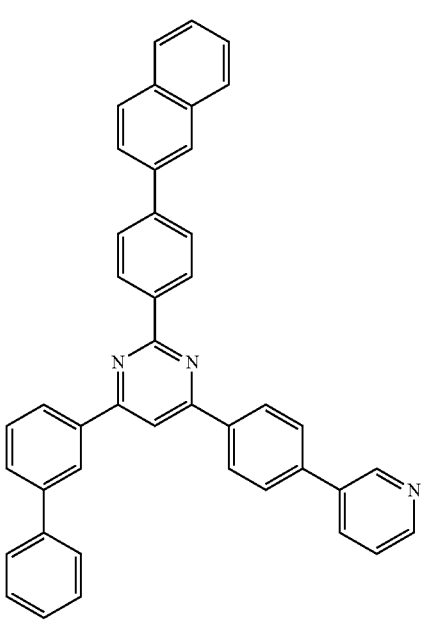
[Chemical Formula 527]
(7-86)
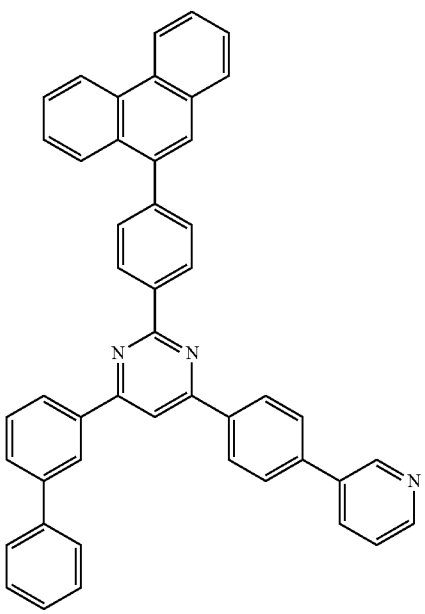

[Chemical Formula 528]
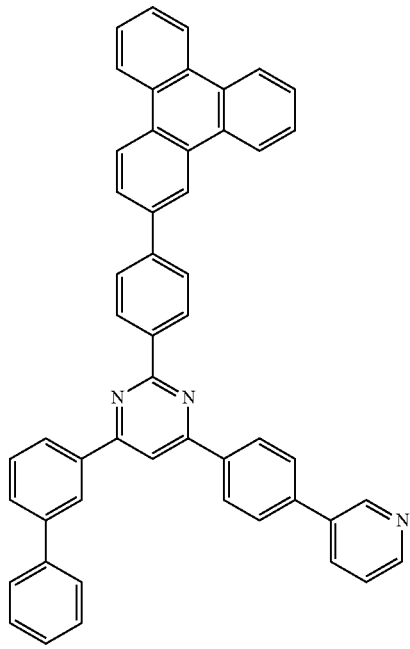
(7-87)
[Chemical Formula 529]
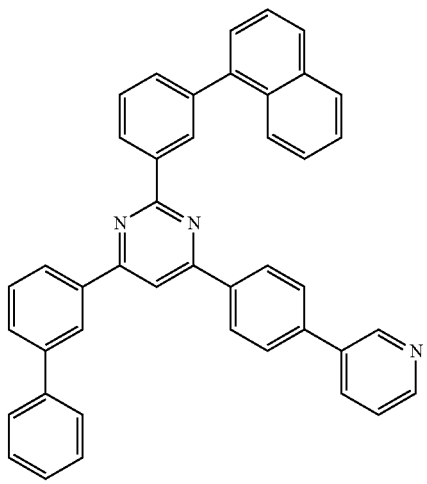
(7-88)
[Chemical Formula 530]
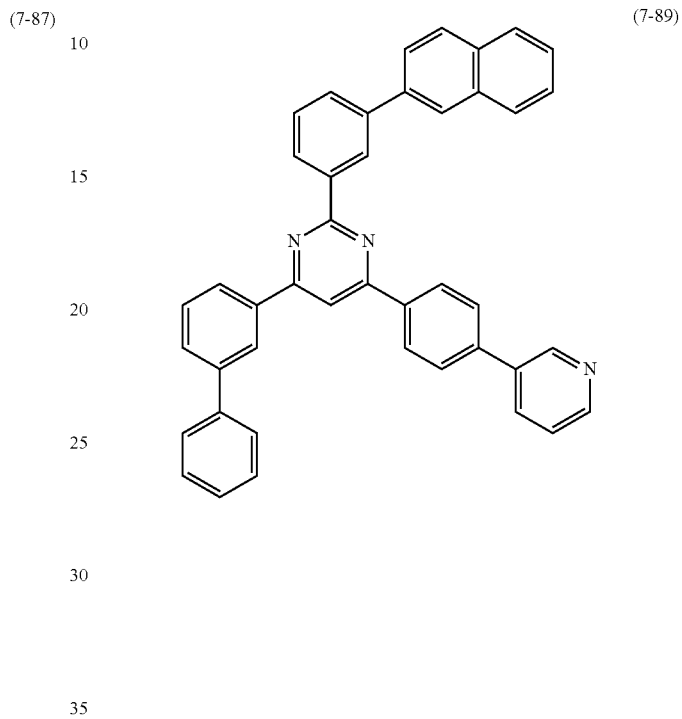
(7-89)
[Chemical Formula 531]
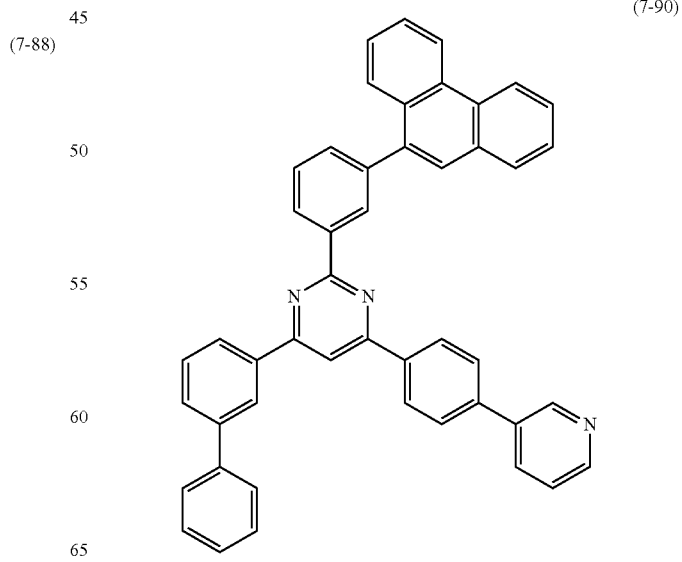
(7-90)

[Chemical Formula 532]
(7-91)
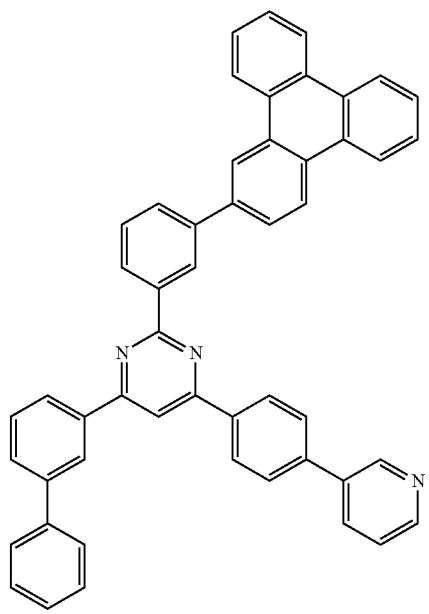
[Chemical Formula 533]
(7-92)
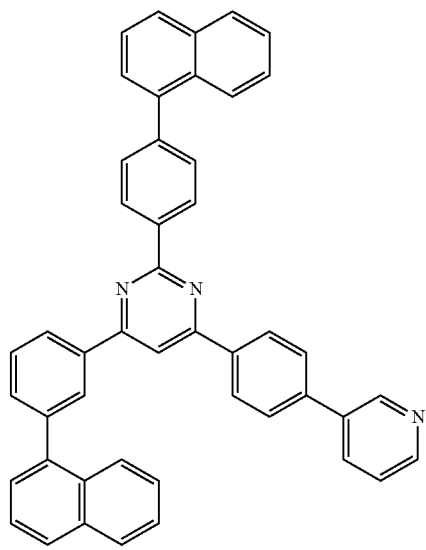
[Chemical Formula 534]
(7-93)
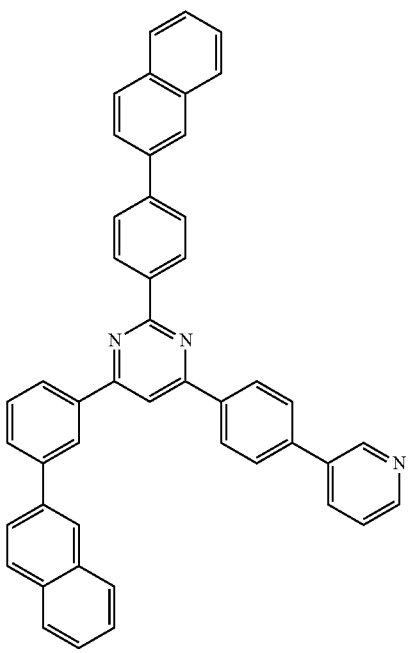
[Chemical Formula 535]
(7-94)
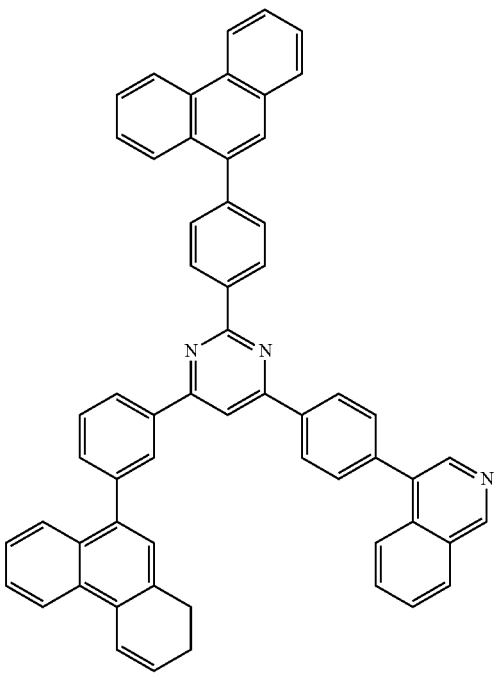

[Chemical Formula 536]
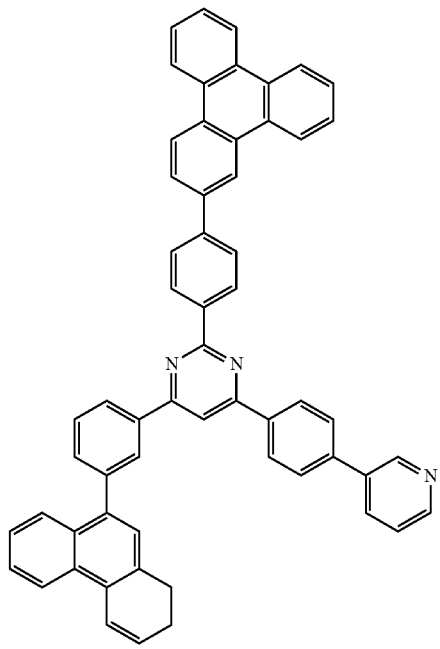
(7-95)
[Chemical Formula 537]
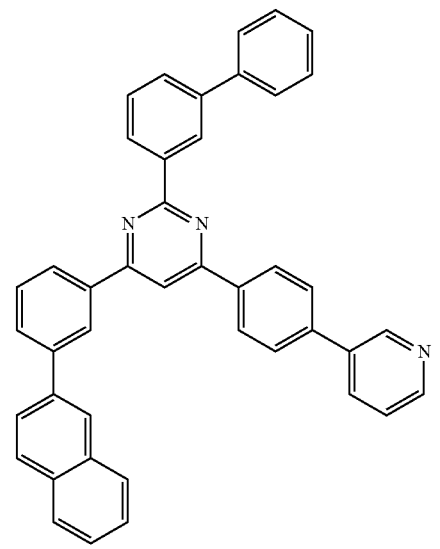
(7-96)
[Chemical Formula 538]
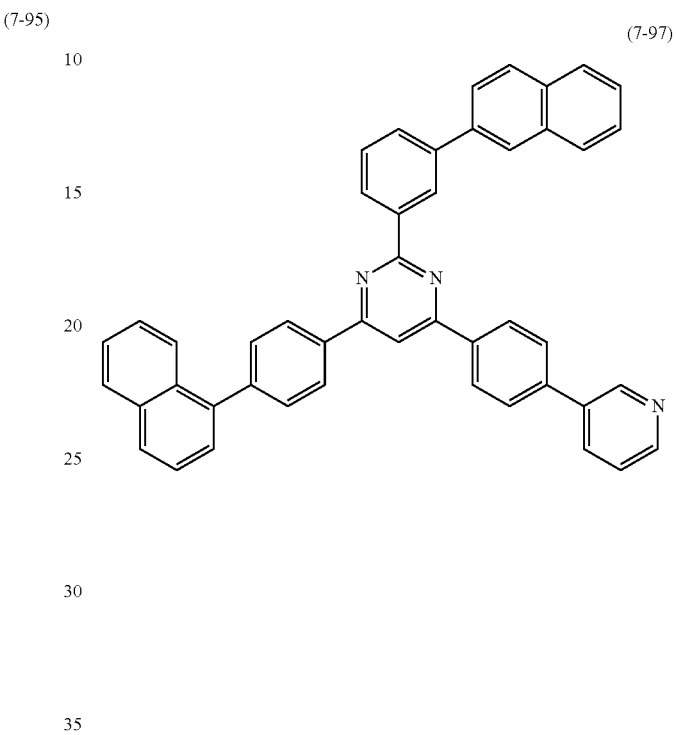
(7-97)
[Chemical Formula 539]
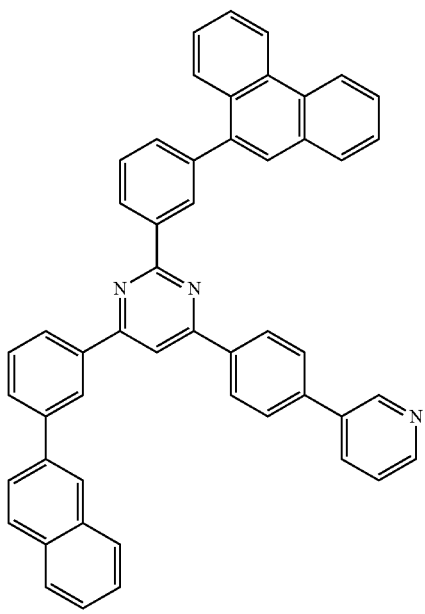
(7-98)

[Chemical Formula 540]
(7-99)
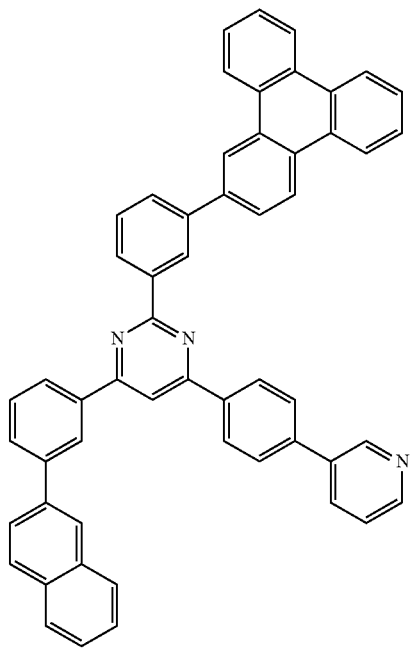
[Chemical Formula 541]
(7-100)
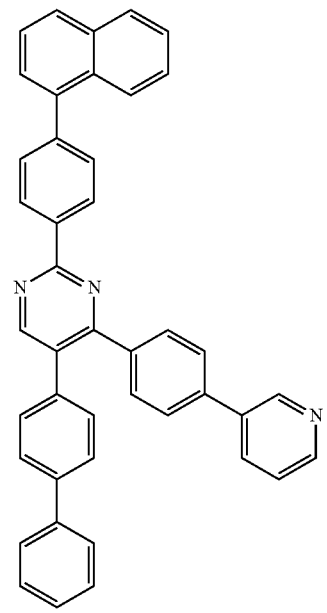
[Chemical Formula 542]
(7-101)
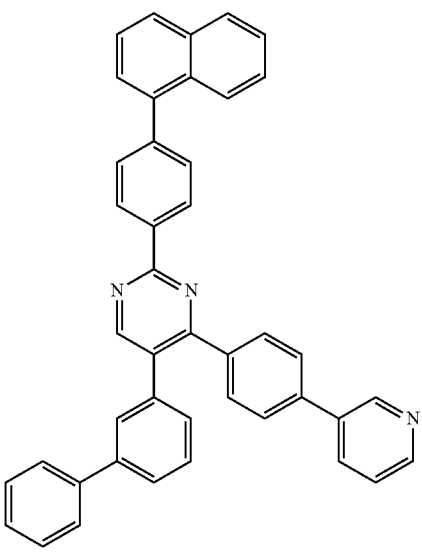
[Chemical Formula 543]
(7-102)
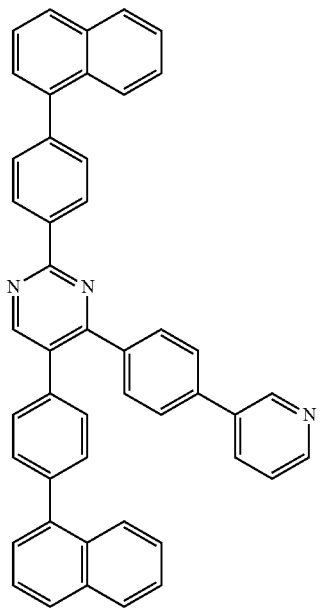

[Chemical Formula 544]
(7-103)
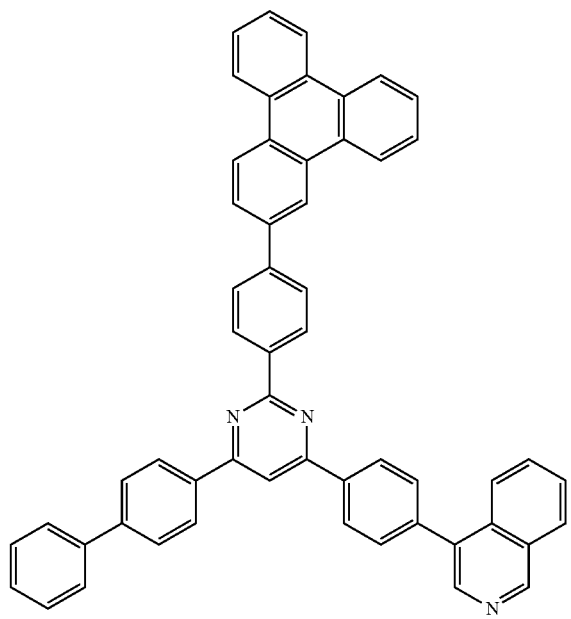
[Chemical Formula 545]
(7-104)
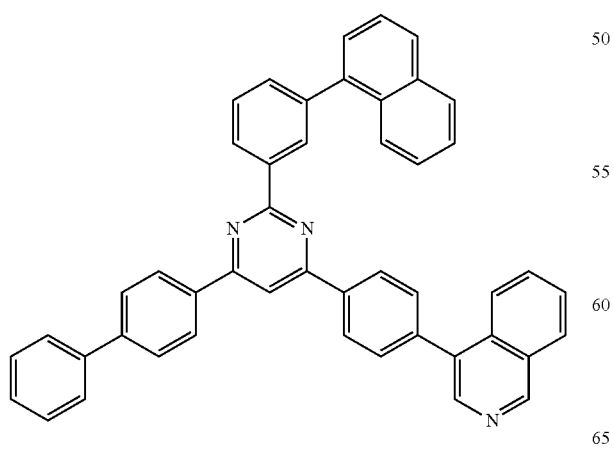
[Chemical Formula 546]
(7-105)
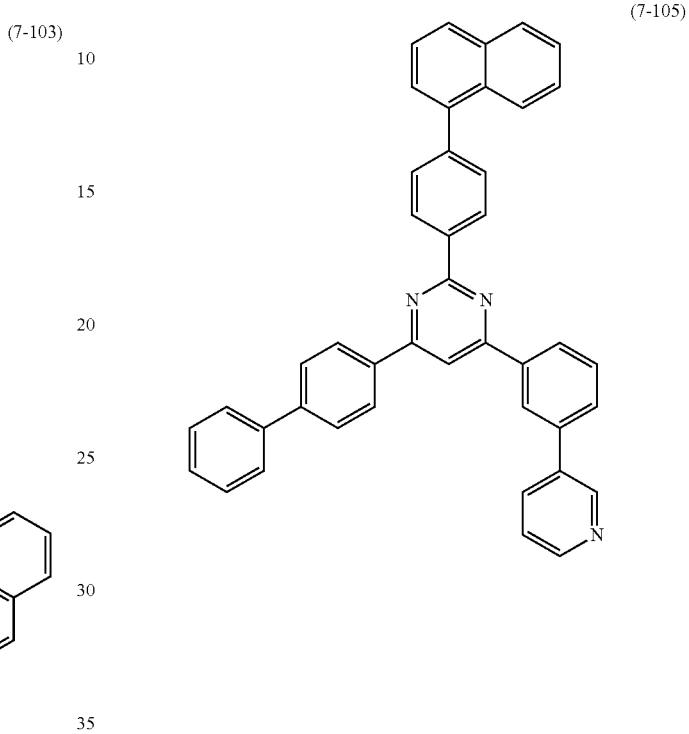
[Chemical Formula 547]
(7-106)
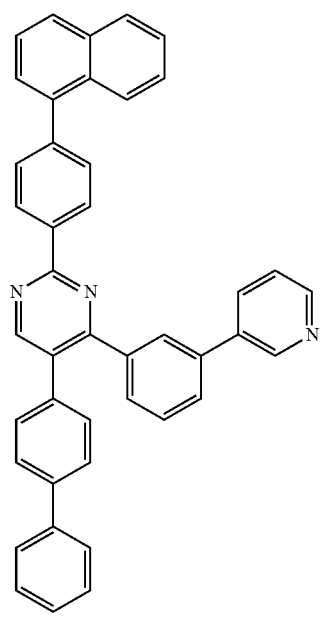

[Chemical Formula 548]
(7-107)
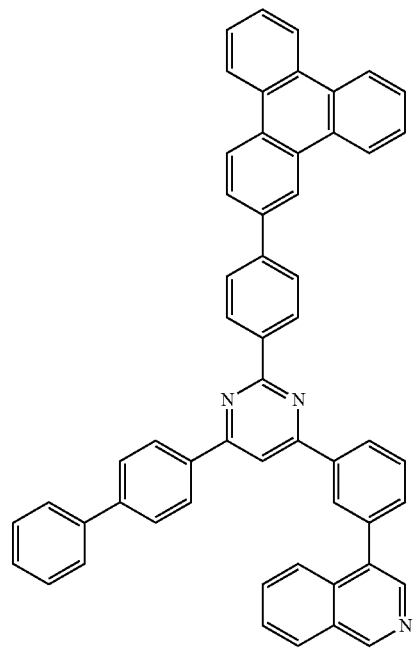
[Chemical Formula 550]
(7-109)
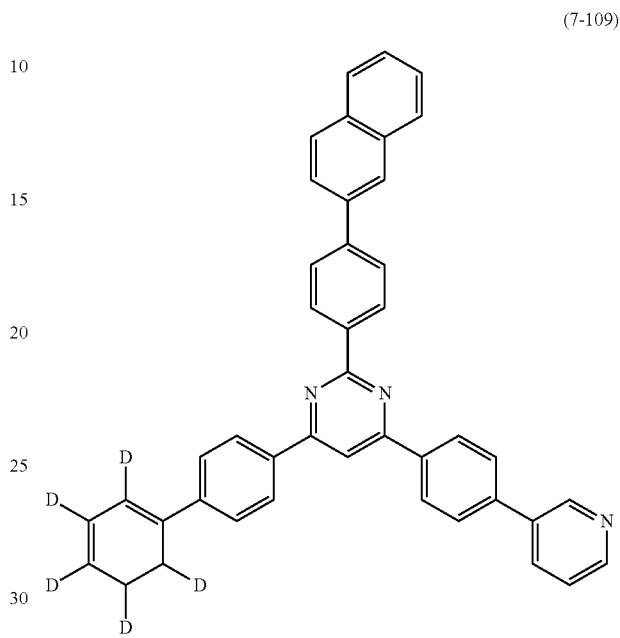
[Chemical Formula 549]
(7-108)
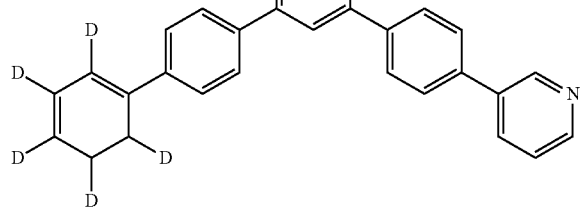
[Chemical Formula 551]
(7-110)
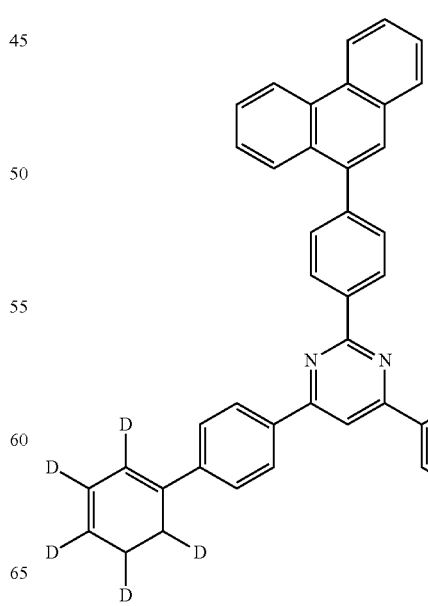

[Chemical Formula 552]
(7-111)
[Chemical Formula 553]
(7-112)
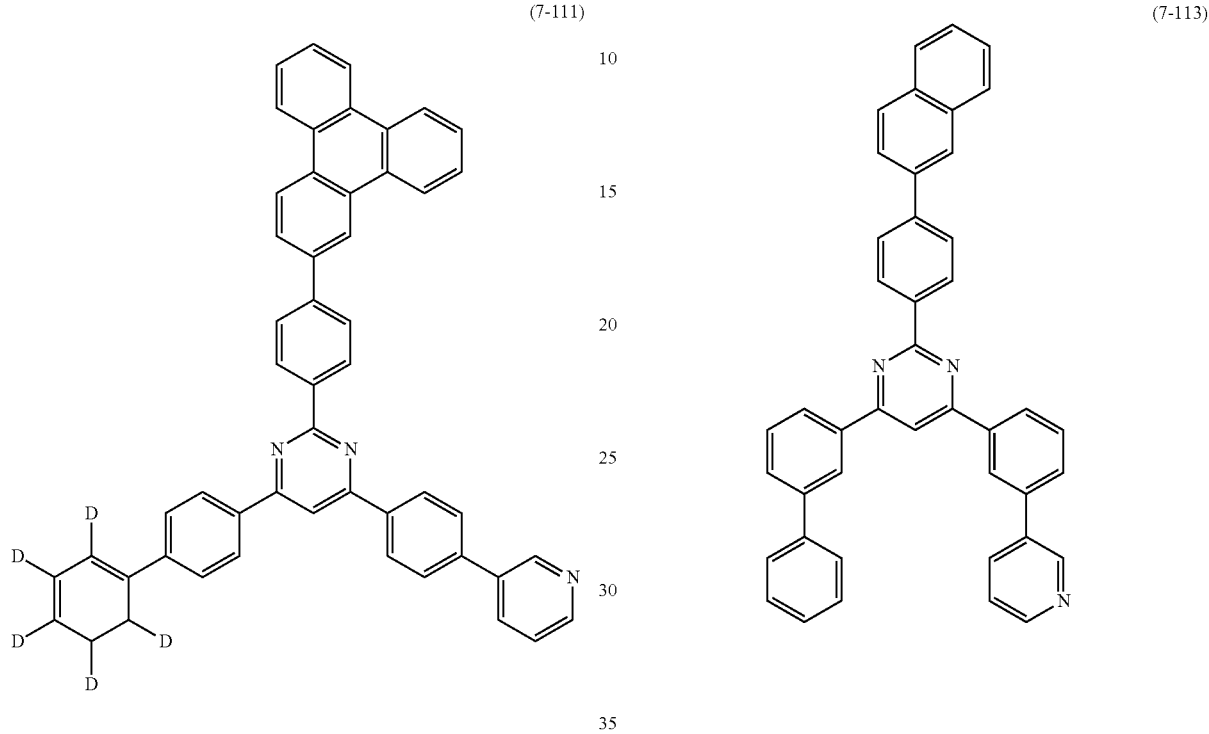
[Chemical Formula 554]
(7-113)
[Chemical Formula 555]
(7-114)
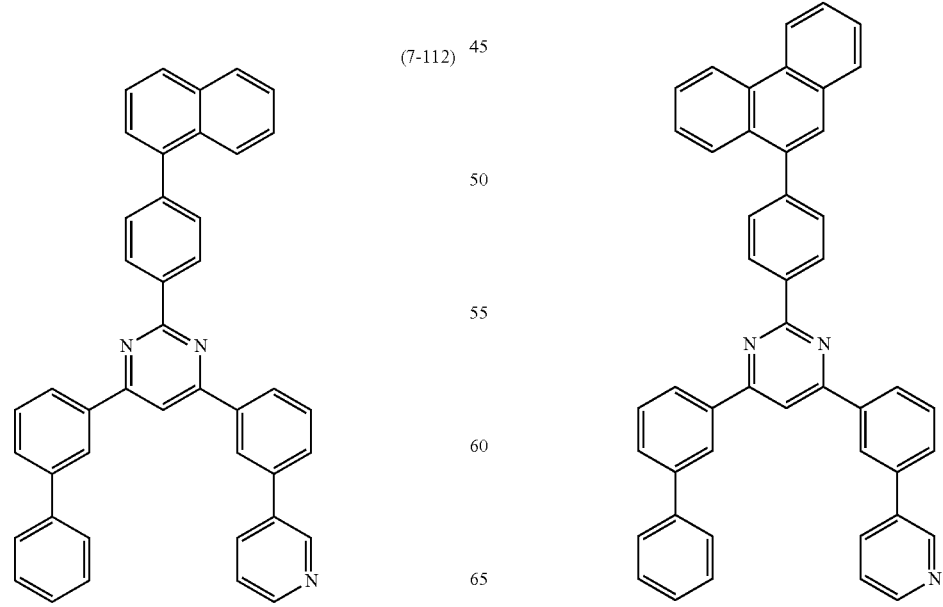

[Chemical Formula 556]
(7-115)
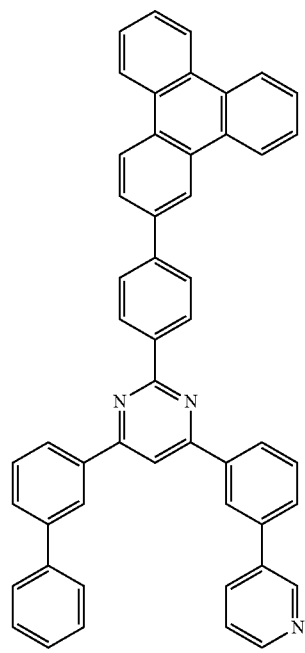
[Chemical Formula 557]
(7-116)
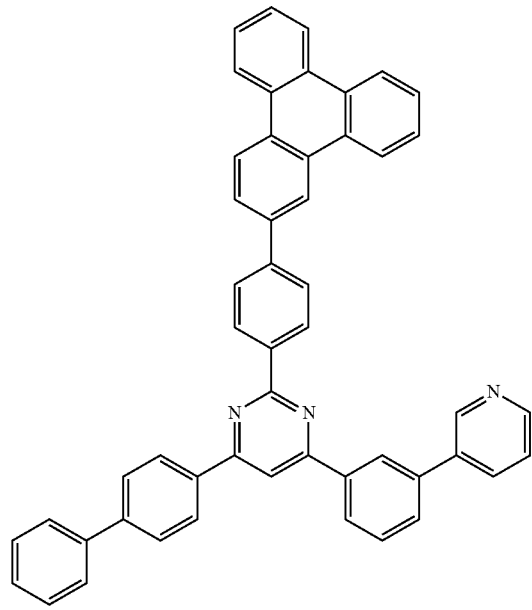
[Chemical Formula 558]
(7-117)
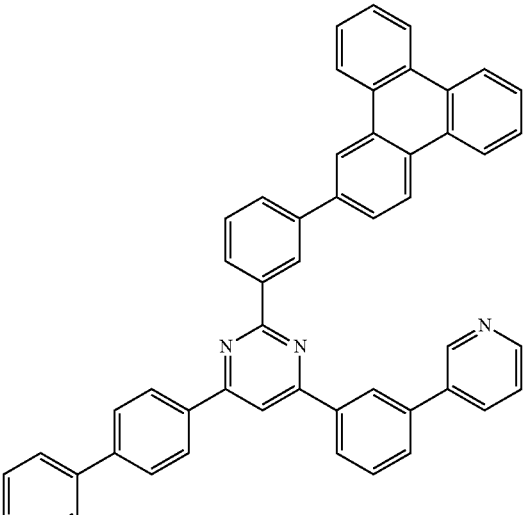
[Chemical Formula 559]
(7-118)
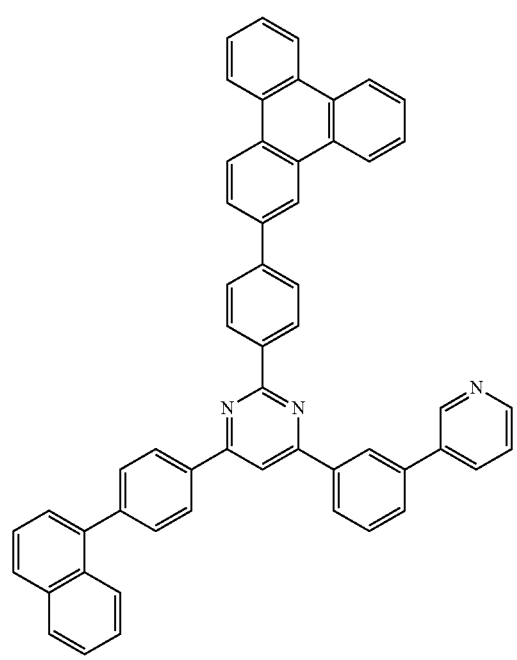

[Chemical Formula 560]
(7-119)
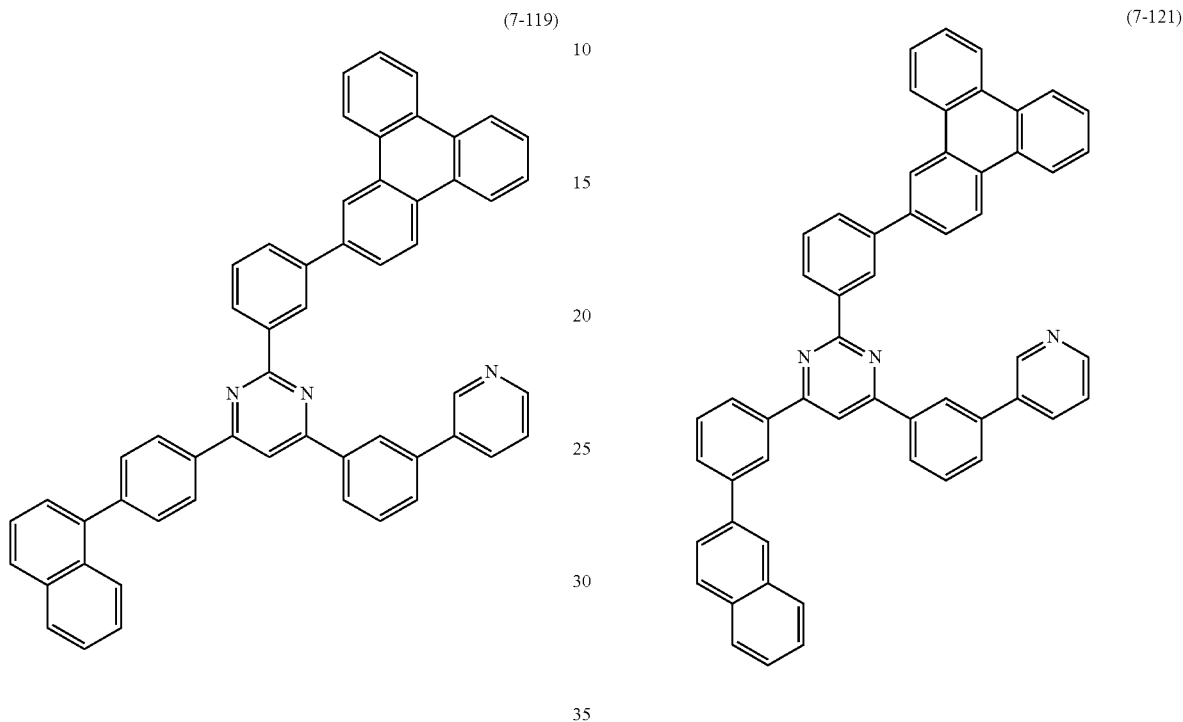
[Chemical Formula 561]
(7-120)
[Chemical Formula 562]
(7-121)
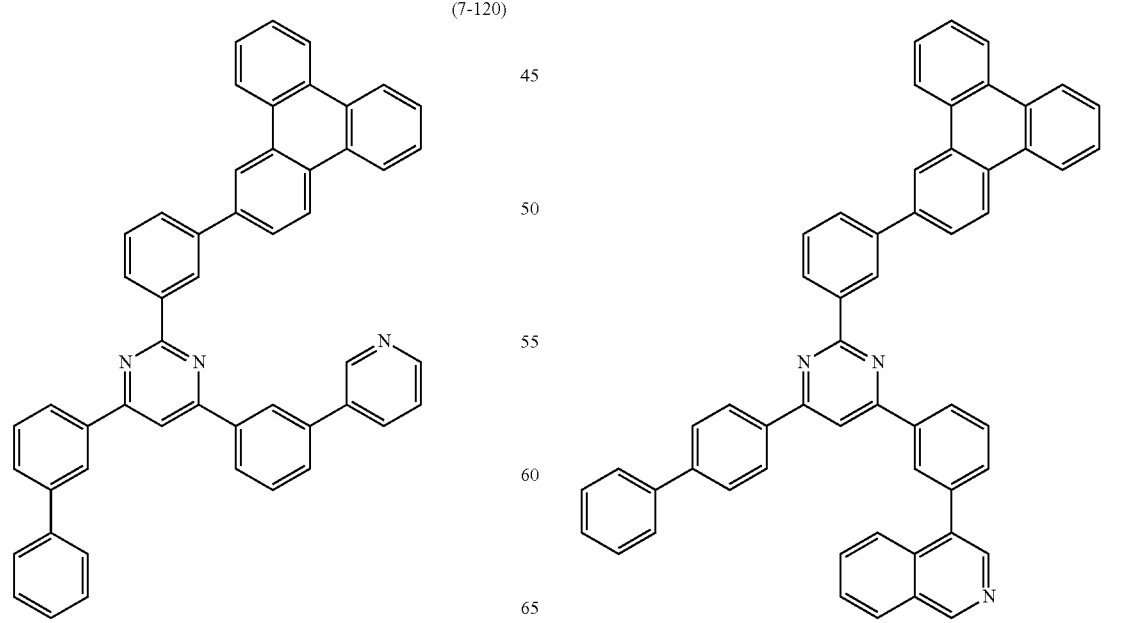
[Chemical Formula 563]
(7-122)

[Chemical Formula 564]
(7-123)
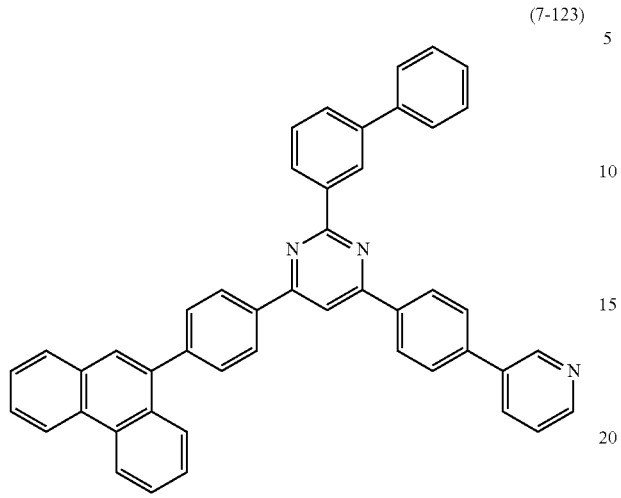
[Chemical Formula 565]
(7-124)
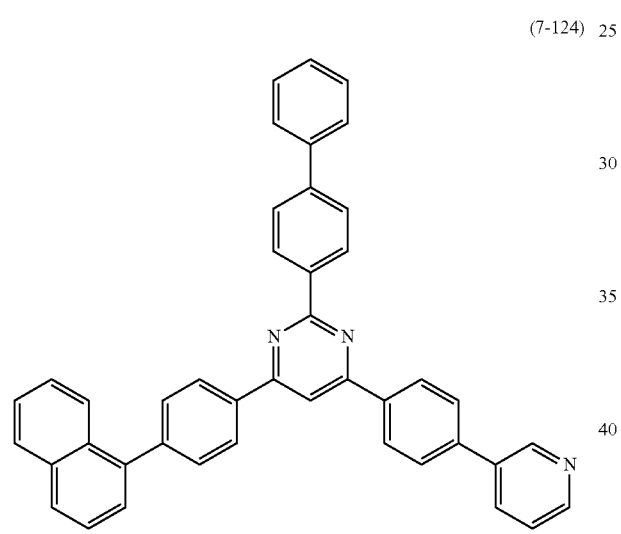
[Chemical Formula 566]
(7-125)
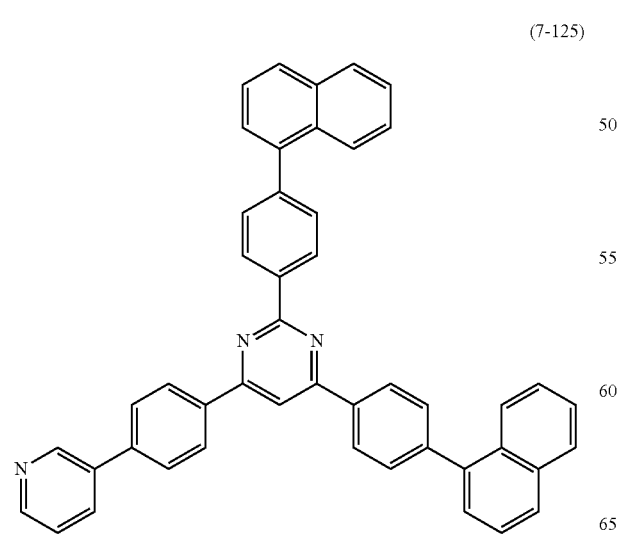
[Chemical Formula 567]
(7-126)
[Chemical Formula 568]
(7-127)
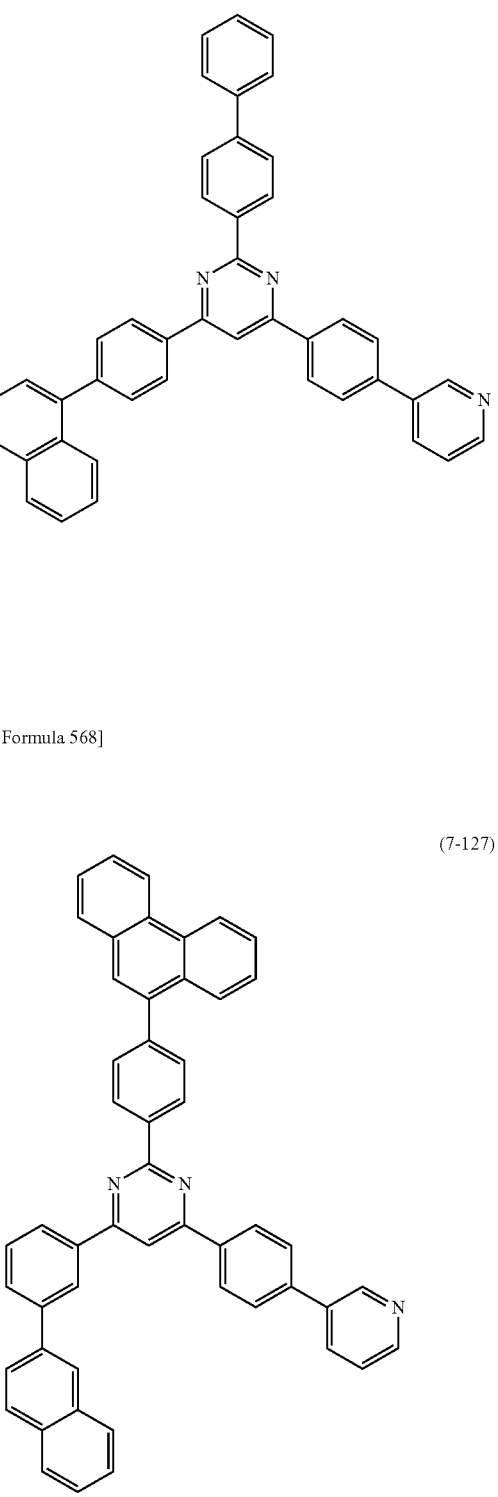

[Chemical Formula 569]
(7-128)
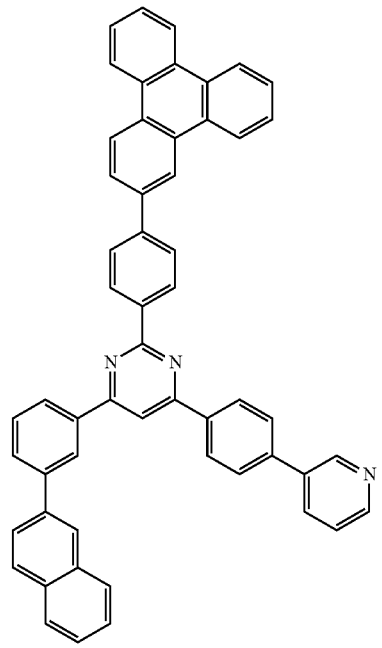
[Chemical Formula 570]
(7-129)
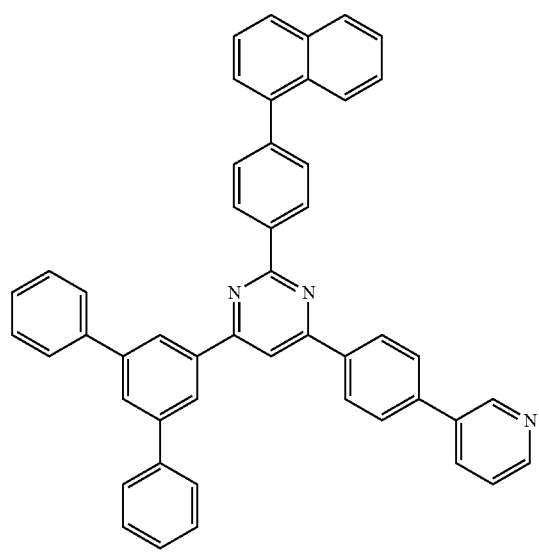
[Chemical Formula 571]
(7-130)
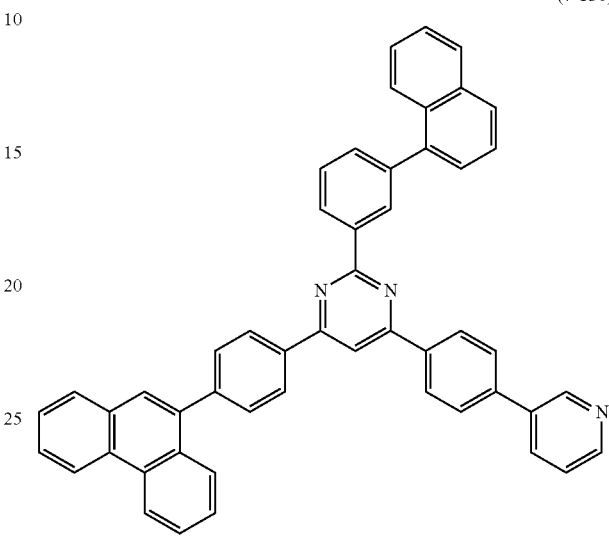
[Chemical Formula 572]
(7-131)
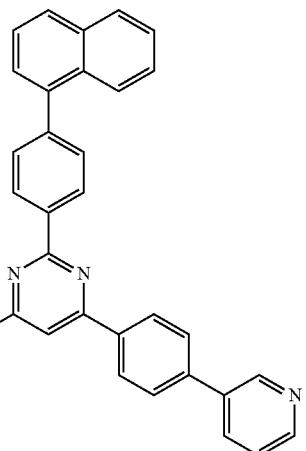

[Chemical Formula 573]
(7-132)
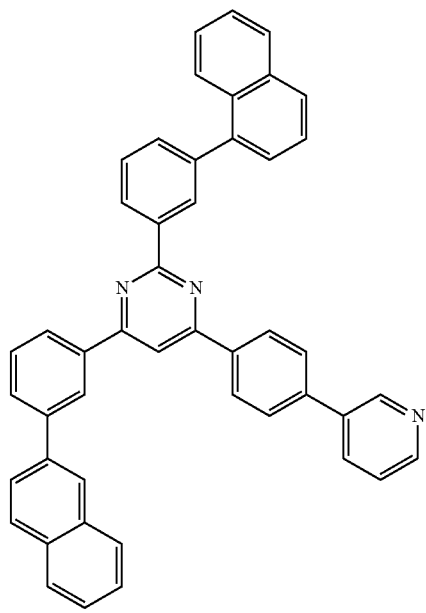
[Chemical Formula 574]
(7-133)
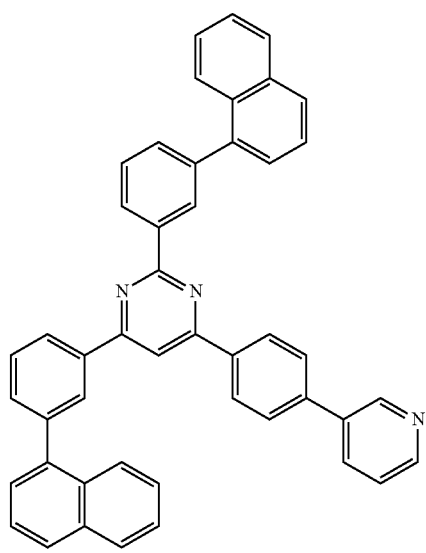
[Chemical Formula 575]
(7-134)
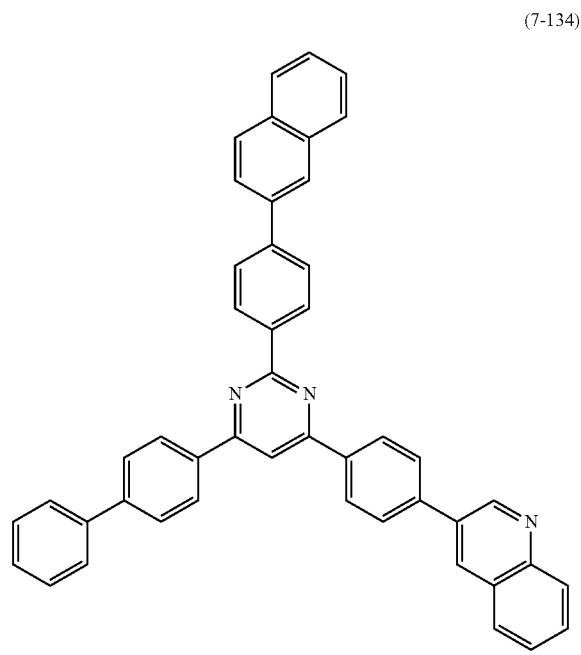
[Chemical Formula 576]
(7-135)
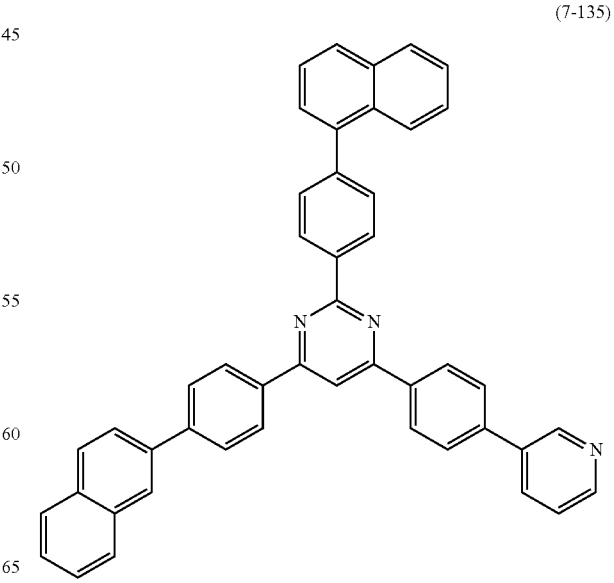

[Chemical Formula 577]
(7-136)
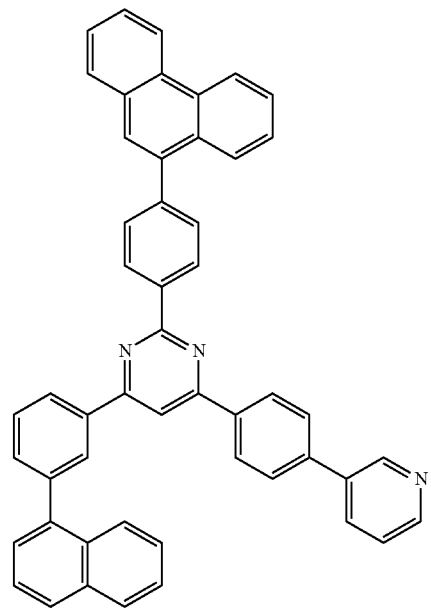
[Chemical Formula 578]
(7-137)
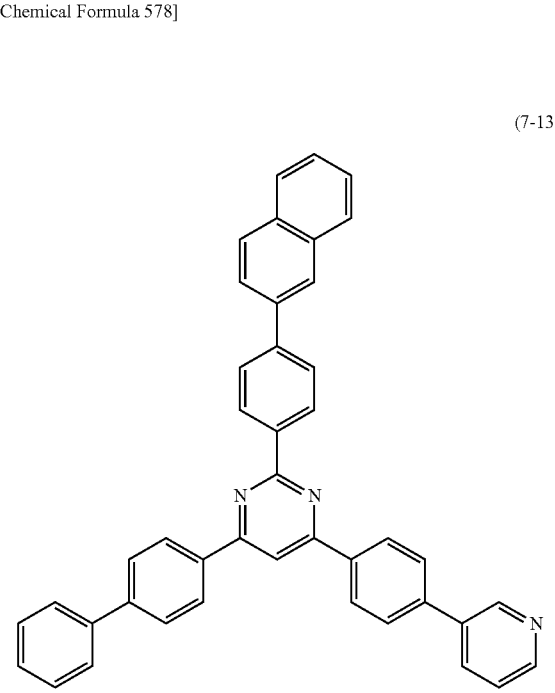
[Chemical Formula 579]
(7-138)
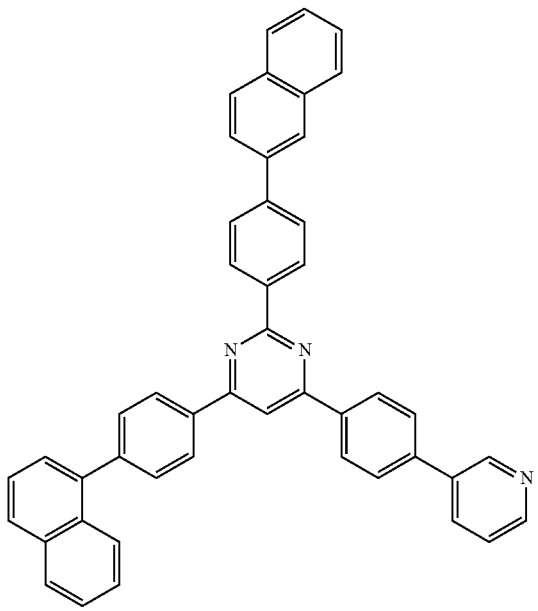
[Chemical Formula 580]
(7-139)
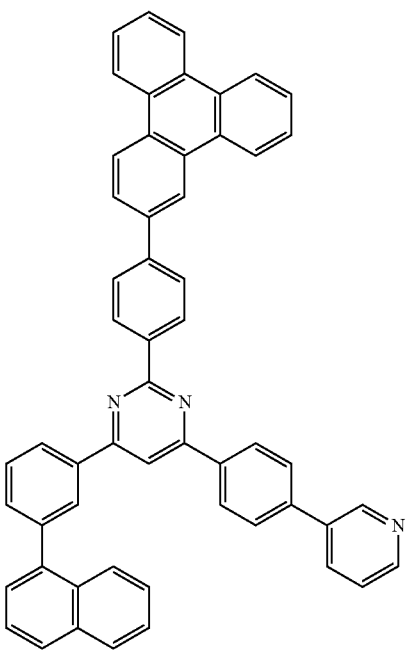

[Chemical Formula 581]
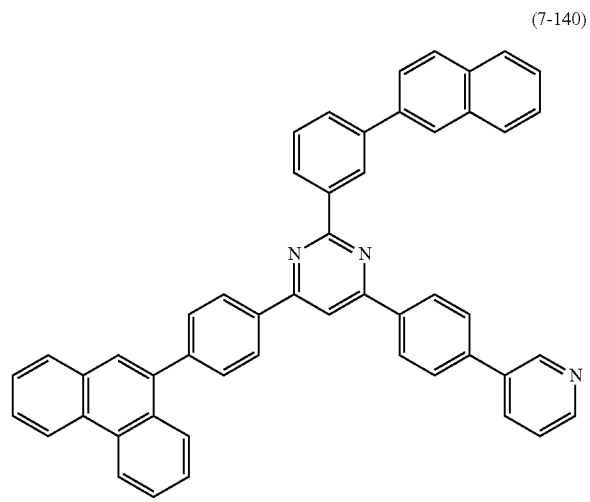
(7-140)
[Chemical Formula 582]
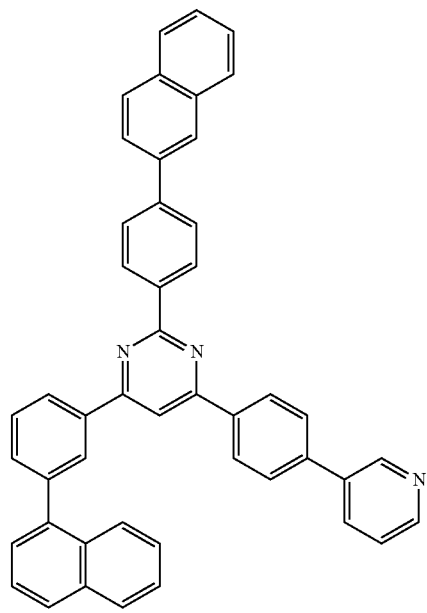
(7-141)
[Chemical Formula 583]
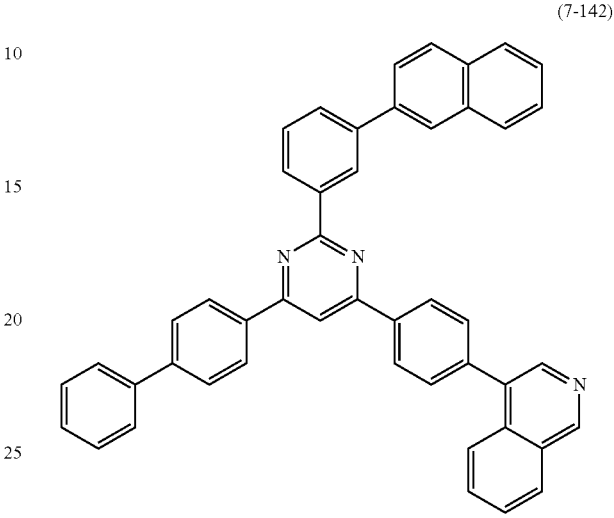
(7-142)
[Chemical Formula 584]
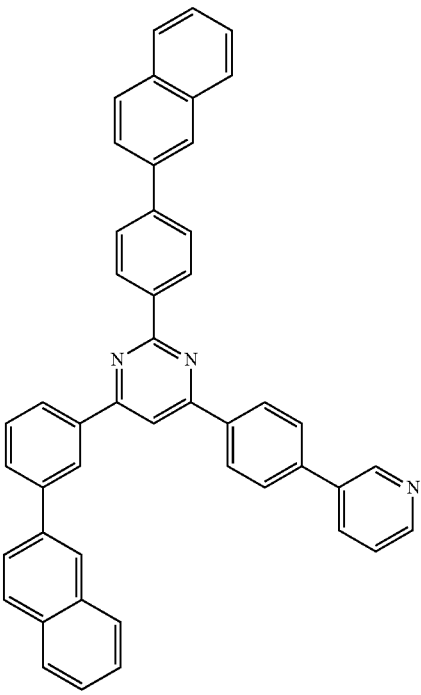
(7-143)

[Chemical Formula 585]
(7-144)
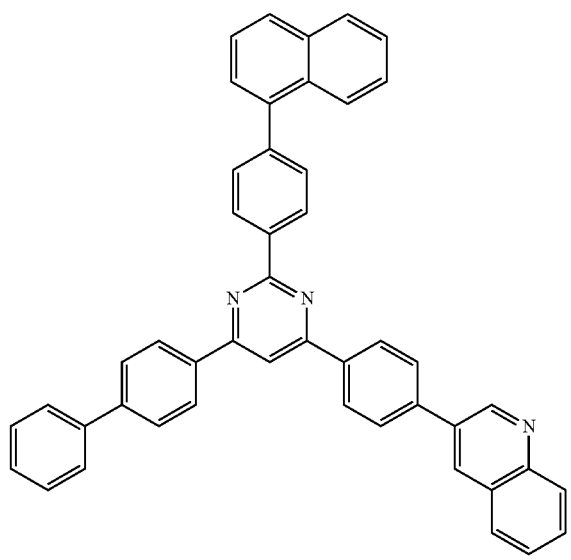
[Chemical Formula 586]
(7-145)
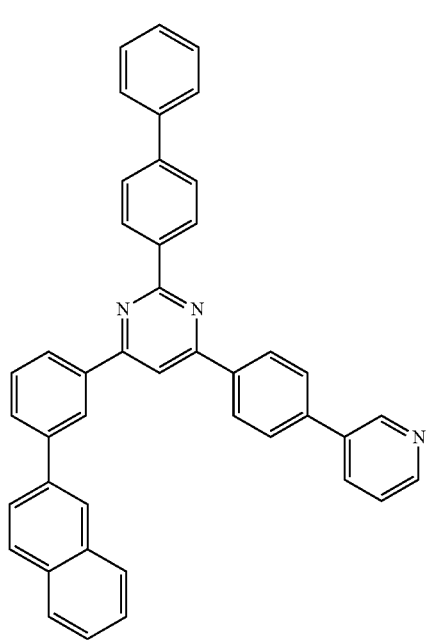
[Chemical Formula 587]
(7-146)
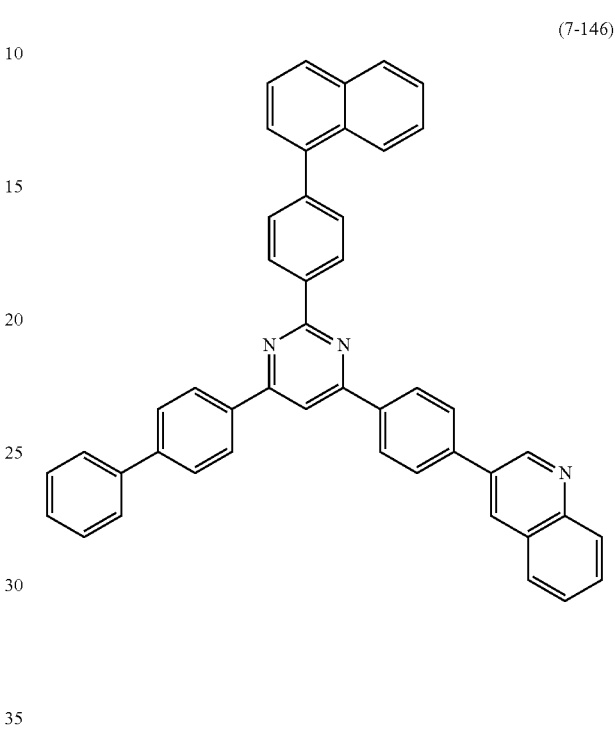
[Chemical Formula 588]
(7-147)
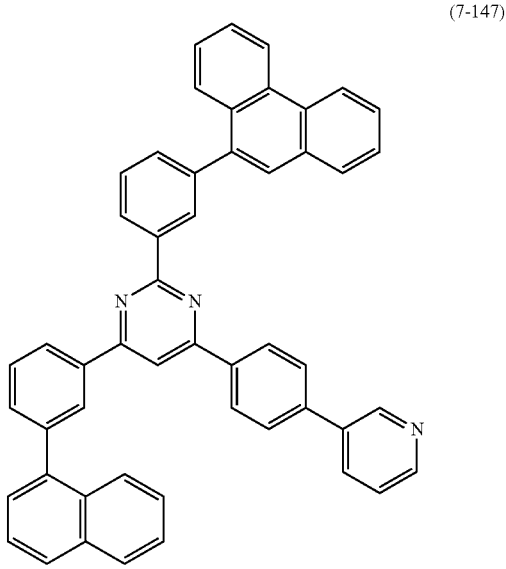

[Chemical Formula 589]
(7-148)
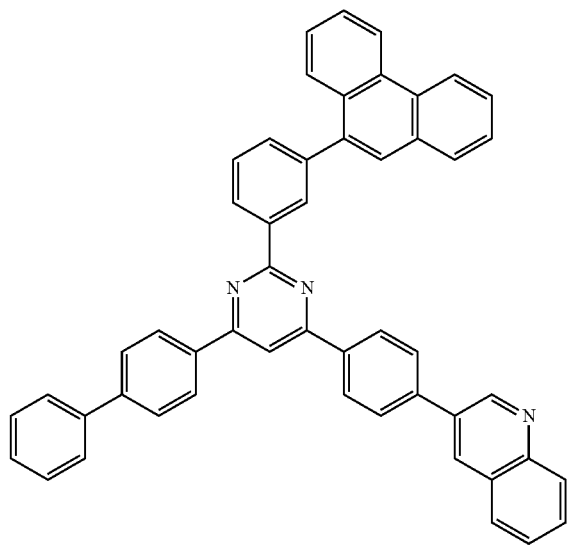
[Chemical Formula 590]
(7-149)
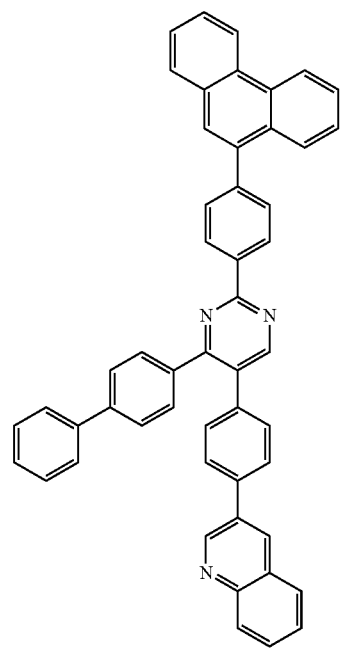
[Chemical Formula 591]
(7-150)
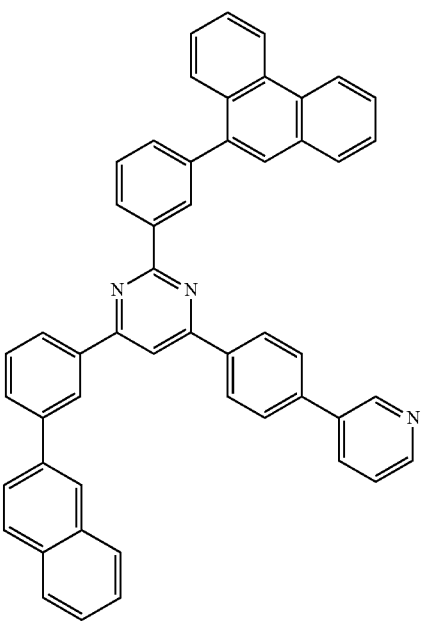
[Chemical Formula 592]
(7-151)
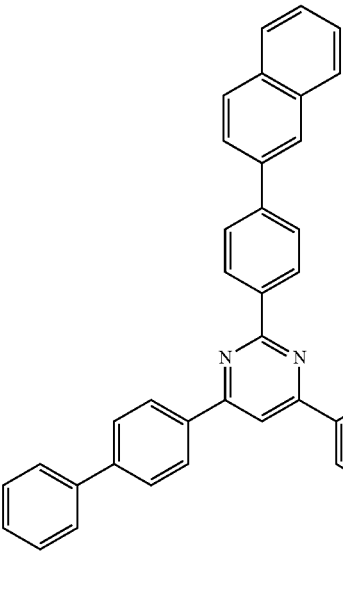

[Chemical Formula 593]
(7-152)
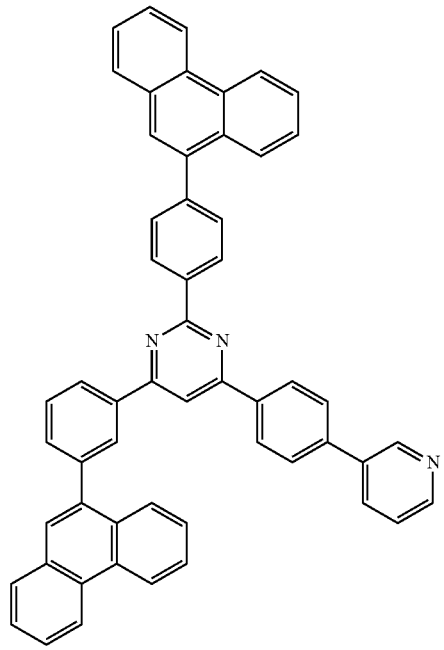
[Chemical Formula 594]
(7-153)
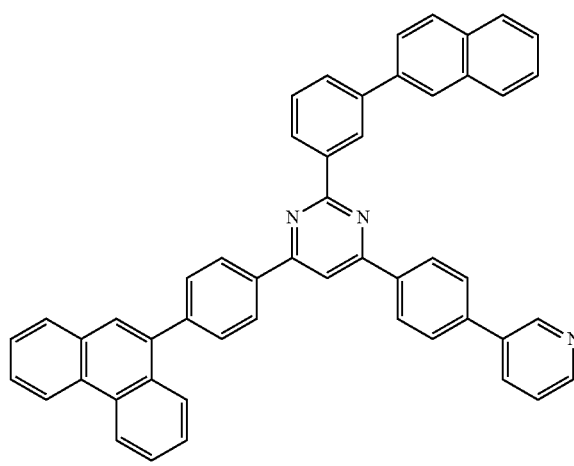
[Chemical Formula 595]
(7-154)
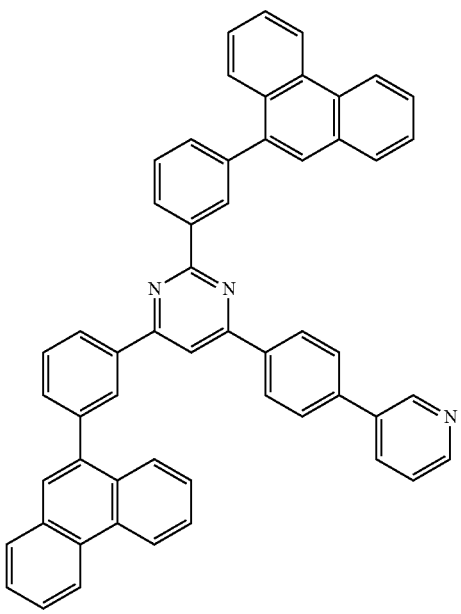
[Chemical Formula 596]
(7-155)
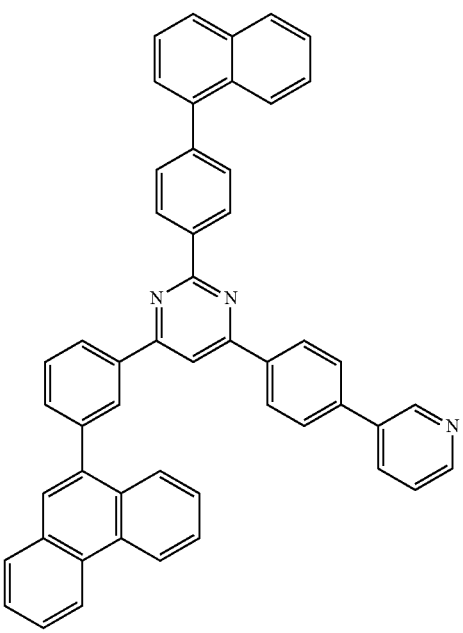

[Chemical Formula 597]
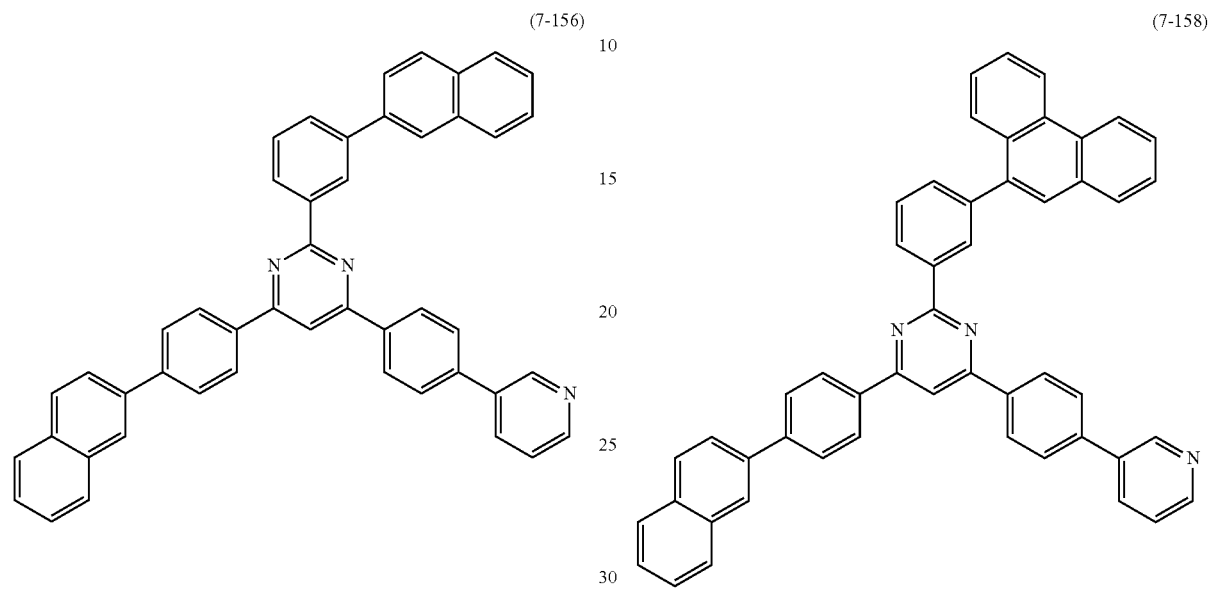
(7-156)
[Chemical Formula 598]
(7-157)
[Chemical Formula 599]
(7-158)
[Chemical Formula 600]
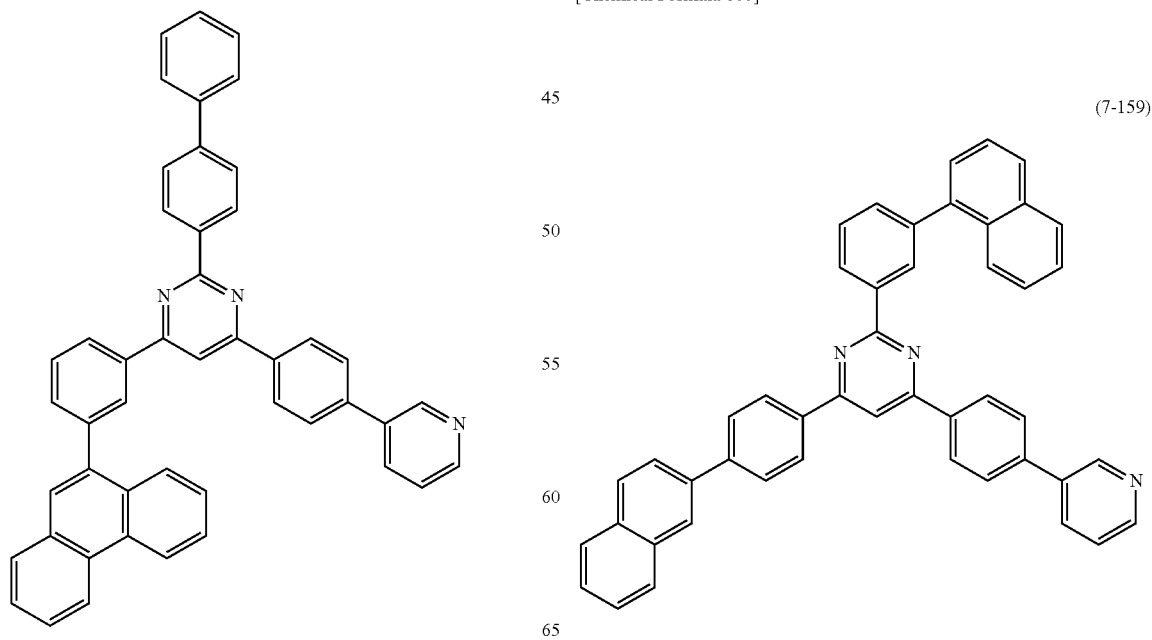
(7-159)

[Chemical Formula 601]
(7-160)
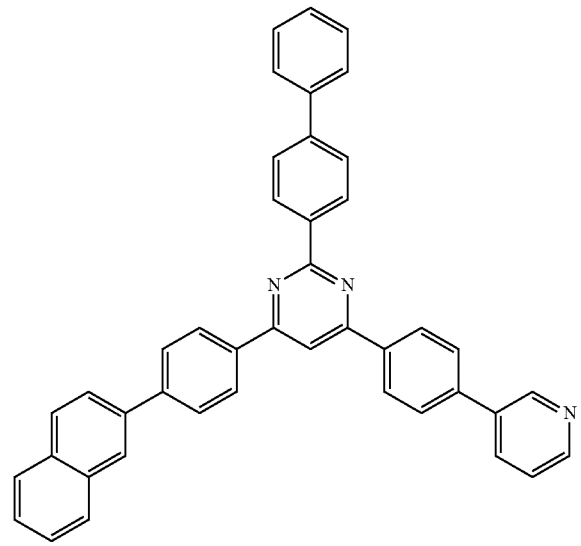
[Chemical Formula 602]
(7-161)
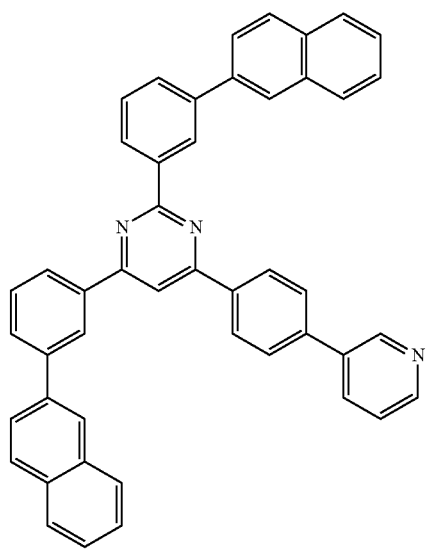
[Chemical Formula 603]
(7-162)
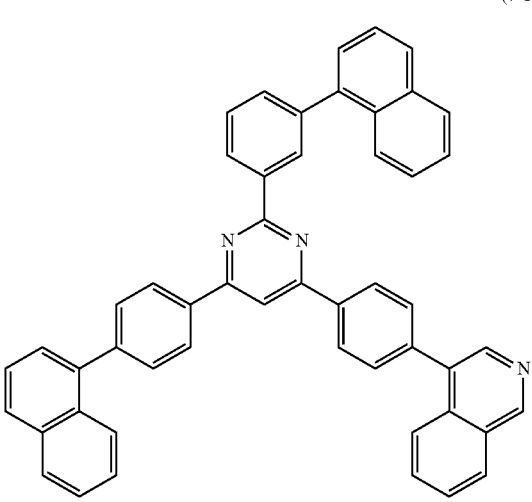
[Chemical Formula 604]
(7-163)
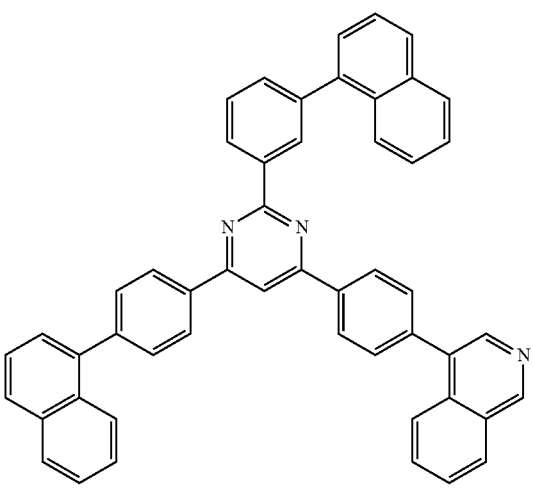
[Chemical Formula 605]
(7-164)
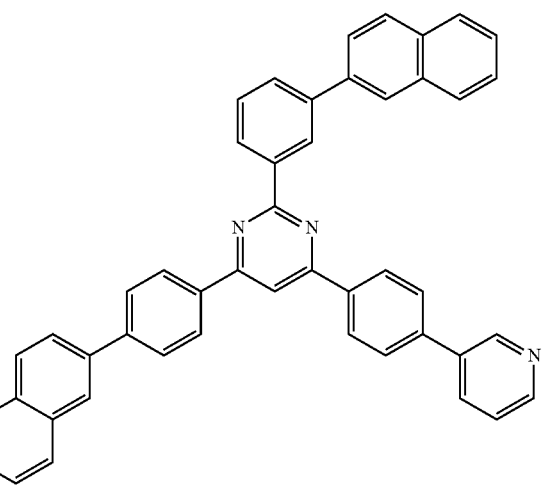

[Chemical Formula 606]
(7-165)
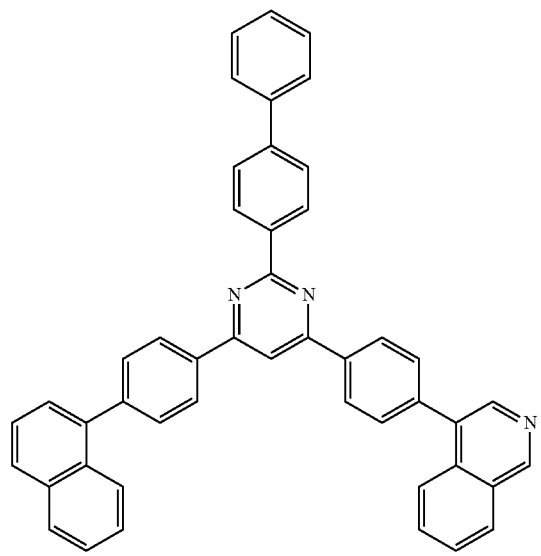
[Chemical Formula 607]
(7-166)
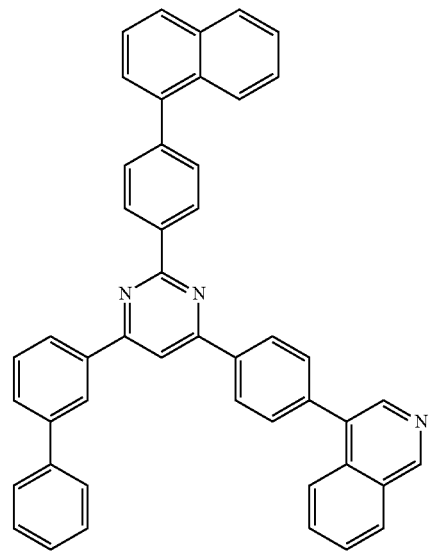
[Chemical Formula 608]
(7-167)
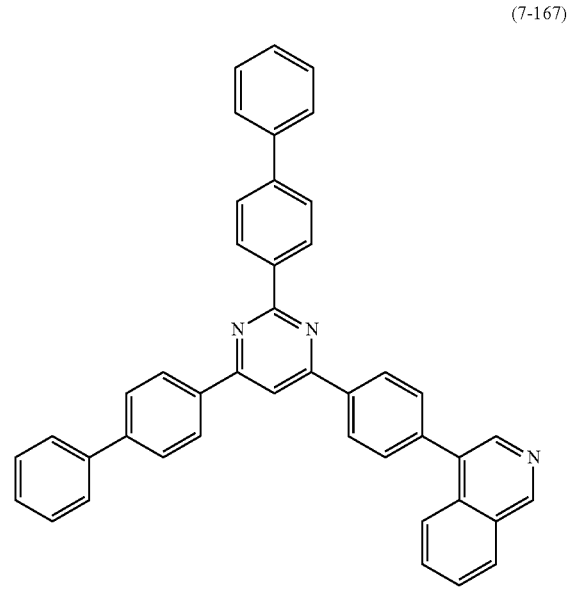
[Chemical Formula 609]
(7-168)
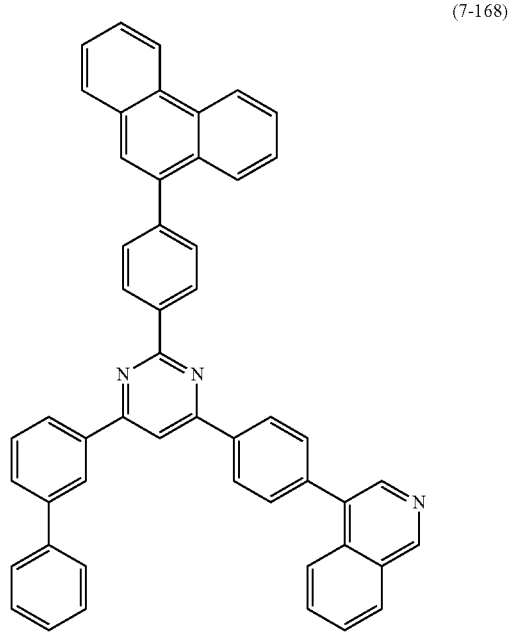

[Chemical Formula 610]
(7-169)
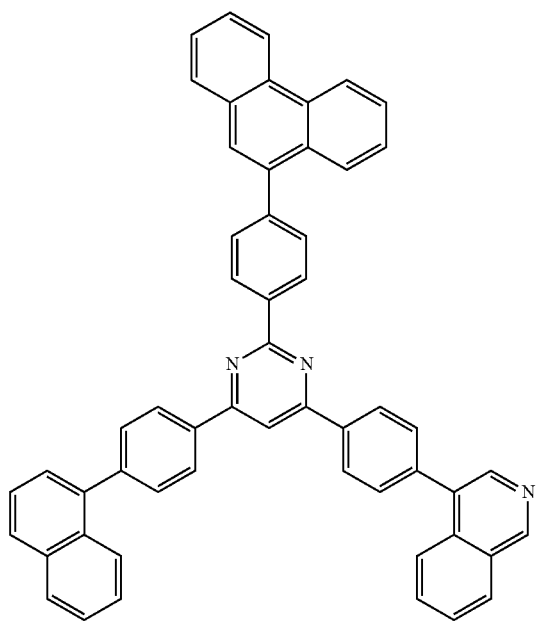
[Chemical Formula 611]
(7-170)
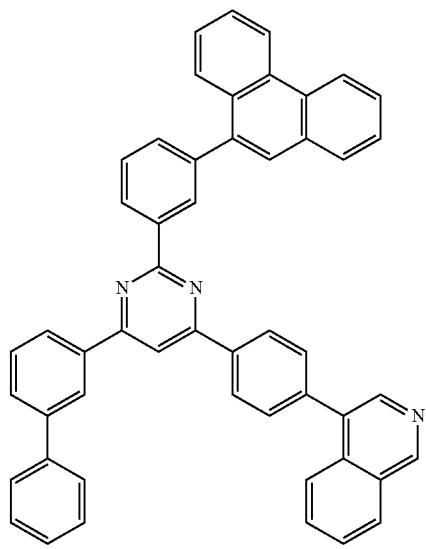
[Chemical Formula 612]
(7-171)
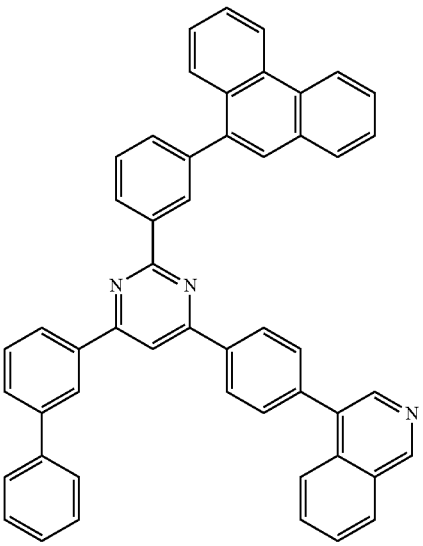
[Chemical Formula 613]
(7-172)
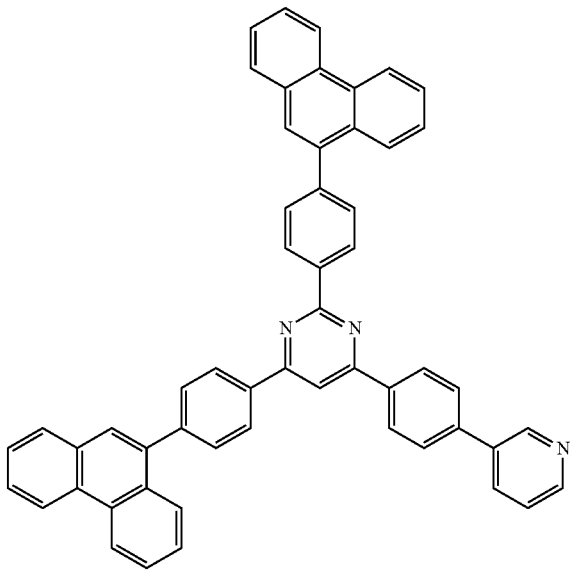

[Chemical Formula 614]
(7-173)
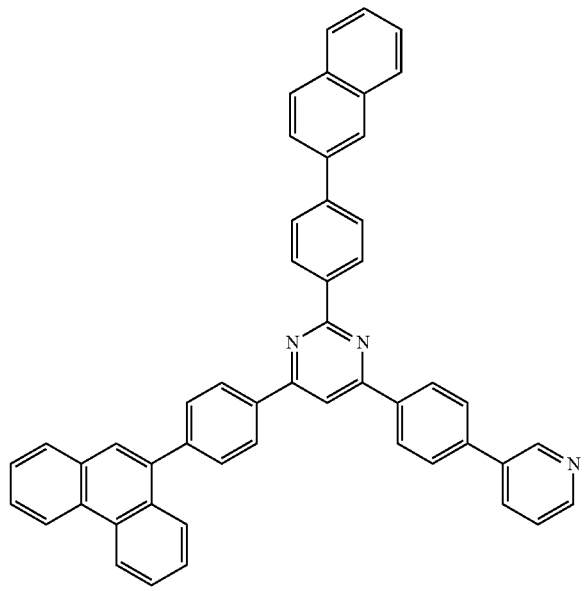
[Chemical Formula 615]
(7-174)
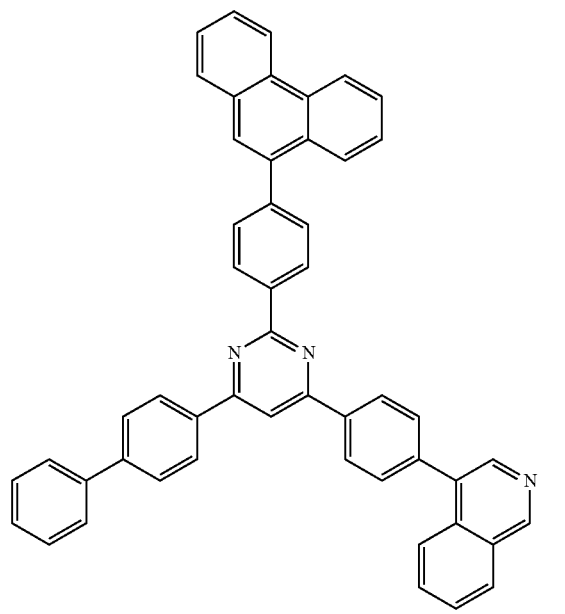
[Chemical Formula 616]
(7-175)
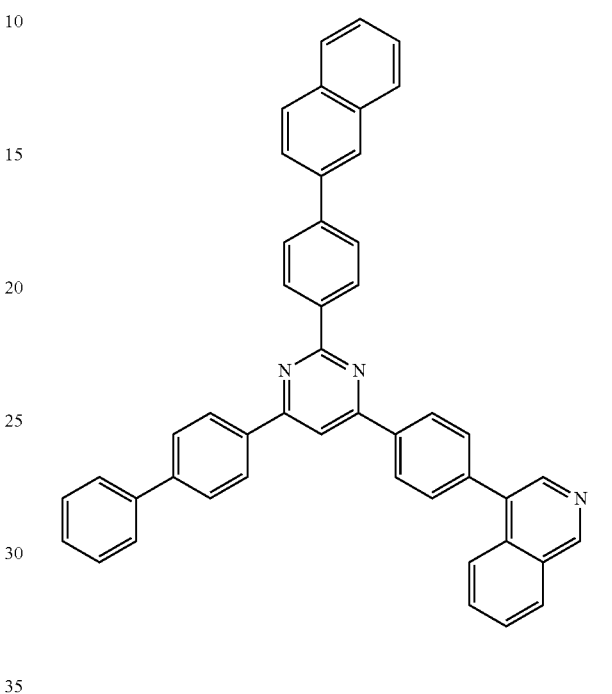
[Chemical Formula 617]
(7-176)
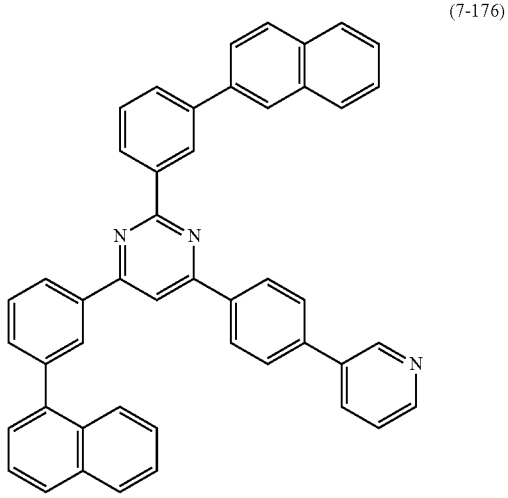

[Chemical Formula 618]
(7-177)
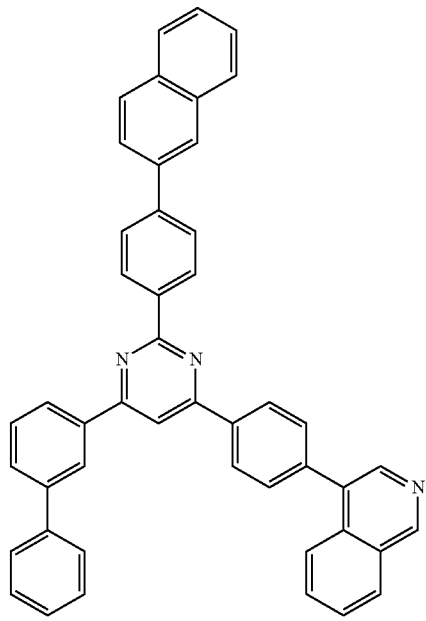
[Chemical Formula 619]
(7-178)
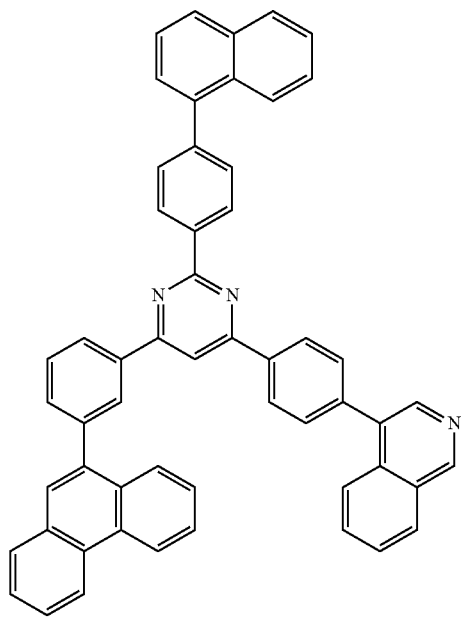
[Chemical Formula 620]
(7-179)
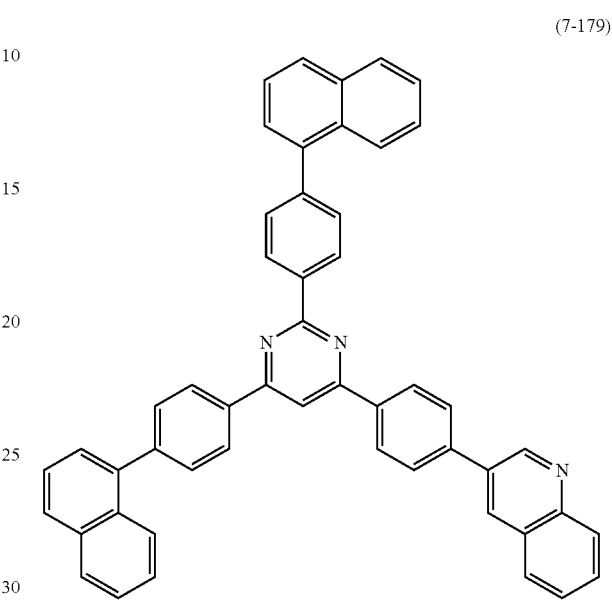
[Chemical Formula 621]
(7-180)
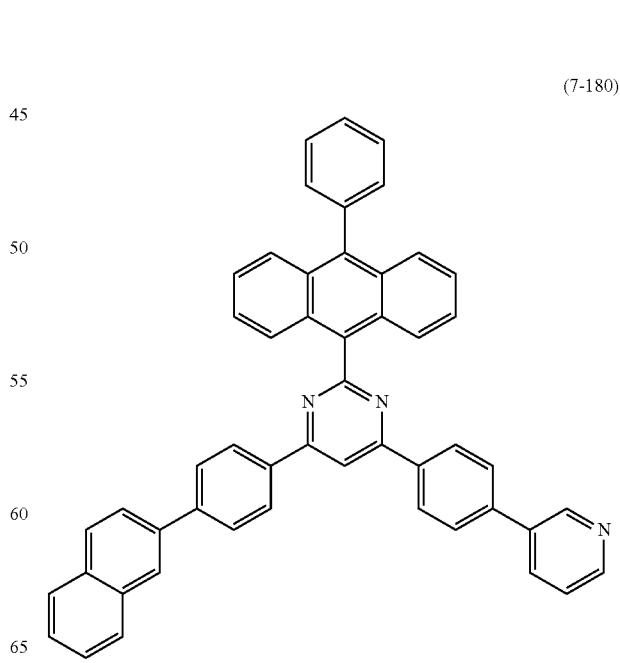

[Chemical Formula 622]
(7-181)
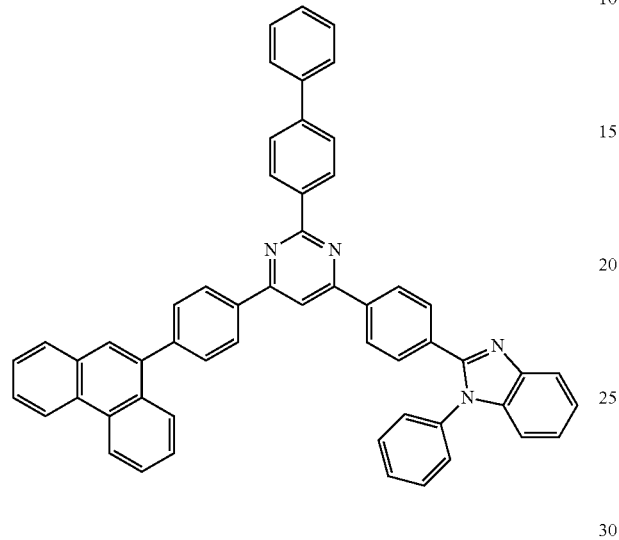
[Chemical Formula 623]
(7-182)
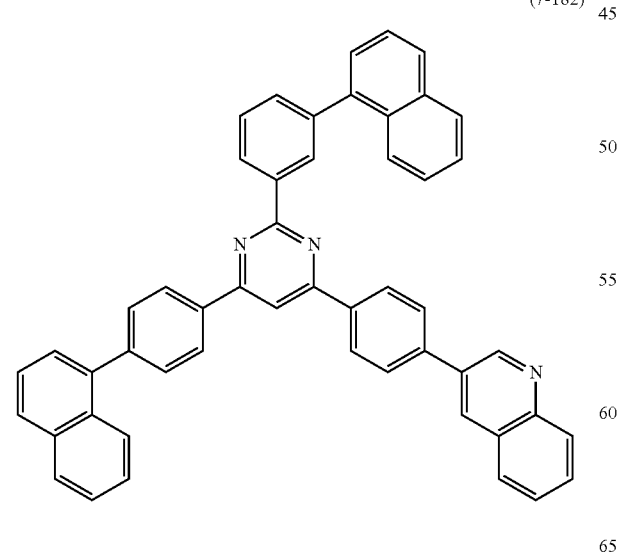
[Chemical Formula 624]
(7-183)
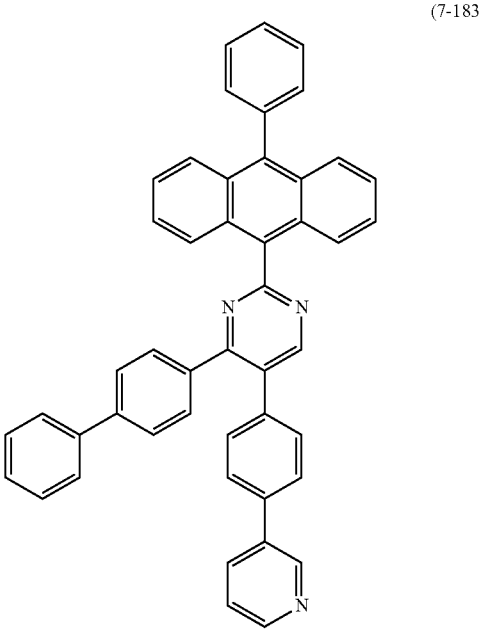
[Chemical Formula 625]
(7-184)
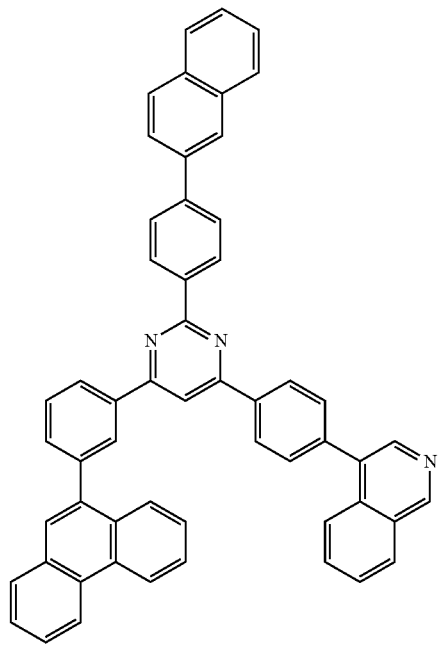

[Chemical Formula 626]
(7-185)
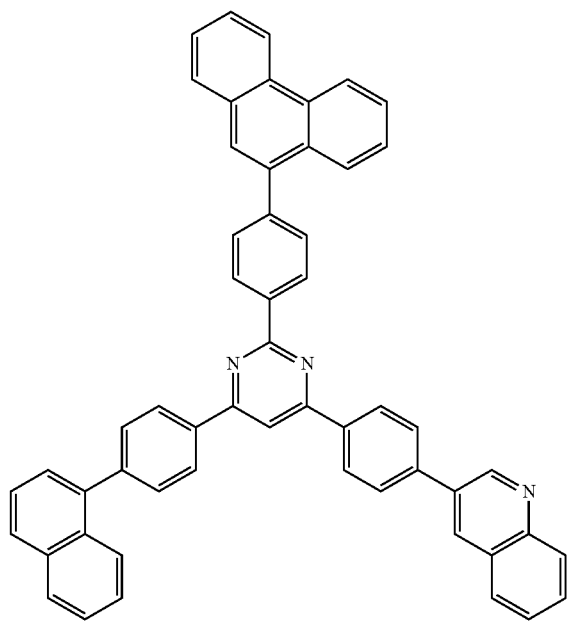
[Chemical Formula 627]
(7-186)
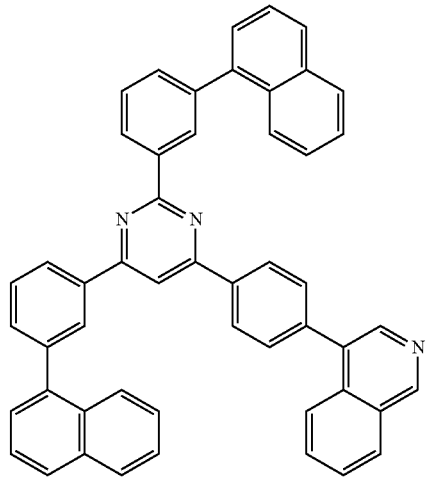
[Chemical Formula 628]
(7-187)
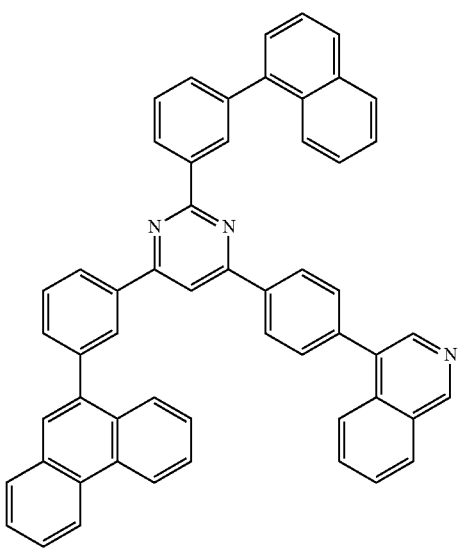
[Chemical Formula 629]
(7-188)
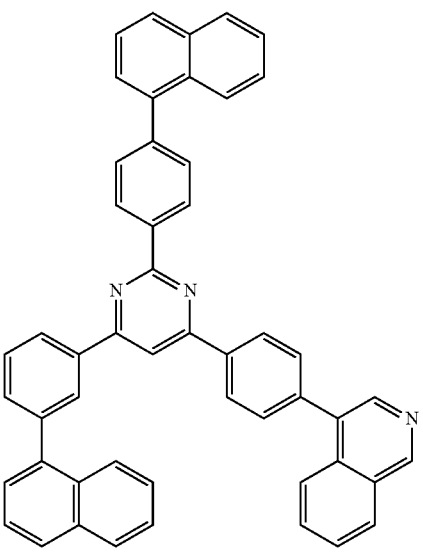

[Chemical Formula 630]

(7-189)

[Chemical Formula 631]

(1-190)

[Chemical Formula 632]

(7-191)

[Chemical Formula 633]

(7-192)

[Chemical Formula 634]
(7-193)
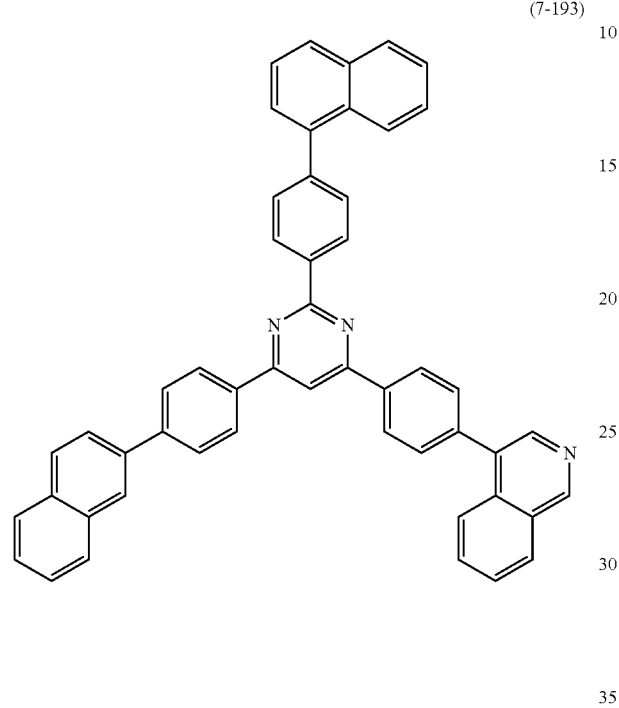
[Chemical Formula 635]
(7-194)
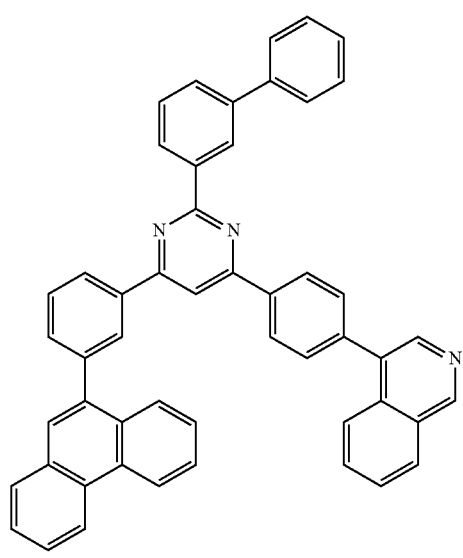
[Chemical Formula 636]
(7-195)
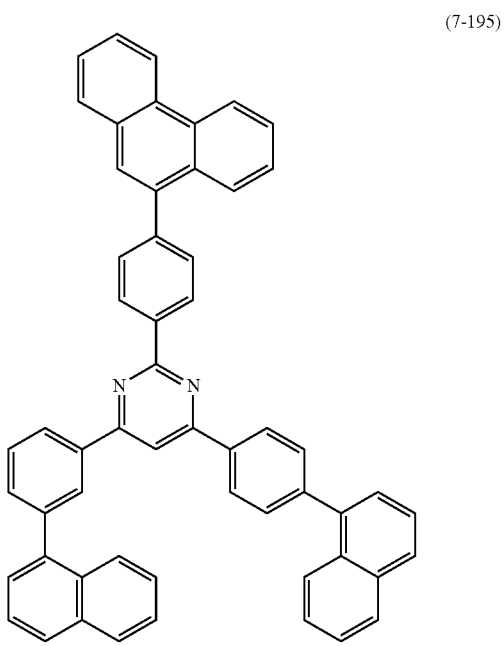
[Chemical Formula 637]
(7-196)
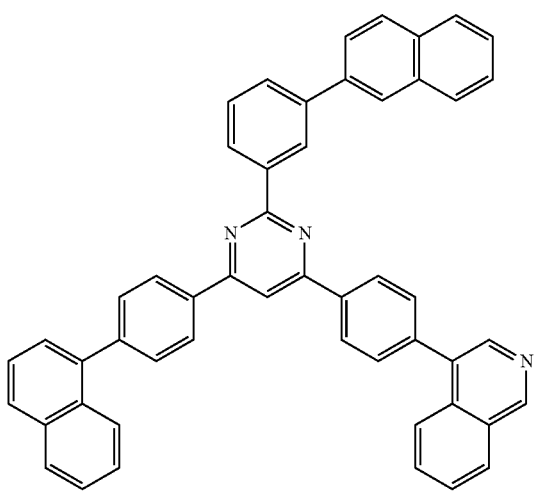

[Chemical Formula 638]
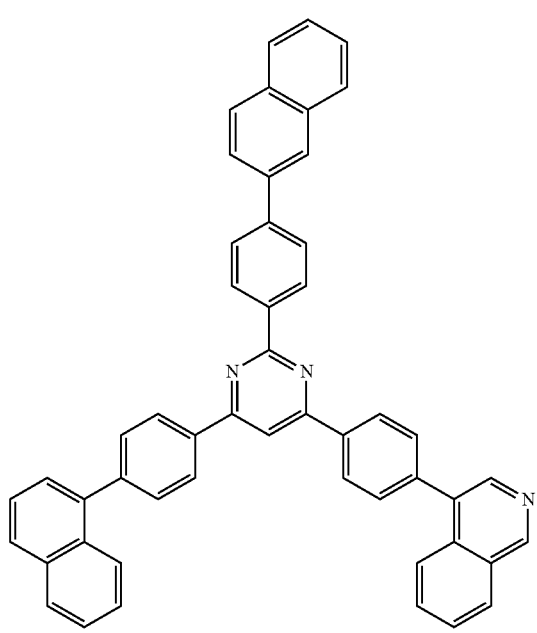
(7-197)
[Chemical Formula 639]
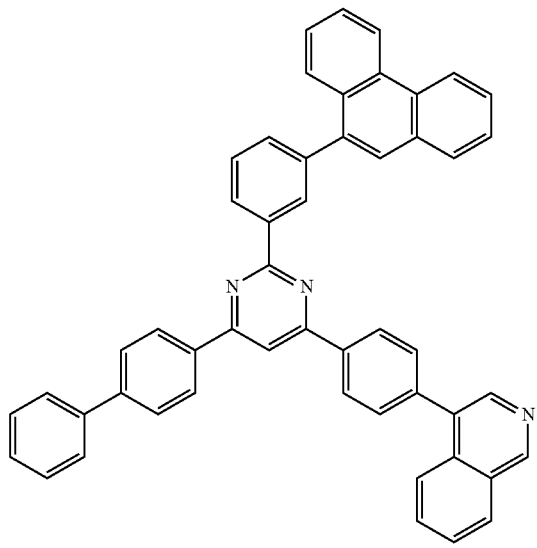
(7-198)
[Chemical Formula 640]
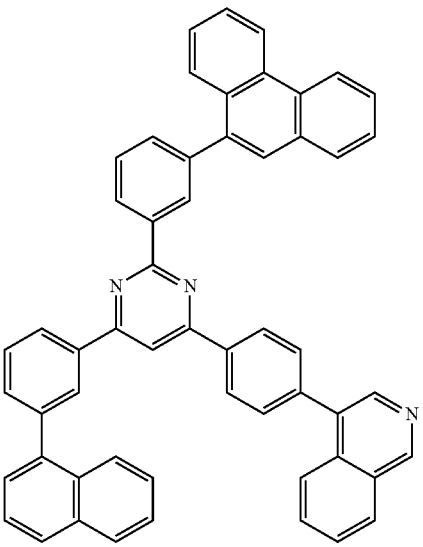
(7-199)
[Chemical Formula 641]
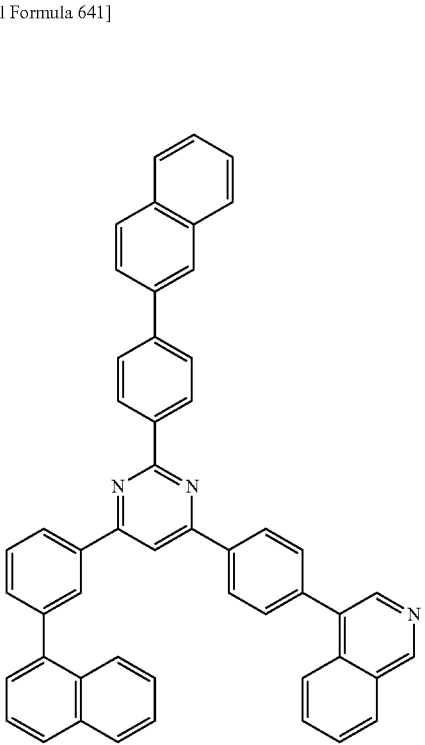
(7-200)

[Chemical Formula 642]
(7-201)
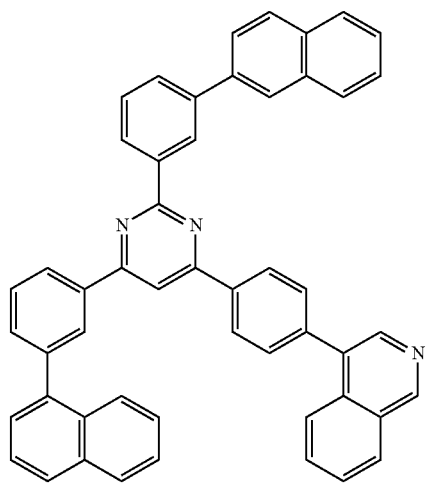
[Chemical Formula 643]
(7-202)
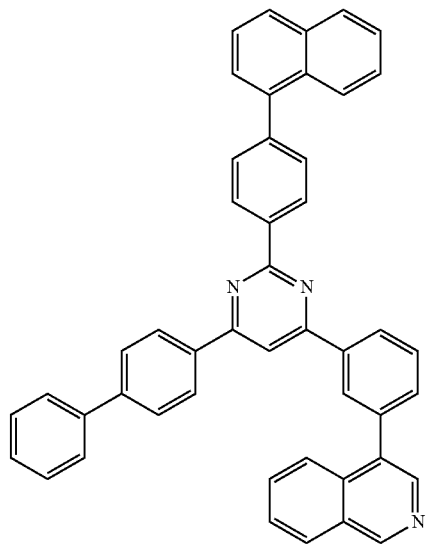
[Chemical Formula 644]
(7-203)
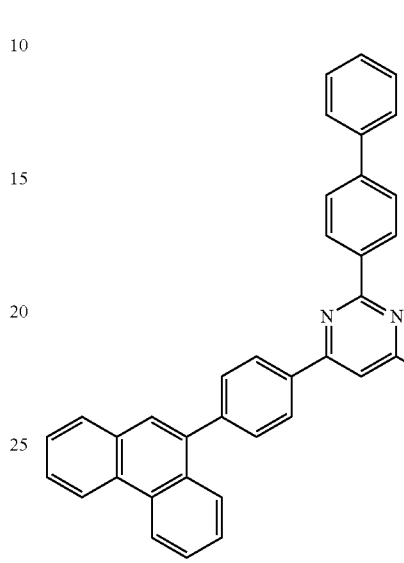
[Chemical Formula 645]
(7-204)
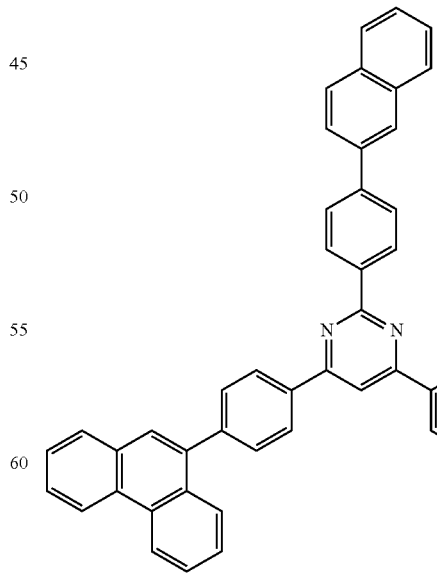

-continued
[Chemical Formula 646]
(7-205)
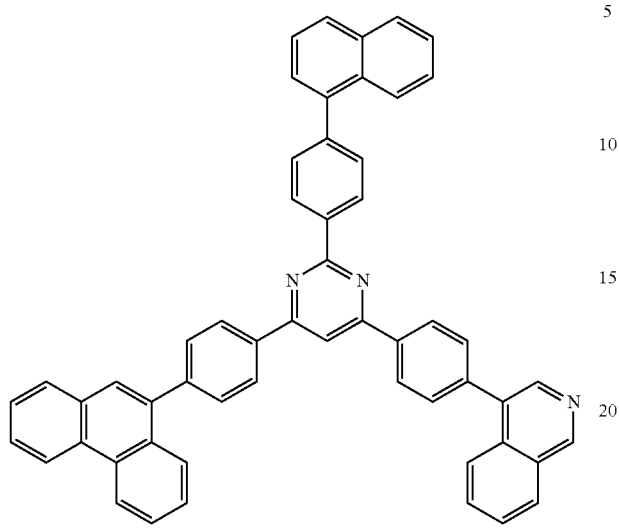
[Chemical Formula 647]
(7-206)
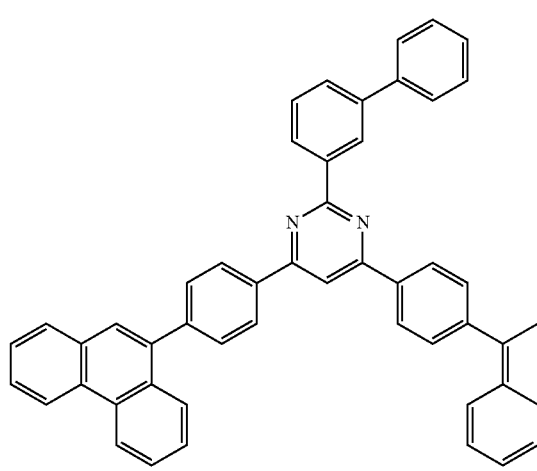
[Chemical Formula 648]
(7-207)
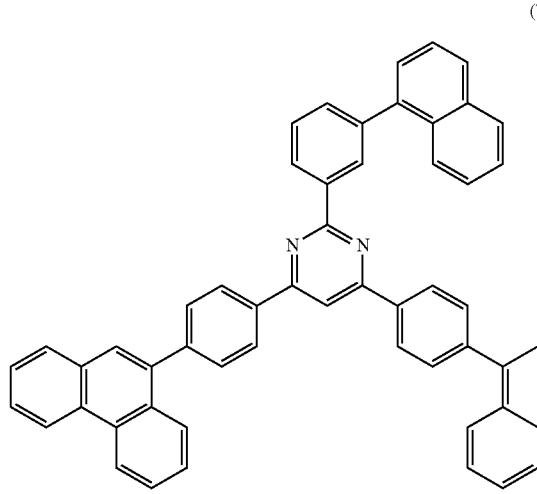
-continued
[Chemical Formula 649]
(7-208)
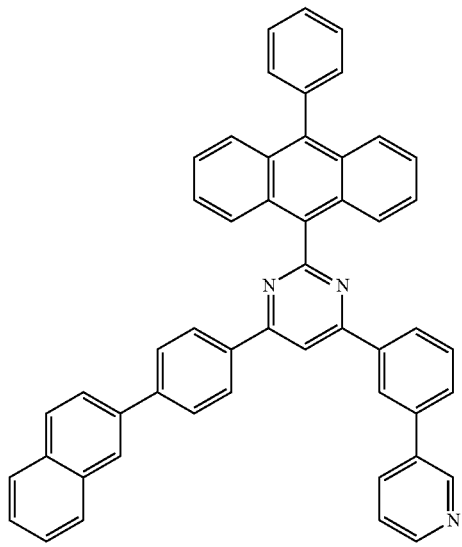
[Chemical Formula 650]
(7-209)
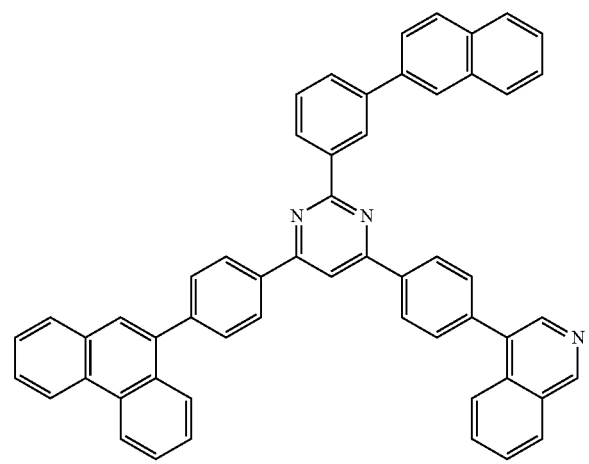
[Chemical Formula 651]
(7-210)

[Chemical Formula 652]
(7-211)
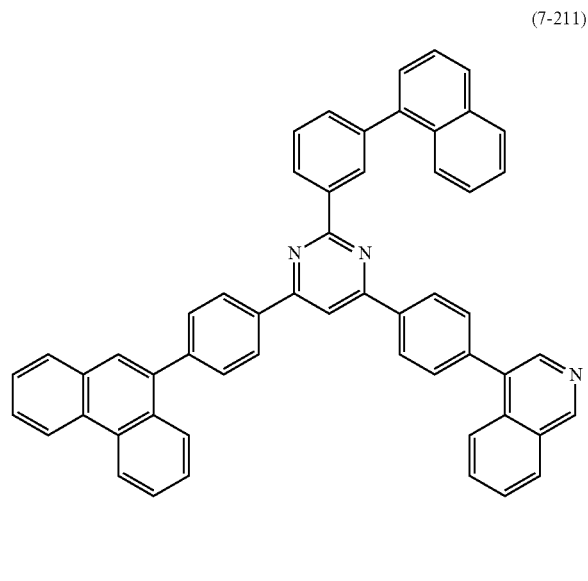
[Chemical Formula 653]
(7-212)
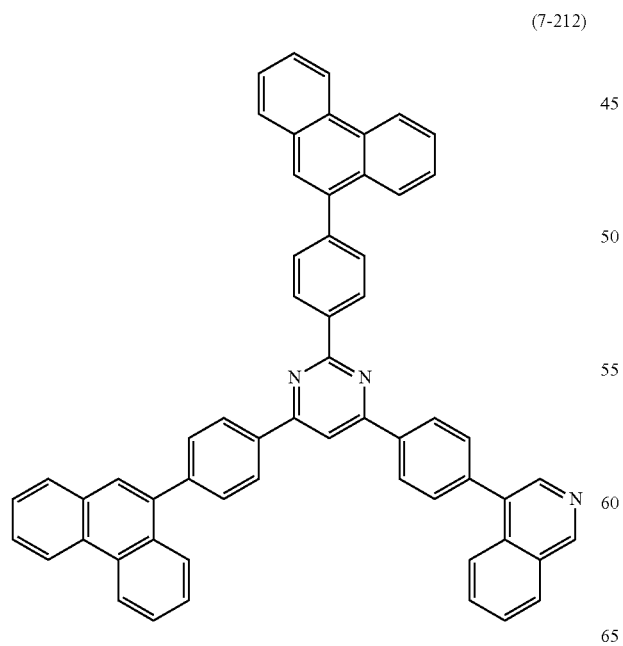
[Chemical Formula 654]
(7-213)
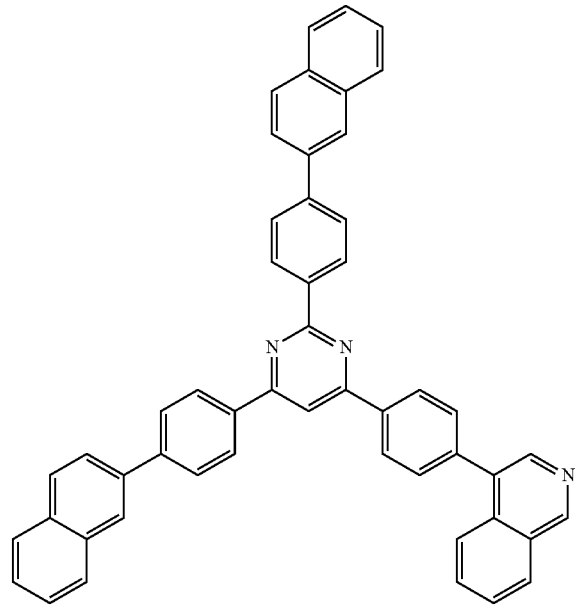
[Chemical Formula 655]
(7-214)
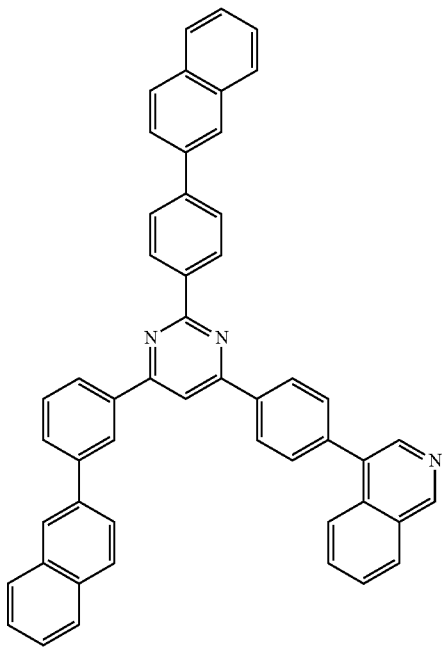

[Chemical Formula 656]
(7-215)
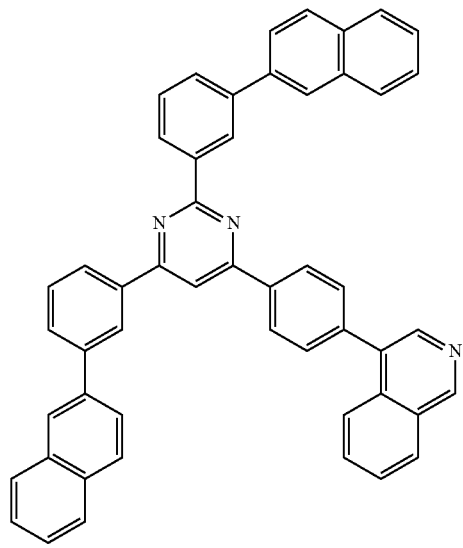
[Chemical Formula 657]
(7-216)
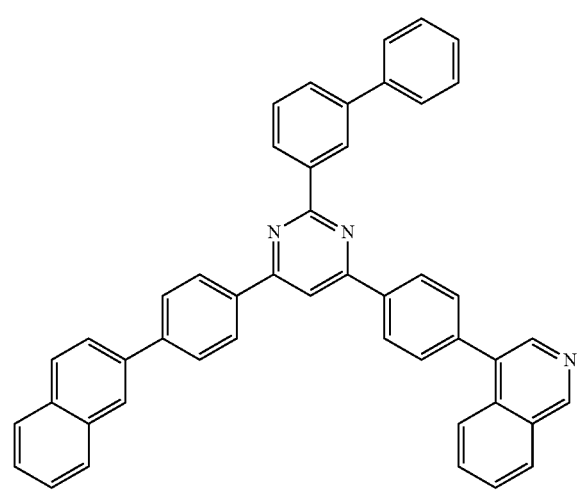
[Chemical Formula 658]
(7-217)
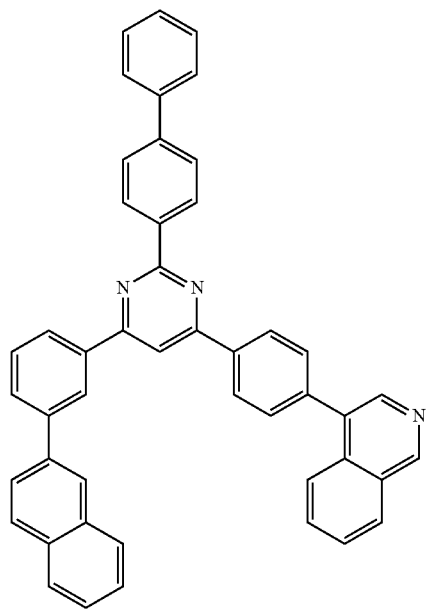
[Chemical Formula 659]
(7-218)
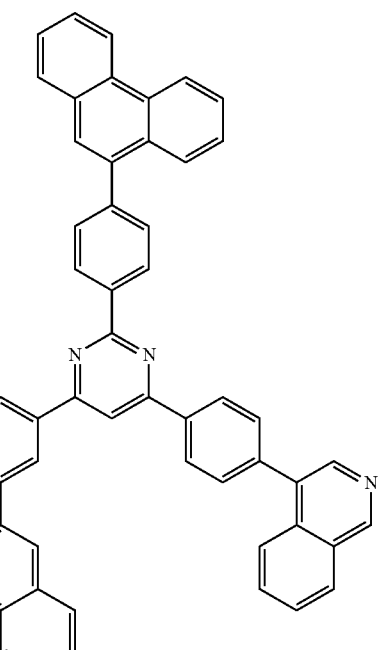

[Chemical Formula 660]
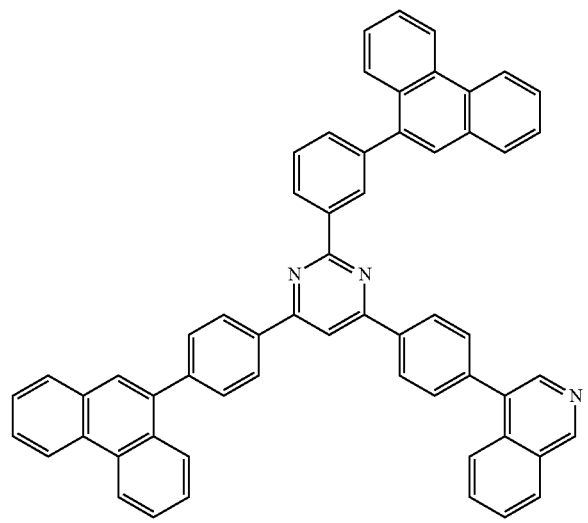
[Chemical Formula 661]
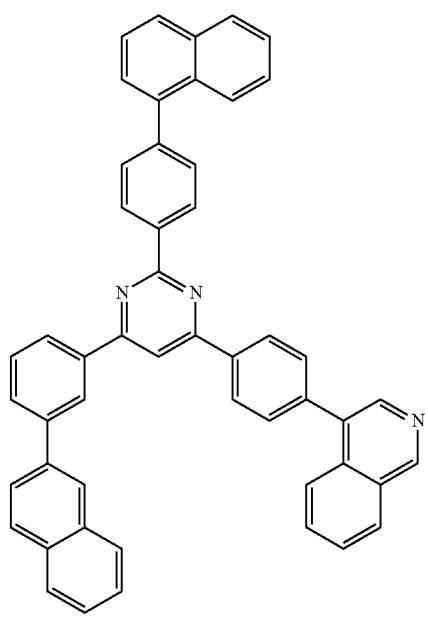
[Chemical Formula 662]
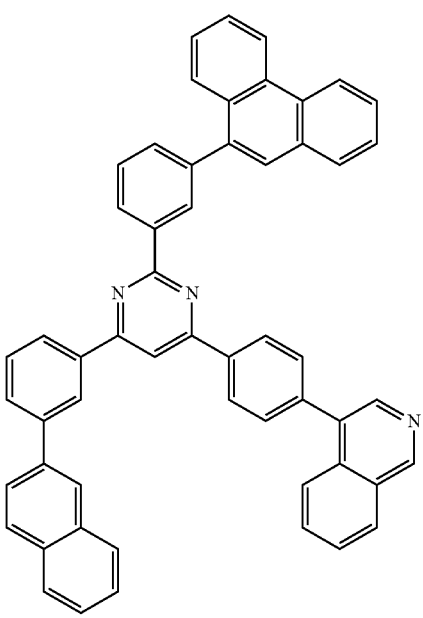
(7-221)
[Chemical Formula 663]
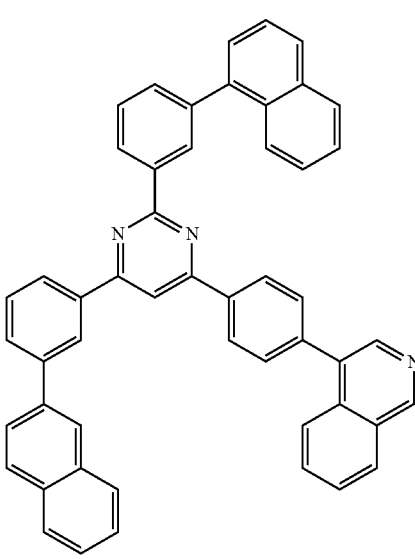
(7-222)

[Chemical Formula 664]
(7-223)
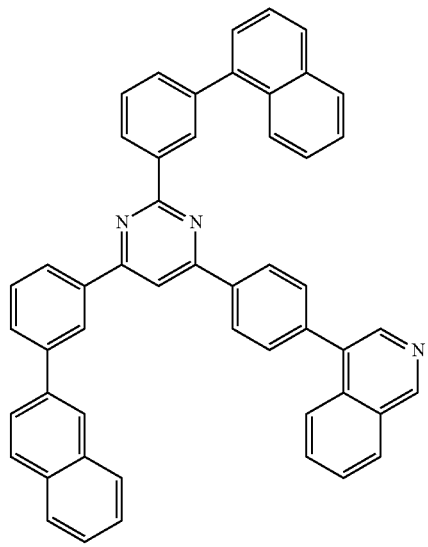
[Chemical Formula 665]
(7-224)
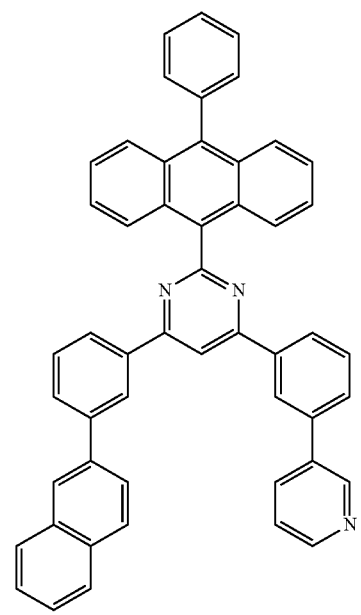
[Chemical Formula 666]
(7-225)
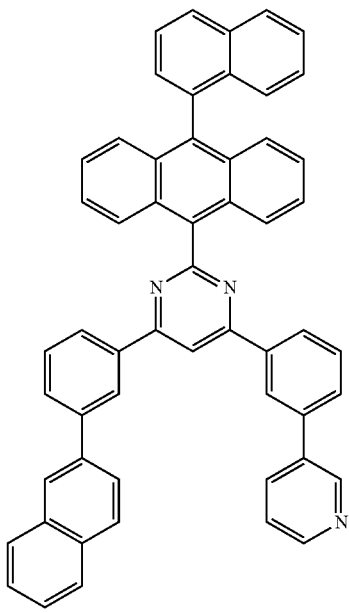
[Chemical Formula 667]
(7-226)
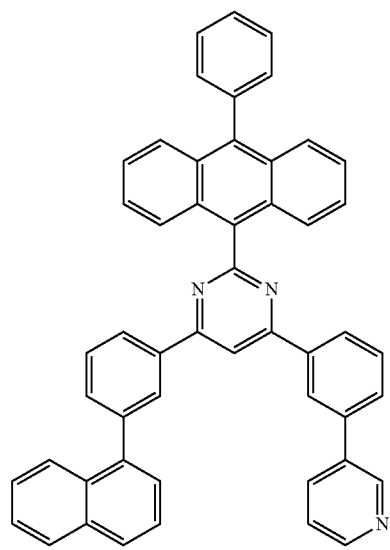

[Chemical Formula 668]
(7-227)
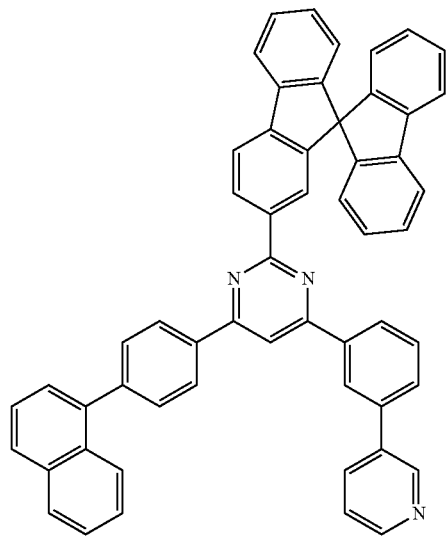
[Chemical Formula 669]
(7-228)
[Chemical Formula 670]
(7-229)
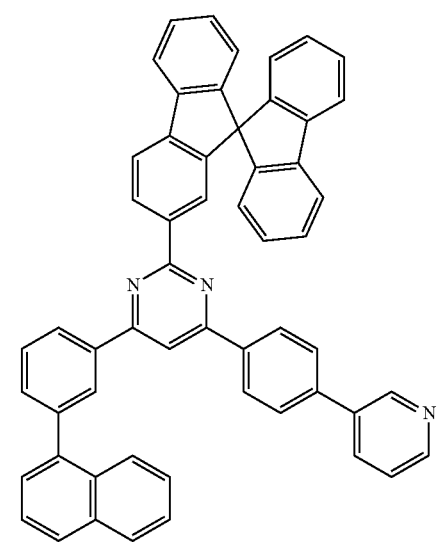
[Chemical Formula 671]
(7-230)
[Chemical Formula 672]
(7-231)
[Chemical Formula 673]
(7-232)
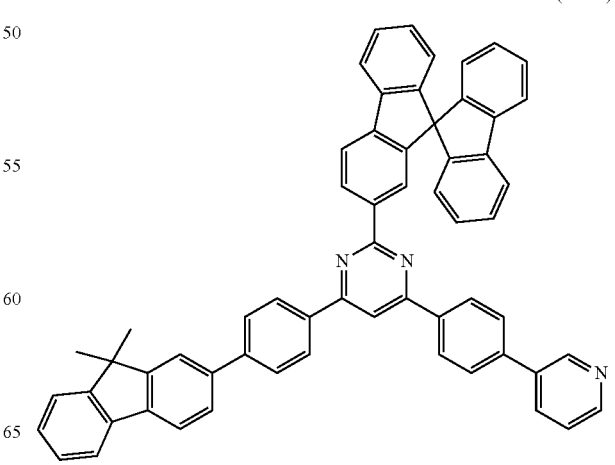

[Chemical Formula 674]
(7-233)
[Chemical Formula 675]
[7-234]
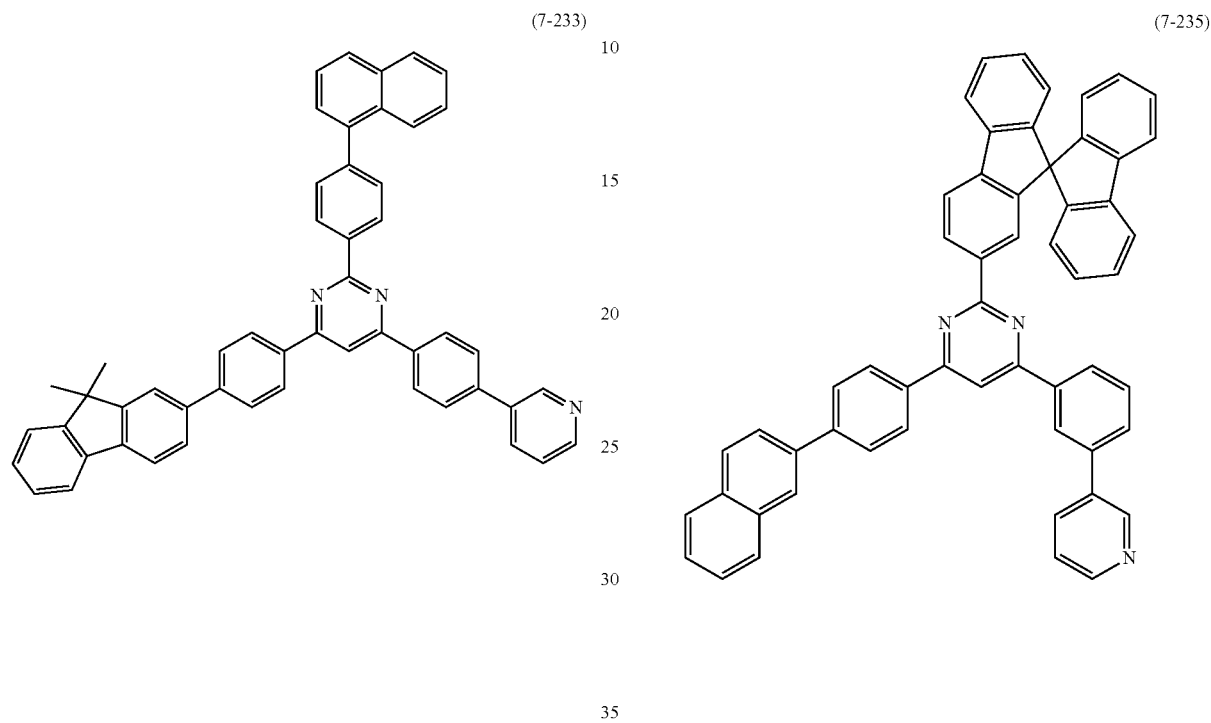
[Chemical Formula 676]
(7-235)
[Chemical Formula 677]
(7-236)
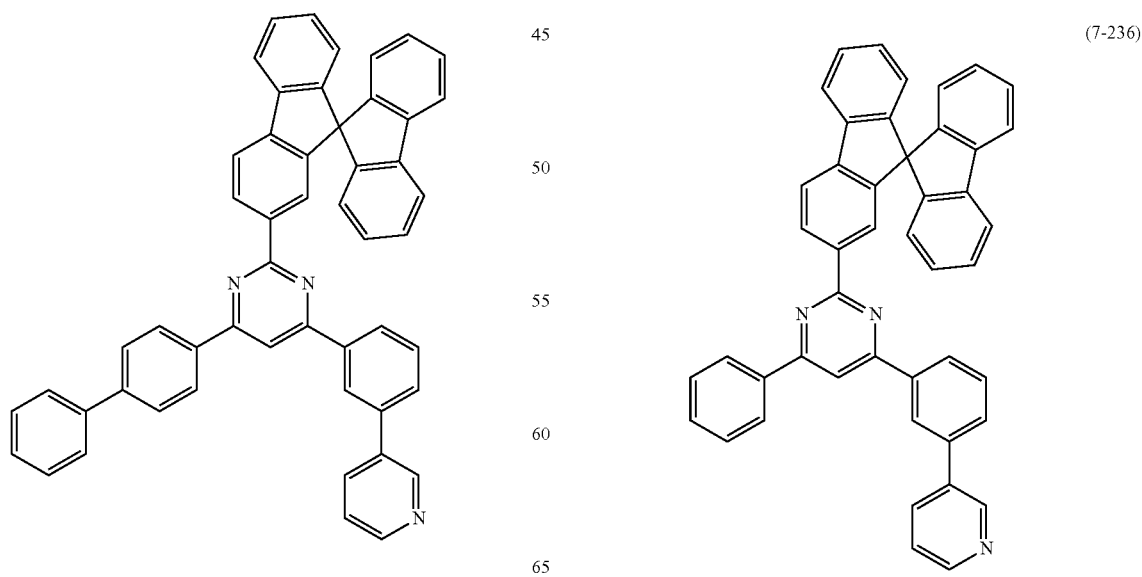

[Chemical Formula 678]
(7-237)
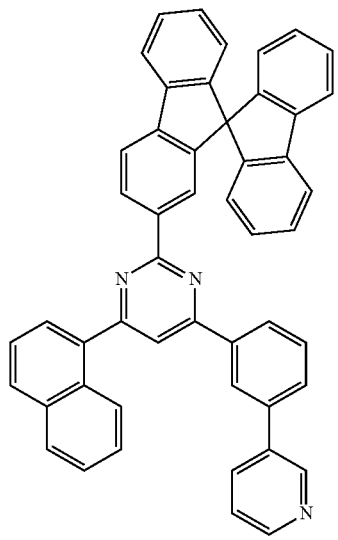
[Chemical Formula 679]
(7-238)
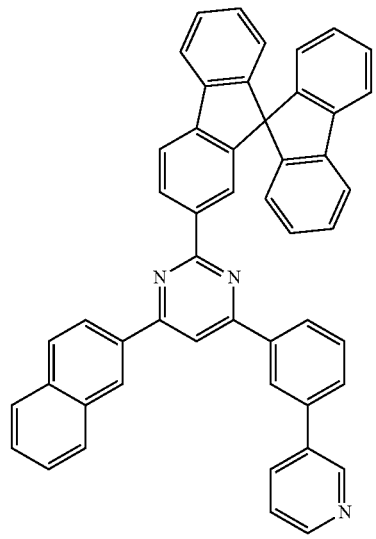
[Chemical Formula 680]
(7-239)
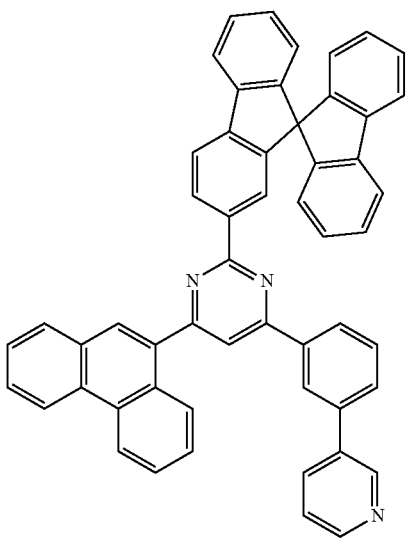
[Chemical Formula 681]
(7-240)
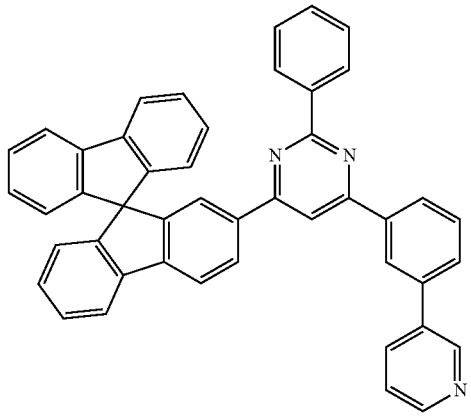
[Chemical Formula 682]
(7-241)
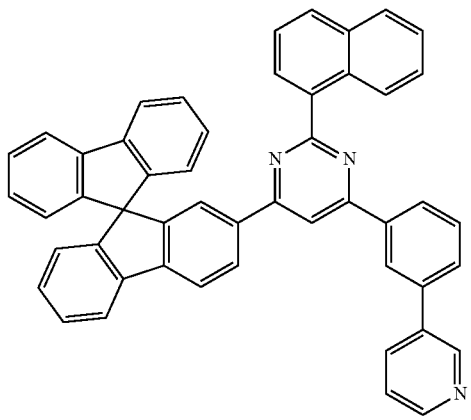

[Chemical Formula 683]
(7-242)
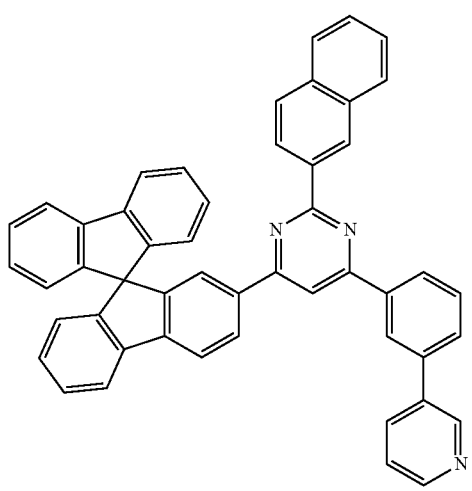
[Chemical Formula 684]
(7-243)
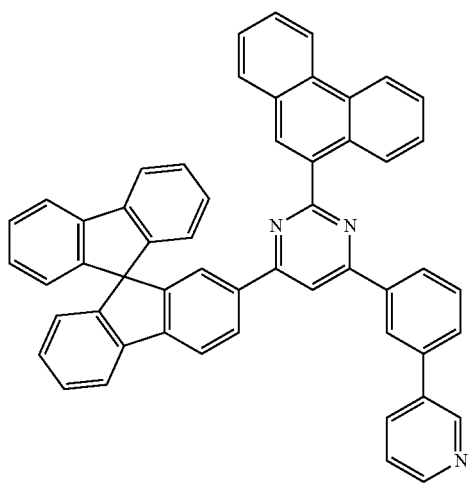
[Chemical Formula 685]
(7-244)
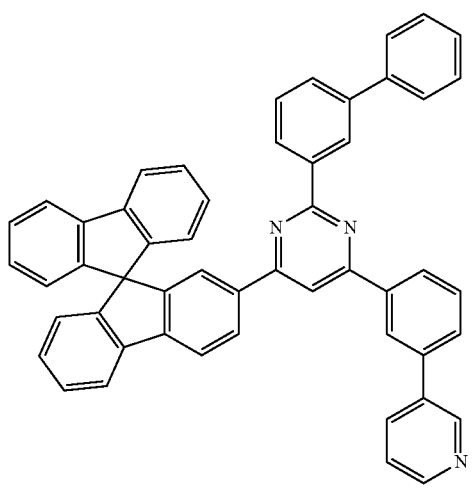
[Chemical Formula 686]
(7-245)
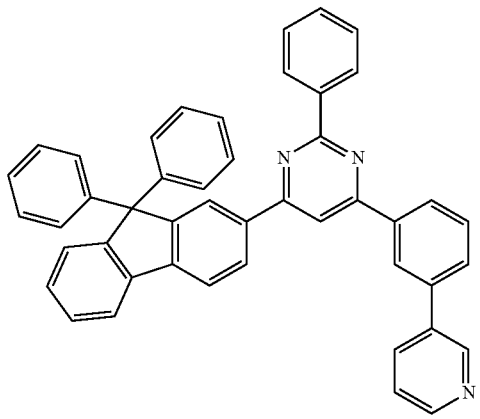
[Chemical Formula 687]
(7-246)
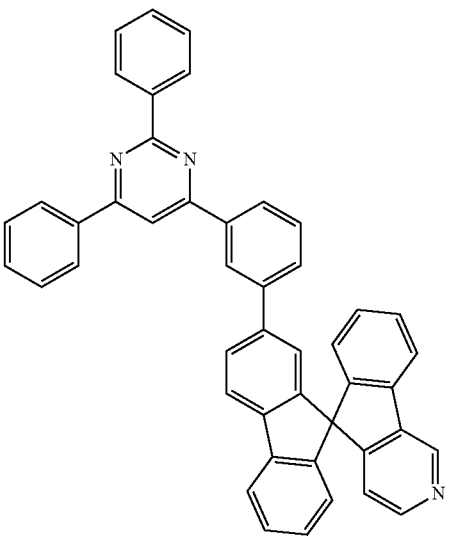
[Chemical Formula 688]
(7-247)
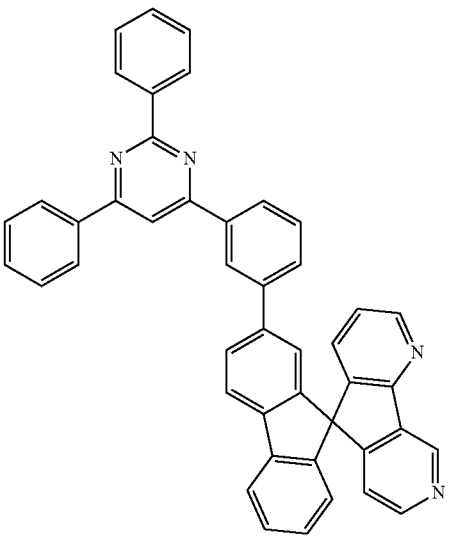

[Chemical Formula 689]
(7-248)
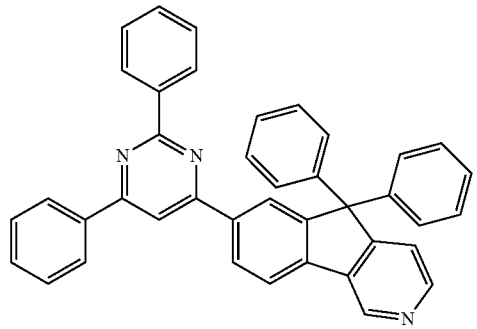
[Chemical Formula 690]
(7-249)
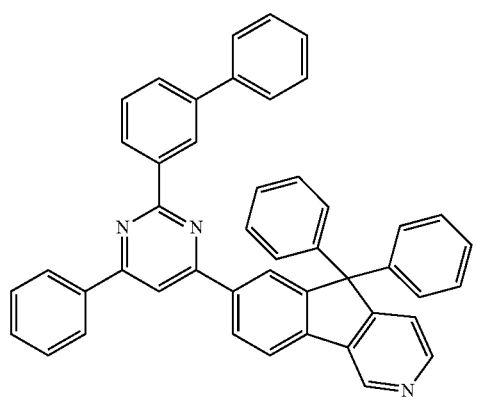
[Chemical Formula 691]
(7-250)
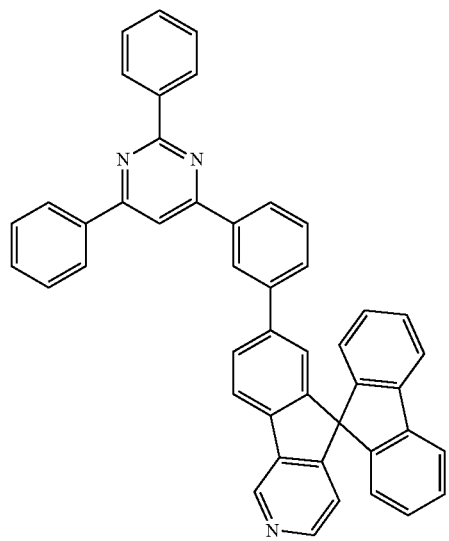
[Chemical Formula 692]
(7-251)
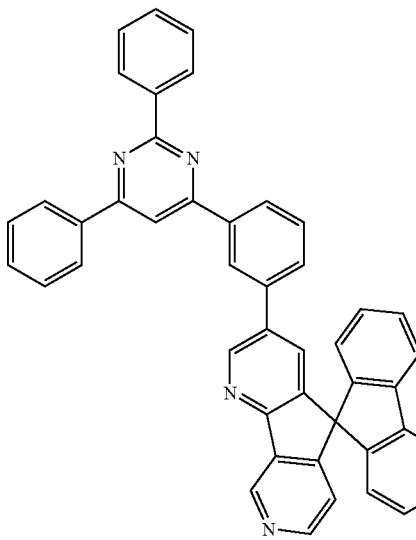
[Chemical Formula 693]
(7-252)
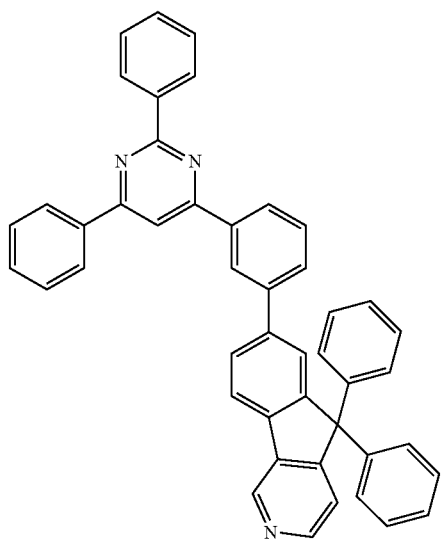

-continued
[Chemical Formula 694]
(7-253)
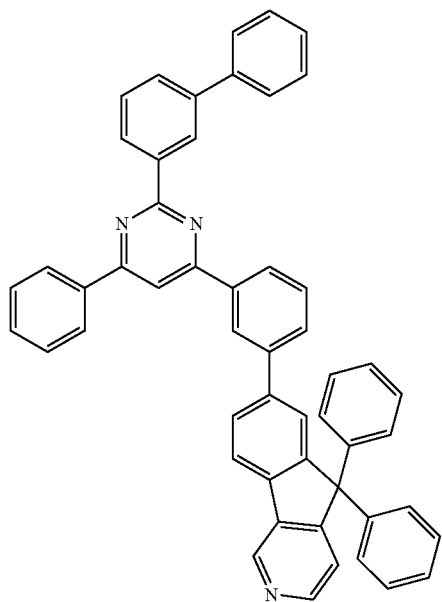
[Chemical Formula 695]
(7-254)
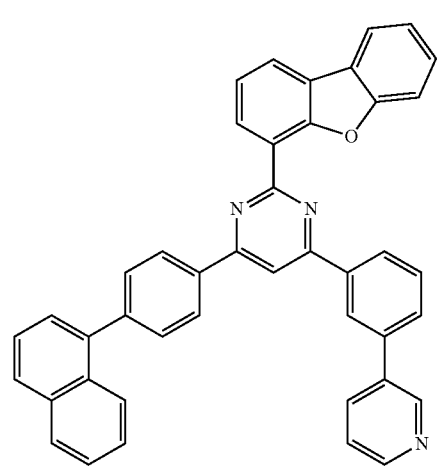
[Chemical Formula 696]
(7-255)
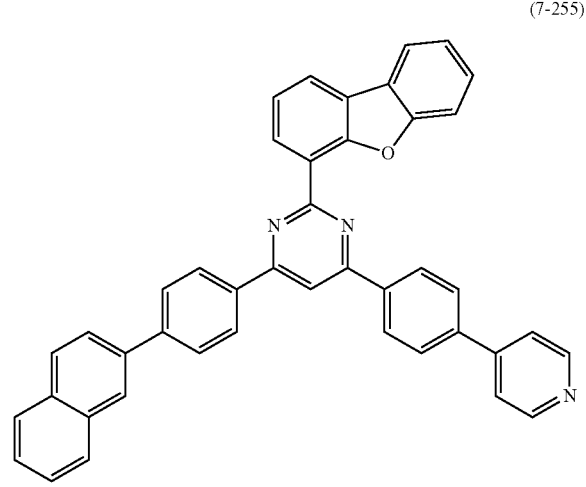
-continued
[Chemical Formula 697]
(7-256)
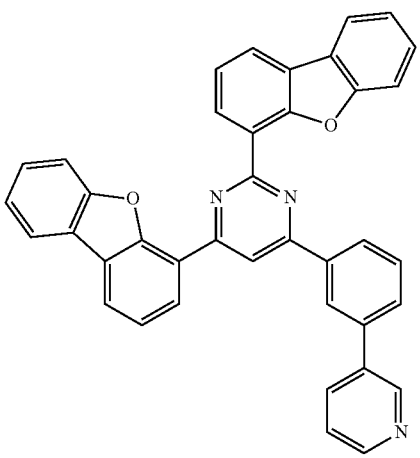
[Chemical Formula 698]
(7-257)
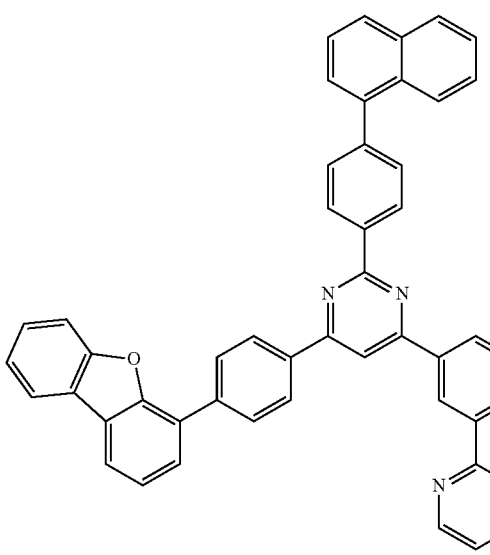
[Chemical Formula 699]
(7-258)
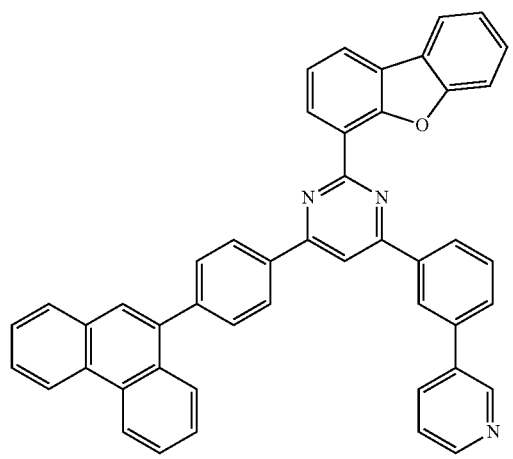

[Chemical Formula 700]
(7-259)
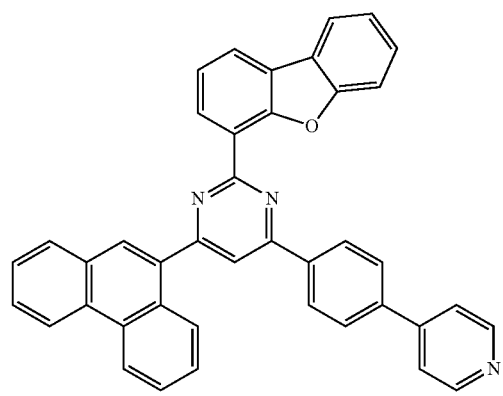
[Chemical Formula 701]
(7-260)
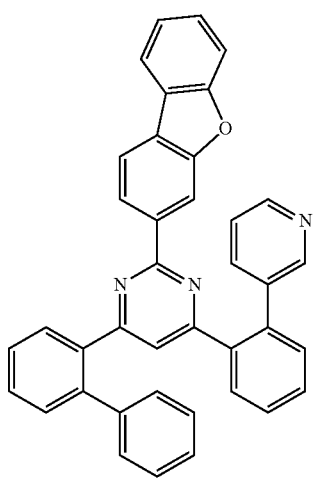
[Chemical Formula 702]
(7-261)
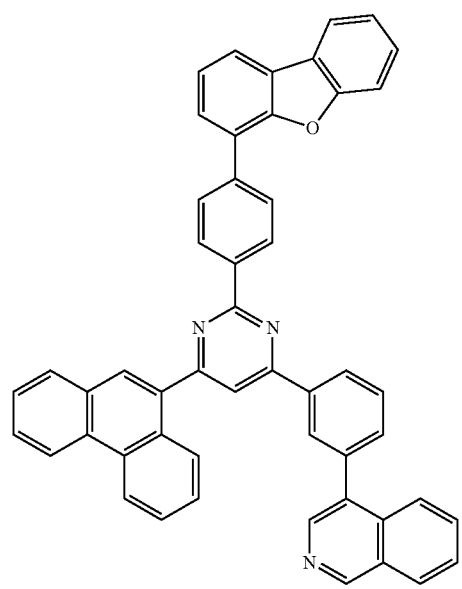
[Chemical Formula 703]
(7-262)
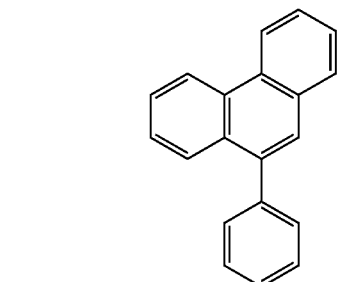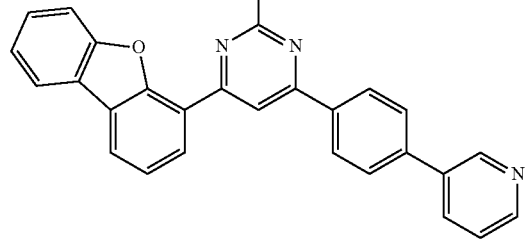
[Chemical Formula 704]
(7-263)
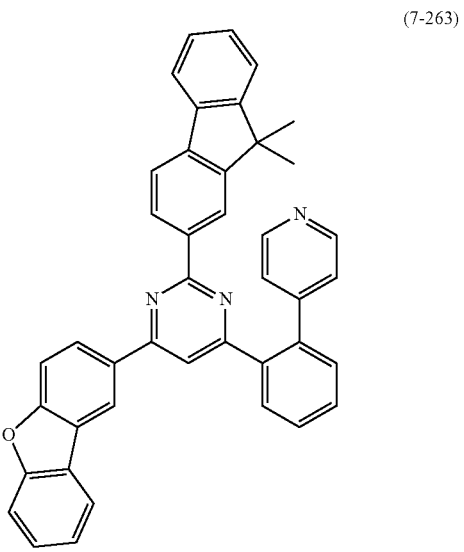

[Chemical Formula 705]

(7-264)

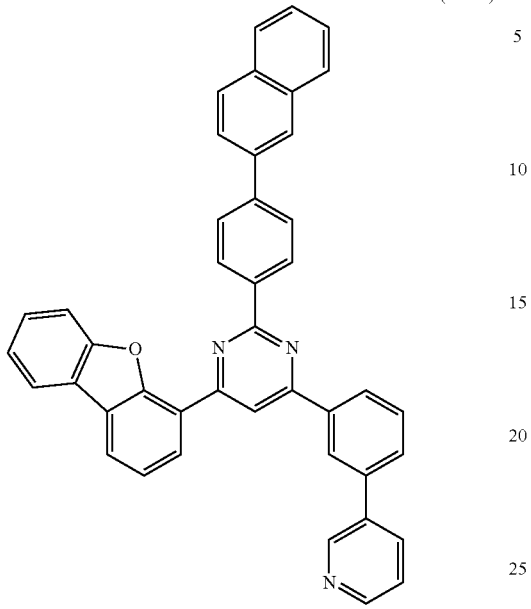

The compounds described above having a pyrimidine ring structure can be synthesized according to a known method (refer to Patent Document 12, for example).

The following presents specific examples of preferred compounds among the compounds of the general formula (9) preferably used in the organic EL device of the present invention and having a benzotriazole ring structure. The present invention, however, is not restricted to these compounds.

[Chemical Formula 706]

(9-1)

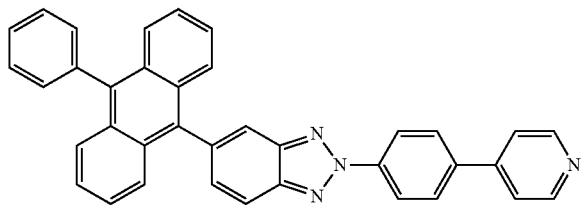

[Chemical Formula 707]

(9-2)

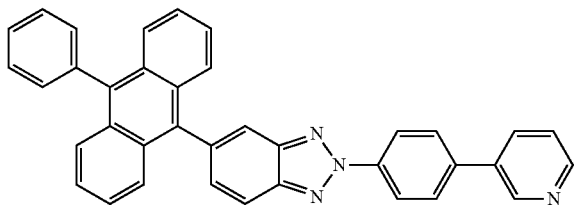

[Chemical Formula 708]

(9-3)

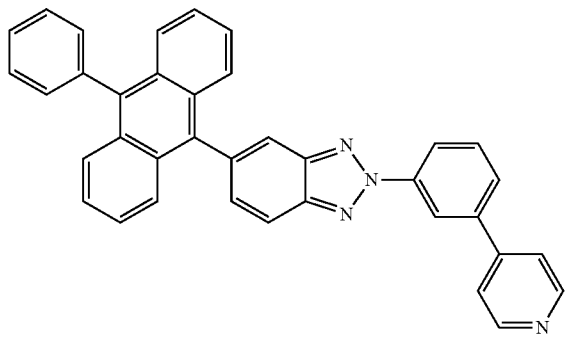

[Chemical Formula 709]

(9-4)

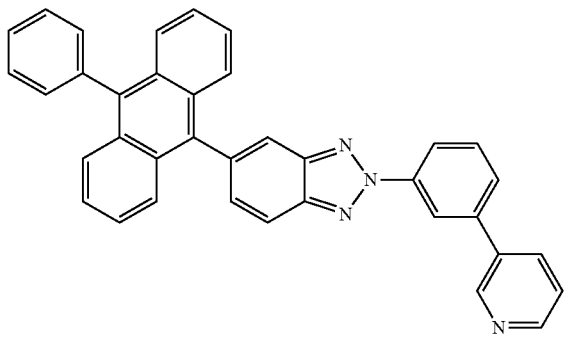

[Chemical Formula 710]
(9-5)
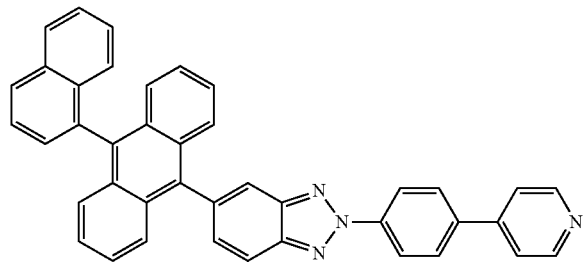
[Chemical Formula 711]
(9-6)
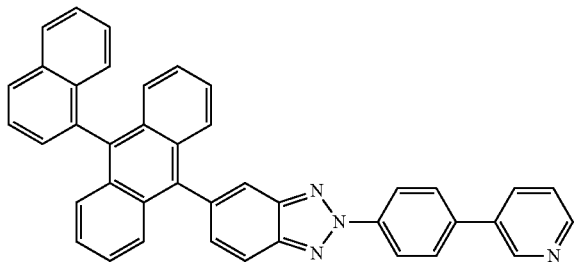
[Chemical Formula 712]
(9-7)
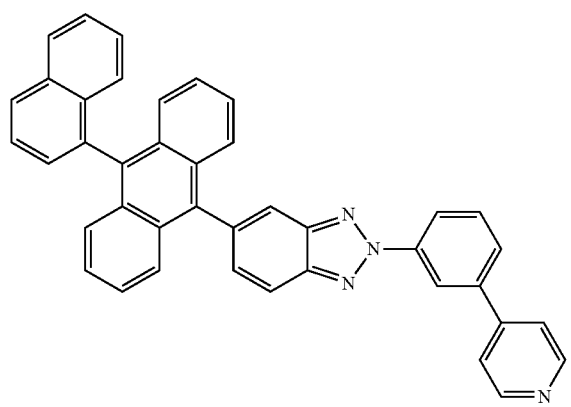
[Chemical Formula 713]
(9-8)
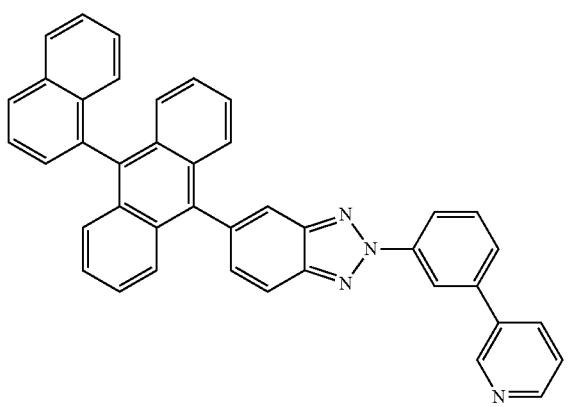
[Chemical Formula 714]
(9-9)
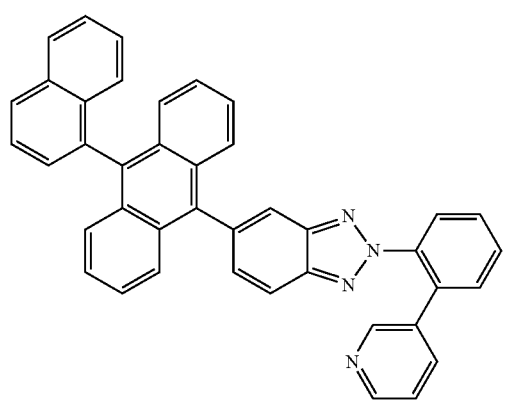
[Chemical Formula 715]
(9-10)
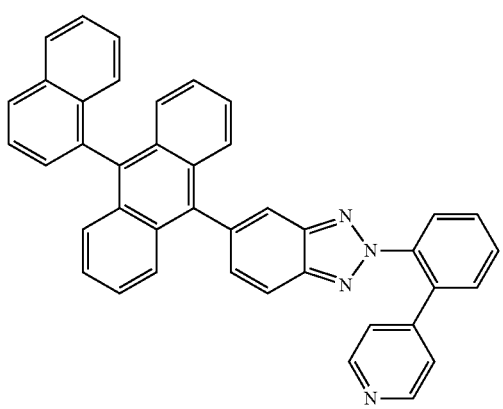
[Chemical Formula 716]
(9-11)
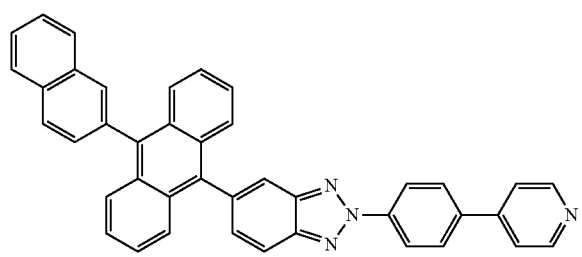
[Chemical Formula 717]
(9-12)
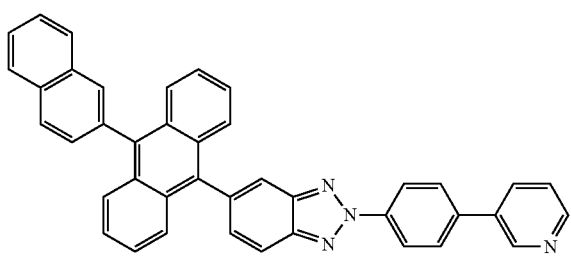

[Chemical Formula 718]
(9-13)
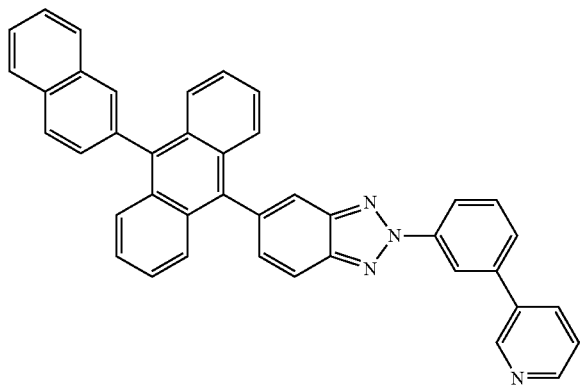
[Chemical Formula 719]
(9-14)
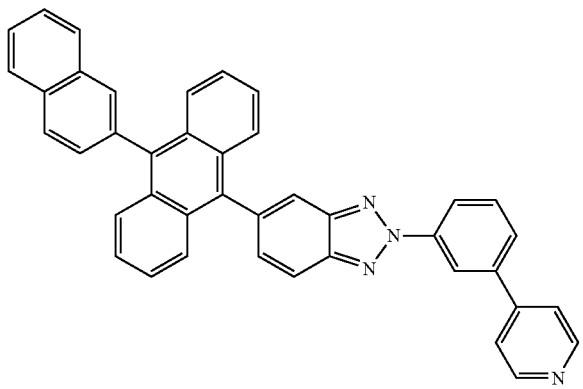
[Chemical Formula 720]
(9-15)
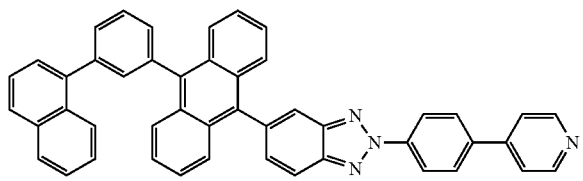
[Chemical Formula 721]
(9-16)
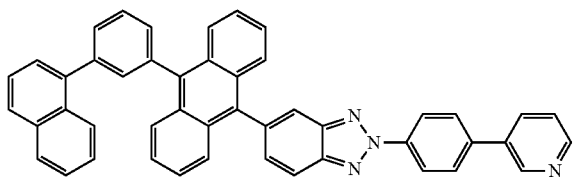
[Chemical Formula 722]
(9-17)
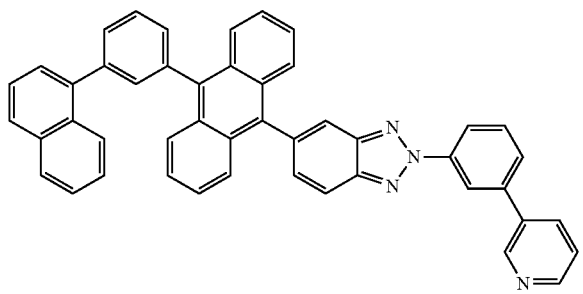
[Chemical Formula 723]
(9-18)
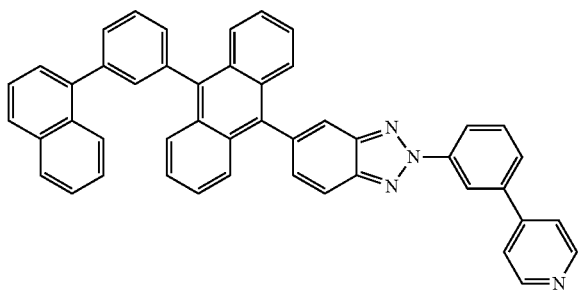
[Chemical Formula 724]
(9-19)
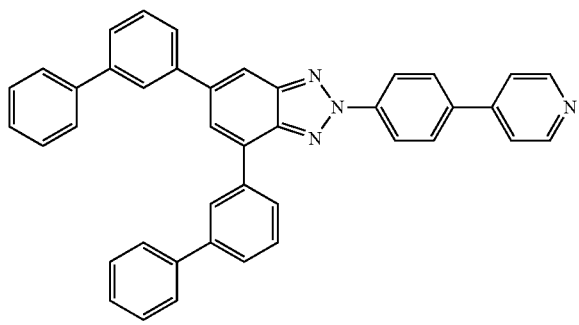
[Chemical Formula 725]
(9-20)
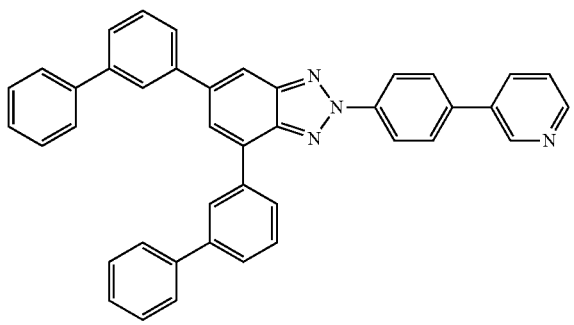

[Chemical Formula 726] [Chemical Formula 727]
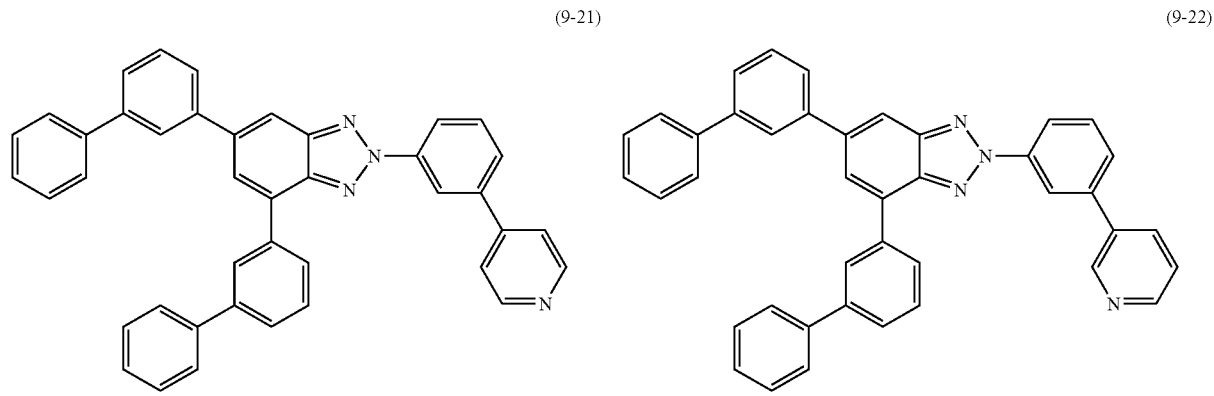
(9-21) (9-22)
[Chemical Formula 728] [Chemical Formula 729]
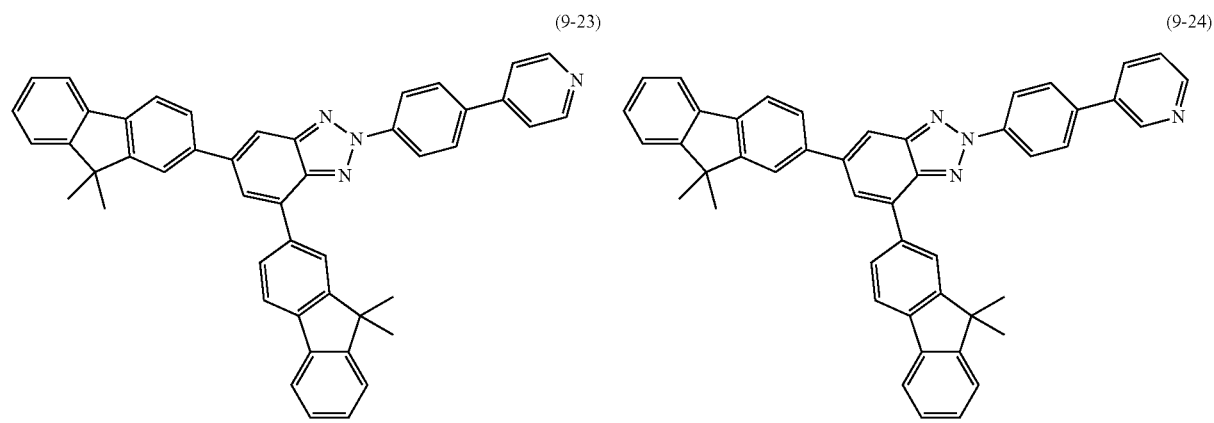
(9-23) (9-24)
[Chemical Formula 730] [Chemical Formula 731]
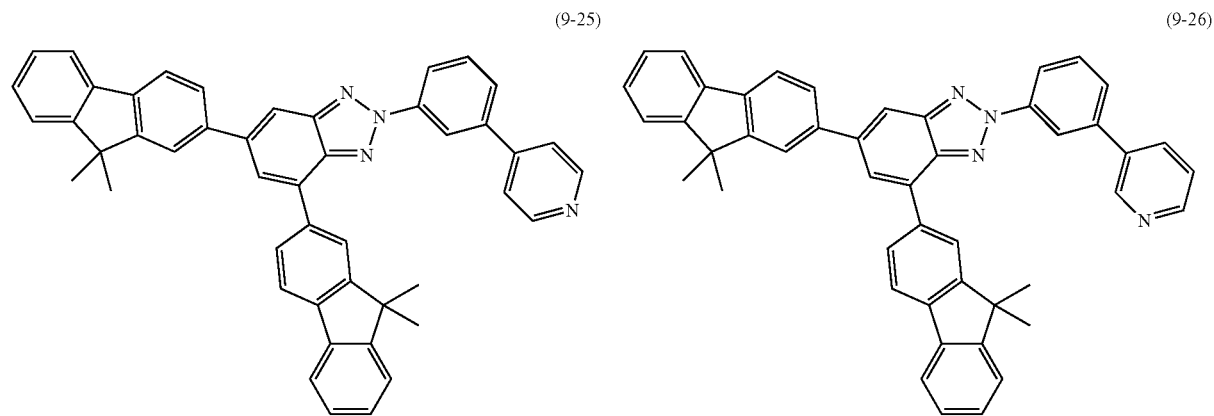
(9-25) (9-26)

[Chemical Formula 732]
(9-27)
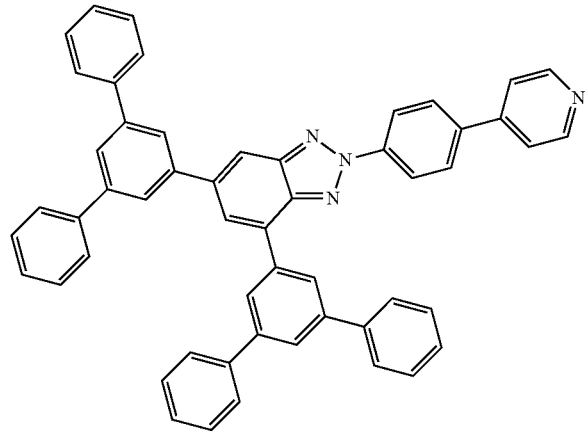
[Chemical Formula 733]
(9-28)
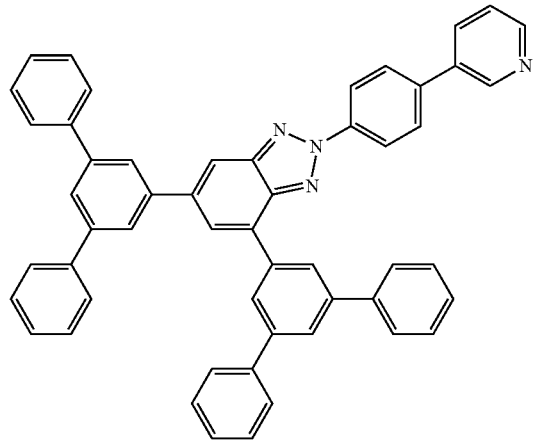
[Chemical Formula 734]
(9-29)
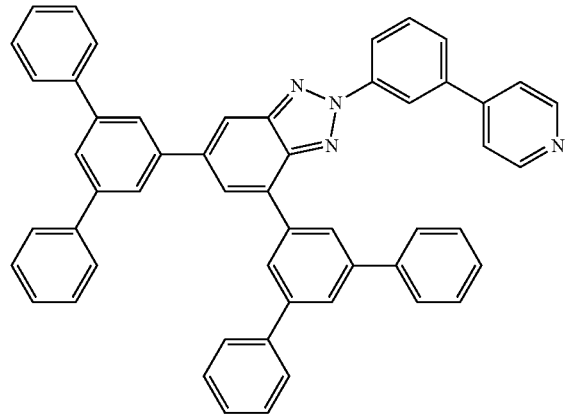
[Chemical Formula 735]
(9-30)
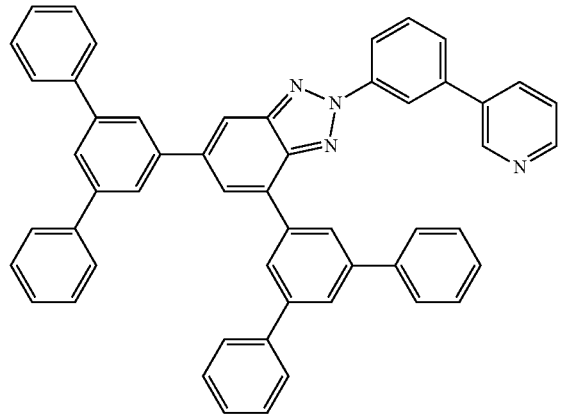
[Chemical Formula 736]
(9-31)
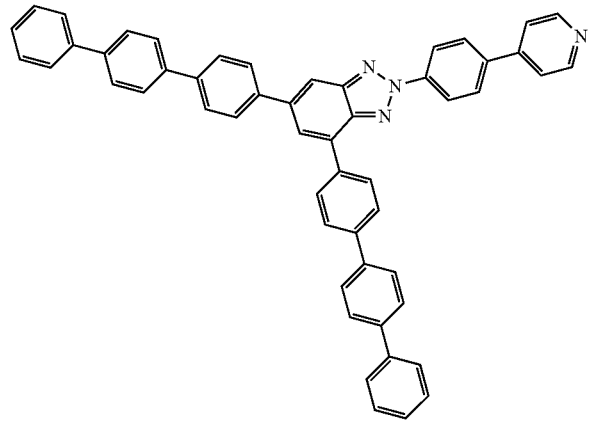
[Chemical Formula 737]
(9-32)
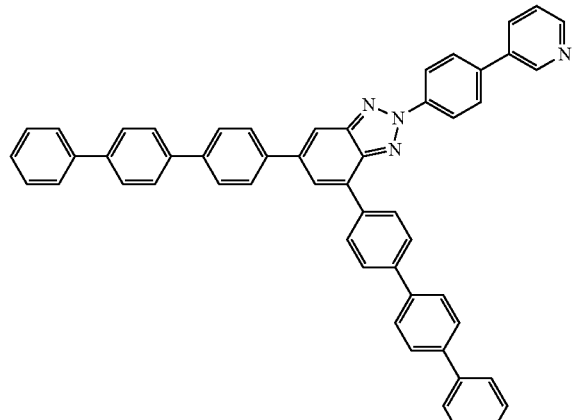

[Chemical Formula 738]
(9-33)
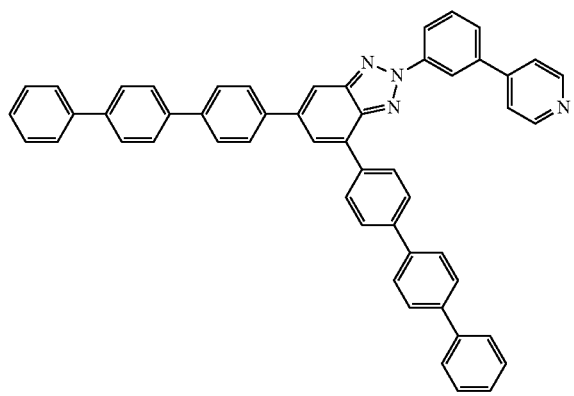
[Chemical Formula 739]
(9-34)
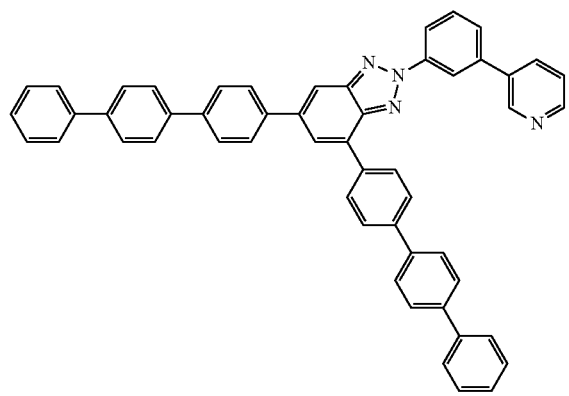
[Chemical Formula 740]
(9-35)
[Chemical Formula 741]
(9-36)
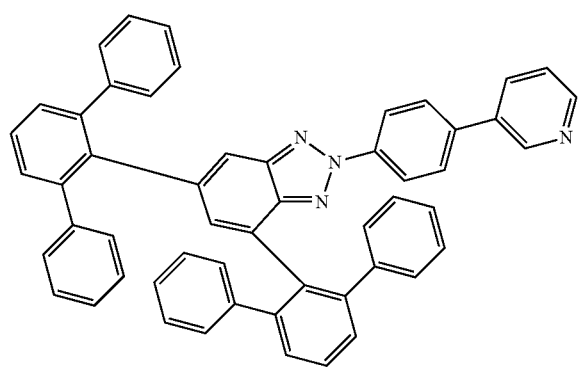
[Chemical Formula 742]
(9-37)
[Chemical Formula 743]
(9-38)
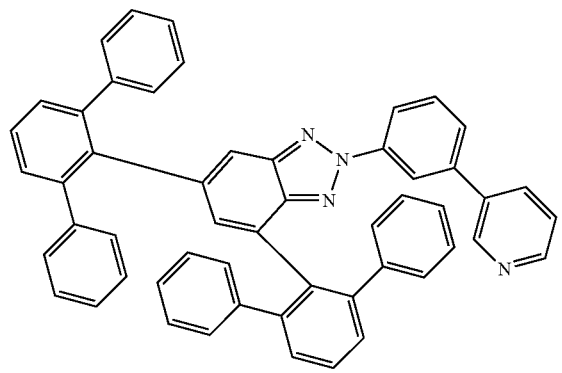
[Chemical Formula 744]
(9-39)
[Chemical Formula 745]
(9-40)
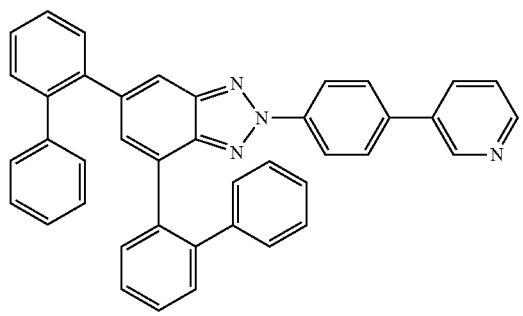

[Chemical Formula 746]
(9-41)
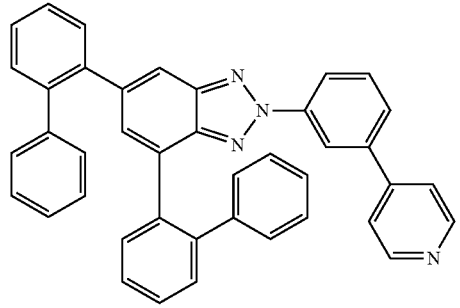
[Chemical Formula 747]
(9-42)
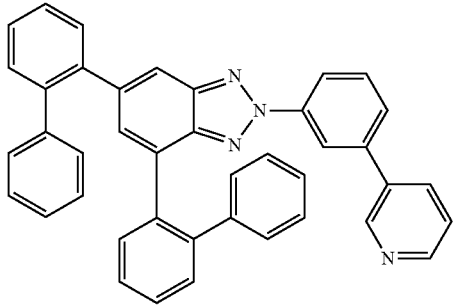
[Chemical Formula 748]
(9-43)
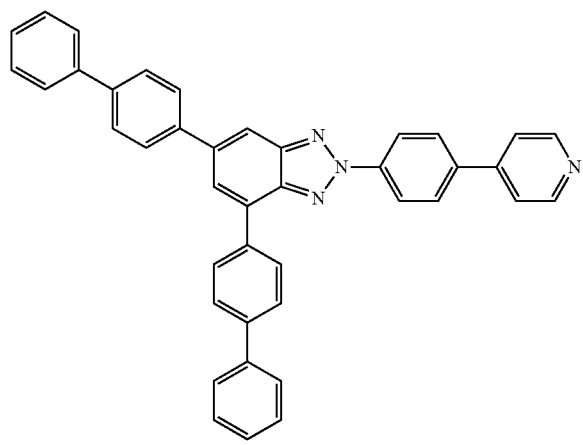
[Chemical Formula 749]
(9-44)
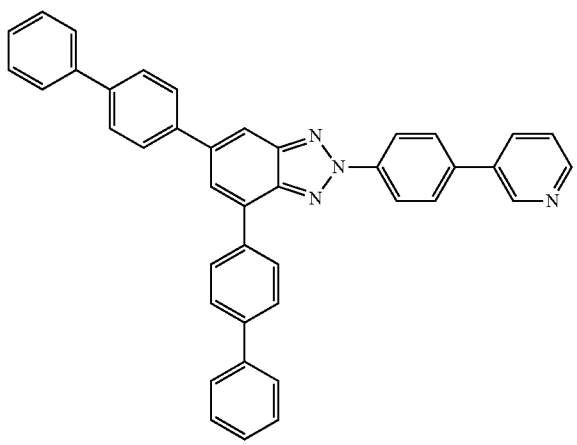
[Chemical Formula 750]
(9-45)
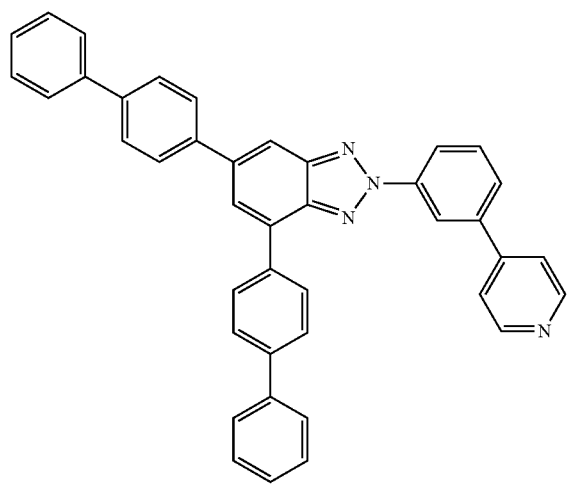
[Chemical Formula 751]
(9-46)
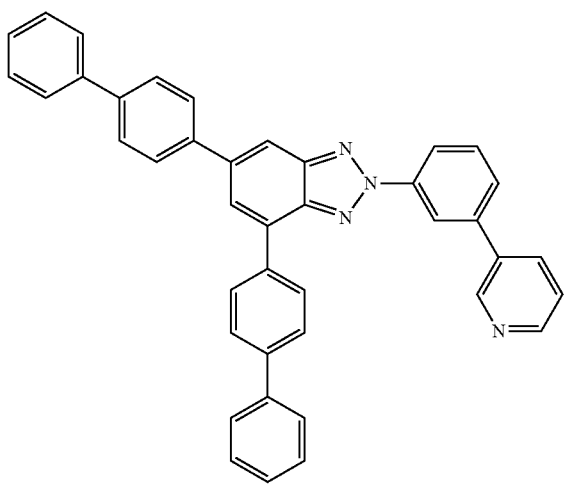

-continued
[Chemical Formula 752]
(9-47)
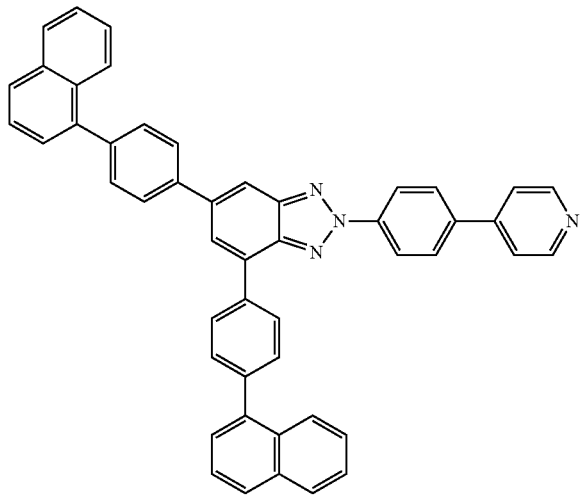
[Chemical Formula 753]
(9-48)
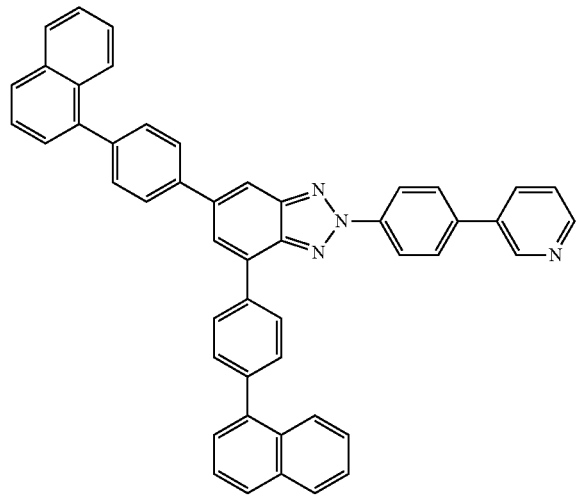
[Chemical Formula 754]
(9-49)
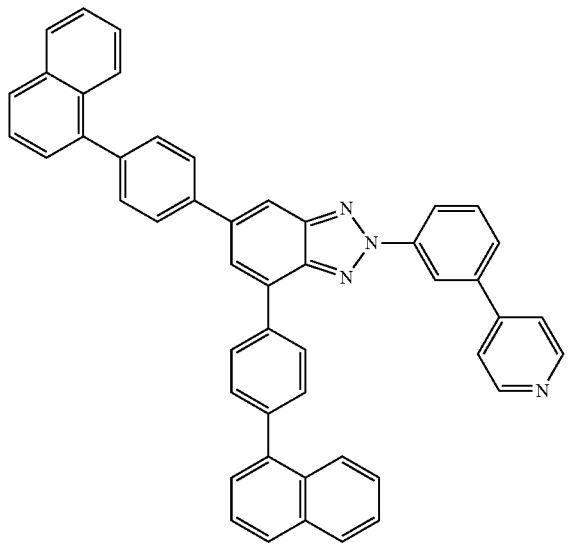
[Chemical Formula 755]
(9-50)
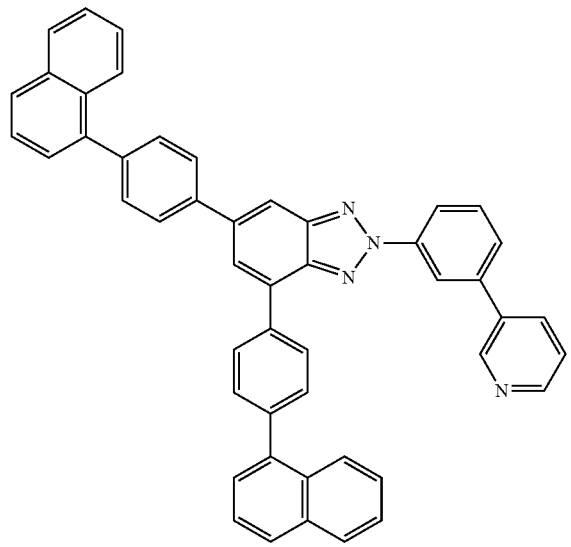
[Chemical Formula 756]
(9-51)
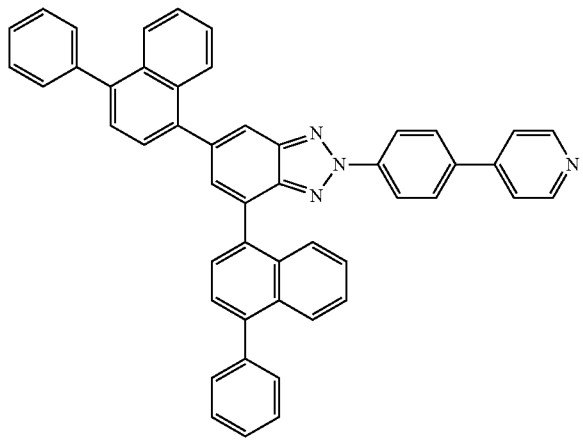
[Chemical Formula 757]
(9-52)
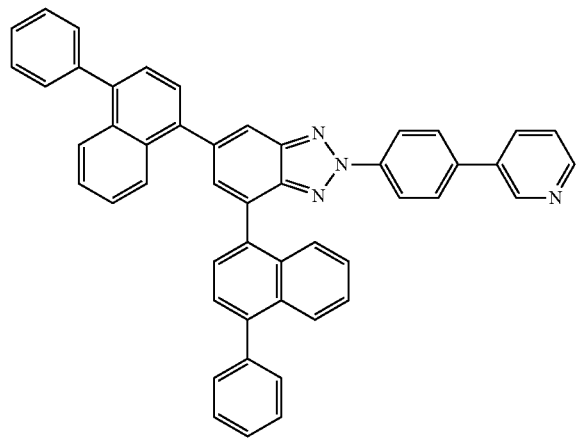

[Chemical Formula 758]
(9-53)
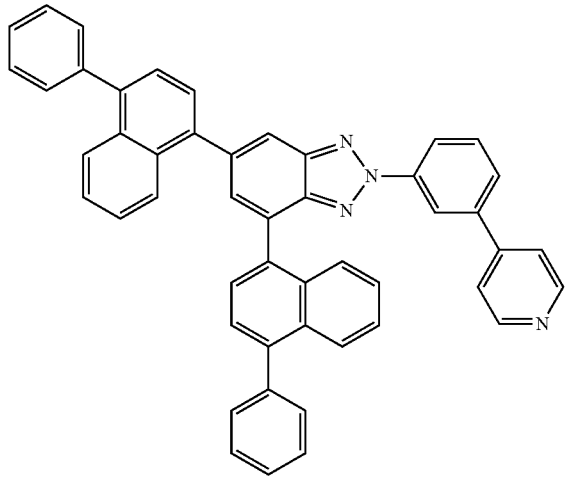
[Chemical Formula 759]
(9-54)
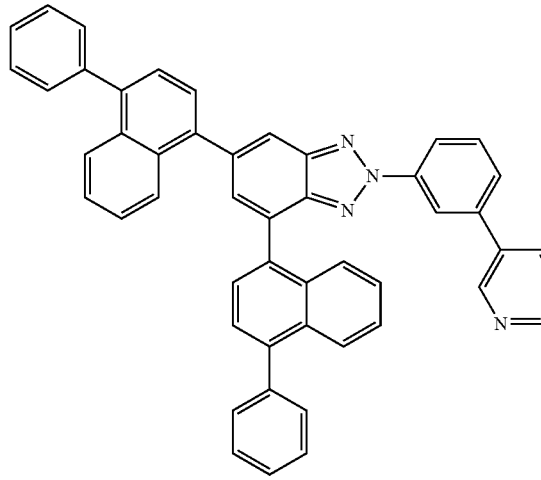
[Chemical Formula 760]
(9-55)
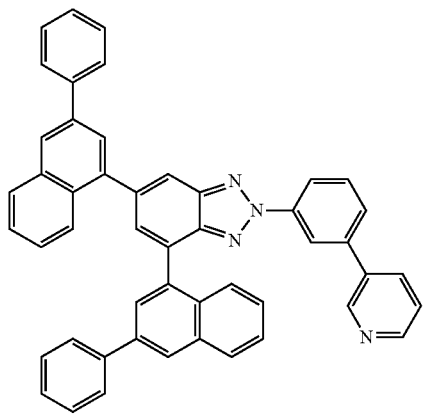
[Chemical Formula 761]
(9-56)
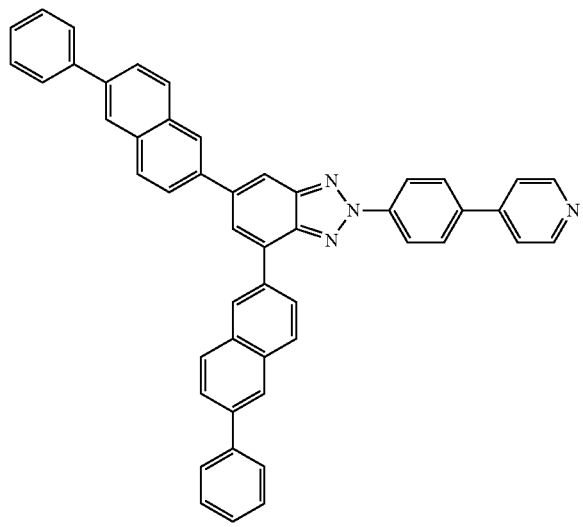

[Chemical Formula 762]
(9-57)
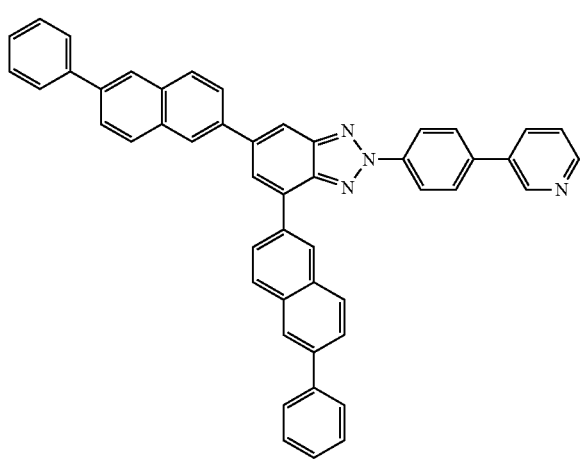
[Chemical Formula 763]
(9-58)
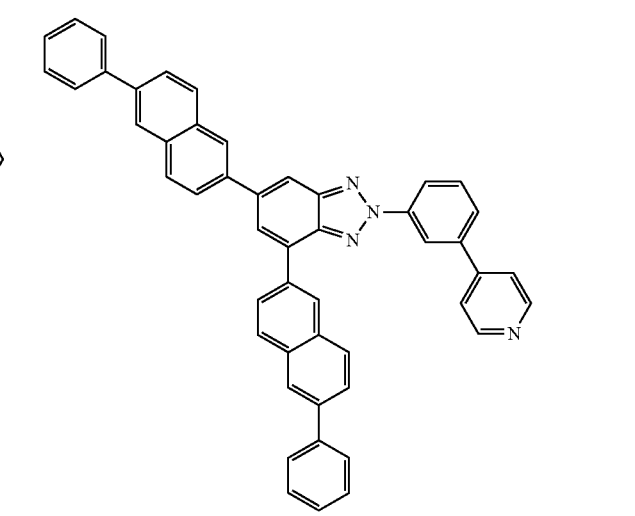
[Chemical Formula 764]
(9-59)
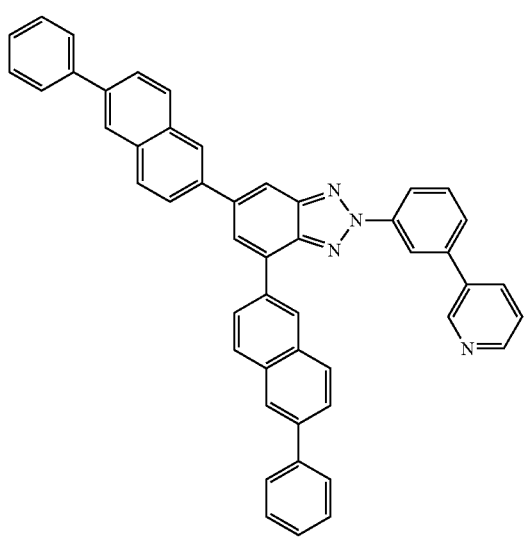
[Chemical Formula 765]
(9-60)
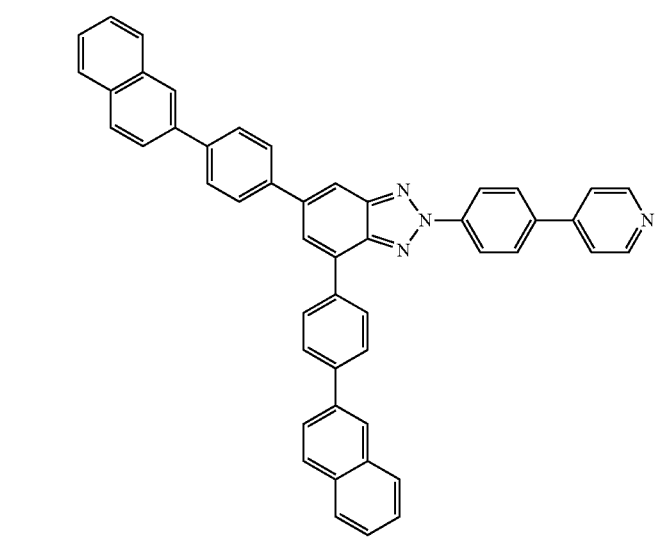

[Chemical Formula 766]
(9-61)
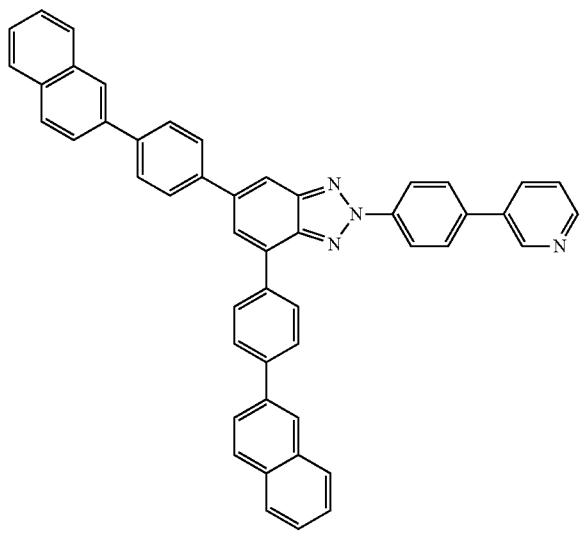
[Chemical Formula 767]
(9-62)
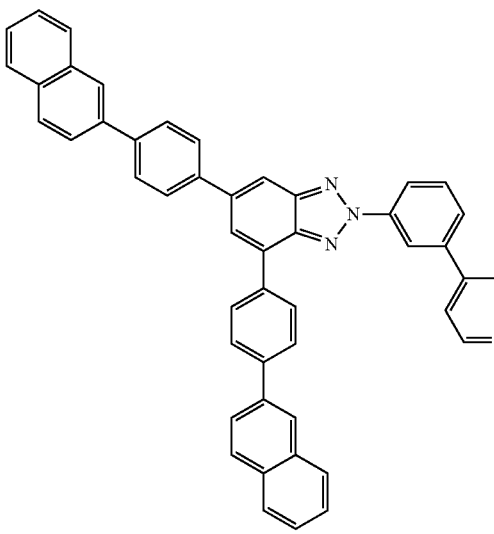
[Chemical Formula 768]
(9-63)
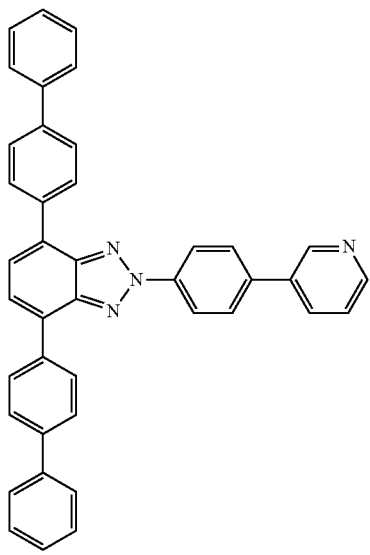
[Chemical Formula 769]
(9-64)
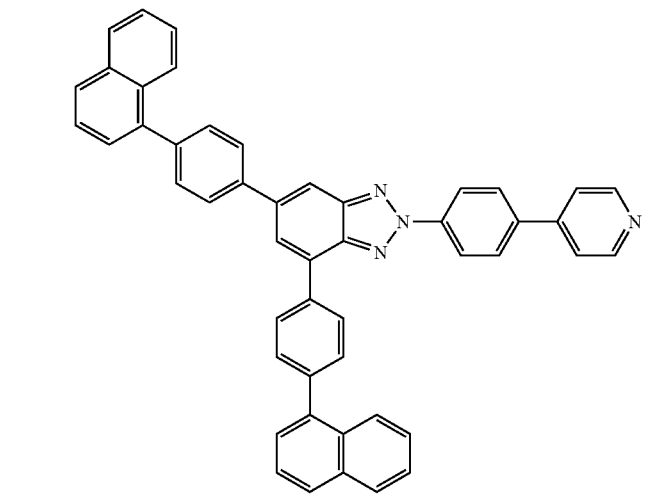

[Chemical Formula 770]

(9-65)

[Chemical Formula 771]

(9-66)

[Chemical Formula 772]

(9-67)

[Chemical Formula 773]

(9-68)

[Chemical Formula 774]
(9-69)
[Chemical Formula 775]
(9-70)
[Chemical Formula 776]
(9-71)
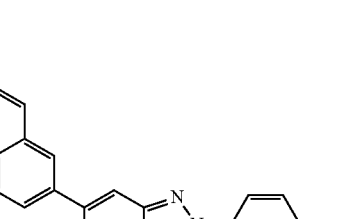
[Chemical Formula 777]
(9-72)
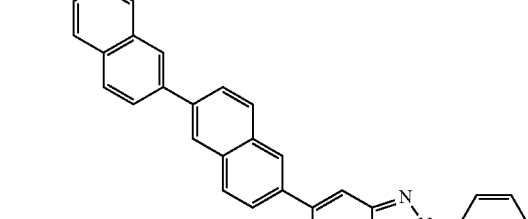

[Chemical Formula 778]
(9-73)
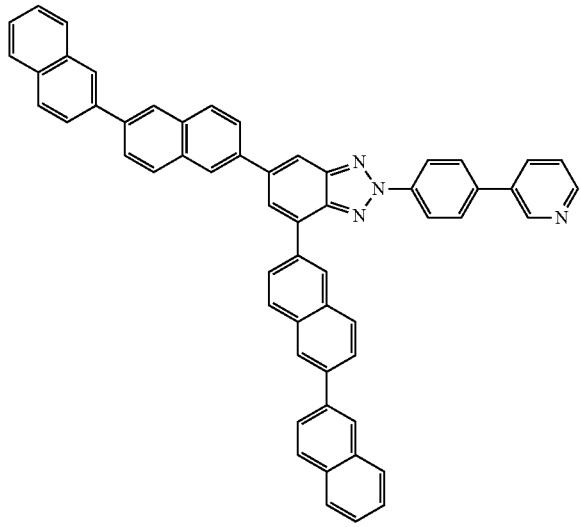
[Chemical Formula 779]
(9-74)
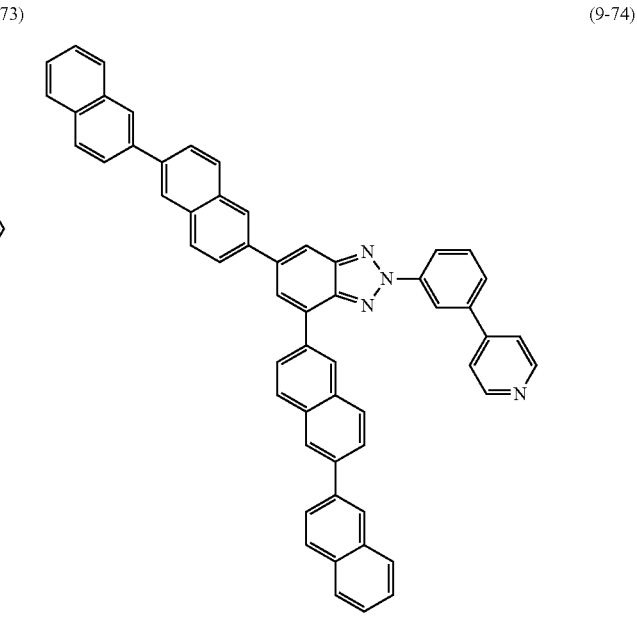
[Chemical Formula 780]
(9-75)
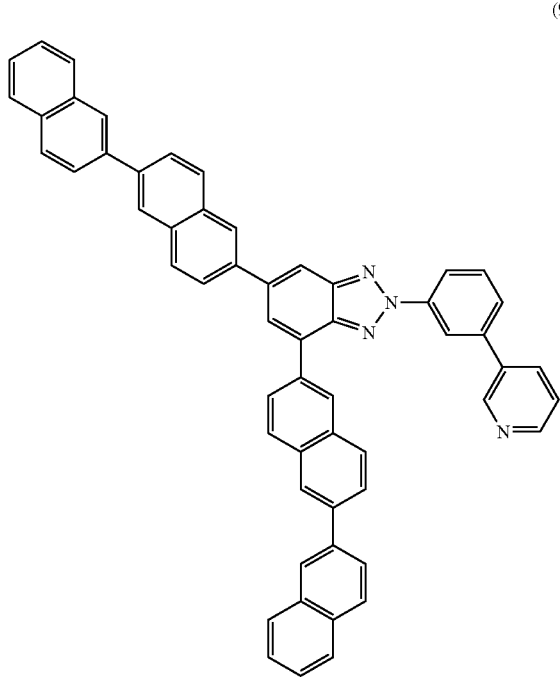
[Chemical Formula 781]
(9-76)
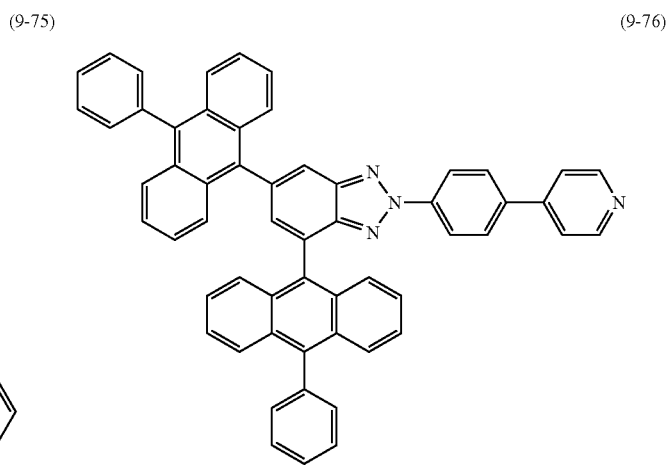

[Chemical Formula 782]
(9-77)
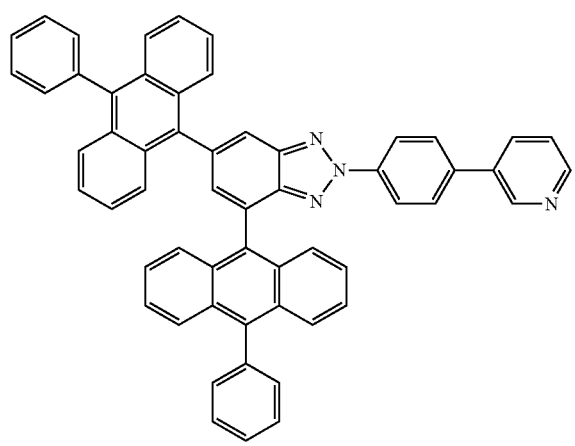
[Chemical Formula 783]
(9-78)
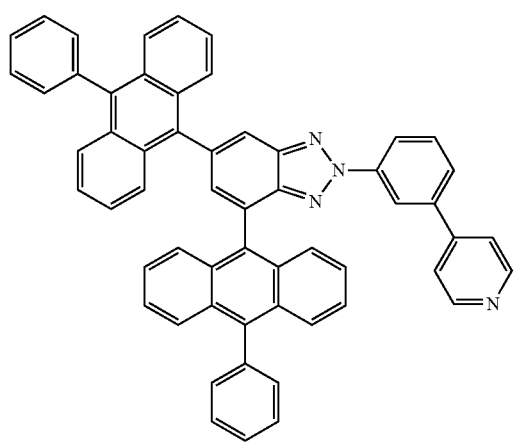
[Chemical Formula 784]
(9-79)
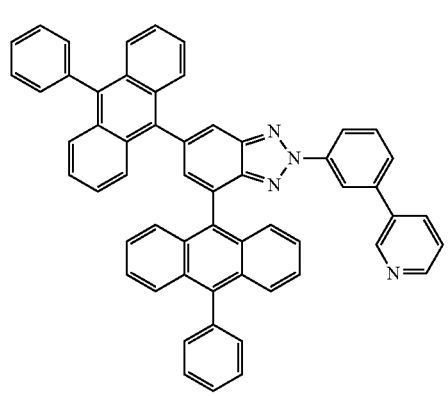
[Chemical Formula 785]
(9-80)
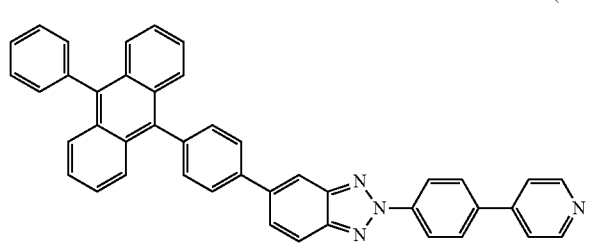
[Chemical Formula 786]
(9-81)
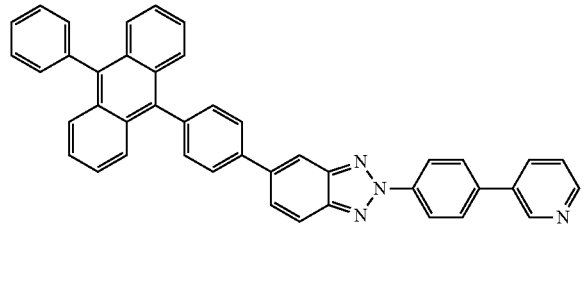
[Chemical Formula 787]
(9-82)
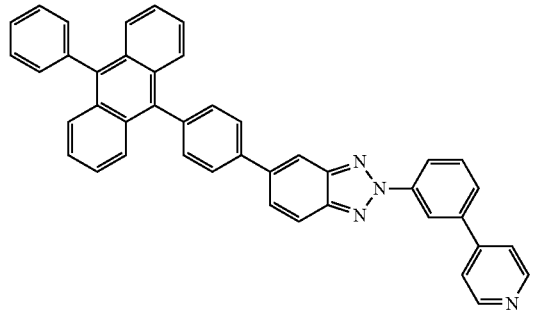

-continued
[Chemical Formula 788]
(9-83)
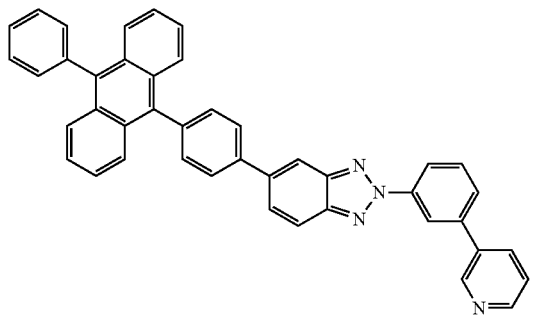
[Chemical Formula 789]
(9-84)
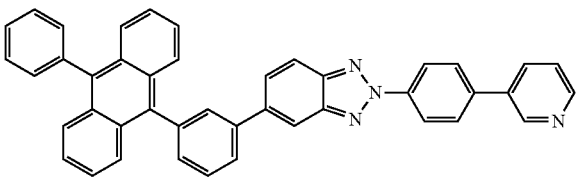
[Chemical Formula 790]
(9-85)
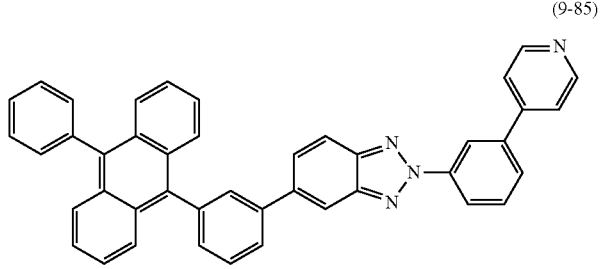
[Chemical Formula 791]
(9-86)
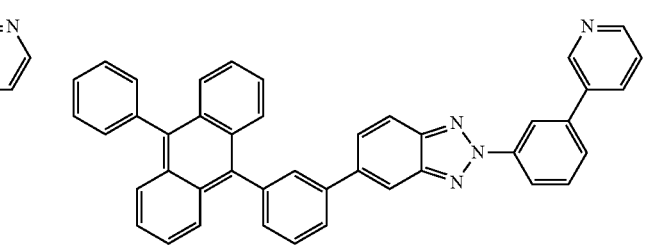
[Chemical Formula 792]
(9-87)
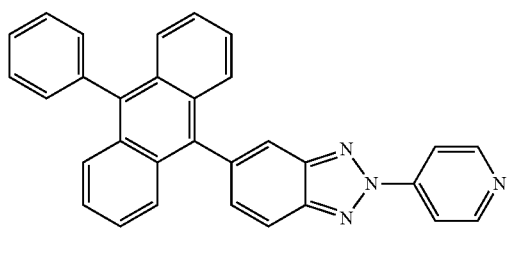
[Chemical Formula 793]
(9-88)
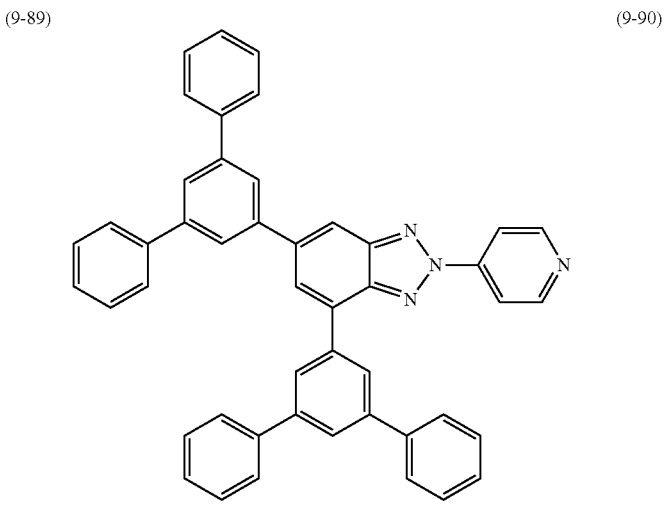
[Chemical Formula 794]
(9-89)
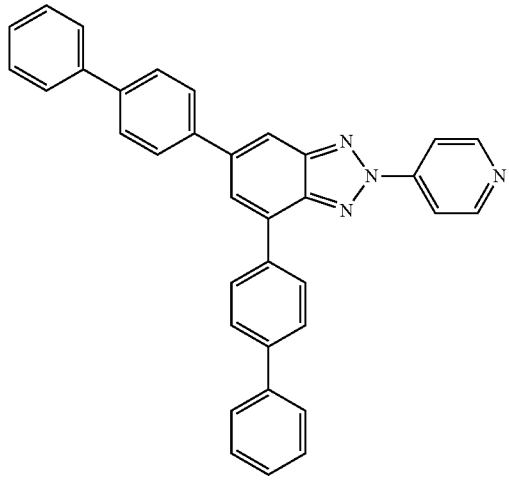
[Chemical Formula 795]
(9-90)

-continued
[Chemical Formula 796]
(9-91)
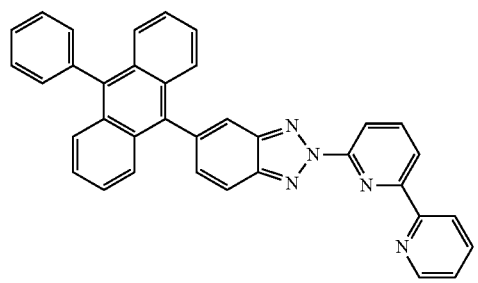
[Chemical Formula 797]
(9-92)
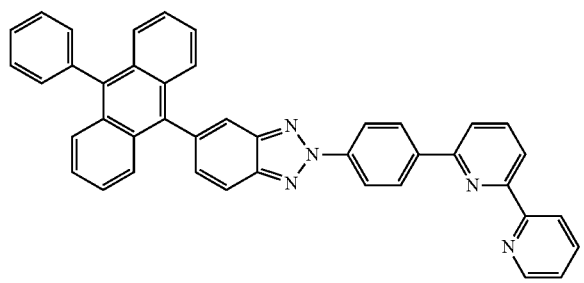
[Chemical Formula 798]
(9-93)
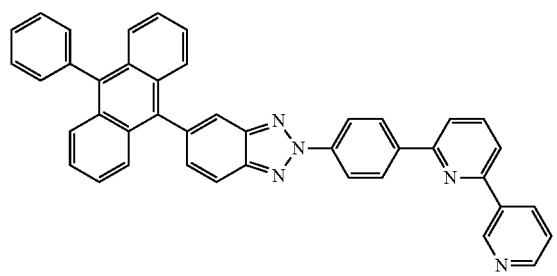
[Chemical Formula 799]
(9-94)
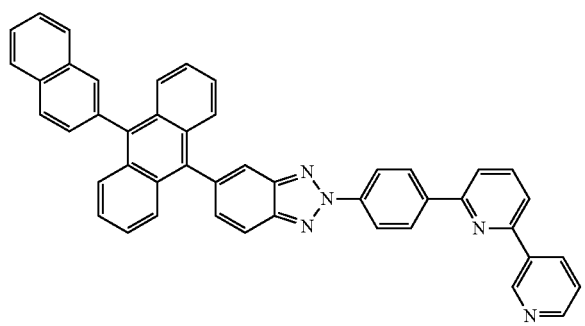
[Chemical Formula 800]
(9-95)
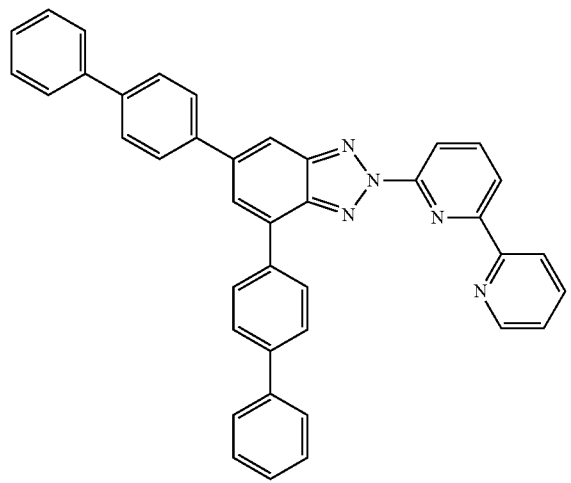
[Chemical Formula 801]
(9-96)
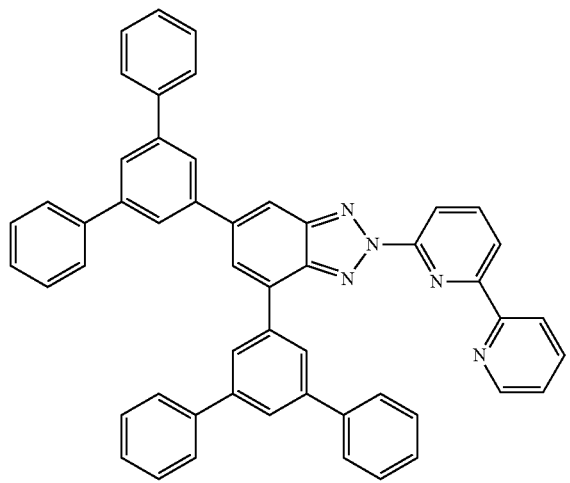

[Chemical Formula 802]
(9-97)
[Chemical Formula 803]
(9-98)
[Chemical Formula 804]
(9-99)
[Chemical Formula 805]
(9-100)
[Chemical Formula 806]
(9-101)
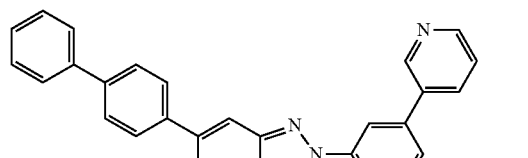
[Chemical Formula 807]
(9-102)
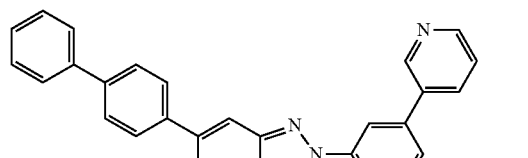

-continued
[Chemical Formula 808]
(9-103)
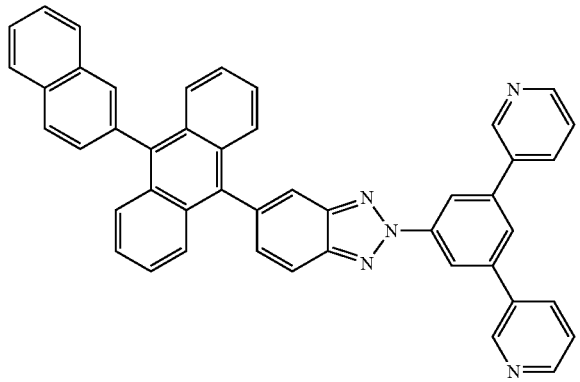
[Chemical Formula 809]
(9-104)
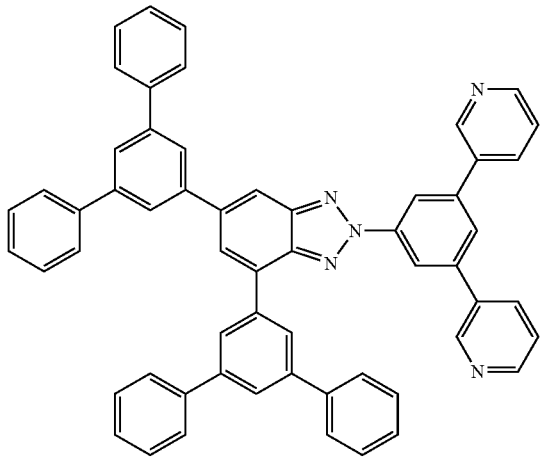
[Chemical Formula 810]
(9-105)
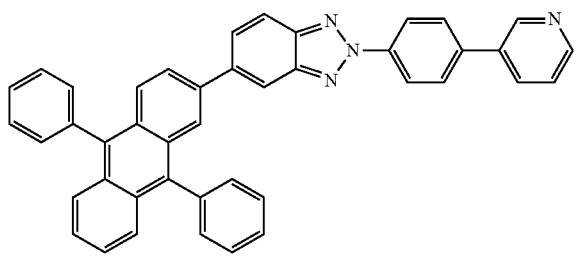
[Chemical Formula 811]
(9-106)
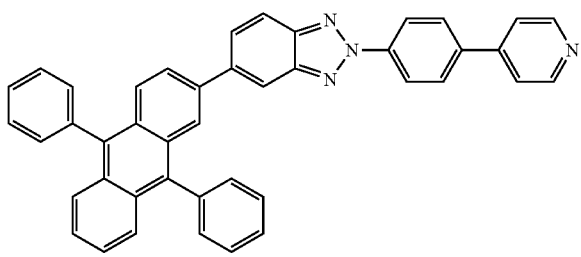
[Chemical Formula 812]
(9-107)
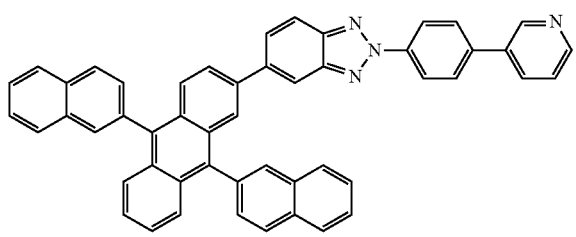
[Chemical Formula 813]
(9-108)
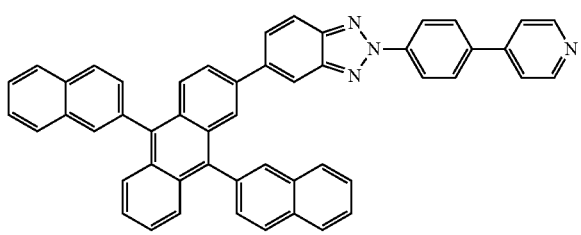
[Chemical Formula 814]
(9-109)
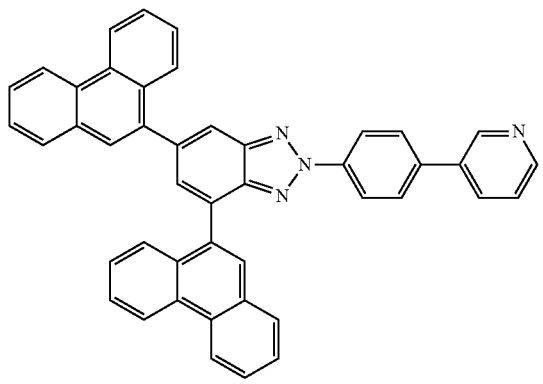
[Chemical Formula 815]
(9-110)
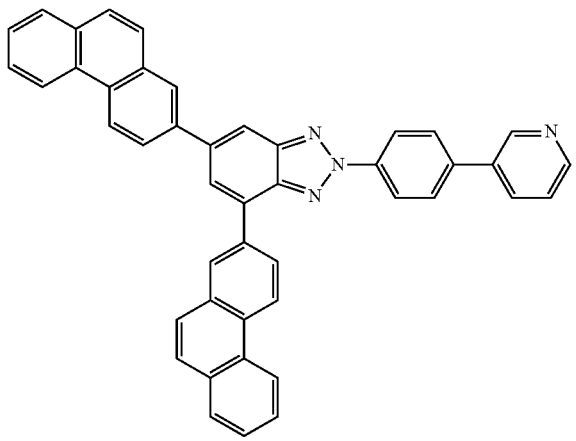

[Chemical Formula 816]
(9-111)
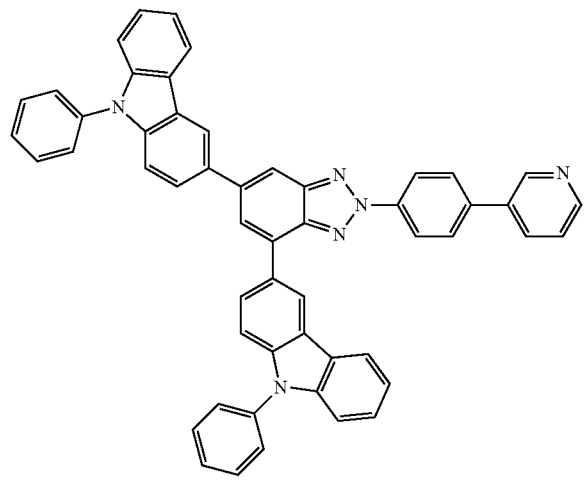
[Chemical Formula 817]
(9-112)
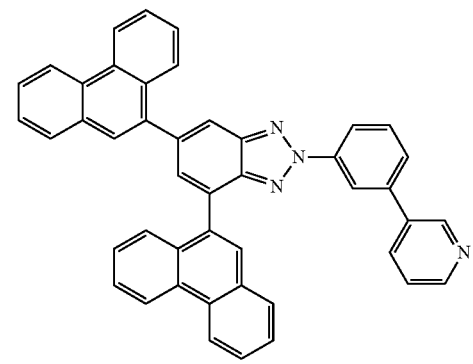
[Chemical Formula 818]
(9-113)
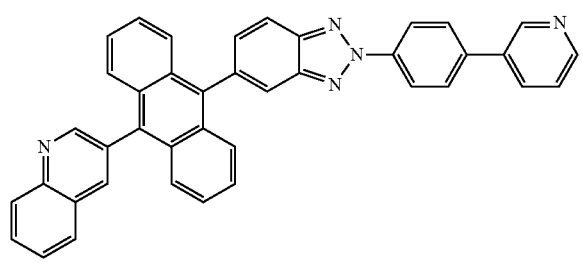
[Chemical Formula 819]
(9-114)
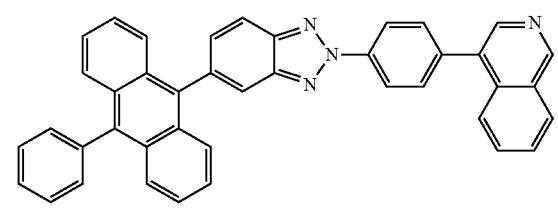
[Chemical Formula 820]
(9-115)
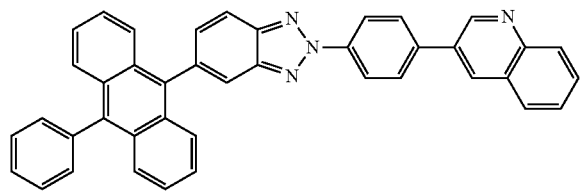
[Chemical Formula 821]
(9-116)
[Chemical Formula 822]
(9-117)
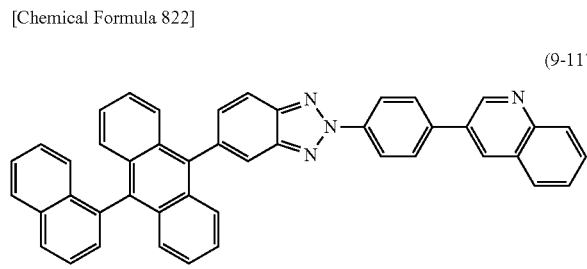
[Chemical Formula 823]
(9-118)
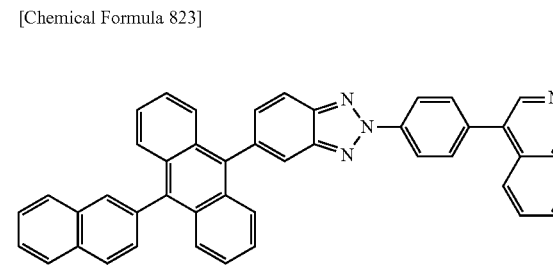
[Chemical Formula 824]
(9-119)
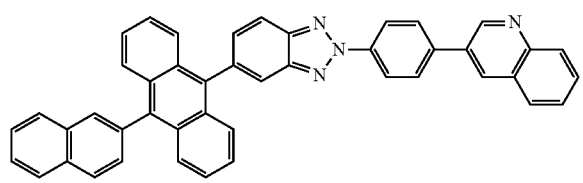
[Chemical Formula 825]
(9-120)
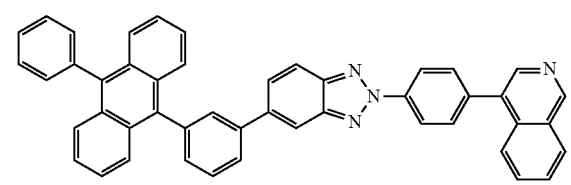

[Chemical Formula 826]
(9-121)
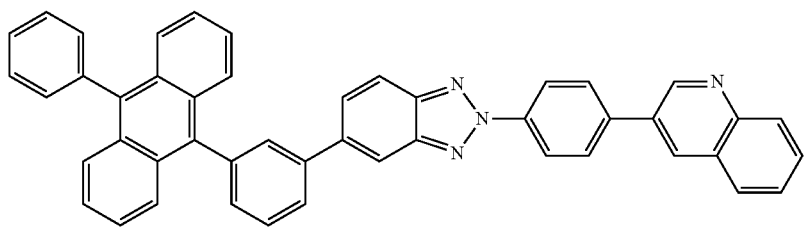
[Chemical Formula 827]
(9-122)
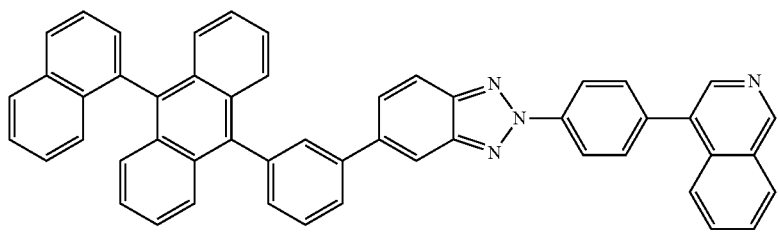
[Chemical Formula 828]
(9-123)
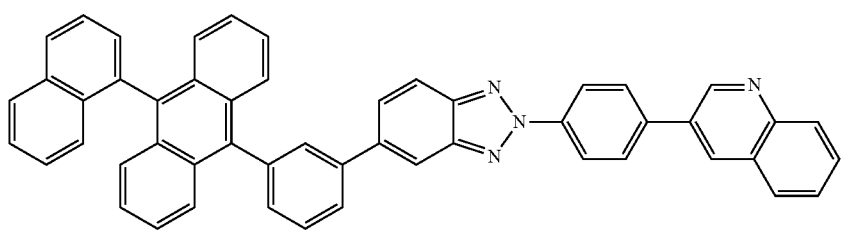
[Chemical Formula 829]
(9-124)
[Chemical Formula 830]
(9-125)
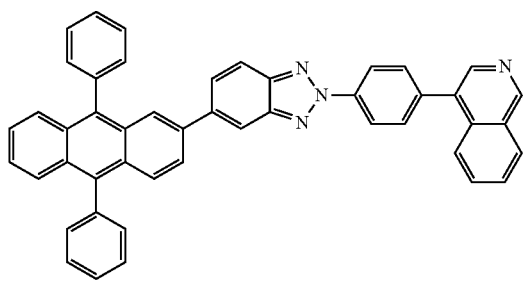
[Chemical Formula 831]
(9-126)
[Chemical Formula 832]
(9-127)
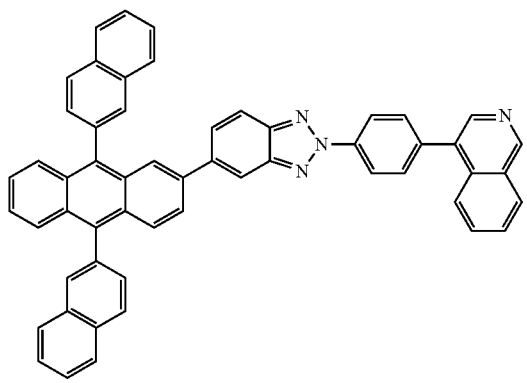
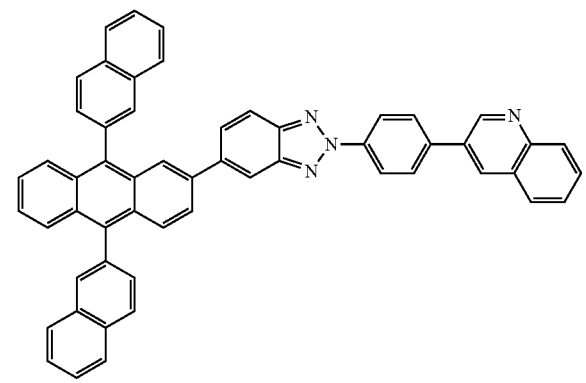

[Chemical Formula 833]
(9-128)
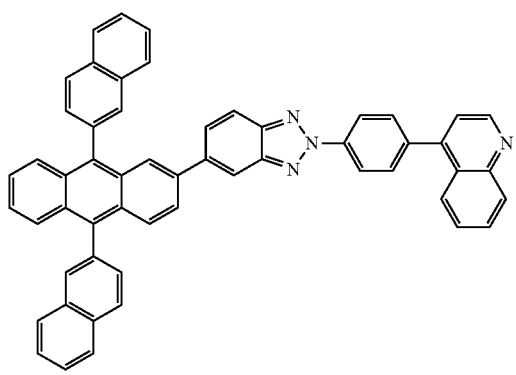
[Chemical Formula 834]
(9-129)
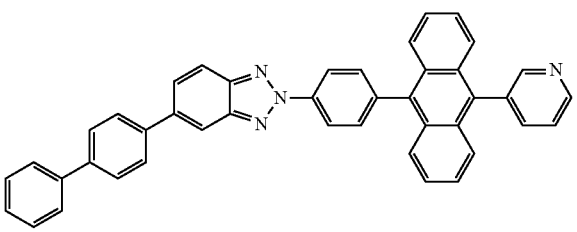
[Chemical Formula 835]
(9-130)
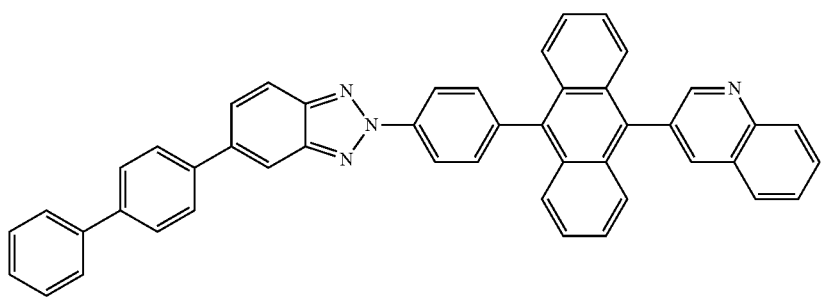
[Chemical Formula 836]
(9-131)
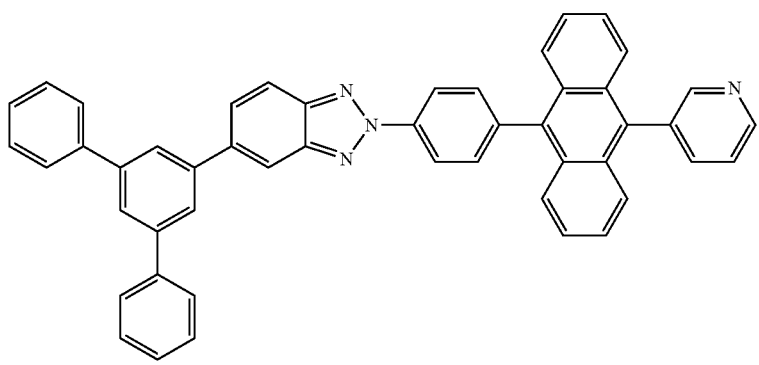
[Chemical Formula 837]
(9-132)
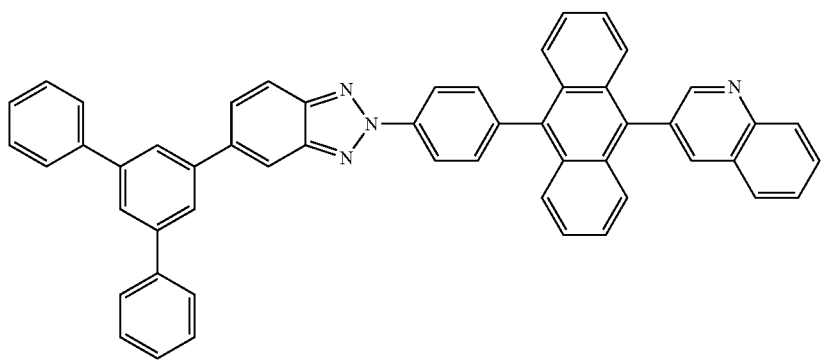

[Chemical Formula 838]
(9-133)
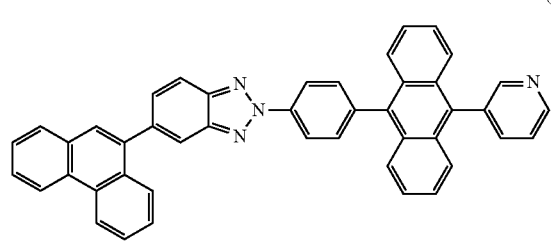
[Chemical Formula 839]
(9-134)
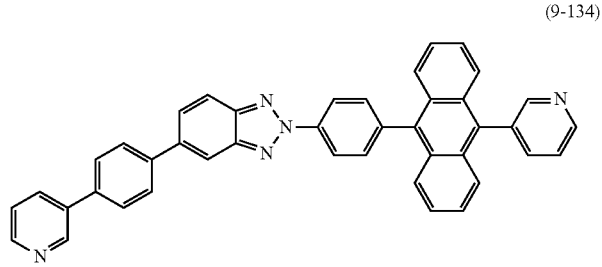
[Chemical Formula 840]
(9-135)
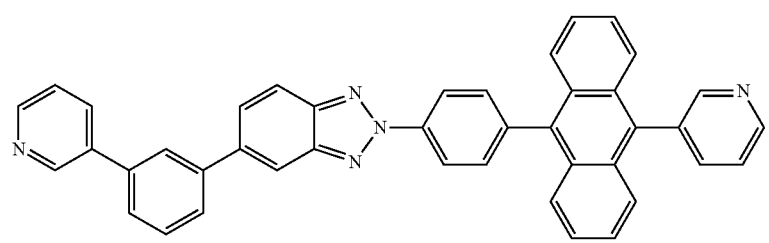
[Chemical Formula 841]
(9-136)
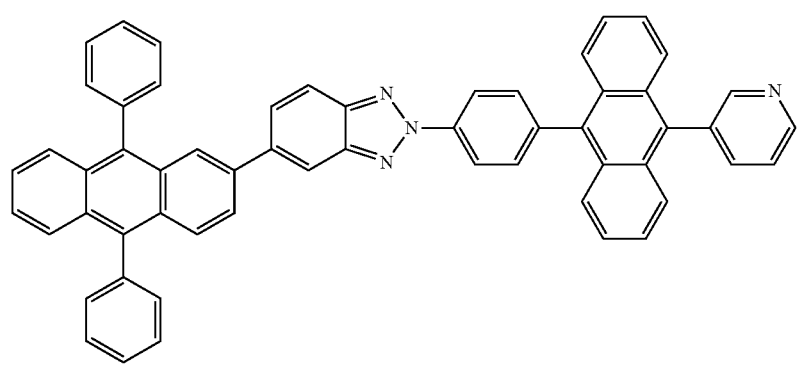
[Chemical Formula 842]
(9-137)
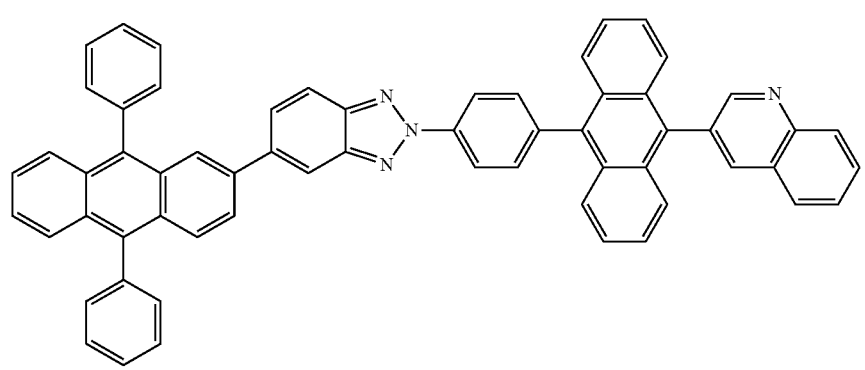

[Chemical Formula 843]
(9-138)
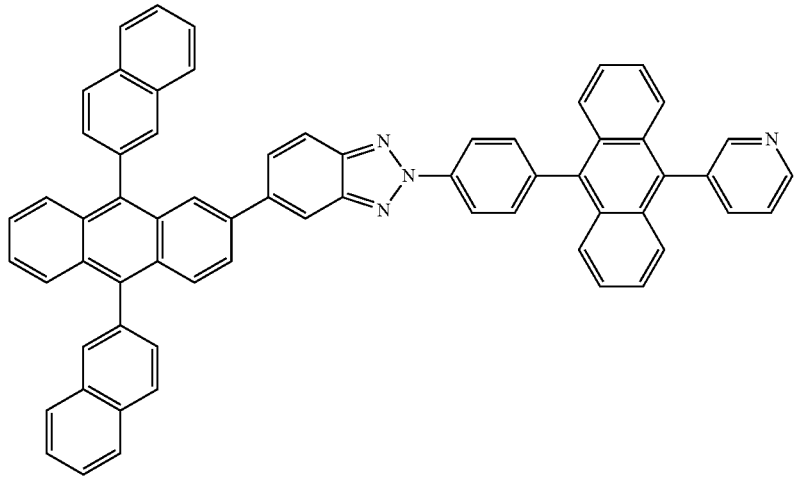
[Chemical Formula 844]
(9-139)
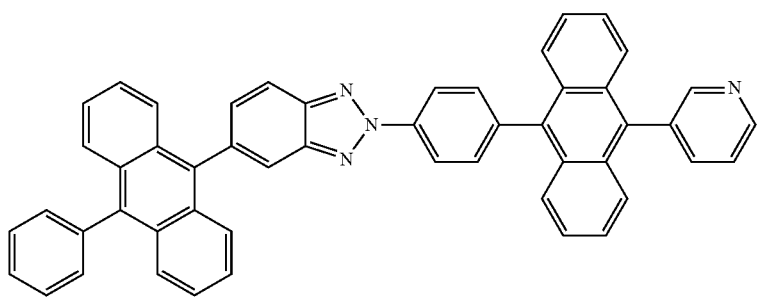
[Chemical Formula 845]
(9-140)
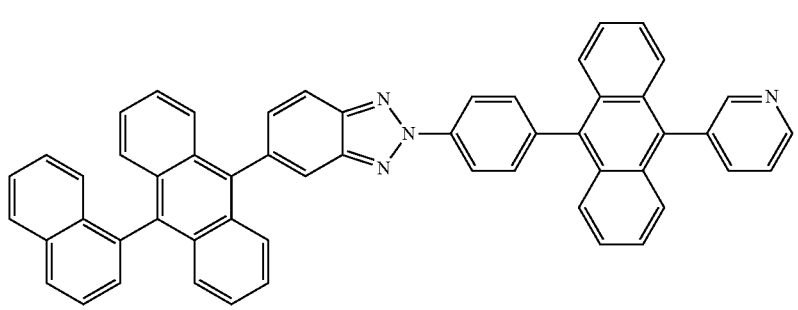
[Chemical Formula 846]
(9-141)
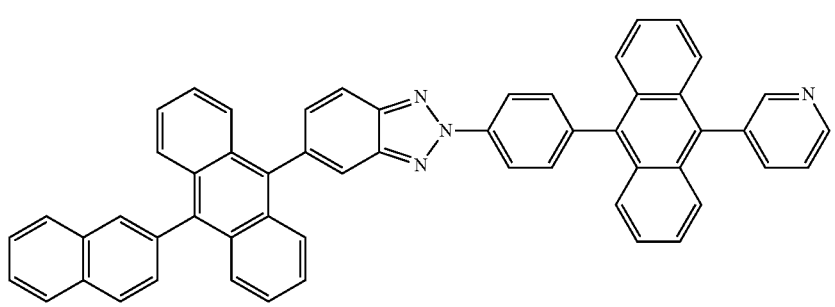

-continued
[Chemical Formula 847]
(9-142)
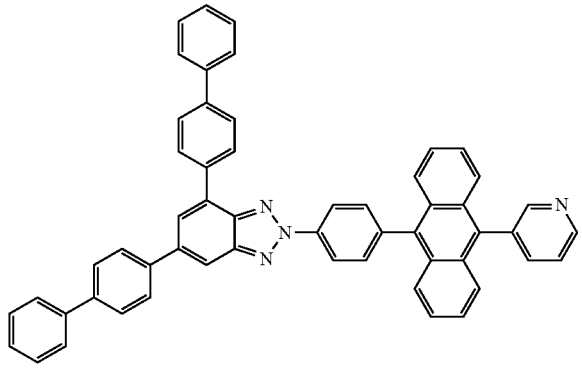
[Chemical Formula 848]
(9-143)
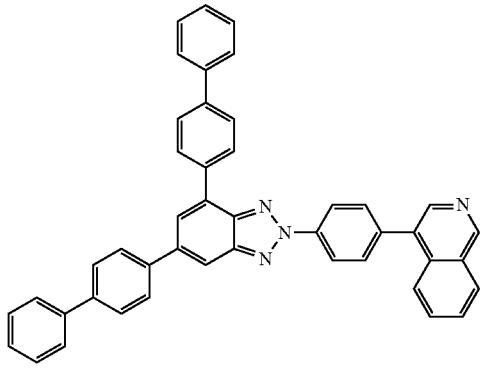
[Chemical Formula 849]
(9-144)
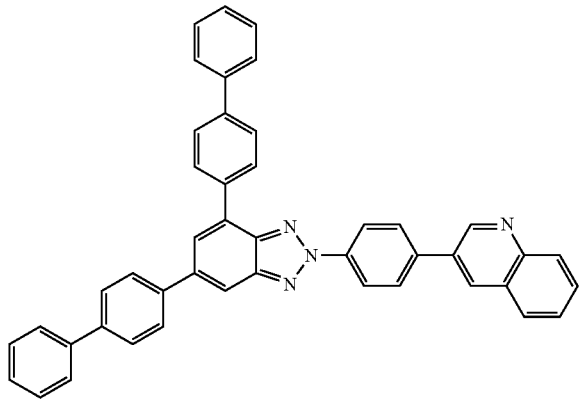
[Chemical Formula 850]
(9-145)
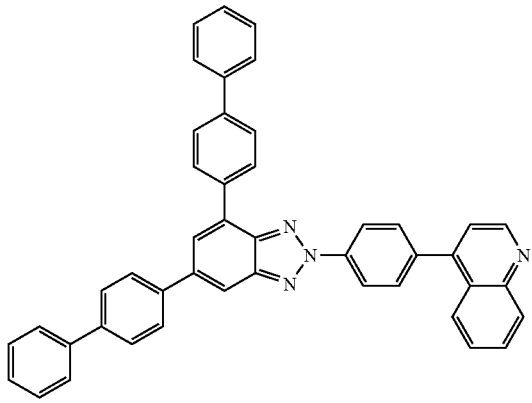
[Chemical Formula 851]
(9-146)
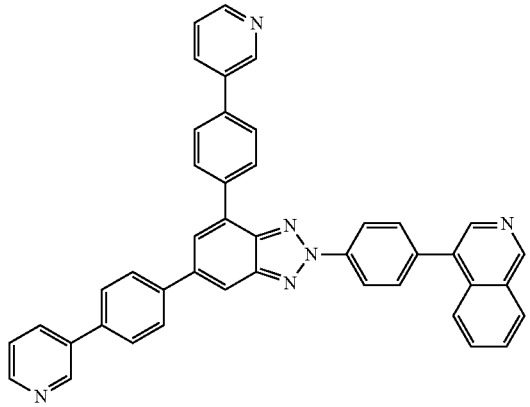
[Chemical Formula 852]
(9-147)
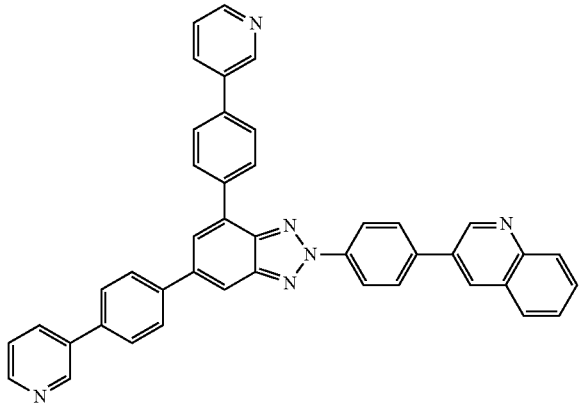

[Chemical Formula 853]
(9-148)
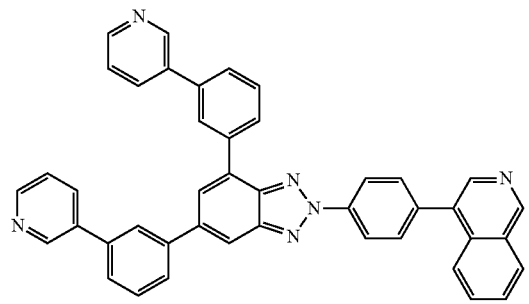
[Chemical Formula 854]
(9-149)
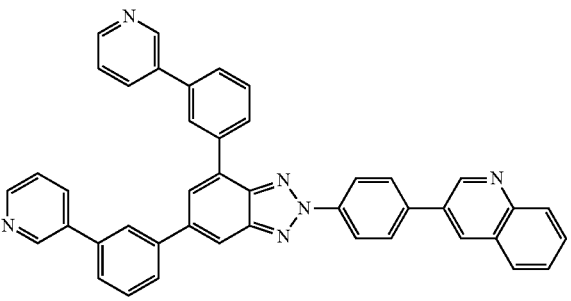
[Chemical Formula 855]
(9-150)
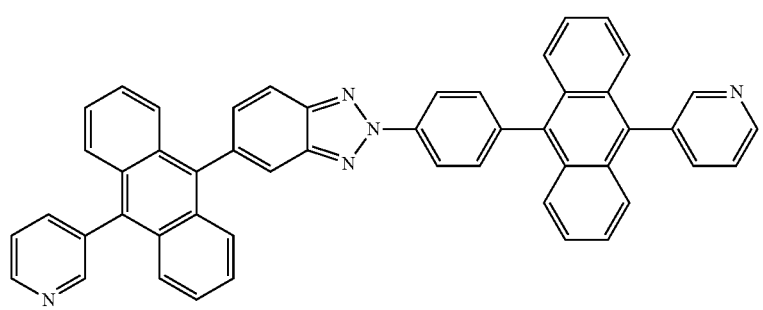
[Chemical Formula 856]
(9-151)
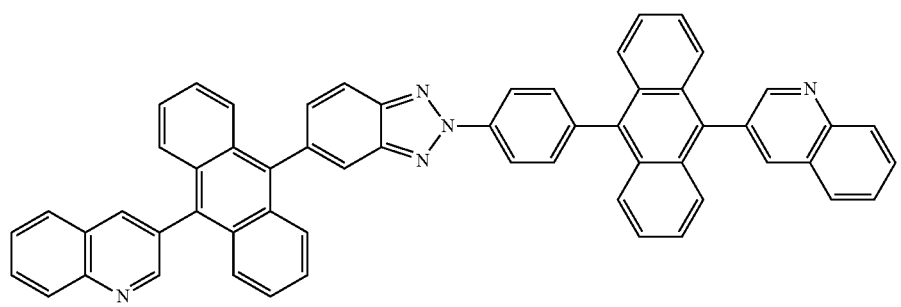
[Chemical Formula 857]
(9-152)
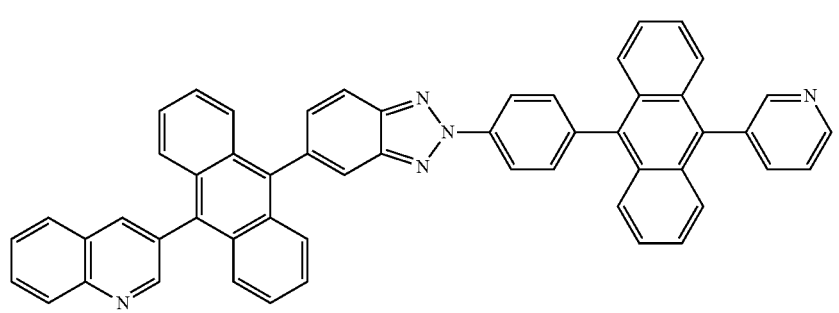

[Chemical Formula 858]
(9-153)
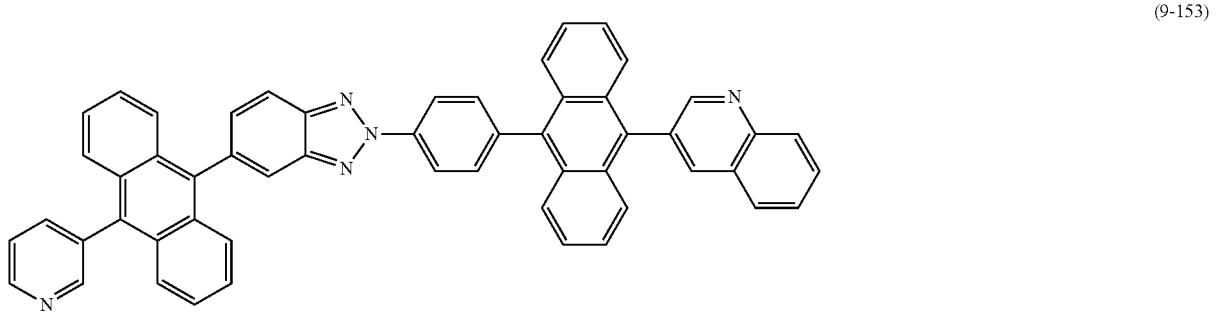
[Chemical Formula 859]
(9-154)
[Chemical Formula 860]
(9-155)
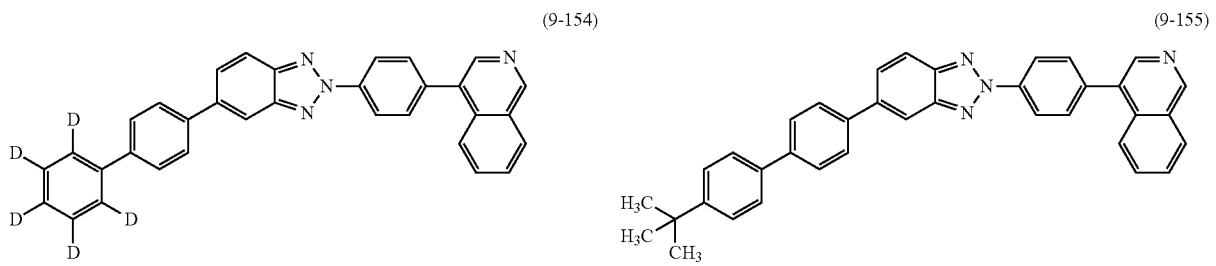
[Chemical Formula 861]
(9-156)
[Chemical Formula 862]
(9-157)
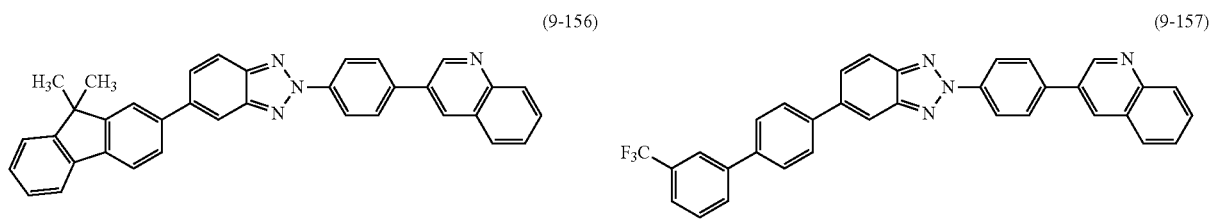
[Chemical Formula 863]
(9-158)
[Chemical Formula 864]
(9-159)
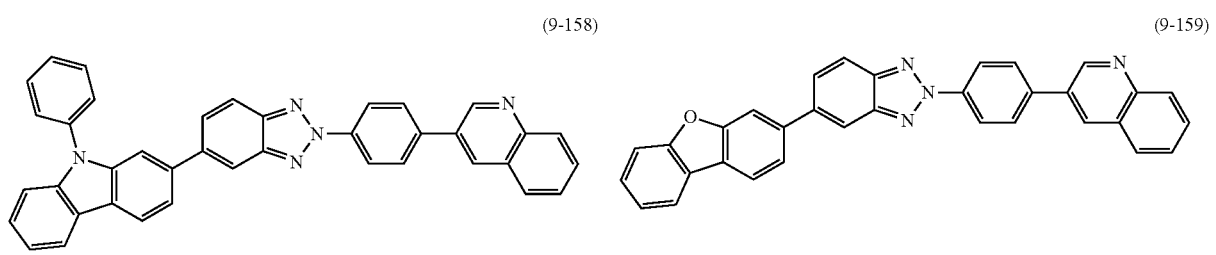
[Chemical Formula 865]
(9-160)
[Chemical Formula 866]
(9-161)
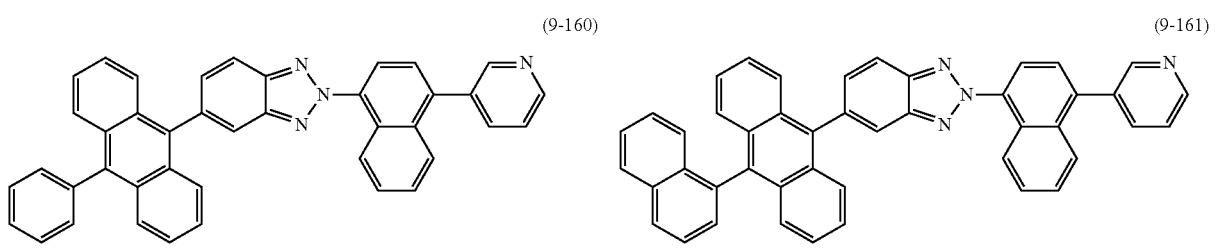

[Chemical Formula 867]
(9-162)
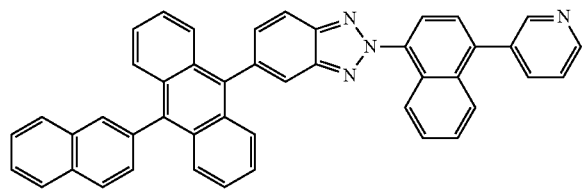
[Chemical Formula 868]
(9-163)
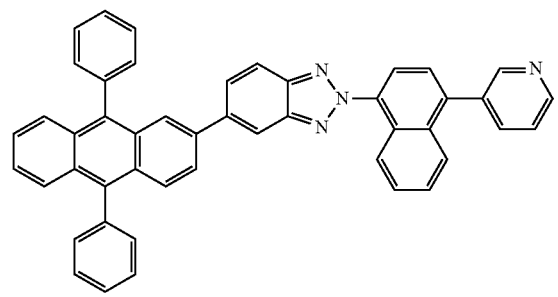
[Chemical Formula 869]
(9-164)
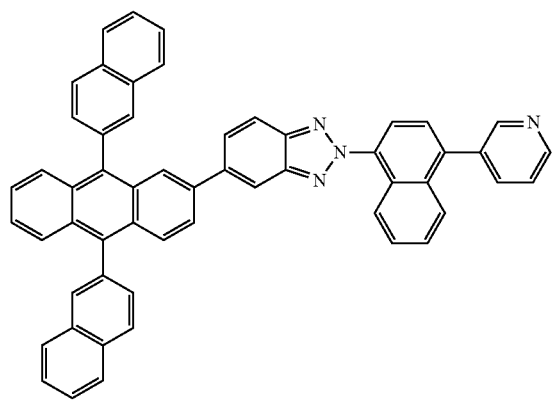
[Chemical Formula 870]
(9-165)
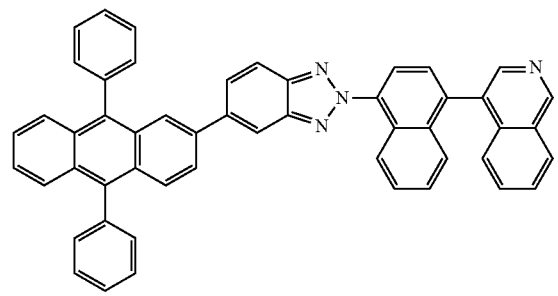
[Chemical Formula 871]
(9-166)
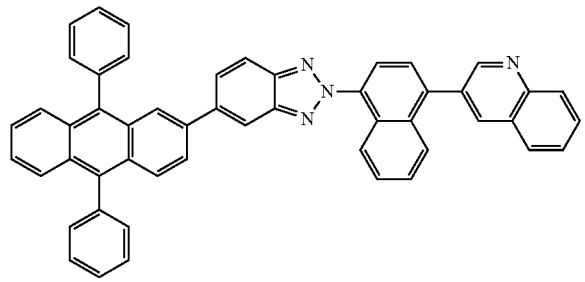
[Chemical Formula 872]
(9-167)
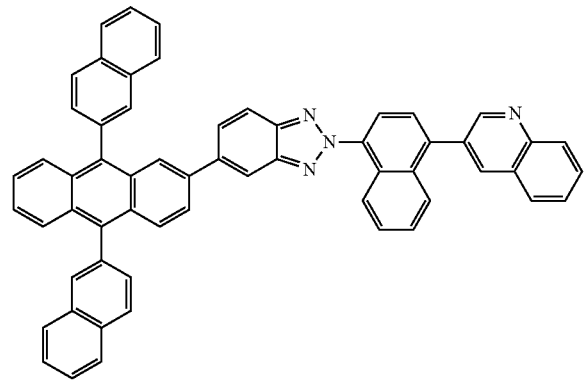
[Chemical Formula 873]
(9-168)
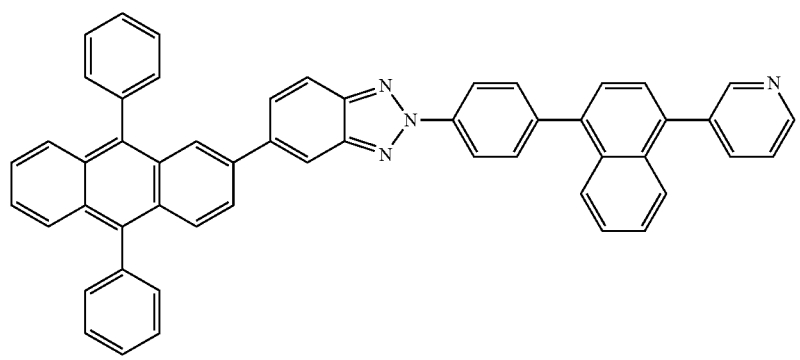

[Chemical Formula 874]
(9-169)
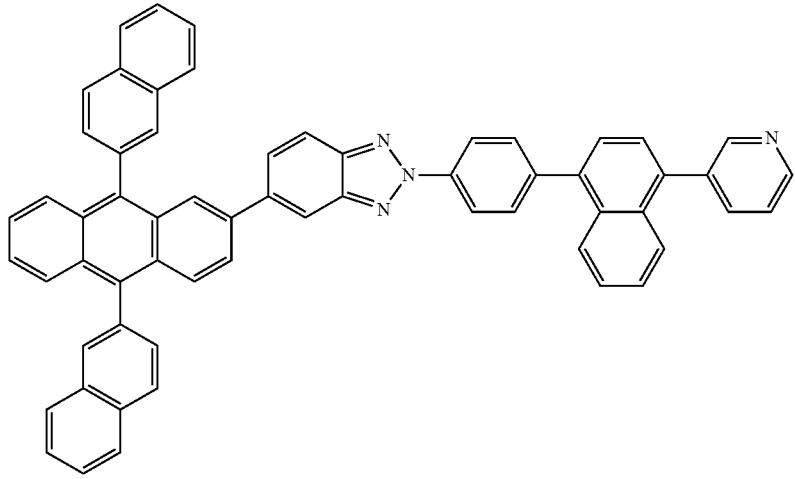
[Chemical Formula 875]
(9-170)
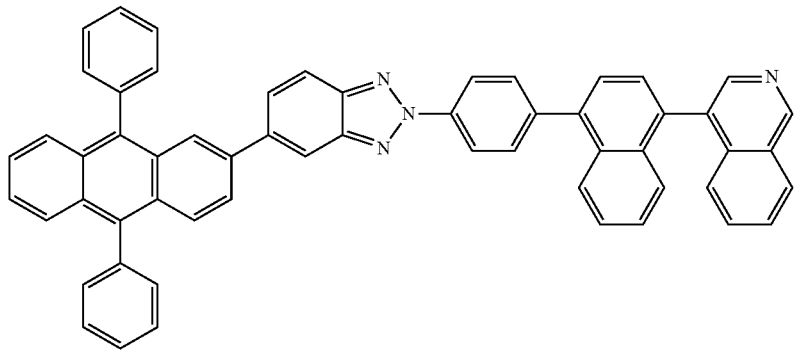
[Chemical Formula 876]
(9-171)
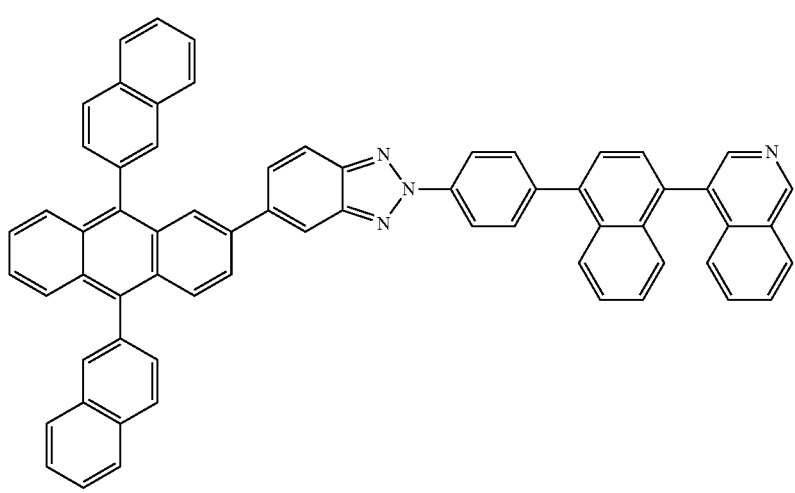

[Chemical Formula 877]

(9-172)

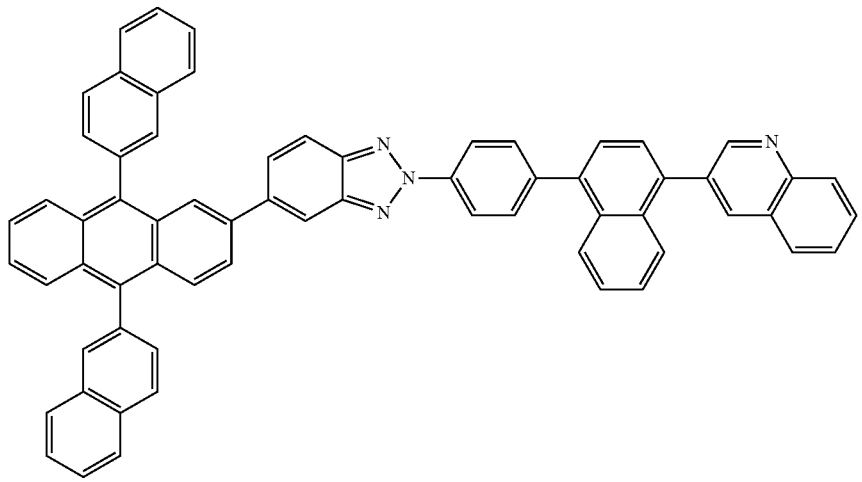

[Chemical Formula 878]

(9-173)

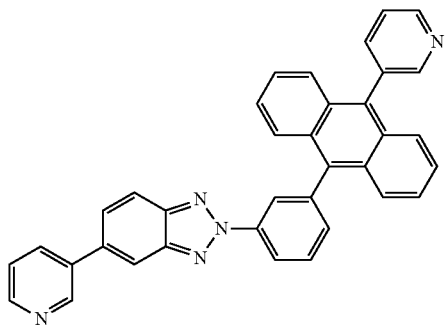

[Chemical Formula 879]

(9-174)

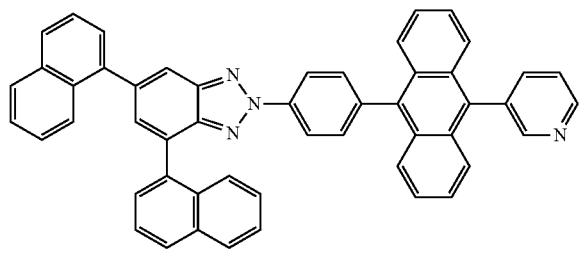

The compounds described above having a benzotriazole ring structure can be synthesized according to a known method (refer to Patent Document 13, for example).

The following presents specific examples of preferred compounds among the arylamine compounds of the general formula (10) preferably used in the organic EL device of the present invention. The present invention, however, is not restricted to these compounds.

[Chemical Formula 880]

(10-1)

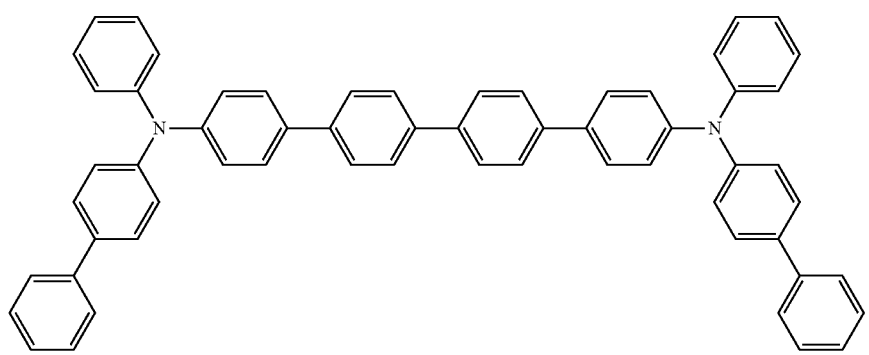

[Chemical Formula 881]
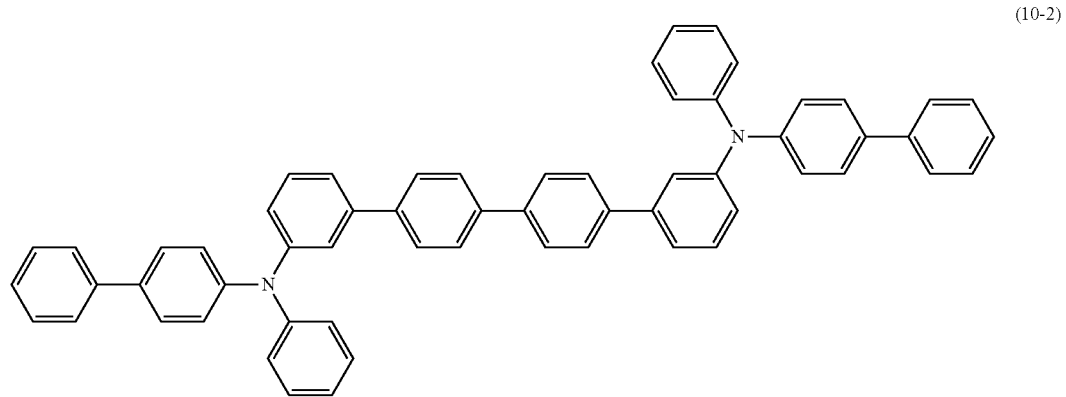
(10-2)
[Chemical Formula 882]
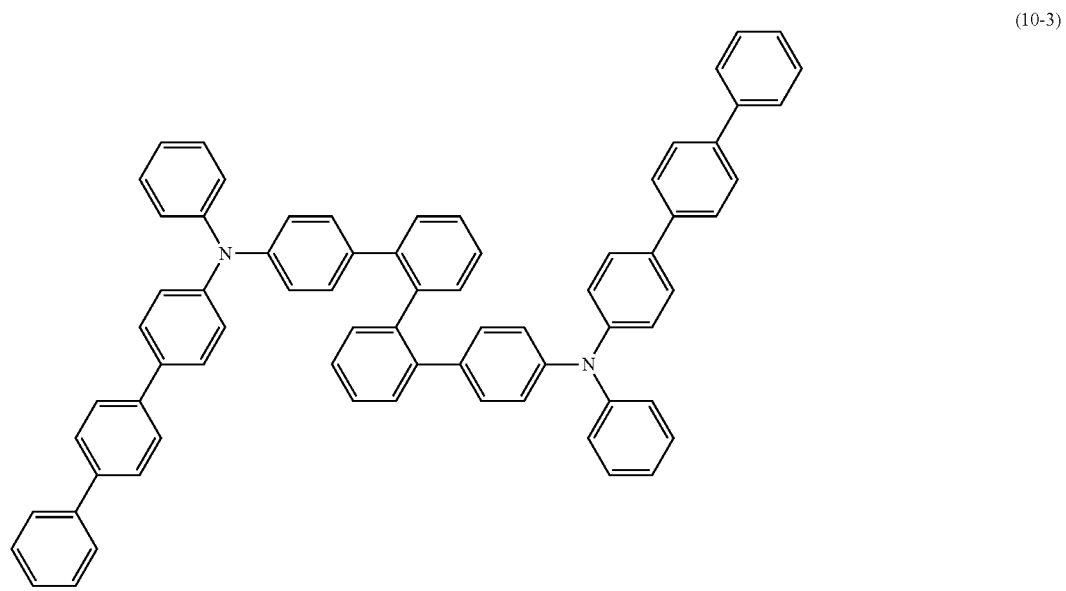
(10-3)
[Chemical Formula 883]
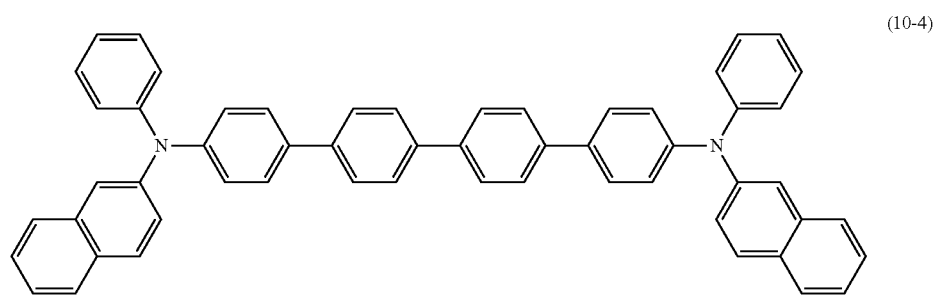
(10-4)

[Chemical Formula 884]
(10-5)
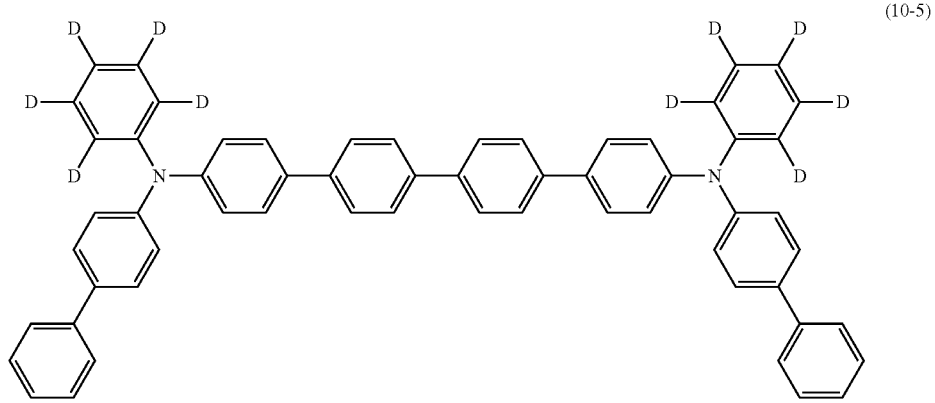
[Chemical Formula 885]
(10-6)
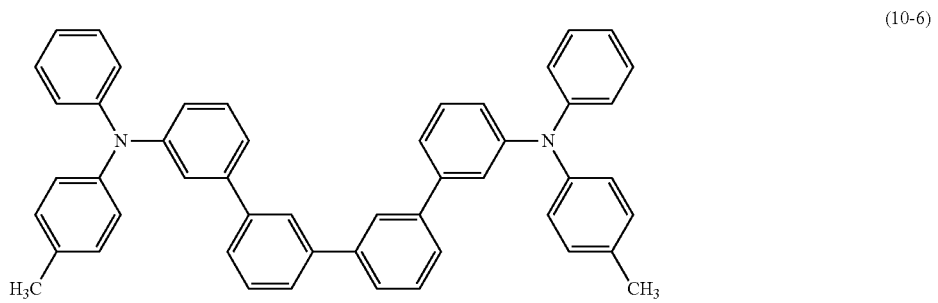
[Chemical Formula 886]
(10-7)
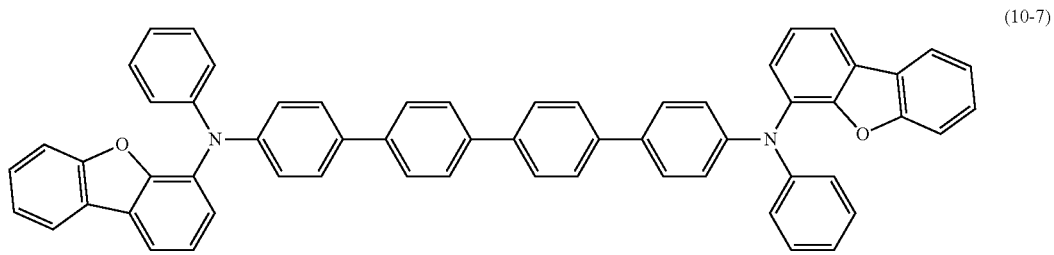
[Chemical Formula 887]
(10-8)
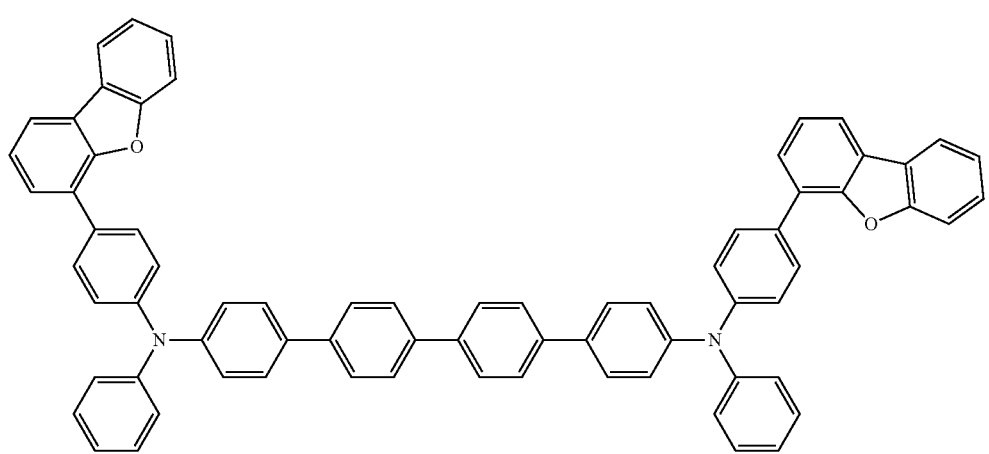

[Chemical Formula 888]
(10-9)
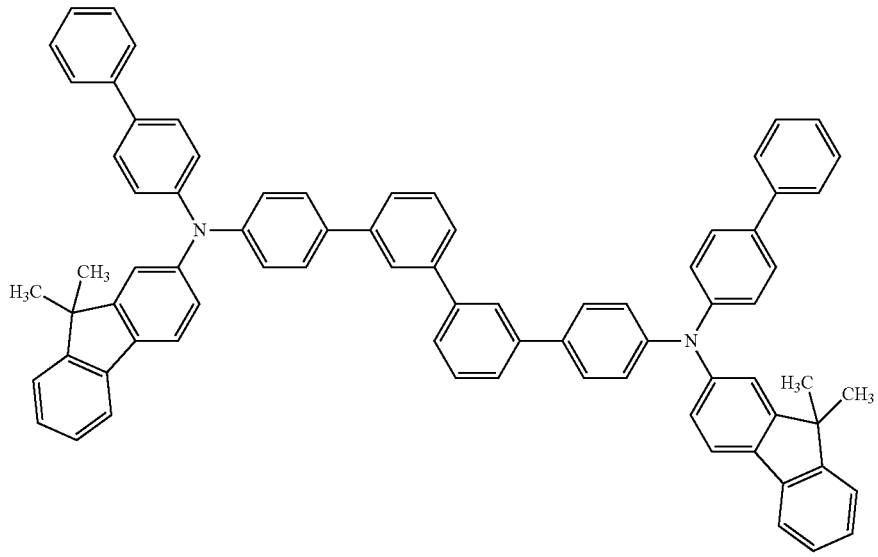
[Chemical Formula 889]
(10-10)
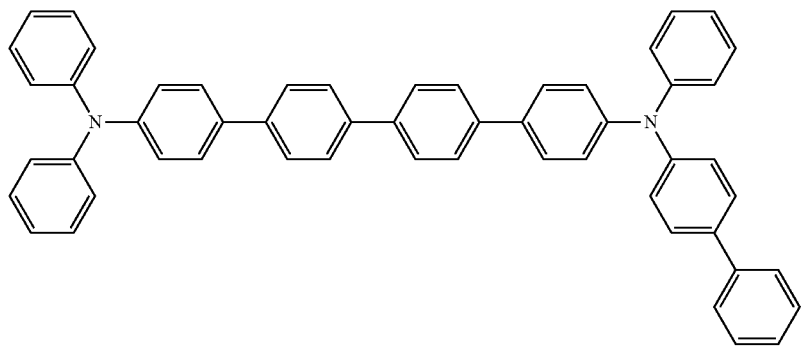
[Chemical Formula 890]
(10-11)
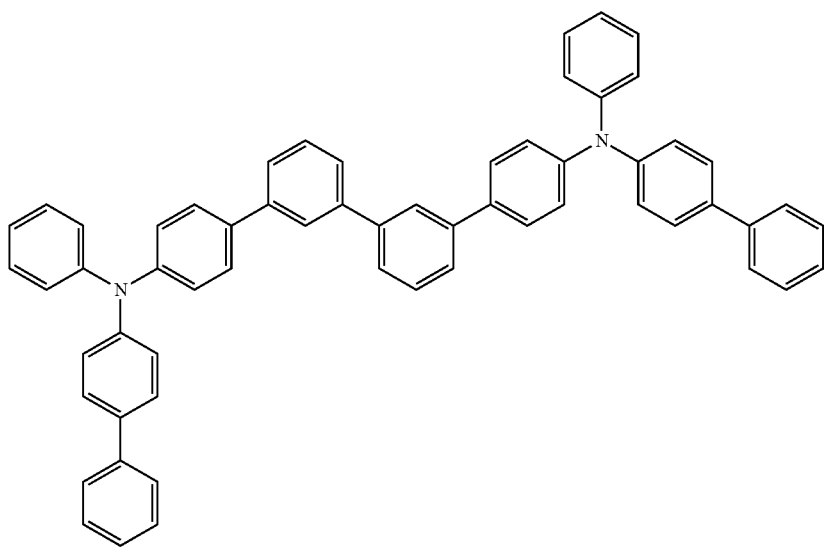

-continued
[Chemical Formula 891]
(10-12)
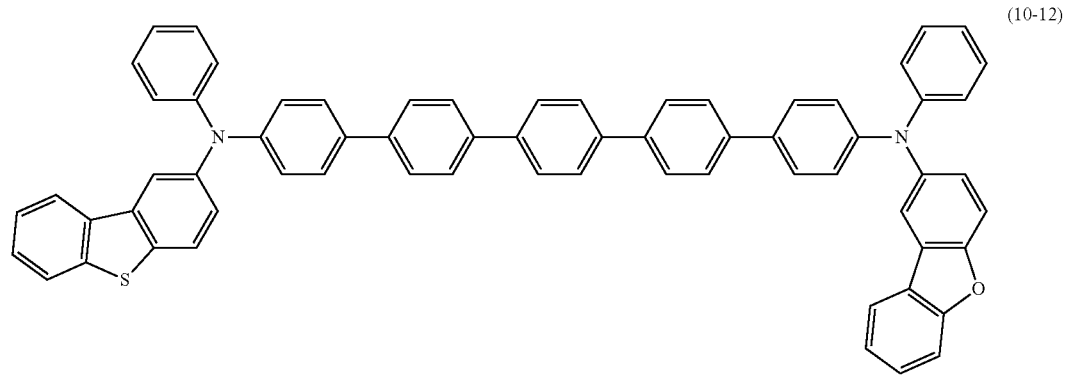
[Chemical Formula 892]
(10-13)
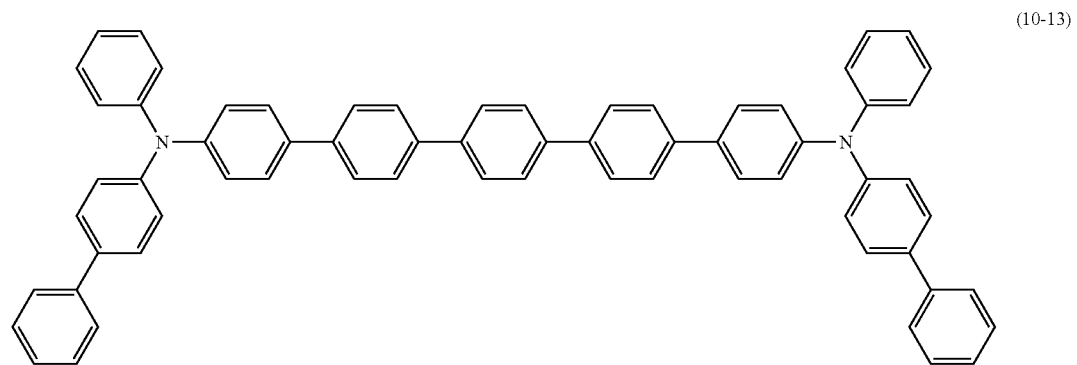
[Chemical Formula 893]
(10-14)
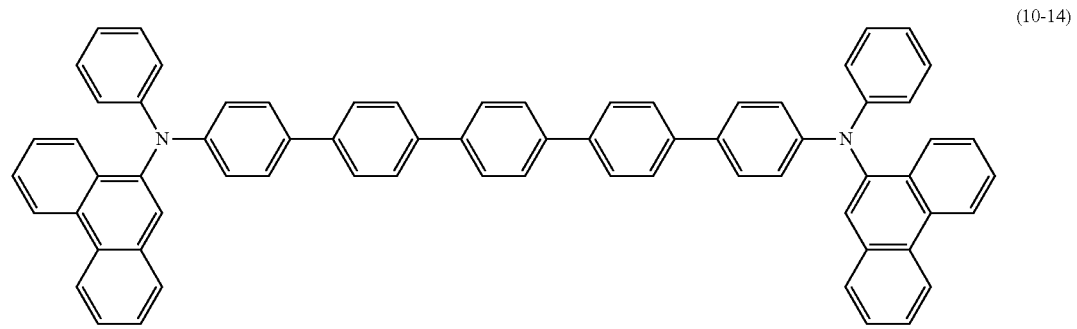
[Chemical Formula 894]
(10-15)
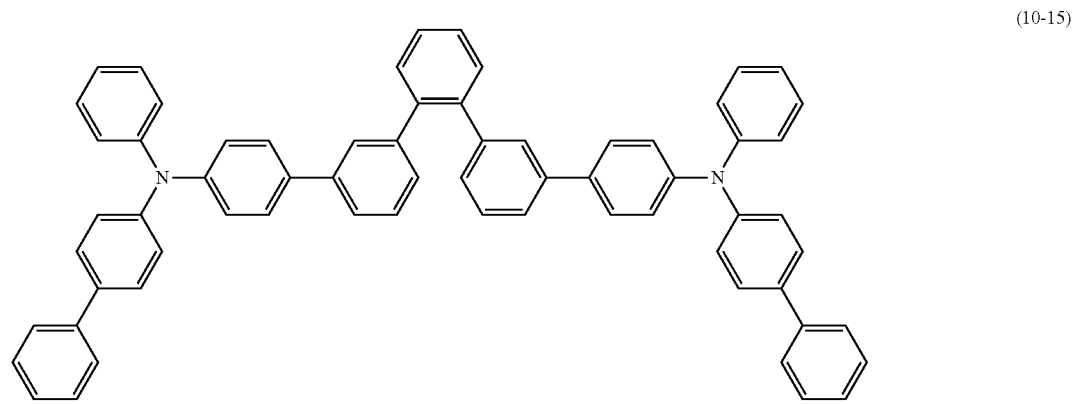

[Chemical Formula 895]
(10-16)
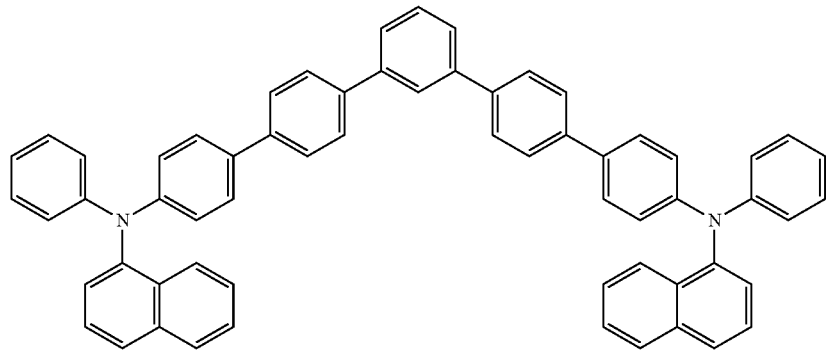
[Chemical Formula 896]
(10-17)
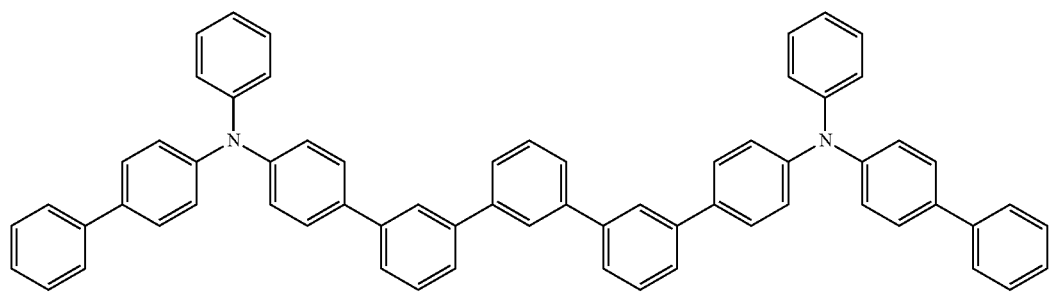
[Chemical Formula 897]
(10-18)
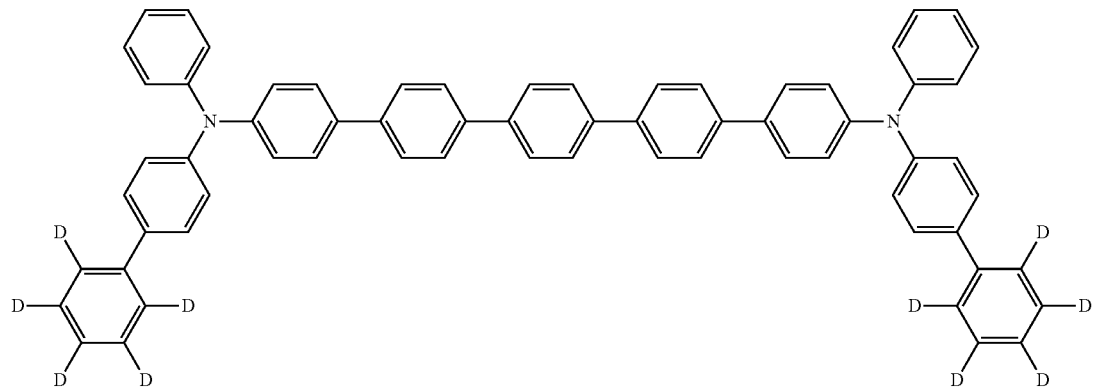
[Chemical Formula 898]
(10-19)
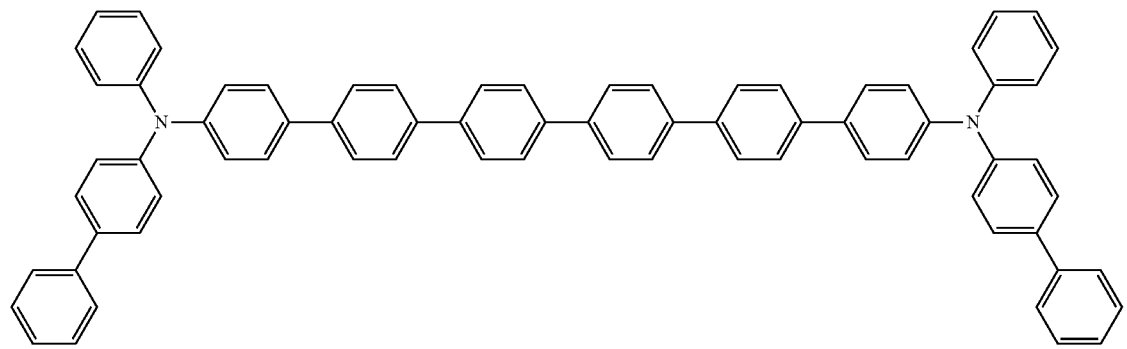

[Chemical Formula 899]
(10-20)
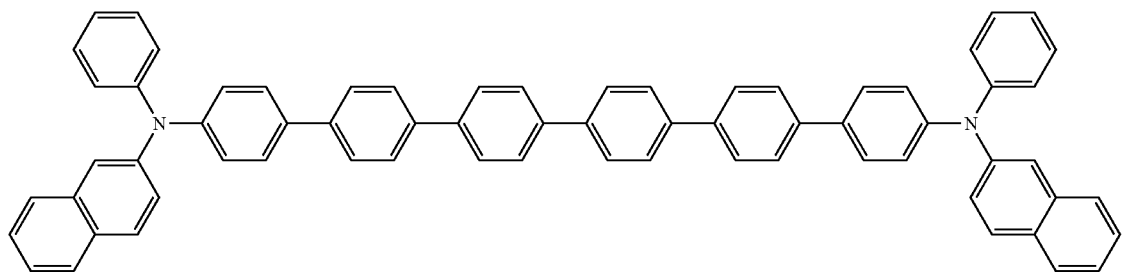
[Chemical Formula 900]
(10-21)
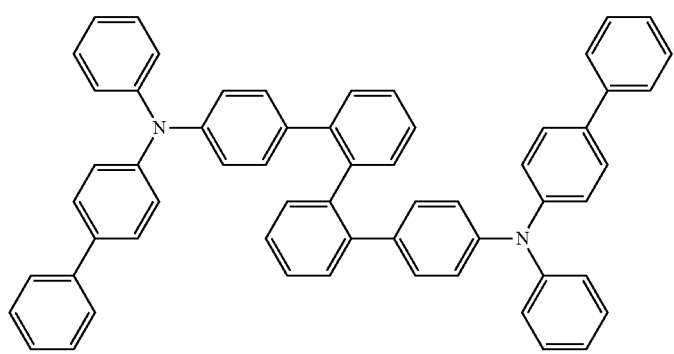
[Chemical Formula 901]
(10-22)
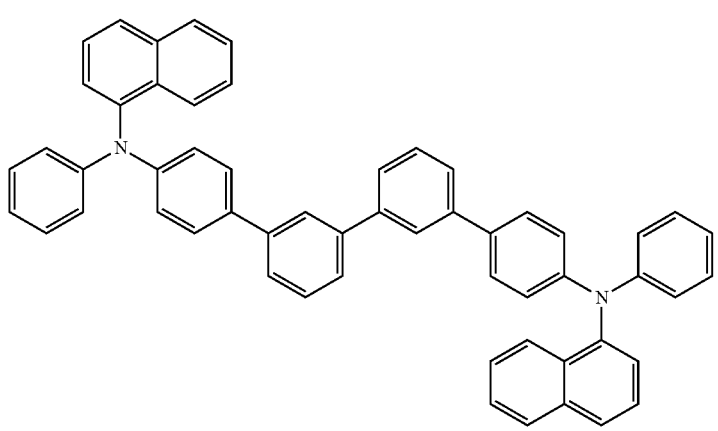
[Chemical Formula 902]
(10-23)
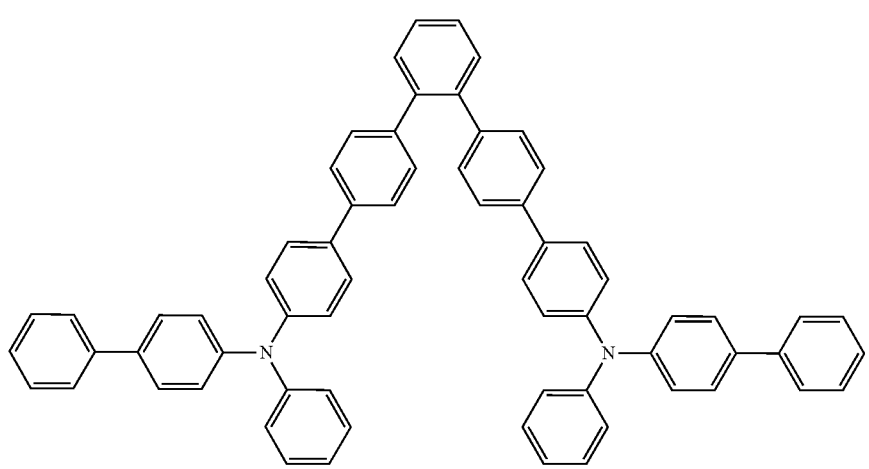

[Chemical Formula 903]
(10-24)
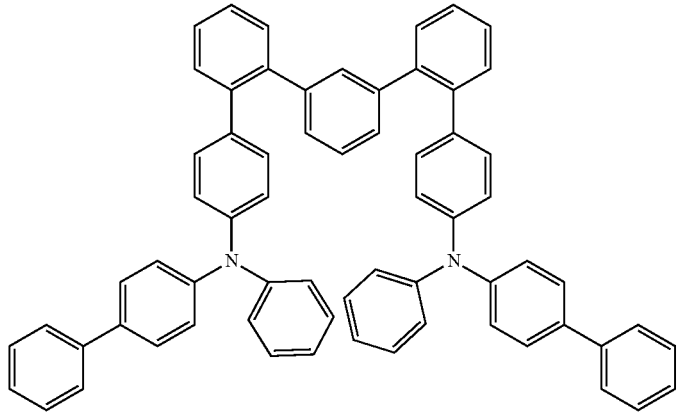
[Chemical Formula 904]
(10-25)
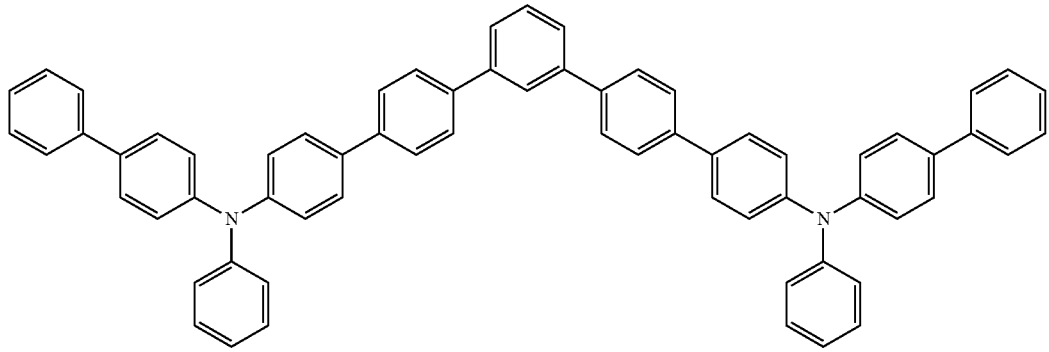
[Chemical Formula 905]
(10-26)
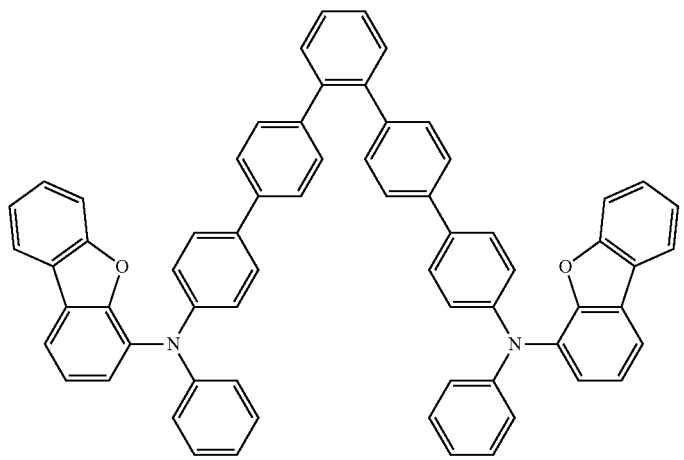

[Chemical Formula 906]
(10-27)
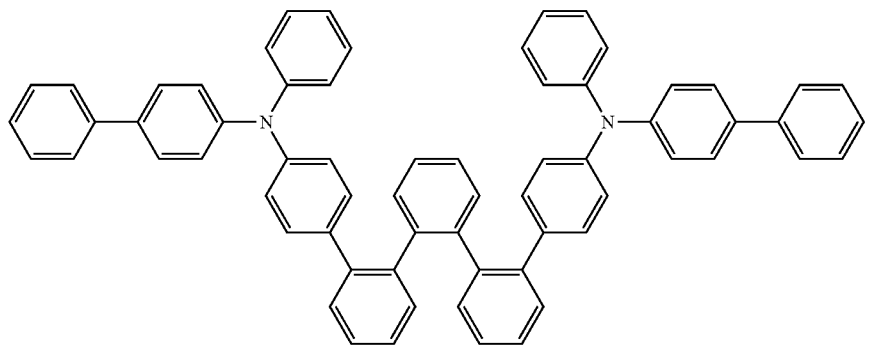
[Chemical Formula 907]
(10-28)
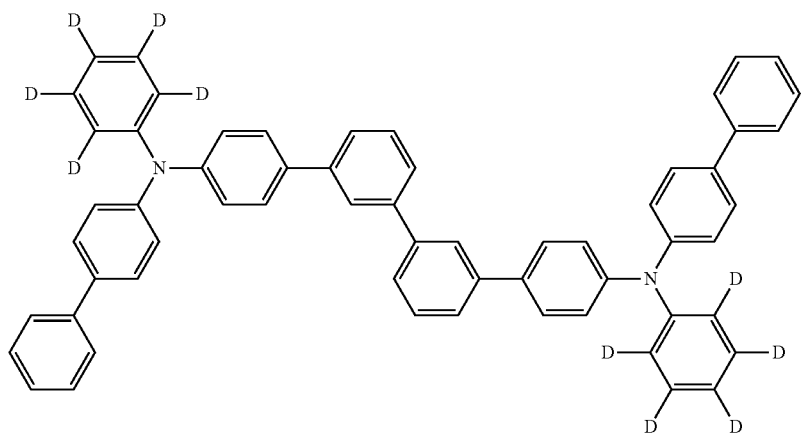
[Chemical Formula 908]
(10-29)
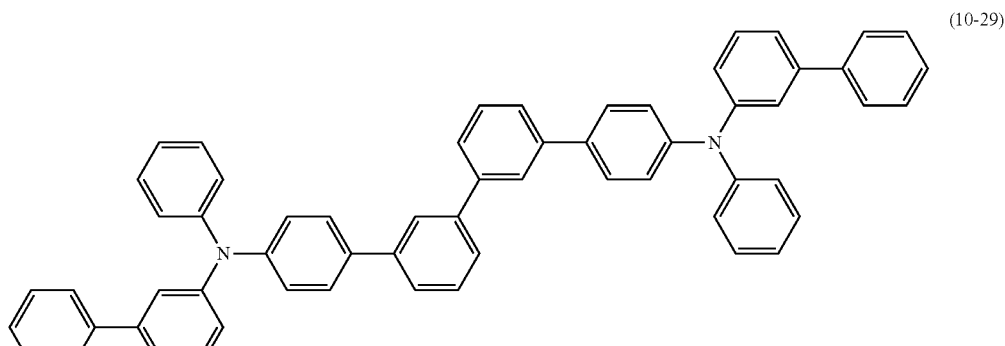
[Chemical Formula 909]
(10-30)
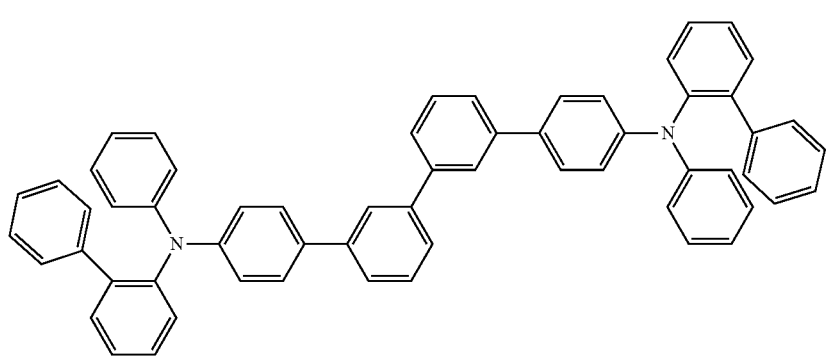

[Chemical Formula 910]
(10-31)
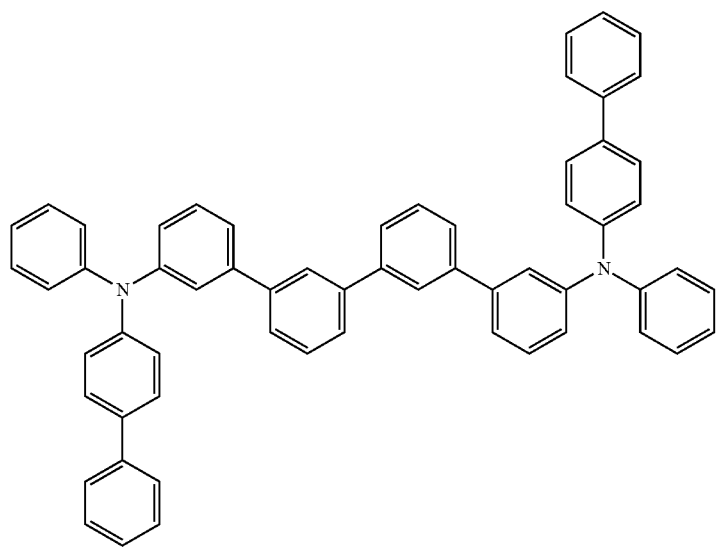
[Chemical Formula 911]
(10-32)
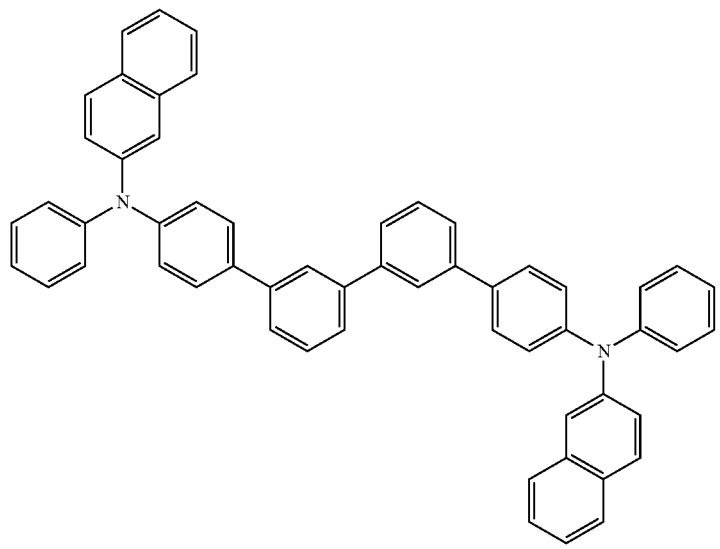
[Chemical Formula 912]
(10-33)
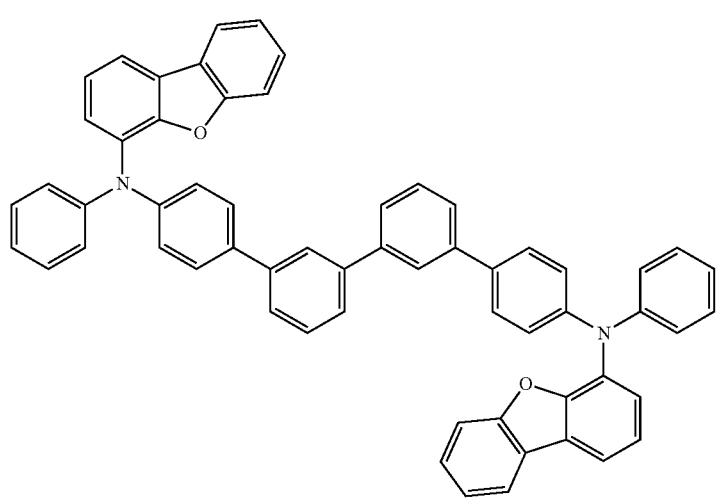

[Chemical Formula 913]
(10-34)
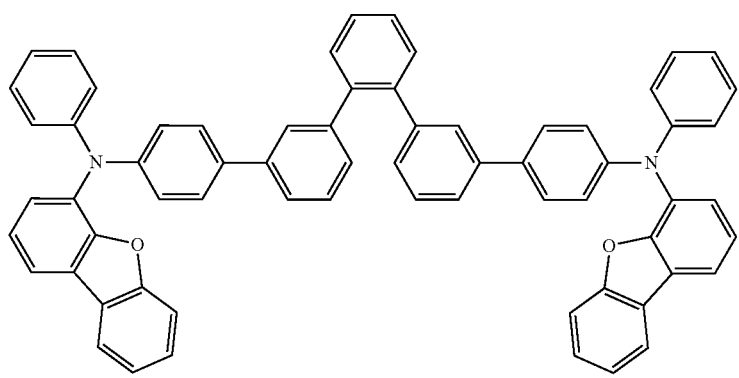
[Chemical Formula 914]
(10-35)
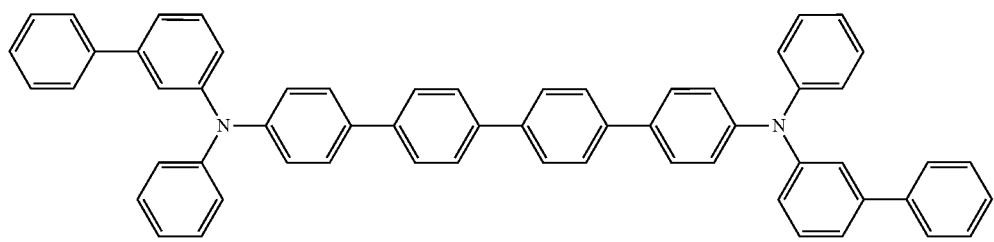
[Chemical Formula 915]
(10-36)
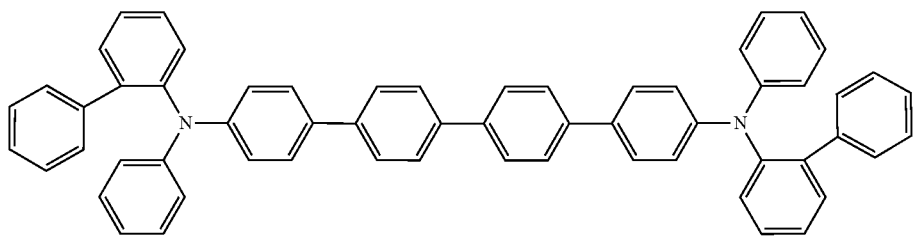
[Chemical Formula 916]
(10-37)
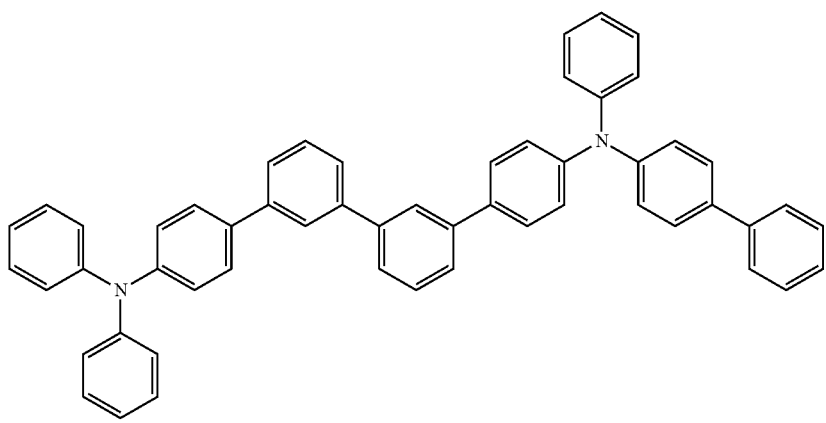

[Chemical Formula 917]

(10-38)

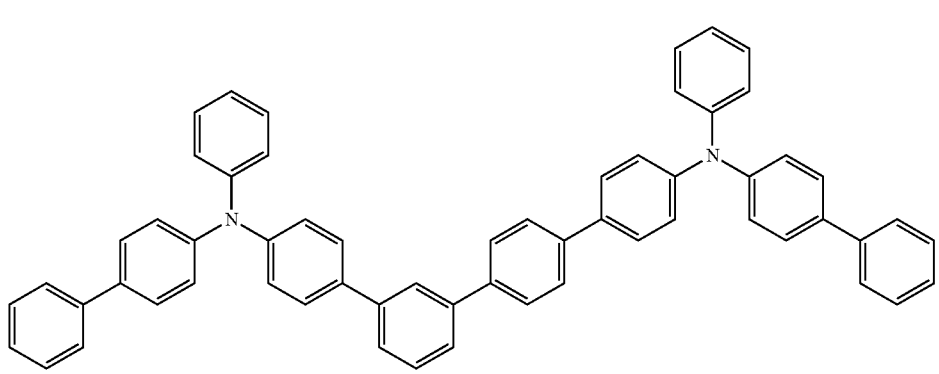

The arylamine compounds of the general formula (5) or the general formula (10) were purified by methods such as column chromatography, adsorption using, for example, a silica gel, activated carbon, or activated clay, recrystallization or crystallization using a solvent, and a sublimation purification method. The compounds were identified by an NMR analysis. A melting point, a glass transition point (Tg), and a work function were measured as material property values. The melting point can be used as an index of vapor deposition, the glass transition point (Tg) as an index of stability in a thin-film state, and the work function as an index of the hole transport capability and the hole blocking capability.

Other compounds used for the organic EL device of the present invention were purified by methods such as column chromatography, adsorption using, for example, a silica gel, activated carbon, or activated clay, and recrystallization or crystallization using a solvent, and finally purified by sublimation.

The melting point and the glass transition point (Tg) were measured by a high-sensitive differential scanning calorimeter (DSC3100SA produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a first hole transport layer, a second hole transport layer, a light emitting layer, an electron transport layer, an electron injection layer, and a cathode successively formed on a substrate, optionally with an electron blocking layer between the second hole transport layer and the light emitting layer, and a hole blocking layer between the light emitting layer and the electron transport layer. Some of the organic layers in the multilayer structure may be omitted, or may serve more than one function. For example, a single organic layer may serve as the electron injection layer and the electron transport layer. Further, the organic layers having a same function may have a laminate structure of two or more layers, for example, the light emitting layers may have a laminate structure of two or more layers, or the electron transport layers may have a laminate structure of two or more layers.

Electrode materials with high work functions such as ITO and gold are used as the anode of the organic EL device of the present invention.

As the hole injection layer of the organic EL device of the present invention, the arylamine compound of the general formula (1) subjected to p-type doping with an electron acceptor is preferably used.

As a hole injection/transport material that can be mixed with or can be used simultaneously with the arylamine compound of the general formula (1), material such as starburst-type triphenylamine derivatives and various triphenylamine tetramers; porphyrin compounds as represented by copper phthalocyanine; accepting heterocyclic compounds such as hexacyanoazatriphenylene; coating-type polymer materials, and the like can be used. These materials may be formed into a thin film by a vapor deposition method or other known methods such as a spin coating method and an inkjet method.

As the first hole transport layer of the organic EL device of the present invention, a hole transport arylamine compound may be used, in addition to the arylamine compound of the general formula (3) and the arylamine compound of the general formula (4). Further, a coating type polymer material, such as poly(3,4-ethylenedioxythiophene) (PEDOT)/poly(styrenesulfonate) (PSS), a polymer compound having a structure of a benzidine derivative as a partial structure thereof, such as TPD, and the like may be used.

As the first hole transport layer of the organic EL device of the present invention, a hole transport arylamine compound is preferably used, and the arylamine compound of the general formula (3) or the arylamine compound of the general formula (4) is more preferably used. The compounds that are not subjected to p-type doping are particularly preferably used.

These may be individually formed into a film, may be used as a single layer formed with another material mixed, or may be formed as a laminated structure of the individually deposited layers, a laminated structure of the mixed layers, or a laminated structure of the individually deposited layer and the mixed layer. These materials may be formed into a thin-film by a vapor deposition method or other known methods such as a spin coating method and an inkjet method.

As the second hole transport layer of the organic EL device of the present invention, a hole transport arylamine compound may be used, in addition to the arylamine compound of the general formula (5) or the general formula (10). Further, a coating type polymer material, such as poly(3,4-ethylenedioxythiophene) (PEDOT)/poly(styrenesulfonate)

(PSS), a polymer compound having a structure of a benzidine derivative as a partial structure thereof, such as TPD, and the like may be used.

As the second hole transport layer of the organic EL device of the present invention, a hole transport arylamine compound is preferably used, and the arylamine compound of the general formula (5) or the general formula (10) is more preferably used. The compounds that are not subjected to p-type doping are particularly preferably used.

These may be individually formed into a film, may be used as a single layer formed with another material mixed, or may be formed as a laminated structure of the individually deposited layers, a laminated structure of the mixed layers, or a laminated structure of the individually deposited layer and the mixed layer. These materials may be formed into a thin-film by a vapor deposition method or other known methods such as a spin coating method and an inkjet method.

As the electron blocking layer of the organic EL device of the present invention, the arylamine compound of the general formula (5) or the general formula (10) is preferably used, and in addition, compounds having an electron blocking effect can be used, for example, a hole transport arylamine compound, such as the arylamine compound of the general formula (3) and the arylamine compound of the general formula (4); carbazole derivatives such as 4,4',4''-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene. These may be individually formed into a film, may be used as a single layer formed with another hole transport material mixed, or may be formed as a laminated structure of the individually deposited layers, a laminated structure of the mixed layers, or a laminated structure of the individually deposited layer and the mixed layer. These materials may be formed into a thin-film by a vapor deposition method or other known methods such as a spin coating method and an inkjet method.

In the organic EL device of the present invention, it is preferable that the electron acceptor in the layer on the side of the light emitting layer with respect to the hole injection layer, particularly the layer adjacent to the light emitting layer (for example, the second hole transport layer and the electron blocking layer) is not subjected to p-type doping.

In layer adjacent to the light emitting layer, an arylamine compound having a high electron blocking capability is preferably used, and the arylamine compound of the general formula (5) or the general formula (10) and the like are preferably used.

The thicknesses of these layers are not particularly limited, as far as the thicknesses are ordinarily used, and may be, for example, 20 to 100 nm for the first hole transport layer, 5 to 30 nm for the second hole transport layer, and 5 to 30 nm for the electron blocking layer.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may be made of a host material and a dopant material. Examples of the host material can be preferably anthracene derivatives. Other examples of the host material can be thiazole derivatives, benzimidazole derivatives, and polydialkyl fluorene derivatives, in addition to the above light-emitting materials. Examples of the dopant material can be preferably pyrene derivatives. Other examples of the dopant material can be quinacridone, coumarin, rubrene, perylene, derivatives thereof, benzopyran derivatives, indenophenanthrene derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes of metals such as iridium and platinum may be used. Examples of the phosphorescent materials include green phosphorescent materials such as $Ir(ppy)_3$, blue phosphorescent materials such as FIrpic and FIr6, and red phosphorescent materials such as $Btp_2Ir(acac)$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2) and 2,2',2''-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, Examples of the light-emitting material may be delayed fluorescent-emitting material such as a CDCB derivative of PIC-TRZ, CC2TA, PXZ-TRZ, 4CzIPN or the like (refer to Non-Patent Document 3, for example).

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproine (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Material used for the electron transport layer of the organic EL device of the present invention can be preferably the compounds of the general formula (6) having an anthracene ring structure, the compounds of the general formula (7) having a pyrimidine ring structure, and the compounds having a benzotriazole ring structure of the general formula (9). Other examples of material can be metal complexes of quinolinol derivatives such as $Alq_3$ and BAlq, various metal complexes, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of N,N-bis(biphenyl-4-yl)-(6-phenylbiphenyl-3-yl)amine (Compound 5-2)

To a reaction vessel having been substituted with nitrogen, 11.8 g of N,N-bis(biphenyl-4-yl)-(6-bromobiphenyl-3-yl)amine, 94 mL of toluene, 2.7 g of phenylboronic acid, and an aqueous solution containing 5.9 g of potassium carbonate dissolved in 36 mL of water in advance were added, through which nitrogen gas was passed under irradiation of ultrasonic wave for 30 minutes. 0.74 g of tetrakistriphenylphosphine palladium was added thereto, and the mixture was heated and stirred at 72° C. for 18 hours. After cooling to room temperature, the organic layer was collected by a liquid separation operation. The organic layer was subjected sequentially to rinsing with water and rinsing with a saturated sodium chloride aqueous solution, and then dried over anhydrous magnesium sulfate and concentrated to provide a crude product. Subsequently, the crude product was purified by column chromatography to provide 8.4 g of white powder of N,N-bis(biphenyl-4-yl)-(6-phenylbiphenyl-3-yl)amine (Compound 5-2) (yield: 72%).

The structure of the obtained white powder was identified by NMR.

$^1$H-NMR (CDCl$_3$) detected 31 hydrogen signals as follows.

δ (ppm)=7.56-7.68 (7H), 7.45-7.52 (4H), 7.14-7.41 (20H)

[Chemical Formula 918]

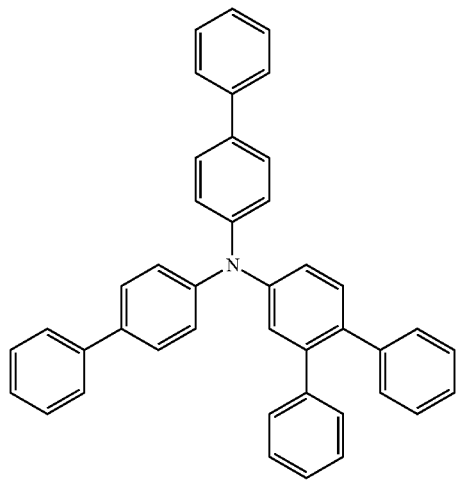

(5-2)

Example 2

Synthesis of N,N-bis(biphenyl-4-yl)-{6-(naphtyl-1-yl)biphenyl-3-yl}amine (Compound 5-3)

The reaction was carried out under the same conditions as in Example 1 except that 1-naphthylboronic acid was used instead of phenylboronic acid to provide 9.2 g of white powder of N,N-bis(biphenyl-4-yl)-{6-(naphtyl-1-yl)biphenyl-3-yl}amine (Compound 5-3) (yield: 61%).

The structure of the obtained white powder was identified by NMR.

$^1$H-NMR (CDCl$_3$) detected 33 hydrogen signals as follows.

δ (ppm)=7.84-7.87 (3H), 7.67-83 (6H), 7.26-7.64 (18H), 7.02-7.04 (6H)

[Chemical Formula 919]

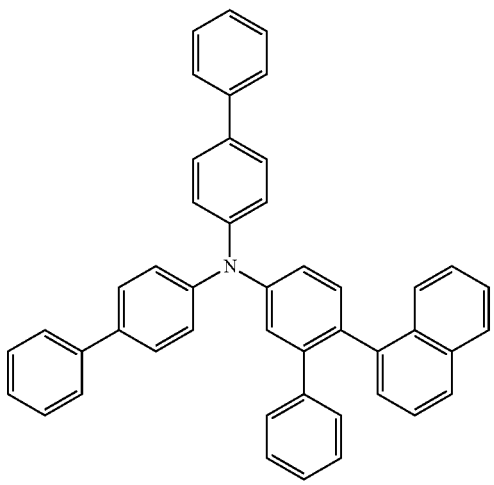

(5-3)

Example 3

Synthesis of N,N-bis(biphenyl-4-yl)-{6-(9,9-dimethylfluoren-2-yl)biphenyl-3-yl}amine (Compound 5-1)

The reaction was carried out under the same conditions as in Example 1 except that (9,9-dimethylfluoren-2-yl)boronic acid was used instead of phenylboronic acid to provide 9.0 g of white powder of N,N-bis(biphenyl-4-yl)-{6-(9,9-dimethylfluoren-2-yl)biphenyl-3-yl}amine (Compound 5-1) (yield: 57%).

The structure of the obtained white powder was identified by NMR.

$^1$H-NMR (CDCl$_3$) detected 39 hydrogen signals as follows.

δ (ppm)=7.56-7.64 (10H), 7.26-50 (18H), 7.02-7.16 (5H), 1.26 (6H)

[Chemical Formula 920]

(5-1)

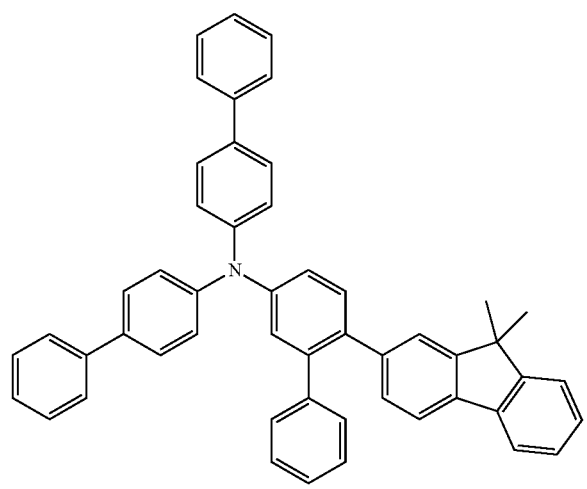

Example 4

Synthesis of N,N-bis(biphenyl-4-yl)-{6-(biphenyl-4-yl)biphenyl-3-yl}amine (Compound 5-4)

The reaction was carried out under the same conditions as in Example 1 except that 4-biphenylboronic acid was used instead of phenylboronic acid to provide 8.6 g of white powder of N,N-bis(biphenyl-4-yl)-{6-(biphenyl-4-yl)biphenyl-3-yl}amine (Compound 5-4) (yield: 64%).

The structure of the obtained white powder was identified by NMR.

$^1$H-NMR (CDCl$_3$) detected 35 hydrogen signals as follows.

δ (ppm)=7.66-7.53 (8H), 7.51-7.15 (27H)

[Chemical Formula 921]

(5-4)

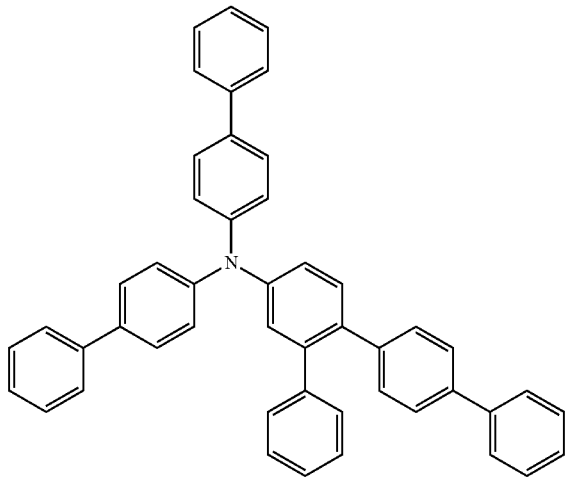

Example 5

Synthesis of N,N-bis(biphenyl-4-yl)-{6-(1,1';4'1''-terphenyl-4-yl)biphenyl-3-yl}amine (Compound 5-9)

The reaction was carried out under the same conditions as in Example 1 except that 4-bromo-1,1';4'1''-terphenyl was used instead of phenylboronic acid, and N,N-bis(biphenyl-4-yl)-{3-phenyl-4-(4,4,5,5-tetramethyl-1,3,2-dioxaboran-2-yl)phenyl}amine was used instead of N,N-bis(biphenyl-4-yl)-(6-bromobiphenyl-3-yl)amine to provide 4.5 g of white powder of N,N-bis(biphenyl-4-yl)-{6-(1,1';4'1''-terphenyl-4-yl)biphenyl-3-yl}amine (Compound 5-9) (yield: 40%).

The structure of the obtained white powder was identified by NMR.

$^1$H-NMR (THF-d$_3$) detected 39 hydrogen signals as follows.

δ (ppm)=7.73-7.58 (15H), 7.46-7.12 (24H)

[Chemical Formula 922]

(5-9)

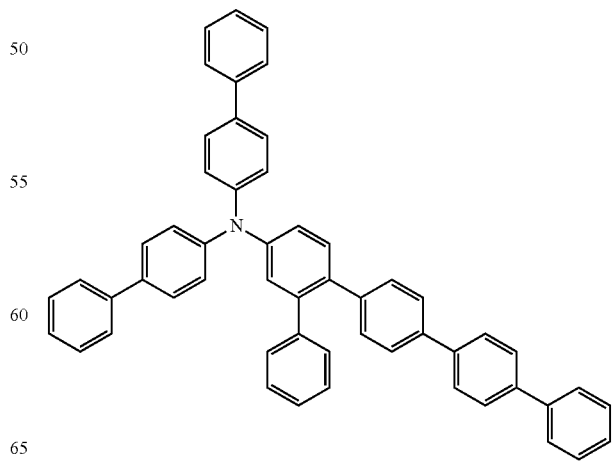

Example 6

Synthesis of N,N-bis(biphenyl-4-yl)-[6-{4-(naphthalen-1-yl)phenyl}biphenyl-3-yl]amine (Compound 5-16)

The reaction was carried out under the same conditions as in Example 1 except that 4-(naphthalen-1-yl)phenylboronic acid was used instead of phenylboronic acid to provide 11.6 g of white powder of N,N-bis(biphenyl-4-yl)-[6-{4-(naphthalen-1-yl)phenyl}biphenyl-3-yl]amine (Compound 5-16) (yield: 77%).

The structure of the obtained white powder was identified by NMR.

$^1$H-NMR (CDCl$_3$) detected 37 hydrogen signals as follows.

δ (ppm)=7.95-7.84 (3H), 7.67-7.18 (34H)

[Chemical Formula 923]

(5-16)

Example 7

Synthesis of N,N-bis(biphenyl-4-yl)-[6-{(9,9-dimethylfluoren-2-yl)phenyl}biphenyl-3-yl]amine (Compound 5-20)

The reaction was carried out under the same conditions as in Example 1 except that 4-(9,9-dimethylfluoren-2-yl)phenylboronic acid was used instead of phenylboronic acid to provide 13.1 g of white powder of N,N-bis(biphenyl-4-yl)-[6-{(9,9-dimethylfluoren-2-yl)phenyl}biphenyl-3-yl]amine (Compound 5-20) (yield: 81%).

The structure of the obtained white powder was identified by NMR.

$^1$H-NMR (CDCl$_3$) detected 43 hydrogen signals as follows.

δ (ppm)=7.78 (2H), 7.68-7.15 (35H), 1.55 (6H)

[Chemical Formula 924]

(5-20)

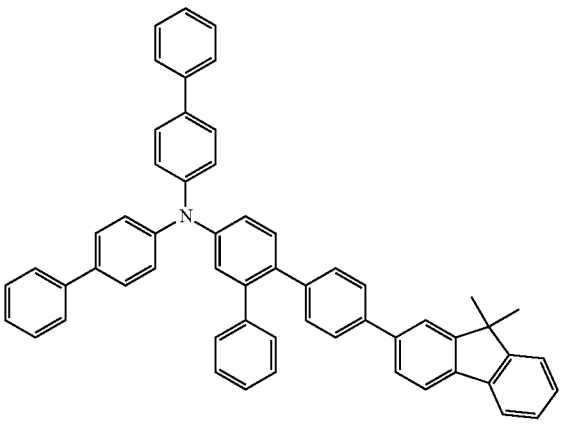

Example 8

Synthesis of N-(biphenyl-4-yl)-N-{6-(biphenyl-4-yl)biphenyl-3-yl}-(9,9-dimethylfluoren-2-yl)amine (Compound 5-56)

The reaction was carried out under the same conditions as in Example 1 except that 4-biphenylboronic acid was used instead of phenylboronic acid, and N-(biphenyl-4-yl)-N-(9,9-dimethylfluoren-2-yl)-(6-bromobiphenyl-3-yl)amine was used instead of N,N-bis(biphenyl-4-yl)-(6-bromobiphenyl-3-yl)amine to provide 17.8 g of white powder of N-(biphenyl-4-yl)-N-{6-(biphenyl-4-yl)biphenyl-3-yl}-(9,9-dimethylfluoren-2-yl)amine (Compound 5-56) (yield: 89%).

The structure of the obtained white powder was identified by NMR.

$^1$H-NMR (CDCl$_3$) detected 39 hydrogen signals as follows.

δ (ppm)=7.72-7.57 (7H), 7.52-7.33 (9H), 7.32-7.19 (17H), 1.45 (6H)

[Chemical Formula 925]

(5-56)

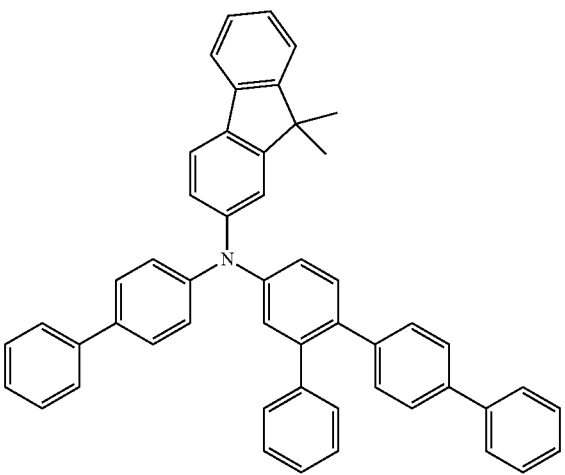

Example 9

Synthesis of N,N-bis(9,9-dimethylfluoren-2-yl)-{6-phenylbiphenyl-3-yl)amine (Compound 5-62)

The reaction was carried out under the same conditions as in Example 1 except that N,N-bis(9,9-dimethylfluoren-2-yl)-(6-bromobiphenyl-3-yl)amine was used instead of N,N-bis(biphenyl-4-yl)-(6-bromobiphenyl-3-yl)amine to provide 11.5 g of white powder of N,N-bis(9,9-dimethylfluoren-2-yl)-{6-phenylbiphenyl-3-yl)amine (Compound 5-62) (yield: 57%).

The structure of the obtained white powder was identified by NMR.

$^1$H-NMR (THF-d$_3$) detected 39 hydrogen signals as follows.

δ (ppm)=7.70-7.63 (3H), 7.44-7.02 (24H), 1.46 (12H)

[Chemical Formula 926]

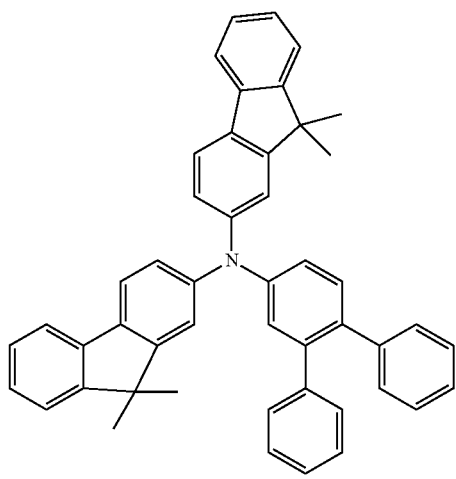

(5-62)

Example 10

Synthesis of N,N-bis(6-phenylbiphenyl-3-yl)-(biphenyl-4-yl)amine (Compound 5-108)

The reaction was carried out under the same conditions as in Example 1 except that N,N-bis(6-bromobiphenyl-3-yl)-(biphenyl-4-yl)amine was used instead of N,N-bis(biphenyl-4-yl)-(6-bromobiphenyl-3-yl)amine to provide 10.2 g of white powder of N,N-bis(6-phenylbiphenyl-3-yl)-(biphenyl-4-yl)amine (Compound 5-108) (yield: 73%).

The structure of the obtained white powder was identified by NMR.

$^1$H-NMR (CDCl$_3$) detected 35 hydrogen signals as follows.

δ (ppm)=7.57-7.66 (4H), 7.10-7.49 (31H)

[Chemical Formula 927]

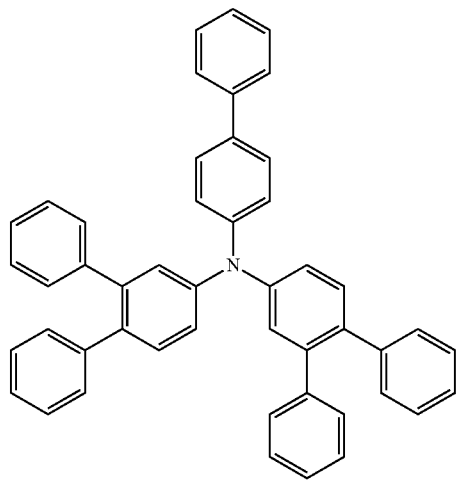

(5-108)

Example 11

Synthesis of N,N,N-tris(6-phenylbiphenyl-3-yl)amine (Compound 5-143)

The reaction was carried out under the same conditions as in Example 1 except that N,N,N-tris(6-bromobiphenyl-3-yl)amine was used instead of N,N-bis(biphenyl-4-yl)-(6-bromobiphenyl-3-yl)amine to provide 11.1 g of white powder of N,N,N-tris(6-phenylbiphenyl-3-yl)amine (Compound 5-143) (yield: 75%).

The structure of the obtained white powder was identified by NMR.

$^1$H-NMR (CDCl$_3$) detected 39 hydrogen signals as follows.

δ (ppm)=7.35-7.42 (6H), 7.15-7.35 (33H)

[Chemical Formula 928]

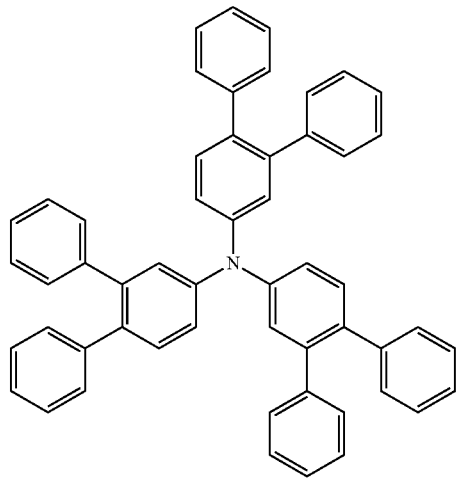

(5-143)

Example 12

Synthesis of N-(biphenyl-4-yl)-N-(6-phenylbiphenyl-3-yl)-(9,9-dimethylfluoren-2-yl)amine (Compound 5-50)

The reaction was carried out under the same conditions as in Example 1 except that N-(biphenyl-4-yl)-N-(9,9-dimethylfluoren-2-yl)-(6-bromobiphenyl-3-yl)amine was used instead of N,N-bis(biphenyl-4-yl)-(6-bromobiphenyl-3-yl)amine to provide 13.6 g of white powder of N-(biphenyl-4-yl)-N-(6-phenylbiphenyl-3-yl)-(9,9-dimethylfluoren-2-yl)amine (Compound 5-50) (yield: 76%).

The structure of the obtained white powder was identified by NMR.

¹H-NMR (CDCl₃) detected 35 hydrogen signals as follows.

δ (ppm)=7.72-7.61 (4H), 7.58 (2H), 7.50-7.09 (29H)

[Chemical Formula 929]

(5-50)

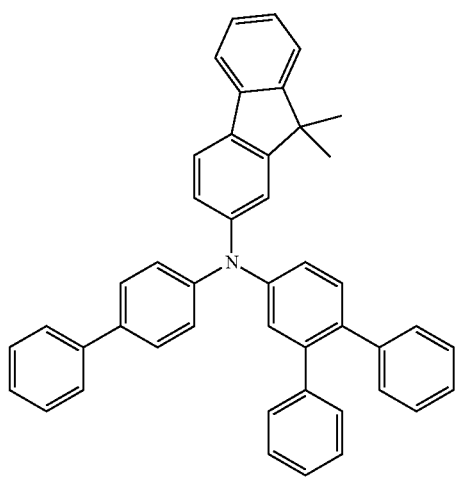

Example 13

Synthesis of N-(9,9-dimethylfluoren-2-yl)-N-{4-(naphthalen-1-yl)phenyl}-(6-phenylbiphenyl-3-yl)amine (Compound 5-63)

The reaction was carried out under the same conditions as in Example 1 except that N-(6-bromobiphenyl-3-yl)-N-(9,9-dimethylfluoren-2-yl)-{4-(naphthalen-1-yl)phenyl}amine was used instead of N,N-bis(biphenyl-4-yl)-(6-bromobiphenyl-3-yl)amine to provide 12.2 g of pale yellowish white powder of N-(9,9-dimethylfluoren-2-yl)-N-{4-(naphthalen-1-yl)phenyl}-(6-phenylbiphenyl-3-yl)amine (Compound 5-63) (yield: 56%).

The structure of the obtained pale yellowish white powder was identified by NMR.

¹H-NMR (CDCl₃) detected 37 hydrogen signals as follows.

δ (ppm)=8.10 (1H), 7.95 (1H), 7.88 (1H), 7.72-7.65 (2H), 7.60-7.10 (26H), 1.50 (6H)

[Chemical Formula 930]

(5-63)

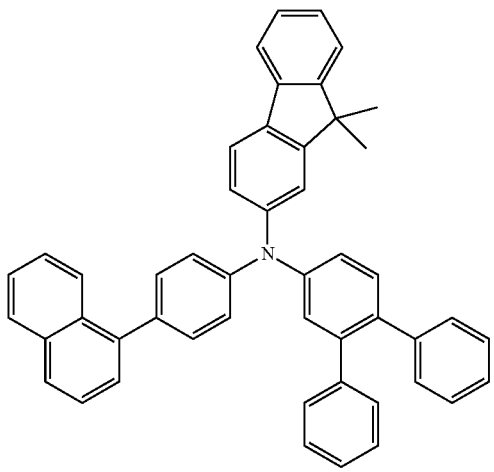

Example 14

Synthesis of N-(9,9-dimethylfluoren-2-yl)-N-{4-(naphthalen-2-yl)phenyl}-(6-phenylbiphenyl-3-yl)amine (Compound 5-64)

The reaction was carried out under the same conditions as in Example 1 except that N-(6-bromobiphenyl-3-yl)-N-(9,9-dimethylfluoren-2-yl)-{4-(naphthalen-2-yl)phenyl}amine was used instead of N,N-bis(biphenyl-4-yl)-(6-bromobiphenyl-3-yl)amine to provide 8.8 g of pale yellowish white powder of N-(9,9-dimethylfluoren-2-yl)-N-{4-(naphthalen-2-yl)phenyl}-(6-phenylbiphenyl-3-yl)amine (Compound 5-64) (yield: 63%).

The structure of the obtained pale yellowish white powder was identified by NMR.

¹H-NMR (CDCl₃) detected 37 hydrogen signals as follows.

δ (ppm)=8.08 (1H), 7.76-7.94 (4H), 7.60-7.71 (4H), 7.13-7.54 (22H), 1.52 (6H)

[Chemical Formula 931]

(5-64)

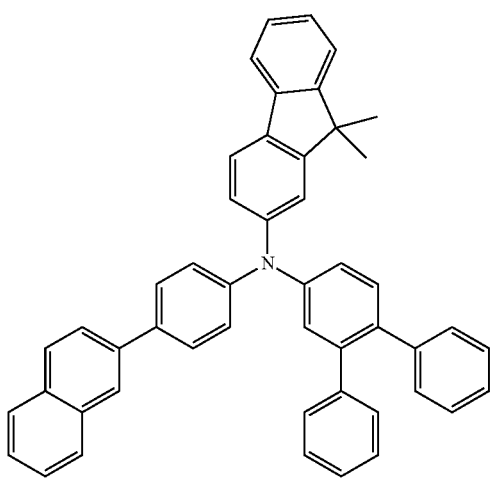

Example 15

Synthesis of N-(biphenyl-4-yl)-N-(9,9-dimethylfluoren-2-yl)-{6-(4-naphthalen-1-ylphenyl)biphenyl-3-yl}amine (Compound 5-65)

The reaction was carried out under the same conditions as in Example 1 except that 4-(naphthalen-1-yl)phenylboronic acid was used instead of phenylboronic acid, and N-(biphenyl-4-yl)-N-(9,9-dimethylfluoren-2-yl)-(6-bromobiphenyl-3-yl)amine was used instead of N,N-bis(biphenyl-4-yl)-(6-bromobiphenyl-3-yl)amine to provide 49.8 g of white powder of N-(biphenyl-4-yl)-N-(9,9-dimethylfluoren-2-yl)-{6-(4-naphthalen-1-ylphenyl)biphenyl-3-yl}amine (Compound 5-65) (yield: 84%).

The structure of the obtained white powder was identified by NMR.

$^1$H-NMR (CDCl$_3$) detected 41 hydrogen signals as follows.

δ (ppm)=7.92 (2H), 7.88 (1H), 7.72-7.18 (38H)

[Chemical Formula 932]

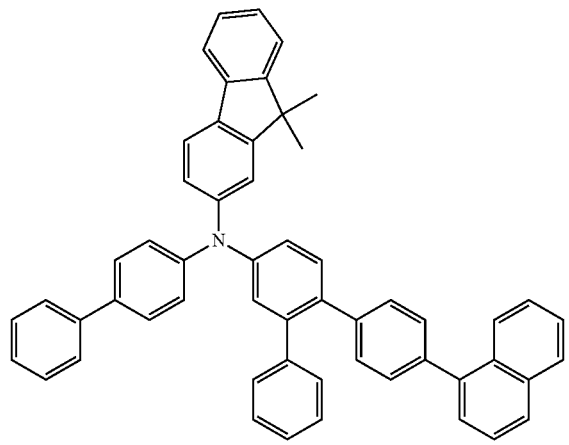

(5-65)

Example 16

Synthesis of N-(biphenyl-4-yl)-N-{4-(naphthalen-1-yl)phenyl}-{6-(biphenyl-4-yl)biphenyl-3-yl)amine (Compound 5-147)

The reaction was carried out under the same conditions as in Example 1 except that 4-biphenylboronic acid was used instead of phenylboronic acid, and N-(biphenyl-4-yl)-N-(6-bromobiphenyl-3-yl)-{4-(naphthalen-1-yl)phenyl}amine was used instead of N,N-bis(biphenyl-4-yl)-(6-bromobiphenyl-3-yl)amine to provide 7.5 g of white powder of N-(biphenyl-4-yl)-N-{4-(naphthalen-1-yl)phenyl}-{6-(biphenyl-4-yl)biphenyl-3-yl)amine (Compound 5-147) (yield: 48%).

The structure of the obtained white powder was identified by NMR.

$^1$H-NMR (CDCl$_3$) detected 37 hydrogen signals as follows.

δ (ppm)=8.08 (1H), 7.95 (1H), 7.88 (1H), 7.68-7.18 (34H)

[Chemical Formula 933]

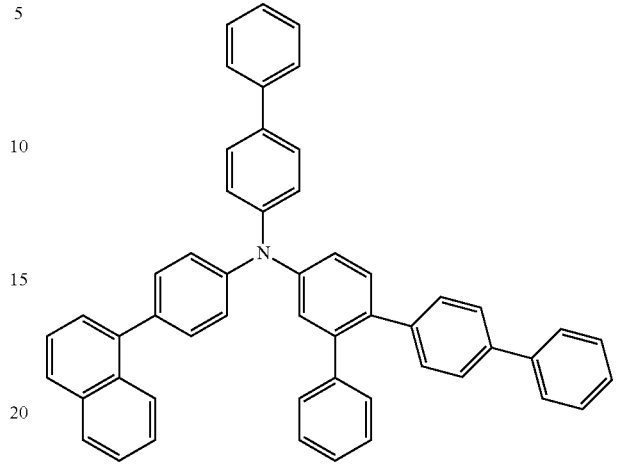

(5-147)

Example 17

Synthesis of N-(biphenyl-4-yl)-N-{4-(naphthalen-1-yl)phenyl}-[6-{4-(naphthalen-1-yl)phenyl}biphenyl-3-yl]amine (Compound 5-148)

The reaction was carried out under the same conditions as in Example 1 except that 4-(naphthalen-1-yl)phenylboronic acid was used instead of phenylboronic acid, and N-(biphenyl-4-yl)-N-{4-(naphthalen-1-yl)phenyl}-(6-bromobiphenyl-3-yl)amine was used instead of N,N-bis(biphenyl-4-yl)-(6-bromobiphenyl-3-yl)amine to provide 8.4 g of pale yellowish white powder of N-(biphenyl-4-yl)-N-{4-(naphthalen-1-yl)phenyl}-[6-{4-(naphthalen-1-yl)phenyl}biphenyl-3-yl]amine (Compound 5-148) (yield: 60%).

The structure of the obtained pale yellowish white powder was identified by NMR.

$^1$H-NMR (CDCl$_3$) detected 39 hydrogen signals as follows.

δ (ppm)=8.09 (1H), 7.98-7.84 (5H), 7.69-7.20 (33H)

[Chemical Formula 934]

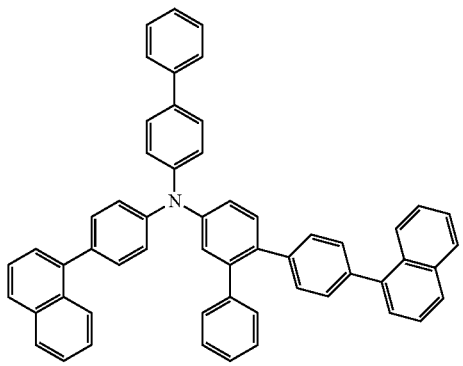

(5-148)

Example 18

Synthesis of N-(biphenyl-4-yl)-N-{4-(naphthalen-1-yl)phenyl}-{6-(p-terphenyl-4-yl)biphenyl-3-yl]amine (Compound 5-150)

The reaction was carried out under the same conditions as in Example 1 except that 4-(p-terphenyl)boronic acid was used instead of phenylboronic acid, and N-(biphenyl-4-yl)-N-{4-(naphthalen-1-yl)phenyl}-(6-bromobiphenyl-3-yl)amine was used instead of N,N-bis(biphenyl-4-yl)-(6-bromobiphenyl-3-yl)amine to provide 6.3 g of pale yellowish white powder of N-(biphenyl-4-yl)-N-{4-(naphthalen-1-yl)phenyl}-{6-(p-terphenyl-4-yl)biphenyl-3-yl]amine (Compound 5-150) (yield: 47%).

The structure of the obtained pale yellowish white powder was identified by NMR.

$^1$H-NMR (CDCl$_3$) detected 41 hydrogen signals as follows.

δ (ppm)=8.12 (1H), 7.98-7.83 (2H), 7.72-7.15 (38H)

[Chemical Formula 935]

(5-150)

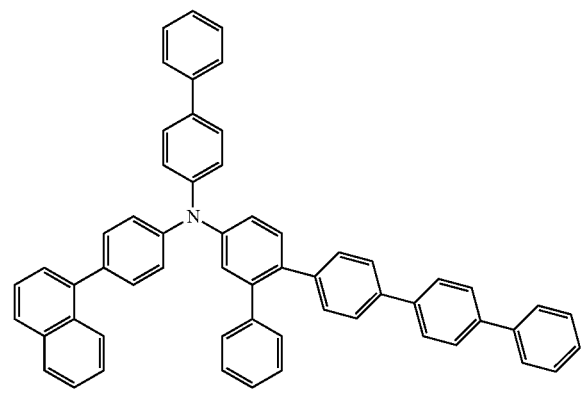

Example 19

Synthesis of N,N-bis(biphenyl-4-yl)-[4-phenyl-3-{4-(naphthalen-1-yl)phenyl}phenyl]amine (Compound 5-152)

To a reaction vessel having been substituted with nitrogen, 13.5 g of 4-bromobiphenyl, 9.0 g of 2-{4-(naphthalen-1-yl)phenyl}-4-aminobiphenyl, 0.11 g of palladium acetate, 0.15 g of a toluene solution (50%) of tri-tert-butylphosphine, and 90 mL of toluene were added, heated, and stirred at 100° C. for 24 hours. After removing insoluble matters by filtering, the filtrate was concentrated to provide a crude product. Subsequently, the crude product was purified by column chromatography to provide 5.4 g of pale yellowish white powder of N,N-bis(biphenyl-4-yl)-[4-phenyl-3-{4-(naphthalen-1-yl)phenyl}phenyl]amine (Compound 5-152) (yield: 33%).

The structure of the obtained pale yellowish white powder was identified by NMR.

$^1$H-NMR (CDCl$_3$) detected 37 hydrogen signals as follows.

δ (ppm)=7.94-7.76 (3H), 7.68-7.15 (34H)

[Chemical Formula 936]

(5-152)

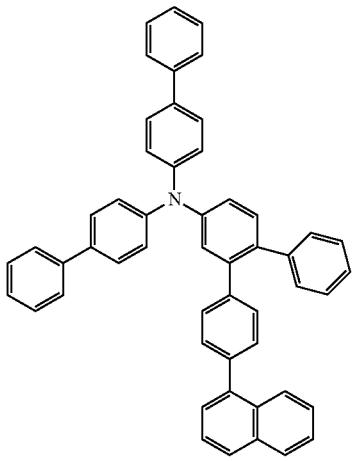

Example 20

Synthesis of N,N-bis(9,9-dimethylfluoren-2-yl)-{6-(biphenyl-4-yl)biphenyl-3-yl)amine (Compound 5-153)

The reaction was carried out under the same conditions as in Example 1 except that 4-biphenylboronic acid was used instead of phenylboronic acid, and N,N-bis(9,9-dimethylfluoren-2-yl)-N-(6-bromobiphenyl-3-yl)amine was used instead of N,N-bis(biphenyl-4-yl)-(6-bromobiphenyl-3-yl)amine to provide 16.7 g of pale yellowish white powder of N,N-bis(9,9-dimethylfluoren-2-yl)-{6-(biphenyl-4-yl)biphenyl-3-yl)amine (Compound 5-153) (yield: 92%).

The structure of the obtained pale yellowish white powder was identified by NMR.

$^1$H-NMR (CDCl$_3$) detected 43 hydrogen signals as follows.

δ (ppm)=7.80-7.59 (6H), 7.51-7.12 (25H), 1.51 (12H)

[Chemical Formula 937]

(5-153)

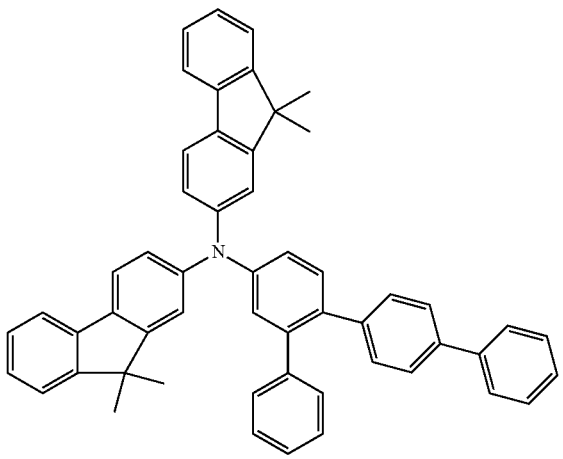

Example 21

Synthesis of N,N-bis{4-(naphthalen-1-yl)phenyl}-{6-(biphenyl-4-yl)biphenyl-3-yl)amine (Compound 5-155)

The reaction was carried out under the same conditions as in Example 1 except that 4-biphenylboronic acid was used instead of phenylboronic acid, and N,N-bis{4-(naphthalen-1-yl)phenyl}-(6-bromobiphenyl-3-yl)amine was used instead of N,N-bis(biphenyl-4-yl)-(6-bromobiphenyl-3-yl)amine to provide 10.6 g of pale yellowish white powder of N,N-bis{4-(naphthalen-1-yl)phenyl}-{6-(biphenyl-4-yl)biphenyl-3-yl)amine (Compound 5-155) (yield: 79%).

The structure of the obtained pale yellowish white powder was identified by NMR.

$^1$H-NMR (CDCl$_3$) detected 39 hydrogen signals as follows.

δ (ppm)=8.08-8.14 (2H), 7.88-7.96 (4H), 7.24-7.64 (33H)

[Chemical Formula 938]

(5-155)

Example 22

Synthesis of N,N-bis{4-(naphthalen-1-yl)phenyl}-[6-{4-(naphthalen-1-yl)phenyl}biphenyl-3-yl]amine (Compound 5-156)

The reaction was carried out under the same conditions as in Example 1 except that 4-(naphthalen-1-yl)phenylboronic acid was used instead of phenylboronic acid, and N,N-bis{4-(naphthalen-1-yl)phenyl}-(6-bromobiphenyl-3-yl)amine was used instead of N,N-bis(biphenyl-4-yl)-(6-bromobiphenyl-3-yl)amine to provide 10.6 g of pale yellowish white powder of N,N-bis{4-(naphthalen-1-yl)phenyl}-[6-{4-(naphthalen-1-yl)phenyl}biphenyl-3-yl]amine (Compound 5-156) (yield: 79%).

The structure of the obtained pale yellowish white powder was identified by NMR.

$^1$H-NMR (CDCl$_3$) detected 41 hydrogen signals as follows.

δ (ppm)=8.14 (2H), 7.99-7.72 (6H), 7.61-7.10 (33H)

[Chemical Formula 939]

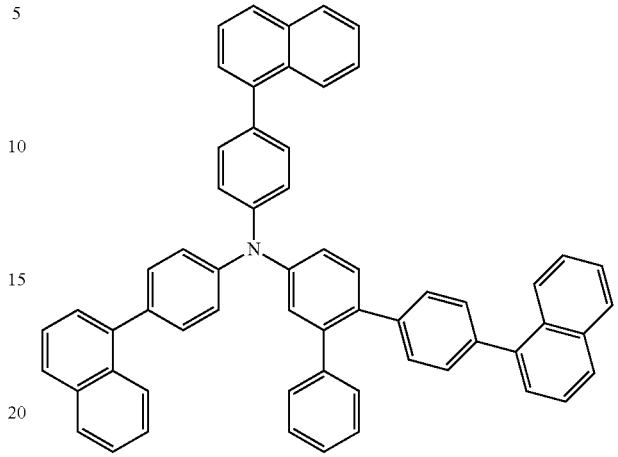

(5-156)

Example 23

Synthesis of N,N-bis{4-(naphthalen-1-yl)phenyl}-[6-{4-(naphthalen-2-yl)phenyl}biphenyl-3-yl]amine (Compound 5-157)

The reaction was carried out under the same conditions as in Example 1 except that 4-(naphthalen-2-yl)phenylboronic acid was used instead of phenylboronic acid, and N,N-bis{4-(naphthalen-1-yl)phenyl}-(6-bromobiphenyl-3-yl)amine was used instead of N,N-bis(biphenyl-4-yl)-(6-bromobiphenyl-3-yl)amine to provide 9.7 g of pale yellowish white powder of N,N-bis{4-(naphthalen-1-yl)phenyl}-[6-{4-(naphthalen-2-yl)phenyl}biphenyl-3-yl]amine (Compound 5-157) (yield: 74%).

The structure of the obtained pale yellowish white powder was identified by NMR.

$^1$H-NMR (CDCl$_3$) detected 41 hydrogen signals as follows.

δ (ppm)=8.08-8.14 (3H), 7.66-7.97 (8H), 7.28-7.66 (30H)

[Chemical Formula 940]

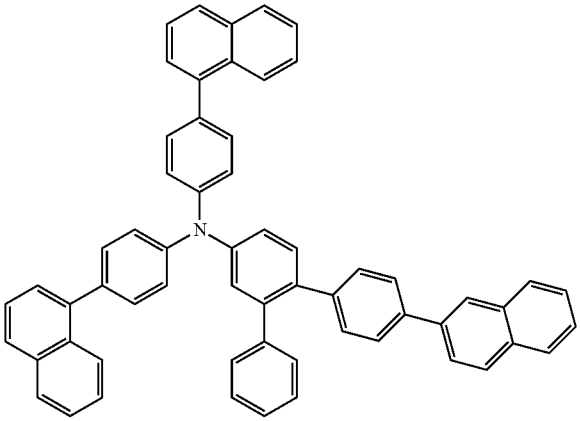

(5-157)

Example 24

Synthesis of N,N-bis{4-(naphthalen-1-yl)phenyl}-{6-(p-terphenyl-4-yl)biphenyl-3-yl)amine (Compound 5-158)

The reaction was carried out under the same conditions as in Example 1 except that pinacol 4-(p-terphenyl)boronate ester was used instead of phenylboronic acid, and N,N-bis{4-(naphthalen-1-yl)phenyl}-(6-bromobiphenyl-3-yl)amine was used instead of N,N-bis(biphenyl-4-yl)-(6-bromobiphenyl-3-yl)amine to provide 6.2 g of pale yellowish white powder of N,N-bis{4-(naphthalen-1-yl)phenyl}-{6-(p-terphenyl-4-yl)biphenyl-3-yl)amine (Compound 5-158) (yield: 63%).

The structure of the obtained pale yellowish white powder was identified by NMR.

$^1$H-NMR (CDCl$_3$) detected 43 hydrogen signals as follows.

δ (ppm)=8.08-8.14 (3H), 7.89-7.95 (4H), 7.25-7.71 (36H)

[Chemical Formula 941]

(5-158)

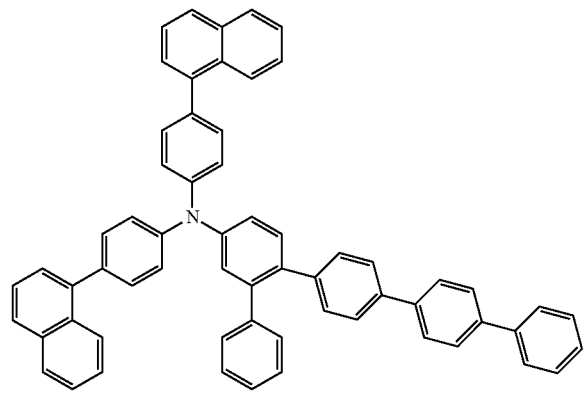

Example 25

Synthesis of N,N-bis{4-(naphthalen-1-yl)phenyl}-{6-(biphenyl-2-yl)biphenyl-3-yl)amine (Compound 5-159)

The reaction was carried out under the same conditions as in Example 1 except that pinacol 2-biphenylboronic acid was used instead of phenylboronic acid, and N,N-bis{4-(naphthalen-1-yl)phenyl}-(6-bromobiphenyl-3-yl)amine was used instead of N,N-bis(biphenyl-4-yl)-(6-bromobiphenyl-3-yl)amine to provide 4.9 g of pale yellowish white powder of N,N-bis{4-(naphthalen-1-yl)phenyl}-{6-(biphenyl-2-yl)biphenyl-3-yl)amine (Compound 5-159) (yield: 48%).

The structure of the obtained pale yellowish white powder was identified by NMR.

$^1$H-NMR (CDCl$_3$) detected 39 hydrogen signals as follows.

δ (ppm)=8.08-8.12 (2H), 7.86-7.94 (4H), 7.00-7.57 (29H), 6.63-6.75 (4H)

[Chemical Formula 942]

(5-159)

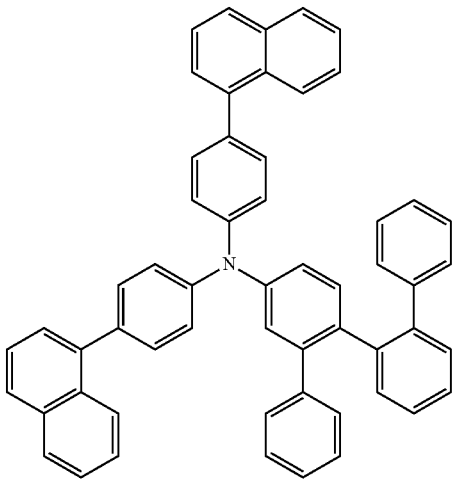

Example 26

Synthesis of N-(biphenyl-4-yl)-N-{4-(9,9-dimethylfluoren-2-yl)phenyl}-(6-phenylbiphenyl-3-yl)amine (Compound 5-160)>

The reaction was carried out under the same conditions as in Example 1 except that N-(biphenyl-4-yl)-N-{4-(9,9-dimethylfluoren-2-yl)phenyl}-(6-bromobiphenyl-3-yl)amine was used instead of N,N-bis(biphenyl-4-yl)-(6-bromobiphenyl-3-yl)amine to provide 8.3 g of white powder of N-(biphenyl-4-yl)-N-{4-(9,9-dimethylfluoren-2-yl)phenyl}-(6-phenylbiphenyl-3-yl)amine (Compound 5-160) (yield: 48%).

The structure of the obtained white powder was identified by NMR.

$^1$H-NMR (CDCl$_3$) detected 39 hydrogen signals as follows.

δ (ppm)=7.79 (2H), 7.69-7.52 (7H), 7.50-7.41 (3H), 7.40-7.10 (21H), 1.57 (6H)

[Chemical Formula 943]

(5-160)

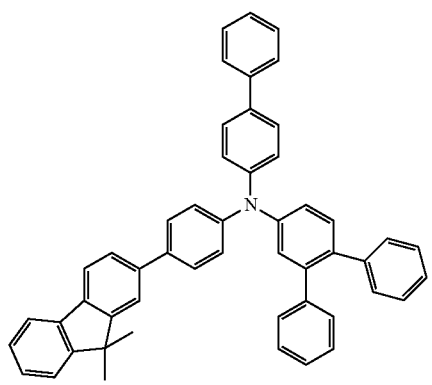

Example 27

Synthesis of N-(biphenyl-4-yl)-N-{4-(9,9-dimethyl-fluoren-2-yl)phenyl}-{6-(biphenyl-3-yl)biphenyl-3-yl)amine (Compound 5-162)

The reaction was carried out under the same conditions as in Example 1 except that 3-biphenylboronic acid was used instead of phenylboronic acid, and N-(biphenyl-4-yl)-N-{4-(9,9-dimethylfluoren-2-yl)phenyl}-(6-bromobiphenyl-3-yl)amine was used instead of N,N-bis(biphenyl-4-yl)-(6-bromobiphenyl-3-yl)amine to provide 8.7 g of white powder of N-(biphenyl-4-yl)-N-{4-(9,9-dimethylfluoren-2-yl)phenyl}-{6-(biphenyl-3-yl)biphenyl-3-yl)amine (Compound 5-162) (yield: 49%).

The structure of the obtained white powder was identified by NMR.

$^1$H-NMR (CDCl$_3$) detected 43 hydrogen signals as follows.

δ (ppm)=7.78 (2H), 7.65-7.46 (6H), 7.45-7.05 (29H), 1.54 (6H)

[Chemical Formula 944]

(5-162)

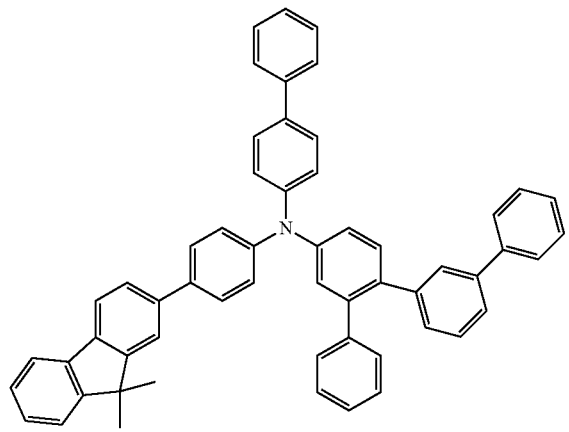

Example 28

Synthesis of N-(biphenyl-4-yl)-N-{4-(naphthalen-2-yl)phenyl}-{6-(biphenyl-4-yl)biphenyl-3-yl)amine (Compound 5-163)

The reaction was carried out under the same conditions as in Example 1 except that 4-biphenylboronic acid was used instead of phenylboronic acid, and N-(biphenyl-4-yl)-N-{4-(naphthalen-2-yl)phenyl}-(6-bromobiphenyl-3-yl)amine was used instead of N,N-bis(biphenyl-4-yl)-(6-bromobiphenyl-3-yl)amine to provide 4.9 g of white powder of N-(biphenyl-4-yl)-N-{4-(naphthalen-2-yl)phenyl}-{6-(biphenyl-4-yl)biphenyl-3-yl)amine (Compound 5-163) (yield: 44%).

The structure of the obtained white powder was identified by NMR.

$^1$H-NMR (CDCl$_3$) detected 37 hydrogen signals as follows.

δ (ppm)=7.73 (1H), 7.61-7.70 (3H), 7.54-7.58 (1H), 7.19-7.52 (32H)

[Chemical Formula 945]

(5-163)

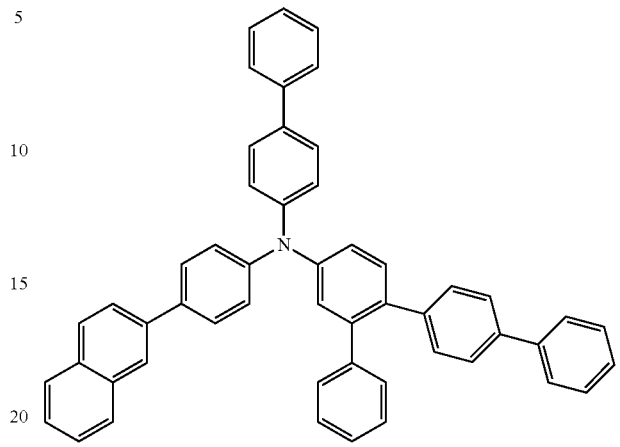

Example 29

Synthesis of N-(biphenyl-4-yl)-N-{4-(naphthalen-2-yl)phenyl}-[6-{4-naphthalen-1-yl)phenyl}biphenyl-3-yl]amine (Compound 5-164)

The reaction was carried out under the same conditions as in Example 1 except that 4-(naphthalen-1-yl)phenylboronic acid was used instead of phenylboronic acid, and N-(biphenyl-4-yl)-N-{4-(naphthalen-2-yl)phenyl}-(6-bromobiphenyl-3-yl)amine was used instead of N,N-bis(biphenyl-4-yl)-(6-bromobiphenyl-3-yl)amine to provide 9.2 g of white powder of N-(biphenyl-4-yl)-N-{4-(naphthalen-2-yl)phenyl}-[6-{4-naphthalen-1-yl)phenyl}biphenyl-3-yl]amine (Compound 5-164) (yield: 740).

The structure of the obtained white powder was identified by NMR.

$^1$H-NMR (CDCl$_3$) detected 39 hydrogen signals as follows.

δ (ppm)=8.10 (1H), 7.89-7.10 (38H)

[Chemical Formula 946]

(5-164)

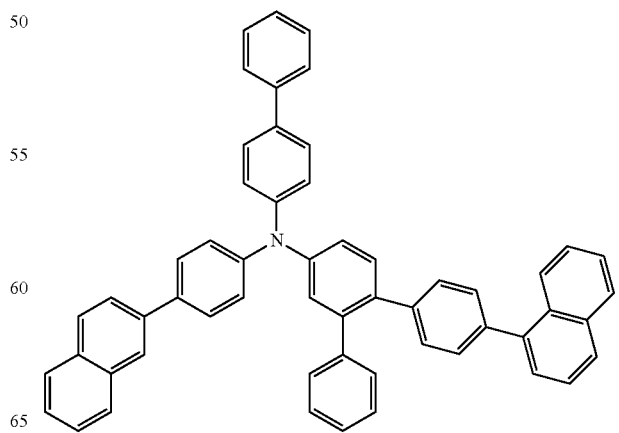

Example 30

Synthesis of N-(biphenyl-4-yl)-N-{4-(naphthalen-2-yl)phenyl}-[6-{4-(naphthalen-2-yl)phenyl}biphenyl-3-yl]amine (Compound 5-165)

The reaction was carried out under the same conditions as in Example 1 except that 4-naphthalen-2-ylphenylboronic acid was used instead of phenylboronic acid, and N-(biphenyl-4-yl)-N-{4-(naphthalen-2-yl)phenyl}-(6-bromobiphenyl-3-yl)amine was used instead of N,N-bis(biphenyl-4-yl)-(6-bromobiphenyl-3-yl)amine to provide 9.8 g of white powder of N-(biphenyl-4-yl)-N-{4-(naphthalen-2-yl)phenyl}-[6-{4-(naphthalen-2-yl)phenyl}biphenyl-3-yl]amine (Compound 5-165) (yield: 70%).

The structure of the obtained white powder was identified by NMR.

$^1$H-NMR (CDCl$_3$) detected 39 hydrogen signals as follows.

δ (ppm)=8.07 (2H), 7.99-7.85 (6H), 7.84-7.40 (15H), 7.39-7.12 (16H)

[Chemical Formula 947]

(5-165)

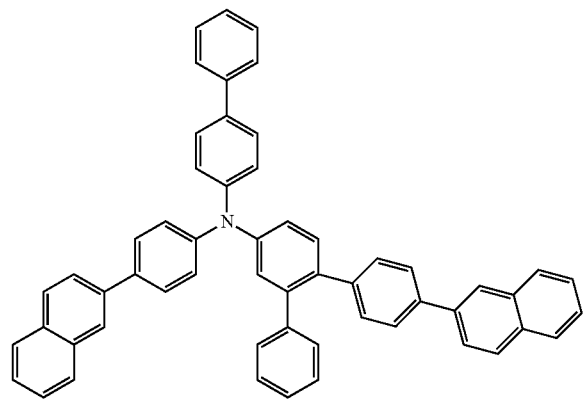

Example 31

Synthesis of N-(biphenyl-4-yl)-N-(9,9-diphenylfluoren-2-yl)-(6-phenylbiphenyl-3-yl)amine (Compound 5-166)>

The reaction was carried out under the same conditions as in Example 1 except that N-(biphenyl-4-yl)-N-(9,9-diphenylfluoren-2-yl)-(6-bromobiphenyl-3-yl)amine was used instead of N,N-bis(biphenyl-4-yl)-(6-bromobiphenyl-3-yl)amine to provide 11.0 g of white powder of N-(biphenyl-4-yl)-N-(9,9-diphenylfluoren-2-yl)-(6-phenylbiphenyl-3-yl)amine (Compound 5-166) (yield: 61%).

The structure of the obtained white powder was identified by NMR.

$^1$H-NMR (CDCl$_3$) detected 39 hydrogen signals as follows.

δ (ppm)=7.60-7.74 (4H), 7.14-7.52 (33H), 7.00-7.03 (2H)

[Chemical Formula 948]

(5-166)

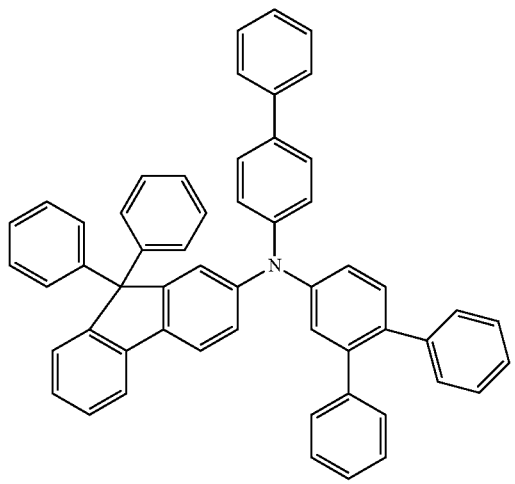

Example 32

Synthesis of N-(p-terphenyl-4-yl)-N-(9,9-dimethylfluoren-2-yl)-(6-phenylbiphenyl-3-yl)amine (Compound 5-167)

The reaction was carried out under the same conditions as in Example 1 except that N-(p-terphenyl-4-yl)-N-(9,9-dimethylfluoren-2-yl)-(6-bromobiphenyl-3-yl)amine was used instead of N,N-bis(biphenyl-4-yl)-(6-bromobiphenyl-3-yl)amine to provide 18.3 g of white powder of N-(p-terphenyl-4-yl)-N-(9,9-dimethylfluoren-2-yl)-(6-phenylbiphenyl-3-yl)amine (Compound 5-167) (yield: 74%).

The structure of the obtained white powder was identified by NMR.

$^1$H-NMR (CDCl$_3$) detected 39 hydrogen signals as follows.

δ (ppm)=7.74-7.52 (10H), 7.51-7.01 (23H), 1.54 (6H)

[Chemical Formula 949]

(5-167)

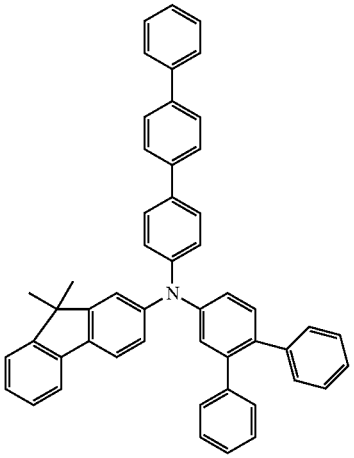

423

Example 33

Synthesis of N-(9,9-dimethylfluoren-2-yl)-N-{4-(naphthalen-2-yl)phenyl}-{6-(biphenyl-4-yl)biphenyl-3-yl}amine (Compound 5-169)

The reaction was carried out under the same conditions as in Example 1 except that 4-biphenylboronic acid was used instead of phenylboronic acid, and N-(9,9-dimethylfluoren-2-yl)-N-{4-(naphthalen-2-yl)phenyl}-(6-bromobiphenyl-3-yl)amine was used instead of N,N-bis(biphenyl-4-yl)-(6-bromobiphenyl-3-yl)amine to provide 10.4 g of white powder of N-(9,9-dimethylfluoren-2-yl)-N-{4-(naphthalen-2-yl)phenyl}-{6-(biphenyl-4-yl)biphenyl-3-yl}amine (Compound 5-169) (yield: 67%).

The structure of the obtained white powder was identified by NMR.

$^1$H-NMR (CDCl$_3$) detected 41 hydrogen signals as follows.

δ (ppm)=8.12 (1H), 7.78-7.92 (4H), 7.60-7.71 (6H), 7.21-7.54 (24H), 1.53 (6H)

[Chemical Formula 950]

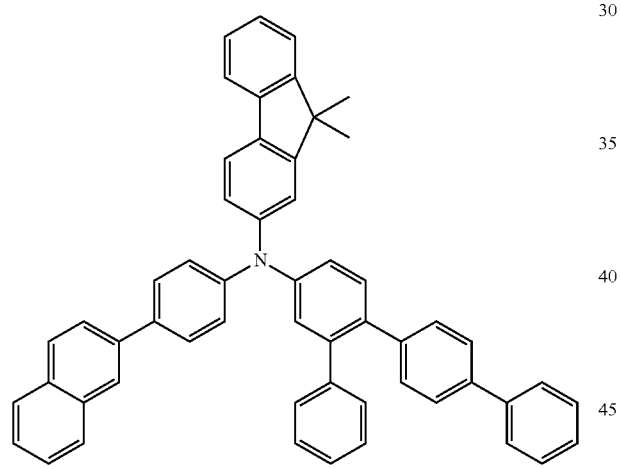

(5-169)

Example 34

Synthesis of N-(biphenyl-4-yl)-N-{4-(naphthalen-2-yl)phenyl}-{2-(biphenyl-4-yl)biphenyl-4-yl)amine (Compound 5-170)

The reaction was carried out under the same conditions as in Example 1 except that N-(biphenyl-4-yl)-N-{4-(naphthalen-2-yl)phenyl}-{2-(biphenyl-4-yl)bromobenzen-4-yl}amine was used instead of N,N-bis(biphenyl-4-yl)-(6-bromobiphenyl-3-yl)amine to provide 10.4 g of white powder of N-(biphenyl-4-yl)-N-{4-(naphthalen-2-yl)phenyl}-{2-(biphenyl-4-yl)biphenyl-4-yl)amine (Compound 5-170) (yield: 67%).

424

The structure of the obtained white powder was identified by NMR.

$^1$H-NMR (CDCl$_3$) detected 37 hydrogen signals as follows.

δ (ppm)=8.08 (1H), 7.81-7.96 (3H), 7.79-7.81 (1H), 7.21-7.73 (32H)

[Chemical Formula 951]

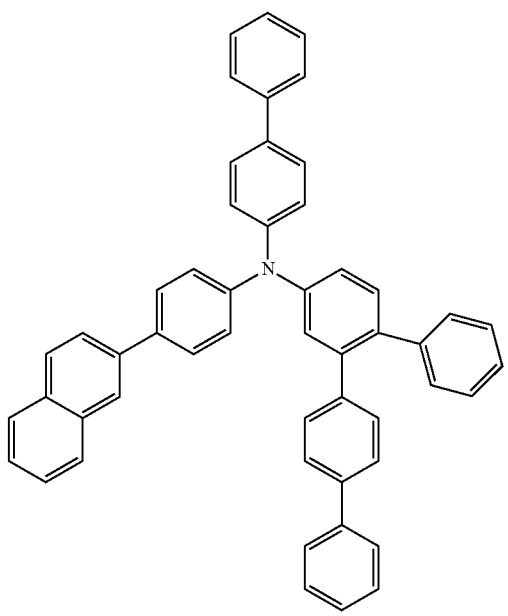

(5-170)

Example 35

Synthesis of N-(biphenyl-4-yl)-N-{4-(naphthalen-2-yl)phenyl}-[2-{4-naphthalen-2-yl)phenyl}biphenyl-4-yl]amine (Compound 5-171)

The reaction was carried out under the same conditions as in Example 1 except that N-(biphenyl-4-yl)-N-{4-(naphthalen-2-yl)phenyl}-[2-{4-(naphthalen-2-yl)phenyl}-(bromo-biphenyl-4-yl)]amine was used instead of N,N-bis(biphenyl-4-yl)-(6-bromobiphenyl-3-yl)amine to provide 10.0 g of white powder of N-(biphenyl-4-yl)-N-{4-(naphthalen-2-yl)phenyl}-[2-{4-naphthalen-2-yl)phenyl}biphenyl-4-yl]amine (Compound 5-171) (yield: 810).

The structure of the obtained white powder was identified by NMR.

$^1$H-NMR (CDCl$_3$) detected 39 hydrogen signals as follows.

δ (ppm)=8.04-8.10 (2H), 7.78-7.96 (8H), 7.24-7.65 (29H)

[Chemical Formula 952]

(5-171)

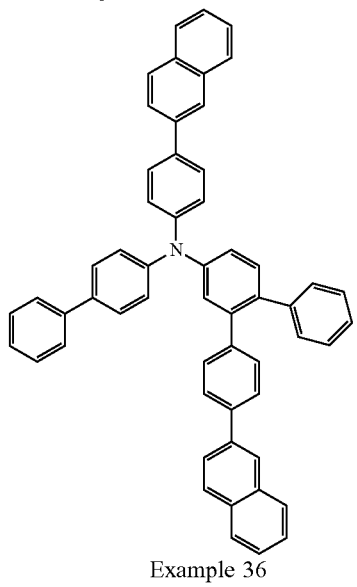

Example 36

Synthesis of N-(biphenyl-4-yl)-N-(9,9-diphenylfluoren-2-yl)-{6-(biphenyl-4-yl)biphenyl-3-yl}amine (Compound 5-174)

The reaction was carried out under the same conditions as in Example 1 except that 4-biphenylboronic acid was used instead of phenylboronic acid, and N-(biphenyl-4-yl)-N-(9,9-diphenylfluoren-2-yl)-(6-bromobiphenyl-3-yl)amine was used instead of N,N-bis(biphenyl-4-yl)-(6-bromobiphenyl-3-yl)amine to provide 6.5 g of white powder of N-(biphenyl-4-yl)-N-(9,9-diphenylfluoren-2-yl)-{6-(biphenyl-4-yl)biphenyl-3-yl}amine (Compound 5-174) (yield: 71%).

The structure of the obtained white powder was identified by NMR.

$^1$H-NMR (CDCl$_3$) detected 43 hydrogen signals as follows.

δ (ppm)=7.61-7.77 (6H), 7.20-7.51 (34H), 7.06-7.11 (3H)

[Chemical Formula 953]

(5-174)

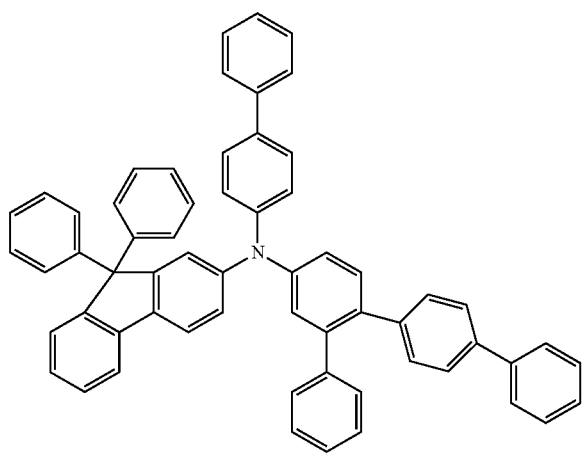

Example 37

Synthesis of N-(biphenyl-4-yl)-N-(9,9-diphenylfluoren-2-yl)-{6-(biphenyl-3-yl)biphenyl-3-yl}amine (Compound 5-175)

The reaction was carried out under the same conditions as in Example 1 except that 3-biphenylboronic acid was used instead of phenylboronic acid, and N-(biphenyl-4-yl)-N-(9,9-diphenylfluoren-2-yl)-(6-bromobiphenyl-3-yl)amine was used instead of N,N-bis(biphenyl-4-yl)-(6-bromobiphenyl-3-yl)amine to provide 8.0 g of white powder of N-(biphenyl-4-yl)-N-(9,9-diphenylfluoren-2-yl)-{6-(biphenyl-3-yl)biphenyl-3-yl}amine (Compound 5-175) (yield: 87%).

The structure of the obtained white powder was identified by NMR.

$^1$H-NMR (CDCl$_3$) detected 43 hydrogen signals as follows.

δ (ppm)=7.70-7.76 (2H), 7.63-7.65 (2H), 7.18-7.54 (36H), 7.08-7.12 (3H)

[Chemical Formula 954]

(5-175)

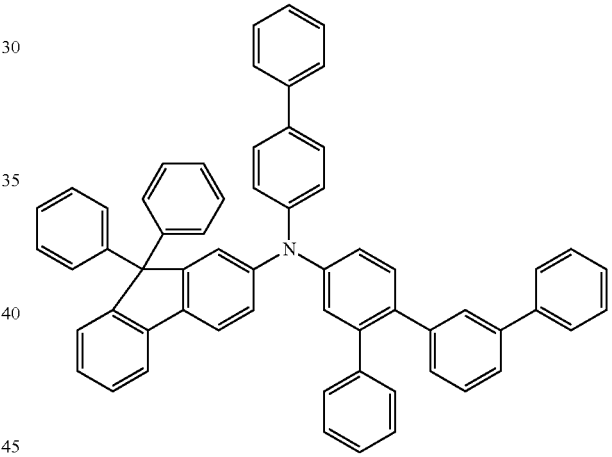

Example 38

Synthesis of N,N-bis(9,9-dimethylfluoren-2-yl)-{6-(biphenyl-3-yl)biphenyl-3-yl)amine (Compound 5-176)

The reaction was carried out under the same conditions as in Example 1 except that 3-biphenylboronic acid was used instead of phenylboronic acid, and N,N-bis(9,9-dimethylfluoren-2-yl)-(6-bromobiphenyl-3-yl)amine was used instead of N,N-bis(biphenyl-4-yl)-(6-bromobiphenyl-3-yl) amine to provide 17.0 g of white powder of N,N-bis(9,9-dimethylfluoren-2-yl)-{6-(biphenyl-3-yl)biphenyl-3-yl) amine (Compound 5-176) (yield: 85%).

The structure of the obtained white powder was identified by NMR.

$^1$H-NMR (CDCl$_3$) detected 43 hydrogen signals as follows.

δ (ppm)=7.30-7.62 (4H), 7.48-7.14 (27H), 1.50 (12H)

[Chemical Formula 955]

(5-176)

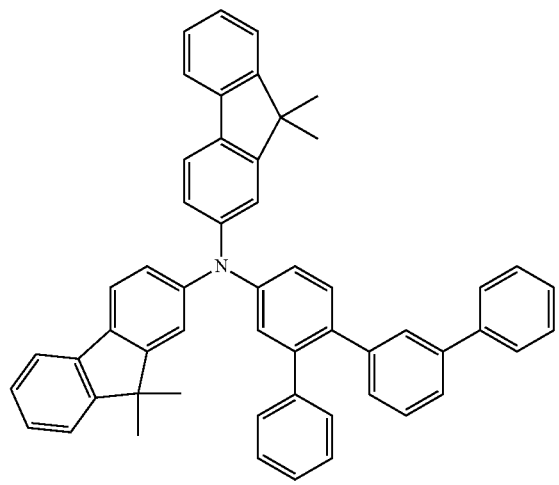

Example 39

Synthesis of N,N-bis(biphenyl-4-yl)-{6-(biphenyl-2-yl)-p-terphenyl-3-yl}amine (Compound 5-179)

The reaction was carried out under the same conditions as in Example 1 except that 2-biphenylboronic acid was used instead of phenylboronic acid, and N,N-bis(biphenyl-4-yl)-(6-bromo-p-terphenyl-3-yl)amine was used instead of N,N-bis(biphenyl-4-yl)-(6-bromobiphenyl-3-yl)amine to provide 9.6 g of white powder of N,N-bis(biphenyl-4-yl)-{6-(biphenyl-2-yl)-p-terphenyl-3-yl}amine (Compound 5-179) (yield: 86%).

The structure of the obtained white powder was identified by NMR.

$^1$H-NMR (CDCl$_3$) detected 39 hydrogen signals as follows.

δ (ppm)=7.54-7.66 (10H), 7.08-7.49 (25H), 6.63-6.74 (4H)

[Chemical Formula 956]

(5-179)

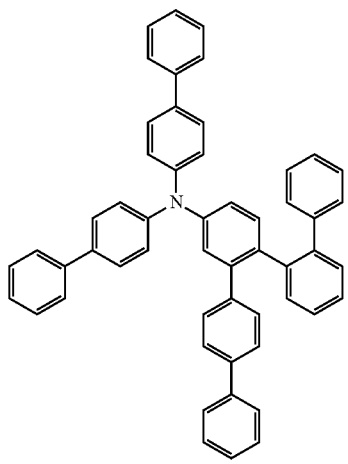

Example 40

Synthesis of N-(biphenyl-4-yl)-N-(9,9-diphenylfluoren-2-yl)-{6-(biphenyl-2-yl)biphenyl-3-yl}amine (Compound 5-180)

The reaction was carried out under the same conditions as in Example 1 except that 2-biphenylboronic acid was used instead of phenylboronic acid, and N-(biphenyl-4-yl)-N-(9,9-diphenylfluoren-2-yl)-(6-bromobiphenyl-3-yl)amine was used instead of N,N-bis(biphenyl-4-yl)-(6-bromobiphenyl-3-yl)amine to provide 5.2 g of white powder of N-(biphenyl-4-yl)-N-(9,9-diphenylfluoren-2-yl)-{6-(biphenyl-2-yl)biphenyl-3-yl}amine (Compound 5-180) (yield: 57%).

The structure of the obtained white powder was identified by NMR.

$^1$H-NMR (CDCl$_3$) detected 43 hydrogen signals as follows.

δ (ppm)=7.60-7.74 (4H), 6.95-7.49 (35H), 6.68-6.71 (2H), 6.54-6.57 (2H)

[Chemical Formula 957]

(5-180)

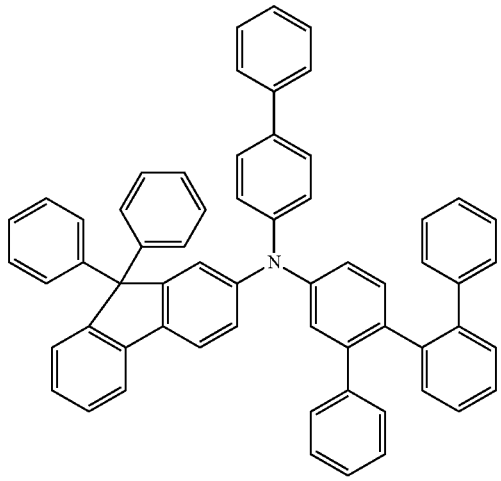

Example 41

Synthesis of N-(9,9-dimethylfluoren-2-yl)-N-{4-(naphthalen-1-yl)phenyl}-{6-(biphenyl-4-yl)biphenyl-3-yl}amine (Compound 5-183)

The reaction was carried out under the same conditions as in Example 1 except that 4-biphenylboronic acid was used instead of phenylboronic acid, and N-(9,9-dimethylfluoren-2-yl)-N-{4-(naphthalen-1-yl)phenyl}-(6-bromobiphenyl-3-yl)amine was used instead of N,N-bis(biphenyl-4-yl)-(6-bromobiphenyl-3-yl)amine to provide 19.9 g of white powder of N-(9,9-dimethylfluoren-2-yl)-N-{4-(naphthalen-1-yl)phenyl}-{6-(biphenyl-4-yl)biphenyl-3-yl}amine (Compound 5-183) (yield: 89%).

The structure of the obtained white powder was identified by NMR.

$^1$H-NMR (CDCl$_3$) detected 41 hydrogen signals as follows.

δ (ppm)=8.10 (1H), 7.93 (1H), 7.88 (1H), 7.71 (2H), 7.65-7.15 (30H), 1.53 (6H)

[Chemical Formula 958]

(5-183)

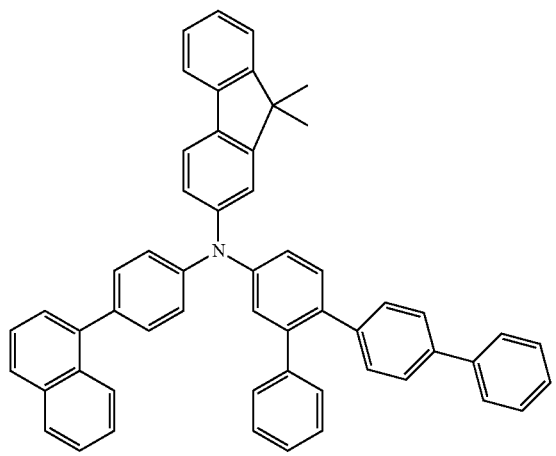

Example 42

Synthesis of N-(9,9-diphenylfluoren-2-yl)-N-{6-(biphenyl-4-yl)biphenyl-3-yl}aniline (Compound 5-217)

The reaction was carried out under the same conditions as in Example 1 except that 4-biphenylboronic acid was used instead of phenylboronic acid, and N-(9,9-diphenylfluoren-2-yl)-N-(6-bromobiphenyl-3-yl)aniline was used instead of N,N-bis(biphenyl-4-yl)-(6-bromobiphenyl-3-yl)amine to provide 4.2 g of white powder of N-(9,9-diphenylfluoren-2-yl)-N-{6-(biphenyl-4-yl)biphenyl-3-yl}aniline (Compound 5-217) (yield: 37%).

The structure of the obtained white powder was identified by NMR.

$^1$H-NMR (CDCl$_3$) detected 39 hydrogen signals as follows.

δ (ppm)=7.76-7.62 (4H), 7.44-7.03 (35H)

[Chemical Formula 959]

(5-217)

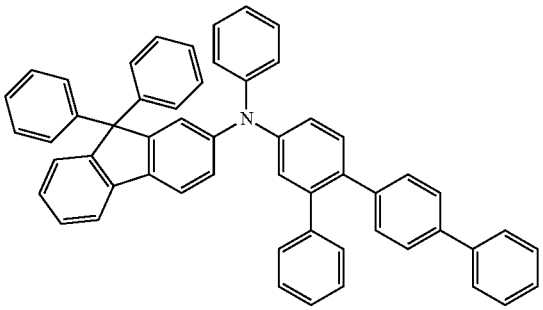

Example 43

Synthesis of N,N-bis{4-(naphthalen-2-yl)phenyl}-[6-{4-(naphthalen-1-yl)phenyl}biphenyl-3-yl]amine (Compound 5-185)

The reaction was carried out under the same conditions as in Example 1 except that 4-(naphthalen-1-yl)phenylboronic acid was used instead of phenylboronic acid, and N,N-bis{4-(naphthalen-2-yl)phenyl}-(6-bromobiphenyl-3-yl)amine was used instead of N,N-bis(biphenyl-4-yl)-(6-bromobiphenyl-3-yl)amine to provide 6.5 g of white powder of N,N-bis{4-(naphthalen-2-yl)phenyl}-[6-{4-(naphthalen-1-yl)phenyl}biphenyl-3-yl]amine (Compound 5-185) (yield: 73%).

The structure of the obtained white powder was identified by NMR.

$^1$H-NMR (CDCl$_3$) detected 41 hydrogen signals as follows.

δ (ppm)=8.11 (2H), 7.98-7.68 (18H), 7.59-7.23 (21H)

[Chemical Formula 960]

(5-185)

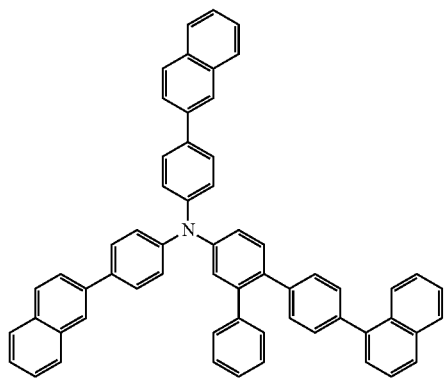

Example 44

Synthesis of N-(biphenyl-4-yl)-N-(phenanthren-9-yl)-(6-phenylbiphenyl-3-yl)amine (Compound 5-187)

The reaction was carried out under the same conditions as in Example 1 except that N-(biphenyl-4-yl)-N-(phenanthren-9-yl)-(6-bromobiphenyl-3-yl)amine was used instead of N,N-bis(biphenyl-4-yl)-(6-bromobiphenyl-3-yl)amine to provide 3.5 g of white powder of N-(biphenyl-4-yl)-N-(phenanthren-9-yl)-(6-phenylbiphenyl-3-yl)amine (Compound 5-187) (yield: 22%).

The structure of the obtained white powder was identified by NMR.

$^1$H-NMR (CDCl$_3$) detected 31 hydrogen signals as follows.

δ (ppm)=8.81-8.70 (2H), 8.17 (1H), 7.83 (1H), 7.78 (1H), 7.74-7.72 (26H)

[Chemical Formula 961]

(5-187)

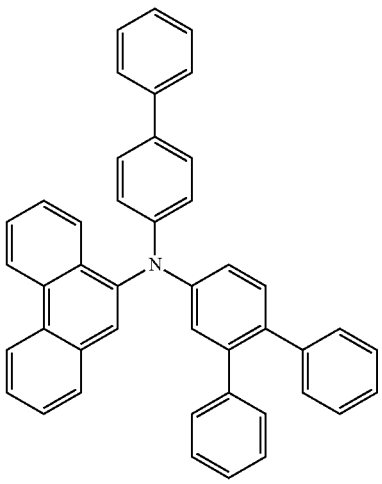

Example 45

Synthesis of N-(biphenyl-4-yl)-N-(phenanthren-9-yl)-N-{6-(biphenyl-4-yl) biphenyl-3-yl)amine (Compound 5-188)

The reaction was carried out under the same conditions as in Example 1 except that 4-biphenylboronic acid was used instead of phenylboronic acid, and N-(biphenyl-4-yl)-N-(phenanthren-9-yl)-(6-bromobiphenyl-3-yl)amine was used instead of N,N-bis(biphenyl-4-yl)-(6-bromobiphenyl-3-yl)amine to provide 13.0 g of white powder of N-(biphenyl-4-yl)-N-(phenanthren-9-yl)-N-{6-(biphenyl-4-yl) biphenyl-3-yl)amine (Compound 5-188) (yield: 77%).

The structure of the obtained white powder was identified by NMR.

$^1$H-NMR (CDCl$_3$) detected 35 hydrogen signals as follows.

δ (ppm)=8.82-8.73 (2H), 8.17 (1H), 7.85 (1H), 7.78 (1H), 7.75-7.09 (30H)

[Chemical Formula 962]

(5-188)

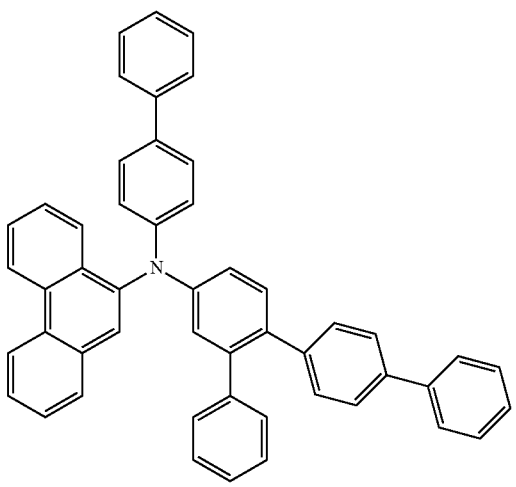

Example 46

Synthesis of N-(biphenyl-4-yl)-N-(9-phenylcarbazol-2-yl)-{6-(biphenyl-4-yl)biphenyl-3-yl)amine (Compound 5-189)

The reaction was carried out under the same conditions as in Example 19 except that 2-bromo-9-phenylcarbazole was used instead of 4-bromobiphenyl, and N-(biphenyl-4-yl)-N-[6-(biphenyl-4-yl)biphenyl-3-yl)amine was used instead of 2-{4-(naphthalen-1-yl)phenyl}-4-aminobiphenyl to provide 18.0 g of white powder of N-(biphenyl-4-yl)-N-(9-phenylcarbazol-2-yl)-{6-(biphenyl-4-yl)biphenyl-3-yl)amine (Compound 5-189) (yield: 85%).

The structure of the obtained white powder was identified by NMR.

$^1$H-NMR (CDCl$_3$) detected 38 hydrogen signals as follows.

δ (ppm)=8.13-8.06 (2H), 7.65-7.59 (4H), 7.57-7.50 (6H), 7.49-7.10 (26H)

[Chemical Formula 963]

(5-189)

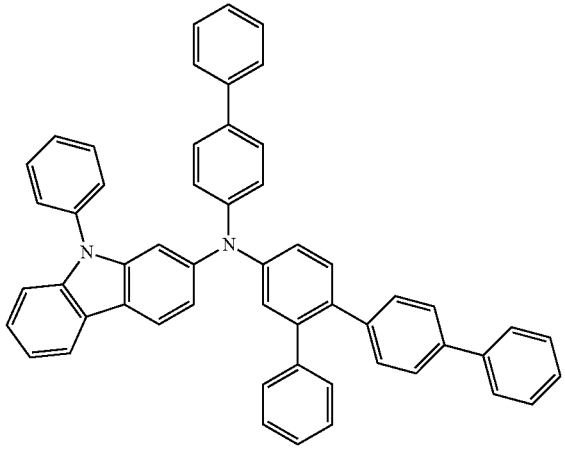

Example 47

Synthesis of N-(biphenyl-4-yl)-N-(9,9'-spirobi[9H-fluoren]-2-yl)-(6-phenylbiphenyl-3-yl)amine (Compound 5-190)

The reaction was carried out under the same conditions as in Example 1 except that N-(biphenyl-4-yl)-N-(9,9'-spirobi[9H-fluoren]-2-yl)-(6-bromobiphenyl-3-yl)amine was used instead of N,N-bis(biphenyl-4-yl)-(6-bromobiphenyl-3-yl)amine to provide 6.0 g of white powder of N-(biphenyl-4-yl)-N-(9,9'-spirobi[9H-fluoren]-2-yl)-(6-phenylbiphenyl-3-yl)amine (Compound 5-190) (yield: 52%).

The structure of the obtained white powder was identified by NMR.

$^1$H-NMR (CDCl$_3$) detected 37 hydrogen signals as follows.

δ (ppm)=7.85-7.72 (4H), 7.57 (2H), 7.49-7.29 (8H), 7.23-6.95 (17H), 6.88-6.82 (4H), 6.80-6.66 (2H)

[Chemical Formula 964]

(5-190)

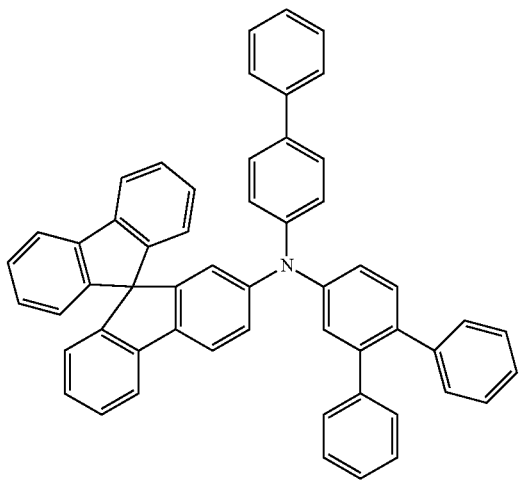

Example 48

The melting points and the glass transition points of the arylamine compounds of the general formula (5) were measured using a high-sensitive differential scanning calorimeter (DSC3100SA, produced by Bruker AXS GmbH).

|  | Melting Point | Glass transition point |
| --- | --- | --- |
| Compound of Example 2 | 242° C. | 103° C. |
| Compound of Example 3 | not observed | 115° C. |
| Compound of Example 4 | not observed | 104° C. |
| Compound of Example 5 | not observed | 117° C. |
| Compound of Example 6 | not observed | 107° C. |
| Compound of Example 7 | 240° C. | 127° C. |
| Compound of Example 8 | not observed | 116° C. |
| Compound of Example 9 | not observed | 119° C. |
| Compound of Example 10 | not observed | 101° C. |
| Compound of Example 11 | not observed | 112° C. |
| Compound of Example 12 | not observed | 102° C. |
| Compound of Example 13 | not observed | 109° C. |
| Compound of Example 14 | 237° C. | 108° C. |
| Compound of Example 15 | not observed | 119° C. |
| Compound of Example 16 | not observed | 109° C. |
| Compound of Example 17 | not observed | 113° C. |
| Compound of Example 18 | not observed | 121° C. |
| Compound of Example 19 | not observed | 111° C. |
| Compound of Example 20 | 246° C. | 132° C. |
| Compound of Example 21 | not observed | 117° C. |
| Compound of Example 22 | not observed | 119° C. |
| Compound of Example 23 | 245° C. | 120° C. |
| Compound of Example 24 | 240° C. | 125° C. |
| Compound of Example 25 | not observed | 107° C. |
| Compound of Example 26 | 244° C. | 113° C. |
| Compound of Example 27 | not observed | 112° C. |
| Compound of Example 28 | not observed | 110° C. |
| Compound of Example 29 | not observed | 112° C. |
| Compound of Example 30 | not observed | 115° C. |
| Compound of Example 31 | not observed | 125° C. |
| Compound of Example 32 | not observed | 114° C. |
| Compound of Example 33 | not observed | 122° C. |
| Compound of Example 34 | not observed | 111° C. |
| Compound of Example 35 | not observed | 119° C. |
| Compound of Example 36 | not observed | 137° C. |
| Compound of Example 37 | not observed | 125° C. |
| Compound of Example 38 | 233° C. | 120° C. |
| Compound of Example 39 | 232° C. | 110° C. |
| Compound of Example 40 | not observed | 126° C. |
| Compound of Example 41 | not observed | 122° C. |
| Compound of Example 42 | not observed | 125° C. |
| Compound of Example 43 | not observed | 116° C. |
| Compound of Example 44 | not observed | 115° C. |
| Compound of Example 45 | not observed | 129° C. |
| Compound of Example 46 | not observed | 121° C. |
| Compound of Example 47 | not observed | 129° C. |

The arylamine compounds of the general formula (5) have glass transition points of 100° C. or higher, which shows that the compounds have a stable thin-film state.

Example 49

A 100 nm-thick vapor-deposited film was fabricated on an ITO substrate using the arylamine compounds of the general formula (5), and the work function thereof was measured using an ionization potential measuring device (PYS-202 produced by Sumitomo Heavy Industries, Ltd.).

|  | Work function |
| --- | --- |
| Compound of Example 1 | 5.68 eV |
| Compound of Example 2 | 5.72 eV |
| Compound of Example 3 | 5.66 eV |
| Compound of Example 4 | 5.67 eV |
| Compound of Example 5 | 5.70 eV |
| Compound of Example 6 | 5.71 eV |
| Compound of Example 7 | 5.66 eV |
| Compound of Example 8 | 5.62 eV |
| Compound of Example 9 | 5.55 eV |
| Compound of Example 10 | 5.72 eV |
| Compound of Example 11 | 5.75 eV |
| Compound of Example 12 | 5.62 eV |
| Compound of Example 13 | 5.62 eV |
| Compound of Example 14 | 5.62 eV |
| Compound of Example 15 | 5.63 eV |
| Compound of Example 16 | 5.73 eV |
| Compound of Example 17 | 5.69 eV |
| Compound of Example 18 | 5.71 eV |
| Compound of Example 19 | 5.72 eV |
| Compound of Example 20 | 5.55 eV |
| Compound of Example 21 | 5.72 eV |
| Compound of Example 22 | 5.73 eV |
| Compound of Example 23 | 5.72 eV |
| Compound of Example 24 | 5.73 eV |
| Compound of Example 25 | 5.73 eV |
| Compound of Example 26 | 5.63 eV |
| Compound of Example 27 | 5.64 eV |
| Compound of Example 28 | 5.69 eV |
| Compound of Example 29 | 5.69 eV |
| Compound of Example 30 | 5.67 eV |
| Compound of Example 31 | 5.66 eV |
| Compound of Example 32 | 5.61 eV |
| Compound of Example 33 | 5.62 eV |
| Compound of Example 34 | 5.70 eV |
| Compound of Example 35 | 5.71 eV |
| Compound of Example 36 | 5.67 eV |
| Compound of Example 37 | 5.68 eV |
| Compound of Example 38 | 5.58 eV |
| Compound of Example 39 | 5.72 eV |
| Compound of Example 40 | 5.64 eV |
| Compound of Example 41 | 5.63 eV |
| Compound of Example 42 | 5.71 eV |
| Compound of Example 43 | 5.68 eV |
| Compound of Example 44 | 5.76 eV |
| Compound of Example 45 | 5.74 eV |
| Compound of Example 46 | 5.60 eV |
| Compound of Example 47 | 5.64 eV |

It is understood that the arylamine compounds of the general formula (5) have favorable energy levels, as compared to a work function of 5.4 eV of the common hole transport materials, such as NPD and TPD, and thus have a favorable hole transport capability.

Example 50

The LUMO levels of the compound of the general formula (6) having an anthracene ring structure, the compound of the general formula (7) having a pyrimidine ring structure, and the compound of the general formula (9) having a benzotriazole ring structure were calculated. The LUMO level was calculated by obtaining the difference in bandgap estimated from the work function of the thin film measured with an ionization potential measuring device and the absorption spectrum of the thin film measured with an ultraviolet-visible absorption spectrum measuring device.

|  | LUMO level |
| --- | --- |
| Compound (6b-1) | 3.26 eV |
| Compound (6c-28) | 3.10 eV |
| Compound (7-126) | 3.26 eV |
| Compound (9-112) | 3.15 eV |

It is understood that the compound of the general formula (6) having an anthracene ring structure, the compound of the general formula (7) having a pyrimidine ring structure, and the compound of the general formula (9) having a benzotriazole ring structure have favorable energy levels, as compared to a LUMO level of 2.70 eV of the known electron transport materials, such as TPBi, and thus have a favorable electron injection capability and a favorable electron transport capability.

Example 51

Synthesis of 4,4'''-bis{(biphenyl-4-yl)phenylamino}-(1,1':4',1'':4'',1'''-quaterphenyl) (Compound 10-1)

To a reaction vessel having been substituted with nitrogen, 18.2 g of N-phenyl-N-{4-(4,4,5,5-tetramethyl-1,3,2-dioxaborolan-2-yl) phenyl}-(1,1'-biphenyl-4-yl)amine, 7.5 g of 4,4'-diiodobiphenyl, 46 mL of a 2 M potassium carbonate aqueous solution, 60 mL of toluene, and 15 mL of ethanol were added, through which nitrogen gas was passed for 1 hour. 1.1 g of tetrakis(triphenylphosphine) palladium was added thereto, and the mixture was heated and stirred at 72° C. for 10 hours. After cooling to room temperature, 60 mL of methanol was added thereto. The solid matter thus deposited was collected by filtration, and rinsed with 100 mL of a mixed solution of methanol/water (5/1, v/v), to which 100 mL of 1,2-dichlorobenzene was then added, and the solid matter was dissolved therein by heating. After removing insoluble matters by filtration, the solution was spontaneously cooled, and 200 mL of methanol was added thereto to deposit a crude product, which was collected by filtration. The crude product was subjected to reflux rinsing with 100 mL of methanol, so as to provide 11.8 g of pale yellow powder of 4,4'''-bis{(biphenyl-4-yl)phenylamino}-(1,1':4',1'':4'',1'''-quaterphenyl) (Compound 10-1) (yield: 81%).

The structure of the obtained pale yellow powder was identified by NMR.

$^1$H-NMR (CDCl$_3$) detected 44 hydrogen signals as follows.

δ (ppm)=7.66-7.77 (8H), 7.50-7.64 (12H), 7.42-7.50 (4H), 7.28-7.38 (6H), 7.20-7.26 (12H), 7.08 (2H)

[Chemical Formula 965]

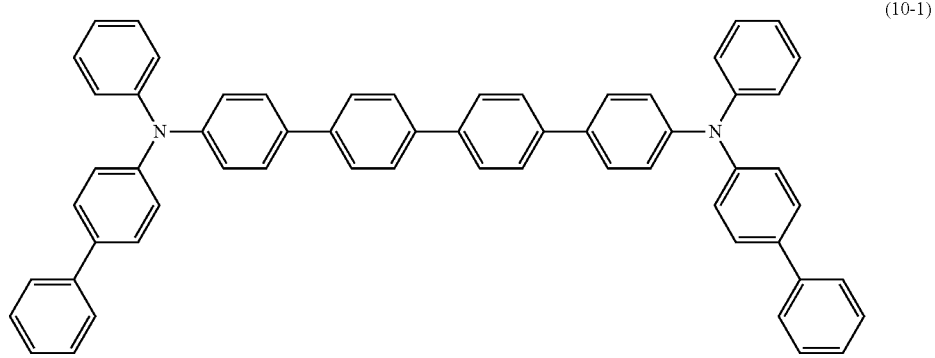

(10-1)

Example 52

Synthesis of 4,4''''-bis{(biphenyl-4-yl)phenylamino}-(1,1':4',1'':4'',1''':4''',1''''-quinquephenyl) (Compound 10-13)

To a reaction vessel having been substituted with nitrogen, 16.3 g of N-phenyl-N-{4-(4,4,5,5-tetramethyl-1,3,2-dioxaborolan-2-yl) phenyl}-(1,1'-biphenyl-4-yl)amine, 8.0 g of 4,4'-diiodoterphenyl, 41 mL of a 2 M potassium carbonate aqueous solution, 64 mL of toluene, and 16 mL of ethanol were added, through which nitrogen gas was passed for 1 hour. 1.0 g of tetrakis(triphenylphosphine) palladium was added thereto, and the mixture was heated and stirred at 72° C. for 18 hours. After cooling to room temperature, 60 mL of methanol was added thereto. The solid matter thus deposited was collected by filtration, and rinsed with 100 mL of a mixed solution of methanol/water (5/1, v/v), to which 100 mL of 1,2-dichlorobenzene was then added, and the solid matter was dissolved therein by heating. After removing insoluble matters by filtration, the solution was spontaneously cooled, and 200 mL of methanol was added thereto to deposit a crude product, which was collected by filtration. The crude product was subjected to reflux rinsing with 100 mL of methanol, so as to provide 9.8 g of pale yellow powder of 4,4''''-bis{(biphenyl-4-yl)phenylamino}-(1,1':4',1'':4'',1''':4''',1''''-quinquephenyl) (Compound 10-13) (yield: 66%).

The structure of the obtained pale yellow powder was identified by NMR.

¹H-NMR (CDCl₃) detected 48 hydrogen signals as follows.

δ (ppm)=7.66-7.80 (12H), 7.50-7.64 (12H), 7.42-7.50 (4H), 7.28-7.38 (6H), 7.20-7.26 (12H), 7.08 (2H)

[Chemical Formula 966]

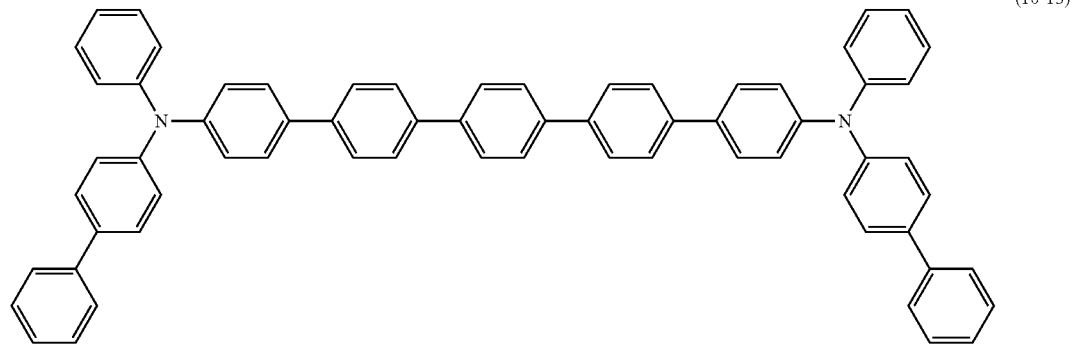

(10-13)

Example 53

Synthesis of 4,4'''-bis{(biphenyl-4-yl)phenylamino}-(1,1':3',1'':3'',1'''-quaterphenyl) (Compound 10-11)

The reaction was carried out under the same conditions as in Example 51 except that 3,3'-dibromobiphenyl was used instead of 4,4'-diiodobiphenyl to provide 16.2 g of pale yellow powder of 4,4'''-bis{(biphenyl-4-yl)phenylamino}-(1,1':3',1'':3'',1'''-quaterphenyl) (Compound 10-11) (yield: 91%).

The structure of the obtained pale yellow powder was identified by NMR.

¹H-NMR (CDCl₃) detected 44 hydrogen signals as follows.

δ (ppm)=7.87 (2H), 7.48-7.66 (18H), 7.39-7.48 (4H), 7.29-7.39 (6H), 7.18-7.26 (12H), 7.08 (2H)

[Chemical Formula 967]

Example 54

Synthesis of 4,4''''-bis{(biphenyl-4-yl)phenylamino}-(1,1':3',1'':2'',1''':3''',1''''-quinquephenyl) (Compound 10-15)

The reaction was carried out under the same conditions as in Example 51 except that 3,3''-dibromo(1,1':2',1''-terphenyl) was used instead of 4,4'-diiodobiphenyl to provide 17.0 g of pale yellow powder of 4,4''''-bis{(biphenyl-4-yl)phenylamino}-(1,1':3',1'':2'',1''':3''',1''''-quinquephenyl) (Compound 10-15) (yield: 92%).

The structure of the obtained pale yellow powder was identified by NMR.

¹H-NMR (CDCl₃) detected 48 hydrogen signals as follows.

δ (ppm)=7.00-7.62 (48H)

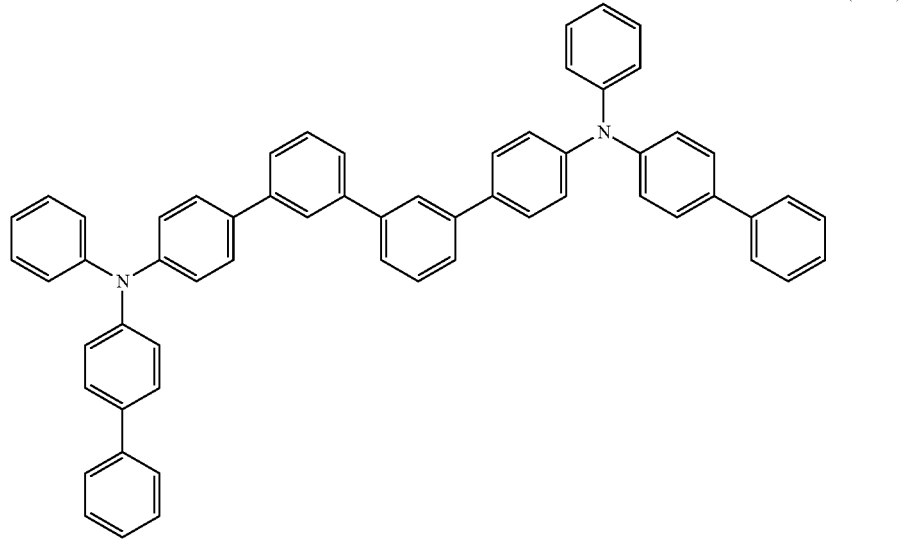

(10-11)

[Chemical Formula 968]

(10-15)

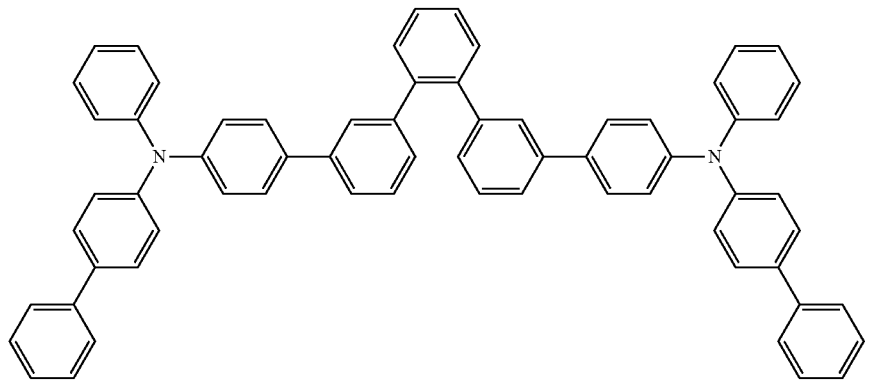

Example 55

Synthesis of 4,4''''-bis{(biphenyl-4-yl)phenylamino}-(1,1':3',1'':3'',1''':3''',1''''-quinquephenyl) (Compound 10-17)

The reaction was carried out under the same conditions as in Example 51 except that 3,3''-dibromo(1,1':3',1''-terphenyl) was used instead of 4,4'-diiodobiphenyl to provide 10.5 g of pale yellow powder of 4,4''''-bis{(biphenyl-4-yl)phenylamino}-(1,1':3',1'':3'',1''':3''',1''''-quinquephenyl) (Compound 10-17) (yield: 57%).

The structure of the obtained pale yellow powder was identified by NMR.

$^1$H-NMR (CDCl$_3$) detected 48 hydrogen signals as follows.

δ (ppm)=7.93 (1H), 7.87 (2H), 7.40-7.72 (24H), 7.16-7.38 (18H), 7.09 (3H)

[Chemical Formula 970]

(10-21)

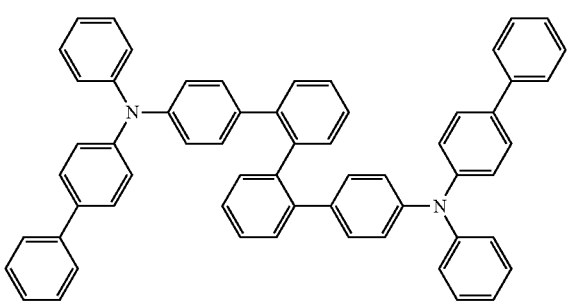

[Chemical Formula 969]

(10-17)

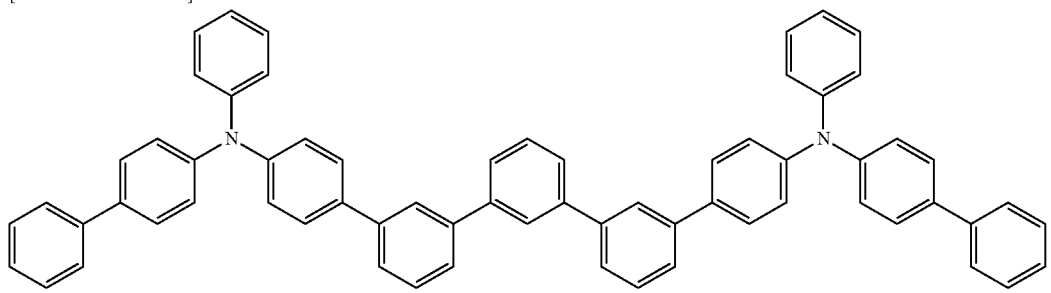

Example 56

Synthesis of 4,4'''-bis{(biphenyl-4-yl)phenylamino}-(1,1':2',1'':2'',1'''-quaterphenyl) (Compound 10-21)

The reaction was carried out under the same conditions as in Example 51 except that 2,2'-dibromobiphenyl was used instead of 4,4'-diiodobiphenyl to provide 9.0 g of pale yellow powder of 4,4'''-bis{(biphenyl-4-yl)phenylamino}-(1,1':2',1'':2'',1'''-quaterphenyl) (Compound 10-21) (yield: 83%).

The structure of the obtained pale yellow powder was identified by NMR.

$^1$H-NMR (CDCl$_3$) detected 44 hydrogen signals as follows.

δ (ppm)=7.45-7.54 (6H), 7.23-7.45 (16H), 7.13-7.22 (4H), 7.05-7.13 (8H), 6.94 (2H), 6.82 (4H), 6.62 (4H)

Example 57

Synthesis of 4,4'''-bis{(naphthalen-1-yl)phenylamino}-(1,1':3',1'':3'',1'''-quaterphenyl) (Compound 10-22)

The reaction was carried out under the same conditions as in Example 51 except that 3,3'-dibromobiphenyl was used instead of 4,4'-diiodobiphenyl, and N-phenyl-N-{4-(4,4,5,5-tetramethyl-1,3,2-dioxaborolan-2-yl) phenyl}-(naphthalen-1-yl)amine was used instead of N-phenyl-N-{4-(4,4,5,5-tetramethyl-1,3,2-dioxaborolan-2-yl) phenyl}-(1,1'-biphenyl-4-yl)amine to provide 4.00 g of pale yellow powder of 4,4'''-bis{(naphthalen-1-yl)phenylamino}-(1,1': 3',1'':3'',1'''-quaterphenyl) (Compound 10-22) (yield: 26%).

The structure of the obtained pale yellow powder was identified by NMR.

¹H-NMR (CDCl₃) detected 40 hydrogen signals as follows.

δ (ppm)=7.99 (2H), 7.92 (2H), 7.78-7.85 (4H), 7.35-7.61 (18H), 7.19-7.28 (4H), 7.06-7.15 (8H), 6.98 (2H)

[Chemical Formula 971]

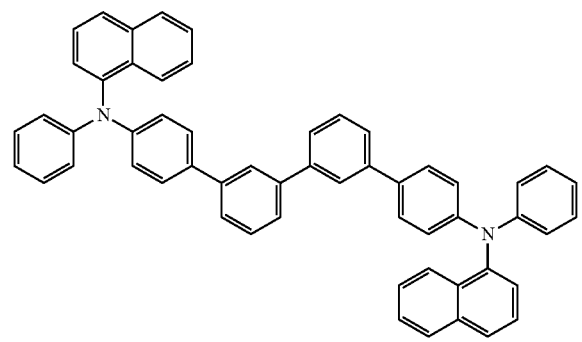

(10-22)

Example 58

Synthesis of 4,4''''-bis{(biphenyl-4-yl)phenylamino}-(1,1':4',1'':2'',1''':4''',1''''-quinquephenyl) (Compound 10-23)

The reaction was carried out under the same conditions as in Example 51 except that 4,4''-dibromo(1,1':2',1''-terphenyl) was used instead of 4,4'-diiodobiphenyl to provide 13.8 g of pale yellow powder of 4,4''''-bis{(biphenyl-4-yl)phenylamino}-(1,1':4',1'':2'',1''':4''',1''''-quinquephenyl) (Compound 10-23) (yield: 62%).

The structure of the obtained pale yellow powder was identified by NMR.

¹H-NMR (CDCl₃) detected 48 hydrogen signals as follows.

δ (ppm)=7.60 (4H), 7.03-7.56 (44H)

[Chemical Formula 972]

Example 59

Synthesis of 4,4''''-bis{(biphenyl-4-yl)phenylamino}-(1,1':2',1'':3'',1''':2''',1''''-quinquephenyl) (Compound 10-24)

The reaction was carried out under the same conditions as in Example 51 except that 2,2''-dibromo(1,1':3',1''-terphenyl) was used instead of 4,4'-diiodobiphenyl to provide 9.7 g of pale yellow powder of 4,4''''-bis{(biphenyl-4-yl)phenylamino}-(1,1':2',1'':3'',1''':2''',1''''-quinquephenyl) (Compound 10-24) (yield: 69%).

The structure of the obtained pale yellow powder was identified by NMR.

¹H-NMR (CDCl₃) detected 48 hydrogen signals as follows.

δ (ppm)=7.30-7.56 (20H), 6.91-7.24 (28H)

[Chemical Formula 973]

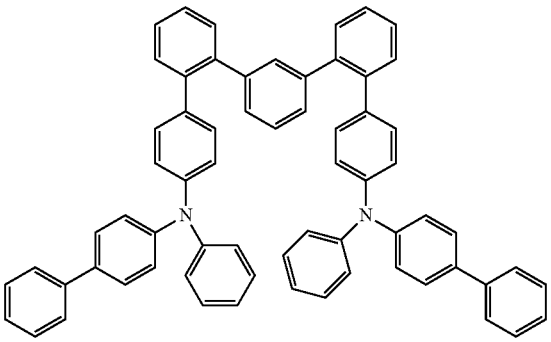

(10-24)

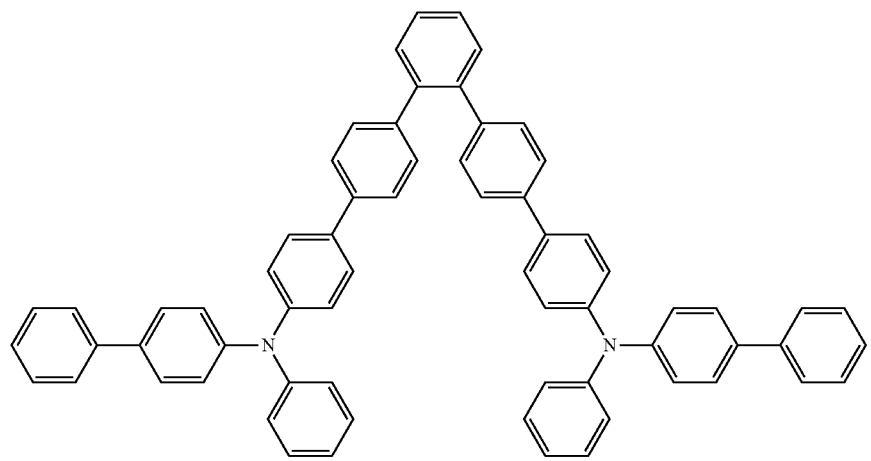

(10-23)

Example 60

Synthesis of 4,4''''-bis{(biphenyl-4-yl)phenylamino}-(1,1':4',1":3",1''':4''',1''''-quinquephenyl) (Compound 10-25)

The reaction was carried out under the same conditions as in Example 51 except that 4,4''-dibromo(1,1':3',1''-terphenyl) was used instead of 4,4'-diiodobiphenyl to provide 16.5 g of pale yellow powder of 4,4''''-bis{(biphenyl-4-yl)phenylamino}-(1,1':4',1":3",1''':4''',1''''-quinquephenyl) (Compound 10-25) (yield: 74%).

The structure of the obtained pale yellow powder was identified by NMR.

$^1$H-NMR (CDCl$_3$) detected 48 hydrogen signals as follows.

δ (ppm)=7.93 (1H), 7.06-7.80 (47H).

[Chemical Formula 974]

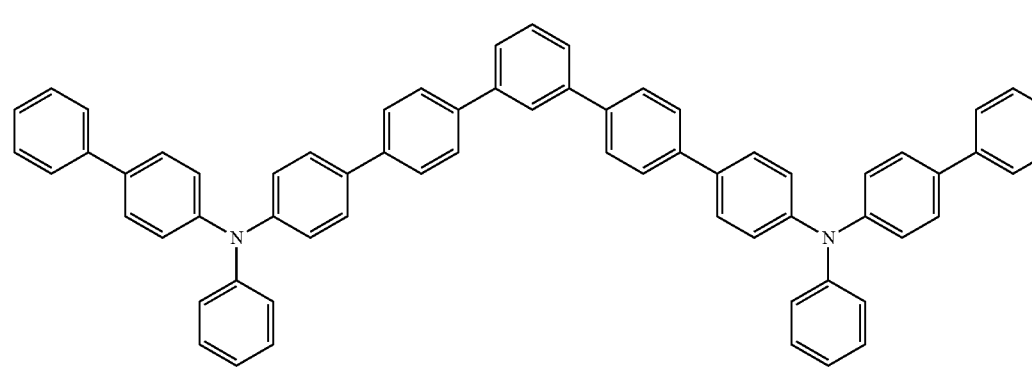

(10-25)

[Chemical Formula 975]

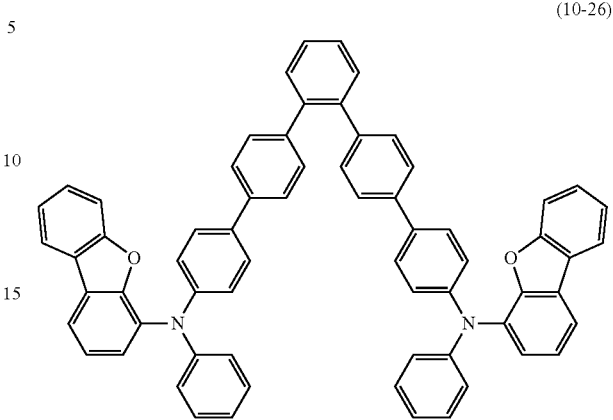

(10-26)

Example 61

Synthesis of 4,4''''-bis{(dibenzofuran-1-yl)phenylamino}-(1,1':4',1":2",1''':4''',1''''-quinquephenyl) (Compound 10-26)

The reaction was carried out under the same conditions as in Example 51 except that N-phenyl-N-{4-(4,4,5,5-tetramethyl-1,3,2-dioxaborolan-2-yl) phenyl}-(dibenzofuran-1-yl)amine was used instead of N-phenyl-N-{4-(4,4,5,5-tetramethyl-1,3,2-dioxaborolan-2-yl) phenyl}-(1,1'-biphenyl-4-yl)amine to provide 14.0 g of pale yellow powder of 4,4''''-bis{(dibenzofuran-1-yl)phenylamino}-(1,1':4',1":2",1''':4''', 1''''-quinquephenyl) (Compound 10-26) (yield: 61%).

The structure of the obtained pale yellow powder was identified by NMR.

$^1$H-NMR (CDCl$_3$) detected 44 hydrogen signals as follows.

δ (ppm)=7.97 (2H), 7.79 (2H), 7.02-7.55 (40H)

Example 62

Synthesis of 4,4''''-bis{(biphenyl-4-yl)phenylamino}-(1,1':2',1":2",1''':2''',1''''-quinquephenyl) (Compound 10-27)

The reaction was carried out under the same conditions as in Example 51 except that 2,2''-dibromo(1,1':2',1''-terphenyl) was used instead of 4,4'-diiodobiphenyl to provide 8.5 g of pale yellow powder of 4,4''''-bis{(biphenyl-4-yl)phenylamino}-(1,1':2',1":2",1''':2''',1''''-quinquephenyl) (Compound 10-27) (yield: 61%).

The structure of the obtained pale yellow powder was identified by NMR.

$^1$H-NMR (CDCl$_3$) detected 48 hydrogen signals as follows.

δ (ppm)=7.62 (4H), 6.78-7.57 (36H), 6.53 (4H), 6.46 (2H), 6.38 (2H)

[Chemical Formula 976]

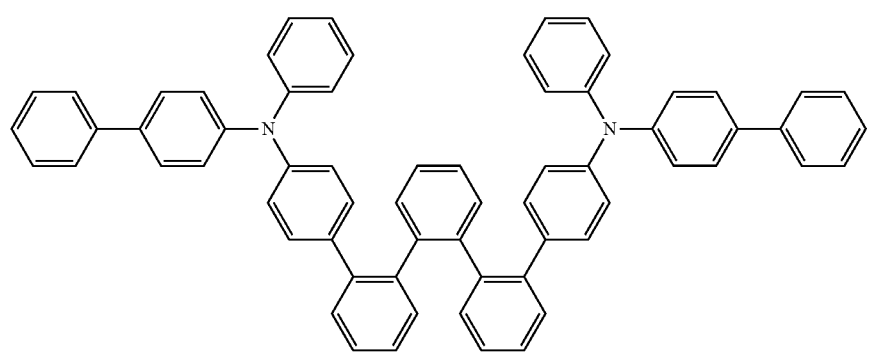

(10-27)

Example 63

Synthesis of 4,4'''-bis{(biphenyl-4-yl)-d$_5$-phenylamino}-(1,1':3',1'':3'',1'''-quaterphenyl) (Compound 10-28)

The reaction was carried out under the same conditions as in Example 51 except that 3,3'-dibromobiphenyl was used instead of 4,4'-diiodobiphenyl, and N-(phenyl-d$_5$)-N-{4-(4,4,5,5-tetramethyl-1,3,2-dioxaborolan-2-yl)phenyl}-(1,1'-biphenyl-4-yl)amine was used instead of N-phenyl-N-{4-(4,4,5,5-tetramethyl-1,3,2-dioxaborolan-2-yl) phenyl}-(1,1'-biphenyl-4-yl)amine to provide 8.7 g of pale yellow powder of 4,4'''-bis{(biphenyl-4-yl)-d$_5$-phenylamino}-(1,1':3',1'':3'',1'''-quaterphenyl) (Compound 10-28) (yield: 68%).

The structure of the obtained pale yellow powder was identified by NMR.

$^1$H-NMR (CDCl$_3$) detected 34 hydrogen signals as follows.

δ (ppm)=7.87 (2H), 7.40-7.66 (20H), 7.30-7.38 (4H), 7.19-7.26 (8H)

Example 64

Synthesis of 4,4'''-bis{(biphenyl-4-yl)phenylamino}-(1,1':3',1'':4'',1'''-quaterphenyl) (Compound 10-38)

The reaction was carried out under the same conditions as in Example 51 except that 3,4'-dibromobiphenyl was used instead of 4,4'-diiodobiphenyl to provide 14.0 g of pale yellow powder of 4,4'''-bis{(biphenyl-4-yl)phenylamino}-(1,1':3',1'':4'',1'''-quaterphenyl) (Compound 10-38) (yield: 84%).

The structure of the obtained pale yellow powder was identified by NMR.

$^1$H-NMR (CDCl$_3$) detected 44 hydrogen signals as follows.

δ (ppm)=7.00-8.00 (44H)

[Chemical Formula 977]

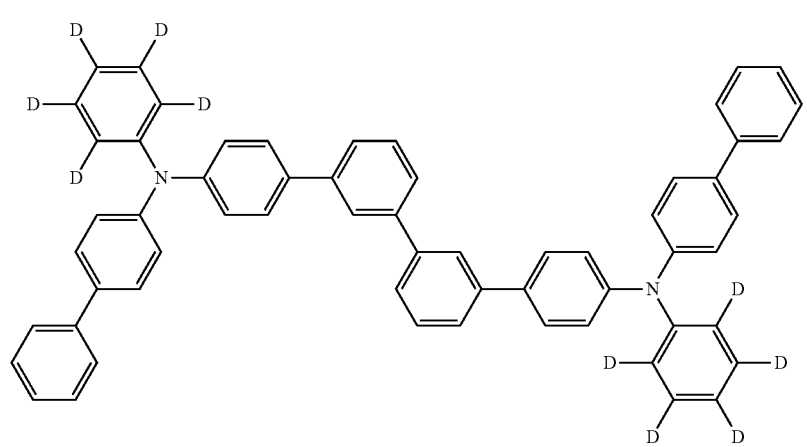

(10-28)

[Chemical Formula 978]

(10-38)

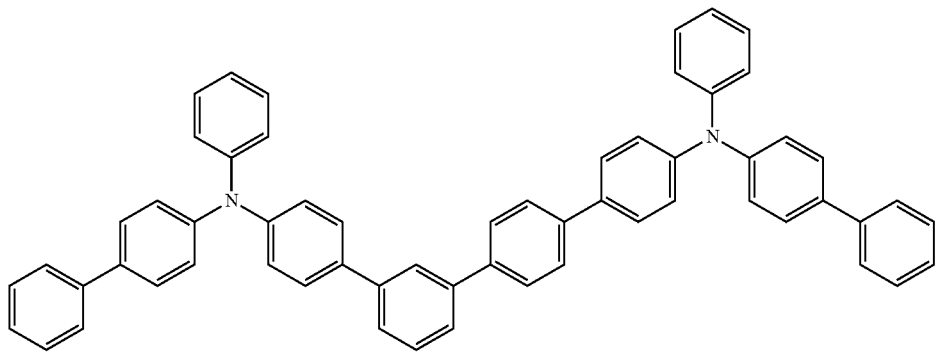

Example 65

The melting points and the glass transition points of the arylamine compounds of the general formula (10) were measured using a high-sensitive differential scanning calorimeter (DSC3100SA, produced by Bruker AXS GmbH).

|  | Melting Point | Glass transition point |
|---|---|---|
| Compound of Example 51 | not observed | 119° C. |
| Compound of Example 52 | not observed | 124° C. |
| Compound of Example 53 | not observed | 114° C. |
| Compound of Example 54 | not observed | 115° C. |
| Compound of Example 55 | not observed | 118° C. |
| Compound of Example 56 | not observed | 111° C. |
| Compound of Example 57 | not observed | 112° C. |
| Compound of Example 58 | not observed | 129° C. |
| Compound of Example 59 | 256° C. | 113° C. |
| Compound of Example 60 | not observed | 126° C. |
| Compound of Example 61 | not observed | 131° C. |
| Compound of Example 62 | not observed | 121° C. |
| Compound of Example 63 | not observed | 113° C. |
| Compound of Example 64 | not observed | 117° C. |

The arylamine compounds of the general formula (10) have glass transition points of 100° C. or higher, which shows that the compounds have a stable thin-film state.

Example 66

A 100 nm-thick vapor-deposited film was fabricated on an ITO substrate using the arylamine compounds of the general formula (10), and the work function thereof was measured using an ionization potential measuring device (PYS-202 produced by Sumitomo Heavy Industries, Ltd.).

|  | Work function |
|---|---|
| Compound of Example 51 | 5.68 eV |
| Compound of Example 52 | 5.69 eV |
| Compound of Example 53 | 5.73 eV |
| Compound of Example 54 | 5.74 eV |
| Compound of Example 55 | 5.77 eV |
| Compound of Example 56 | 5.73 eV |
| Compound of Example 57 | 5.81 eV |
| Compound of Example 58 | 5.71 eV |
| Compound of Example 59 | 5.74 eV |
| Compound of Example 60 | 5.72 eV |
| Compound of Example 61 | 5.74 eV |
| Compound of Example 62 | 5.73 eV |

-continued

|  | Work function |
|---|---|
| Compound of Example 63 | 5.76 eV |
| Compound of Example 64 | 5.74 eV |

It is understood that the arylamine compounds of the general formula (10) have favorable energy levels, as compared to a work function of 5.4 eV of the common hole transport materials, such as NPD and TPD, and thus have a favorable hole transport capability.

Example 67

The organic EL device, as shown in FIG. 1, was fabricated by vapor-depositing a hole injection layer 3, a first hole transport layer 4, a second hole transport layer 5, a light emitting layer 6, an electron transport layer 7, an electron injection layer 8, and a cathode (aluminum. electrode) 9 in this order on a glass substrate 1 on which an ITO electrode was formed as a transparent anode 2 beforehand.

Specifically, the glass substrate 1 having ITO having a film thickness of 150 nm formed thereon was subjected to ultrasonic washing in isopropyl alcohol for 20 minutes and then dried for 10 minutes on a hot plate heated to 200° C. Thereafter, after performing an UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, an electron acceptor (Acceptor-1) of the structural formula below and Compound (1-1) of the structural formula below were formed in a film thickness of 30 nm by dual vapor deposition at a vapor deposition rate ratio of Acceptor-1/Compound (1-1)=3/97. As the first hole transport layer 4 on the hole injection layer 3, Compound (1-1) of the structural formula below was formed in a film thickness of 35 nm. As the second hole transport layer 5 on the first hole transport layer 4, Compound (5-4) of Example 4 was formed in a film thickness of 5 nm. As the light emitting layer 6 on the second hole transport layer 5, Compound EMD-1 of the structural formula below and Compound EMH-1 of the structural formula below were formed in a film thickness of 20 nm by dual vapor deposition at a vapor deposition rate ratio of EMD-1/EMH-1=3/97. As the electron transport layer 7 on the light emitting layer 6, Compound (6b-1) having an anthracene ring structure of the structural formula below and Compound ETM-1 of the structural formula below were formed in a film thickness of 30 nm by dual vapor deposition at a vapor deposition rate ratio of Compound (6b-1)/ETM-1=50/50. As the electron injection layer 8 on the electron transport layer 7, lithium fluoride was formed in a film thickness of 1 nm. Finally, aluminum was vapor-deposited in a thickness of 100 nm to form the cathode 9. The characteristics of the thus fabricated organic EL device were measured in the atmosphere at an ordinary temperature. Table 1 summarizes the results of the measurement of emission characteristics performed by applying a direct current voltage to the fabricated organic EL device.

[Chemical Formula 979]

(Acceptor-1)

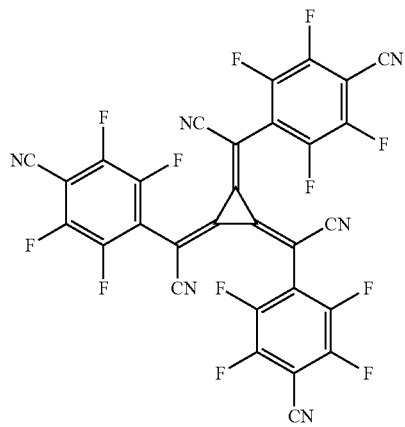

[Chemical Formula 980]

(1-1)

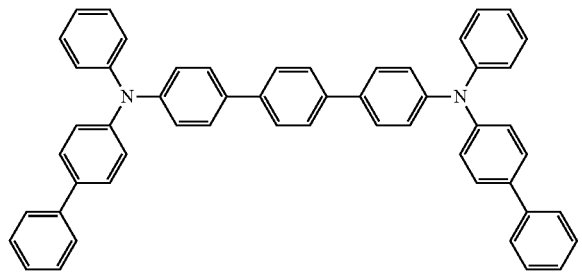

[Chemical Formula 981]

(5-4)

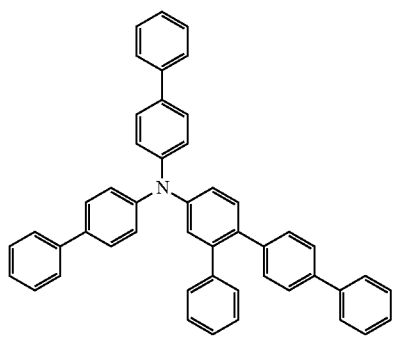

[Chemical Formula 982]

(EMD-1)

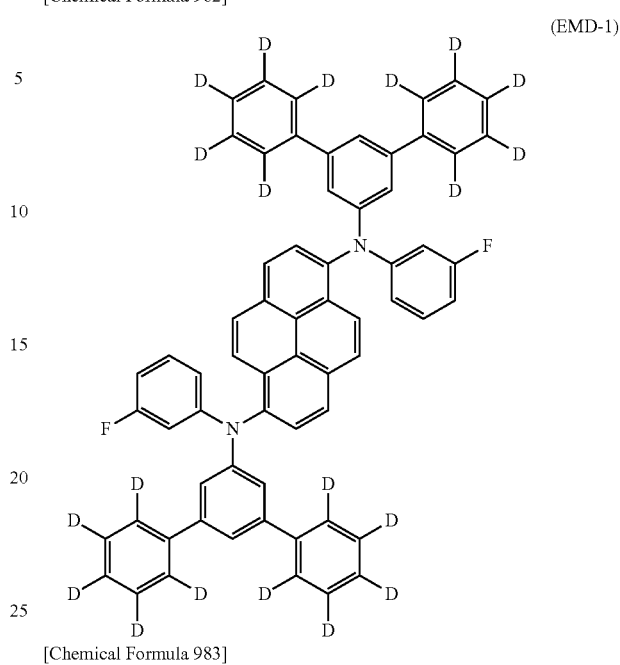

[Chemical Formula 983]

(EMH-1)

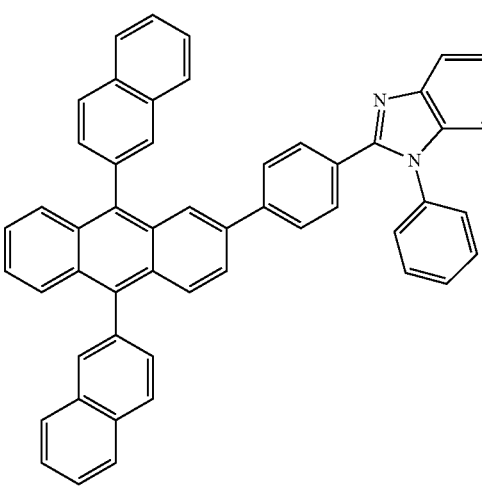

[Chemical Formula 984]

(6b-1)

-continued

[Chemical Formula 985]

(ETM-1)

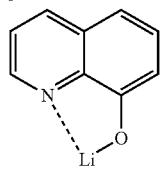

Example 68

An organic EL device was fabricated under the same conditions used in Example 67, except that Compound (6c-28) having an anthracene ring structure of the structural formula below was used as the material of the electron transport layer 7 instead of Compound (6b-1) having an anthracene ring structure of the above structural formula, and Compound (6c-28) and Compound ETM-1 of the above structural formula were formed in a film thickness of 30 nm by dual vapor deposition at a vapor deposition rate ratio of Compound (6c-28)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

[Chemical Formula 986]

(6c-28)

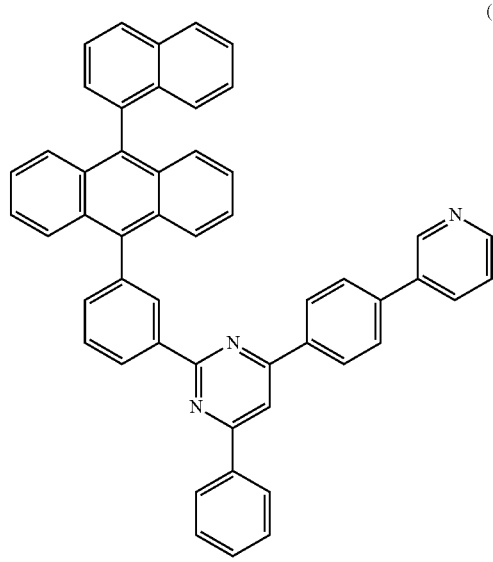

Example 69

An organic EL device was fabricated under the same conditions used in Example 67, except that Compound (7-126) having a pyrimidine ring structure of the structural formula below was used as the material of the electron transport layer 7 instead of Compound (6b-1) having an anthracene ring structure of the above structural formula, and Compound (7-126) and Compound ETM-1 of the above structural formula were formed in a film thickness of 30 nm by dual vapor deposition at a vapor deposition rate ratio of Compound (7-126)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

[Chemical Formula 987]

(7-126)

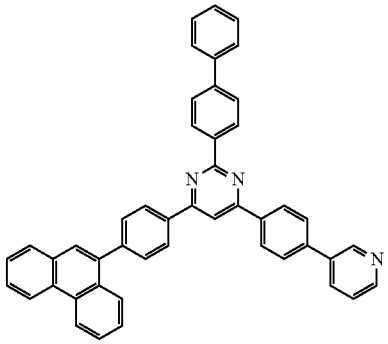

Example 70

An organic EL device was fabricated under the same conditions used in Example 67, except that Compound (9-112) having a benzotriazole ring structure of the structural formula below was used as the material of the electron transport layer 7 instead of Compound (6b-1) having an anthracene ring structure of the above structural formula, and Compound (9-112) and Compound ETM-1 of the above structural formula were formed in a film thickness of 30 nm by dual vapor deposition at a vapor deposition rate ratio of Compound (9-112)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

[Chemical Formula 988]

(9-112)

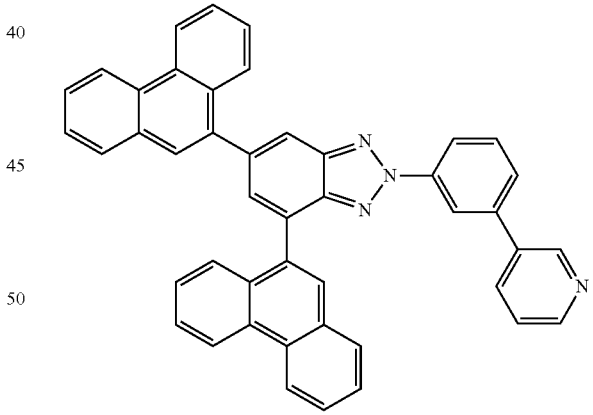

Example 71

An organic EL device was fabricated under the same conditions used in Example 67, except that Compound (10-11) of Example 53 was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

[Chemical Formula 989]

(10-11)

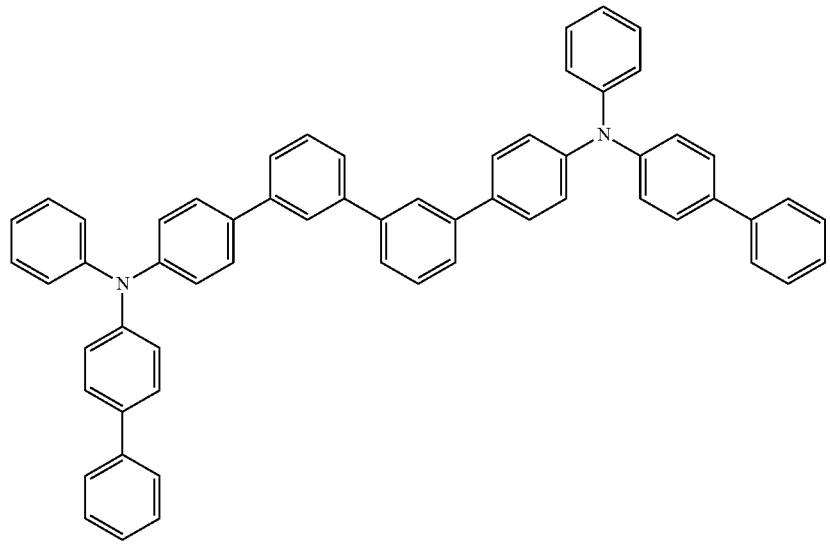

Example 72

An organic EL device was fabricated under the same conditions used in Example 67, except that Compound (10-23) of Example 58 was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 73

An organic EL device was fabricated under the same conditions used in Example 67, except that Compound (10-38) of Example 64 was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

[Chemical Formula 990]

(10-23)

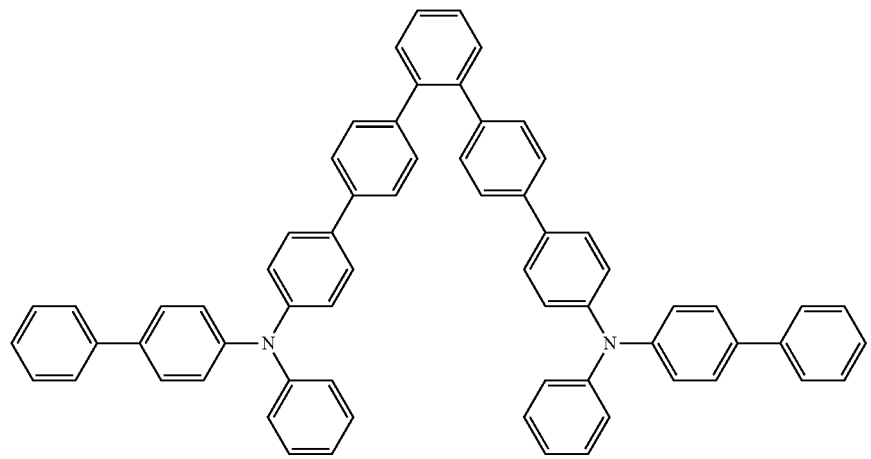

[Chemical Formula 991]

(10-38)

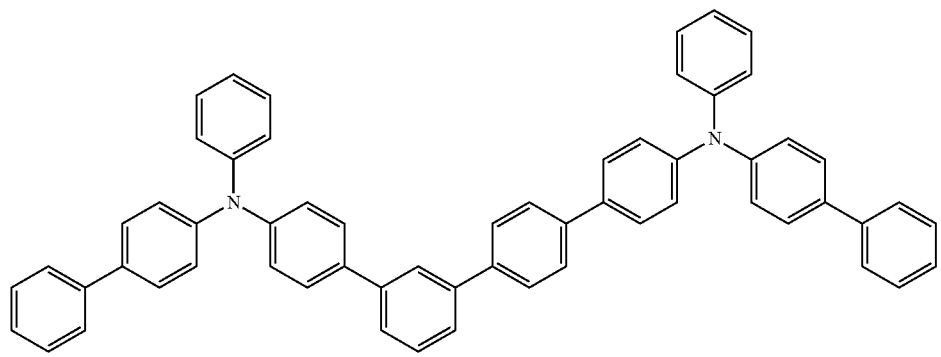

Example 74

An organic EL device was fabricated under the same conditions used in Example 71, except that Compound (6c-28) having an anthracene ring structure of the above structural formula was used as the material of the electron transport layer 7 instead of Compound (6b-1) having an anthracene ring structure of the above structural formula, and Compound (6c-28) and Compound ETM-1 of the above structural formula were formed in a film thickness of 30 nm by dual vapor deposition at a vapor deposition rate ratio of Compound (6c-28)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 75

An organic EL device was fabricated under the same conditions used in Example 72, except that Compound (6c-28) having an anthracene ring structure of the above structural formula was used as the material of the electron transport layer 7 instead of Compound (6b-1) having an anthracene ring structure of the above structural formula, and Compound (6c-28) and Compound ETM-1 of the above structural formula were formed in a film thickness of 30 nm by dual vapor deposition at a vapor deposition rate ratio of Compound (6c-28)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 76

An organic EL device was fabricated under the same conditions used in Example 73, except that Compound (6c-28) having an anthracene ring structure of the above structural formula was used as the material of the electron transport layer 7 instead of Compound (6b-1) having an anthracene ring structure of the above structural formula, and Compound (6c-28) and Compound ETM-1 of the above structural formula were formed in a film thickness of 30 nm by dual vapor deposition at a vapor deposition rate ratio of Compound (6c-28)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 77

An organic EL device was fabricated under the same conditions used in Example 71, except that Compound (7-126) having a pyrimidine ring structure of the above structural formula was used as the material of the electron transport layer 7 instead of Compound (6b-1) having an anthracene ring structure of the above structural formula, and Compound (7-126) and Compound ETM-1 of the above structural formula were formed in a film thickness of 30 nm by dual vapor deposition at a vapor deposition rate ratio of Compound (7-126)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 78

An organic EL device was fabricated under the same conditions used in Example 72, except that Compound (7-126) having a pyrimidine ring structure of the above structural formula was used as the material of the electron transport layer 7 instead of Compound (6b-1) having an anthracene ring structure of the above structural formula, and Compound (7-126) and Compound ETM-1 of the above structural formula were formed in a film thickness of 30 nm by dual vapor deposition at a vapor deposition rate ratio of Compound (7-126)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 79

An organic EL device was fabricated under the same conditions used in Example 73, except that Compound (7-126) having a pyrimidine ring structure of the above structural formula was used as the material of the electron transport layer 7 instead of Compound (6b-1) having an anthracene ring structure of the above structural formula, and Compound (7-126) and Compound ETM-1 of the above structural formula were formed in a film thickness of 30 nm by dual vapor deposition at a vapor deposition rate ratio of Compound (7-126)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 80

An organic EL device was fabricated under the same conditions used in Example 71, except that Compound (9-112) having a benzotriazole ring structure of the above structural formula was used as the material of the electron transport layer 7 instead of Compound (6b-1) having an anthracene ring structure of the above structural formula, and Compound (9-112) and Compound ETM-1 of the above structural formula were formed in a film thickness of 30 nm by dual vapor deposition at a vapor deposition rate ratio of Compound (9-112)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 81

An organic EL device was fabricated under the same conditions used in Example 72, except that Compound (9-112) having a benzotriazole ring structure of the above structural formula was used as the material of the electron transport layer 7 instead of Compound (6b-1) having an anthracene ring structure of the above structural formula, and Compound (9-112) and Compound ETM-1 of the above structural formula were formed in a film thickness of 30 nm by dual vapor deposition at a vapor deposition rate ratio of Compound (9-112)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Example 82

An organic EL device was fabricated under the same conditions used in Example 73, except that Compound (9-112) having a benzotriazole ring structure of the above structural formula was used as the material of the electron transport layer 7 instead of Compound (6b-1) having an anthracene ring structure of the above structural formula, and Compound (9-112) and Compound ETM-1 of the above structural formula were formed in a film thickness of 30 nm by dual vapor deposition at a vapor deposition rate ratio of Compound (9-112)/ETM-1=50/50. The characteristics of the thus fabricated organic EL device were measured in the atmosphere at an ordinary temperature. Table 1 summarizes the results of the measurement of emission characteristics performed by applying a direct current voltage to the fabricated organic EL device.

Comparative Example 1

For comparison, an organic EL device was fabricated under the same conditions used in Example 67, except that Compound (1-1) of the above structural formula was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

Comparative Example 2

For comparison, an organic EL device was fabricated under the same conditions used in Example 68, except that Compound (1-1) of the above structural formula was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

Comparative Example 3

For comparison, an organic EL device was fabricated under the same conditions used in Example 69, except that Compound (1-1) of the above structural formula was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

Comparative Example 4

For comparison, an organic EL device was fabricated under the same conditions used in Example 70, except that Compound (1-1) of the above structural formula was used as the material of the second hole transport layer 5 instead of Compound (5-4) of Example 4, and formed in a film thickness of 5 nm. The characteristics of the thus fabricated organic EL device were measured in the atmosphere at an ordinary temperature. Table 1 summarizes the results of the measurement of emission characteristics performed by applying a direct current voltage to the fabricated organic EL device.

Table 1 summarizes the results of the measurement of device lifetime performed with organic EL devices fabricated in Examples 67 to 82 and Comparative Examples 1 to 4. The device lifetime was measured as the time elapsed until the emission luminance of 2,000 cd/m² (initial luminance) at the start of emission was attenuated to 1,900 cd/m² (corresponding to attenuation to 95% with respect to the initial luminance as 100%, 95% attenuation) when carrying out constant current driving.

TABLE 1

| | Hole injection layer | First hole transport layer | Second hole transport layer | Light emitting layer | Electron transport layer | Voltage (V) (@ 10 mA/cm$^2$) | Luminance (cd/m$^2$) (@ 10 mA/cm$^2$) | Luminous efficiency (cd/A) (@ 10 mA/cm$^2$) | Power efficiency (lm/W) (@ 10 mA/cm$^2$) | Device lifetime (Attenuation to 95%) |
|---|---|---|---|---|---|---|---|---|---|---|
| Example 67 | Compound 1-1/ Acceptor-1 | Compound 1-1 | Compound 5-4 | EMD-1/EMH-1 | Compound 6b-1/ ETM-1 | 3.91 | 674 | 6.73 | 5.41 | 114 hours |
| Example 68 | Compound 1-1/ Acceptor-1 | Compound 1-1 | Compound 5-4 | EMD-1/EMH-1 | Compound 6c-28/ ETM-1 | 3.85 | 779 | 7.79 | 6.36 | 196 hours |
| Example 69 | Compound 1-1/ Acceptor-1 | Compound 1-1 | Compound 5-4 | EMD-1/EMH-1 | Compound 7-126/ ETM-1 | 3.74 | 781 | 7.81 | 6.57 | 108 hours |
| Example 70 | Compound 1-1/ Acceptor-1 | Compound 1-1 | Compound 5-4 | EMD-1/EMH-1 | Compound 9-112/ ETM-1 | 3.92 | 762 | 7.64 | 6.12 | 126 hours |
| Example 71 | Compound 1-1/ Acceptor-1 | Compound 1-1 | Compound 10-11 | EMD-1/EMH-1 | Compound 6b-1/ ETM-1 | 3.88 | 701 | 7.00 | 5.67 | 202 hours |
| Example 72 | Compound 1-1/ Acceptor-1 | Compound 1-1 | Compound 10-23 | EMD-1/EMH-1 | Compound 6b-1/ ETM-1 | 3.94 | 690 | 6.88 | 5.49 | 184 hours |
| Example 73 | Compound 1-1/ Acceptor-1 | Compound 1-1 | Compound 10-38 | EMD-1/EMH-1 | Compound 6b-1/ ETM-1 | 3.90 | 675 | 6.73 | 5.42 | 215 hours |
| Example 74 | Compound 1-1/ Acceptor-1 | Compound 1-1 | Compound 10-11 | EMD-1/EMH-1 | Compound 6c-28/ ETM-1 | 3.84 | 780 | 7.78 | 6.37 | 177 hours |
| Example 75 | Compound 1-1/ Acceptor-1 | Compound 1-1 | Compound 10-23 | EMD-1/EMH-1 | Compound 6c-28/ ETM-1 | 3.89 | 785 | 7.81 | 6.34 | 143 hours |
| Example 76 | Compound 1-1/ Acceptor-1 | Compound 1-1 | Compound 10-38 | EMD-1/EMH-1 | Compound 6c-28/ ETM-1 | 3.83 | 760 | 7.48 | 6.14 | 187 hours |
| Example 77 | Compound 1-1/ Acceptor-1 | Compound 1-1 | Compound 10-11 | EMD-1/EMH-1 | Compound 7-126/ ETM-1 | 3.82 | 782 | 7.80 | 6.42 | 195 hours |
| Example 78 | Compound 1-1/ Acceptor-1 | Compound 1-1 | Compound 10-23 | EMD-1/EMH-1 | Compound 7-126/ ETM-1 | 3.87 | 805 | 8.03 | 6.52 | 156 hours |
| Example 79 | Compound 1-1/ Acceptor-1 | Compound 1-1 | Compound 10-38 | EMD-1/EMH-1 | Compound 7-126/ ETM-1 | 3.80 | 775 | 7.75 | 6.41 | 184 hours |
| Example 80 | Compound 1-1/ Acceptor-1 | Compound 1-1 | Compound 10-11 | EMD-1/EMH-1 | Compound 9-112/ ETM-1 | 3.92 | 761 | 7.59 | 6.06 | 138 hours |
| Example 81 | Compound 1-1/ Acceptor-1 | Compound 1-1 | Compound 10-23 | EMD-1/EMH-1 | Compound 9-112/ ETM-1 | 3.94 | 750 | 7.49 | 5.97 | 143 hours |
| Example 82 | Compound 1-1/ Acceptor-1 | Compound 1-1 | Compound 10-38 | EMD-1/EMH-1 | Compound 9-112/ ETM-1 | 3.92 | 732 | 7.30 | 5.58 | 156 hours |
| Comparative Example 1 | Compound 1-1/ Acceptor-1 | Compound 1-1 | Compound 1-1 | EMD-1/EMH-1 | Compound 6b-1/ ETM-1 | 3.80 | 610 | 6.10 | 5.04 | 60 hours |
| Comparative Example 2 | Compound 1-1/ Acceptor-1 | Compound 1-1 | Compound 1-1 | EMD-1/EMH-1 | Compound 6c-28/ ETM-1 | 3.79 | 690 | 6.90 | 5.73 | 54 hours |
| Comparative Example 3 | Compound 1-1/ Acceptor-1 | Compound 1-1 | Compound 1-1 | EMD-1/EMH-1 | Compound 7-126/ ETM-1 | 3.73 | 697 | 6.98 | 5.89 | 71 hours |
| Comparative Example 4 | Compound 1-1/ Acceptor-1 | Compound 1-1 | Compound 1-1 | EMD-1/EMH-1 | Compound 9-112/ ETM-1 | 3.88 | 675 | 6.77 | 5.48 | 45 hours |

As shown in Table 1, in the comparison of Examples 67 and 71 to 73 and Comparative Example 1 having the same combination of materials of the electron transport layer, the luminous efficiency upon passing an electric current with a current density of 10 mA/cm$^2$ was 6.10 cd/A for the organic EL device of Comparative Example 1, whereas was a high efficiency of 6.73 to 7.00 cd/A for the organic EL devices of Examples 67 and 71 to 73. The power efficiency was 5.04 lm/W for the organic EL device of Comparative Example 1, whereas was a high efficiency of 5.41 to 5.67 lm/W for the organic EL devices of Examples 67 and 71 to 73. The device lifetime (95% attenuation) was 60 hours for the organic EL device of Comparative Example 1, whereas was a largely increased lifetime of 114 to 215 hours for the organic EL devices of Examples 67 and 71 to 73.

As shown in Table 1, in the comparison of Examples 68 and 74 to 76 and Comparative Example 2 having the same combination of materials of the electron transport layer, the luminous efficiency upon passing an electric current with a current density of 10 mA/cm$^2$ was 6.90 cd/A for the organic EL device of Comparative Example 2, whereas was a high efficiency of 7.48 to 7.81 cd/A for the organic EL devices of Examples 68 and 74 to 76. The power efficiency was 5.73 lm/W for the organic EL device of Comparative Example 2, whereas was a high efficiency of 6.14 to 6.37 lm/W for the organic EL devices of Examples 68 and 74 to 76. The device lifetime (95% attenuation) was 54 hours for the organic EL device of Comparative Example 2, whereas was a largely increased lifetime of 143 to 196 hours for the organic EL devices of Examples 68 and 74 to 76.

As shown in Table 1, in the comparison of Examples 69 and 77 to 79 and Comparative Example 3 having the same combination of materials of the electron transport layer, the luminous efficiency upon passing an electric current with a current density of 10 mA/cm$^2$ was 6.98 cd/A for the organic EL device of Comparative Example 3, whereas was a high efficiency of 7.75 to 8.03 cd/A for the organic EL devices of Examples 69 and 77 to 79. The power efficiency was 5.89 lm/W for the organic EL device of Comparative Example 3, whereas was a high efficiency of 6.41 to 6.57 lm/W for the organic EL devices of Examples 69 and 77 to 79. The device lifetime (95% attenuation) was 71 hours for the organic EL device of Comparative Example 3, whereas was a largely increased lifetime of 156 to 198 hours for the organic EL devices of Examples 69 and 77 to 79.

As shown in Table 1, in the comparison of Examples 70 and 80 to 82 and Comparative Example 4 having the same combination of materials of the electron transport layer, the luminous efficiency upon passing an electric current with a current density of 10 mA/cm$^2$ was 6.77 cd/A for the organic EL device of Comparative Example 4, whereas was a high efficiency of 7.30 to 7.64 cd/A for the organic EL devices of Examples 70 and 80 to 82. The power efficiency was 5.48 lm/W for the organic EL device of Comparative Example 4, whereas was a high efficiency of 5.85 to 6.12 lm/W for the organic EL devices of Examples 70 and 80 to 82. The device lifetime (95% attenuation) was 45 hours for the organic EL device of Comparative Example 4, whereas was a largely increased lifetime of 126 to 156 hours for the organic EL devices of Examples 70 and 80 to 82.

It has been found that in the organic EL devices of the present invention, for injecting and transporting holes efficiently from the anode, the particular arylamine compound (having the particular structure) doped with an electron acceptor is used as the material of the hole injection layer, the hole transport layer is formed of two layers including the first hole transport layer and the second hole transport layer, and the particular arylamine compounds (having the particular structures) not doped with an electron acceptor are combined for the two layers, and furthermore the compound having an anthracene ring structure having the particular structure, the compound having a pyrimidine ring structure having the particular structure, or the compound having a benzotriazole ring structure having the particular structure is used as the material of the electron transport layer, so as to improve the carrier balance in the organic EL device, thereby achieving an organic EL device having a higher luminous efficiency and a longer lifetime than the conventional organic EL devices.

INDUSTRIAL APPLICABILITY

The organic EL device of the present invention using the particular arylamine compound (having the particular structure) doped with an electron acceptor as the material of the hole injection layer, and having the combination of the particular arylamine compound (having the particular structure) with the compound having an anthracene ring structure having the particular structure, the compound having a pyrimidine ring structure having the particular structure, or the compound having a benzotriazole ring structure having the particular structure has an improved luminous efficiency and an improved durability of the organic EL device, and can be applied, for example, to home electric appliances and illuminations.

DESCRIPTION OF REFERENCE NUMERAL

1 Glass substrate
2 Transparent anode
3 Hole injection layer
4 First hole transport layer
5 Second hole transport layer
6 Light emitting layer
7 Electron transport layer
8 Electron injection layer
9 Cathode

The invention claimed is:
1. An organic electroluminescent device comprising at least an anode, a hole injection layer, a first hole transport layer, a second hole transport layer, a light emitting layer, an electron transport layer, and a cathode, in this order, wherein the hole injection layer contains an arylamine compound of the following general formula (1) and an electron acceptor:

[Chemical Formula 1]

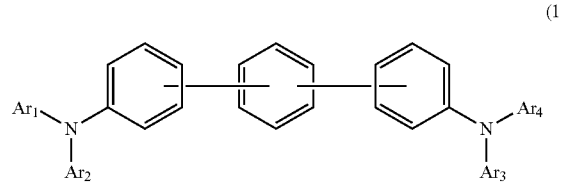

(1)

wherein Ar$_1$ to Ar$_4$ may be the same or different, and represent a substituted or unsubstituted aromatic hydrocarbon group, a substituted or unsubstituted aromatic heterocyclic group, or a substituted or unsubstituted condensed polycyclic aromatic group;
and wherein the electron transport layer has a LUMO level of 2.9 to 3.4 eV.

2. The organic EL device according to claim 1, wherein the electron acceptor is an electron acceptor selected from trisbromophenylamine hexachloroantimony, tetracyanoquinodimethane (TCNQ), 2,3,5,6-tetrafluoro-tetracyano-1,4-benzoquinodimethane (F4TCNQ), and a radialene derivative.

3. The organic EL device according to claim 1, wherein the electron acceptor is a radialene derivative of the following general formula (2):

[Chemical Formula 2]

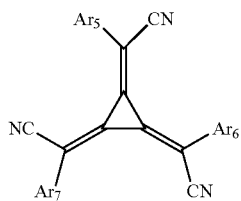

(2)

wherein $Ar_5$ to $Ar_7$ may be the same or different, and represent an aromatic hydrocarbon group, an aromatic heterocyclic group, or a condensed polycyclic aromatic group, having an electron acceptor group as a substituent.

4. The organic EL device according to claim 1, wherein the first hole transport layer or the second hole transport layer contains only a hole transport arylamine compound.

5. The organic EL device according to claim 1, wherein the first hole transport layer and the second hole transport layer each contain only a hole transport arylamine compound.

6. The organic EL device according to claim 4, wherein the first hole transport layer contains an arylamine compound having a structure in which two to six triphenylamine structures are joined within a molecule via a single bond or a divalent group that does not contain a heteroatom.

7. The organic EL device according to claim 6, wherein the arylamine compound having a structure in which two to six triphenylamine structures are joined within a molecule via a single bond or a divalent group that does not contain a heteroatom is an arylamine compound of the following general formula (3):

[Chemical Formula 3]

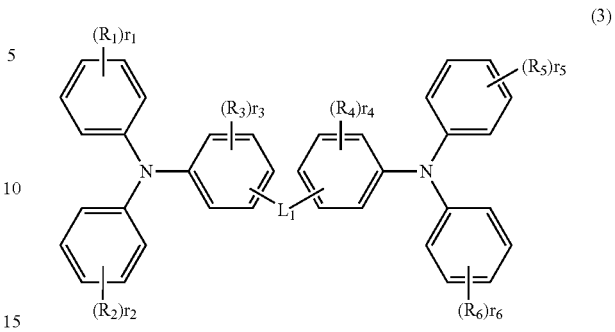

(3)

wherein $R_1$ to $R_6$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_1$ to $r_6$ may be the same or different, $r_1$, $r_2$, $r_5$, and $r_6$ representing an integer of 0 to 5, and $r_3$ and $r_4$ representing an integer of 0 to 4, where when $r_1$, $r_2$, $r_5$, and $r_6$ are an integer of 2 to 5, or when $r_3$ and $r_4$ are an integer of 2 to 4, $R_1$ to $R_6$, a plurality of which bind to the same benzene ring, may be the same or different and may bind to each other via a single bond, substituted or unsubstituted methylene, an oxygen atom, or a sulfur atom to form a ring; and $L_1$ represents a divalent linking group or a single bond.

8. The organic EL device according to claim 6, wherein the arylamine compound having a structure in which two to six triphenylamine structures are joined within a molecule via a single bond or a divalent group that does not contain a heteroatom is an arylamine compound of the following general formula (4):

[Chemical Formula 4]

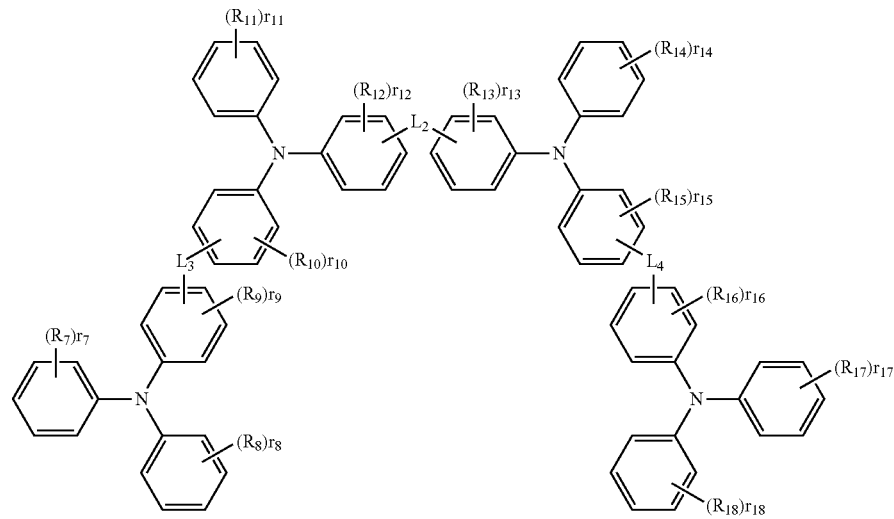

(4)

wherein $R_7$ to $R_{18}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_7$ to $r_{18}$ may be the same or different, $r_7$, $r_8$, $r_{11}$, $r_{14}$, $r_{17}$, and $r_{18}$ representing an integer of 0 to 5, and $r_9$, $r_{10}$, $r_{12}$, $r_{13}$, $r_{15}$, and $r_{16}$ representing an integer of 0 to 4, where when $r_7$, $r_8$, $r_{11}$, $r_{14}$, $r_{17}$, and $r_{18}$ are an integer of 2 to 5, or when $r_9$, $r_{10}$, $r_{12}$, $r_{13}$, $r_{15}$, and $r_{16}$ are an integer of 2 to 4, $R_7$ to $R_{18}$, a plurality of which bind to the same benzene ring, may be the same or different and may bind to each other via a single bond, substituted or unsubstituted methylene, an oxygen atom, or a sulfur atom to form a ring; and $L_2$, $L_3$, and $L_4$ may be the same or different, and represent a divalent linking group or a single bond.

9. The organic EL device according to claim 4, wherein the second hole transport layer contains an arylamine compound of the following general formula (5):

[Chemical Formula 5]

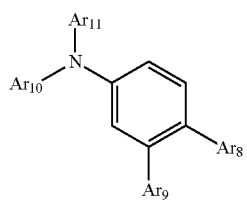

(5)

wherein $Ar_8$ to $Ar_{11}$ may be the same or different, and represent a substituted or unsubstituted aromatic hydrocarbon group, a substituted or unsubstituted aromatic heterocyclic group, or a substituted or unsubstituted condensed polycyclic aromatic group.

10. The organic EL device according to claim 4, wherein the second hole transport layer contains an arylamine compound of the following general formula (10):

[Chemical Formula 6]

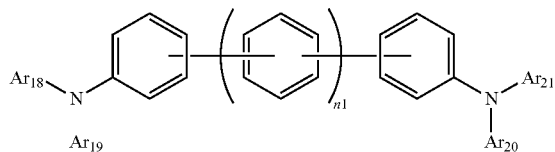

(10)

wherein $Ar_{18}$ to $Ar_{21}$ may be the same or different, and represent a substituted or unsubstituted aromatic hydrocarbon group, a substituted or unsubstituted aromatic heterocyclic group, or a substituted or unsubstituted condensed polycyclic aromatic group; and n1 represents an integer of 2 to 4.

11. The organic EL device according to claim 1, wherein the electron transport layer contains a compound of the following formula (6) having an anthracene ring structure:

[Chemical Formula 7]

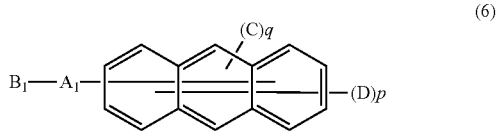

(6)

wherein $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; $B_1$ represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group; and p represents 7 or 8, and q represents 1 or 2 while maintaining a relationship that a sum of p and q is 9.

12. The organic EL device according to claim 1, wherein the electron transport layer contains a compound of the following general formula (7) having a pyrimidine ring structure:

[Chemical Formula 8]

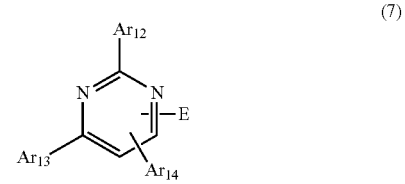

(7)

wherein $Ar_{12}$ represents a substituted or unsubstituted aromatic hydrocarbon group, a substituted or unsubstituted aromatic heterocyclic group, or a substituted or unsubstituted condensed polycyclic aromatic group; $Ar_{13}$ and $Ar_{14}$ may be the same or different, and represent a hydrogen atom, a substituted or unsubstituted aromatic hydrocarbon group, a substituted or unsubstituted aromatic heterocyclic group, or a substituted or unsubstituted condensed polycyclic aromatic group; and E represents a monovalent group of the following structural formula (8), where $Ar_{13}$ and $Ar_{14}$ are not simultaneously a hydrogen atom:

[Chemical Formula 9]

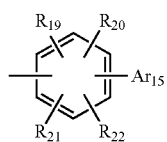
(8)

wherein $Ar_{15}$ represents a substituted or unsubstituted aromatic heterocyclic group; and $R_{19}$ to $R_{22}$ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group, where $R_{19}$ to $R_{22}$ may bind to $Ar_{15}$ via a single bond, substituted or unsubstituted methylene, an oxygen atom, or a sulfur atom to form a ring.

13. The organic EL device according to claim 1, wherein the electron transport layer contains a compound of the following general formula (9) having a benzotriazole ring structure:

[Chemical Formula 10]

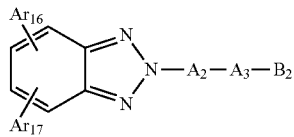
(9)

wherein $Ar_{16}$ represents a substituted or unsubstituted aromatic hydrocarbon group, a substituted or unsubstituted aromatic heterocyclic group, or a substituted or unsubstituted condensed polycyclic aromatic group; $Ar_{17}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group; $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; $A_3$ represents a divalent group of substituted or unsubstituted condensed polycyclic aromatics, or a single band; and $B_2$ represents a substituted or unsubstituted aromatic heterocyclic group.

14. The organic EL device according to claim 1, wherein the light emitting layer contains a blue light emitting dopant.

15. The organic EL device according to claim 14, wherein the light emitting layer contains a pyrene derivative as the blue light emitting dopant.

16. The organic EL device according to claim 1, wherein the light emitting layer contains an anthracene derivative.

17. The organic EL device according to claim 16, wherein the light emitting layer contains a host material which is the anthracene derivative.

18. The organic EL device according to claim 2, wherein the electron acceptor is a radialene derivative of the following general formula (2):

[Chemical Formula 2]

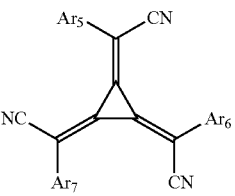
(2)

wherein $Ar_5$ to $Ar_7$ may be the same or different, and represent an aromatic hydrocarbon group, an aromatic heterocyclic group, or a condensed polycyclic aromatic group, having an electron acceptor group as a substituent.

19. The organic EL device according to claim 2, wherein the first hole transport layer or the second hole transport layer contains only a hole transport arylamine compound.

* * * * *